United States Patent
Delhomel et al.

(10) Patent No.: US 11,052,092 B2
(45) Date of Patent: Jul. 6, 2021

(54) N-{[2-(PIPERIDIN-1-YL)PHENYL](PHENYL)METHYL}-2-(3-OXO-3,4-DIHYDRO-2H-1,4-BENZOXAZIN-7-YL)ACETAMIDE DERIVATIVES AND RELATED COMPOUNDS AS ROR-GAMMA MODULATORS FOR TREATING AUTOIMMUNE DISEASES

(71) Applicant: Genfit, Loos (FR)

(72) Inventors: Jean-Francois Delhomel, Arras (FR); Enrico Perspicace, Phalempin (FR); Zouher Majd, Ennetieres-en-Weppes (FR); Peggy Parroche, Loos (FR); Robert Walczak, Lille (FR)

(73) Assignee: Genfit, Loos (FR)

( * ) Notice: Subject to any disclaimer, the term of this patent is extended or adjusted under 35 U.S.C. 154(b) by 0 days.

(21) Appl. No.: 16/481,233

(22) PCT Filed: Jan. 29, 2018

(86) PCT No.: PCT/EP2018/052172
§ 371 (c)(1),
(2) Date: Jul. 26, 2019

(87) PCT Pub. No.: WO2018/138362
PCT Pub. Date: Aug. 2, 2018

(65) Prior Publication Data
US 2019/0365768 A1    Dec. 5, 2019

(30) Foreign Application Priority Data

Jan. 27, 2017 (EP) ..... 17305093
Jun. 29, 2017 (EP) ..... 17178888

(51) Int. Cl.
| | | |
|---|---|---|
| C07D 215/227 | (2006.01) |
| A61K 31/536 | (2006.01) |
| A61P 37/02 | (2006.01) |
| A61K 31/192 | (2006.01) |
| A61K 31/357 | (2006.01) |
| A61K 31/39 | (2006.01) |
| A61K 31/40 | (2006.01) |
| A61K 31/405 | (2006.01) |
| A61K 31/428 | (2006.01) |
| A61K 31/4439 | (2006.01) |
| A61K 31/454 | (2006.01) |
| A61K 31/47 | (2006.01) |
| A61K 31/4709 | (2006.01) |
| A61K 31/498 | (2006.01) |
| A61K 31/5377 | (2006.01) |
| C07D 401/12 | (2006.01) |
| C07D 405/12 | (2006.01) |
| C07D 405/14 | (2006.01) |
| C07D 407/12 | (2006.01) |
| C07D 411/12 | (2006.01) |
| C07D 411/14 | (2006.01) |
| C07D 413/12 | (2006.01) |
| C07D 413/14 | (2006.01) |
| C07D 417/12 | (2006.01) |
| C07D 417/14 | (2006.01) |

(52) U.S. Cl.
CPC ......... *A61K 31/536* (2013.01); *A61K 31/192* (2013.01); *A61K 31/357* (2013.01); *A61K 31/39* (2013.01); *A61K 31/40* (2013.01); *A61K 31/405* (2013.01); *A61K 31/428* (2013.01); *A61K 31/4439* (2013.01); *A61K 31/454* (2013.01); *A61K 31/47* (2013.01); *A61K 31/4709* (2013.01); *A61K 31/498* (2013.01); *A61K 31/5377* (2013.01); *A61P 37/02* (2018.01); *C07D 215/227* (2013.01); *C07D 401/12* (2013.01); *C07D 405/12* (2013.01); *C07D 405/14* (2013.01); *C07D 407/12* (2013.01); *C07D 411/12* (2013.01); *C07D 411/14* (2013.01); *C07D 413/12* (2013.01); *C07D 413/14* (2013.01); *C07D 417/12* (2013.01); *C07D 417/14* (2013.01)

(58) Field of Classification Search
CPC ..... A61K 31/536
See application file for complete search history.

(56) References Cited

U.S. PATENT DOCUMENTS 9,902,725 B2 * 2/2018 Delhomel ............... A61P 37/00
2005/0113576 A1    5/2005 Lee et al.

FOREIGN PATENT DOCUMENTS

| EP | 0591830 A1 | 4/1994 |
| GB | 1033389 A | 6/1966 |
| JP | S5973554 A | 4/1984 |
| JP | H11310560 A | 11/1999 |
| WO | WO-97/08155 A1 | 3/1997 |

(Continued)

OTHER PUBLICATIONS

Hashimoto et al "Bischler-Napieralski Reaction of N [2-(2-Bromo-4,5-Dialkyloxyphenyl)Ethyl]N-(1-Phenylethyl)-2-(2-Bromo-4,5-Dimethoxyphenyl)Acetamides" Heterocycles vol. 57, pp. 2149-2161, 2002.

(Continued)

*Primary Examiner* — Paul V Ward
(74) *Attorney, Agent, or Firm* — Cesari & McKenna, LLP

(57) ABSTRACT

The present invention provides e.g. N-{[2-(piperidin-1-yl)phenyl](phenyl)methyl}-2-(3-oxo-3,4-dihydro-2H-1,4-benzoxazin-7-yl)acetamide derivatives and related compounds as ROR-gamma modulators for treating e.g. autoimmune diseases, autoimmune-related diseases, inflammatory diseases, metabolic diseases, fibrotic diseases or cholestatic diseases, such as e.g. arthritis and asthma.

16 Claims, 37 Drawing Sheets

(56) References Cited

FOREIGN PATENT DOCUMENTS

WO  WO-2008/109180 A2    9/2008
WO  WO-2016/102633 A1    6/2016

OTHER PUBLICATIONS

Takaba et al "Asymmetric Synthesis of (R)-1-(2-Methoxy-3,4-Methylenedioxybenyzl)-2-Methyl-6,7-Methylenedioxy-1,2,3,4-Tetrahydroisoquinoline (So-Called "Fumarizine")" Heterocycles vol. 43, pp. 1777-1786, 1996.

Uemura et al "Pd(OAc)$_2$-Catalyzed Lactonization of Arylacetamides Involving Oxidation of C—H Bonds" Chemistry Letters vol. 44, pp. 621-623, 2015.

* cited by examiner

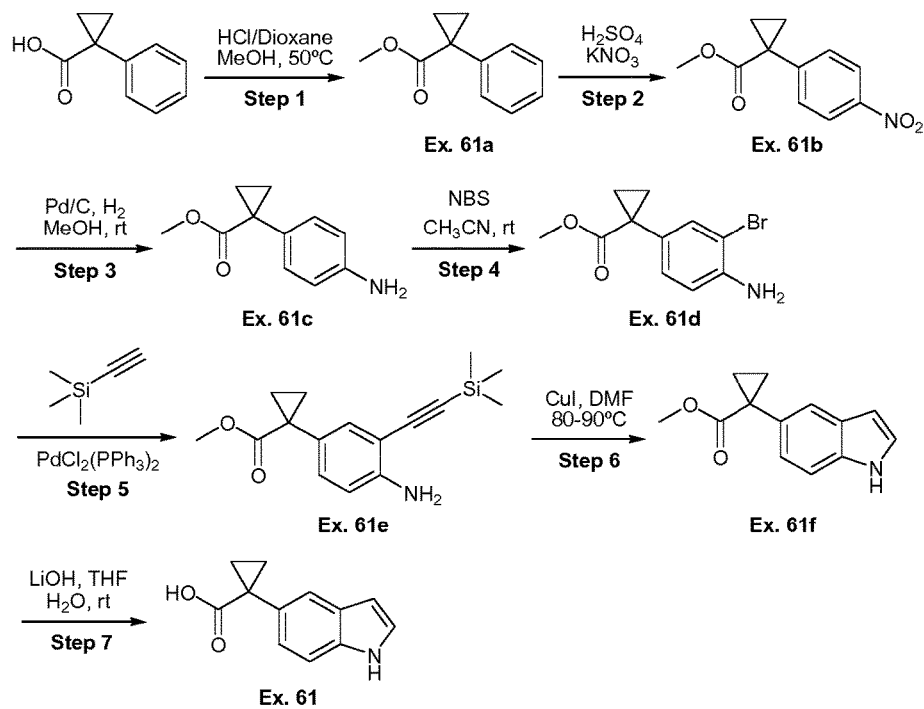
FIGURE 1BQ (Ex.61)
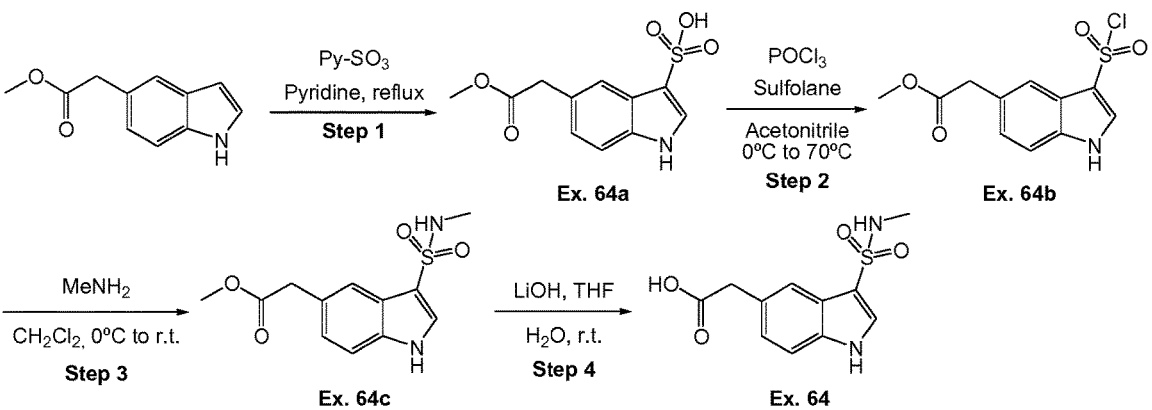
FIGURE 1BT (Ex.64)

FIGURE 1BU (Ex.65)
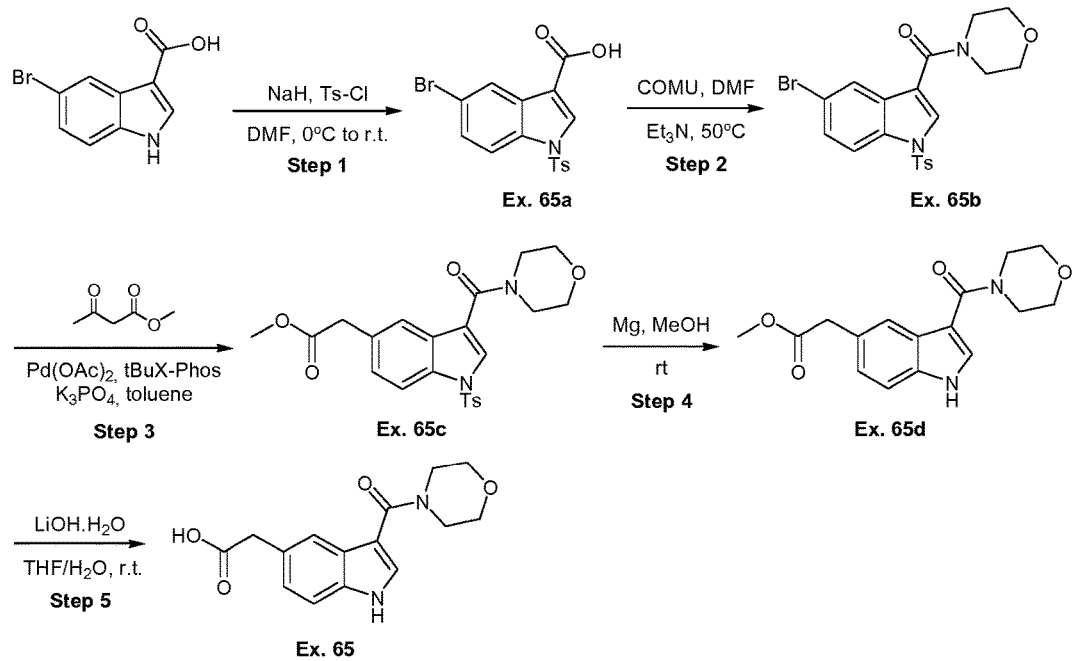
FIGURE 1BW (Ex.67)
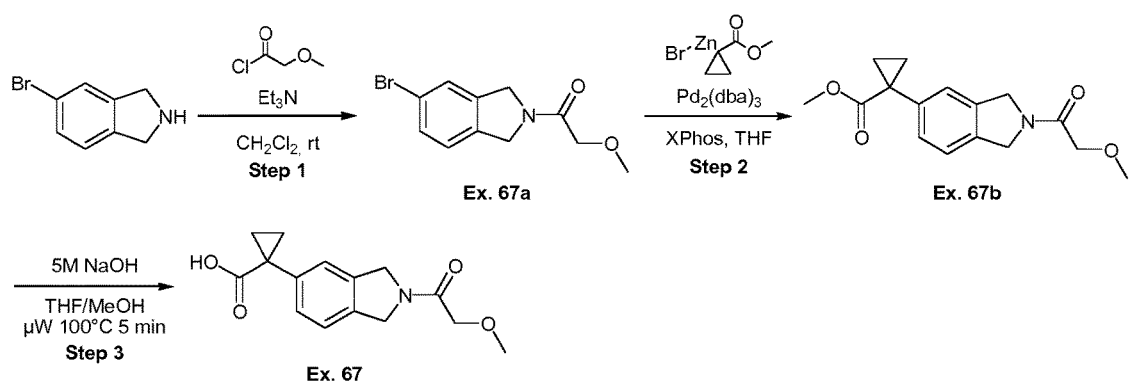

FIGURE 1BX (Ex.68)
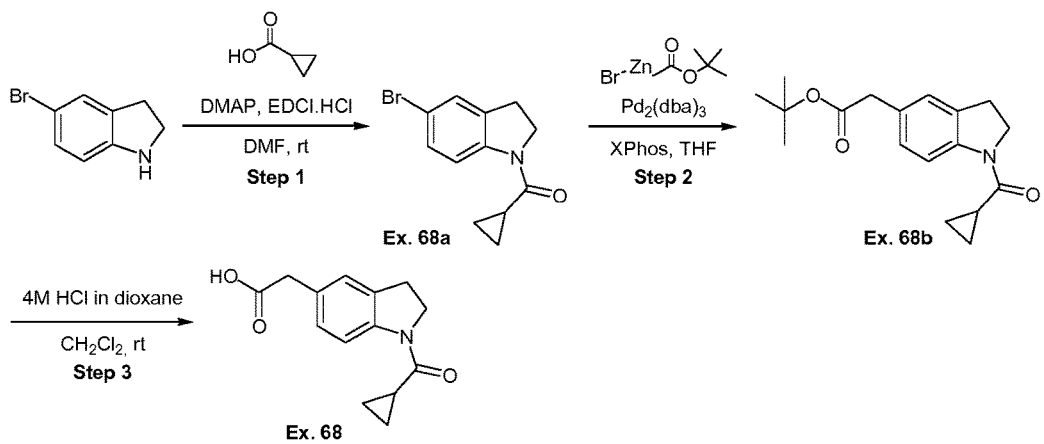
FIGURE 1BY (Ex.69)
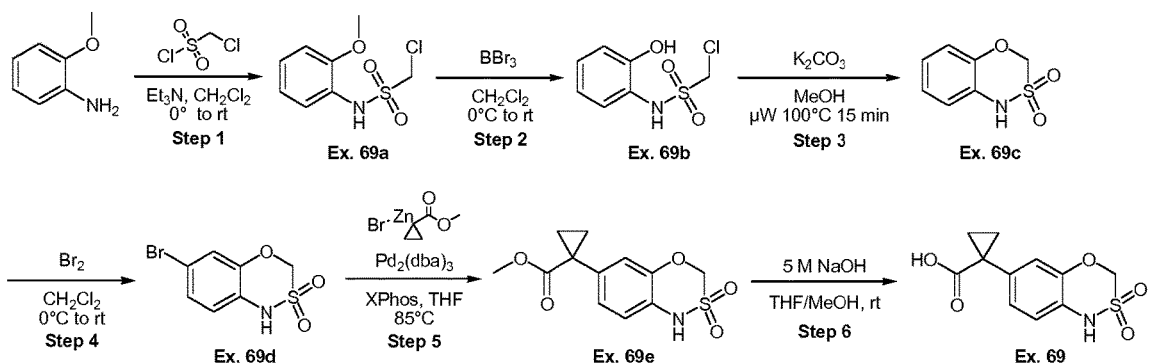
FIGURE 1BZ (Ex.70)
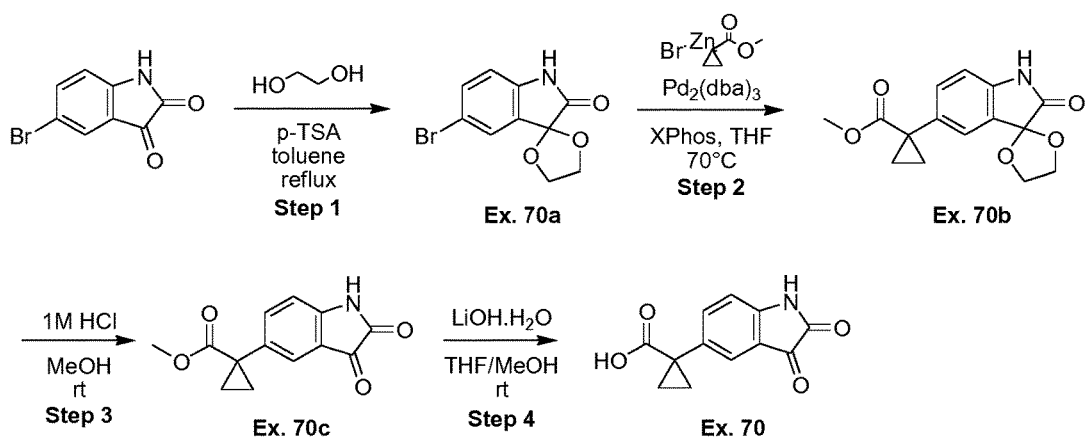

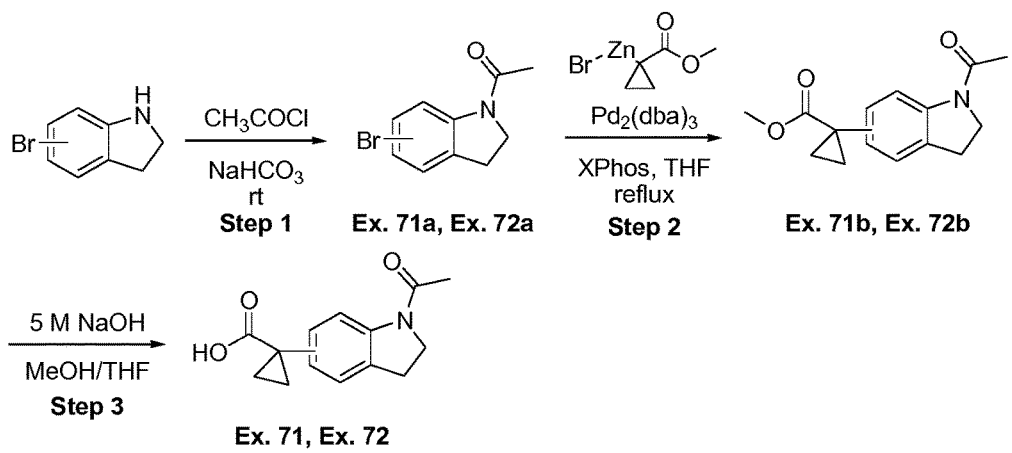
FIGURE 1CA (Ex.71) & FIGURE 1CB (Ex.72)
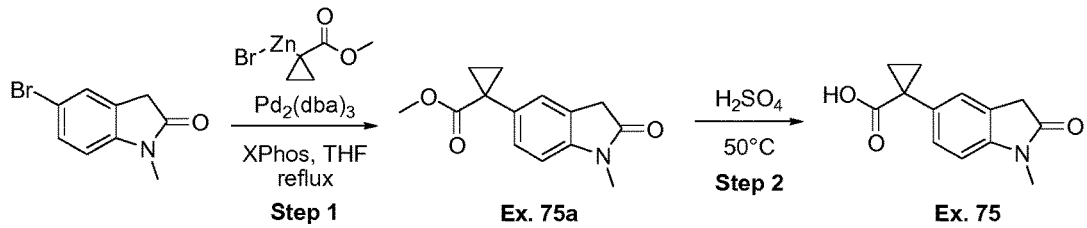
FIGURE 1CE (Ex.75)
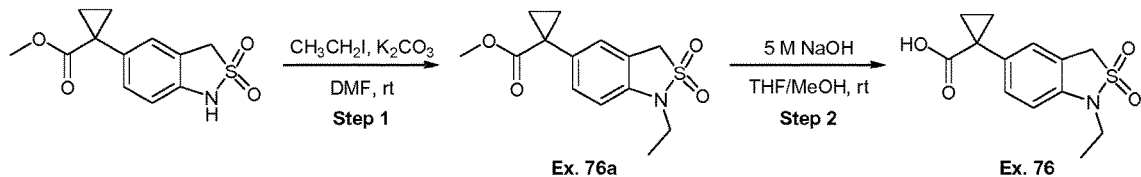
FIGURE 1CF (Ex.76)

FIGURE 1CL (Ex.82)
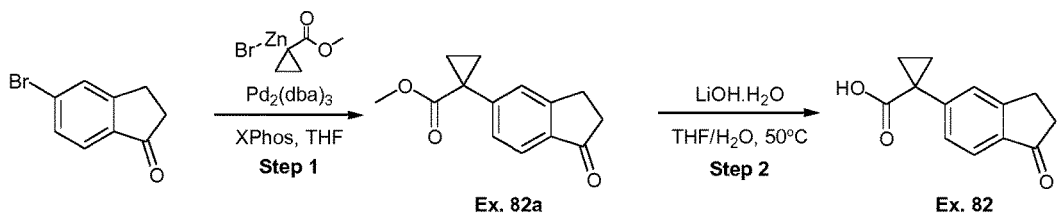
FIGURE 1CN (Ex.84)
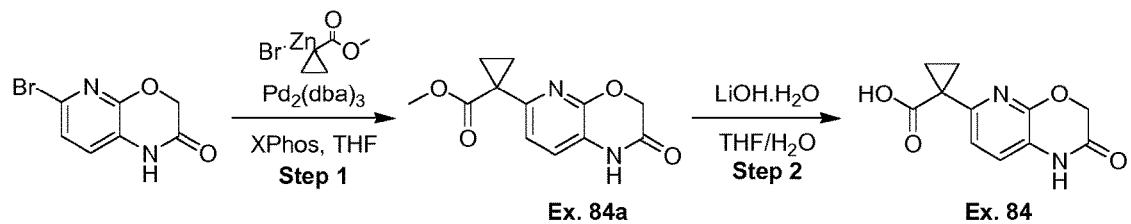
FIGURE 1CO (Ex.85)
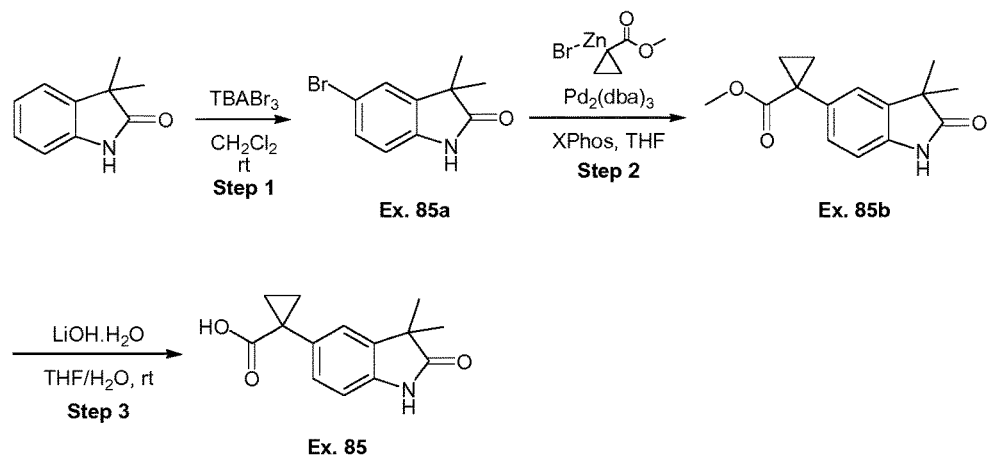

FIGURE 1CP (Ex.86)
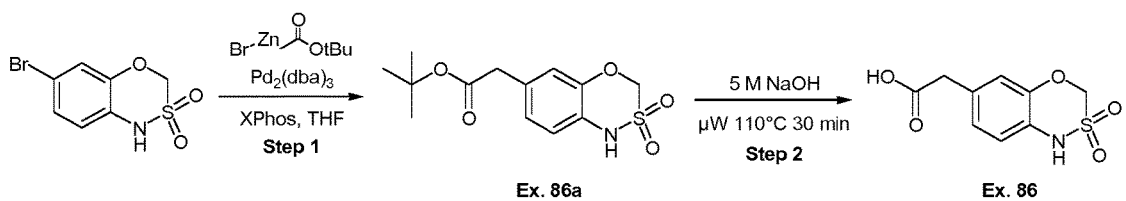
FIGURE 1CR (Ex.88)
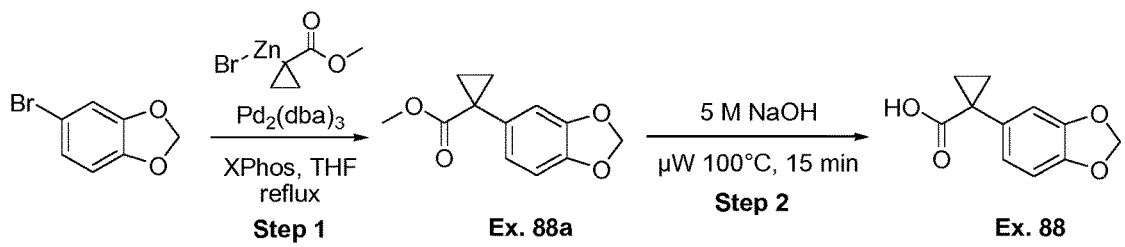
FIGURE 1CU (Ex.91)
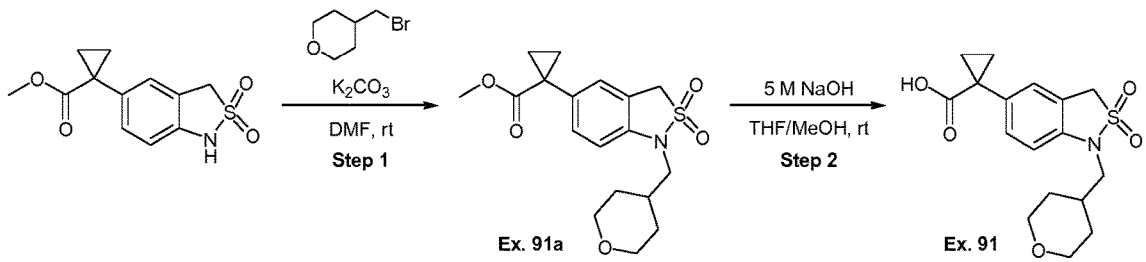
FIGURE 1CV (Ex.92)
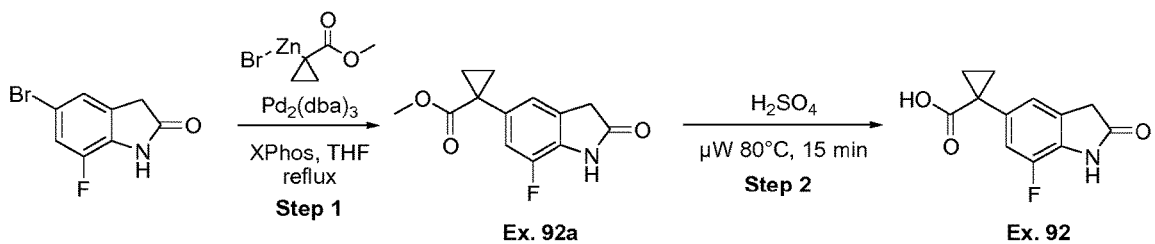

FIGURE 1CW (Ex.93)
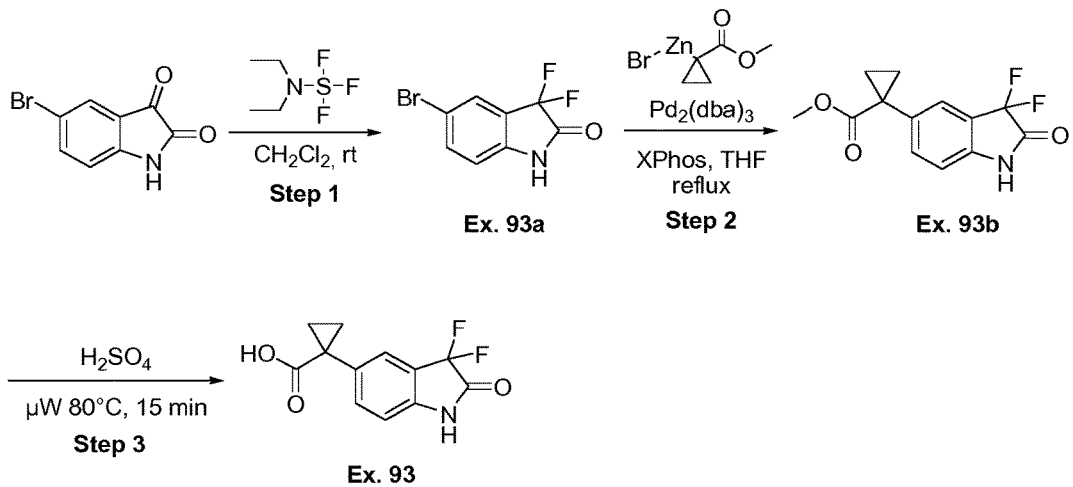
FIGURE 1CX (Ex.94)
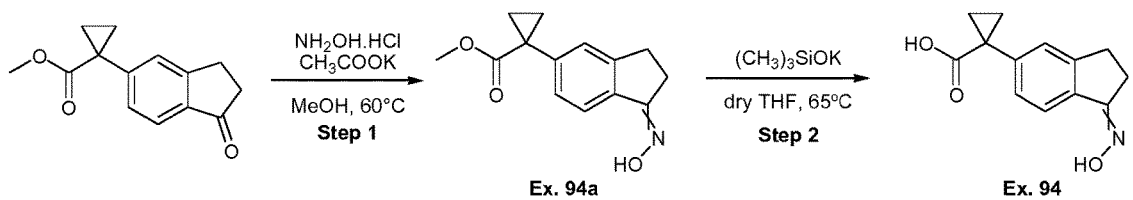
FIGURE 1CY (Ex.95)
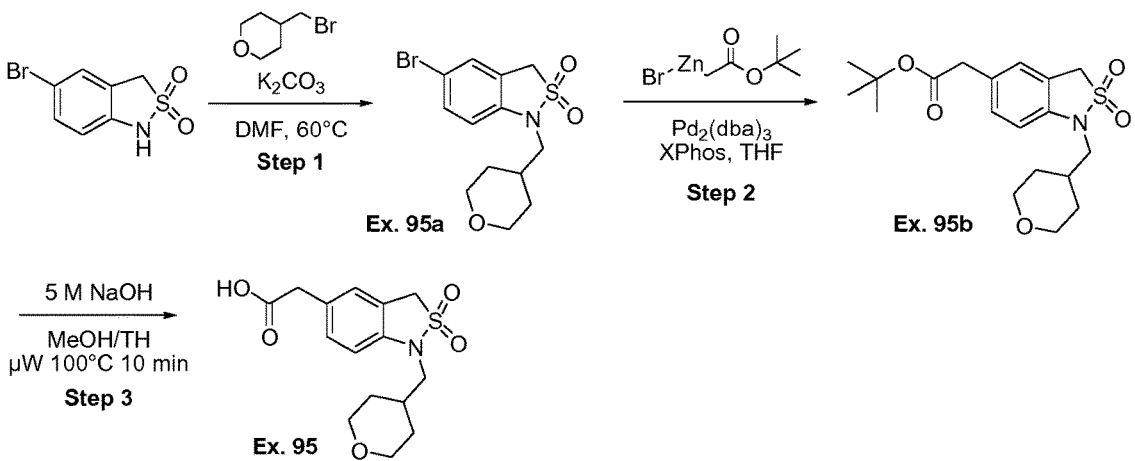

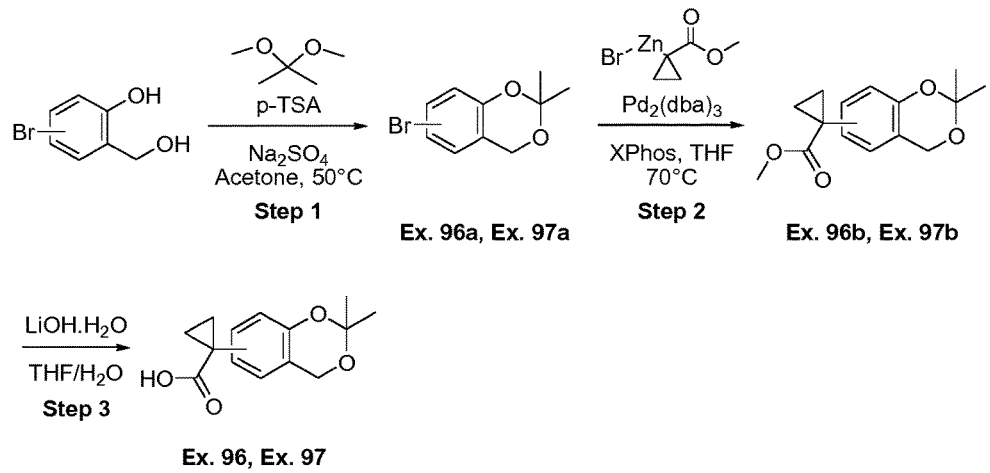
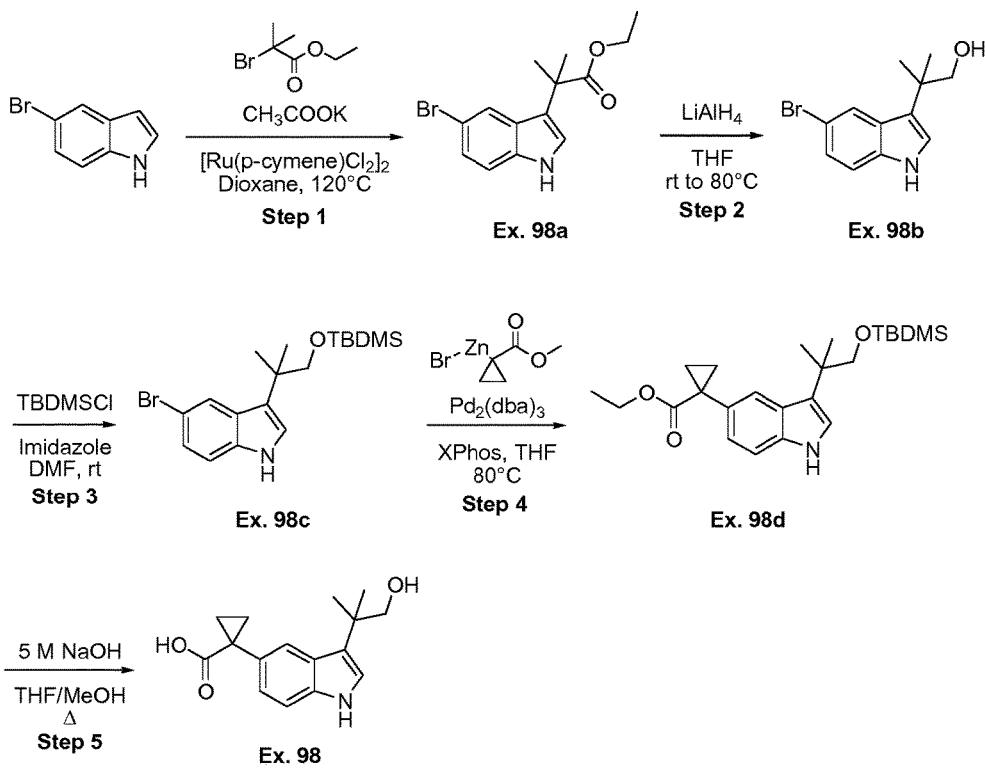

FIGURE 1DD (Ex.100)
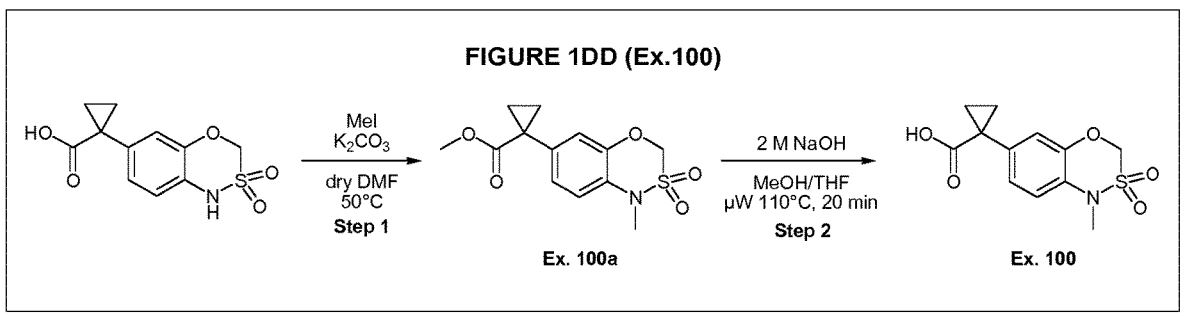
FIGURE 1DF (Ex.102)
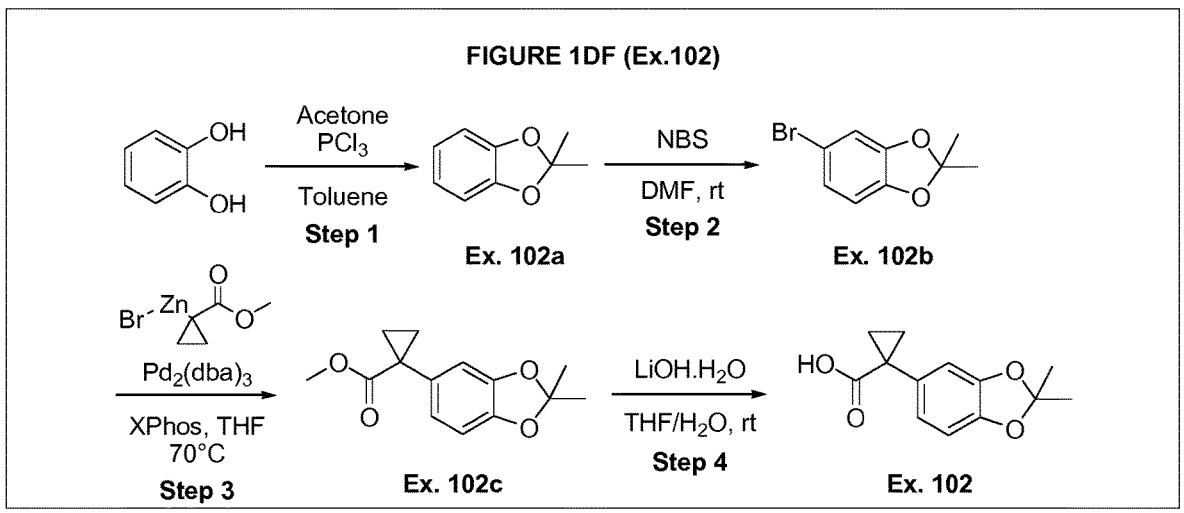

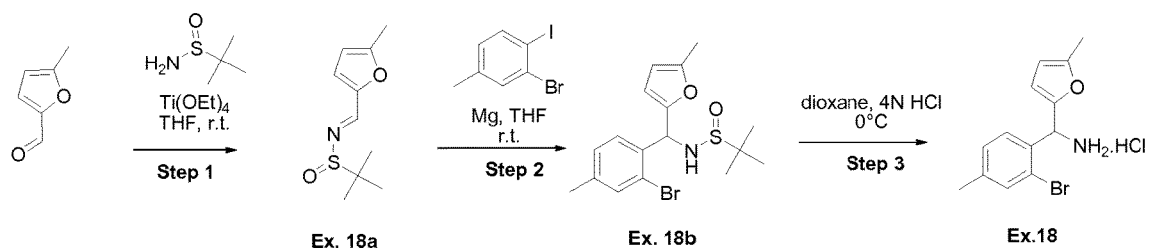
FIGURE 2A (Ex.18)
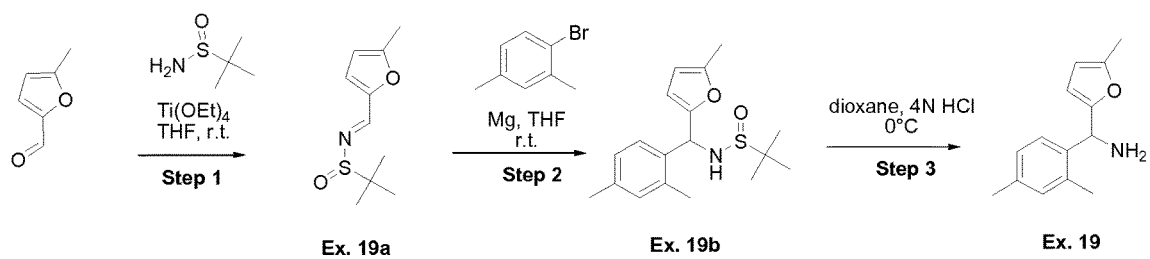
FIGURE 2B (Ex.19)
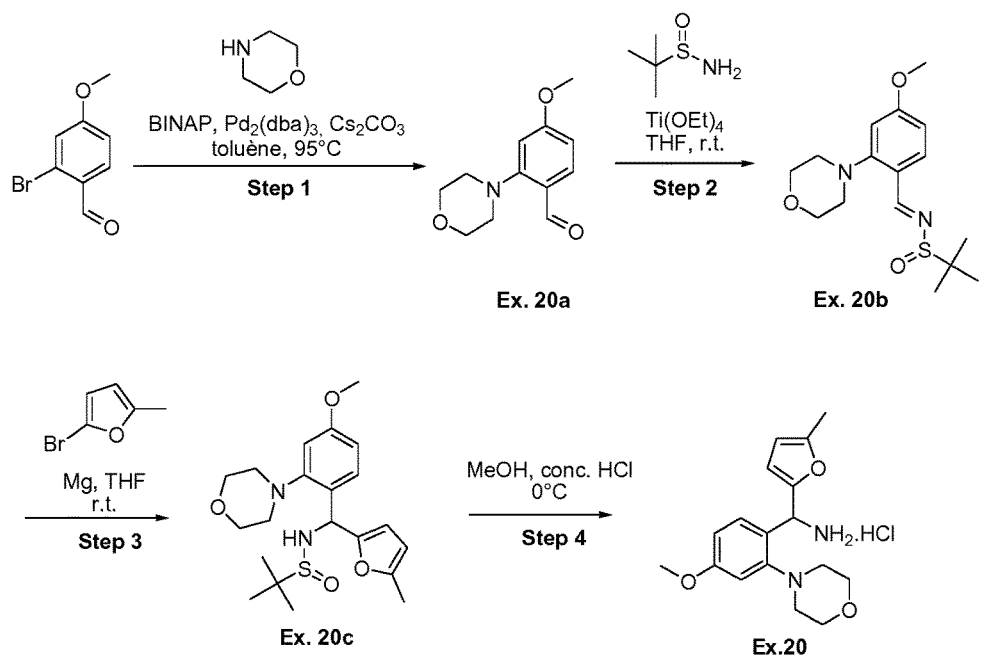
FIGURE 2C (Ex.20)

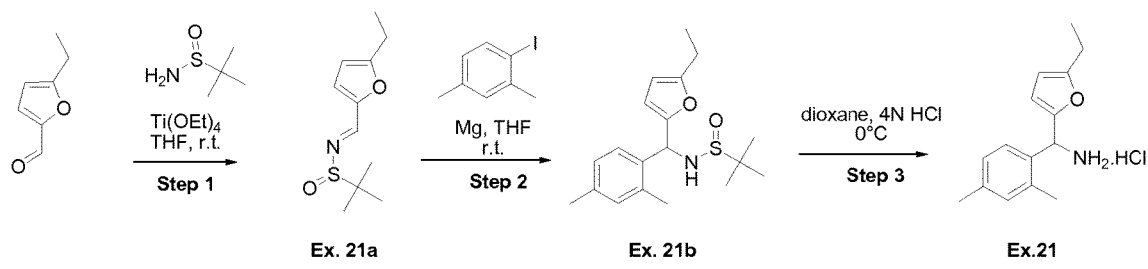
FIGURE 2D (Ex.21)
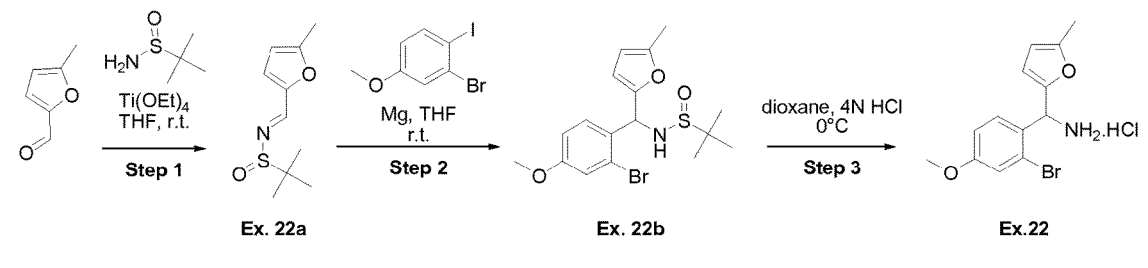
FIGURE 2E (Ex.22)
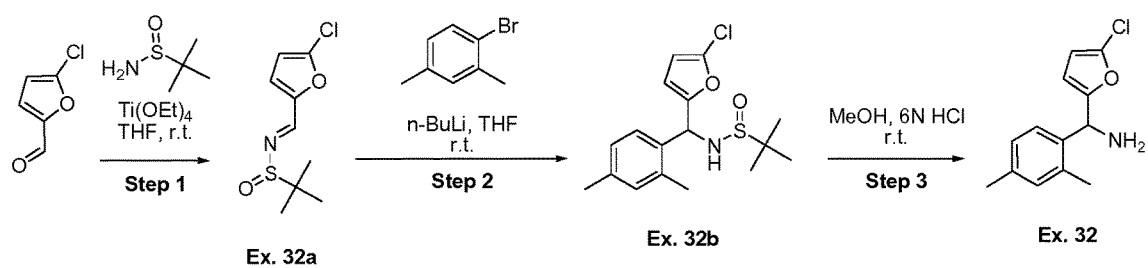
FIGURE 2F (Ex.32)
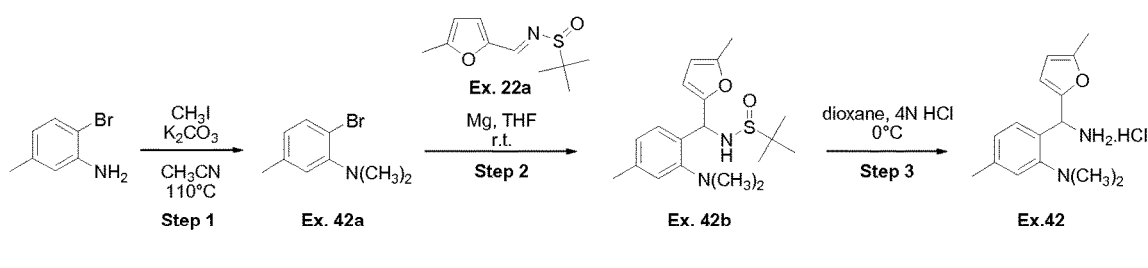
FIGURE 2G (Ex.42)

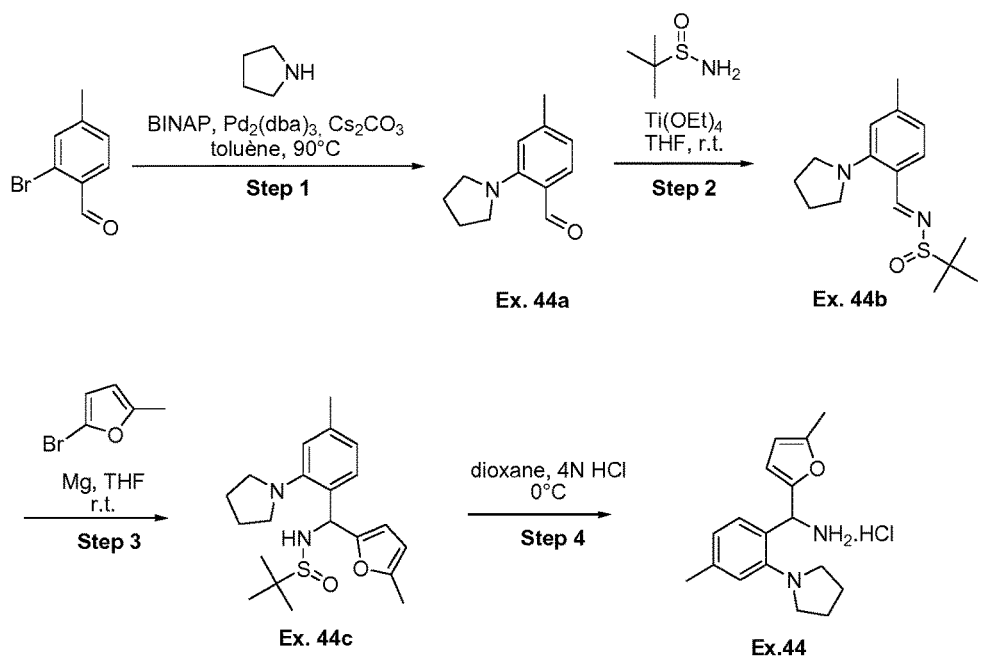
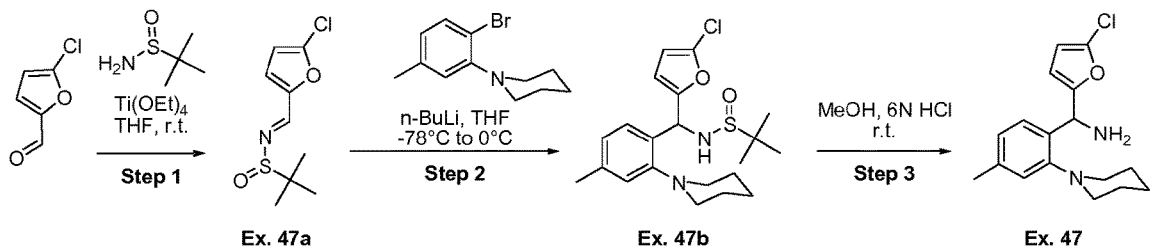

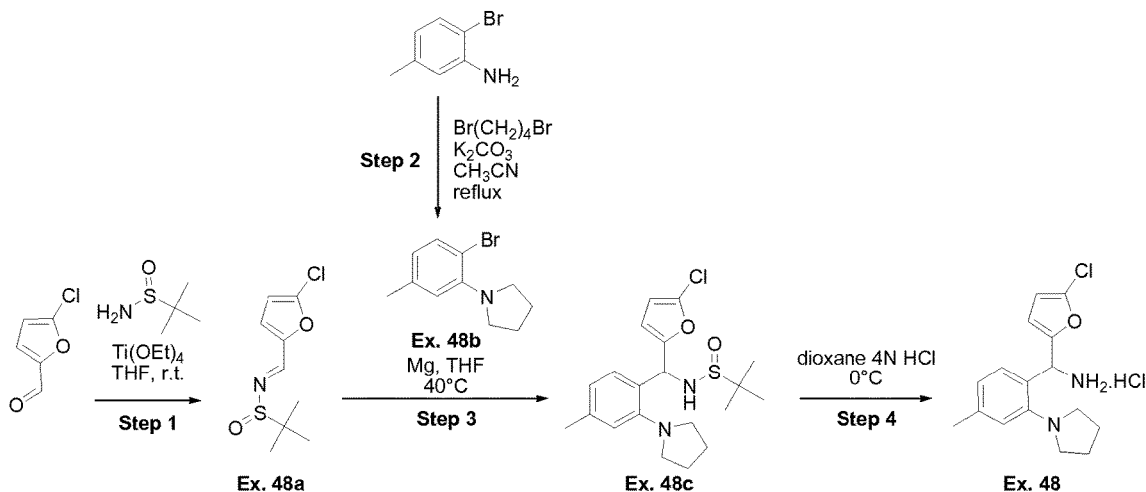
FIGURE 2J (Ex.48)
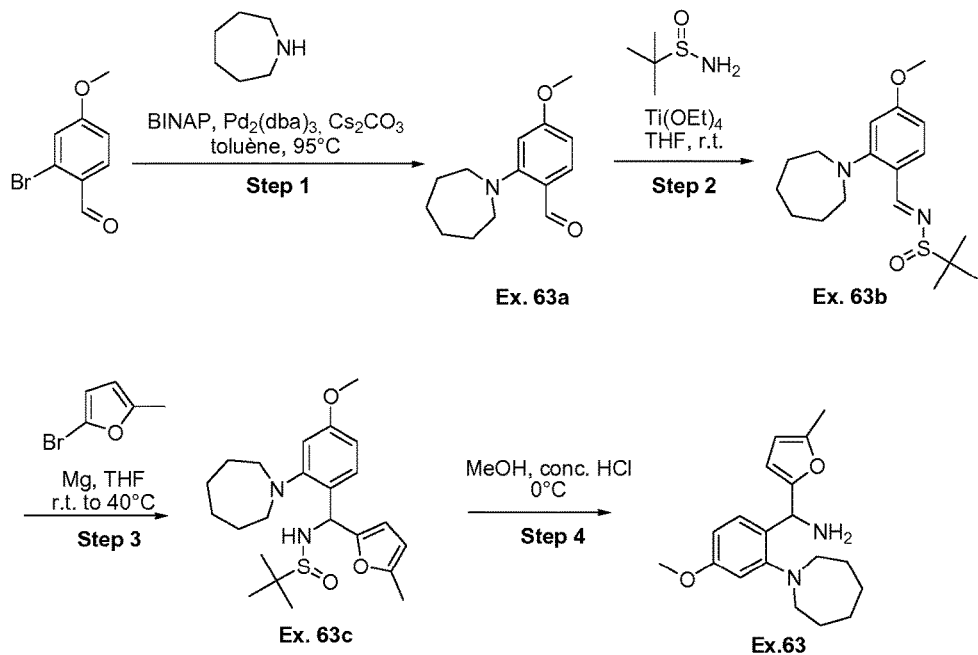
FIGURE 2K (Ex.63)

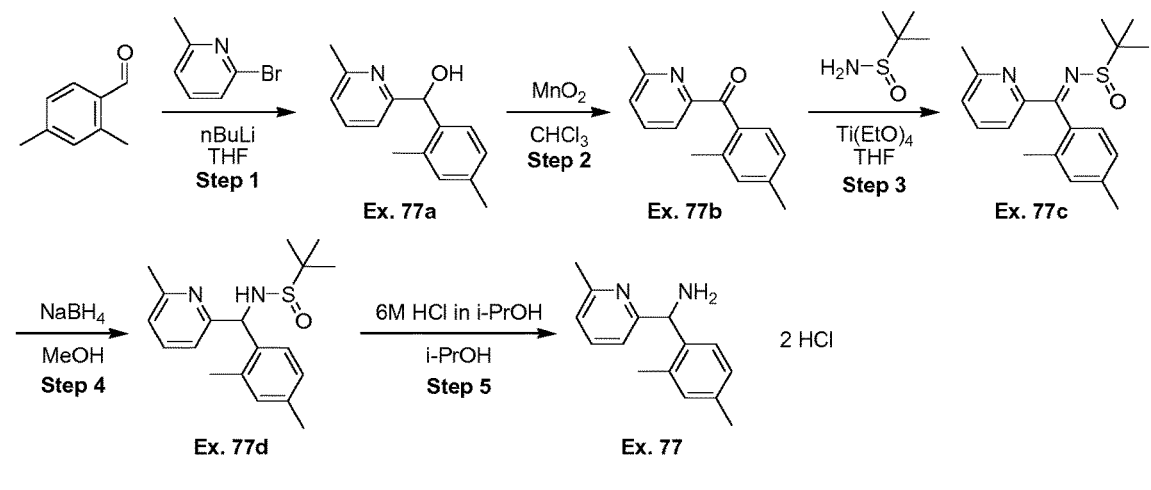
FIGURE 2L (Ex.77)
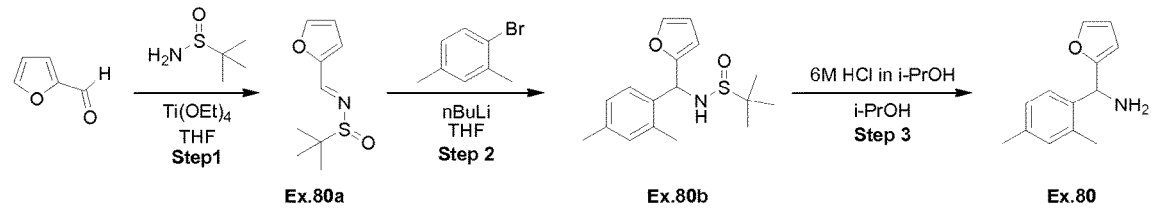
FIGURE 2N (Ex.80)
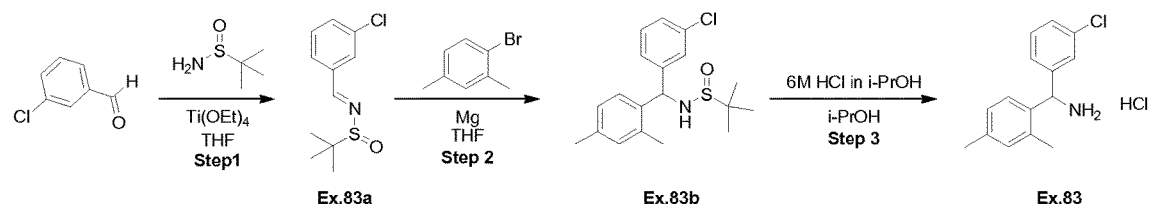
FIGURE 2O (Ex.83)

FIGURE 2P (Ex.87)
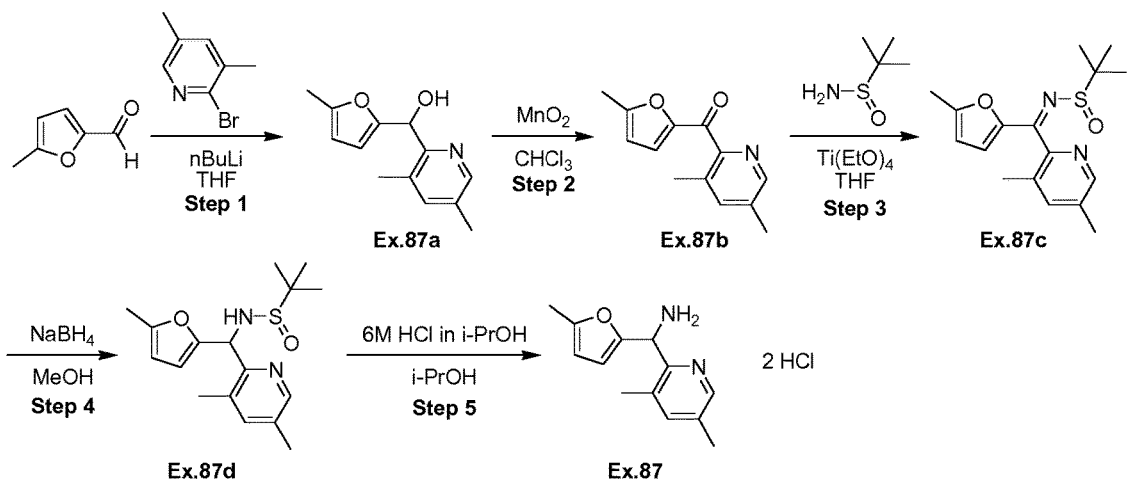
FIGURE 2Q (Ex.99)
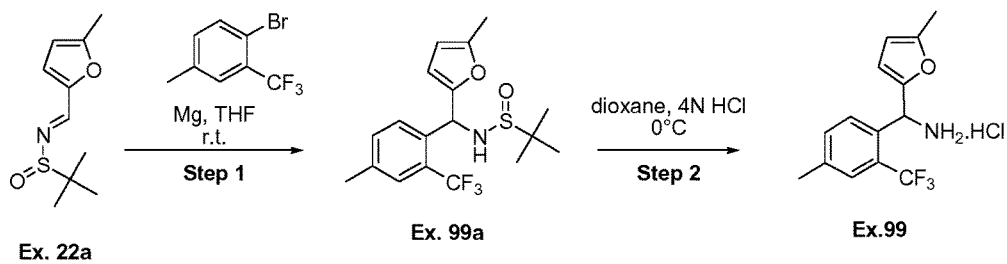
FIGURE 2R (Ex.101)
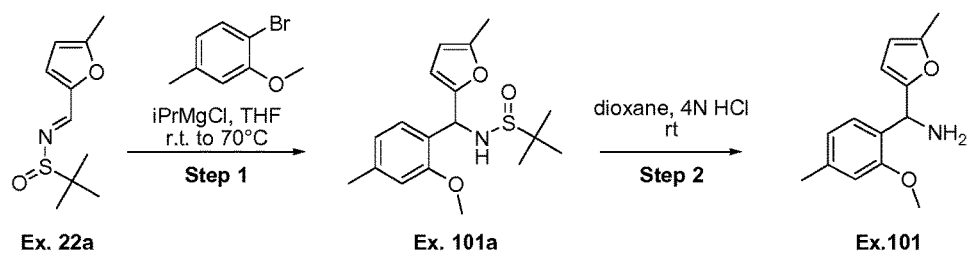

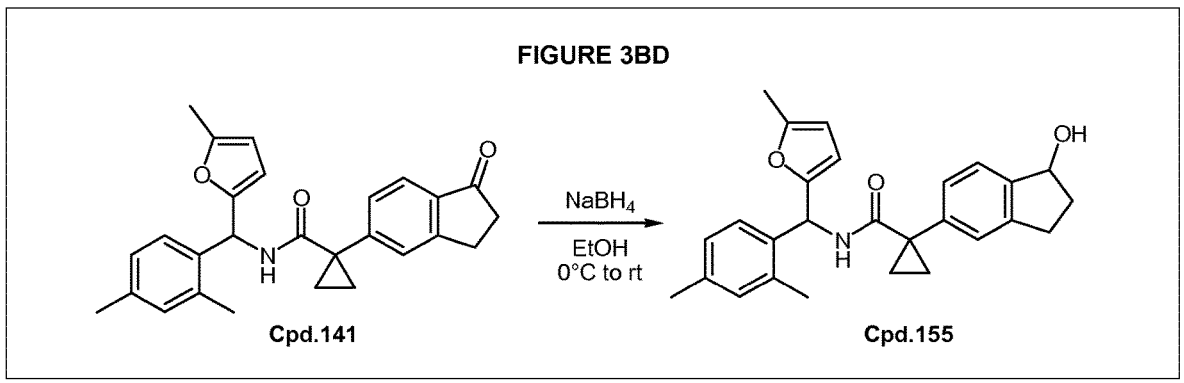
FIGURE 4A
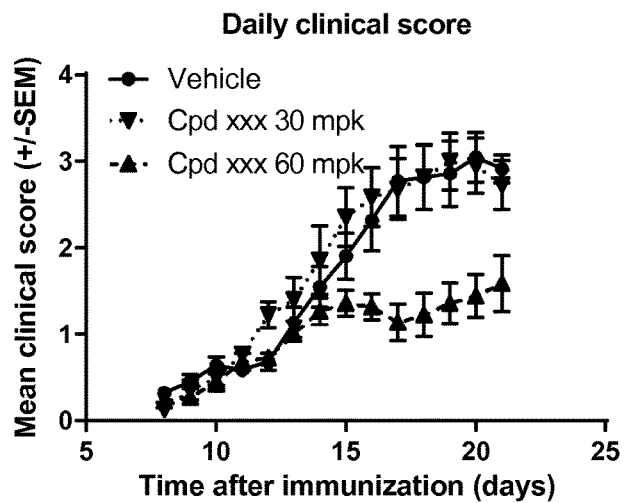
FIGURE 4B
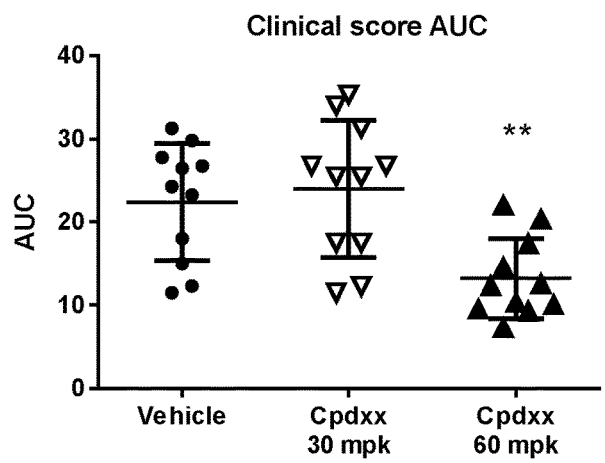

N-{[2-(PIPERIDIN-1-YL)PHENYL](PHENYL) METHYL}-2-(3-OXO-3,4-DIHYDRO-2H-1,4-BENZOXAZIN-7-YL)ACETAMIDE DERIVATIVES AND RELATED COMPOUNDS AS ROR-GAMMA MODULATORS FOR TREATING AUTOIMMUNE DISEASES

CROSS-REFERENCE TO RELATED APPLICATIONS

This application is the National Stage of International Application No. PCT/EP2018/052172, filed Jan. 29, 2018, which claims priority to European Application No. 17305093.1, filed Jan. 27, 2017, and European Application No. 17178888.8, filed Jun. 29, 2017. The contents of these prior applications are hereby incorporated by reference herein in their entirety.

TECHNICAL FIELD

The present invention relates to novel compounds that are modulators of RORgamma and the pharmaceutical use of such compounds.

BACKGROUND

The retinoic acid-related orphan receptor γ (RORγ) is a member of the ROR subfamily of nuclear receptors which includes three genes; RORA, RORB and RORC (also known as RORγ). rory gene encodes two isoforms RORγ1 and RORγ2 (also termed RORγt). RORγ1 is preferentially expressed in skeletal muscle and several other tissues, including pancreas, thymus, prostate, liver and testis (Hirose et al, 1994; Ortiz et al, 1995). RORγt is restricted to several distinct immune cell types (He et al, 1998). This immune system-specific isoform (RORγt) is the key lineage-defining transcription factor for the differentiation program of T helper type 17 (Th17) cells, a subset of CD4+ T-helper and the most prominent cells in producing a number of inflammatory cytokines, such as IL-17A, IL-17F, IL-22, and IL-23 considered as important pathogenic factors for many immune and inflammatory diseases. During the disease process Th17 cells are activated and are responsible for recruiting other inflammatory cell types, such as neutrophils, to mediate pathology in the target tissues (Korn et al, 2009). RORγt is also able to induce IL-17A and IL-17F in naïve CD4+ T-helper, NKT and iNKT cells (Rachitskaya et al, 2008), γδT cells (Murdoch & Lloyd, 2010), CD8+ Tcells (Liu et al, 2007) and CD4-CD8+TCRab+T cells (Crispin et al, 2008). RORγt is also expressed in and is required for the generation of LTi cells (Eberl et al, 2004), which are central to the development of lymphoid organs such as lymph node and Peyer's patch (Lipp & Muller, 2004).

Overexpression of RORγt in naïve CD4+ T cells was demonstrated to drive the induction and development of Th17 cells. In contrast, RORγt deficiency in mice completely impairs Th17 cell differentiation and induces resistance to the development of autoimmune diseases, such as experimental autoimmune encephalomyelitis (EAE) a model of multiple sclerosis (Dang et al, 2011; Yang et al, 2008) or experimental autoimmune myocarditis (EAM) (Yamashita et al, 2011). In the same manner, mice lacking IL-17 are resistant to development of EAE, and collagen-induced arthritis (CIA), a model of rheumatoid arthritis. IL-17 neutralization with a targeted antibody suppresses autoimmune inflammation, joint damage, and bone destruction (Furuzawa-Carballeda et al, 2007; Lubberts et al, 2004; Stockinger et al, 2007). Moreover, blocking Th17 pathway demonstrated good efficacy in patients with some chronic inflammatory diseases. For example, the anti-p40 monoclonal antibody Ustekinumab (Stelara) that targets Th17 and Th1 through IL-23 and IL-12 respectively, has been approved for the treatment of moderate to severe plaque psoriasis in adult patients and showed a clinical (phase Iib) efficacy in refractory Crohn diseased patients (Tuskey & Behm, 2014).

Small molecule RORγt modulators have therapeutic effects in preclinical disease models. In particular, compounds TMP778 and SR1001 were efficacious in psoriasis and multiple sclerosis models, respectively, when administered by injection (Skepner et al, 2014; Solt et al, 2011). Recently, Vitae Pharma has announced that a small molecule RORgt inverse agonist VTP-43742 reduced the Psoriasis Area Severity Index (PASI) score and plasma IL-17 levels, relative to placebo, in patients with moderate to severe psoriasis.

To summarise, RORγt activity modulation results in the modulation of IL-17 dependent immune and inflammatory responses.

Currently, there is considerable evidence suggesting that RORγt/IL-17 component is closely associated with a range of chronic inflammatory diseases such as multiple sclerosis (MS), psoriasis, inflammatory bowel diseases (IBD), rheumatoid arthritis (RA), uveitis and lung diseases. Compounds able to modulate RORγt activity are also expected to provide a therapeutic benefit in the treatment of numerous medical disorders, including autoimmune, inflammatory, fibrotic and cholestatic disorders, such as asthma, ankylosing spondylitis, autoimmune cardiomyopathy, autoimmune hepatitis, Crohn's disease, chronic obstructive proliferative disease (COPD), diabetes mellitus type 1, lupus erythematosus, lupus nephritis, multiple sclerosis, psoriasis, psoriatic arthritis, rheumatoid arthritis, ulcerative colitis, myocarditis, pulmonary fibrosis (idiopathic pulmonary, interstitial lung, cystic and progressive massive fibrosis), Non Alcoholic Fatty Liver Disease (NAFLD), NonAlcoholic SteatoHepatitis (NASH) and Alcoholic SteatoHepatitis (ASH), cardiac fibrosis and heart myocardial and endomyocardial fibrosis, arterial fibrosis, atherosclerosis/restenosis, intestinal fibrosis (occurs for example in Crohn's disease and collagenous colitis), kidney fibrosis, scleroderma and systemic sclerosis Primary Biliary Cholangitis (PBC), primary sclerosisng cholangitis (PSC), biliary atresia, Progressive familial intrahepatic cholestasis (PFIC), Hepatitis (hepatitis A, hepatitis B, hepatitis C).

The present invention describes novel RORγt modulators, their preparation and their use in therapy, in particular in the treatment of immune, inflammatory, metabolic, fibrotic and cholestatic diseases.

SUMMARY OF INVENTION

RORγ inverse agonists were proposed in Skepner et al., 2014 who allegedly showed that compound T was efficacious in psoriasis model when administered by injection.

Recently, data from a Phase 2a proof-of-concept clinical trial with RORgt inverse agonist (VTP-43742) were reported (Vitae Pharma press release).

VTP-43742 demonstrated a clear signal of efficacy, with patients in the 350 mg dose group achieving a 24 percent reduction in the Psoriasis Area Severity Index (PASI) score relative to placebo. In the 700 mg dose group, patients achieved a 30 percent placebo-adjusted PASI score reduction.

The present invention provides novel compounds that are modulators of RORγ and have the following formula (I):

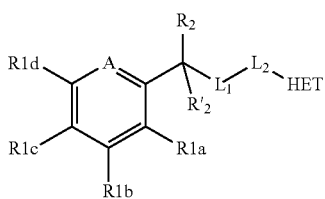

In a particular embodiment, the novel compounds have the following formula (Ia):

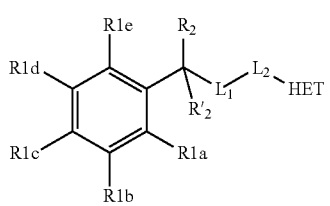

The present invention also provides pharmaceutical compositions comprising the compounds of formula (I) or (Ia), since they modulate RORγ in vitro and in cellular models, indicating that these compounds have properties of pharmaceutical interest. Accordingly, further objects of the invention include methods of treatment comprising the administration of said pharmaceutical composition for the treatment of RORγ-related diseases such as autoimmune, inflammatory diseases, metabolic, fibrotic and cholestatic diseases.

The present invention also provides a compound of formula (I) or (Ia), for use as a medicament.

The present invention also provides a compound of formula (I) or (Ia), for use in a method for the treatment of RORγ-related diseases.

Further objects of the present invention, including preferred compounds of formula (I) or (Ia), methods of preparing compounds of formula (I) or (Ia) and preferred medical uses or methods, in combination or not with other compounds, are provided in the Detailed Description.

DESCRIPTION OF THE FIGURES

Abbreviations Used in the Figures and in the Text:
ACLF acute-on-chronic liver failure
ADME absorption, distribution, metabolism, and excretion
ALF acute liver failure
ASH Alcoholic SteatoHepatitis
AUC area under the curve
BINAP 2,2'-Bis(diphenylphosphino)-1,1'-binaphthalene
BOC tButylOxyCarbonyl
CD Cluster of Differentiation
CDCl3 deuterated chloroform
CFA Complete Freund's Adjuvant
CHCl3 chloroform
CH2Cl2 Dichloromethane
CIA collagen-induced arthritis
CMC CarboxyMethyl Cellulose
CNS Conserved non coding sequence
COPD chronic obstructive proliferative disease
Cpd: Compound
Cs2CO3 Cesium Carbonate
di-tert-butyl X-Phos 2-di-tert-butylphosphino-2',4',6'-triisopropylbiphenyl
DMAP 4-(DiMethylAmino)Pyridine
DMEM Dulbecco's modified Eagle's medium
DMF DiMethylFormamide
DMSO DiMethyl SulfOxide
EAE Experimental Autoimmune Encephalomyelitis
EAM Experimental Autoimmune Myocarditis
EDCl.HCl N-Ethyl-N'-(3-Dimethylaminopropyl)Carbodilmide HydroChloride
EDTA ethylene-diamine tetra-acetic acid
equiv equivalent
Et2O Diethyl ether
Et3N Triethylamine
EtOAc Ethyl acetate
EtOH Ethanol
H2O water
H2SO4 sulfuric acid
HCl Hydrochloric acid
HNO3 nitric acid
HPLC High Performance Liquid Chromatography
HTAB hexadecyltrimethyl ammonium bromide
IBD inflammatory bowel disease
ICP intrahepatic cholestasis of pregnancy
$IC_{50}$ Half maximal inhibitory concentration
IL-12 interleukin 12
IL-17 interleukin 17
IL-22 interleukin 22
IL-23 interleukin 23
iPrOH isopropanol
IUPAC International Union of Pure and Applied Chemistry
K2CO3 potassium carbonate
LCMS Liquid Chromatography-Mass Spectrometry
Me3SiCl Trimethylsilyl chloride
MeOH Methanol
mg miligramme
MgSO4 Magnesium sulphate
min minute
mL milliliter
µL microliter
MOG Myelin Oligodendrocyte Glycoprotein
mp melting point
MS multiple sclerosis
NAFLD non-alcoholic fatty liver disease
NaHCO3 Sodium bicarbonate
NaN3 sodium azide
NaOH sodium hydroxide
NASH NonAlcoholic SteatoHepatitis
NH4Cl ammonium chloride
NMR nuclear magnetic resonance
NR Nuclear Receptor
PASI psoriasis area and severity index
PBC primary biliary cholangitis
PBS phosphate-buffered saline
PCR Polymerase Chain Reaction
Pd2(dba)3 Tris(dibenzylideneacetone)dipalladium(0)
Pd/C palladium on carbon
Pd(OAc)2 Palladium(II) acetate
PdCl2(dppf)2 1,1'-Bis(diphenylphosphino)ferrocene]dichloropalladium(II)
PFIC progressive familial intrahepatic cholestasis
PMA Phorbol 12-Myristate 13-Acetate
ppm parts-per-million
PSC primary sclerosing cholangitis
PTX pertussis toxin PyBOP (benzotriazol-1-yloxy)tripyrrolidinophosphonium hexafluorophosphate
RA rheumatoid arthritis
RPMI Roswell Park Memorial Institute medium
ROR Retinoic Acid-Related Orphan Receptor
rt room temperature
sat. saturated
SIRS systemic inflammatory response syndrome
SPF Specific Pathogen Free
TFA trifluoroacetic acid
Th1 T helper 1
Th17 T helper 17
THF TetraHydroFuran
TLC Thin-Layer Chromatography
UV ultra-violet
XPhos Dicyclohexylphosphino-2',4',6'-triisopropylbiphenyl
μW Microwave FIGS. 1 and 2—Intermediate Compounds for the Synthesis of the Compounds of Formula (I) or (Ia)

Intermediates are independently generated for the synthesis of compounds of formula (I) or (Ia): for example 2-(3-oxo-3,4-dihydro-2H-1,4-benzoxazin-7-yl)acetic acid Ex.2 (FIG. 1AA), 2-(2,3-dioxo-1,2,3,4-tetrahydroquinoxalin-6-yl)acetic acid Ex.11 (FIG. 1AB), 2-(3-oxo-3,4-dihydro-2H-1,4-benzoxazin-6-yl)acetic acid Ex.12 (FIG. 1AC), 2-(2,2-difluoro-3-oxo-3,4-dihydro-2H-1,4-benzoxazin-7-yl)acetic acid Ex.13 (FIG. 1AD), 2-(2-oxo-2,3-dihydro-1H-indol-5-yl)acetic acid Ex.14 (FIG. 1AE), 2-(2,2-dimethyl-3-oxo-3,4-dihydro-2H-1,4-benzoxazin-7-yl)acetic acid Ex.15 (FIG. 1AF), 2-(2,2-dioxo-1,3-dihydro-2,1-benzothiazol-5-yl)acetic acid hydrochloride Ex.17 (FIG. 1AG), 2-(2-oxo-1,2,3,4-tetrahydroquinolin-6-yl)acetic acid Ex.23 (FIG. 1AH), 2-(1-methyl-2-oxo-2,3-dihydro-1H-indol-5-yl)acetic acid Ex.24 (FIG. 1AI), 2-(3-hydroxy-1,3-dimethyl-2-oxo-2,3-dihydro-1H-indol-5-yl)acetic acid Ex.25 (FIG. 1AI), 2-(1,3,3-trimethyl-2-oxo-2,3-dihydro-1H-indol-5-yl)acetic acid Ex.26 (FIG. 1AI), 2-(2-methanesulfonyl-2,3-dihydro-1H-isoindol-5-yl)acetic acid Ex.27 (FIG. 1AJ), 2-(2-methanesulfonyl-2,3-dihydro-1H-isoindol-4-yl)acetic acid Ex.28 (FIG. 1AK), 2-(1-oxo-2,3-dihydro-1H-inden-5-yl)acetic acid Ex.29 (FIG. 1AL), 2-(7-methyl-2-oxo-2,3-dihydro-1H-indol-5-yl)acetic acid Ex.30 (FIG. 1AM), 2-[2-oxo-3-(propan-2-ylidene)-2,3-dihydro-1H-indol-5-yl]acetic acid Ex.31 (FIG. 1AN), 1-(2-methanesulfonyl-2,3-dihydro-1H-isoindol-5-yl)cyclopropane-1-carboxylic acid Ex.33 (FIG. 1AO), 2-[3-(2-hydroxyethyl)-1H-indol-5-yl]acetic acid Ex.34 (FIG. 1AP) 1-(3-oxo-3,4-dihydro-2H-1,4-benzoxazin-7-yl)cyclopropane-1-carboxylic acid Ex.35 (FIG. 1AQ), 1-[3-(2-hydroxyethyl)-1H-indol-5-yl]cyclopropane-1-carboxylic acid Ex.36 (FIG. 1AR), 1-(2-oxo-2,3-dihydro-1H-indol-5-yl)cyclopropane-1-carboxylic acid Ex.37 (FIG. 1AS), 1-(2,2-dioxo-1,3-dihydro-2,1-benzothiazol-5-yl)cyclopropane-1-carboxylic acid Ex.38 (FIG. 1AT), 2-(3-methyl-1H-indol-5-yl)acetic acid Ex.39 (FIG. 1AU), 1-(1-methyl-2,2-dioxo-1,3-dihydro-2-benzothiazol-5-yl)cyclopropane-1-carboxylic acid Ex.40 (FIG. 1AV), 1-{1-[2-(benzyloxy)ethyl]-2,3-dihydro-1H-indol-5-yl}cyclopropane-1-carboxylic acid Ex.41 (FIG. 1AW), 1-(2,2-dioxo-1,3-dihydro-2-benzothiophen-5-yl)cyclopropane-1-carboxylic acid Ex.43 (FIG. 1AY), 2-(2,2-dioxo-1,3-dihydro-2-benzothiophen-5-yl)acetic acid Ex.46 (FIG. 1BB), 2-(3-oxo-2,3-dihydro-1H-inden-5-yl)acetic acid Ex.51 (FIG. 1BG), 2-(2-ethoxy-1H-1,3-benzodiazol-5-yl)acetic acid Ex.52 (FIG. 1BH), 2-[6-(methylsulfanyl)naphthalen-2-yl]acetic acid Ex.53 (FIG. 1BI), 2-[2-(ethylsulfanyl)-1H-1,3-benzodiazol-5-yl]acetic acid Ex.54 (FIG. 1BJ), 2-[2-(morpholin-4-yl)-1H-1,3-benzodiazol-5-yl]acetic acid Ex.55 (FIG. 1BK), 1-(1-cyclopropanecarbonyl-2,3-dihydro-1H-indol-5-yl)cyclopropane-1-carboxylic acid Ex.56 (FIG. 1BL), 2-{1-[3-(tert-butoxy)-3-oxopropyl]-1H-indol-5-yl}acetic acid Ex.57 (FIG. 1BM), 2-[3-(2-methanesulfonylethyl)-1H-indol-5-yl]acetic acid Ex.58 (FIG. 1BN), 2-[3-(2-methanesulfonylacetyl)-1H-indol-5-yl]acetic acid Ex.59 (FIG. 1BO), 1-(1H-indol-5-yl)cyclopropane-1-carboxylic acid Ex.61 (FIG. 1BQ), 2-[3-(methylsulfamoyl)-1H-indol-5-yl]acetic acid Ex.64 (FIG. 1BT), 2-[3-(morpholine-4-carbonyl)-1H-indol-5-yl]acetic acid Ex.65 (FIG. 1BU), 1-[2-(2-methoxyacetyl)-2,3-dihydro-1H-isoindol-5-yl]cyclopropane-1-carboxylic acid Ex.67 (FIG. 1BW), 2-(1-cyclopropanecarbonyl-2,3-dihydro-1H-indol-5-yl)acetic acid Ex.68 (FIG. 1BX), 1-(2,2-dioxo-1,3-dihydro-4,2,1-benzoxathiazin-6-yl)cyclopropane-1-carboxylic acid Ex.69 (FIG. 1BY), 1-(2,3-dioxo-2,3-dihydro-1H-indol-5-yl)cyclopropane-1-carboxylic acid Ex.70 (FIG. 1BZ), 1-(1-acetylindolin-5-yl)cyclopropanecarboxylic acid=1-(1-acetyl-2,3-dihydro-1H-indol-5-yl)cyclopropane-1-carboxylic acid Ex.71 (FIG. 1CA), 1-(2-acetylisoindolin-5-yl)cyclopropanecarboxylic acid=1-(2-acetyl-2,3-dihydro-1H-isoindol-5-yl)cyclopropane-1-carboxylic acid Ex.72 (FIG. 1CB), 1-(1-methyl-2-oxo-2,3-dihydro-1H-indol-5-yl)cyclopropane-1-carboxylic acid Ex.75 (FIG. 1CE), 1-(1-ethyl-2,2-dioxo-1,3-dihydro-2,1-benzothiazol-5-yl)cyclopropane-1-carboxylic acid Ex.76 (FIG. 1CF), 1-(1-oxo-2,3-dihydro-1H-inden-5-yl)cyclopropane-1-carboxylic acid Ex.82 (FIG. 1CL), 1-{2-oxo-1H,2H,3H-pyrido[2,3-b][1,4]oxazin-6-yl}cyclopropane-1-carboxylic acid Ex.84 (FIG. 1CN), 1-(3,3-dimethyl-2-oxo-2,3-dihydro-1H-indol-5-yl)cyclopropane-1-carboxylic acid Ex.85 (FIG. 1CO), 2-(2,2-dioxo-1,3-dihydro-4,2,1-benzoxathiazin-6-yl)acetic acid Ex.86 (FIG. 1CP), 1-(2H-1,3-benzodioxol-5-yl)cyclopropane-1-carboxylic acid Ex.88 (FIG. 1CR), 1-[1-(oxan-4-ylmethyl)-2,2-dioxo-1,3-dihydro-2,1-benzothiazol-5-yl]cyclopropane-1-carboxylic acid Ex.91 (FIG. 1CU), 1-(7-fluoro-2-oxo-2,3-dihydro-1H-indol-5-yl)cyclopropane-1-carboxylic acid Ex.92 (FIG. 1CV), 1-(3,3-difluoro-2-oxo-2,3-dihydro-1H-indol-5-yl)cyclopropane-1-carboxylic acid Ex.93 (FIG. 1CW), 1-[1-(hydroxyimino)-2,3-dihydro-1H-inden-5-yl]cyclopropane-1-carboxylic acid Ex.94 (FIG. 1CX), 2-[1-(oxan-4-ylmethyl)-2,2-dioxo-1,3-dihydro-2,1-benzothiazol-5-yl]acetic acid Ex.95 (FIG. 1CY), 1-(2,2-dimethyl-2,4-dihydro-1,3-benzodioxin-7-yl)cyclopropane-1-carboxylic acid Ex.96 (FIG. 1CZ), 1-(2,2-dimethyl-2,4-dihydro-1,3-benzodioxin-6-yl)cyclopropane-1-carboxylic acid Ex.97 (FIG. 1DA), 1-[3-(1-hydroxy-2-methylpropan-2-yl)-1H-indol-5-yl]cyclopropane-1-carboxylic acid Ex.98 (FIG. 1DB), 1-(1-methyl-2,2-dioxo-1,3-dihydro-4,2,1-benzoxathiazin-6-yl)cyclopropane-1-carboxylic acid (FIG. 1DD) and 1-(2,2-dimethyl-2H-1,3-benzodioxol-5-yl)cyclopropane-1-carboxylic acid (FIG. 1DF).

In a same manner were synthetised (2-bromo-4-methylphenyl)(5-methylfuran-2-yl)methanamine hydrochloride Ex.18 (FIG. 2A), (2,4-dimethylphenyl)(5-methylfuran-2-yl)methanamine Ex.19 (FIG. 2B), [4-methoxy-2-(morpholin-4-yl)phenyl](5-methylfuran-2-yl)methanamine hydrochloride Ex.20 (FIG. 2C), (2,4-dimethylphenyl)(5-ethylfuran-2-yl)methanamine hydrochloride Ex.21 (FIG. 2D), (2-bromo-4-methoxyphenyl)(5-methylfuran-2-yl)methanamine Ex.22 (FIG. 2E), (5-chlorofuran-2-yl)(2,4-dimethylphenyl)methanamine Ex.32 (FIG. 2F), 2-[amino(5-methylfuran-2-yl)methyl]-N,N,5-trimethylaniline hydrochloride Ex.42 (FIG. 2G), [4-methyl-2-(pyrrolidin-1-yl)phenyl](5-methylfuran-2-yl)methanamine hydrochloride Ex.44 (FIG. 2H), (5-chlorofuran-2-yl)[4-methyl-2-(piperidin-1-yl)phenyl]methanamine Ex.47 (FIG. 2I), (5-chlorofuran-2-yl)[4-methyl-2-

(pyrrolidin-1-yl)phenyl]methanamine hydrochloride Ex.48 (FIG. 2J), [2-(azepan-1-yl)-4-methoxyphenyl](5-methylfuran-2-yl)methanamine Ex.63 (FIG. 2K), (2,4-dimethylphenyl)(6-methylpyridin-2-yl)methanamine dihydrochloride Ex.77 (FIG. 2L), (2,4-dimethylphenyl)(furan-2-yl) methanamine Ex.80 (FIG. 2N), (3-chlorophenyl)(2,4-dimethylphenyl)methanamine hydrochloride Ex.83 (FIG. 2O), (3,5-dimethylpyridin-2-yl)(5-methylfuran-2-yl)methanamine dihydrochloride Ex.87 (FIG. 2P), [4-methyl-2-(trifluoromethyl)phenyl](5-methylfuran-2-yl)methanamine hydrochloride Ex.99 (FIG. 2Q) and (2-methoxy-4-methylphenyl)(5-methylfuran-2-yl)methanamine Ex.101 (FIG. 2R).

FIG. 3—General Synthesis Scheme of Compounds of Formula (I) or (Ia)

Compounds of formula (I) or (Ia) are generated using the Protocol A summarized in FIG. 3.

FIG. 4—Effect of Compounds According to the Invention on Clinical Score.

Clinical score from MOG-induced EAE mice determined daily by a visual inspection of behavior. FIG. 4A shows the mean of EAE disease course in mice treated with vehicle or Cpd. 24 at 30 and 60 mpk. FIG. 4B shows the AUC of clinical disease curves for all mice treated with vehicle or Cpd.24 at 30 and 60 mpk; horizontal line: median value. Error bars: SEM; P=0.005 by 2-Way ANOVA. **P<0.01.

FIG. 5—Effect of compounds according to the invention on psoriasis model.

Figure 5A:
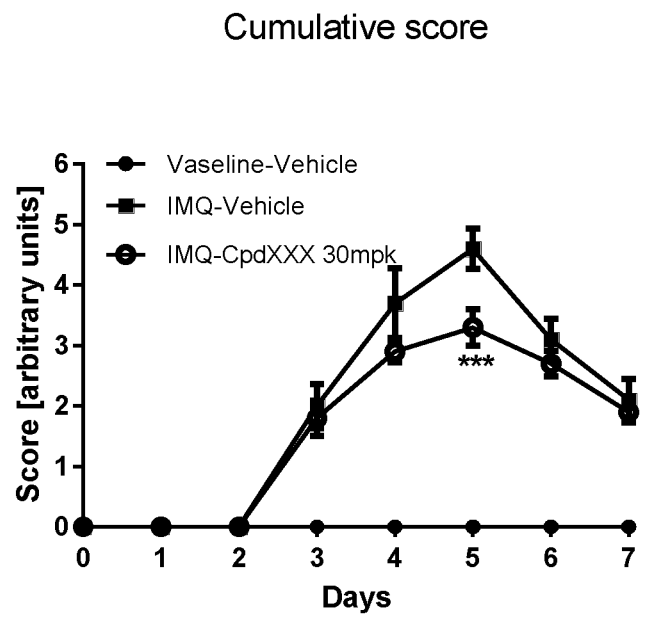
Figure 5B:
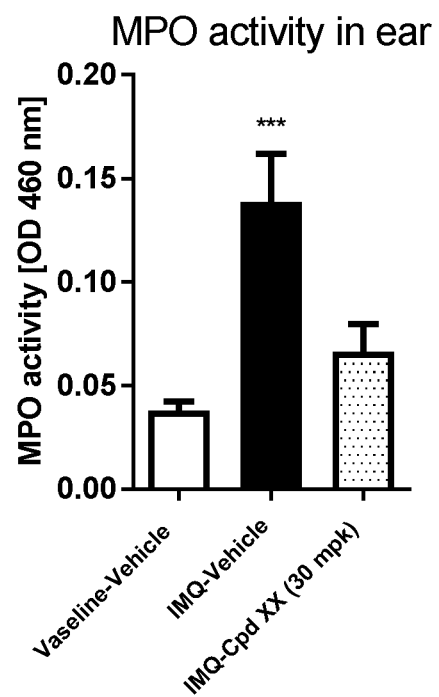

FIG. 5A shows the effect of Cpd. 24 oral administrations (30 mpk) on cumulative clinical score evolution during the course of the experiment. FIG. 5B shows the effect of Cpd. 24 oral administrations (30 mpk) on MPO activity. Statistical evaluation of differences between the experimental groups was determined by using two-way Anova followed by a Bonferroni post test. *** p<0.001, IMQ-Vehicle compared with IMQ-Cpd. 24 at 30 mpk.

DETAILED DESCRIPTION OF THE INVENTION

The present invention provides novel compounds that are modulators of RORgamma. These compounds, and pharmaceutical compositions comprising the same, are suitable for treating any disease wherein the RORgamma activity is involved, for instance in multiple autoimmune, inflammatory, metabolic, fibrotic and cholestatic disorders.

Compounds of Formula (I)

According to a first aspect, the present invention relates to a compound of formula (I), or a pharmaceutically acceptable salt thereof:

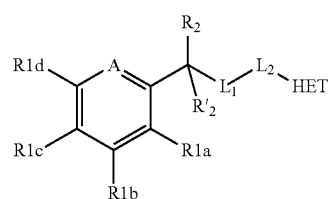

(I)

in which,

A is a C—R1e group or a nitrogen atom;
R1a is a halogen atom, a nitrile group, a nitro group (NO2), a (C1-C6) alkyl group, a (C1-C6) alkyloxy group, a (C1-C6) alkylthio group, a —NH2 group, a (C1-C6) alkylamino group, a (C1-C6)dialkylamino group or a heterocyclic group;

R1b is a hydrogen atom, a (C1-C6)alkyloxy group, a (C1-C6)alkyl group or a heterocyclic group;

R1c is a hydrogen atom, a halogen atom, a (C1-C6)alkyl group, a (C1-C6)alkyloxy group, a (C1-C6)alkylthio group, a heterocyclic group, a cyano group, an amido group or a hydroxyl group;

R1d and R1e are, independently, a hydrogen atom, a halogen atom, a (C1-C6)alkyloxy group or an (C1-C6)alkyl group;

R2 is an unsubstituted, branched (C3-C6)alkyl group; an (C2-C6)alkynyl group; a (C3-C14)cycloalkyl group; an (C6-C14)aryl group optionally substituted by a (C1-C6)alkyl group or a halogen; a 5-membered hetoaryl group containing an oxygen or a nitrogen atom optionally substituted by a (C1-C6)alkyl group or a halogen; or a 6-membered heteroaryl group containing at least one nitrogen atom optionally substituted by a (C1-C6)alkyl group or a halogen;

R'2 is a hydrogen atom; an (C1-C6)alkyl group; an (C2-C6)alkynyl group; a (C3-C14)cycloalkyl group; a (C6-C14)aryl group optionally substituted by a (C1-C6)alkyl group or a halogen; or a heterocyclic group optionally substituted by a (C1-C6)alkyl group or a halogen;

or R2 and R2' can form, together with the carbon atom to which they are attached, a cycloalkyl group or a heterocycloalkyl group;

L1 is a —NH—CO— or —CO—NH— group;
L2 represents a CR4R'4 group;
R4 and R'4 are independently, a hydrogen atom or a (C1-C6)alkyl group;

or R4 and R'4 can form, together with the carbon atom to which they are attached, a cycloalkyl group;

HET is a bicyclic group of formulae (II'), (II") or (II'''):

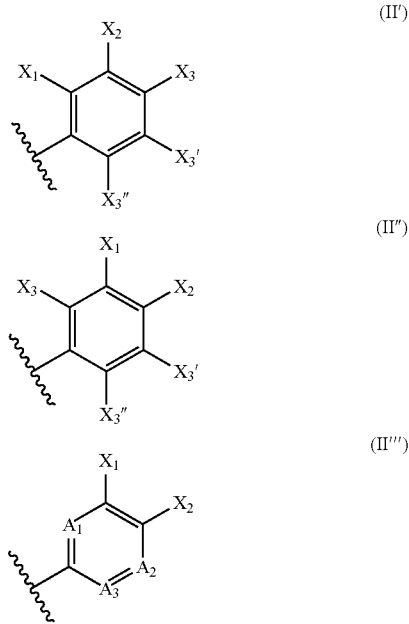

in which:

A1 is a nitrogen atom or a CX3 group;
A2 is a nitrogen atom or a CX3' group;
A3 is a nitrogen atom or a CX3" group;

wherein one and only one of A1, A2 and A3 is a nitrogen atom;

X1 and X2 form together, with the carbons of the ring to which they are attached:
- an unsaturated 5- to 8-membered ring optionally interrupted by at least one group selected from N—R8; an oxygen atom; a sulfur atom; a SO2 group; a CO group; and a —N—SO2-R7- group with R7 being a (C1-C4)alkyl group; or
- a saturated 5- to 8-membered ring interrupted by at least one group selected in the group consisting of a nitrogen atom; an oxygen atom; a sulfur atom; a SO2 group; a CHOH; a CO group; and a —N—SO2-R7- group with R7 being a (C1-C4)alkyl group;

R8 is a hydrogen atom; a (C1-C6) alkyl group optionally substituted by a COOH group, a COO(C1-C6)alkyl or a heterocycloalkyle group; a COR9 group or a SO2R9 group;

R9 is a (C1-C6)alkyl or a heterocycloalkyle, said 5- to 8-membered saturated or unsaturated rings are optionally substituted by at least one radical selected in the group consisting of:
- a (C1-C6)alkyl group optionally substituted by at least one hydroxyl, morpholino, tetrahydropyran, SO2R5, or NH—SO2-R5 group, R5 being a hydrogen or a (C1-C6)alkyl group; with the proviso that two hydroxyl groups cannot be attached to the same carbon atom;
- a (C2-C6)alkenyl group optionally substituted by at least one hydroxyl, or a heterocyclic group;
- a fluorine atom;
- a =N—NRR' group with R and R' being independently a hydrogen or a (C1-C6)alkyl group;
- a =NR" group with R" being a hydrogen, a (C1-C6)alkyl group or a hydroxy;
- a OR6 group or a SR6 group, R6 being a hydrogen atom or a (C1-C6)alkyl group;
- a COR10 group, R10 being a morpholino group or a tetrahydropyran group, or R10 being an alkyl optionally substituted, by a SO2R11 group, or a N—SO2-R11 group, R11 being a (C1-C6)alkyl; and
- a =CH—R'" with R'" being a heteroaryl optionally substituted by at least one substituent selected from a (C1-C6)alkyl and a NRR' with R and R' are such as above defined; and X3, X3' and X3" are, independently, a hydrogen, a halogen atom, or a (C1-C6)alkyl group.

In particular embodiments, in the compound of formula (I) of the present invention:
- a (C1-C6)alkyl group may be a substituted or unsubstituted (C1-C6)alkyl group, in particular a substituted or unsubstituted (C1-C4)alkyl group;
- a (C1-C6)alkyloxy group may be a substituted or unsubstituted (C1-C6)alkyloxy group, in particular a substituted or unsubstituted (C1-C4)alkyloxy group;
- a (C6-C14)aryl group may be a substituted or unsubstituted (C6-C14)aryl group;
- a heterocyclic group may be a substituted or unsubstituted heterocycloalkyl or heteroaryl group.

The present invention also includes stereoisomers (diastereoisomers, enantiomers), pure or mixed, as well as racemic mixtures and geometric isomers, or tautomers of compounds of formula (I). The invention further includes salts, solvates (in particular hydrates) and polymorphs or crystalline forms of the compounds of formula (I).

In a particular embodiment, A is a C—R1e group.

In a further particular embodiment, R1a is a halogen atom, a nitrile group, a nitro group (NO2), a (C1-C6)alkyl group, a (C1-C6)alkyloxy group, a (C1-C6)alkylthio group, an amino group, a (C1-C6)alkylamino group, a (C1-C6)dialkylamino group, a piperidinyl group, a pyrrolidinyl group, an azepanyl group, a piperazinyl group, or a morpholinyl group, wherein said piperidinyl, pyrrolidinyl, azepanyl, piperazinyl or morpholinyl group can be optionally substituted by at least one (C1-C6)alkyl groups. In a further particular embodiment, R1a is a halogen atom, a nitrile group, a nitro group (NO2), a (C1-C6)alkyl group, a (C1-C6)alkyloxy group, a (C1-C6)alkylthio group, an amino group, a (C1-C6)alkylamino group, a (C1-C6)dialkylamino group, a piperidinyl group, a pyrrolidinyl group or an azepanyl group, wherein said piperidinyl, pyrrolidinyl or azepanyl group can be optionally substituted by at least one (C1-C6)alkyl groups. In another particular embodiment, R1a is selected in the group consisting of a halogen atom (such as a bromine atom), a (C1-C6)alkyl group (such as a methyl or a CF3 group), a (C1-C6)dialkylamino group (such as dimethylamino group, a piperidinyl group (such as a piperidin-1-yl group), a piperazinyl group (such as a piperazin-1-yl) and an azepanyl group (such as an azepan-1-yl). In a further particular embodiment, R1a is selected in the group consisting of a halogen atom (such as a bromine atom), a (C1-C6)alkyl group (such as a methyl group), a piperidinyl group (such as a piperidin-1-yl group) or a piperazinyl group (such as a piperazin-1-yl). In another particular embodiment, R1a is a halogen, group, a (C1-C6) alkyl group, a piperidinyl group (such as a piperidin-1-yl group), a morpholinyl group (such as morpholin-4-yl group), a pyrrolidinyl group (such as a pyrrolidin-1-yl group), a piperazinyl group (such as a piperazin-1-yl), or an azepanyl group (such as an azepan-1-yl). In a particular embodiment, R1a is a halogen atom, a (C1-C6)alkyl group, a piperidinyl group (such as a piperidin-1-yl group), a morpholinyl group (such as morpholin-4-yl group) or a pyrrolidinyl group (such as a pyrrolidin-1-yl group).

In a particular embodiment, R1b is a hydrogen atom.

In a particular embodiment, R1c is a hydrogen atom, an (C1-C6)alkyl group, or an (C1-C6)alkyloxy group. In another particular embodiment, R1c is a (C1-C6)alkyl group (such as a methyl group), or a (C1-C6)alkyloxy group (such as a methoxy group).

In a particular embodiment, R1d is a hydrogen atom.

In a particular embodiment, R1e is a hydrogen atom.

In a further particular embodiment, R1b, R1d and R1e are hydrogen atoms. In a further variant, R1b, R1d and R1e are hydrogen atoms and R1c is a (C1-C6)alkyl group (such as a methyl group) or a (C1-C6)alkyloxy group (such as a methoxy group).

In another embodiment, R2 is a (C3-C6)alkyl group, a (C3-C14)aryl group, or a heteroaryl group.

In a further embodiment, R2 is a (C6-C14)aryl group or a heteroaryl group. In a particular variant, R2 is selected in the group consisting of a phenyl group, a furanyl group and a pyridinyl group, wherein the substituents of said phenyl, furanyl and pyridinyl group may be unsubstituted or substituted, such as by at least one group selected in the group consisting of (C1-C6)alkyl groups (e.g. at least one methyl group, such as one or two methyl groups) and halogen atoms (e.g. chlorine, such as one or two chlorine atoms). Illustratively, R2 may be a phenyl group, a methylphenyl group, a dimethylphenyl group (such as a 2,4-dimethylphenyl group), a chlorophenyl group (such as a 3-chlorophenyl group), a furanyl group (such as a furan-2-yl group), a methylfuranyl group (such as a 5-methylfuran-2-yl group), a chlorofuranyl group (such as a 5-chlorofuranyl group), a pyridinyl group (such as a pyridine-2-yl group) or a methylpyridinyl group (such as a 6-methylpyridin-2-yl group). In a particular embodiment, R2 is selected in the group consisting of a dimethylphenyl group (such as a 2,4-dimethylphenyl group), a chlorophenyl group (such as a 3-chlorophenyl group), a furanyl group (such as a furan-2-yl group), a methylfuranyl group (such as a 5-methylfuran-2-yl group), a chlorofuranyl group (such as a 5-chlorofuranyl group) and a methylpyridinyl group (such as a 6-methylpyridin-2-yl group). In a particular embodiment, R2 is a furanyl group, such as a furan-2-yl group, which is unsubstituted, or substituted with a least one (C1-C6)alkyl group, in particular at least one methyl group, such as a 5-methylfuran-2-yl group.

In another embodiment, R'2 is a hydrogen atom.

In another particular embodiment, R2 is an (C3-C6)alkyl group, an (C6-C14)aryl group, or a heteroaryl group, and R'2 is a hydrogen atom.

In a further particular embodiment, the invention relates to a compound of formula (I) wherein:

R1a is a halogen atom, a nitrile group, a nitro group (NO2), a (C1-C6)alkyl group, a (C1-C6)alkyloxy group, a (C1-C6)alkylthio group, an amino group, a (C1-C6)alkylamino group, a (C1-C6)dialkylamino group, a piperidinyl group, a morpholinyl group, a pyrrolidinyl group, a piperazinyl group, or an azepanyl group, wherein said piperidinyl, morpholinyl, pyrrolidinyl, piperazinyl, or azepanyl group can be optionally substituted by at least one (C1-C6) alkyl groups;

R1b is a hydrogen atom;

R1c is a hydrogen atom, a (C1-C6)alkyl group, or a (C1-C6)alkyloxy group;

R2 is a (C3-C6)alkyl group, an (C6-C14)aryl group, or a heteroaryl group, and R'2 is a hydrogen atom.

In a further particular embodiment, the invention relates to a compound of formula (I) wherein:

R1a is a halogen atom, a nitrile group, a nitro group (NO2), a (C1-C6)alkyl group, a (C1-C6)alkyloxy group, a (C1-C6)alkylthio group, an amino group, a (C1-C6)alkylamino group, a (C1-C6)dialkylamino group, a piperidinyl group, a morpholinyl group or a pyrrolidinyl group, wherein said piperidinyl or pyrrolidinyl, can be optionally substituted by at least one (C1-C6)alkyl groups;

R1b is a hydrogen atom;

R1c is a hydrogen atom, a (C1-C6)alkyl group, or a (C1-C6)alkyloxy group;

R2 is a (C3-C6)alkyl group, an (C6-C14)aryl group, or a heteroaryl group, and R'2 is a hydrogen atom.

In a particular embodiment, HET is a group selected in the following list:

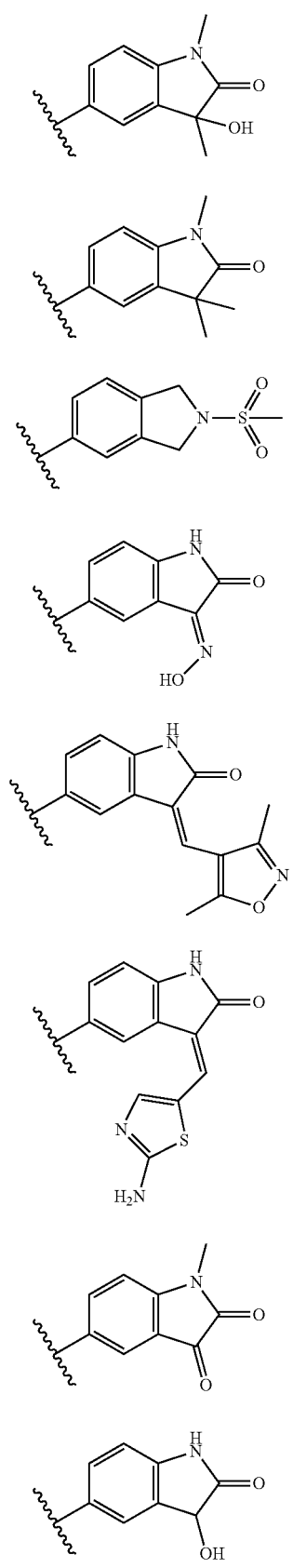
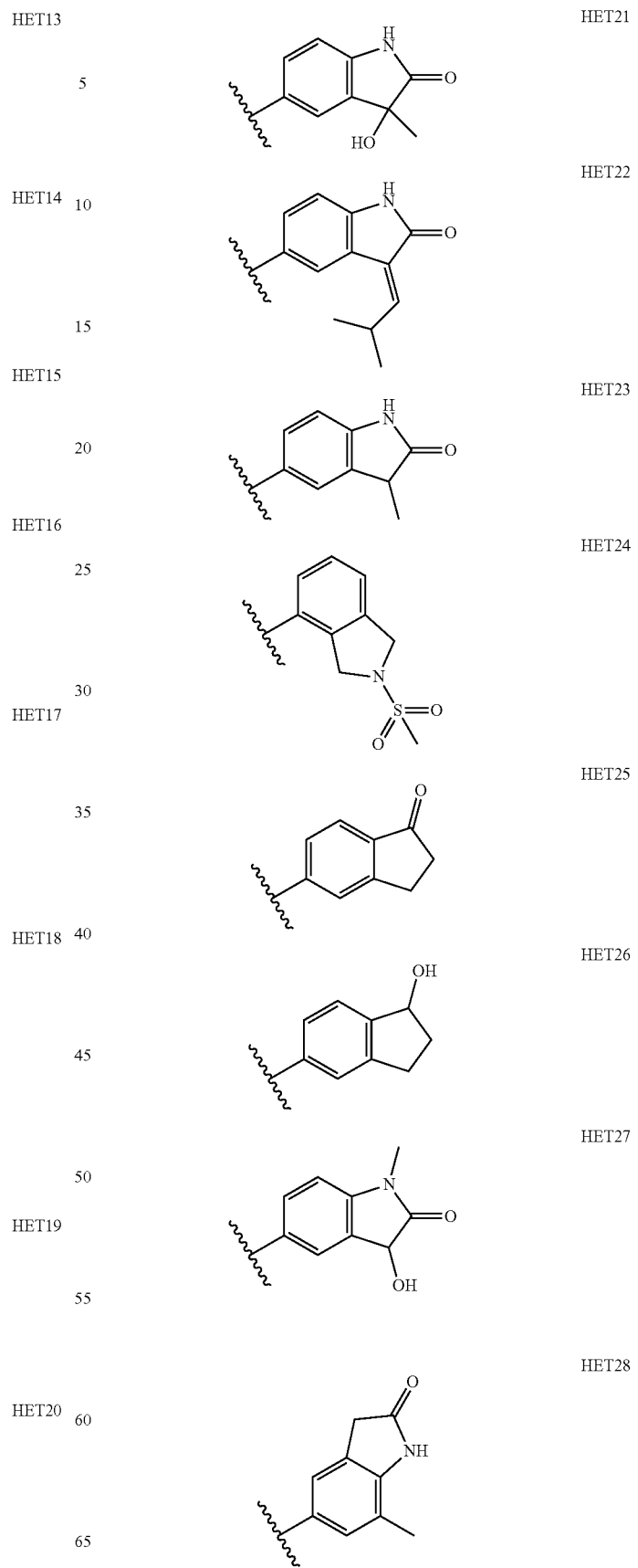

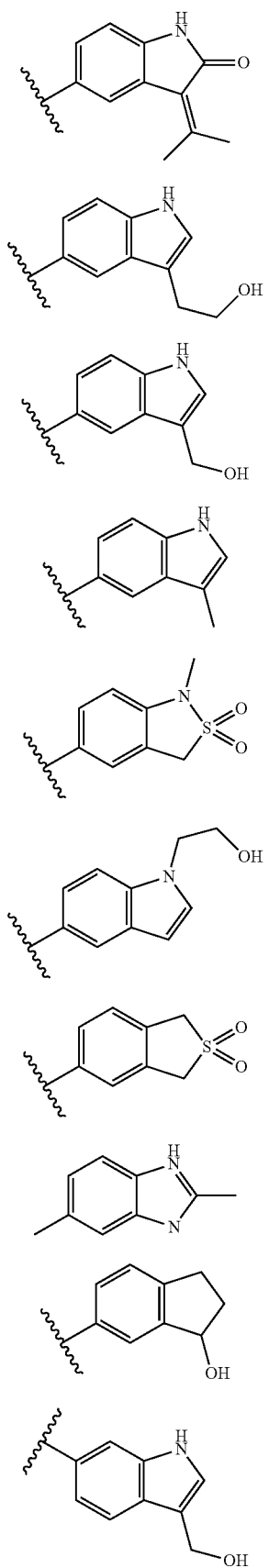
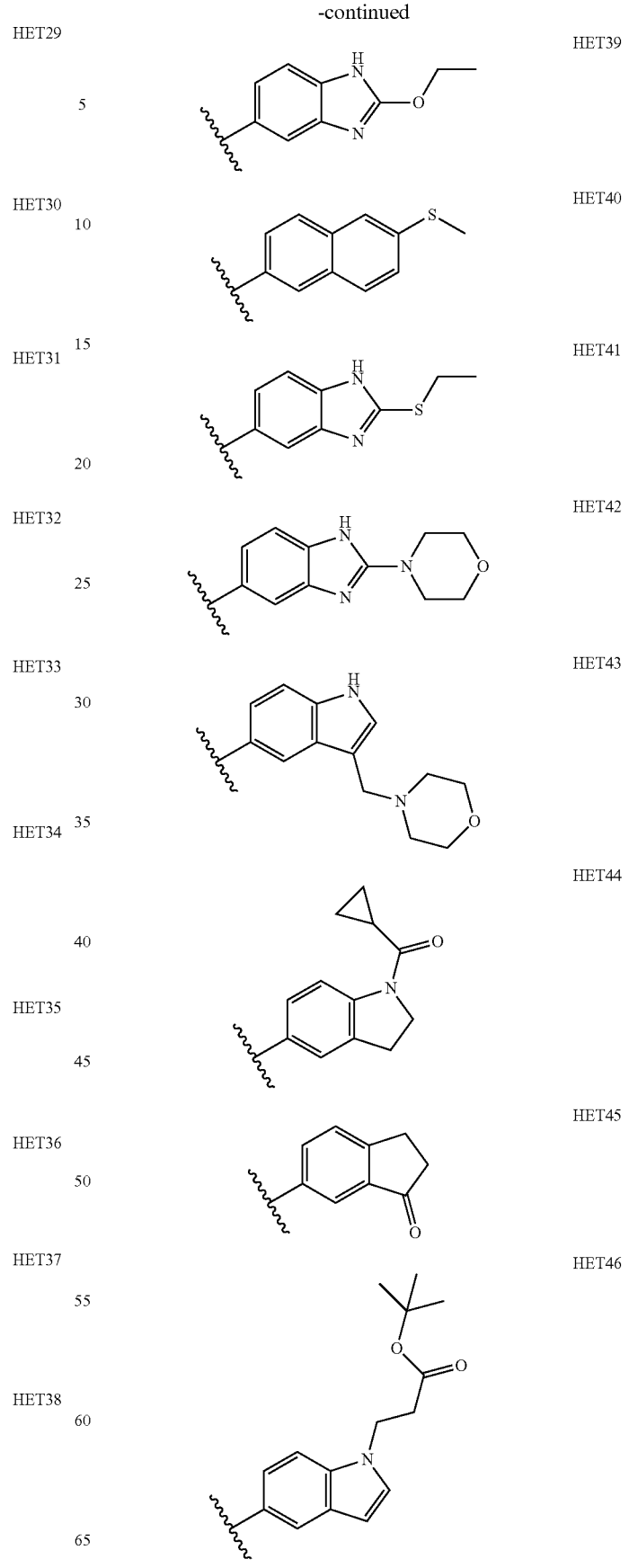

US 11,052,092 B2

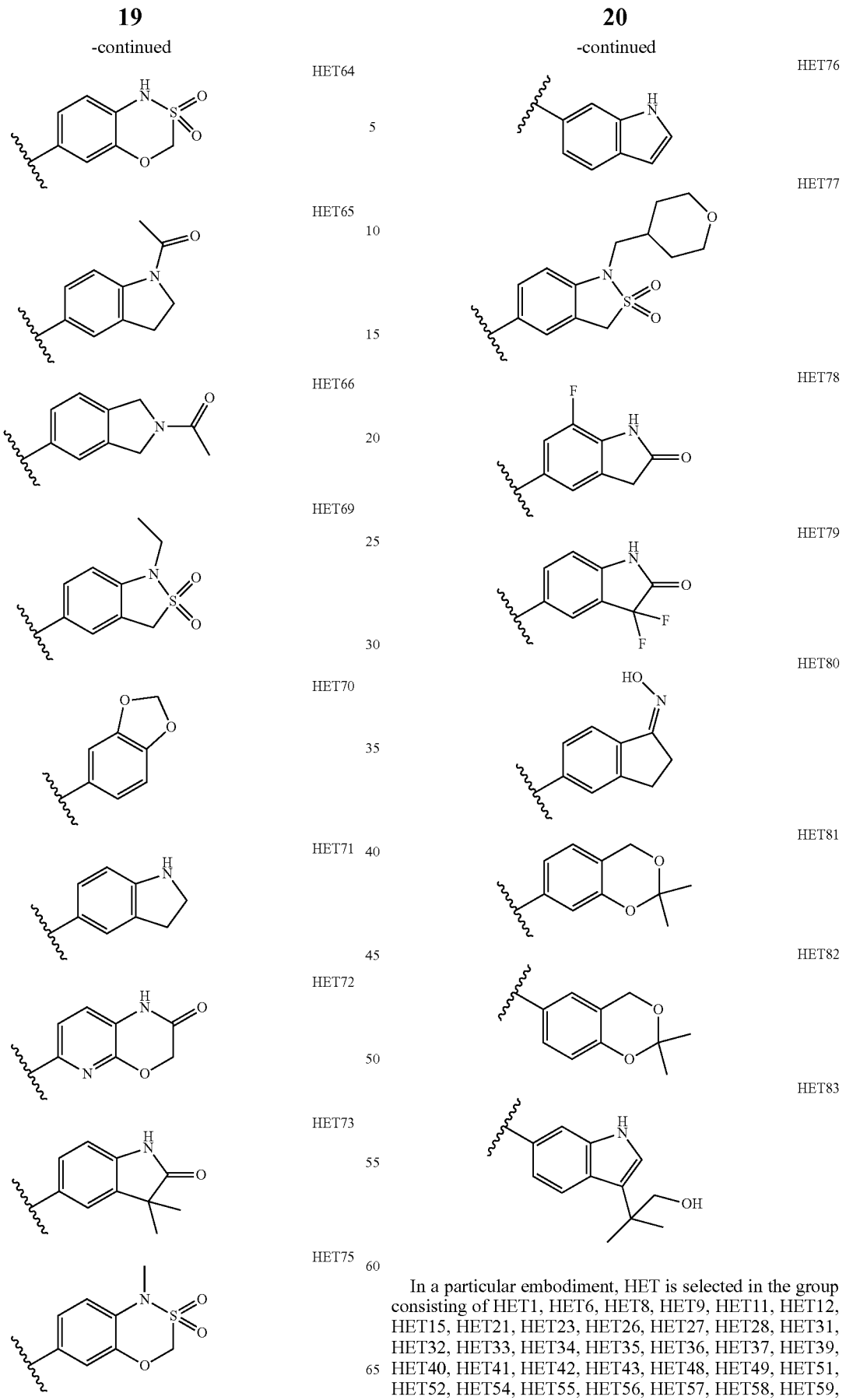
In a particular embodiment, HET is selected in the group consisting of HET1, HET6, HET8, HET9, HET11, HET12, HET15, HET21, HET23, HET26, HET27, HET28, HET31, HET32, HET33, HET34, HET35, HET36, HET37, HET39, HET40, HET41, HET42, HET43, HET48, HET49, HET51, HET52, HET54, HET55, HET56, HET57, HET58, HET59, HET60, HET61, HET64, HET65, HET66, HET69, HET70, HET71, HET72, HET73, HET78, HET80 and HET83. In a further particular embodiment, HET is selected in the group consisting of HET1, HET6, HET30, HET38, HET44, HET47 and HET77.

In a particular embodiment, L1 is a NH—CO group.

In a particular embodiment, L2 is a CR4R'4 group (such as a cyclopropyl group of formula (III) or cyclobutyl of formula (IV)

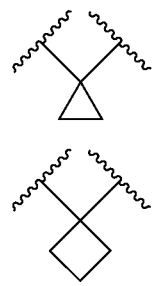

In a particular embodiment, L2 is a cyclopropyl group of formula (III).

In a further particular embodiment, L1 is a NH—CO group, and L2 is a (C1-C6)alkyl group or a (C3-C14) cycloalkylgroup. In a particular embodiment, L1 is a NH—CO group and L2 is a CH2 group or a cyclopropyl group of formula (III). In a particular embodiment, the invention relates to a compound of formula (I), in which:

A is a CR1e group;

R1a is a halogen atom (such as bromine), a (C1-C6)alkyl group (such as a methyl or ethyl group, in particular a methyl group), a piperidinyl group (such as a piperidin-1-yl group), a morpholinyl group (such as a morpholin-4-yl), a pyrrolidinyl group (such as a pyrrolidin-1-yl group), or a piperazinyl group (such as a piperazin-1-yl), or an azepanyl group (such as an azepan-1-yl), wherein said piperidinyl, morpholinyl, or pyrrolidinyl group can be optionally substituted by at least one (C1-C6)alkyl groups;

R1b is a hydrogen atom;

R1c is a hydrogen, a (C1-C6)alkyl group (such as a methyl or ethyl group, in particular a methyl group), or a (C1-C6)alkoxy group (such as a methoxy or a an ethoxy group, in particular a methoxy group);

R1d and R1e are hydrogen atoms;

R2 is a (C3-C6)alkyl group (such as an isobutyl group), a phenyl group or a heterocyclic group (such as a substituted or unsubstituted furanyl group, in particular a 5-methylfuranyl group or a 5-ethylfuranyl group, more particularly a 5-methylfuran-2-yl group);

L1 represents a NH—CO group,

L2 is a CH2 group or a cyclopropyl group of formula (III);

HET is selected in the group consisting of:

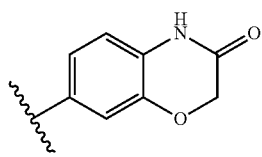
HET1

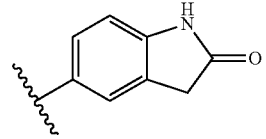
HET6

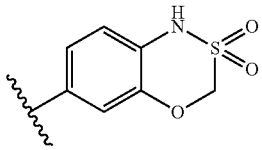
HET64

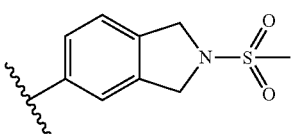
HET15

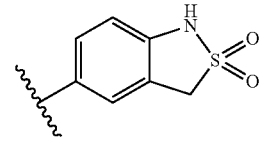
HET9

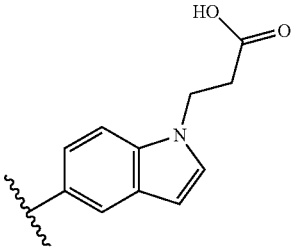
HET47

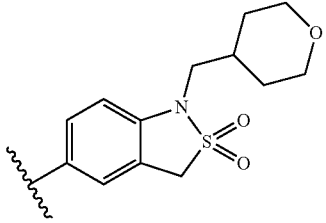
HET77

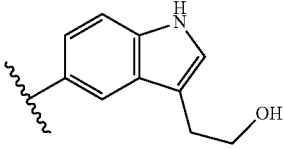
HET30

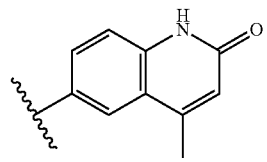
HET2

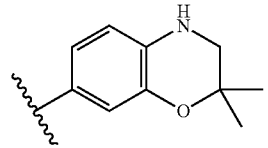
HET7

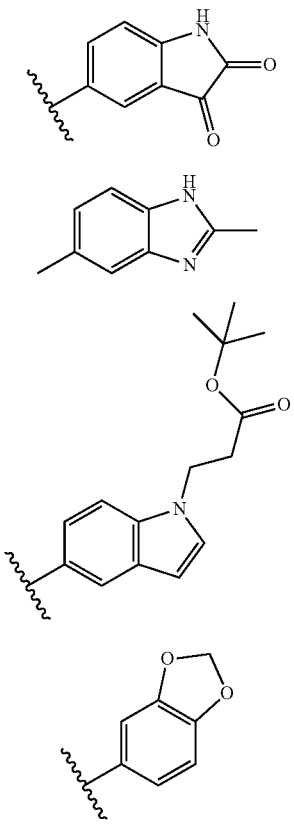

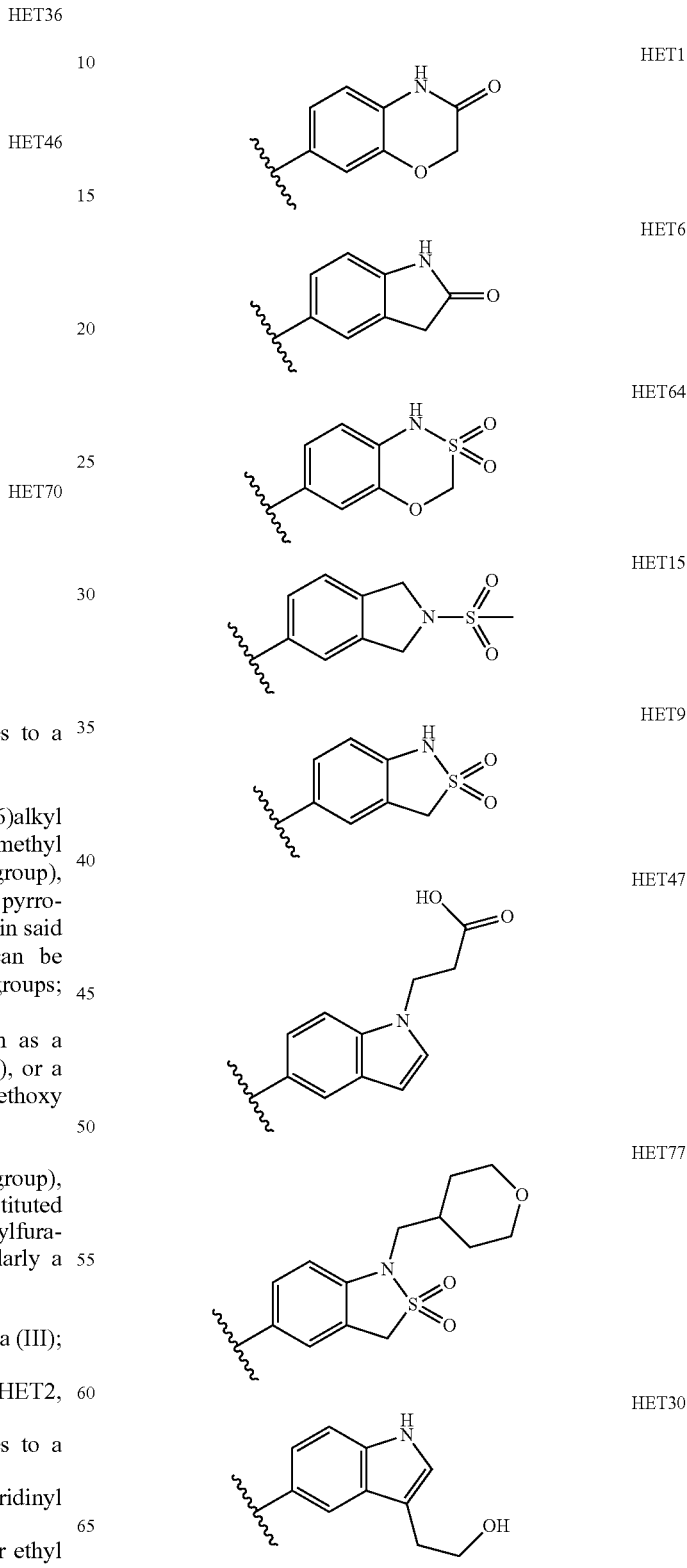

In a particular embodiment, the invention relates to a compound of formula (I), in which:

A is a CR1e group;

R1a is a halogen atom (such as bromine), a (C1-C6)alkyl group (such as a methyl or ethyl group, in particular a methyl group), a piperidinyl group (such as a piperidin-1-yl group), a morpholinyl group (such as a morpholin-4-yl) or a pyrrolidinyl group (such as a pyrrolidin-1-yl group), wherein said piperidinyl, morpholinyl, or pyrrolidinyl group can be optionally substituted by at least one (C1-C6)alkyl groups;

R1b is a hydrogen atom;

R1c is a hydrogen, a (C1-C6)alkyl group (such as a methyl or ethyl group, in particular a methyl group), or a (C1-C6)alkoxy group (such as a methoxy or a an ethoxy group, in particular a methoxy group);

R1d and R1e are hydrogen atoms;

R2 is a (C3-C6)alkyl group (such as an isobutyl group), a phenyl group or a heterocyclic group (such as a substituted or unsubstituted furanyl group, in particular a 5-methylfuranyl group or a 5-ethylfuranyl group, more particularly a 5-methylfuran-2-yl group);

L1 represents a NH—CO group,

L2 is a CH2 group or a cyclopropyl group of formula (III); and

HET is selected in the group consisting of HET1, HET2, HET6, HET7, HET8 and HET9.

In a particular embodiment, the invention relates to a compound of formula (I), in which:

R1a is a heterocyclic group (in particular a piperidinyl group (such as a piperidin-1-yl group));

R1c is a (C1-C6)alkyl group (such as a methyl or ethyl group, in particular a methyl group);

R2 is a heterocyclic group (such as a substituted or unsubstituted furanyl group, in particular a 5-methylfuranyl group or a 5-ethylfuranyl group, more particularly a 5-methylfuran-2-yl group);

L1 represents a NH—CO group,

L2 is a CH2 group or a cyclopropyl group of formula (III);

HET is selected in the group consisting of:

-continued

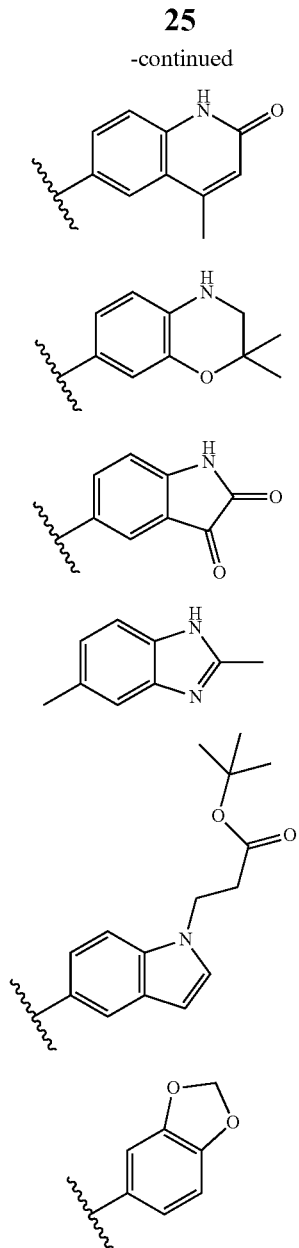

HET2

HET7

HET8

HET36

HET46

HET70

HET being in particular selected in the group consisting of HET1, HET2, HET6, HET7, HET8 and HET9.

In a particular embodiment, the invention relates to a compound of formula (I), in which:

R1a is a heterocyclic group (in particular a piperidinyl group (such as a piperidin-1-yl group)) or a (C1-C6)alkyl group (such as a methyl or ethyl group, in particular a methyl group);

R1c is a (C1-C6)alkyl group (such as a methyl or ethyl group, in particular a methyl group);

R2 is a heterocyclic group (such as a substituted or unsubstituted furanyl group, in particular a 5-methylfuranyl group or a 5-ethylfuranyl group or a 5-chlorofuranyl, more particularly a 5-chlorofuran-2-yl group);

L1 represents a NH—CO group; and

L2 is a CR4R'4 group (such as a cyclopropyl group of formula (III) or cyclobutyl of formula (IV)

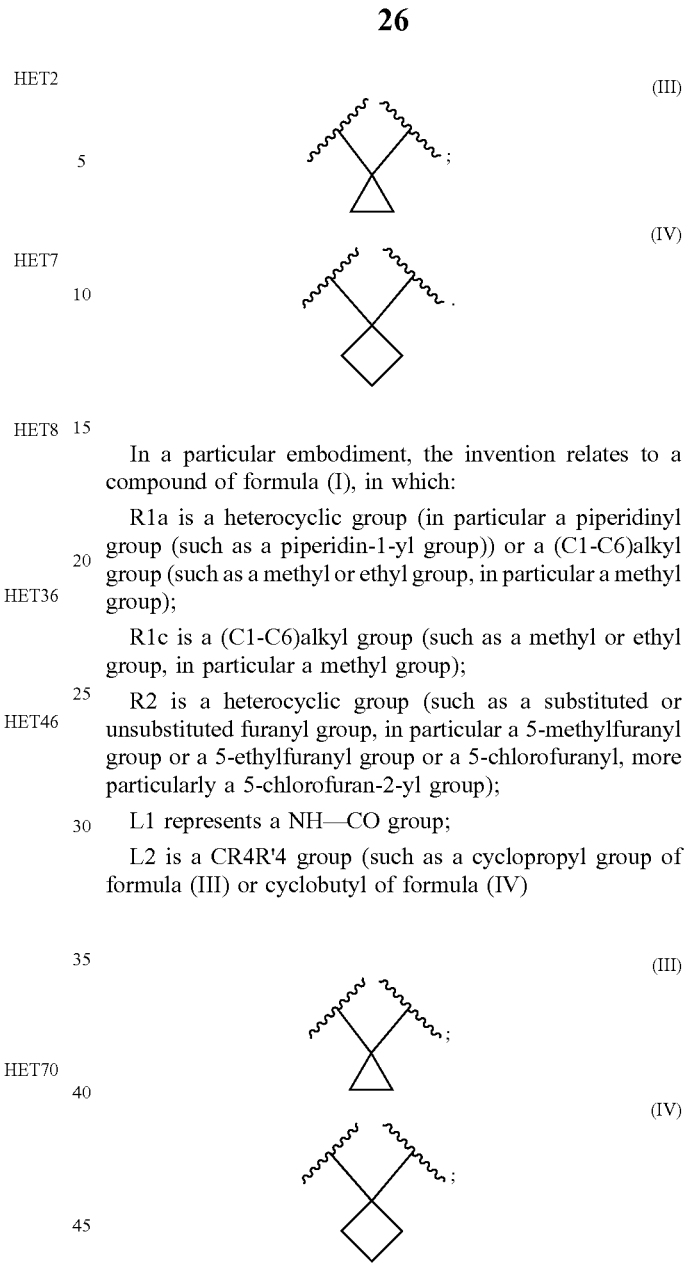

(III)

(IV)

In a particular embodiment, the invention relates to a compound of formula (I), in which:

R1a is a heterocyclic group (in particular a piperidinyl group (such as a piperidin-1-yl group)) or a (C1-C6)alkyl group (such as a methyl or ethyl group, in particular a methyl group);

R1c is a (C1-C6)alkyl group (such as a methyl or ethyl group, in particular a methyl group);

R2 is a heterocyclic group (such as a substituted or unsubstituted furanyl group, in particular a 5-methylfuranyl group or a 5-ethylfuranyl group or a 5-chlorofuranyl, more particularly a 5-chlorofuran-2-yl group);

L1 represents a NH—CO group;

L2 is a CR4R'4 group (such as a cyclopropyl group of formula (III) or cyclobutyl of formula (IV)

(III)

(IV)

and

HET is selected in the group consisting of the following HET groups:

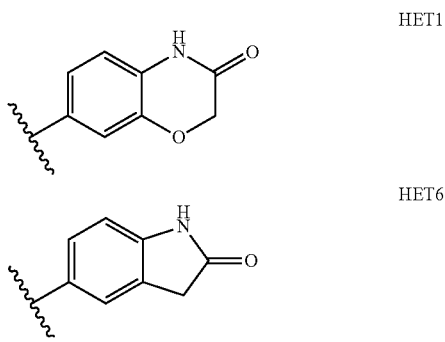

HET1

HET6

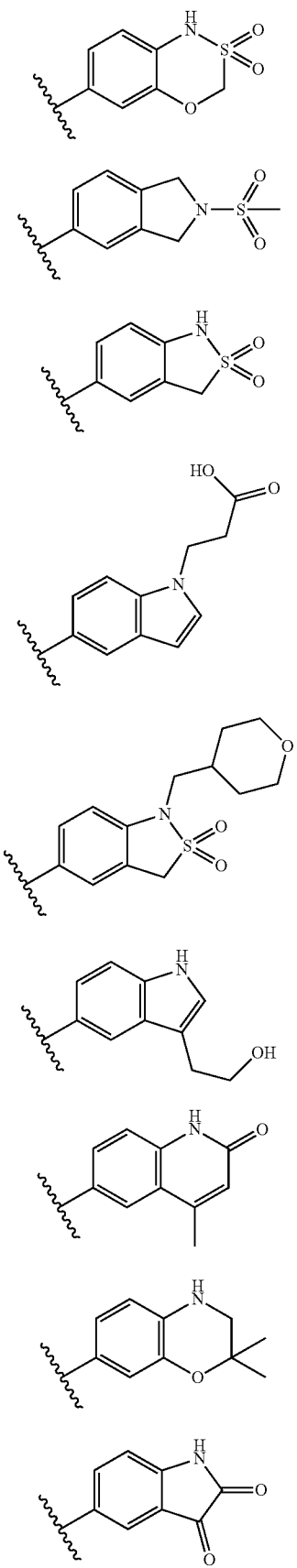

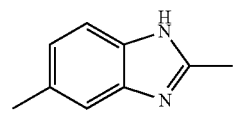

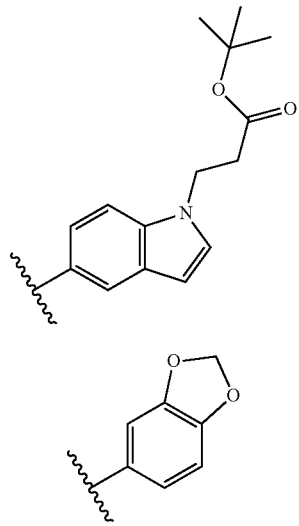

In a particular embodiment of the compound of formula (I):

R1a represents a halogen, in particular a bromine atom; a (C1-C6)alkyl group, in particular a methyl group; a heterocyclic group, in particular a piperadin-1-yl group, a piperazin-1-yl group, or an azepan-1-yl group; a di(C1-C6)alkylamaino group, in particular a N(CH3)2 group;

R1 b, R1d and R1e represent hydrogen atoms;

R1c is a (C1-C6)alkyl group, in particular a methyl group, or a (C1-C6)alkyloxy group, in particular a methoxy group;

R2 represents a 5 membered heteroaryl group containing an oxygen or a nitrogen atom optionally substituted by a (C1-C6)alkyl group or a halogen, in particular a furan-1-yl group, a 5-methylfuran-2-yl group or a 5-chlorofuran-2-yl group; a (C6-C14)aryl group optionally substituted by a (C1-C6)alkyl group, in particular a phenyl group optionally substituted by one or more methyl group or by a chlorine atom; or a heterocyclic group optionally substituted by a (C1-C6)alkyl group, in particular a 6-methylpyridin-2-yl;

R'2 is a hydrogen atom;

L1 represents a NH—CO group; and

L2 represents a (C1-C6)alkyl group, in particular a —CH2-group, or a a CR4R'4 group, in particular a cyclopropyl group of formula (III)

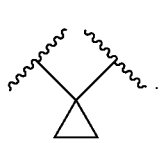

(III)

In a particular embodiment of the compound of formula (I):

R1a represents a halogen, in particular a bromine atom; a (C1-C6)alkyl group, in particular a methyl group; a heterocyclic group, in particular a piperadin-1-yl group, or a piperazin-1-yl group;

R1b, R1d and R1e represent a hydrogen atom;
R1c is a (C1-C6)alkyl group, in particular a methyl group;
R2 represents a 5 membered heteroaryl group containing an oxygen or a nitrogen atom optionally substituted by a (C1-C6)alkyl group or a halogen, in particular a 5-methyl-furan-2-yl group or a 5-chlorofuran-2-yl group;
R'2 is a hydrogen atom;
L1 represents a NH—CO group;
L2 represents a (C1-C6)alkyl group, in particular a —CH2- group, or a a CR4R'4 group, in particular a cyclopropyl group of formula (III)

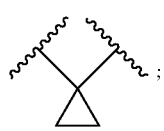

and
HET is HET1, HET6, HET30, HET38, HET44, HET47, HET67 or HET77.

Compounds of formula (Ia)

In a second aspect, the present invention relates to a compound of formula (Ia), or a pharmaceutically acceptable salt thereof:

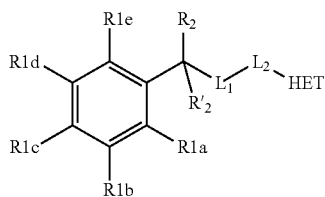

R1a is a hydrogen atom, a halogen atom, a nitrile group, a nitro group (NO2), a (C1-C6) alkyl group, a (C1-C6) alkyloxy group, a (C1-C6) alkylthio group, a —NH2 group, a (C1-C6) alkylamino group, a (C1-C6)dialkylamino group, or a heterocyclic group;
R1b is a hydrogen atom, a (C1-C6)alkyloxy group, a (C1-C6)alkyl group or a heterocyclic group;
R1c is a hydrogen atom, a halogen atom, a (C1-C6)alkyl group, a (C1-C6)alkyloxy group, a (C1-C6)alkylthio group, a heterocyclic group, a cyano group, an amido group or a hydroxyl group;
R1d and R1e are, independently, a hydrogen atom, a halogen atom, a (C1-C6)alkyloxy group or an (C1-C6)alkyl group;
R2 is a (C1-C6)alkyl group, a (C2-C6)alkynyl group, a (C3-C14)cycloalkyl group, a (C6-C14)aryl group or a heterocyclic group optionally substituted by a (C1-C6)alkyl group or a halogen;
R'2 is a hydrogen atom, a (C1-C6)alkyl group, a (C2-C6) alkynyl group, a (C3-C14)cycloalkyl group, a (C6-C14)aryl group or a heterocyclic group optionally substituted by a (C1-C6)alkyl group or a halogen;
or R2 and R2' can form, together with the carbon atom to which they are attached, a cycloalkyl group or a heterocycloalkyl group;
L1 is a NR3-CO—CH2, NR3-CO—, NR3-CO—C(CH3)2, CO—NH—CH2, CO—NH or CO—NH—C(CH3)2 group;

R3 represents a hydrogen atom or a (C1-C6)alkyl group;
L2 represents a bond, a (C1-C6)alkyl group, a (C3-C14) cycloalkylgroup, or a CR4R'4 group;
R4 and R'4 are independently, a hydrogen atom, or a (C1-C6)alkyl group;
R4 and R'4 can form, together with the carbon atom to which they are attached, a cycloalkyl group;
HET is a bicyclic group of formula (II') or (II"):

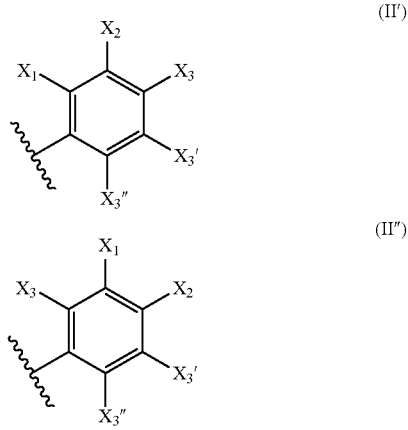

in which:
X1 and X2 form together, with the carbons of the phenyl ring where they are attached, a saturated or unsaturated 5- to 8-membered ring optionally interrupted by at least one group selected in the group consisting of a nitrogen atom, an oxygen atom, a sulfur atom, a N—SO2-R7 group, with R7 being a (C1-C6)alkyl group, a SO2 group, or a CO group; said 5- to 8-membered ring is optionally substituted by at least one radical selected in the group consisting of:
 a (C1-C6)alkyl group optionally substituted by at least one hydroxy; or a (C2-C6)alkenyl group optionally substituted by at least one hydroxy,
 a halogen atom,
 a =N—NRR' group, with R and R' being independently a hydrogen or a (C1-C6)alkyl group,
 a =NR" group, with R" being a hydrogen, a (C1-C6)alkyl group or a hydroxy;
 a hydroxyl group, and
 a =CH—R''' group, with R''' being a heteroaryl optionally substituted by at least one substituent selected from a (C1-C6)alkyl and a NRR' group with R and R' are such as above defined; and
X3, X3' and X3" are, independently, a hydrogen or a (C1-C6)alkyl group.

In particular embodiments, in the compound of formula (Ia) of the present invention:
 a (C1-C6)alkyl group may be a substituted or unsubstituted (C1-C6)alkyl group, in particular a substituted or unsubstituted (C1-C4)alkyl group;
 a (C1-C6)alkyloxy group may be a substituted or unsubstituted (C1-C6)alkyloxy group, in particular a substituted or unsubstituted (C1-C4)alkyloxy group;
 a (C6-C14)aryl group may be a substituted or unsubstituted (C6-C14)aryl group;
 a heterocyclic group may be a substituted or unsubstituted heterocycloalkyl or heteroaryl group.

The present invention also includes stereoisomers (diastereoisomers, enantiomers), pure or mixed, as well as racemic mixtures and geometric isomers, or tautomers of compounds of formula (Ia). The invention further includes salts, solvates (in particular hydrates) and polymorphs or crystalline forms of the compounds of formula (Ia).

According to a particular embodiment, the invention relates to a compound of formula (Ia) wherein R1a is a hydrogen atom, a halogen atom, a nitrile group, a nitro group (NO2), a (C1-C6)alkyl group, a (C1-C6) alkyloxy group, a (C1-C6)alkylthio group, an amino group, a (C1-C6)alkylamino group, a (C1-C6)dialkylamino group, a piperidinyl group, a pyrrolidinyl group, an azepanyl group, a piperazinyl group, or a morpholinyl group, wherein said piperidinyl, pyrrolidinyl, azepanyl, piperazinyl or morpholinyl group can be optionally substituted by at least one (C1-C6)alkyl groups. In a further particular embodiment, R1a is a hydrogen atom, a halogen atom, a nitrile group, a nitro group (NO2), a (C1-C6)alkyl group, a (C1-C6)alkyloxy group, a (C1-C6)alkylthio group, an amino group, a (C1-C6)alkylamino group, a (C1-C6)dialkylamino group, a piperidinyl group, a pyrrolidinyl group or an azepanyl group, wherein said piperidinyl, pyrrolidinyl or azepanyl group can be optionally substituted by at least one (C1-C6) alkyl groups. In another particular embodiment, R1a is selected in the group consisting of a halogen atom (such as a bromine atom), a (C1-C6)alkyl group (such as a methyl or a CF3 group), a (C1-C6)dialkylamino group (such as dimethylamino group, a piperidinyl group (such as a piperidin-1-yl group), a piperazinyl group (such as a piperazin-1-yl) and an azepanyl group (such as an azepan-1-yl). In a further particular embodiment, R1a is selected in the group consisting of a halogen atom (such as a bromine atom), a (C1-C6)alkyl group (such as a methyl group), a piperidinyl group (such as a piperidin-1-yl group) or a piperazinyl group (such as a piperazin-1-yl).

In another particular embodiment, R1a is a hydrogen atom, a halogen, group, a (C1-C6)alkyl group, a piperidinyl group (such as a piperidin-1-yl group), a morpholinyl group (such as morpholin-4-yl group), a pyrrolidinyl group (such as a pyrrolidin-1-yl group), a piperazinyl group (such as a piperazin-1-yl), or an azepanyl group (such as an azepan-1-yl). In a particular embodiment, R1a is a hydrogen atom, a halogen, group, a (C1-C6)alkyl group), a piperidinyl group (such as a piperidin-1-yl group), a morpholinyl group (such as morpholin-4-yl group) or a pyrrolidinyl group (such as a pyrrolidin-1-yl group).

In a particular embodiment, R1b is a hydrogen atom.

In a particular embodiment, R1c is a hydrogen atom, an (C1-C6)alkyl group, or an (C1-C6)alkyloxy group. In another particular embodiment, R1c is a (C1-C6)alkyl group (such as a methyl group), or a (C1-C6)alkyloxy group (such as a methoxy group).

In a particular embodiment, R1d is a hydrogen atom.

In a particular embodiment, R1e is a hydrogen atom.

In a further particular embodiment, R1b, R1d and R1e are hydrogen atoms. In a further variant, R1b, R1d and R1e are hydrogen atoms and R1c is a (C1-C6)alkyl group (such as a methyl group) or a (C1-C6)alkyloxy group (such as a methoxy group).

In another embodiment, R2 is a (C1-C6)alkyl group, a (C6-C14)aryl group, or a heteroaryl group.

In a further embodiment, R2 is a (C6-C14)aryl group or a heteroaryl group. In a particular variant, R2 is selected in the group consisting of a phenyl group, a furanyl group and a pyridinyl group, wherein the substituents of said phenyl, furanyl and pyridinyl group may be unsubstituted or substituted, such as by at least one group selected in the group consisting of (C1-C6)alkyl groups (e.g. at least one methyl group, such as one or two methyl groups) and halogen atoms (e.g. chlorine, such as one or two chlorine atoms). Illustratively, R2 may be a phenyl group, a methylphenyl group, a dimethylphenyl group (such as a 2,4-dimethylphenyl group), a chlorophenyl group (such as a 3-chlorophenyl group), a furanyl group (such as a furan-2-yl group), a methylfuranyl group (such as a 5-methylfuran-2-yl group), a chlorofuranyl group (such as a 5-chlorofuranyl group), a pyridinyl group (such as a pyridine-2-yl group) or a methylpyridinyl group (such as a 6-methylpyridin-2-yl group). In a particular embodiment, R2 is selected in the group consisting of a dimethylphenyl group (such as a 2,4-dimethylphenyl group), a chlorophenyl group (such as a 3-chlorophenyl group), a furanyl group (such as a furan-2-yl group), a methylfuranyl group (such as a 5-methylfuran-2-yl group), a chlorofuranyl group (such as a 5-chlorofuranyl group) and a methylpyridinyl group (such as a 6-methylpyridin-2-yl group). In a particular embodiment, R2 is a furanyl group, such as a furan-2-yl group, which is unsubstituted, or substituted with a least one (C1-C6)alkyl group, in particular at least one methyl group, such as a 5-methylfuran-2-yl group.

In another embodiment, R'2 is a hydrogen atom.

In another particular embodiment, R2 is a (C1-C6)alkyl group, a (C6-C14)aryl group, or a heteroaryl group, and R'2 is a hydrogen atom.

In a further particular embodiment, the invention relates to a compound of formula (Ia) wherein:

R1a is a hydrogen atom, a halogen atom, a nitrile group, a nitro group (NO2), a (C1-C6)alkyl group, a (C1-C6) alkyloxy group, a (C1-C6)alkylthio group, an amino group, a (C1-C6)alkylamino group, a (C1-C6)dialkylamino group, a piperidinyl group, a morpholinyl group, a pyrrolidinyl group, a piperazinyl group, or an azepanyl group, wherein said piperidinyl, morpholinyl, pyrrolidinyl, piperazinyl, or azepanyl group can be optionally substituted by at least one (C1-C6)alkyl groups;

R1b is a hydrogen atom;

R1c is a hydrogen atom, a (C1-C6)alkyl group, or a (C1-C6)alkyloxy group;

R2 is a (C1-C6)alkyl group, an (C6-C14)aryl group, or a heteroaryl group, and R'2 is a hydrogen atom.

In a further particular embodiment, the invention relates to a compound of formula (Ia) wherein:

R1a is a hydrogen atom, a halogen atom, a nitrile group, a nitro group (NO2), a (C1-C6)alkyl group, a (C1-C6) alkyloxy group, a (C1-C6)alkylthio group, an amino group, a (C1-C6)alkylamino group, a (C1-C6)dialkylamino group, a piperidinyl group, a morpholinyl group or a pyrrolidinyl group, wherein said piperidinyl or pyrrolidinyl, can be optionally substituted by at least one (C1-C6)alkyl groups;

R1b is a hydrogen atom;

R1c is a hydrogen atom, a (C1-C6)alkyl group, or a (C1-C6)alkyloxy group;

R2 is a (C1-C6)alkyl group, an (C6-C14)aryl group, or a heteroaryl group, and R'2 is a hydrogen atom.

In a particular embodiment, HET is a group selected in the following list:

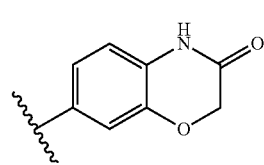

HET1

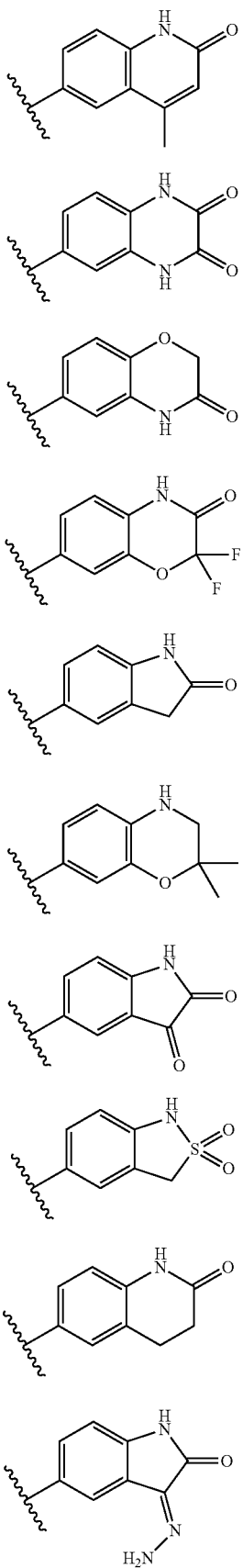
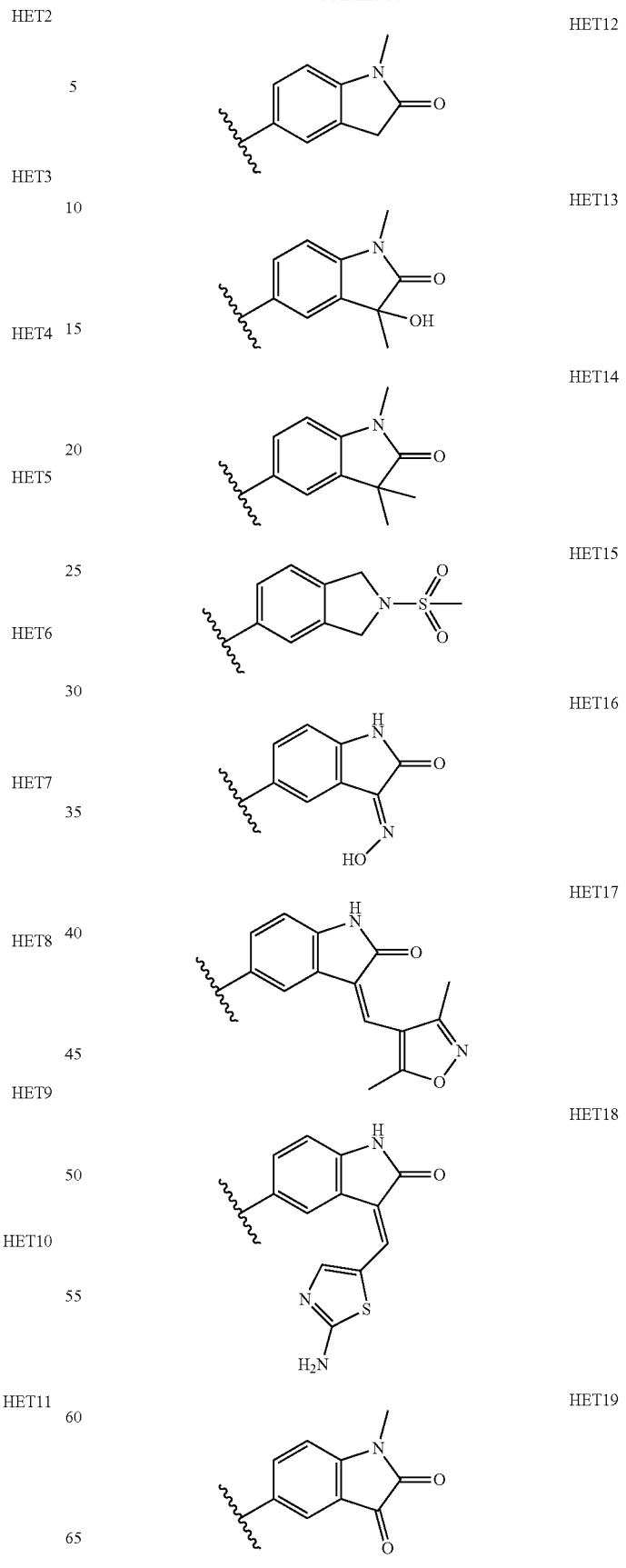

HET20 
HET21 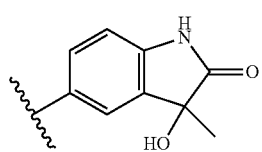
HET22 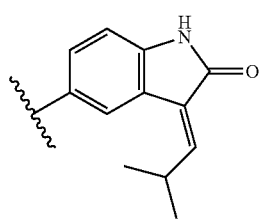
HET23 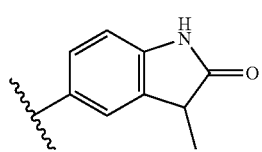
HET24 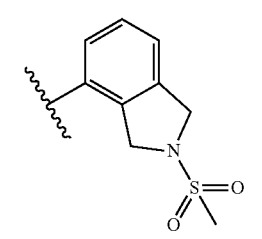
HET25 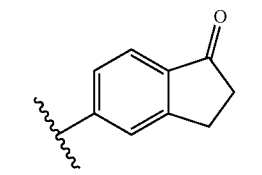
HET26 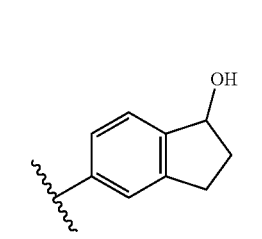
HET27 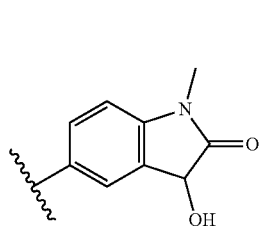
HET28 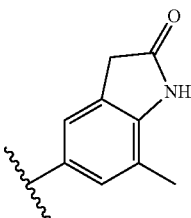
HET29 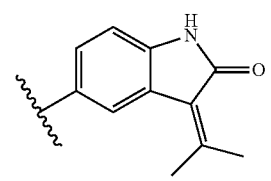
HET30 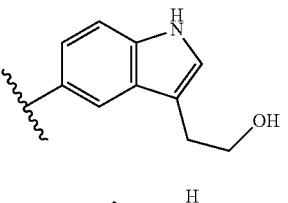
HET31 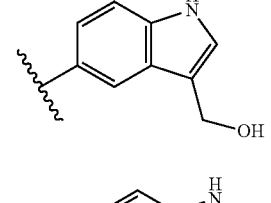
HET32 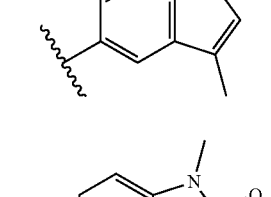
HET33 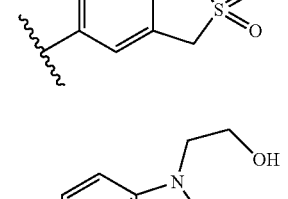
HET34 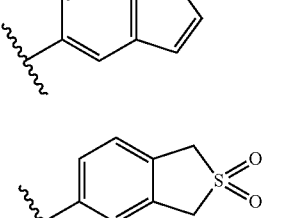
HET35 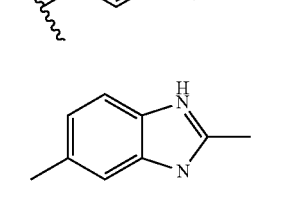
HET36

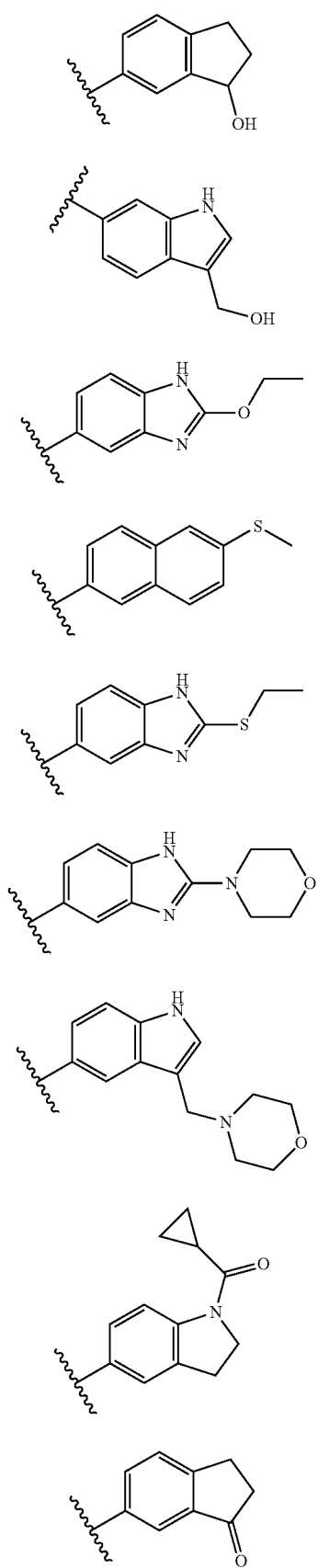
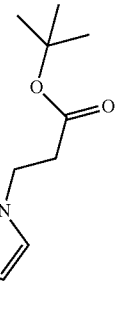
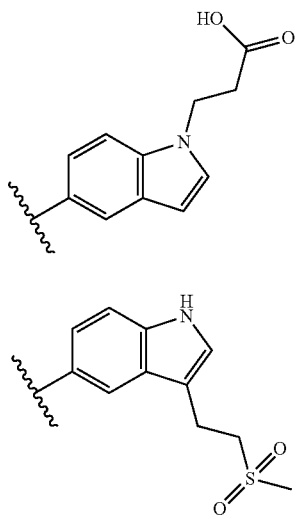
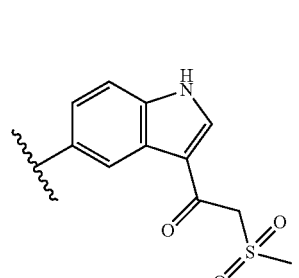
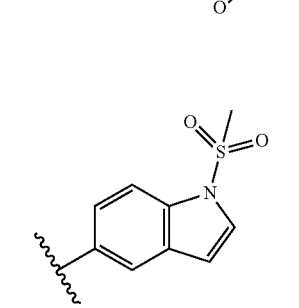
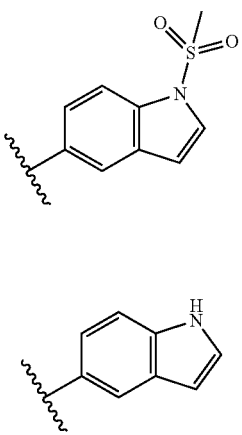
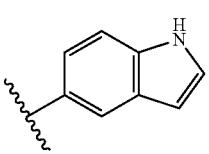

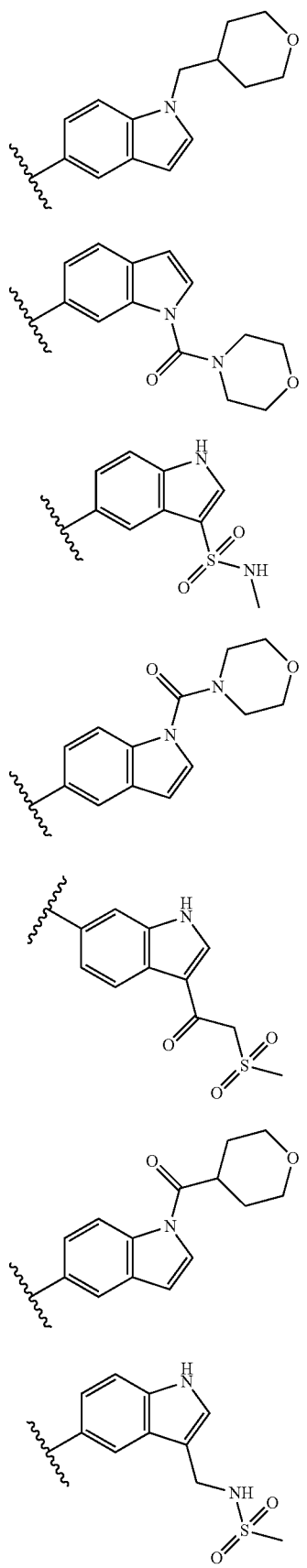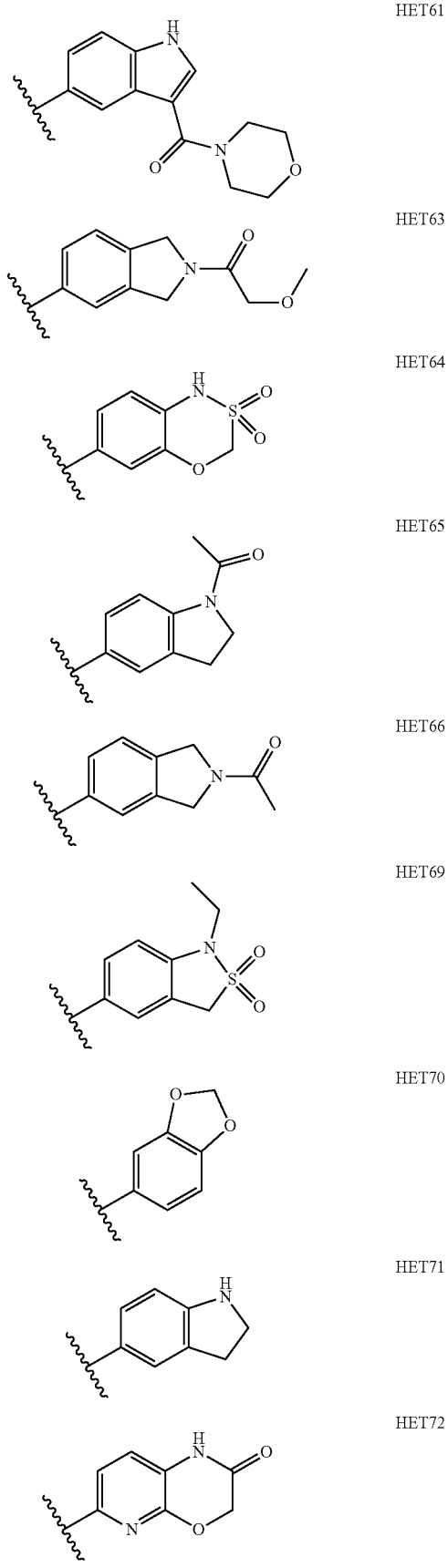

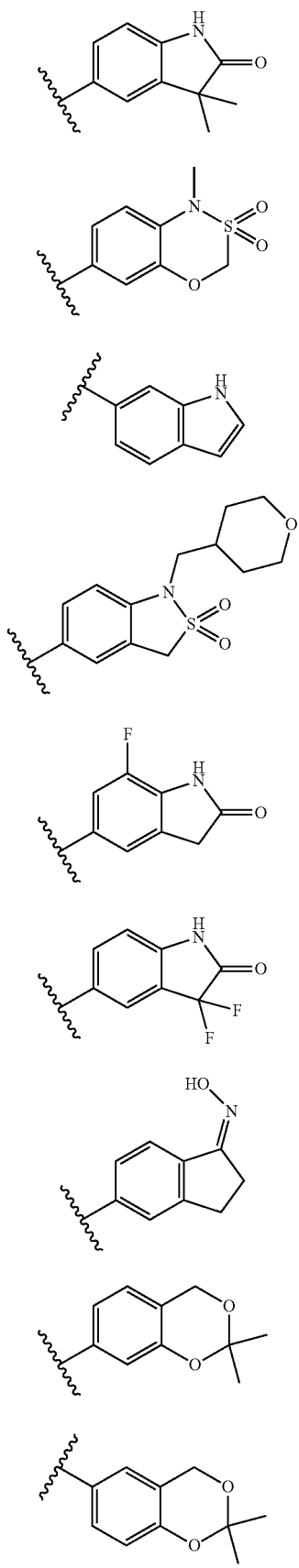
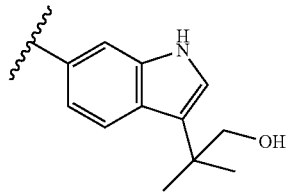
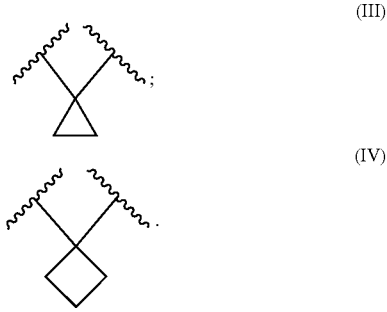

In a particular embodiment, HET is a group selected in group consisting of HET1 to HET44.

In a particular embodiment, HET is selected in the group consisting of HET1, HET6, HET8, HET9, HET11, HET12, HET15, HET21, HET23, HET26, HET27, HET28, HET31, HET32, HET33, HET34, HET35, HET36, HET37, HET39, HET40, HET41, HET42, HET43, HET48, HET49, HET51, HET52, HET54, HET55, HET56, HET57, HET58, HET59, HET60, HET61, HET64, HET65, HET66, HET69, HET70, HET71, HET72, HET73, HET78, HET80 and HET83. In a further particular embodiment, HET is selected in the group consisting of HET1, HET6, HET30, HET38, HET44, HET47 and HET77.

In a particular embodiment, L1 is a NR3-CO—CH2, NR3-CO—C(CH3)2, CO—NH—CH2, or CO—NH—C(CH3)2 group. In a further particular embodiment, L1 is a NR3-CO—CH2 group. In another particular embodiment, R3 is a hydrogen atom.

In another embodiment, L1 is a NH—CO group.

In a particular embodiment, L2 is a CR4R'4 group (such as a cyclopropyl group of formula (III) or cyclobutyl of formula (IV)

$$\text{(III)}$$

$$\text{(IV)}$$

In a particular embodiment, L2 is a cyclopropyl group of formula (III).

In a further particular embodiment, L1 is NR3-CO group or CO—NH group, in particular a NH—CO group, and L2 is a (C1-C6)alkyl group or a (C3-C14)cycloalkylgroup. In a particular embodiment, L1 is a NH—CO group and L2 is a CH2 group or a cyclopropyl group of formula (III).

In a particular embodiment, the invention relates to a compound of formula (Ia), in which:

R1a is a halogen atom (such as bromine), a (C1-C6)alkyl group (such as a methyl or ethyl group, in particular a methyl group), a piperidinyl group (such as a piperidin-1-yl group), a morpholinyl group (such as a morpholin-4-yl), a pyrrolidinyl group (such as a pyrrolidin-1-yl group), or a piperazinyl group (such as a piperazin-1-yl), or an azepanyl group (such as an azepan-1-yl), wherein said piperidinyl, morpholinyl, piperazinyl, azepanyl or pyrrolidinyl group can be optionally substituted by at least one (C1-C6)alkyl group;

R1b is a hydrogen atom;

R1c is a hydrogen, a (C1-C6)alkyl group (such as a methyl or ethyl group, in particular a methyl group), or a (C1-C6)alkoxy group (such as a methoxy or a an ethoxy group, in particular a methoxy group);

R1d and R1e are hydrogen atoms;

R2 is a (C1-C6)alkyl group (such as an isobutyl group), a phenyl group or a heterocyclic group (such as a substituted or unsubstituted furanyl group, in particular a 5-methylfuranyl group or a 5-ethylfuranyl group, more particularly a 5-methylfuran-2-yl group);

L1 represents a NH—CO—CH2 group, L2 is a bond; HET is chosen in the list:

HET1
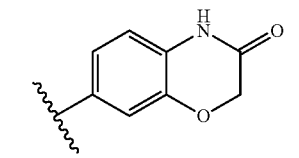

HET6

HET64
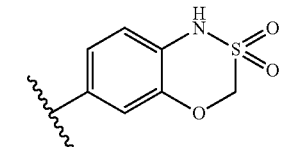

HET15
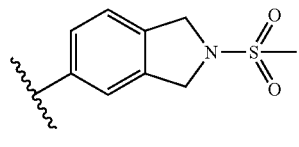

HET9
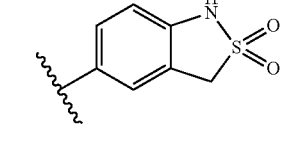

HET47
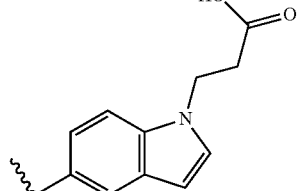

HET77
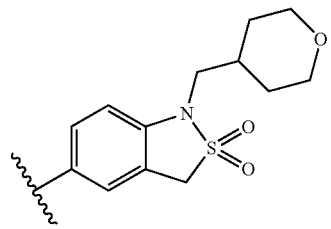

-continued

HET30
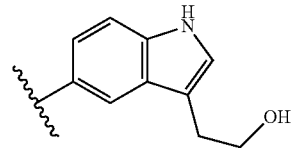

HET2
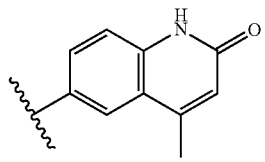

HET7
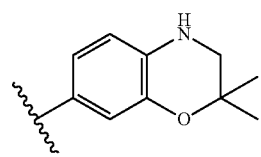

HET8
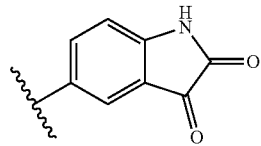

HET36
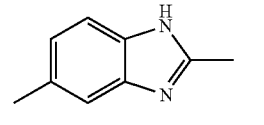

HET46
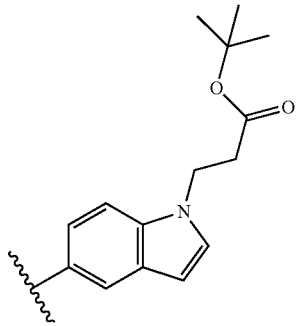

HET70
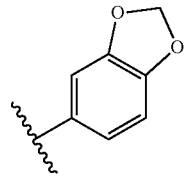

In a particular embodiment, the invention relates to a compound of formula (Ia), in which:

A is a CR1e group;

R1a is a halogen atom (such as bromine), a (C1-C6)alkyl group (such as a methyl or ethyl group, in particular a methyl group), a piperidinyl group (such as a piperidin-1-yl group), a morpholinyl group (such as a morpholin-4-yl) or a pyrrolidinyl group (such as a pyrrolidin-1-yl group), wherein said piperidinyl, morpholinyl, or pyrrolidinyl group can be optionally substituted by at least one (C1-C6)alkyl groups;

R1b is a hydrogen atom;

R1c is a hydrogen, a (C1-C6)alkyl group (such as a methyl or ethyl group, in particular a methyl group), or a (C1-C6)alkoxy group (such as a methoxy or a an ethoxy group, in particular a methoxy group);

R1d and R1e are hydrogen atoms;

R2 is a (C1-C6)alkyl group (such as an isobutyl group), a phenyl group or a heterocyclic group (such as a substituted or unsubstituted furanyl group, in particular a 5-methylfuranyl group or a 5-ethylfuranyl group, more particularly a 5-methylfuran-2-yl group);

L1 represents a NH—CO—CH2 group, L2 is a bond;

HET is selected in the group consisting of HET1, HET2, HET6, HET7, HET8 and HET9.

In a particular embodiment, the invention relates to a compound of formula (Ia), in which:

R1a is a heterocyclic group (in particular a piperidinyl group (such as a piperidin-1-yl group));

R1c is a (C1-C6)alkyl group (such as a methyl or ethyl group, in particular a methyl group);

R2 is a heterocyclic group (such as a substituted or unsubstituted furanyl group, in particular a 5-methylfuranyl group or a 5-ethylfuranyl group, more particularly a 5-methylfuran-2-yl group);

L represents a NH—CO—CH2 group, L2 is a bond;

HET is chosen in the list:

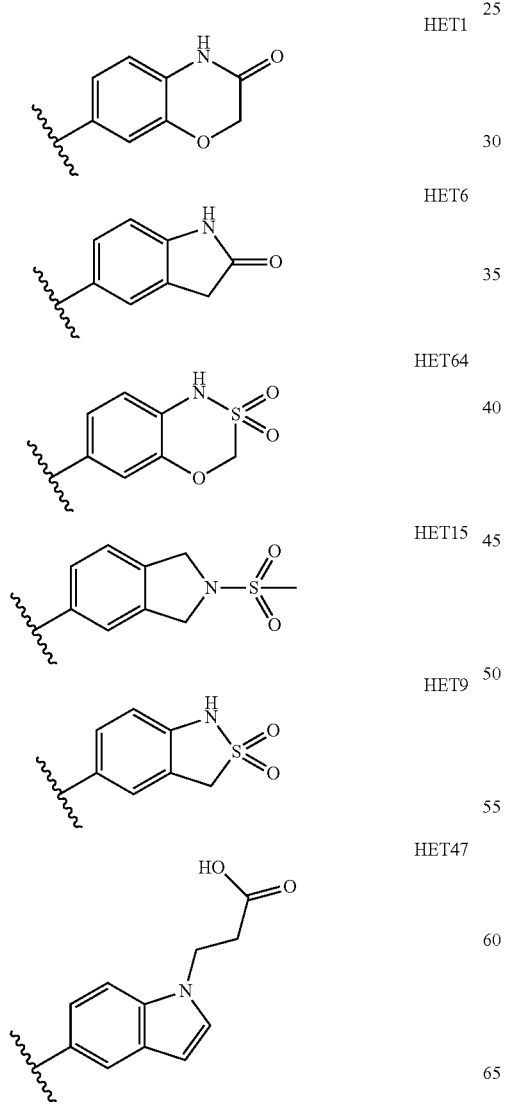

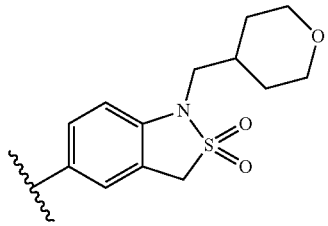

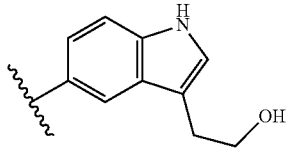

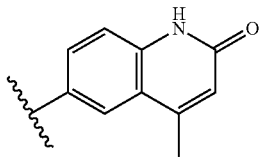

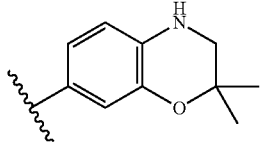

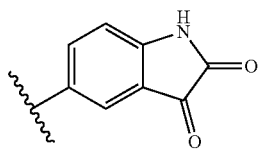

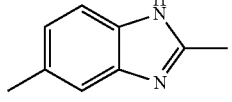

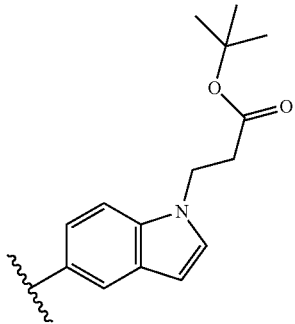

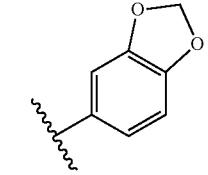

HET being in particular selected in the group consisting of HET1, HET2, HET6, HET7, HET8 and HET9.

In a particular embodiment, the invention relates to a compound of formula (Ia), in which:

R1a is a heterocyclic group (in particular a piperidinyl group (such as a piperidin-1-yl group)) or a (C1-C6)alkyl group (such as a methyl or ethyl group, in particular a methyl group);

R1c is a (C1-C6)alkyl group (such as a methyl or ethyl group, in particular a methyl group);

R2 is a heterocyclic group (such as a substituted or unsubstituted furanyl group, in particular a 5-methylfuranyl group or a 5-ethylfuranyl group or a 5-chlorofuranyl, more particularly a 5-chlorofuran-2-yl group);

L1 represents a NH—CO— group, L2 is a CR4R'4 group (such as a cyclopropyl group of formula (III) or cyclobutyl of formula (IV)

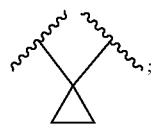 (III)

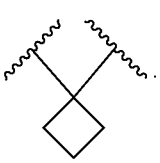 (IV)

In a particular embodiment, the invention relates to a compound of formula (Ia), in which:

R1a is a heterocyclic group (in particular a piperidinyl group (such as a piperidin-1-yl group)) or a (C1-C6)alkyl group (such as a methyl or ethyl group, in particular a methyl group);

R1c is a (C1-C6)alkyl group (such as a methyl or ethyl group, in particular a methyl group);

R2 is a heterocyclic group (such as a substituted or unsubstituted furanyl group, in particular a 5-methylfuranyl group or a 5-ethylfuranyl group or a 5-chlorofuranyl, more particularly a 5-chlorofuran-2-yl group);

L1 represents a NH—CO group;

L2 is a CR4R'4 group (such as a cyclopropyl group of formula (III) or cyclobutyl group of formula (IV)

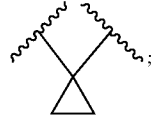 (III)

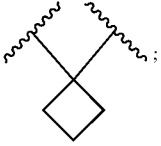 (IV)

and

HET is selected in the group consisting of the following HET groups:

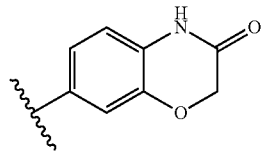 HET1

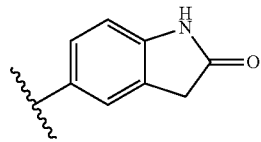 HET6

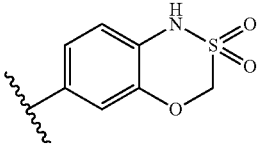 HET64

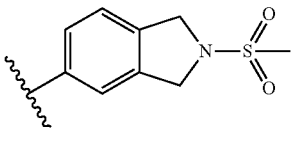 HET15

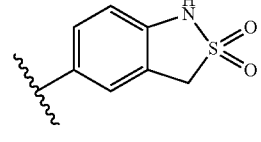 HET9

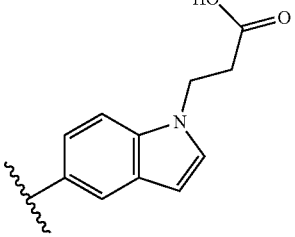 HET47

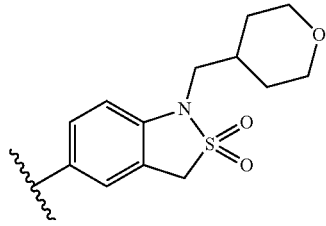 HET77

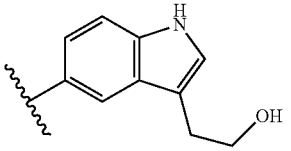 HET30

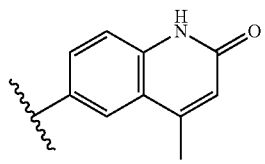 HET2

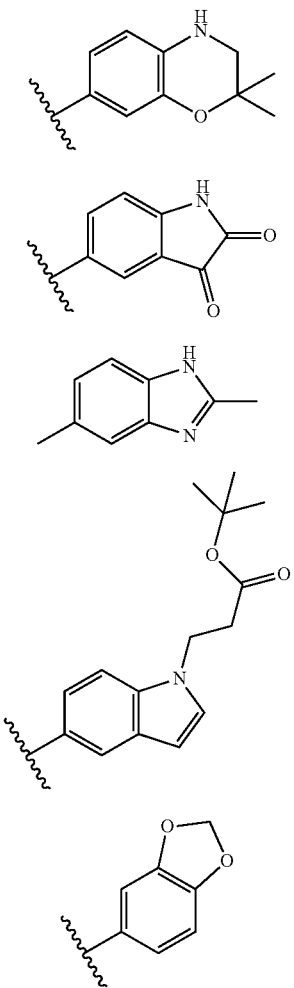

In a particular embodiment of the compound of formula (Ia):

R1a represents a halogen, in particular a bromine atom; a (C1-C6)alkyl group, in particular a methyl group; a heterocyclic group, in particular a piperadin-1-yl group, a piperazin-1-yl group, or an azepan-1-yl group; a di(C1-C6)alkylamaino group, in particular a N(CH3)2 group;

R1b, R1d and R1e represent a hydrogen atom;

R1c is a (C1-C6)alkyl group, in particular a methyl group, or a (C1-C6)alkyloxy group, in particular a methoxy group R2 represents a 5 membered hetoaryl group containing an oxygen or a nitrogen atom optionally substituted by a (C1-C6)alkyl group or a halogen, in particular a furan-1-yl group, a 5-methylfuran-2-yl group or a 5-chlorofuran-2-yl group; a (C6-C14)aryl group optionally substituted by a (C1-C6)alkyl group, in particular a phenyl group optionally substituted by one or more methyl group or by a chlorine atom; or a heterocyclic group optionally substituted by a (C1-C6)alkyl group, in particular a 6-methylpyridin-2-yl;

R'2 is a hydrogen atom;

L1 represents a NH—CO group; and

L2 represents a (C1-C6)alkyl group, in particular a —CH2- group, or a a CR4R'4 group, in particular a cyclopropyl group of formula (III)

$$\text{(III)}$$

In a particular embodiment of the compound of formula (Ia):

R1a represents a halogen, in particular a bromine atom; a (C1-C6)alkyl group, in particular a methyl group; a heterocyclic group, in particular a piperadin-1-yl group, or a piperazin-1-yl group;

R1b, R1d and R1e represent a hydrogen atom;

R1c is a (C1-C6)alkyl group, in particular a methyl group;

R2 represents a 5 membered hetoaryl group containing an oxygen or a nitrogen atom optionally substituted by a (C1-C6)alkyl group or a halogen, in particular a 5-methylfuran-2-yl group or a 5-chlorofuran-2-yl group;

R'2 is a hydrogen atom;

L1 represents a NH—CO group;

L2 represents a (C1-C6)alkyl group, in particular a —CH2- group, or a a CR4R'4 group, in particular a cyclopropyl group of formula (III)

$$\text{(III)}$$

and

HET is HET1, HET6, HET30, HET38, HET44, HET47, HET67 or HET77.

Particular Embodiments and Aspects of the Invention

The term "alkyl" refers to a saturated hydrocarbon radical that is linear or branched, substituted or not, having preferably from one to six, and even more preferably from one to four carbon atoms, such as methyl, ethyl, n-propyl, isopropyl, n-butyl, isobutyl, tert-butyl, or sec-butyl. The alkyl group can be optionally substituted by one or more halogen atoms, by an (C6-C14)aryl group or by a (C3-C14)cycloalkyl group. Further possible substituents of an alkyl group also include one or more substituents selected from a —NH₂ group, a (C1-C6)alkylamino group, a (C1-C6)dialkylamino group, and a (C2-C6)alkynyl group.

The term alkynyl denotes linear or branched hydrocarbon groups containing from 2 to 6 carbon atoms and containing at least one triple bond. Examples of alkynyl containing from 3 to 6 carbon atoms are 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the isomeric forms thereof.

The terms "alkyloxy" and "alkylthio" refer to an alkyl group as defined above that is linked to the remainder of the compound by an oxygen or sulfur atom, respectively.

The term "(C1-C6)alkylamino" refers to a —NH—(C1-C6)alkyl group. In a particular embodiment, the alkyl group of the alkylamino group may be substituted or not with a (C3-C14)cycloalkyl group, a (C6-C14)aryl group, a heterocyclic group, or an (C1-C6)alkyloxycarbonyl group.

The term "(C1-C6)dialkylamino" refers to a —NRR' group where R and R' independently represent a (C1-C6) alkyl group as defined above. In a particular embodiment, the alkyl groups of the dialkylamino group may independently be substituted or not with a (C3-C14)cycloalkyl group, a (C6-C14)aryl group, a heterocyclic group, or a (C1-C6)alkyloxycarbonyl group.

The term "cycloalkyl" designates a substituted or unsubstituted alkyl group that forms one cycle having preferably from three to fourteen carbon atoms, and more preferably five to six carbon atoms, such as cyclopropyl, cyclopentyl and cyclohexyl. The cycloalkyl group of the present invention may be unsubstituted, or substituted, for example with a (C1-C6)alkyl group, in particular with a (C1-C6)alkyl group substituted with one or more halogen atoms, such as the CF3 group.

The term "cycloalkylamino" refers to a —NH—(C3-C14) cycloalkyl group or a —N((C1-C6)alkyl)(C3-C14)cycloalkyl group.

The term "amino group" designates a —NH$_2$ group.

The term "hydroxyl group" refers to a —OH group.

The term "carbonyl" designates a CO group.

The term "carbonyl(C1-C6)alkyl" designates a CO—(C1-C6)alkyl group.

The term "amido" designates a CO—NH2 group.

The term "alkylamido" designates a CO—NH—(C1-C6) alkyl group.

The term "(C1-C6)dialkylamido" designates a CO—NRR' group, R and R' representing a (C1-C6)alkyl group as defined above.

A sulfone group designates a SO2 group; The term "aryl" designates an aromatic group, substituted or not, having preferably from six to fourteen carbon atoms such as phenyl, a-naphtyl, b-naphtyl, or biphenyl.

The term "heterocyclic" refers to a heterocycloalkyl group or a heteroaryl group. The term "heterocycloalkyl" group refers to a cycloalkyl as indicated above that further comprises one or several heteroatoms selected among nitrogen, oxygen or sulfur. They generally comprise from four to fourteen carbon atoms, such as morpholinyl, piperazinyl, piperidinyl, pyrrolidinyl, tetrahydropyranyl, dithiolanyl and azepanyl groups. In a particular embodiment, the heterocycloalkyl group is a 5-, 6- or 7-membered cycle. The term "heteroaryl" refers to an aryl group as indicated above, substituted or not, that further comprises one or several heteroatoms selected among nitrogen, oxygen or sulfur. They generally comprise from four to fourteen carbon atoms. In a particular embodiment, the heteroaryl group is a 5-, 6- or 10-membered heteroaryl group. Representative heteroaryl groups include a pyridinyl, pyrimidinyl, furanyl, thiophenyl, quinoleinyl, and isoquinoleinyl group.

The aryl group or the heterocyclic group can be optionally substituted by one or more halogen atom(s), (C1-C6)alkyl group(s), or (C1-C6)alkyloxy group(s). By halogen atom, an atom of bromine, chlorine, fluorine or iodine is understood, in particular an atom of bromine, chlorine or fluorine.

Specific compounds according to the invention include:

| | |
|---|---|
| Cpd. 1 | N-{[4-methyl-2-(piperidin-1-yl)phenyl](phenyl)methyl}-2-(3-oxo-3,4-dihydro-2H-1,4-benzoxazin-7-yl)acetamide; |
| Cpd. 2 | N-{[4-methyl-2-(morpholin-4-yl)phenyl](phenyl)methyl}-2-(3-oxo-3,4-dihydro-2H-1,4-benzoxazin-7-yl)acetamide; |
| Cpd. 3 | 2-(3-oxo-3,4-dihydro-2H-1,4-benzoxazin-7-yl)-N-{phenyl[2-(piperidin-1-yl)phenyl]methyl}acetamide; |
| Cpd. 4 | N-{[4-methoxy-2-(piperidin-1-yl)phenyl](phenyl)methyl}-2-(3-oxo-3,4-dihydro-2H-1,4-benzoxazin-7-yl)acetamide; |
| Cpd. 5 | 2-(3-oxo-3,4-dihydro-2H-1,4-benzoxazin-7-yl)-N-{phenyl[2-(pyrrolidin-1-yl)phenyl]methyl}acetamide; |
| Cpd. 6 | N-{3-methyl-1-[2-(piperidin-1-yl)phenyl]butyl}-2-(3-oxo-3,4-dihydro-2H-1,4-benzoxazin-7-yl)acetamide; |
| Cpd. 7 | N-{[2-(morpholin-4-yl)phenyl](phenyl)methyl}-2-(3-oxo-3,4-dihydro-2H-1,4-benzoxazin-7-yl)acetamide; |
| Cpd. 8 | N-{[4-methyl-2-(morpholin-4-yl)phenyl](phenyl)methyl}-2-(4-methyl-2-oxo-1,2-dihydroquinolin-6-yl)acetamide; |
| Cpd. 9 | N-[(2,4-dimethylphenyl)(phenyl)methyl]-2-(4-methyl-2-oxo-1,2-dihydroquinolin-6-yl)acetamide; |
| Cpd. 10 | N-{[4-methoxy-2-(piperidin-1-yl)phenyl](phenyl)methyl}-2-(4-methyl-2-oxo-1,2-dihydroquinolin-6-yl)acetamide; |
| Cpd. 11 | N-{[4-methyl-2-(piperidin-1-yl)phenyl](phenyl)methyl}-2-(4-methyl-2-oxo-1,2-dihydroquinolin-6-yl)acetamide; |
| Cpd. 12 | 2-(2,3-dioxo-1,2,3,4-tetrahydroquinoxalin-6-yl)-N-{phenyl[2-(piperidin-1-yl)phenyl]methyl}acetamide; |
| Cpd. 13 | 2-(3-oxo-3,4-dihydro-2H-1,4-benzoxazin-6-yl)-N-{phenyl[2-(piperidin-1-yl)phenyl]methyl}acetamide; |
| Cpd. 14 | 2-(2,2-difluoro-3-oxo-3,4-dihydro-2H-1,4-benzoxazin-7-yl)-N-{phenyl[2-(piperidin-1-yl)phenyl]methyl}acetamide; |
| Cpd. 15 | 2-(2-oxo-2,3-dihydro-1H-indol-5-yl)-N-{phenyl[2-(piperidin-1-yl)phenyl]methyl}acetamide; |
| Cpd. 16 | N-{[4-methyl-2-(piperidin-1-yl)phenyl](phenyl)methyl}-2-(2-oxo-2,3-dihydro-1H-indol-5-yl)acetamide; |
| Cpd. 17 | N-{[2-(morpholin-4-yl)phenyl](phenyl)methyl}-2-(2-oxo-2,3-dihydro-1H-indol-5-yl)acetamide; |
| Cpd. 18 | N-{[4-methyl-2-(morpholin-4-yl)phenyl](phenyl)methyl}-2-(2-oxo-2,3-dihydro-1H-indol-5-yl)acetamide; |
| Cpd. 19 | 2-(2,2-dimethyl-3-oxo-3,4-dihydro-2H-1,4-benzoxazin-7-yl)-N-{phenyl[2-(piperidin-1-yl)phenyl]methyl}acetamide; |
| Cpd. 20 | 2-(2,3-dioxo-2,3-dihydro-1H-indol-5-yl)-N-{phenyl[2-(piperidin-1-yl)phenyl]methyl}acetamide; |
| Cpd. 21 | 2-(2,2-dimethyl-3-oxo-3,4-dihydro-2H-1,4-benzoxazin-7-yl)-N-{[4-methyl-2-(morpholin-4-yl)phenyl](phenyl)methyl}acetamide; |
| Cpd. 22 | 2-(2,3-dioxo-2,3-dihydro-1H-indol-5-yl)-N-{[4-methoxy-2-(piperidin-1-yl)phenyl](phenyl)methyl}acetamide; |
| Cpd. 23 | 2-(2,3-dioxo-2,3-dihydro-1H-indol-5-yl)-N-{[4-methyl-2-(piperidin-1-yl)phenyl](5-methylfuran-2-yl)methyl}acetamide; |

-continued

| | |
|---|---|
| Cpd. 24 | N-{[4-methyl-2-(piperidin-1-yl)phenyl](5-methylfuran-2-yl)methyl}-2-(2-oxo-2,3-dihydro-1H-indol-5-yl)acetamide; |
| Cpd. 25 | 2-(2,2-dimethyl-3-oxo-3,4-dihydro-2H-1,4-benzoxazin-7-yl)-N-{[4-methyl-2-(piperidin-1-yl)phenyl](5-methylfuran-2-yl)methyl}acetamide; |
| Cpd. 26 | 2-(2,2-dioxo-1,3-dihydro-2,1-benzothiazol-5-yl)-N-{phenyl[2-(piperidin-1-yl)phenyl]methyl}acetamide; |
| Cpd. 27 | 2-(2,2-dioxo-1,3-dihydro-2,1-benzothiazol-5-yl)-N-{[4-methyl-2-(piperidin-1-yl)phenyl](5-methylfuran-2-yl)methyl}acetamide; |
| Cpd. 28 | N-[(2-bromo-4-methylphenyl)(5-methylfuran-2-yl)methyl]-2-(2,2-dioxo-1,3-dihydro-2,1-benzothiazol-5-yl)acetamide; |
| Cpd. 29 | N-[(2,4-dimethylphenyl)(5-methylfuran-2-yl)methyl]-2-(2-oxo-2,3-dihydro-1H-indol-5-yl)acetamide; |
| Cpd. 30 | 2-(2,2-dimethyl-3-oxo-3,4-dihydro-2H-1,4-benzoxazin-7-yl)-N-{[4-methoxy-2-(morpholin-4-yl)phenyl](5-methylfuran-2-yl)methyl}acetamide; |
| Cpd. 31 | N-[(2-bromo-4-methylphenyl)(5-methylfuran-2-yl)methyl]-2-(3-oxo-3,4-dihydro-2H-1,4-benzoxazin-7-yl)acetamide; |
| Cpd. 32 | N-[(2,4-dimethylphenyl)(5-ethylfuran-2-yl)methyl]-2-(3-oxo-3,4-dihydro-2H-1,4-benzoxazin-7-yl)acetamide; |
| Cpd. 33 | N-[(2,4-dimethylphenyl)(5-methylfuran-2-yl)methyl]-2-(3-oxo-3,4-dihydro-2H-1,4-benzoxazin-7-yl)acetamide; |
| Cpd. 34 | N-[(2-bromo-4-methoxyphenyl)(5-methylfuran-2-yl)methyl]-2-(3-oxo-3,4-dihydro-2H-1,4-benzoxazin-7-yl)acetamide; |
| Cpd. 35 | N-{[4-methyl-2-(piperidin-1-yl)phenyl](5-methylfuran-2-yl)methyl}-2-(3-oxo-3,4-dihydro-2H-1,4-benzoxazin-7-yl)acetamide; |
| Cpd. 36 | N-[(2-bromo-4-methylphenyl)(5-methylfuran-2-yl)methyl]-2-(2-oxo-1,2,3,4-tetrahydroquinolin-6-yl)acetamide; |
| Cpd. 37 | 2-(3-hydrazinylidene-2-oxo-2,3-dihydro-1H-indol-5-yl)-N-{[4-methyl-2-(piperidin-1-yl)phenyl](5-methylfuran-2-yl)methyl}acetamide; |
| Cpd. 38 | N-{[4-methyl-2-(piperidin-1-yl)phenyl](5-methylfuran-2-yl)methyl}-2-(1-methyl-2-oxo-2,3-dihydro-1H-indol-5-yl)acetamide; |
| Cpd. 39 | 2-(3-hydroxy-1,3-dimethyl-2-oxo-2,3-dihydro-1H-indol-5-yl)-N-{[4-methyl-2-(piperidin-1-yl)phenyl](5-methylfuran-2-yl)methyl}acetamide; |
| Cpd. 40 | N-{[4-methyl-2-(piperidin-1-yl)phenyl](5-methylfuran-2-yl)methyl}-2-(1,3,3-trimethyl-2-oxo-2,3-dihydro-1H-indol-5-yl)acetamide; |
| Cpd. 41 | 2-(2-methanesulfonyl-2,3-dihydro-1H-isoindol-5-yl)-N-{[4-methyl-2-(piperidin-1-yl)phenyl](5-methylfuran-2-yl)methyl}acetamide; |
| Cpd. 42 | 2-[3-(hydroxyimino)-2-oxo-2,3-dihydro-1H-indol-5-yl]-N-{[4-methyl-2-(piperidin-1-yl)phenyl](5-methylfuran-2-yl)methyl}acetamide; |
| Cpd. 43 | 2-{3-[(dimethyl-1,2-oxazol-4-yl)methylidene]-2-oxo-2,3-dihydro-1H-indol-5-yl}-N-{[4-methyl-2-(piperidin-1-yl)phenyl](5-methylfuran-2-yl)methyl}acetamide; |
| Cpd. 44 | 2-{3-[(2-amino-1,3-thiazol-5-yl)methylidene]-2-oxo-2,3-dihydro-1H-indol-5-yl}-N-{[4-methyl-2-(piperidin-1-yl)phenyl](5-methylfuran-2-yl)methyl}acetamide; |
| Cpd. 45 | 2-(1-methyl-2,3-dioxo-2,3-dihydro-1H-indol-5-yl)-N-{[4-methyl-2-(piperidin-1-yl)phenyl](5-methylfuran-2-yl)methyl}acetamide; |
| Cpd. 46 | 2-(3-hydroxy-2-oxo-2,3-dihydro-1H-indol-5-yl)-N-{[4-methyl-2-(piperidin-1-yl)phenyl](5-methylfuran-2-yl)methyl}acetamide; |
| Cpd. 47 | 2-(3-hydroxy-3-methyl-2-oxo-2,3-dihydro-1H-indol-5-yl)-N-{[4-methyl-2-(piperidin-1-yl)phenyl](5-methylfuran-2-yl)methyl}acetamide; |
| Cpd. 48 | N-{[4-methyl-2-(piperidin-1-yl)phenyl](5-methylfuran-2-yl)methyl}-2-[(3E)-3-(2-methylpropylidene)-2-oxo-2,3-dihydro-1H-indol-5-yl]acetamide; |
| Cpd. 49 | N-{[4-methyl-2-(piperidin-1-yl)phenyl](5-methylfuran-2-yl)methyl}-2-(3-methyl-2-oxo-2,3-dihydro-1H-indol-5-yl)acetamide; |
| Cpd. 50 | 2-(2-methanesulfonyl-2,3-dihydro-1H-isoindol-4-yl)-N-{[4-methyl-2-(piperidin-1-yl)phenyl](5-methylfuran-2-yl)methyl}acetamide; |
| Cpd. 51 | N-{[4-methyl-2-(piperidin-1-yl)phenyl](5-methylfuran-2-yl)methyl}-2-(1-oxo-2,3-dihydro-1H-inden-5-yl)acetamide; |
| Cpd. 52 | 2-(1-hydroxy-2,3-dihydro-1H-inden-5-yl)-N-{[4-methyl-2-(piperidin-1-yl)phenyl](5-methylfuran-2-yl)methyl}acetamide; |
| Cpd. 53 | 2-(3-hydroxy-1-methyl-2-oxo-2,3-dihydro-1H-indol-5-yl)-N-{[4-methyl-2-(piperidin-1-yl)phenyl](5-methylfuran-2-yl)methyl}acetamide; |
| Cpd. 54 | N-{[4-methyl-2-(piperidin-1-yl)phenyl](5-methylfuran-2-yl)methyl}-2-(7-methyl-2-oxo-2,3-dihydro-1H-indol-5-yl)acetamide; |
| Cpd. 55 | N-{[4-methyl-2-(piperidin-1-yl)phenyl](5-methylfuran-2-yl)methyl}-2-[2-oxo-3-(propan-2-ylidene)-2,3-dihydro-1H-indol-5-yl]acetamide; |
| Cpd. 56 | N-[(5-chlorofuran-2-yl)(2,4-dimethylphenyl)methyl]-1-(2-methanesulfonyl-2,3-dihydro-1H-isoindol-5-yl)cyclopropane-1-carboxamide; |
| Cpd. 57 | 2-[3-(2-hydroxyethyl)-1H-indol-5-yl]-N-{[4-methyl-2-(piperidin-1-yl)phenyl](5-methylfuran-2-yl)methyl}acetamide; |
| Cpd. 58 | 2-[3-(hydroxymethyl)-1H-indol-5-yl]-N-{[4-methyl-2-(piperidin-1-yl)phenyl](5-methylfuran-2-yl)methyl}acetamide; |
| Cpd. 59 | N-[(2,4-dimethylphenyl)(5-methylfuran-2-yl)methyl]-1-(3-oxo-3,4-dihydro-2H-1,4-benzoxazin-7-yl)cyclopropane-1-carboxamide; |
| Cpd. 60 | N-[(2,4-dimethylphenyl)(5-methylfuran-2-yl)methyl]-1-[3-(2-hydroxyethyl)-1H-indol-5-yl]cyclopropane-1-carboxamide; |
| Cpd. 61 | N-[(2,4-dimethylphenyl)(5-methylfuran-2-yl)methyl]-1-(2-oxo-2,3-dihydro-1H-indol-5-yl)cyclopropane-1-carboxamide; |
| Cpd. 62 | N-[(5-chlorofuran-2-yl)(2,4-dimethylphenyl)methyl]-1-[3-(2-hydroxyethyl)-1H-indol-5-yl]cyclopropane-1-carboxamide; |

-continued

| | |
|---|---|
| Cpd. 63 | N-[(2,4-dimethylphenyl)(5-methylfuran-2-yl)methyl]-1-(2,2-dioxo-1,3-dihydro-2,1-benzothiazol-5-yl)cyclopropane-1-carboxamide; |
| Cpd. 64 | 2-(3-methyl-1H-indol-5-yl)-N-{[4-methyl-2-(piperidin-1-yl)phenyl](5-methylfuran-2-yl)methyl}acetamide; |
| Cpd. 65 | N-[(2,4-dimethylphenyl)(5-methylfuran-2-yl)methyl]-1-(2-methanesulfonyl-2,3-dihydro-1H-isoindol-5-yl)cyclopropane-1-carboxamide; |
| Cpd. 66 | 1-[3-(2-hydroxyethyl)-1H-indol-5-yl]-N-{[4-methyl-2-(piperidin-1-yl)phenyl](5-methylfuran-2-yl)methyl}cyclopropane-1-carboxamide; |
| Cpd. 67 | N-{[4-methyl-2-(piperidin-1-yl)phenyl](5-methylfuran-2-yl)methyl}-2-(3-oxo-2,3-dihydro-1H-inden-5-yl)acetamide; |
| Cpd. 68 | N-[(2-bromo-4-methylphenyl)(5-methylfuran-2-yl)methyl]-2-[1-(oxan-4-ylmethyl)-2,2-dioxo-1,3-dihydro-2,1-benzothiazol-5-yl]acetamide; |
| Cpd. 69 | N-[(2,4-dimethylphenyl)(5-methylfuran-2-yl)methyl]-1-[1-(2-hydroxyethyl)-1H-indol-5-yl]cyclopropane-1-carboxamide; |
| Cpd. 70 | N-[(2,4-dimethylphenyl)(5-methylfuran-2-yl)methyl]-1-(1-methyl-2,2-dioxo-1,3-dihydro-2,1-benzothiazol-5-yl)cyclopropane-1-carboxamide; |
| Cpd. 71 | N-{[2-(dimethylamino)-4-methylphenyl](5-methylfuran-2-yl)methyl}-1-(2,2-dioxo-1,3-dihydro-2,1-benzothiazol-5-yl)cyclopropane-1-carboxamide; |
| Cpd. 72 | N-[(5-chlorofuran-2-yl)(2,4-dimethylphenyl)methyl]-1-(2,2-dioxo-1,3-dihydro-2-benzothiophen-5-yl)cyclopropane-1-carboxamide; |
| Cpd. 73 | 1-(2-methanesulfonyl-2,3-dihydro-1H-isoindol-5-yl)-N-{[4-methyl-2-(pyrrolidin-1-yl)phenyl](5-methylfuran-2-yl)methyl}cyclopropane-1-carboxamide; |
| Cpd. 74 | N-[(2,4-dimethylphenyl)(5-methylfuran-2-yl)methyl]-1-(2,2-dioxo-1,3-dihydro-2-benzothiophen-5-yl)cyclopropane-1-carboxamide; |
| Cpd. 75 | 2-(2-methyl-1H-1,3-benzodiazol-5-yl)-N-{[4-methyl-2-(piperidin-1-yl)phenyl](phenyl)methyl}acetamide; |
| Cpd. 76 | N-{[2-(dimethylamino)-4-methylphenyl](5-methylfuran-2-yl)methyl}-1-(2-methanesulfonyl-2,3-dihydro-1H-isoindol-5-yl)cyclopropane-1-carboxamide; |
| Cpd. 77 | N-[(2-bromo-4-methylphenyl)(5-methylfuran-2-yl)methyl]-2-(2-methyl-1H-1,3-benzodiazol-5-yl)acetamide; |
| Cpd. 78 | 2-(2,2-dioxo-1,3-dihydro-2-benzothiophen-5-yl)-N-{[4-methyl-2-(piperidin-1-yl)phenyl](5-methylfuran-2-yl)methyl}acetamide; |
| Cpd. 79 | N-[(5-chlorofuran-2-yl)[4-methyl-2-(piperidin-1-yl)phenyl]methyl]-2-(2-methanesulfonyl-2,3-dihydro-1H-isoindol-5-yl)acetamide; |
| Cpd. 80 | N-[(5-chlorofuran-2-yl)[4-methyl-2-(pyrrolidin-1-yl)phenyl]methyl]-1-(2-methanesulfonyl-2,3-dihydro-1H-isoindol-5-yl)cyclopropane-1-carboxamide; |
| Cpd. 81 | N-[(2-bromo-4-methylphenyl)(phenyl)methyl]-2-(2-methyl-1H-1,3-benzodiazol-5-yl)acetamide; |
| Cpd. 82 | 2-(2-methyl-1H-1,3-benzodiazol-5-yl)-N-{[4-methyl-2-(pyrrolidin-1-yl)phenyl](phenyl)methyl}acetamide; |
| Cpd. 83 | N-[(5-chlorofuran-2-yl)[4-methyl-2-(piperidin-1-yl)phenyl]methyl]-2-(2-oxo-2,3-dihydro-1H-indol-5-yl)acetamide; |
| Cpd. 84 | 2-[(3Z)-3-hydrazinylidene-2-oxo-2,3-dihydro-1H-indol-5-yl]-N-{[4-methyl-2-(piperidin-1-yl)phenyl](5-methylfuran-2-yl)methyl}acetamide; |
| Cpd. 85 | 2-(3-hydroxy-2,3-dihydro-1H-inden-5-yl)-N-{[4-methyl-2-(piperidin-1-yl)phenyl](5-methylfuran-2-yl)methyl}acetamide; |
| Cpd. 86 | N-[(5-chlorofuran-2-yl)(2,4-dimethylphenyl)methyl]-1-(2-oxo-2,3-dihydro-1H-indol-5-yl)cyclopropane-1-carboxamide; |
| Cpd. 87 | N-[(5-chlorofuran-2-yl)(2,4-dimethylphenyl)methyl]-1-(2,2-dioxo-1,3-dihydro-2,1-benzothiazol-5-yl)cyclopropane-1-carboxamide; |
| Cpd. 88a | 2-(1H-indol-6-yl)-N-((4-methyl-2-(piperidin-1-yl)phenyl)(5-methylfuran-2-yl)methyl)acetamide; |
| Cpd. 88 | 2-[3-(hydroxymethyl)-1H-indol-6-yl]-N-{[4-methyl-2-(piperidin-1-yl)phenyl](5-methylfuran-2-yl)methyl}acetamide; |
| Cpd. 89a | 1-(1H-indol-5-yl)-N-((4-methyl-2-(piperidin-1-yl)phenyl)(5-methylfuran-2-yl)methyl)cyclopropanecarboxamide; |
| Cpd. 89 | 1-[3-(hydroxymethyl)-1H-indol-5-yl]-N-{[4-methyl-2-(piperidin-1-yl)phenyl](5-methylfuran-2-yl)methyl}cyclopropane-1-carboxamide; |
| Cpd. 90 | N-[(2-bromo-4-methylphenyl)(phenyl)methyl]-2-(2-ethoxy-1H-1,3-benzodiazol-5-yl)acetamide; |
| Cpd. 91 | N-{[4-methyl-2-(piperidin-1-yl)phenyl](5-methylfuran-2-yl)methyl}-2-[6-(methylsulfanyl)naphthalen-2-yl]acetamide; |
| Cpd. 92 | N-[(2-bromo-4-methylphenyl)(phenyl)methyl]-2-[2-(ethylsulfanyl)-1H-1,3-benzodiazol-5-yl]acetamide; |
| Cpd. 93 | N-{[4-methyl-2-(piperidin-1-yl)phenyl](5-methylfuran-2-yl)methyl}-2-[2-(morpholin-4-yl)-1H-1,3-benzodiazol-5-yl]acetamide; |
| Cpd. 94 | N-{[4-methyl-2-(piperidin-1-yl)phenyl](5-methylfuran-2-yl)methyl}-2-[3-(morpholin-4-ylmethyl)-1H-indol-5-yl]acetamide; |
| Cpd. 95 | 1-(1-cyclopropanecarbonyl-2,3-dihydro-1H-indol-5-yl)-N-[(2,4-dimethylphenyl)(5-methylfuran-2-yl)methyl]cyclopropane-carboxamide; |
| Cpd. 96 | tert-butyl 3-{5-[({[4-methyl-2-(piperidin-1-yl)phenyl](5-methylfuran-2-yl)methyl}carbamoyl)methyl]-1H-indol-1-yl}propanoate; |
| Cpd. 97 | 3-{5-[({[4-methyl-2-(piperidin-1-yl)phenyl](5-methylfuran-2-yl)methyl}carbamoyl)methyl]-1H-indol-1-yl}propanoic acid; |
| Cpd. 98 | 2-[3-(2-methanesulfonylethyl)-1H-indol-5-yl]-N-{[4-methyl-2-(piperidin-1-yl)phenyl](5-methylfuran-2-yl)methyl}acetamide; |

| | |
|---|---|
| Cpd. 99 | tert-butyl 3-[5-({[(2,4-dimethylphenyl)(5-methylfuran-2-yl)methyl]carbamoyl}methyl)-1H-indol-1-yl]propanoate; |
| Cpd. 100 | tert-butyl 3-[5-({[(2-bromo-4-methylphenyl)(5-methylfuran-2-yl)methyl]carbamoyl}methyl)-1H-indol-1-yl]propanoate; |
| Cpd. 101 | 3-[5-({[(2,4-dimethylphenyl)(5-methylfuran-2-yl)methyl]carbamoyl}methyl)-1H-indol-1-yl]propanoic acid; |
| Cpd. 102 | 3-[5-({[(2-bromo-4-methylphenyl)(5-methylfuran-2-yl)methyl]carbamoyl}methyl)-1H-indol-1-yl]propanoic acid; |
| Cpd. 103 | 2-[3-(2-methanesulfonylacetyl)-1H-indol-5-yl]-N-{[4-methyl-2-(piperidin-1-yl)phenyl](5-methylfuran-2-yl)methyl}acetamide; |
| Cpd. 104 | N-[(2-bromo-4-methylphenyl)(5-methylfuran-2-yl)methyl]-2-[3-(2-methanesulfonylacetyl)-1H-indol-5-yl]acetamide; |
| Cpd. 106a | 2-(1H-indol-5-yl)-N-{[4-methyl-2-(piperidin-1-yl)phenyl](5-methylfuran-2-yl)methyl}acetamide; |
| Cpd. 106 | 2-(1-methanesulfonyl-1H-indol-5-yl)-N-{[4-methyl-2-(piperidin-1-yl)phenyl](5-methylfuran-2-yl)methyl}acetamide; |
| Cpd. 107 | N-[(2,4-dimethylphenyl)(5-methylfuran-2-yl)methyl]-2-[3-(2-methanesulfonylacetyl)-1H-indol-5-yl]acetamide; |
| Cpd. 108 | N-[(2,4-dimethylphenyl)(5-methylfuran-2-yl)methyl]-1-(1H-indol-5-yl)cyclopropane-1-carboxamide; |
| Cpd. 110 | tert-butyl 3-{5-[({[2-(azepan-1-yl)-4-methoxyphenyl](5-methylfuran-2-yl)methyl}carbamoyl)methyl]-1H-indol-1-yl}propanoate; |
| Cpd. 111 | 3-{5-[({[2-(azepan-1-yl)-4-methoxyphenyl](5-methylfuran-2-yl)methyl}carbamoyl)methyl]-1H-indol-1-yl}propanoic acid; |
| Cpd. 112 | N-[(5-chlorofuran-2-yl)[4-methyl-2-(pyrrolidin-1-yl)phenyl]methyl]-2-[3-(2-methanesulfonylethyl)-1H-indol-5-yl]acetamide; |
| Cpd. 113 | N-{[4-methyl-2-(piperidin-1-yl)phenyl](5-methylfuran-2-yl)methyl}-2-[1-(oxan-4-ylmethyl)-1H-indol-5-yl]acetamide; |
| Cpd. 114 | N-{[4-methyl-2-(piperidin-1-yl)phenyl](5-methylfuran-2-yl)methyl}-2-[1-(morpholine-4-carbonyl)-1H-indol-6-yl]acetamide; |
| Cpd. 115 | N-{[4-methyl-2-(piperidin-1-yl)phenyl](5-methylfuran-2-yl)methyl}-2-[3-(methylsulfamoyl)-1H-indol-5-yl]acetamide; |
| Cpd. 116 | N-{[4-methyl-2-(piperidin-1-yl)phenyl](5-methylfuran-2-yl)methyl}-2-[1-(morpholine-4-carbonyl)-1H-indol-5-yl]acetamide; |
| Cpd. 117 | 2-[3-(2-methanesulfonylacetyl)-1H-indol-6-yl]-N-{[4-methyl-2-(piperidin-1-yl)phenyl](5-methylfuran-2-yl)methyl}acetamide; |
| Cpd. 118 | N-{[4-methyl-2-(piperidin-1-yl)phenyl](5-methylfuran-2-yl)methyl}-2-[1-(oxane-4-carbonyl)-1H-indol-5-yl]acetamide; |
| Cpd. 119 | 1-[3-(methanesulfonamidomethyl)-1H-indol-5-yl]-N-{[4-methyl-2-(piperidin-1-yl)phenyl](5-methylfuran-2-yl)methyl}cyclopropane-1-carboxamide; |
| Cpd. 120 | N-{[4-methyl-2-(piperidin-1-yl)phenyl](5-methylfuran-2-yl)methyl}-2-[3-(morpholine-4-carbonyl)-1H-indol-5-yl]acetamide; |
| Cpd. 122 | N-[(2,4-dimethylphenyl)(5-methylfuran-2-yl)methyl]-1-[2-(2-methoxyacetyl)-2,3-dihydro-1H-isoindol-5-yl]cyclopropane-1-carboxamide; |
| Cpd. 123 | 2-(1-cyclopropanecarbonyl-2,3-dihydro-1H-indol-5-yl)-N-{[4-methyl-2-(piperidin-1-yl)phenyl](5-methylfuran-2-yl)methyl}acetamide; |
| Cpd. 124 | N-[(2,4-dimethylphenyl)(5-methylfuran-2-yl)methyl]-1-(2,2-dioxo-1,3-dihydro-4,2,1-benzoxathiazin-6-yl)cyclopropane-1-carboxamide |
| Cpd. 125 | N-[(2,4-dimethylphenyl)(5-methylfuran-2-yl)methyl]-1-(2,3-dioxo-2,3-dihydro-1H-indol-5-yl)cyclopropane-1-carboxamide; |
| Cpd. 126 | 1-(1-acetyl-2,3-dihydro-1H-indol-5-yl)-N-[(2,4-dimethylphenyl)(5-methylfuran-2-yl)methyl]cyclopropane-1-carboxamide |
| Cpd. 127 | 1-(2-acetyl-2,3-dihydro-1H-isoindol-5-yl)-N-[(2,4-dimethylphenyl)(5-methylfuran-2-yl)methyl]cyclopropane-1-carboxamide; |
| Cpd. 130 | N-[(2,4-dimethylphenyl)(5-methylfuran-2-yl)methyl]-1-(1-methyl-2-oxo-2,3-dihydro-1H-indol-5-yl)cyclopropane-1-carboxamide; |
| Cpd. 131 | N-[(2-bromo-4-methylphenyl)(5-methylfuran-2-yl)methyl]-1-(2,2-dioxo-1,3-dihydro-4,2,1-benzoxathiazin-6-yl)cyclopropane-1-carboxamide; |
| Cpd. 132 | N-[(2,4-dimethylphenyl)(5-methylfuran-2-yl)methyl]-1-(1-ethyl-2,2-dioxo-1,3-dihydro-2,1-benzothiazol-5-yl)cyclopropane-1-carboxamide; |
| Cpd. 133 | N-{[2-(dimethylamino)-4-methylphenyl](5-methylfuran-2-yl)methyl}-1-(1-methyl-2,2-dioxo-1,3-dihydro-2,1-benzothiazol-5-yl)cyclopropane-1-carboxamide; |
| Cpd. 134 | N-[(5-chlorofuran-2-yl)(2,4-dimethylphenyl)methyl]-1-(3-oxo-3,4-dihydro-2H-1,4-benzoxazin-7-yl)cyclopropane-1-carboxamide; |
| Cpd. 135 | N-[(2-bromo-4-methylphenyl)(5-methylfuran-2-yl)methyl]-1-(3-oxo-3,4-dihydro-2H-1,4-benzoxazin-7-yl)cyclopropane-1-carboxamide; |
| Cpd. 136 | N-[(2,4-dimethylphenyl)(6-methylpyridin-2-yl)methyl]-1-(3-oxo-3,4-dihydro-2H-1,4-benzoxazin-7-yl)cyclopropane-1-carboxamide; |
| Cpd. 137 | 1-(2H-1,3-benzodioxol-5-yl)-N-[(2,4-dimethylphenyl)(5-methylfuran-2-yl)methyl]cyclopropane-1-carboxamide; |
| Cpd. 139 | N-[(2,4-dimethylphenyl)(furan-2-yl)methyl]-1-(3-oxo-3,4-dihydro-2H-1,4-benzoxazin-7-yl)cyclopropane-1-carboxamide; |
| Cpd. 140 | N-[(4-chlorophenyl)(2,4-dimethylphenyl)methyl]-1-(3-oxo-3,4-dihydro-2H-1,4-benzoxazin-7-yl)cyclopropane-1-carboxamide; |
| Cpd. 141 | N-[(2,4-dimethylphenyl)(5-methylfuran-2-yl)methyl]-1-(1-oxo-2,3-dihydro-1H-inden-5-yl)cyclopropane-1-carboxamide; |

| | |
|---|---|
| Cpd. 142 | 1-(2,3-dihydro-1H-indol-5-yl)-N-[(2,4-dimethylphenyl)(5-methylfuran-2-yl)methyl]cyclopropane-1-carboxamide; |
| Cpd. 143 | N-[(3-chlorophenyl)(2,4-dimethylphenyl)methyl]-1-(3-oxo-3,4-dihydro-2H-1,4-benzoxazin-7-yl)cyclopropane-1-carboxamide; |
| Cpd. 144 | N-[(2,4-dimethylphenyl)(5-methylfuran-2-yl)methyl]-1-{2-oxo-1H,2H,3H-pyrido[2,3-b][1,4]oxazin-6-yl}cyclopropane-1-carboxamide; |
| Cpd. 145 | N-[(5-chlorofuran-2-yl)[4-methyl-2-(piperidin-1-yl)phenyl]methyl]-1-(3-oxo-3,4-dihydro-2H-1,4-benzoxazin-7-yl)cyclopropane-1-carboxamide; |
| Cpd. 146 | 1-(3,3-dimethyl-2-oxo-2,3-dihydro-1H-indol-5-yl)-N-[(2,4-dimethylphenyl)(5-methylfuran-2-yl)methyl]cyclopropane-1-carboxamide; |
| Cpd. 147 | N-[(2-bromo-4-methoxyphenyl)(5-methylfuran-2-yl)methyl]-1-(2,2-dioxo-1,3-dihydro-4,2,1-benzoxathiazin-6-yl)cyclopropane-1-carboxamide; |
| Cpd. 148 | N-{[2-(dimethylamino)-4-methylphenyl](5-methylfuran-2-yl)methyl}-1-(2,2-dioxo-1,3-dihydro-4,2,1-benzoxathiazin-6-yl)cyclopropane-1-carboxamide; |
| Cpd. 149 | N-[(5-chlorofuran-2-yl)(2,4-dimethylphenyl)methyl]-1-(2,2-dioxo-1,3-dihydro-4,2,1-benzoxathiazin-6-yl)cyclopropane-1-carboxamide; |
| Cpd. 150 | N-[(2-bromo-4-methylphenyl)(5-methylfuran-2-yl)methyl]-2-(2,2-dioxo-1,3-dihydro-4,2,1-benzoxathiazin-6-yl)acetamide; |
| Cpd. 152 | 3-[5-(1-{[(2,4-dimethylphenyl)(5-methylfuran-2-yl)methyl]carbamoyl}cyclopropyl)-1H-indol-1-yl]propanoic acid; |
| Cpd. 153 | N-[(3,5-dimethylpyridin-2-yl)(5-methylfuran-2-yl)methyl]-1-(2,2-dioxo-1,3-dihydro-4,2,1-benzoxathiazin-6-yl)cyclopropane-1-carboxamide; |
| Cpd. 154 | 3-{5-[1-({[4-methyl-2-(piperidin-1-yl)phenyl](5-methylfuran-2-yl)methyl}carbamoyl)cyclopropyl]-1H-indol-1-yl}propanoic acid; |
| Cpd. 155 | N-[(2,4-dimethylphenyl)(5-methylfuran-2-yl)methyl]-1-(1-hydroxy-2,3-dihydro-1H-inden-5-yl)cyclopropane-1-carboxamide; |
| Cpd. 156 | N-{[2-(dimethylamino)-4-methylphenyl](5-methylfuran-2-yl)methyl}-1-(3-oxo-3,4-dihydro-2H-1,4-benzoxazin-7-yl)cyclopropane-1-carboxamide; |
| Cpd. 157 | N-[(2,4-dimethylphenyl)(5-methylfuran-2-yl)methyl]-1-[1-(oxan-4-ylmethyl)-2,2-dioxo-1,3-dihydro-2,1-benzothiazol-5-yl]cyclopropane-1-carboxamide; |
| Cpd. 158 | N-[(2,4-dimethylphenyl)(5-methylfuran-2-yl)methyl]-1-(7-fluoro-2-oxo-2,3-dihydro-1H-indol-5-yl)cyclopropane-1-carboxamide; |
| Cpd. 159 | 1-(3,3-difluoro-2-oxo-2,3-dihydro-1H-indol-5-yl)-N-[(2,4-dimethylphenyl)(5-methylfuran-2-yl)methyl]cyclopropane-1-carboxamide; |
| Cpd. 160 | N-[(5-chlorofuran-2-yl)(2,4-dimethylphenyl)methyl]-1-(1-methyl-2,2-dioxo-1,3-dihydro-2,1-benzothiazol-5-yl)cyclopropane-1-carboxamide; |
| Cpd. 161 | 1-(2H-1,3-benzodioxol-5-yl)-N-[(2-bromo-4-methylphenyl)(5-methylfuran-2-yl)methyl]cyclopropane-1-carboxamide; |
| Cpd. 162 | N-{[4-methyl-2-(piperidin-1-yl)phenyl](5-methylfuran-2-yl)methyl}-1-[1-(oxan-4-ylmethyl)-2,2-dioxo-1,3-dihydro-2,1-benzothiazol-5-yl]cyclopropane-1-carboxamide; |
| Cpd. 163 | N-[(2-bromo-4-methylphenyl)(5-methylfuran-2-yl)methyl]-1-[1-(oxan-4-ylmethyl)-2,2-dioxo-1,3-dihydro-2,1-benzothiazol-5-yl]cyclopropane-1-carboxamide; |
| Cpd. 164 | 1-(2H-1,3-benzodioxol-5-yl)-N-{[4-methyl-2-(piperidin-1-yl)phenyl](5-methylfuran-2-yl)methyl}cyclopropane-1-carboxamide; |
| Cpd. 165 | N-[(2,4-dimethylphenyl)(5-methylfuran-2-yl)methyl]-1-[1-(hydroxyimino)-2,3-dihydro-1H-inden-5-yl]cyclopropane-1-carboxamide; |
| Cpd. 166 | N-[(2,4-dimethylphenyl)(5-methylfuran-2-yl)methyl]-2-[1-(oxan-4-ylmethyl)-2,2-dioxo-1,3-dihydro-2,1-benzothiazol-5-yl]acetamide; |
| Cpd. 167 | N-{[4-methyl-2-(piperidin-1-yl)phenyl](5-methylfuran-2-yl)methyl}-2-[1-(oxan-4-ylmethyl)-2,2-dioxo-1,3-dihydro-2,1-benzothiazol-5-yl]acetamide; |
| Cpd. 168 | 1-(2,2-dimethyl-2,4-dihydro-1,3-benzodioxin-7-yl)-N-[(2,4-dimethylphenyl)(5-methylfuran-2-yl)methyl]cyclopropane-1-carboxamide; |
| Cpd. 169 | 1-(2,2-dimethyl-2,4-dihydro-1,3-benzodioxin-6-yl)-N-[(2,4-dimethylphenyl)(5-methylfuran-2-yl)methyl]cyclopropane-1-carboxamide; |
| Cpd. 170 | N-[(2,4-dimethylphenyl)(5-methylfuran-2-yl)methyl]-1-[3-(1-hydroxy-2-methylpropan-2-yl)-1H-indol-5-yl]cyclopropane-1-carboxamide; |
| Cpd. 171 | 1-(2,2-dioxo-1,3-dihydro-4,2,1-benzoxathiazin-6-yl)-N-{[4-methyl-2-(trifluoromethyl)phenyl](5-methylfuran-2-yl)methyl}cyclopropane-1-carboxamide; |
| Cpd. 172 | N-[(2,4-dimethylphenyl)(5-methylfuran-2-yl)methyl]-1-(1-methyl-2,2-dioxo-1,3-dihydro-4,2,1-benzoxathiazin-6-yl)cyclopropane-1-carboxamide; |
| Cpd. 173 | N-[(2-bromo-4-methylphenyl)(5-methylfuran-2-yl)methyl]-1-(1-methyl-2,2-dioxo-1,3-dihydro-4,2,1-benzoxathiazin-6-yl)cyclopropane-1-carboxamide; |
| Cpd. 174 | 1-(2,2-dioxo-1,3-dihydro-4,2,1-benzoxathiazin-6-yl)-N-[(2-methoxy-4-methylphenyl)(5-methylfuran-2-yl)methyl]cyclopropane-1-carboxamide; and |
| Cpd. 175 | 1-(2,2-dimethyl-2H-1,3-benzodioxol-5-yl)-N-[(2,4-dimethylphenyl)(5-methylfuran-2-yl)methyl]cyclopropane-1-carboxamide. |

In the present invention, the terms "RORgamma", "RORγ" and "RORg" are used interchangeably.

"RORγ modulator" refers to a chemical compound that modulates, either directly or indirectly, the activity of RORγ. In particular, the RORγ modulator modulates, in particular inhibits or activates, more particularly inhibits, either directly or indirectly, the activity of RORγ. RORγ modulators include antagonists, inverse agonists and agonists of RORγ, in particular antagonists and inverse agonists.

RORgamma modulators can be used as medicinal products. Consequently, the present invention provides a compound of formula (I) or (Ia) for use as a medicament.

The present invention further provides a pharmaceutical composition comprising a compound of formula (I) or (Ia) and a pharmaceutically acceptable carrier. A compound of formula (I) or (Ia), optionally in combination with one or more other therapeutically active substances, may be used in methods for treating diseases for which the modulation of RORgamma has positive effects in a subject in need thereof.

The present invention further provides a compound of formula (I) or (Ia) for use in the treatment of a RORγ related-disease. The invention also provides a method for treating a RORγ related-disease comprising the administration of a therapeutically effective amount of a compound of formula (I) or (Ia) to a subject in need thereof. The invention further provides the use of a compound of formula (I) or (Ia), in the manufacture of a medicament for use in the treatment of a RORγ related-disease.

The compounds of the invention may in particular be used in the treatment of a RORγ related-disease such as an autoimmune or autoimmune-related disease, inflammation-related disease, metabolic disease and/or fibrotic disease, cholestatic, cholestasis-related disease or a cancer. In a particular embodiment, the compound of formula (I) or (Ia) is used in the treatment of an autoimmune or autoimmune-related disease, an inflammation-related disease, a metabolic disease, a fibrotic disease, a cholestatic disease or a cholestasis-related disease.

The term "autoimmune disease" is used to designate a condition that arises from an abnormal immune response of the body against substances and tissues normally present in the body. The disease may be restricted to certain organs (e.g. pancreas, in type I diabetes or thyroid gland in autoimmune thyroiditis) or involve a particular tissue in different places (e.g. in Goodpasture's disease, affection of the basement membrane in the lung and the kidney).

The term "inflammation" is used to designate a condition that arise from a protective response involving host cells, blood vessels, and proteins and other mediators which may serve to eliminate the cause of cell/tissue injury, as well as the necrotic cells/tissues resulting from the original insult, and to initiate the process of repair. The inflammatory reaction may be manifested by pain, heat, redness, swelling, blood vessels dilatation, blood flow increase and loss of function.

Fibrosis is a pathologic process, which includes scar formation and over production of extracellular matrix, by the connective tissue, as a response to tissue damage. Damage to tissue can result from a variety of stimuli including autoimmune reactions and mechanical injury. This can be a reactive, benign, or pathological state that occurs in an organ or tissue. In response to injury this is called scarring and if fibrosis arises from a single cell line this is called a fibroma. Physiologically the deposit of connective tissue can obliterate the architecture and function of the underlying organ or tissue.

Cholestasis is defined as a decrease in bile flow due to impaired secretion by hepatocytes (hepato-cellular cholestasis) or to obstruction of bile flow through intra- or extra-hepatic bile ducts (obstructive cholestasis). In clinical practice, cholestasis is any condition in which the flow of bile from the liver is slowed or blocked.

Cancers are a large family of diseases that involve abnormal cell growth with the potential to invade or spread to other parts of the body. IL-17, which is produced by several types of cells, including immune cells, where IL-17 expression relies on RORgt, is known to contribute to malignant transformation and metastasis of several cancers.

Examples of autoimmune diseases, autoimmune-related diseases, inflammatory diseases, metabolic diseases, fibrotic diseases, cholestatic diseases and cancers include arthritis, asthma, severe, glucocorticoid-nonresponsive asthma, asthma exacerbations due to ongoing and/or past pulmonary infection, Addison's disease, allergy, agammaglobulinemia, alopecia areata, ankylosing spondylitis, atherosclerosis, atopic allergy, atopic dermatitis, autoimmune cardiomyopathy, autoimmune enteropathy, autoimmune hemolytic anemia, autoimmune hepatitis, autoimmune lymphoproliferative syndrome, autoimmune pancreatitis, autoimmune peripheral neuropathy, Crohn's disease, Celiac disease, colitis, chronic inflammatory demyelinating polyneuropathy, chronic obstructive pulmonary disease (COPD), dermatomyositis, diabetes mellitus type 1, diffuse cutaneous systemic sclerosis, eczema, gastrointestinal disorder, Goodpasture's syndrome, Graves' disease, Guillain-Barre syndrome, Hashimoto's encephalopathy, Hashimoto's thyroiditis, idiopathic thrombocytopenic purpura, inflammatory bowel disease (IBD), irritable bowel syndrome, lupus, lupus erythematosus, lupus nephritis, mixed connective tissue disease, Kawasaki disease, multiple sclerosis, neuromyelitis optica, myasthenia gravis, narcolepsy, optic neuritis, osteoarthritis, pemphigus vulgaris, pernicious anaemia, polymyositis, psoriasis, psoriatic arthritis, reactive arthritis, relapsing polychondritis, respiratory disorder, rheumatoid arthritis, rheumatic fever, Sjorgen's syndrome, systemic lupus erythematosus, transverse myelitis, undifferentiated connective tissue disease, ulcerative colitis, uveitis, vasculitis, Wegener's granulomatosis, systemic inflammatory response syndrome (SIRS), sepsis, Behcets disease, allergic contact dermatitis, cutaneous lupus erythematosus, dry eye and glomerulonephritis, myocarditis, acute liver failure (ALF), including acute-on-chronic liver failure (ACLF), pulmonary fibrosis (idiopathic pulmonary, interstitial lung, cystic and progressive massive fibrosis), liver fibrosis and cirrhosis of diverse etiologies (congenital, of autoimmune origin, induced by cardiometabolic diseases, alcohol consumption, cholestasis, drugs, infectious agents, trauma, radiation), metabolic syndrome, non-alcoholic fatty liver disease (NAFLD), NonAlcoholic SteatoHepatitis (NASH) and Alcoholic SteatoHepatitis (ASH), cardiac fibrosis and heart myocardial and endomyocardial fibrosis, arterial fibrosis, atherosclerosis/restenosis, mediastinal fibrosis (soft tissue of the mediastinum), macular degeneration, retinal and vitreal retinopathy, ocular scarring, cataract, Alzheimer's disease, cancer, local, disseminated or metastatic cancer, scleroderma, glioblastoma, myelofibrosis (bone marrow), retroperitoneal fibrosis (soft tissue of the retroperitoneum), nephrogenic systemic fibrosis (skin, joints, eyes, and internal organs), keloid (skin), intestinal fibrosis (occurs for example in Crohn's disease and collagenous colitis), kidney fibrosis, scleroderma and systemic sclerosis (skin, lungs, kidneys, heart, and gastrointestinal tract), arthrofibrosis (knee, shoulder, other joints), Peyronie's disease (penis), Dupuytren's contracture (hands and fingers), some forms of adhesive capsulitis (shoulder), obesity, Primary Biliary Cholangitis (PBC), Primary Sclerosing Cholangitis (PSC), Intarhepatic Cholestasis of Pregnancy (ICP), Progressive Familial Intrahepatic Cholestasis (PFIC), Biliary atresia, Cholelithiasis, Infectious cholangitis, Cholangitis associated with Langerhans cell histiocytosis, Alagille syndrome, Nonsyndromic ductal paucity, Hepatitis (hepatitis A, hepatitis B, hepatitis C), Alpha1-antitrypsin deficiency, Inborn errors of bile acid synthesis, Drug-induced cholestasis, Total parenteral nutrition (TPN)-associated cholestasis, breast cancer and breast cancer metastasis, pancreatic cancer and pancreatic cancer metastasis, pancreatic ductal adenocarcinoma, liver cancer and liver cancer metastasis, hepatocellular carcinoma, lung cancer and lung cancer metastasis, non-small-cell lung cancer, colorectal cancer and colorectal cancer metastasis, colorectal carcinoma, prostate cancer and prostate cancer metastasis, gallbladder cancer and gallbladder cancer metastasis.

In particular, RORg modulators may be used in the treatment of asthma, ankylosing spondylitis, autoimmune cardiomyopathy, autoimmune hepatitis, crohn's disease, chronic obstructive proliferative disease (COPD), diabetes mellitus type 1, lupus erythematosus, lupus nephritis, multiple sclerosis, psoriasis, psoriatic arthritis, rheumatoid arthritis, ulcerative colitis, myocarditis, pulmonary fibrosis (idiopathic pulmonary, interstitial lung, cystic and progressive massive fibrosis), non-alcoholic fatty liver disease (NAFLD), non-alcoholic steato-hepatitis (NASH) and alcoholic steatoHepatitis (ASH), cardiac fibrosis and heart myocardial and endomyocardial fibrosis, arterial fibrosis, atherosclerosis/restenosis, intestinal fibrosis (occurs for example in crohn's disease and collagenous colitis), kidney fibrosis, scleroderma, systemic sclerosis, primary biliary cholangitis (PBC), hepatitis (hepatitis A, hepatitis B, hepatitis C), colon cancer, small-cell lung cancer, non-small cell lung cancer, prostate cancer, renal cancer, ovarian cancer, bladder cancer, stomach cancer, liver cancer, testis cancer, uterus cancer, leukemia, adenocarcinoma, melanoma and cancer of central nervous system tissue.

The term "treatment" or "treating" refers to therapy, prevention, or prophylaxis of a disorder in a subject in need thereof. The treatment involves the administration of a pharmaceutical composition to subjects (e.g. patients) having a declared disorder to prevent, cure, delay, reverse, or slow down the progression of the disorder, improving thereby the condition of patients. A treatment may also be administered to subjects that are either healthy or at risk of developing a disorder such as an autoimmune, inflammatory, fibrotic or cholestatic disorder.

The term "subject" refers to a mammal and more particularly a human. The subjects to be treated according to the invention can be appropriately selected on the basis of several criteria associated with autoimmune, inflammatory, fibrotic and cholestatic pathological processes such as previous and/or present drug treatments, associated pathologies, genotype, exposure to risk factors, as well as any other relevant biomarker that can be evaluated by means of any suitable immunological, biochemical, or enzymatic method.

The Examples show how Compounds of formula (I) or (Ia) can be produced and tested.

The details of the general methods of synthesis and purification of intermediate products for Compounds of formula (I) or (Ia) are provided in Example 1.

Specific reaction intermediates can be synthesized and purified from compounds that may be already available commercially or that can be readily synthesized.

The details of the general methods of synthesis and purification of Compounds of formula (I) or (Ia) are provided in Example 2.

Figure 3A:
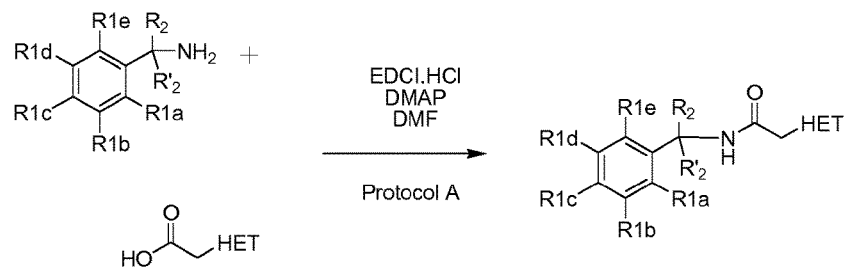
Figure 3A:
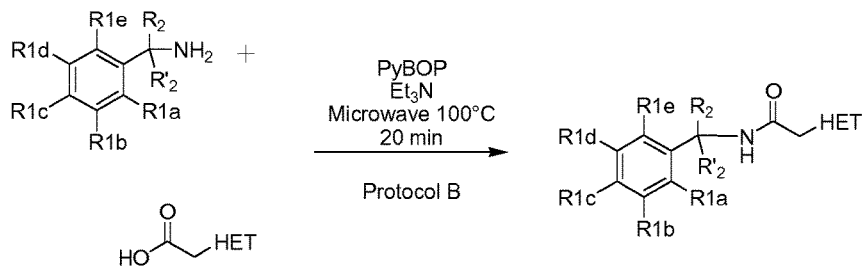
Figure 3A:
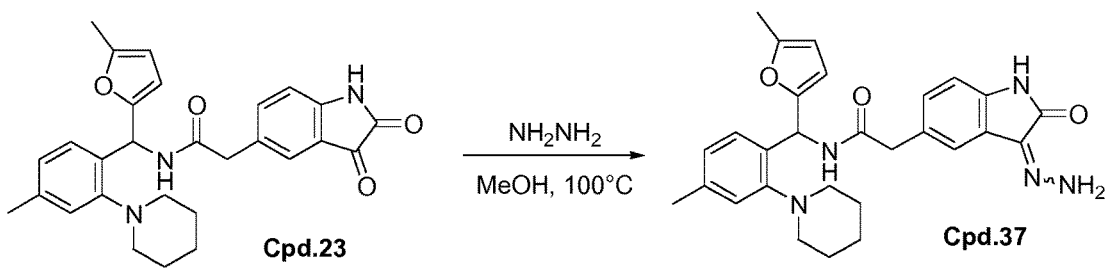
Figure 3A:
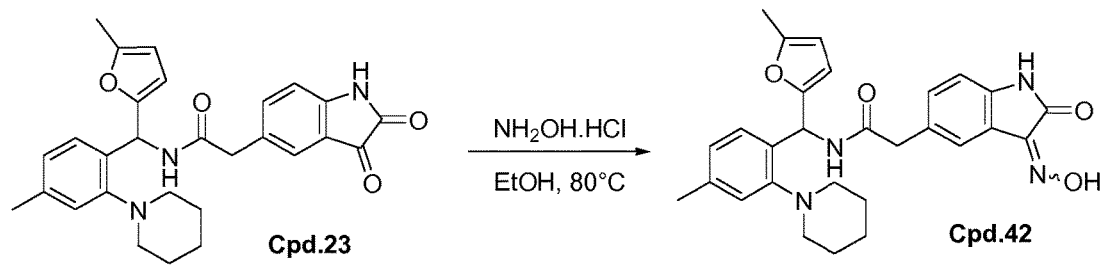
Figure 3A:
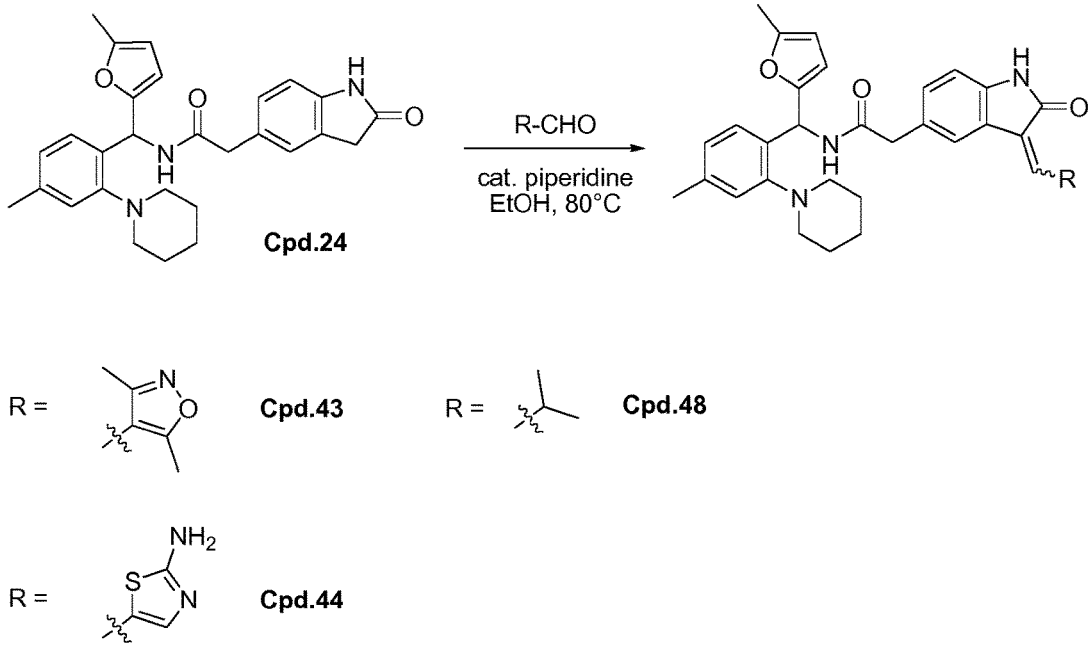
Figure 3A:
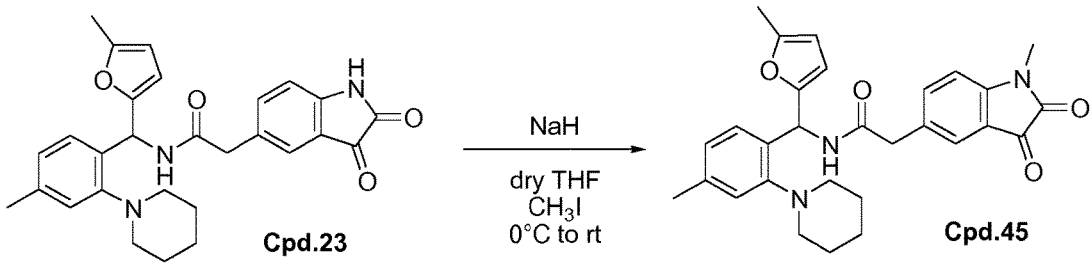
Figure 3A:
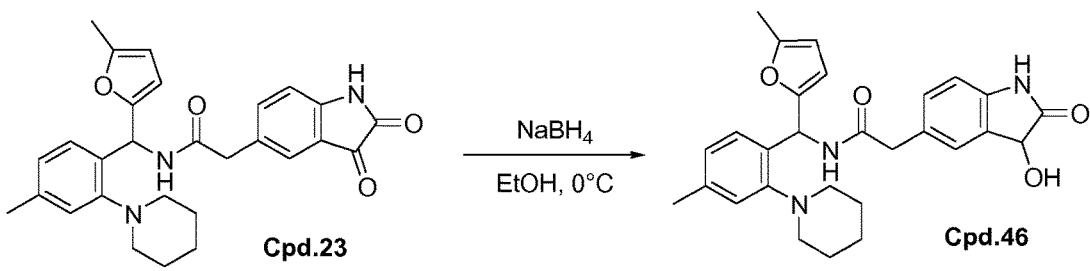
Figure 3A:
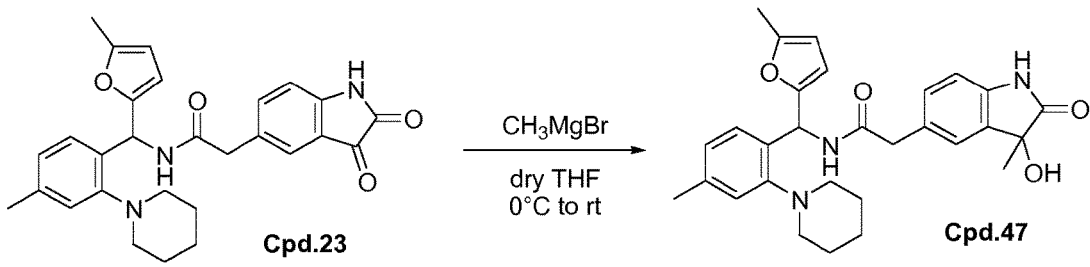
Figure 3A:
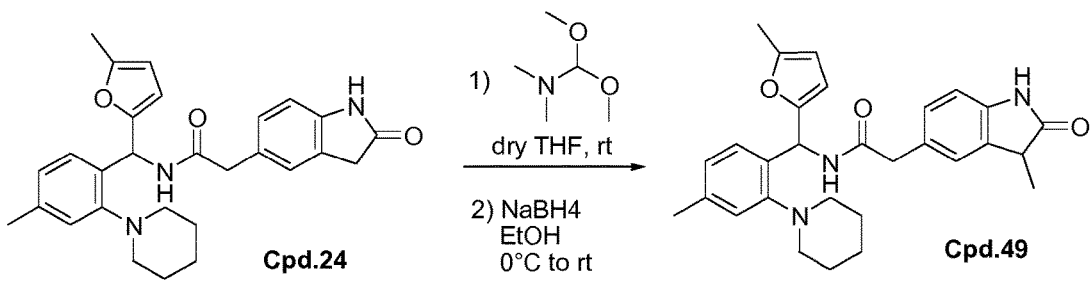
Figure 3A:
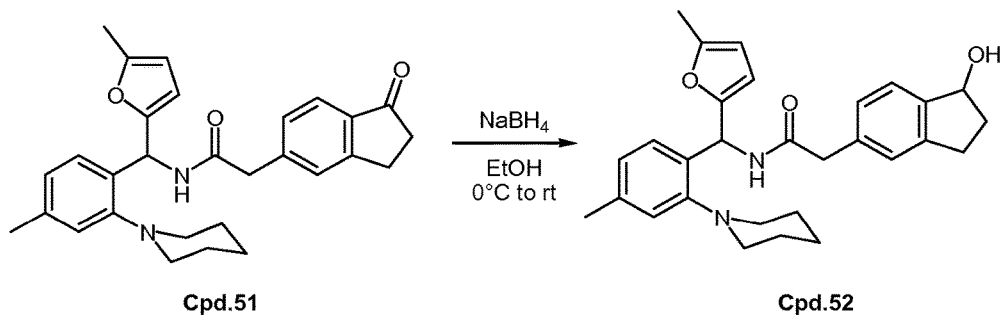
Figure 3A:
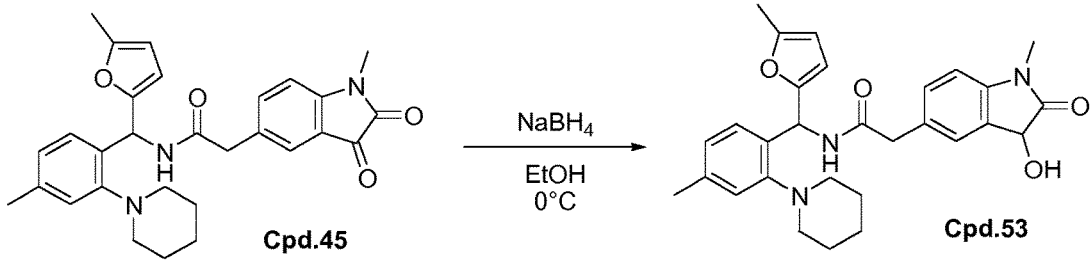
Figure 3A:
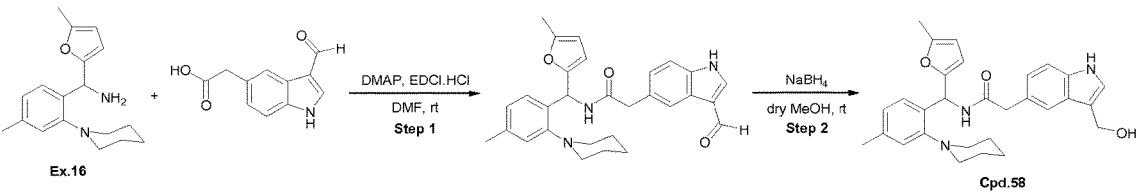
Figure 3A:
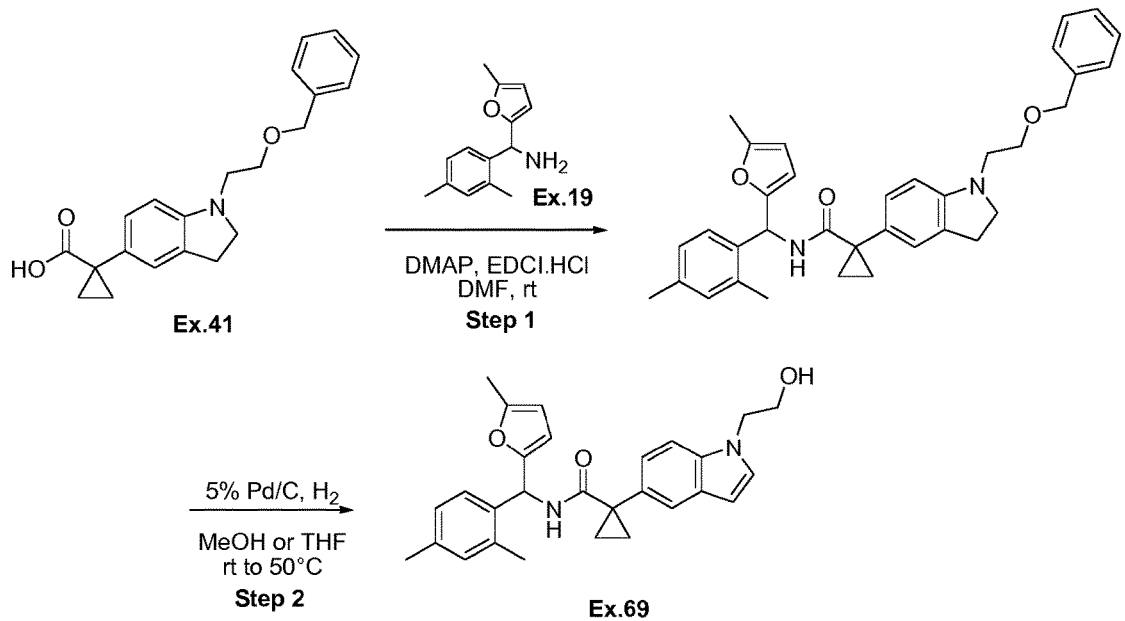
Figure 3A:
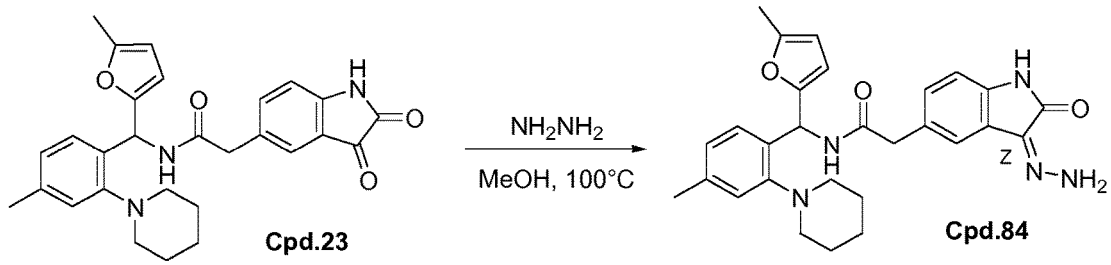
Figure 3A:
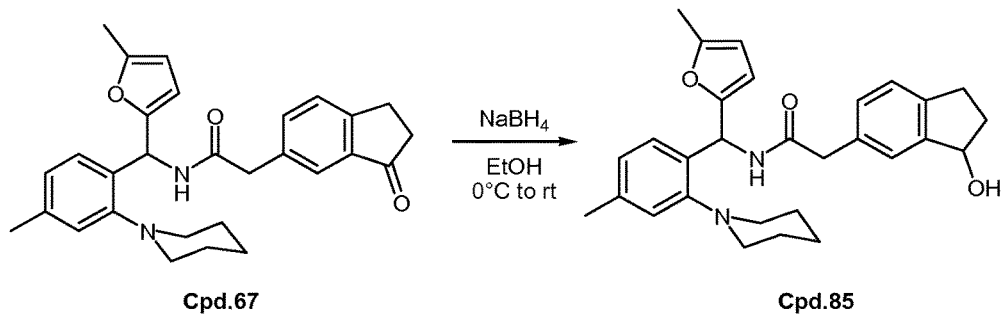
Figure 3A:
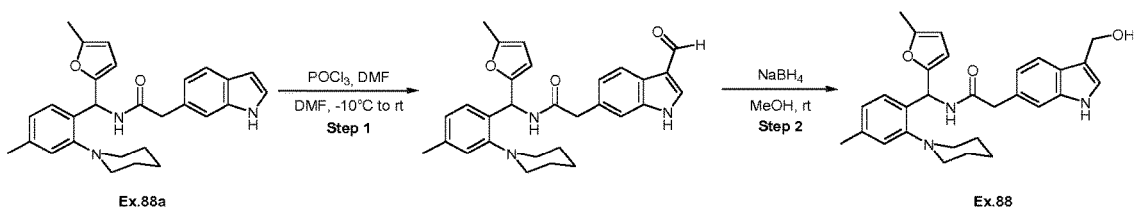
Figure 3A:
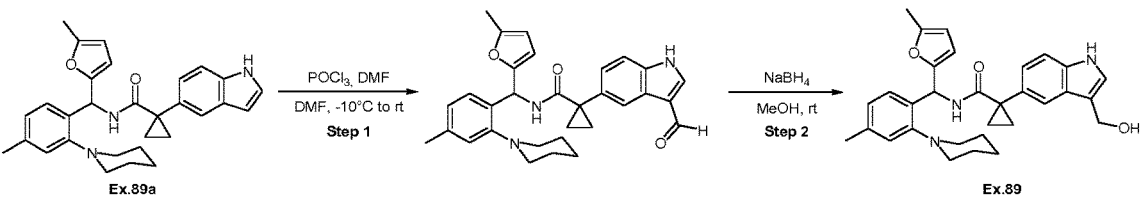
Figure 3A:
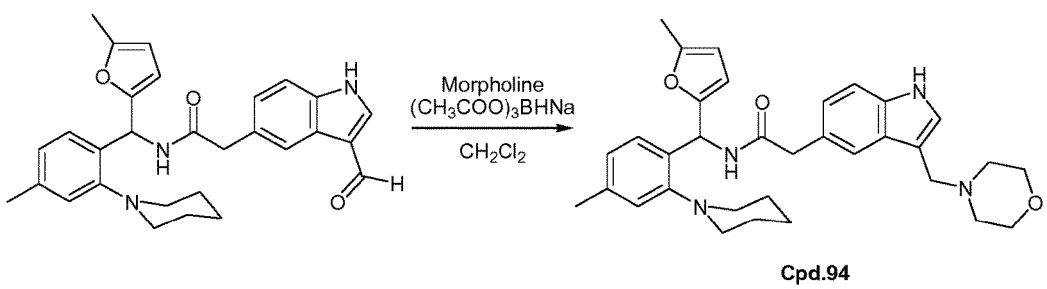
Figure 3A:
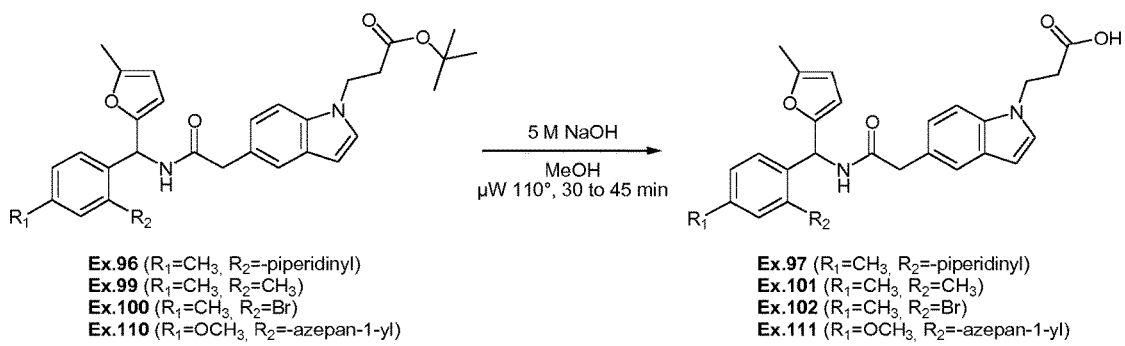
Figure 3A:
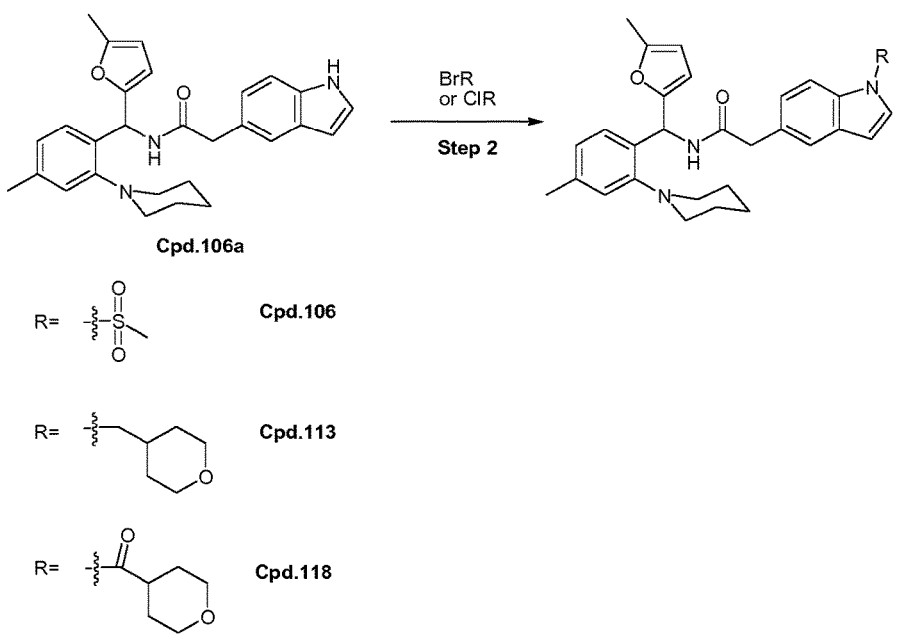
Figure 3A:
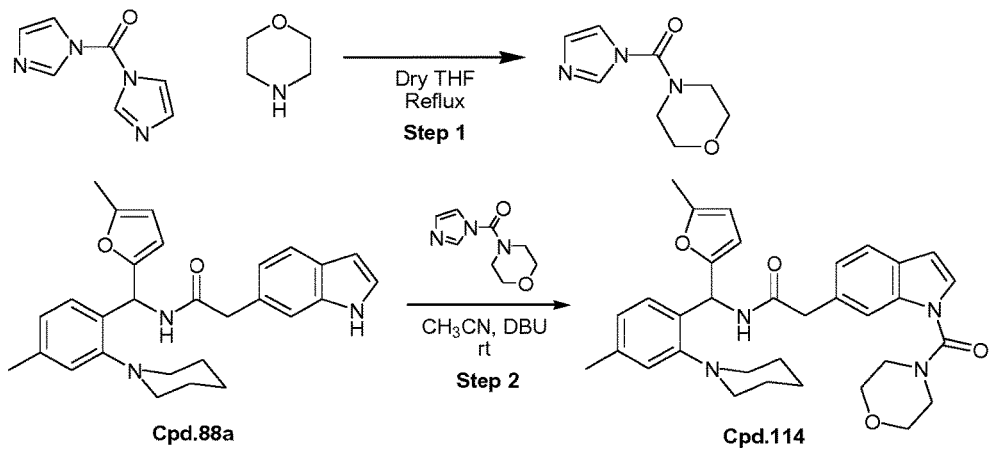
Figure 3A:
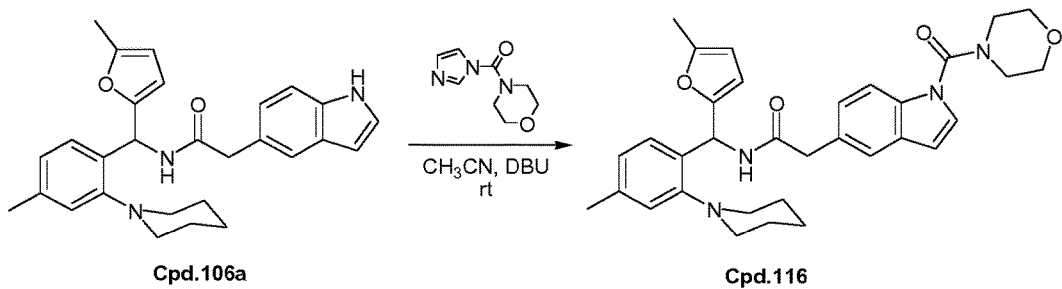
Figure 3A:
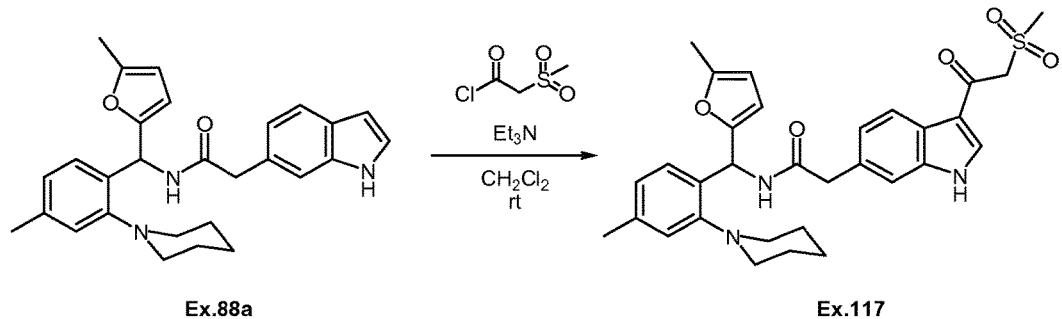
Figure 3A:
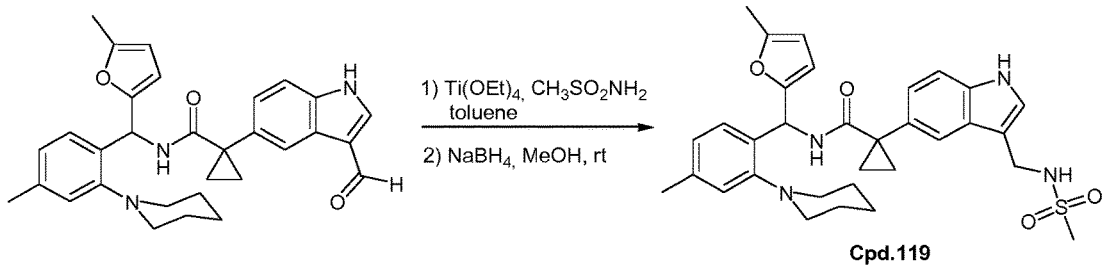

General schemes of synthesis of the compounds of formula (I) or (Ia) are presented in FIG. 3A.

The functional groups optionally present in the reaction intermediates that are generated for obtaining the desired compounds of formula (I) or (Ia) can be protected, either permanently, or temporarily, by protective groups, which ensure unequivocal synthesis of the desired compounds. The reactions of protection and deprotection are carried out according to techniques well known by a person skilled in the art or such as those described in the literature, as in the book "Greene's Protective Groups in Organic Synthesis" (Wuts & Greene, 2007).

The compounds according to the invention may contain one or more asymmetric centers. The present invention includes stereoisomers (diastereoisomers, enantiomers), pure or mixed, as well as racemic mixtures and geometric isomers, or tautomers of compounds of formula (I) or (Ia). When an enantiomerically pure (or enriched) mixture is desired, it can be obtained either by purification of the final product or of chiral intermediates, or by asymmetric synthesis according to methods known by a person skilled in the art (using for example chiral reactants and catalysts). Certain compounds according to the invention can have various stable tautomeric forms and all these forms and mixtures thereof are included in the invention. The techniques for obtaining and characterizing the stereoisomers, pure or mixed, as well as racemic mixtures and geometric isomers, or tautomers are described in the literature, such as in the book "Chirality in Drug Design and Development" (Reddy & Mehvar, 2004).

The compounds of formula (I) or (Ia) can be purified by precipitation or solid/liquid extraction after evaporation of the reaction medium. Further or other purification step can be performed by chromatography over silica gel or by crystallization, when the compound is stable as a solid form, by applying techniques well known in the literature or, more in general, for chemicals (Armarego & Chai, 2009).

Moreover, the required purification and/or (re-)crystallization steps that are appropriate for isolating compounds of formula (I) or (Ia) from the reaction mixture, can be used for obtaining amorphous, polymorphous, mono- or poly-crystalline forms. Such polymorphisms may present distinct pharmacological and/or chemical properties, for example in terms of solubility, intrinsic dissolution rate, melting temperature, bioavailability, and/or possible transition from a polymorphic state to another one in pharmaceutical compositions and/or biological fluids.

The (re-)crystallisation assays can be performed in panels of different solvents (such as isopropanol, acetone, methanol, diisopropyl ether or water) or mixture thereof, and by applying different conditions, such as reaction volumes or temperatures. The resulting samples can be analyzed by different techniques such as microscopy, calorimetry, and/or spectroscopy that allow establishing the features of a particular crystalline form, such as structure, solubility, stability or conversion to other forms (Bauer, 2004; Erdemir et al, 2007; Morissette et al, 2004; Yin & Grosso, 2008).

Such a polymorphism study allows characterizing the crystalline form of a compound that is pharmaceutically acceptable for both pharmacological and manufacturing points of view.

Certain compounds of formula (I) or (Ia) can be isolated in the form of zwitterions and each of these forms is included in the invention, as well as mixtures thereof.

Compounds of formula (I) or (Ia) and their salts can be stable in liquid or solid forms. The present invention includes all solid and liquid forms of formula (I) or (Ia), which includes the amorphous, polymorphic, mono- and poly-crystalline forms. In particular, the compounds of formula (I) or (Ia) can exist in the free form or in the solvated form, i.e. in the form of associations or combinations with one or more molecules of a solvent, for example with pharmaceutically acceptable solvents such as water (hydrates) or ethanol. The present invention also includes the prodrugs of the compounds according to the invention which, after administration to a subject, are converted to the compounds as described in the invention or to their metabolites having therapeutic activities comparable to the compounds according to the invention.

Specific compounds of formula (I) or (Ia) can comprise at least one atom of the structure that is replaced by an isotope (radioactive or not). Examples of isotopes that can be included in the structure of the compounds according to the invention can be selected from hydrogen, carbon, nitrogen, oxygen, sulphur such as $^2$H, $^3$H, $^{13}$C, $^{14}$C, $^{15}$N, $^{18}$O, $^{17}$O, $^{35}$S respectively. When non-radioactive, the stable isotope can be selectively incorporated in the structure in place of hydrogen (in the case of deuterium) or carbon (in the case of $^{13}$C) not only as means of performing absorption, distribution, metabolism, and excretion (ADME) studies but also as means for obtaining compounds that may retain the desired biochemical potency and selectivity of the original compound while the metabolic fate is substantially altered. In some favourable cases, this modification has the potential to have a positive impact effect on safety, efficacy and/or tolerability of the original compound (Mutlib, 2008). Otherwise radioactive isotopes $^3$H and $^{14}$C are particularly preferred as they are easy to prepare and detect in studies of the bioavailability in vivo of the substances. The heavy isotopes (such as $^2$H) are particularly preferred as they are used as internal standards in analytical studies and as possible variants of pharmaceutical interest.

Compounds of formula (I) or (Ia) can be obtained as specific salts, hydrates, and polymorphs that can be obtained during the final purification step of the compound or, in the case of salts, by incorporating the salt into the previously purified compound. The selection of a compound of formula (I) or (Ia) that is produced according to the methods of the Invention as an optimal candidate for drug development can be automated for a comprehensive biopharmaceutical characterization at the scale-up stage and for the solid or liquid formulation that is appropriate for the desired route of administration and therapeutic indication (Kumar et al, 2007; Mahato & Narang, 2011; Stahl & Wermuth, 2002).

In view of their use as medicinal products, the compounds of formula (I) or (Ia) can be formulated as pharmaceutically acceptable salts obtained from organic or inorganic bases or acids of such compounds. Alternatively, the compounds of formula (I) or (Ia) can be formulated as pharmaceutically acceptable hydrates or polymorphs of such compounds. These salts, hydrates, and polymorphs can be obtained during the final purification step of the compound or, in the case of salts, by incorporating the salt into the previously purified compound (Stahl & Wermuth, 2002).

These salts can be prepared with pharmaceutically acceptable acids but the salts of other acids useful for purifying or isolating the compounds of formula (I) or (Ia) also form part of the invention. In particular, when the compounds according to the invention are in the form of a salt, it is a salt of an alkali metal, in particular a salt of sodium or of potassium, or a salt of an alkaline-earth metal, in particular magnesium or calcium, or a salt with an organic amine, more particularly with an amino acid such as arginine or lysine.

The present invention further provides pharmaceutical compositions comprising a compound of formula (I) or (Ia), or a pharmaceutically acceptable salt thereof, and optionally at least one pharmaceutically acceptable carrier or diluent. The pharmaceutical compositions comprising a compound of formula (I) or (Ia) may comprise one or several excipients or vehicles acceptable within a pharmaceutical context (e.g., for liquid formulations, saline solutions, physiological solutions, isotonic solutions).

A further object of the invention are methods of preparing such pharmaceutical compositions, comprising admixing a compound of formula (I) or (Ia), with at least one pharmaceutically acceptable carrier, vehicle, or diluent. These methods involve, for example, conventional mixing, dissolving, granulation, dragee-making, levigating, emulsifying, encapsulating, entrapping, lyophilizing processes or spray drying (Gennaro, 2000; Rowe et al, 2003).

The phrase "pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability.

The term "carrier", "vehicle", or "excipient" refers to any substance, not itself a therapeutic agent, that is added to a pharmaceutical composition to be used as a carrier, vehicle, and/or diluent for the delivery of a therapeutic agent to a subject in order to improve its handling or storage properties or to permit or facilitate formation of a dosage unit of the composition into a discrete article. The pharmaceutical compositions of the invention, either individually or in combination, can comprise one or several agents or vehicles chosen among dispersants, solubilisers, stabilisers, preservatives, etc. Agents or vehicles useful for these formulations (liquid and/or injectable and/or solid) are particularly methylcellulose, hydroxymethylcellulose, polysorbate 80, mannitol, gelatin, lactose, vegetable oils, liposomes, etc. Acceptable excipients can be chosen among disintegrants, binding agents, adhesives, wetting agents, lubricants, glidants, flavors, dyes, fragrances, stearic acid, magnesium oxide, sodium and calcium salts of phosphoric and sulfuric acids, magnesium carbonate, talc, gelatin, lactose, sucrose, starches, polymers, such as polyvinyl alcohol and polyethylene glycols, and other pharmaceutically acceptable materials added to improve taste, odor or appearance of the composition.

The compounds can be made up in solid or liquid form, such as tablets, capsules, powders, syrups, elixirs and the like, aerosols, sterile solutions, suspensions or emulsions, and the like. The composition may be presented in a solid preformulation composition wherein the active ingredients are dispersed evenly throughout the composition so that the composition may be readily subdivided into equally effective dosage forms such as tablets, pills and capsules. Additionally, the combined compositions may be delivered using sustained-release formulations.

The compositions can be formulated as injectable suspensions, gels, oils, pills, suppositories, powders, gel caps, capsules, aerosols, etc., eventually by means of galenic forms or devices assuring a prolonged and/or slow release. For this kind of formulation, agents such as cellulose, carbonates or starches can advantageously be used. The compositions of the present invention can also be formulated in the form of liposome delivery systems, such as small unilamellar vesicles, large unilamellar vesicles, and multilamellar vesicles. Liposomes can be formed from a variety of lipids, including but not limited to amphipathic lipids such as phosphatidylcholines, sphingomyelins, phophatidylcholines, cardiolipins, phosphatidylethanolamines, phosphatidylserines, phosphatidylglycerols, phosphatidic acids, phosphatidylinositols, diacyl trimethylammonium propanes, diacyl dimethylammonium propanes, and stearylamine, neutral lipids such as triglycerides, and combinations thereof.

The pharmaceutical combination of the invention can be administered in a systematic or parenteral way, by using oral, topical, perlingual, nasal, rectal, transmucosal, transdermal, intestinal, intramuscular, intravenously, subcutaneous, intraarterial, intraperitoneal, intrapulmonary or intraocular route, by using methods known in the art.

Formulations for oral administration may be in the form of aqueous solutions and suspensions, in addition to solid tablets and capsule formulations. The aqueous solutions and suspensions may be prepared from sterile powders or granules. The compounds may be dissolved in water, polyethylene glycol, propylene glycol, ethanol, corn oil, cottonseed oil, peanut oil, sesame oil, benzyl alcohol, sodium chloride, and/or various buffers.

For administration by inhalation, the pharmaceutical compositions comprising a compound of formula (I) or (Ia) are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, 1,1,1,2-tetrafluoroethane, 1,1,1,2,3,3,3-heptafluoropropane, carbon dioxide or other suitable gas, alone or in combination. Pressurized aerosols may be formulated as suspensions or solutions, and include an appropriate propellant formulation, and various excipients, such as surfactants, co-solvents, etc. In the case of a pressurized aerosol the dosage unit may be determined by providing a valve to deliver a metered amount. Capsules and cartridges of e.g. gelatin for use in an inhaler or insufflators may be formulated containing a powder mix of the compound and a suitable powder base such as lactose or starch.

The tablets or pills of the composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of material can be used for such enteric layers or coatings, such materials including a number of polymeric acids with such as shellac and cellulose acetate.

The liquid forms in which the pharmaceutical compositions can be incorporated for oral administration or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin. The liquid forms in suitably flavored suspending or dispersing agents may also include the synthetic and natural gums, for example, tragacanth, acacia, methylcellulose and the like. For parenteral administration, sterile suspensions and solutions are desired. A person skilled in the art will take care to select the possible compound or compounds to be added to these compositions in such a way that the advantageous properties intrinsically attaching to the present invention are not or substantially not altered by the addition envisaged, as is also explained in the literature, for example in the book "Pharmaceutical Dosage Forms and Drug Delivery" (2007; edited by Mahato R; published by CRC Press).

A pharmaceutical composition as disclosed herein is understood to be useful for treating a RORγ related-disease, that is, the active ingredients are contained in an amount to achieve their intended purpose. At this scope, a compound of formula (I) or (Ia) should be administered in an effective amount by using a pharmaceutical composition as above-defined. Administration can be performed daily or even several times per day, if necessary, and in an amount that can be optimal or suboptimal, if they are compared with dosages that are normally used for such compounds.

The term "effective amount" refers to an amount of the compound sufficient to produce the desired therapeutic result. In particular the compounds of formula (I) or (Ia) are administered in amounts that are sufficient to display a desired effect.

Optimal dosages of compounds of formula (I) or (Ia) to be administered may be readily determined by those skilled in the art, and will vary with the particular compound used, the strength of the preparation, the mode of administration, and the severity of the condition to be treated. In addition, factors associated with the particular patient being treated, including patient age, weight, diet and time of administration, will result in the need to adjust dosages and interval. The frequency and/or dose relative to the simultaneous or separate administrations can be adapted by one of ordinary skill in the art, in function of the patient, the pathology, the form of administration, etc. For instance, a compound of formula (I) or (Ia) should be provided in a dosage that allows its administration in the amount 0.01 mg/day to 1000 mg/day, preferably from 0.1 mg/day to 10 mg/day.

The compounds of formula (I) or (Ia) can advantageously be formulated and/or administered in combination with one or more other therapeutically active substances, marketed or under development, that are selected according to a specific autoimmune, inflammatory, fibrotic or cholestatic disorder or any other disorders that may be found associated to said disorder in medical settings and that should be also treated. Such a combined administration includes two possibilities: the two agents are administered to a subject at substantially similar times; or the two agents are administered to a subject at different times, at independent intervals that may or may not overlap or coincide. As such, the invention also relates to a kit-of-parts, comprising a compound of the invention, in association with another therapeutically active agent, for their simultaneous, separate or sequential use in the therapy, in particular in the treatment of an autoimmune, inflammatory, fibrotic or cholestatic disorder.

The invention also relates to a pharmaceutical composition comprising a compound of formula (I) or (Ia) and at least one other therapeutically active agent.

A non-exhaustive list of active agents that may be advantageously formulated and/or administered with compounds of formula (I) or (Ia) includes:
 anti-inflammatory;
 anti-oxidant agents;
 immunosuppressor agents;
 agents used in the treatment of asthma;
 agents used in the treatment of psoriasis;
 agents used in the treatment of respiratory diseases;
 hepatoprotective agents;
 agents used in the treatment of heart failure or coronary insufficiency Anti-hypertensive and hypotensive agents;
 anti-coagulant, vasodilators,
 anti-ischemic agents;
 agents used in the treatment of metabolic diseases, such as anti-diabetic, hypolipidemic, hypocholesterolemic, anti-atherosclerotic and anti-obesity agents.
 anti-viral agents;
 anti-cancer agents and cancer prevention agents;
 anti-cholestatic agents;
 anti-fibrotic agents;
 anti-NAFLD agents;
 anti-NASH agents.

In a particular embodiment, the invention relates to the use of a compound of formula (I) or (Ia) in combination with an anti-fibrotic, anti-NAFLD or anti-NASH agent. Therefore, the invention relates to a first combination product comprising:

a) a RORgamma modulator, such as a compound of formula (I) or (Ia) or a pharmaceutically acceptable salt thereof; and b) another therapeutically active agent.

In a particular embodiment, the other therapeutically active agent is an anti-fibrotic, anti-NAFLD or anti-NASH agent. In another particular embodiment, the other therapeutically active agent is a PPAR activator as defined below.

In a particular embodiment, the combination product is a composition comprising the RORgamma modulator and the other therapeutically active agent, and a pharmaceutically acceptable carrier.

In another embodiment, the combination product is a kit of parts comprising components a) and b) of the combination product. The kit of parts of the invention is for sequential, separate or simultaneous use in the treatment of any of the diseases mentioned above.

In another aspect, the invention relates to a combination of a RORγ modulator and a PPAR activator. In a particular embodiment, the invention relates to a composition comprising a RORγ modulator and a PPAR activator. In another embodiment, the invention relates to a kit-of-parts comprising a RORγ modulator and a PPAR activator, for simultanate, separate or sequential use.

The PPARs (α, β/(herein after δ), γ) belong to the hormone-activated nuclear receptor family. The PPARs, or "Peroxisome Proliferator Activated Receptors", are nuclear receptors from the superfamily of transcription factors activated by the following ligands: steroids/thyroid hormones/retinoids. To date, three PPAR isotypes have been identified in mice and humans: PPARα, PPARδ and PPARγ. While PPAR β/δ expression in humans appears to be ubiquitous, PPARα and γ exhibit a differential tissue distribution (Braissant O and Wahli W, 1998). PPARα is expressed in cells with high fatty acid catabolic activity and in cells with high peroxisomal activity (hepatocytes, cardiomyocytes, renal proximal tubules, intestinal mucosa). PPAR β/δ is expressed ubiquitously and abundantly in most tissues. As far as PPARγ expression is concerned, it is limited mainly to adipose tissue, certain immune system cells and retina and is present in only trace amounts in other organs (Braissant O and Wahli W, 1998).

Taking the example of PPARα, its action is mediated by a class of compounds such as the fibrates which have a lipid-lowering effect. Natural ligands have also been identified such as for example fatty acids, eicosanoids (leukotriene B4) and 8(S)-hydroxyeicosatetraenoic acid (Kliewer S A et al., 1997). The PPARs have been associated primarily with lipid and glucose metabolism. PPAR activators, such as fibrates, enable a regulation of plasma cholesterol and triglyceride concentrations via activation of PPARα (Hourton D et al., 2001). Fibrate therapy leads to an increase in fatty acid oxidation in liver. Fibrates also decrease the synthesis of triglycerides (Staels B and Auwerx J, 1998). PPARα activators are also capable of correcting hyperglycemia and insulin level. Fibrates also reduce adipose tissue mass through a mechanism which is independent of food intake and leptin gene expression (Guerre-Millo M et al., 2000). The therapeutic interest of PPARγ agonists has been widely investigated in the treatment of type 2 diabetes (Spiegelman B M, 1998). It has been shown that PPARγ agonists restore insulin sensitivity in target tissues and reduce plasma glucose, lipid and insulin levels both in animal models of type 2 diabetes and in humans (Ram V J, 2003). PPAR activation by ligands also plays a role in regulating the expression of genes that participate in processes such as inflammation, angiogenesis, cell proliferation and differentiation, apoptosis and the activities of iNOS, MMPase and TIMPs. Activation of PPARα in keratinocytes results in a cessation of their proliferation and expression of genes involved in differentiation (Komuves L G et al., 2000). The PPARs have anti-inflammatory properties because they negatively interfere with transcription mechanisms involving other transcription factors like NF-κB or transcriptional activators like STAT and AP-1 (Desvergne B and Wahli W, 1999). Said anti-inflammatory and anti-proliferative properties make the PPARδ (and particularly PPARα) interesting therapeutic targets for the treatment of diseases such as vascular occlusive diseases (atherosclerosis, etc.), hypertension, diseases related to neovascularization (diabetic retinopathy, etc.), inflammatory diseases (inflammatory bowel disease, psoriasis, etc.) and neoplastic diseases (carcinogenesis, etc.).

The combination of the invention may be used as a medicament. In a particular embodiment, the combination is used for the treatment of one of the diseases mentioned above. The RORγ modulator and the PPAR activator are each administered to a subject in need thereof in a therapeutically effective amount.

In a particular embodiment, the ROR modulator in the combination is a compound of formula (I) or (Ia).

In a particular embodiment, the PPAR activator in the combination is a PPARα, PPARδ, PPARγ, PPARα/δ (or dual PPARα/δ), PPARα/γ (or dual PPARα/γ), PPARγ/δ (or dual PPARγ/δ), or PPARα/γ/δ (or pan-PPAR) activator.

In a particular embodiment, the PPAR alpha agonist is a fibrate such as fenofibrate, ciprofibrate, pemafibrate, gemfibrozil, clofibrate, binifibrate, clinofibrate, clofibric acid, nicofibrate, pirifibrate, plafibride, ronifibrate, theofibrate, tocofibrate or SR10171.

In a particular embodiment, the PPAR gamma agonist is a glitazone (or thiazolidinedione) such as Rosiglitazone, Pioglitazone, deuterated pioglitazone, efatutazone, ATx08-001, OMS-405, CHS-131, THR-0921, SER-150-DN, KDT-501, GED-0507-34-Levo, CLC-3001 or ALL-4.

In a particular embodiment, the PPAR delta agonist is GW501516 (Endurabol or ({4-[({4-methyl-2-[4-(trifluoromethyl)phenyl]-1,3-thiazol-5-yl}methyl)sulfanyl]-2-methylphenoxy}acetic acid)), MBX8025 (Seladelpar or {2-methyl-4-[5-methyl-2-(4-trifluoromethyl-phenyl)-2H-[I, 2,3]triazol-4-ylmethylsylfanyl]-phenoxy}-acetic acid), GW0742 ([4-[[[2-[3-fluoro-4-(trifluoromethyl)phenyl]-4-methyl-5-thiazolyl]methyl]thio]-2-methyl phenoxy]acetic acid), L165041, HPP-593 or NCP-1046.

In a particular embodiment, the PPAR alpha/gamma dual agonist is a glitazar such as Saroglitazar, Aleglitazar, Muraglitazar, Tesaglitazar or DSP-8658.

In a particular embodiment, the PPAR alpha/delta dual agonist is Elafibranor (GFT505) or T913659.

In a particular embodiment, the PPAR gamma/delta dual agonist is a conjugated linoleic acid (CLA) or T3D-959.

In a particular embodiment, the PPAR alpha/gamma/delta pan agonist is IVA337, TTA (tetradecylthioacetic acid), Bavachinin, GW4148, GW9135, Bezafibrate, Lobeglitazone or CSO38.

In a more particular embodiment, the PPAR activator is a compound of formula (II), or a pharmaceutically acceptable salt thereof:

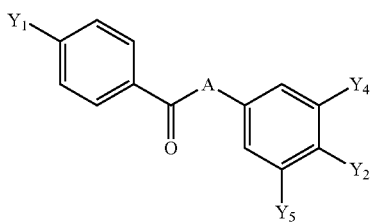

(II)

in which:
Y1 represents a halogen, a Ra, or Ga—Ra group;
A represents a CH═CH or a CH2-CH2 group;
Y2 represents a Gb-Rb group;
Ga and Gb, identical or different, represent an atom of oxygen or sulfur;
Ra represents a hydrogen atom, an unsubstituted (C1-C6) alkyl group, a (C6-C14)aryl group or a (C1-C6)alkyl group that is substituted by one or more halogen atoms, a (C1-C6)alkoxy or a (C1-C6)alkylthio group, (C3-C14)cycloalkyl groups, (C3-C14)cycloalkylthio groups or heterocyclic groups;
Rb represents a (C1-C6)alkyl group substituted by at least a —COORc group, wherein Rc represents a hydrogen atom, or a (C1-C6)alkyl group that is substituted or not by one or more halogen atoms, (C3-C14)cycloalkyl groups, or heterocyclic groups; and
Y4 and Y5, identical or different, representing a (C1-C6) alkyl group that is substituted or not by one or more halogen atoms, (C3-C14)cycloalkyl groups or heterocyclic groups.

In a particular embodiment of the compound of formula (II):
Y1 represents a halogen, a Ra, or a Ga—Ra group;
A represents a CH═CH group;
Y2 represents a Gb-Rb group;
Ga and Gb, identical or different, represent an atom of oxygen or sulfur;
Ra represents a (C1-C6)alkyl or (C3-C14)cycloalkyl group, in particular a (C1-C7)alkyl or (C3-C14)cycloalkyl group substituted or not by one or more halogen atoms;
Rb represents a (C1-C6)alkyl group substituted by a —COOR3 group, wherein Rc represents a hydrogen atom or an alkyl group having from one to four carbon atoms; and
Y4 and Y5 independently represent a (C1-C4)alkyl group.

In a particular embodiment of the compound of formula (II):
Y1 represents a Ra or Ga—Ra group;
A represents a CH2-CH2 group;
Y2 represents a Gb-Rb group;
Ga represents an atom of oxygen or sulfur and Gb represents an atom of oxygen;
Ra represents a (C1-C6)alkyl or (C3-C7)cycloalkyl group;
Rb represents a (C1-C6)alkyl group substituted by at least a —COORc group, wherein Rc represents a hydrogen atom or (C1-C4)alkyl group; and
Y4 and Y5 independently represent a (C1-C4)alkyl group.

In a particular embodiment of the compound of formula (II):
Y1 represents a halogen atom or a Ra or Ga—Ra group;
A represents a CH2-CH2 group;
Y2 represents a Gb-Rb group;
Ga represents an atom of oxygen or sulfur and Gb represents an atom of oxygen;

Ra represents a (C1-C6)alkyl or (C3-C14)cycloalkyl group that is substituted by one or more halogen atoms;
Rb represents a (C1-C6)alkyl group substituted or not by one or more halogen atoms and substituted by at least a —COORc group, wherein Rc represents a hydrogen atom or a (C1-C4)alkyl group; and
Y4 and Y5 represent a (C1-C4)alkyl group.

In a particular embodiment of the compound of formula (II), Gb is an oxygen atom and Rb is (C1-C6)alkyl group substituted by a —COORc group, wherein Rc represents a hydrogen atom or an unsubstituted linear or branched (C1-C4)alkyl group.

In a particular embodiment of the compound of formula (II), Y1 is a (C1-C6)alkylthio group that comprises a (C1-C6)alkyl group that is linear or branched that is substituted or not by one or more halogen atoms.

In a particular embodiment, the compound of formula (II) is selected in the group consisting of 1-[4-methylthiophenyl]-3-[3,5-dimethyl-4-carboxydimethylmethyloxy phenyl] prop-2-en-1-one (Elafibranor or GFT505), 1-[4-methylthiophenyl]-3-[3,5-dimethyl-4-isopropyloxy carbonyldimethylmethyloxyphenyl]prop-2-en-1-one, 1-[4-methylthiophenyl]-3-[3,5-dimethyl-4-tertbutyloxycarbonyldimethylmethyloxyphenyl]prop-2-en-1-one, 1-[4-trifluoromethyl phenyl]-3-[3,5-dimethyl-4-tertbutyloxycarbonyldimethylmethyloxyphenyl]prop-2-en-1-one, 1-[4-trifluoromethylphenyl]-3-[3,5-dimethyl-4-carboxydimethylmethyloxyphenyl]prop-2-en-1-one, 1-[4-trifluoromethyl oxyphenyl]-3-[3,5-dimethyl-4-tertbutyloxycarbonyldimethylmethyloxy phenyl]prop-2-en-1-one, 1-[4-trifluoromethyloxyphenyl]-3-[3,5-dimethyl-4-carboxydimethylmethyloxyphenyl]prop-2-en-1-one, 2-[2,6-dimethyl-4-[3-[4-(methylthio)phenyl]-3-oxo-propyl] phenoxy]-2-methylpropanoic acid, and 2-[2,6-dimethyl-4-[3-[4-(methylthio) phenyl]-3-oxo-propyl]phenoxy]-2-methyl-propanoic acid isopropyl ester.

In a more particular embodiment, the PPAR activator is 1-[4-methylthiophenyl]-3-[3,5-dimethyl-4-carboxydimethylmethyloxy phenyl]prop-2-en-1-one (or Elafibranor-GFT505), or a pharmaceutically acceptable salt thereof.

In a particular aspect, the invention relates to a combination product comprising:
i) a RORgamma modulator, in particular a compound of formula (I) or (Ia) or a pharmaceutically acceptable salt thereof;
ii) a PPAR activator, in particular a compound of formula (II) or a pharmaceutically acceptable salt thereof, in particular Elafibranor or a pharmaceutically acceptable salt thereof.

In a particular embodiment, the combination product is a composition comprising:
i) a RORgamma modulator, in particular a compound of formula (I) or (Ia) or a pharmaceutically acceptable salt thereof; and
ii) a PPAR activator, in particular a compound of formula (II) or a pharmaceutically acceptable salt thereof, in particular Elafibranor or a pharmaceutically acceptable salt thereof; and
iii) a pharmaceutically acceptable carrier.

In a particular embodiment, the combination product is a kit of parts comprising:
i) a RORgamma modulator, in particular a compound of formula (I) or (Ia) or a pharmaceutically acceptable salt thereof; and
ii) a PPAR activator, in particular a compound of formula (II) or a pharmaceutically acceptable salt thereof, in particular Elafibranor or a pharmaceutically acceptable salt thereof;

for sequential, separate or simultaneous use in the treatment of any of the diseases mentioned above.

Several other advantages of the invention will rise in the reading of the following examples; they should be considered as illustrative data and not as limitative ones.

EXAMPLES

Chemical names follow IUPAC nomenclature. Starting materials and solvents were purchased from commercial suppliers (Acros Organic, Sigma Aldrich, Combi-Blocks, Fluorochem, Fluka, Alfa Aesar or Lancaster) and were used as received without further purification. Some starting materials can be readily synthesized by a person skilled in the art. Air and moisture sensitive reactions were carried out under an inert atmosphere of nitrogen, and glassware was oven-dried. No attempts were made to optimize reaction yields. Thin-layer chromatography (TLC) was done on Merck silica gel 60 UV254 (250 µm) plates. Visualization was accomplished with UV light. Column chromatography was performed on Geduran silica gel 60 (40-63 µm) from Merck. Melting points (mp) were recorded with a Büchi Melting Point B-545 and are uncorrected. All microwave irradiation experiments were carried out in a Biotage Initiator microwave apparatus. $^1$H spectra were recorded on Bruker Advance I spectrometer at 300 MHz. Chemical shifts (δ) are reported in ppm (parts per million), by reference to the hydrogenated residues of deuterated solvent as internal standard: 2.50 ppm for DMSO-d6, 7.26 ppm for CDCl3, and 3.31, and 4.78 for Methanol-d4. The spectral splitting patterns are designated as follows: s, singlet; d, doublet; dd, doublet of doublets; ddd, doublet of doublet of doublets; t, triplet; dt, doublet of triplets; q, quartet; m, multiplet; br s, broad singlet. Coupling constants (J) are quoted to the nearest 0.1 Hz. All tested compounds exhibited ≥95% chemical purity assessed by HPLC on a Merck HITACHI Lachrom L-7000 series and Merck HITACHI diode array detector L-7455 with a Waters column Symmetry C18 (3.5 µm, 4.6*75 mm) and using a gradient of MeOH/Millipore water containing 0.1% of formic acid. Chromatograms were analyzed with Lachrom software version 890-8800-09. Mass spectrometry measurements were performed on Alliance 2695 and DAD detector 2998 equipped with an Acquity QDa detector from Waters using a Waters column Symmetry C18 (3.5 µm, 4.6*75 mm) and using a gradient of MeOH/Millipore water containing 0.1% of formic acid (chromatograms were analyzed with Empower 3 software) or they were performed on apparatus equipped with Waters 2545 binary gradient module, Waters 2489 UV/Visible detector and Acquity QDa detector using a Waters column Symmetry C18 (3.5 µm, 4.6*75 mm) and using a gradient of MeOH/Millipore water containing 0.1% of formic acid (chromatograms were analyzed with MassLynx 4.1). Preparative HPLC were performed on apparatus equipped with Waters 2545 binary gradient module, Waters 2489 UV/Visible detector, Acquity QDa detector and Waters 2767 sample manager using a Waters column SymmetryPrep C18 (7 µm, 19*150 mm) and using a gradient of MeOH/Millipore water containing 0.1% of formic acid (chromatograms were analyzed with MassLynx 4.1). All solvents are HPLC grade.

The compounds of the invention are prepared according to the general methods and general protocols of synthesis given below. Representative procedures suitable for the preparation of compounds of formula (I) or (Ia) are outlined in the Reaction Schemes for intermediate (FIG. 1 and FIG. 2) and final (FIG. 3) compounds. Reagents and conditions may be adapted and additional steps employed to produce further compounds encompassed in the present invention having alternative substituent groups, or for achieving such compounds at higher yield and/or of higher purity.

Example 1: Synthesis of Intermediates for the Synthesis of Compounds According to the Invention In the following, compounds termed "Ex. X" are intermediate compounds used for the synthesis of compounds of the present invention.

The general treatments and purification steps are carried out according to techniques well known by a person skilled in the art or such as those described in the literature: the reaction was quenched either with water, brine or sat. NH4Cl. Excess or solvent used for the reaction was removed under reduced pressure. The aqueous layer was extracted three times with a non-water miscible solvent (e.g. Et2O, EtOAc, CH2Cl2). The organic layer was dried over MgSO4, filtered and the solution was concentrated under reduced pressure. Purification of the crude material was realized either by double extraction using conc. HCl and/or NaOH 2N, by hydrochloride formation or by purification on silica gel column chromatography using standard mixture systems (cyclohexane/EtOAc, CH2Cl2/MeOH and CH2Cl2/EtOAc).

Figure 1A:
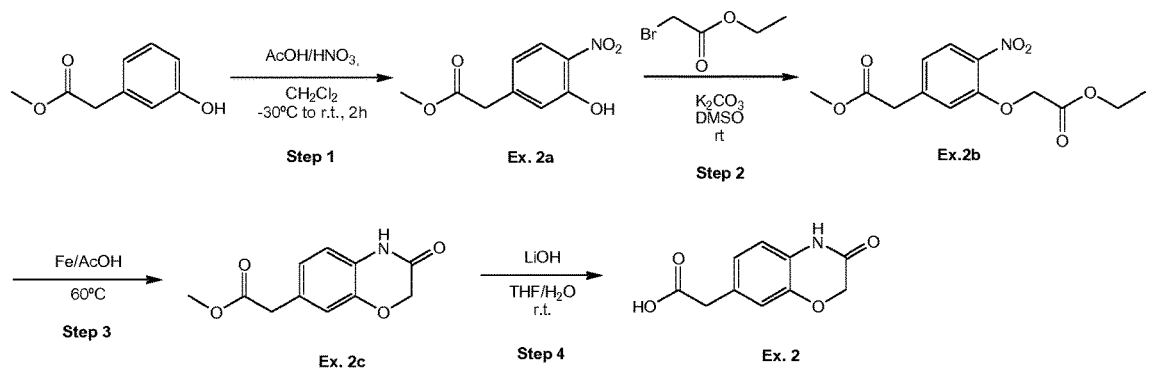
Figure 1A:
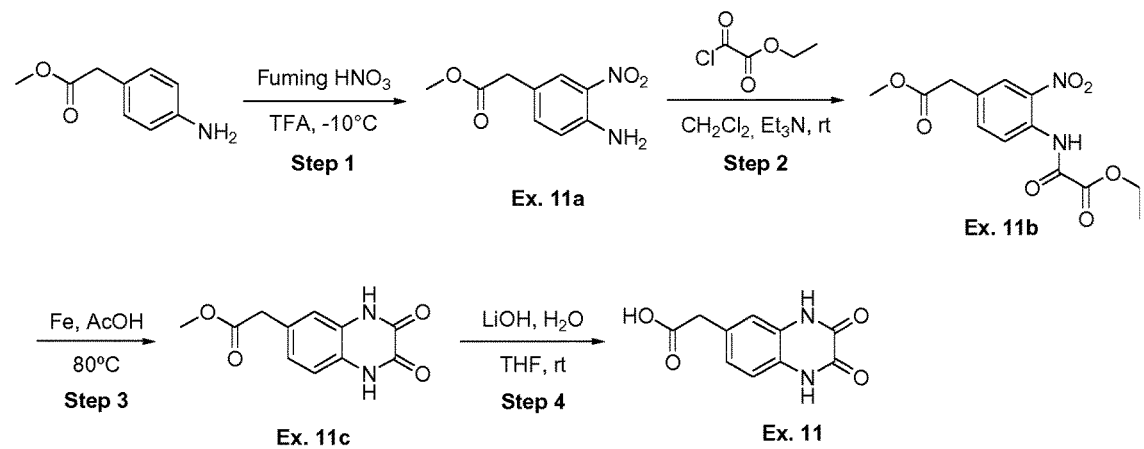
Figure 1A:
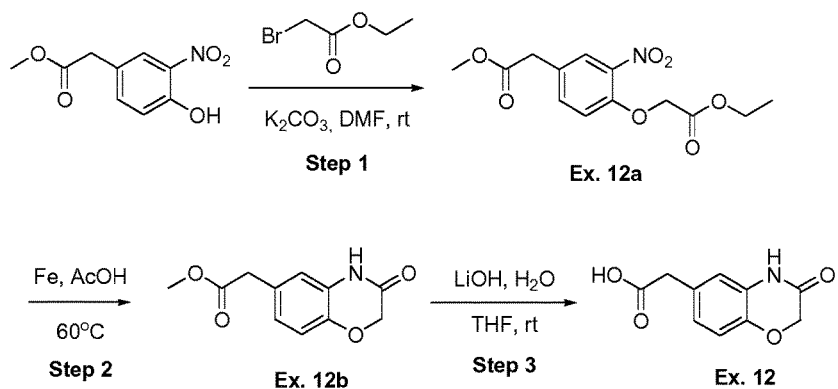
Figure 1A:
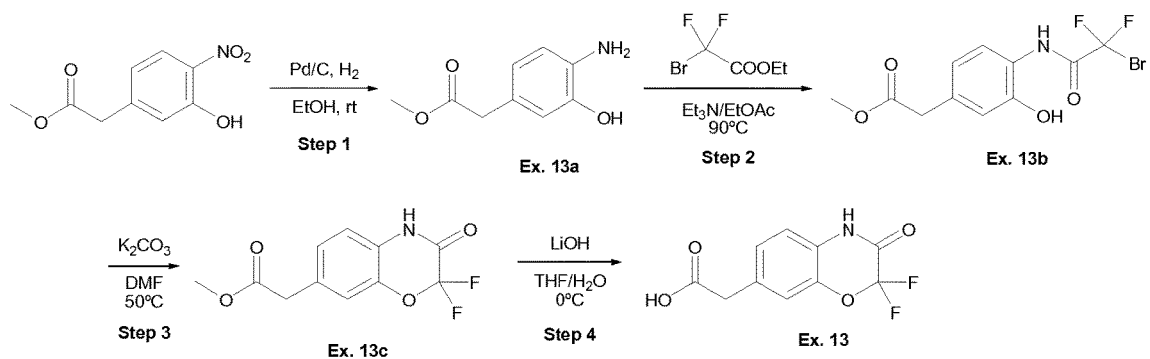
Figure 1A:
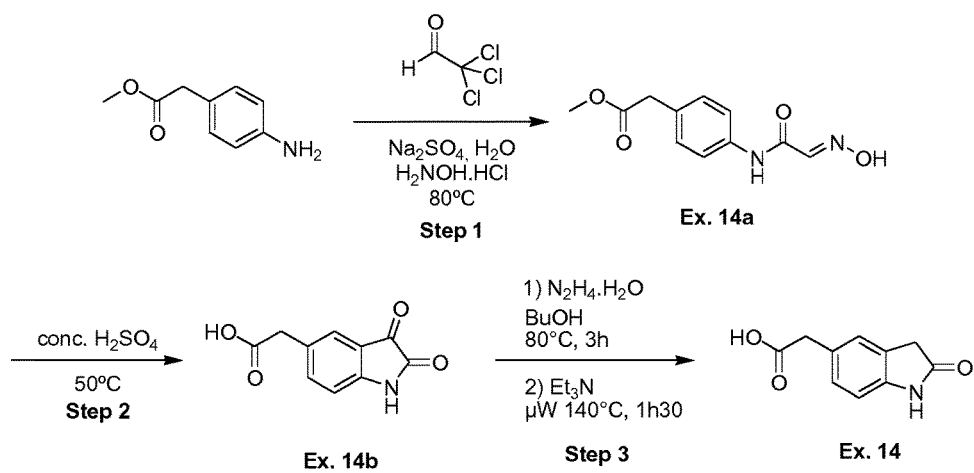
Figure 1A:
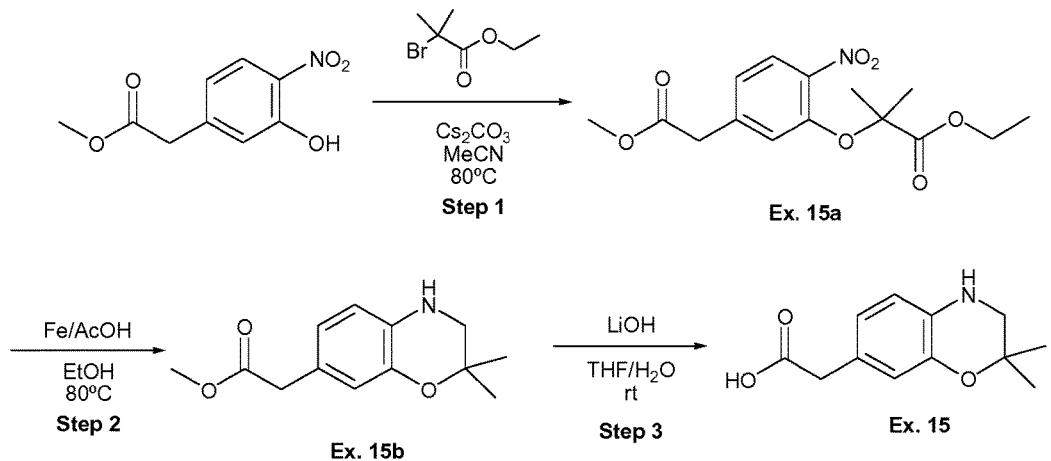
Figure 1A:
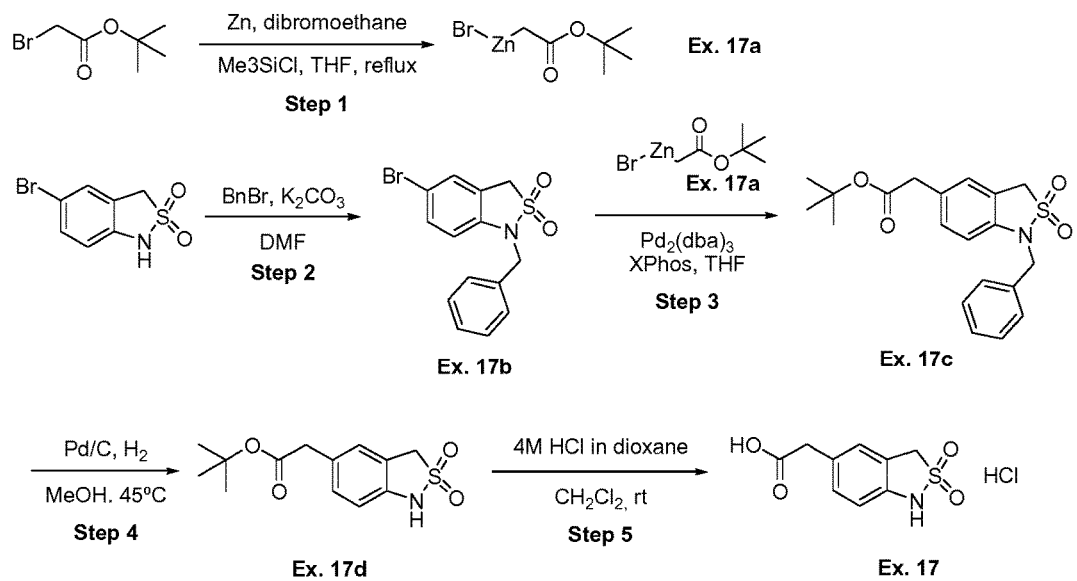
Figure 1A:
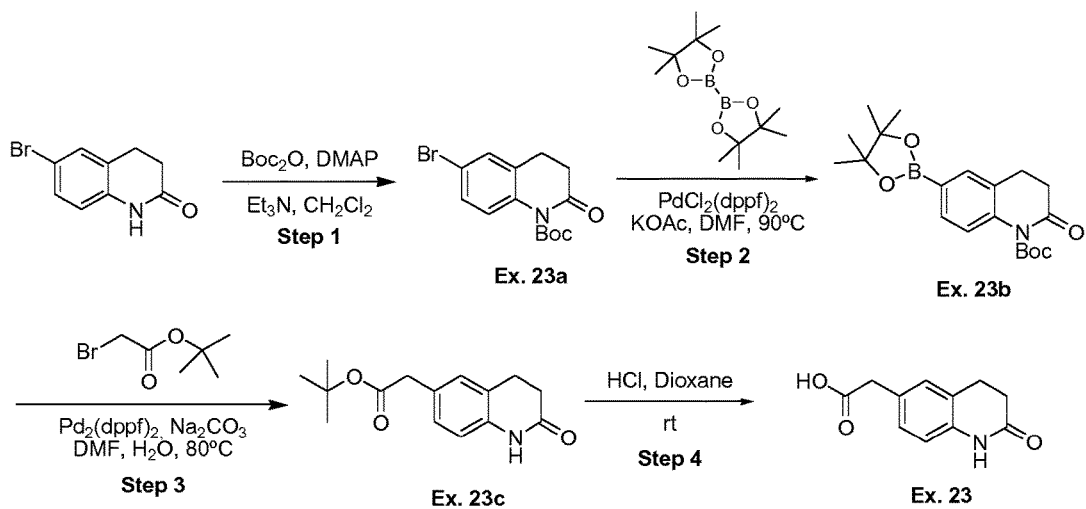
Figure 1A:
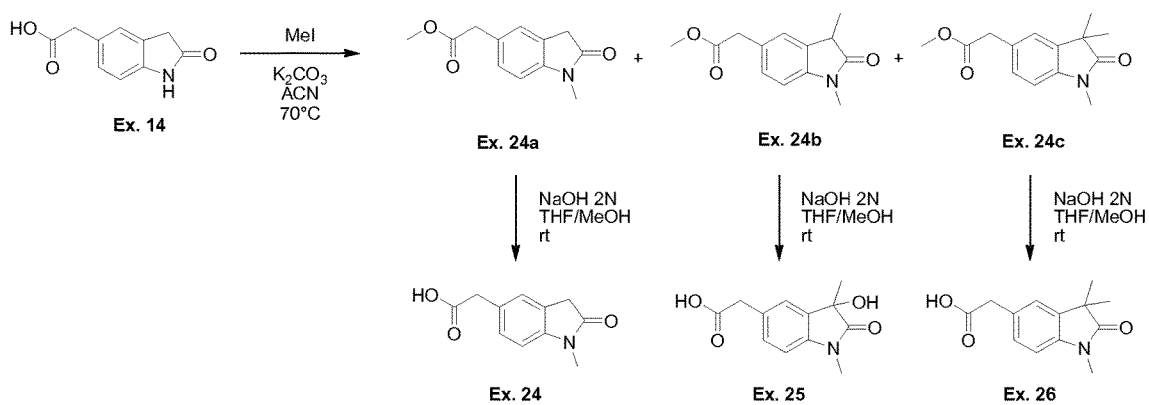
Figure 1A:
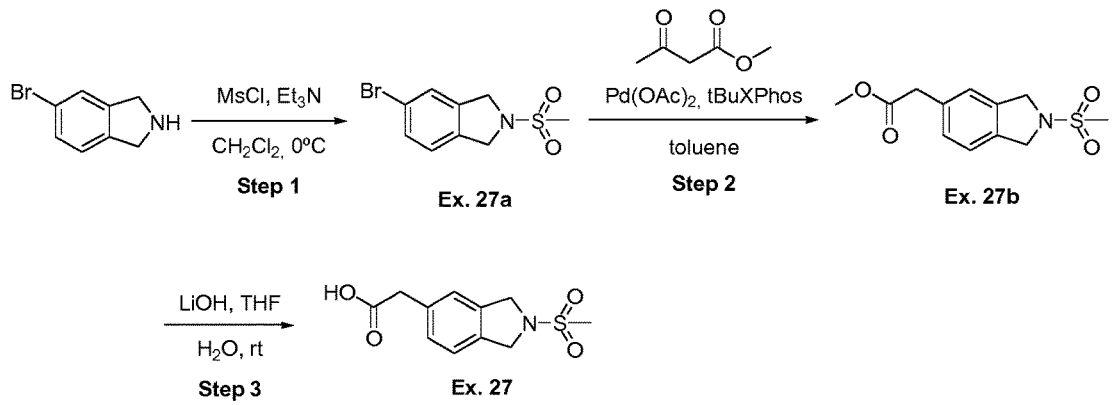
Figure 1A:
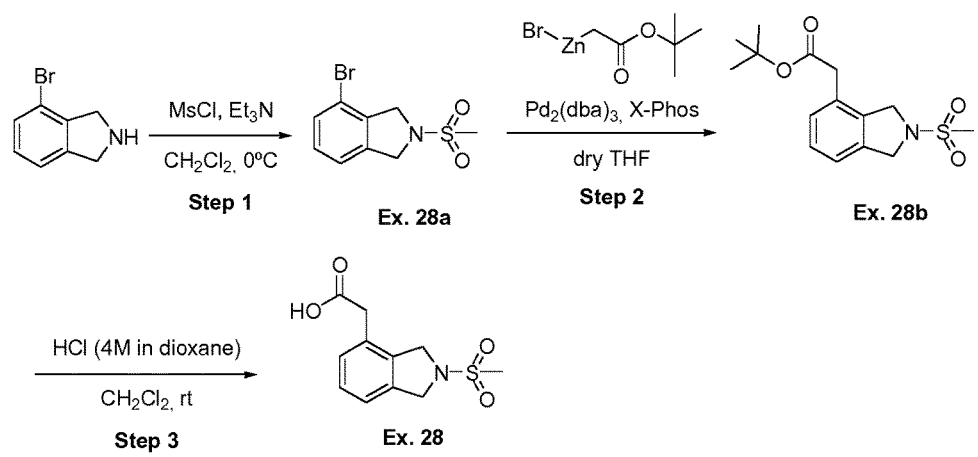
Figure 1A:
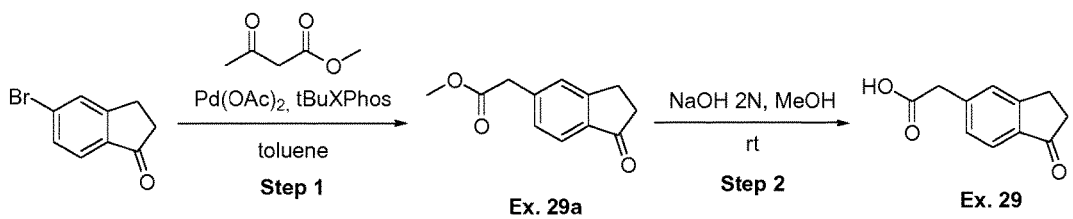
Figure 1A:
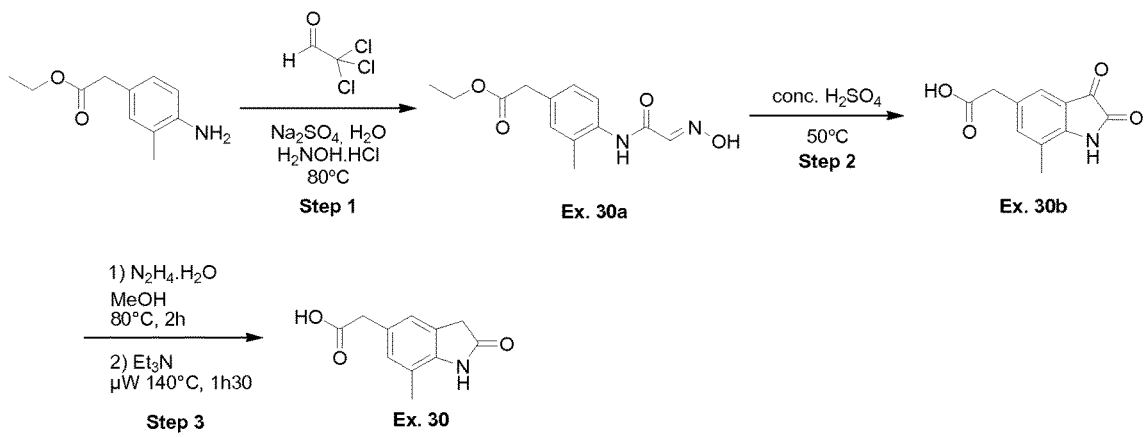
Figure 1A:
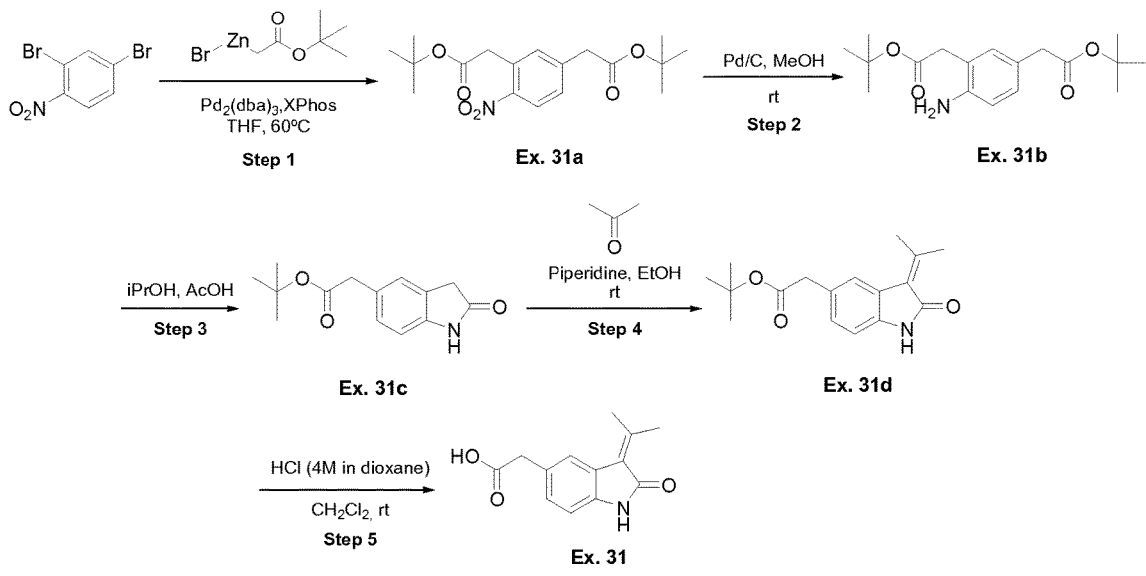
Figure 1A:
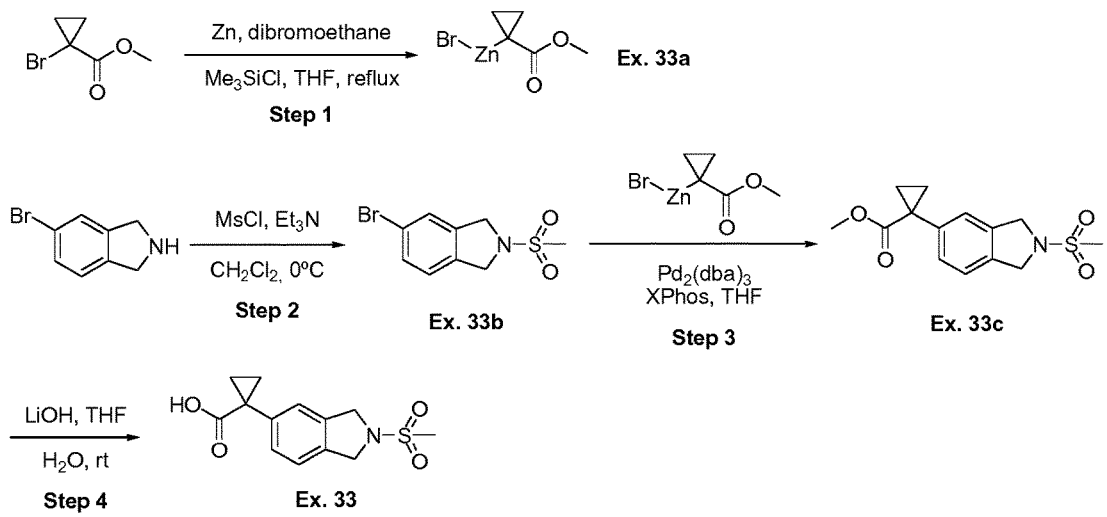
Figure 1A:
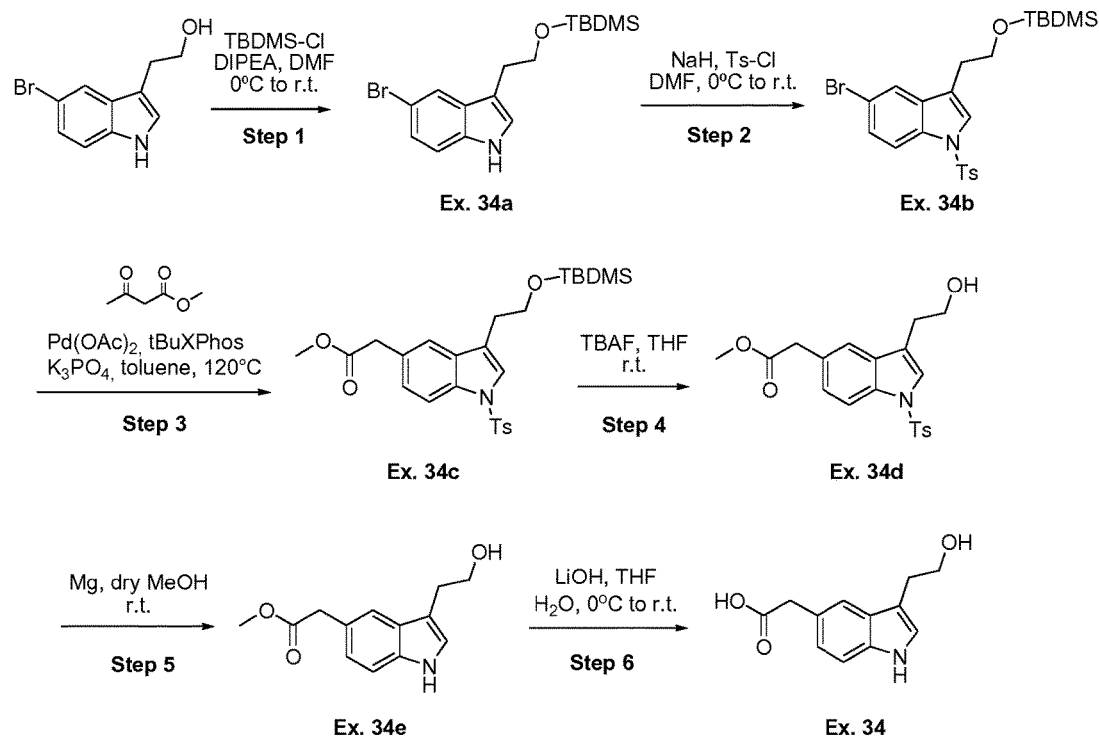
Figure 1A:
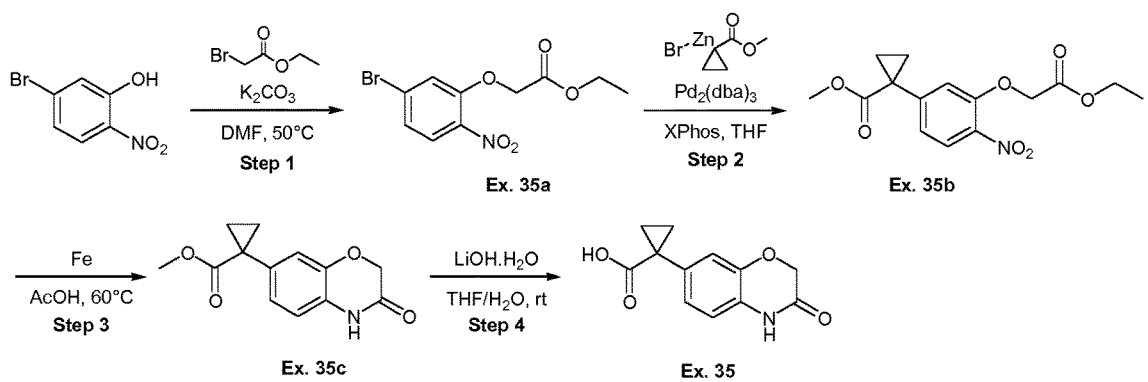
Figure 1A:
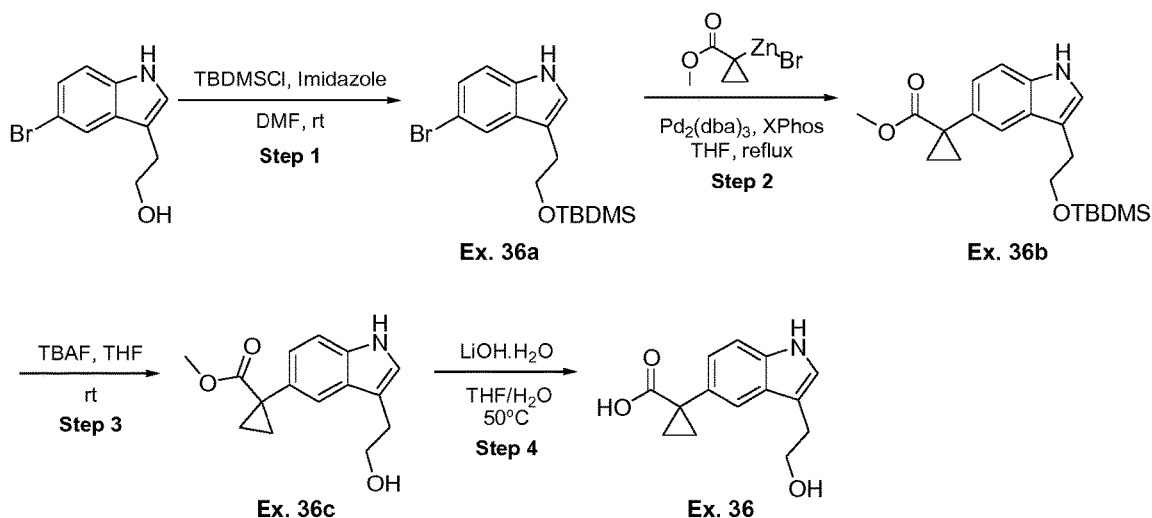
Figure 1A:
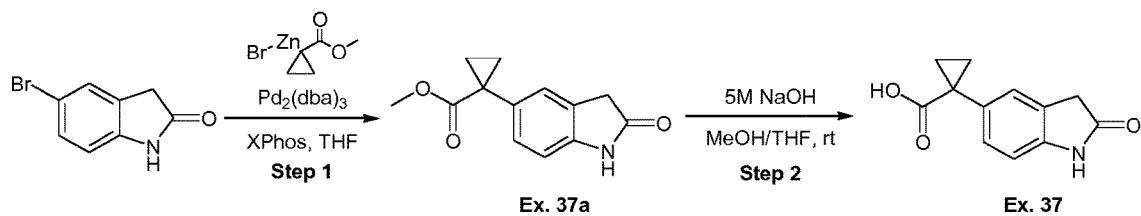
Figure 1A:
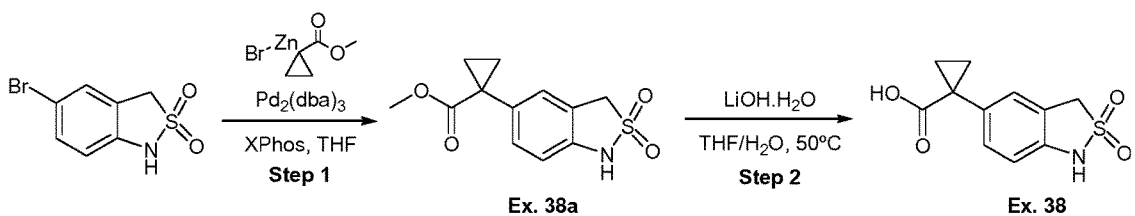
Figure 1A:
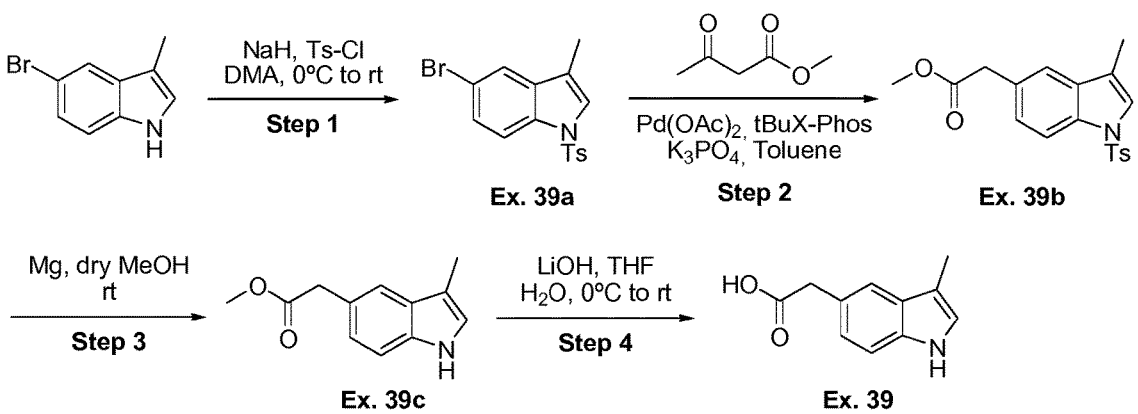
Figure 1A:
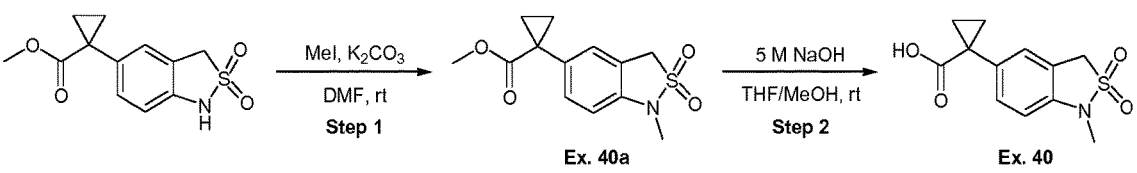
Figure 1A:
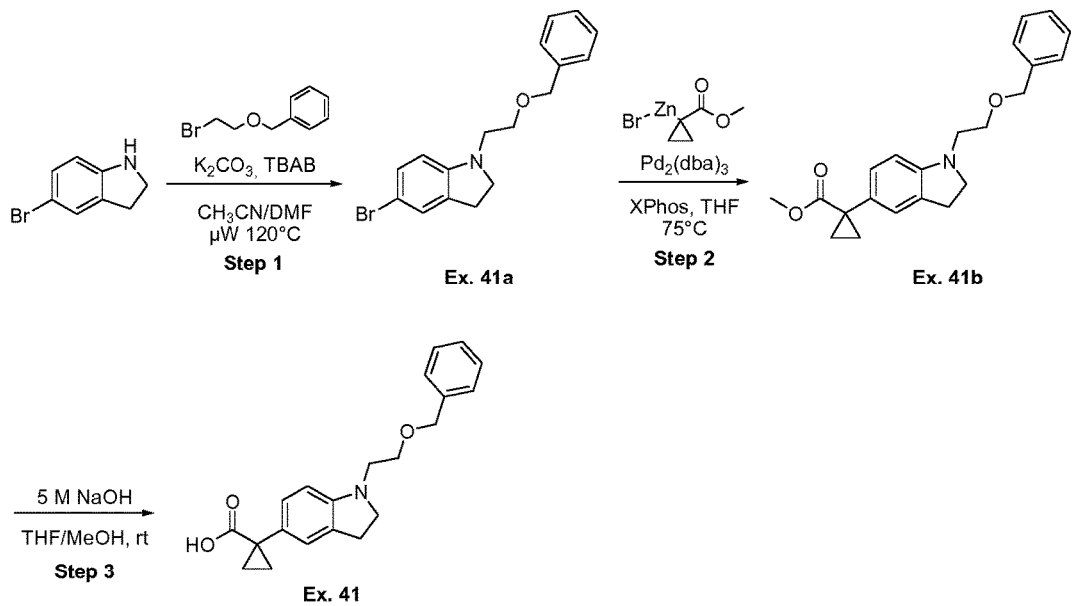
Figure 1A:
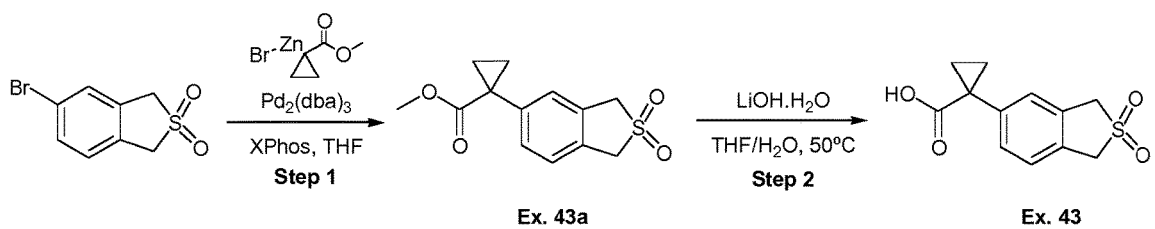

Example 1a: Synthesis of Acid Intermediates for the Synthesis of Compounds According to the Invention Intermediate Ex.2: 2-(3-oxo-3,4-dihydro-2H-1,4-benzoxazin-7-yl)acetic acid (FIG. 1AA)

TABLE 1.1

| Cpd. | Starting compounds, Reaction conditions and purification, Yield, Appearance, $^1$H NMR (solvent) data |
|---|---|
| Ex. 2a | methyl 2-(3-hydroxy-4-nitrophenyl)acetate<br>Step 1: methyl 2-(3-hydroxyphenyl)acetate (9.0 g, 54.18 mmol) was dissolved in CH2Cl2 (180 mL) and glacial acetic acid (70 mL). The mixture was cooled to −30° C. and a solution of nitric acid 65% (3.78 mL, 54.18 mmol) in glacial acetic acid (75 mL) was added dropwise over 30 min. maintaining the temperature below −25° C. When the addition was complete the mixture was allowed to warm up to rt and stirred at rt for 1 h. The mixture was quenched into a stirred mixture of CH2Cl2/H2O (400 mL/400 mL). The phases were separated, the organic layer was washed with sat. NaHCO3 and brine, was dried over MgSO4, filtered and the solution was concentrated to dryness. The crude material was purified by silica gel column chromatography eluting with heptane and a gradient of heptane/EtOAc from [100:0] to [60:40]. The product fractions were concentrated to dryness to afford methyl 2-(3-hydroxy-4-nitrophenyl)acetate (2.64 g, 23%) as |

TABLE 1.1-continued

| Cpd. | Starting compounds, Reaction conditions and purification, Yield, Appearance, $^1$H NMR (solvent) data |
|---|---|
| | yellow oil which solidified upon standing at rt.<br>1H NMR (300 MHz, DMSO-d6, d in ppm): 3.63 (s, 3H), 3.76 (S, 2H), 6.89 (d, 1H, J = 9.0 Hz), 7.05 (s, 1H), 7.86 (d, 1H, J = 9.0 Hz), 10.93 (s, 1H). |
| Ex. 2b | ethyl 2-[5-(2-methoxy-2-oxoethyl)-2-nitrophenoxy]acetate<br>Step 2: methyl 2-(3-hydroxy-4-nitrophenyl)acetate Ex. 2a (2.50 g, 11.80 mmol) was dissolved in DMSO (25 mL), ethyl bromoacetate (1.44 mL, 12.8 mmol) and K2CO3 (1.77 g, 12.8 mmol) were added and the mixture was stirred at rt for 16 h. The mixture was quenched with water and the aqueous layer was extracted with EtOAc. The organic layer was dried over MgSO4, filtered and the solution was concentrated to dryness. The crude material was purified by silica gel column chromatography eluting with heptane and a gradient of heptane/EtOAc from [100:0] to [80:20]. The product fractions were concentrated to dryness to afford ethyl 2-[5-(2-methoxy-2-oxoethyl)-2-nitrophenoxy]acetate (3.29 g, 94%) as yellow oil which solidified upon standing at rt.<br>1H NMR (300 MHz, CDCl3, d in ppm): 1.31 (t, 3H, J = 6.0 Hz), 3.67 (s, 2H), 3.73 (s, 3H), 4.29 (q, 2H, J = 6.0 Hz), 4.79 (s, 2H), 6.96 (s, 1H), 7.03 (d, 1H, J = 9.0 Hz), 7.86 (d, 1H, J = 9.0 Hz). |
| Ex. 2c | methyl 2-(3-oxo-3,4-dihydro-2H-1,4-benzoxazin-7-yl)acetate<br>Step 3: ethyl 2-[5-(2-methoxy-2-oxoethyl)-2-nitrophenoxy]acetate Ex. 2b (3.20 g, 10.8 mmol) was dissolved in glacial acetic acid (50 mL) and iron powder (1.81 g, 32.4 mmol) was added. The mixture was heated to 70-80° C. for 2 h. The mixture was concentrated to approx. half its volume. Water was added and the resulting suspension was stirred at rt for 30 min. The solid was collected by filtration and washed with water until it was white. The solid was dried under vacuum to constant weight and adsorbed onto silica gel for purification by column chromatography eluting with EtOAc (100%). The product fractions were combined and concentrated to dryness to afford methyl 2-(3-oxo-3,4-dihydro-2H-1,4-benzoxazin-7-yl)acetate (1.69 g, 71%) as white solid.<br>1H NMR (300 MHz, DMSO-d6, d in ppm): 3.58-3.60 (m, 5H), 4.55 (s, 2H), 6.83-6.85 (m, 3H), 10.67 (s, 1H). |
| Ex. 2 | 2-(3-oxo-3,4-dihydro-2H-1,4-benzoxazin-7-yl)acetic acid<br>Step 4: methyl 2-(3-oxo-3,4-dihydro-2H-1,4-benzoxazin-7-yl)acetate Ex. 2c (1.68 g, 7.59 mmol) was dissolved in a mixture of methanol (20 mL), THF (20 mL) and water (10 mL) to afford a clean yellow solution and lithium hydroxide monohydrate (640 mg, 15.2 mmol) was added to the mixture. The solution was stirred at rt for 60 h. The organic solvents were removed under vaccum and 2M HCl was added dropwise to the residues until pH 3 was reached. A white precipitate was formed, collected by filtration, washed with water and dried under vacuum to constant weight to afford 2-(3-oxo-3,4-dihydro-2H-1,4-benzoxazin-7-yl)acetic acid (1.30 g, 83%) as white solid.<br>1H NMR (300 MHz, DMSO-d6, d in ppm): 3.47 (s, 2H), 4.55 (s, 2H), 6.82-6.85 (m, 3H), 10.65 (s, 1H), 12.29 (br(s), 1H). |

Intermediate Ex.11: 2-(2,3-dioxo-1,2,3,4-tetrahydro-quinoxalin-6-yl)acetic acid (FIG. 1AB)

TABLE 1.2

| Cpd. | Starting compounds, Reaction conditions and purification, Yield, appearance, $^1$H NMR (solvent) data |
|---|---|
| Ex. 11a | methyl 2-(4-amino-3-nitrophenyl)acetate<br>Step 1: methyl 2-(4-aminophenyl)acetate (17.70 g, 107.0 mmol) was dissolved in TFA (red dark solution) and cooled to −10° C. Then fuming HNO3 (4.76 mL, 112.0 mmol) was added dropwise. The reaction mixture was warmed to rt and stirred for 18 h. TFA was evaporated and the residue was neutralized with sat. NaHCO3 and solid NaHCO3. The aqueous layer was extracted with EtOAc. The organic layer was dried over MgSO4, filtered and the solution was concentrated to dryness. The crude material was purified by silica gel column chromatography eluting with heptane and a gradient of heptane/EtOAc from [100:0] to [80:20] to afford the desired product (12.30 g, 55%) as yellow solid.<br>1H NMR (300 MHz, CDCl3, d in ppm): 3.55 (s, 2H), 3.71 (s, 3H), 6.04 (s, 2H), 6.79 (d, 1H, J = 8.6 Hz), 7.31 (dd, 1H, J = 8.5 Hz, J = 1.8 Hz), 8.02 (s, 1H). |
| Ex. 11b | methyl 2-(4-(ethyl carbamoylformyl)-3-nitrophenyl)acetate<br>Step 2: to a solution of methyl 2-(4-amino-3-nitrophenyl)acetate Ex. 11a (1.50 g, 7.14 mmol) in CH2Cl2 (28 mL) and triethylamine (2.25 mL, 10.71 mmol) was added dropwise ethyl oxalylchloride (1.47 mL, 12.84 mmol) at 0° C. The reaction mixture was stirred at rt for 18 h. The reaction was quenched with brine. The aqueous layer was extracted with EtOAc. The organic layer was dried over MgSO4, filtered and the solution was concentrated to dryness. The crude material was purified by silica gel column chromatography eluting with heptane and a gradient of heptane/EtOAc from [100:0] to [70:30] to give methyl 2-(4-(ethyl carbamoylformyl)-3-nitrophenyl)acetate (1.55 g, 70%). |

TABLE 1.2-continued

| Cpd. | Starting compounds, Reaction conditions and purification, Yield, appearance, ¹H NMR (solvent) data |
|---|---|
| | 1H NMR (300 MHz, DMSO-d6, d in ppm): 1.33 (t, 3H, J = 7.1 Hz), 3.61 (s, 3H), 3.65 (s, 2H), 4.34 (d, 2H, J = 7.1 Hz), 7.70 (d, 1H, J = 8.6 Hz), 8.01 (d, 1H, J = 8.4 Hz), 8.08 (s, 1H), 11.35 (s, 1H). |
| Ex. 11c | methyl 2-(1,2,3,4-tetrahydro-2,3-dioxoquinoxalin-7-yl)acetate<br>Step 3: to a solution of methyl 2-(4-(ethyl carbamoylformyl)-3-nitrophenyl)acetate Ex. 11b (1.55 g, 4.99 mmol) in AcOH (23 mL) was added at rt iron powder (975 mg, 17.45 mmol). The reaction mixture was warmed to 78° C. for 4 h. The reaction mixture was filtered and quenched with sat. NaHCO3. The aqueous layer was extracted with iPrOH/CHCl3 [1:1]. The organic layer was dried over MgSO4, filtered and the solution was concentrated to dryness. The crude material was purified by silica gel column chromatography eluting with heptane and a gradient of heptane/EtOAc from [100:0] to [0:100], then a gradient of EtOAc/MeOH from [100:0] to [30:70] to afford the title compound (669 mg, 57%).<br>1H NMR (300 MHz, DMSO-d6, d in ppm): 3.60 (s, 3H), 3.65 (s, 2H), 6.97 (d, 1H, J = 9.0 Hz), 7.02 (s, 1H), 7.07 (d, 1H, J = 9.0 Hz). |
| Ex. 11 | 2-(2,3-dioxo-1,2,3,4-tetrahydroquinoxalin-6-yl)acetic acid<br>Step 4: to a solution of methyl 2-(1,2,3,4-tetrahydro-2,3-dioxoquinoxalin-7-yl)acetate Ex. 11c (669 mg, 2.86 mmol) in THF (28 mL) and water (14 mL) was added lithium hydroxide monohydrate (367 mg, 8.57 mmol) at 0° C. The reaction mixture was stirred for 5 h. The organic solvent was evaporated under vacuum and the aqueous layer was treated with 2M HCl until pH 5 was reached. The precipitate formed was filtered-off, washed with water and dried under vacuum at 60° C. for 24 h to afford 2-(2,3-dioxo-1,2,3,4-tetrahydroquinoxalin-6-yl)acetic acid (549 mg, 87%) as pale yellow solid.<br>1H NMR (300 MHz, DMSO-d6, d in ppm): 3.53 (s, 2H), 6.97 (d, 1H, J = 8.0 Hz), 7.02 (s, 1H), 7.05 (d, 1H, J = 8.1 Hz), 11.89 (d, 2H, J = 4.1 Hz), 12.14-12.55 (m, 1H). |

Intermediate Ex.12: 2-(3-oxo-3,4-dihydro-2H-1,4-benzoxazin-6-yl)acetic acid (FIG. 1AC)

TABLE 1.3

| Cpd. | Starting compounds, Reaction conditions and purification, Yield, appearance, ¹H NMR (solvent) data |
|---|---|
| Ex. 12a | ethyl 2-[4-(2-methoxy-2-oxoethyl)-2-nitrophenoxy]acetate<br>Step 1: to a suspension of methyl 2-(4-hydroxy-3-nitrophenyl)acetate (2.5 g, 11.84 mmol) and K2CO3 (1.97 g, 14.21 mmol) in DMF (36 mL) was added methyl bromoacetate (1.62 mL, 14.21 mmol). Then the reaction mixture was stirred at rt over the weekend. Water and EtOAc were added. The two layers were partitioned. The organic layer was dried over MgSO4, filtered and the solution was concentrated to dryness. The crude material was purified by silica gel column chromatography eluting with heptane and a gradient of heptane/EtOAc to from [100:0] to [80:20]. The product fractions were combined and concentrated to dryness to afford the desired product (6.05 g, 80%) as brown solid. |
| Ex. 12b | 2-(3,4-dihydro-3-oxo-2H-benzo[b][1,4]oxazin-6-yl)acetate<br>Step 2: iron powder (1.82 g, 32.67 mmol) was added to the mixture of ethyl 2-[4-(2-methoxy-2-oxoethyl)-2-nitrophenoxy]acetate Ex. 12a (3.09 g, 10.89 mmol) acid in glacial acetic acid (35 mL). The reaction mixture was heated at 80° C. for 3 h. The mixture was concentrated to approx. half its volume. Water and EtOAc were added. The organic layer was separated, concentrated and purified by silica gel column chromatography eluting with heptane and a gradient of heptane/EtOAc from [100:1] to [1:1]. The product fractions were combined and concentrated to dryness to afford methyl 2-(3,4-dihydro-3-oxo-2H-benzo[b][1,4]oxazin-6-yl)acetate (2.30 g, 96%) as white solid. |
| Ex. 12 | 2-(3,4-dihydro-3-oxo-2H-benzo[b][1,4]oxazin-6-yl)acetic acid<br>Step 3: lithium hydroxide monohydrate (910 mg, 21.60 mmol) was added to the mixture of methyl 2-(3,4-dihydro-3-oxo-2H-benzo[b][1,4]oxazin-6-yl)acetate Ex. 12b (2.30 g, 10.80 mmol) in THF (32 mL) and water (16 mL). The reaction mixture was stirred at rt for 16 h. 1N HCl was added to the reaction mixture until pH = 2 was reached. The solid formed was collected by filtration, washed with water and with Et2O. The solid was dried under vacuum at 60° C. to constant weight to afford 2-(3,4-dihydro-3-oxo-2H-benzo[b][1,4]oxazin-6-yl)acetic acid (1.53 g, 68%) as white solid.<br>1H NMR (300 MHz, DMSO-d6, d in ppm): 3.47 (s, 2H), 4.54 (s, 2H), 6.78-6.80 (m, 2H), 6.87 (d, 1H, J = 8.5 Hz), 10.69 (s, 1H), 12.30 (br(s), 1H). |

Intermediate Ex.13: 2-(2,2-difluoro-3-oxo-3,4-di-hydro-2H-1,4-benzoxazin-7-yl)acetic acid (FIG. 1AD)

TABLE 1.4

| Cpd. | Starting compounds, Reaction conditions and purification, Yield, appearance, $^1$H NMR (solvent) data |
|---|---|
| Ex. 13a | methyl 2-(3-amino-4-hydroxyphenyl)acetate<br>Step 1: methyl 2-(4-hydroxy-3-nitrophenyl)acetate (1.2 g, 5.68 mmol) was dissolved in EtOH (17 mL). The mixture was stirring at rt under nitrogen atmosphere. Then Pd/C 10% (568 mg) was added and the nitrogen atmosphere was replaced by hydrogen. The reaction mixture was stirred at rt for 16 h (hydrogen balloon). The suspension was filtered through a pad of Celite and concentrated to dryness to afford the desired product (1.00 g, 97%) as white solid. |
| Ex. 13b | methyl 2-[3-(2-bromo-2,2-difluoroacetamido)-4-hydroxyphenyl]acetate<br>Step 2: to a suspension of methyl 2-(3-amino-4-hydroxyphenyl)acetate Ex. 13a (840 mg, 4.64 mmol) and triethylamine (711 µL, 5.10 mmol) in EtOAc (7 mL) was added ethyl bromodifluoroacetate (660 µL, 5.10 mmol) under nitrogen atmosphere. The reaction mixture was heated at 90° C. for 2 h. EtOAc and water were added to the mixture to quench the reaction. The two phases were partitionated. The organic layer was dried over MgSO4, filtered and the solution was concentrated under reduced pressure. The crude material was purified by silica gel column chromatography eluting with heptane and a gradient of heptane/EtOAc from [100:0] to [8:2]. The product fractions were combined and concentrated to dryness to afford methyl 2-[3-(2-bromo-2,2-difluoroacetamido)-4-hydroxyphenyl]acetate (1.14 g, 72%) as white solid. |
| Ex. 13c | methyl 2-(2,2-difluoro-3-oxo-3,4-dihydro-2H-1,4-benzoxazin-6-yl)acetate<br>Step 3: to a mixture of methyl 2-[3-(2-bromo-2,2-difluoroacetamido)-4-hydroxyphenyl]acetate Ex. 13b (1.14 g, 3.37 mmol) in DMF (10 mL) was added K2CO3 (560 mg, 4.04 mmol). The reaction mixture was heated at 50° C. for 3 h. EtOAc and water were added to quench the reaction. The organic layer was separated, concentrated and purified by silica gel column chromatography eluting with heptane and a gradient of heptane/EtOAc from [100:0] to [8:2]. The product fractions were combined and concentrated to dryness to afford methyl 2-(2,2-difluoro-3-oxo-3,4-dihydro-2H-1,4-benzoxazin-6-yl)acetate (850 mg, 98%) as yellow solid. |
| Ex. 13 | 2-(2,2-difluoro-3-oxo-3,4-dihydro-2H-1,4-benzoxazin-7-yl)acetic acid<br>Step 4: methyl 2-(2,2-difluoro-3-oxo-3,4-dihydro-2H-1,4-benzoxazin-6-yl)acetate Ex. 13c (850 mg, 3.30 mmol) was added to the mixture of lithium hydroxide monohydrate (280 mg, 6.60 mmol) in THF (10 mL) and water (5 mL). The reaction mixture was stirred at rt for 16 h. TLC showed still starting material. A further 1 equiv of lithium hydroxide monohydrate was added to the reaction mixture. The suspension was stirred at rt for additional 16 h. 1M HCl was added to quench the reaction and until pH = 2 was reached, a brown oil was formed which was separated from the aqueous layer. The crude material was purified by silica gel column chromatography eluting with CH2Cl2 and a gradient of CH2Cl2/MeOH from [100:0] to [9:1]. The product fractions were combined and concentrated to dryness. The resulting solid was triturated with water, filtered, washed with Et2O and dried under vacuum at 60° C. to constant weight yielding 2-(2,2-difluoro-3-oxo-3,4-dihydro-2H-1,4-benzoxazin-7-yl)acetic acid (805 mg, quantitative).<br>1H NMR (300 MHz, DMSO-d6, d in ppm): 3.57 (s, 2H), 7.10 (br(s), 1H), 7.17-7.19 (m, 2H), 7.95 (s, 1H), 12.22 (br(s), 1H). |

Intermediate Ex.14: 2-(2-oxo-2,3-dihydro-1H-indol-5-yl)acetic acid (FIG. 1AE)

TABLE 1.5

| Cpd. | Starting compounds, Reaction conditions and purification, Yield, appearance, $^1$H NMR (solvent) data |
|---|---|
| Ex. 14a | 2-{4-[2-(N-hydroxyimino)acetamido]phenyl}acetic acid<br>Step 1: sodium sulfate (9.69 g, 139.50 mmol) was added to 2,2,2-trichloroacetaldehyde (9.05 g, 61.38 mmol) in water (56 mL). The mixture was stirred at rt for 15 min. Ethyl 2-(4-aminophenyl)acetate (10 g, 55.80 mmol) dissolved in 1N HCl (56 mL) was added dropwise to the previous solution followed by hydroxylamine hydrochloride (9.69 g, 139.50 mmol) dissolved in water (56 mL). The reaction mixture was heated at 80° C. for 3 h. After cooling to rt, the solid formed was collected by filtration, washed with water and dried under vacuum until constant weight affording 2-{4-[2-(N-hydroxyimino)acetamido]phenyl}acetic acid (9.60 g, 77%) as pale brown solid. |

TABLE 1.5-continued

| Cpd. | Starting compounds, Reaction conditions and purification, Yield, appearance, $^1$H NMR (solvent) data |
|---|---|
| | 1H NMR (300 MHz, DMSO-d6, d in ppm): 3.51 (s, 2H), 7.19 (d, 2H, J = 8.5 Hz), 7.60 (d, 2H, J = 8.6 Hz), 7.64 (s, 1H), 10.14 (s, 1H), 12.14 (s, 1H), 12.26 (br(s), 1H). |
| Ex. 14b | 2-(2,3-dioxo-2,3-dihydro-1H-indol-5-yl)acetic acid<br>Step 2: 2-{4-[2-(N-hydroxyimino)acetamido]phenyl}acetic acid Ex. 14a (9.58 g, 43.12 mmol) was added portionwise to a solution of conc. H2SO4 (50 mL) which was heated at 30° C. After addition, the reaction mixture was heated at 50° C. for 18 h. The solution was cooled to rt and poured into ice. The precipitate was collected by filtration, washed with water and dried under vacuum until constant weight yielding 2-(2,3-dioxo-2,3-dihydro-1H-indol-5-yl)acetic acid (5.90 g, 67%) as red solid.<br>1H NMR (300 MHz, DMSO-d6, d in ppm): 3.56 (s, 2H), 6.85 (d, 1H, J = 8.0 Hz), 7.39 (d, 1H, J = 1.7 Hz), 7.46 (dd, 1H, J = 8.0 Hz, J = 1.8 Hz), 10.99 (s, 1H). |
| Ex. 14 | 2-(2-oxo-2,3-dihydro-1H-indol-5-yl)acetic acid<br>Step 3: a solution of 2-(2,3-dioxo-2,3-dihydro-1H-indol-5-yl)acetic acid Ex. 14b (600 mg, 2.92 mmol) and hydrazine 50% in water (w/w) (206 mg, 3.22 mmol) in butanol (24 mL) were placed in a microwave vial. The reaction mixture was heated at 80° C. for 3 h. After conversion of all starting material, triethylamine(2.44 mL, 17.55 mmol) was added. The vial was screwed with a cap and then heated at 140° C. for 1 h 30 under microwave irradiation. The solvent was removed under reduced pressure. The residue was triturated with Et2O and filtered-off to give 2-(2-oxo-2,3-dihydro-1H-indol-5-yl)acetic acid (485 mg, 87%) as pale brown solid.<br>1H NMR (300 MHz, DMSO-d6, d in ppm): 3.47 (m, 4H), 6.73 (d, 1H, J = 7.9 Hz), 7.03 (d, 1H, J = 7.9 Hz), 7.08 (s, 1H), 10.30 (s, 1H). |

Intermediate Ex.15: 2-(2,2-dimethyl-3-oxo-3,4-dihydro-2H-1,4-benzoxazin-7-yl)acetic acid (FIG. 1AF)

TABLE 1.6

| Cpd. | Starting compounds, Reaction conditions and purification, Yield, appearance, $^1$H NMR (solvent) data |
|---|---|
| Ex. 15a | -ethyl 2-[5-(2-methoxy-2-oxoethyl)-2-nitrophenoxy]-2-methylpropanoate<br>Step 1: the previously synthesized methyl 2-(4-hydroxy-3-nitrophenyl)acetate (4.50 g, 21.31 mmol) was dissolved in acetonitrile (65 mL). Ethyl 2-bromoisobutyrate (3.75 mL, 25.57 mmol) and Cs2CO3 (8.33 g, 25.57 mmol) were added and the mixture was heated at 80° C. for 36 h. The mixture was diluted with EtOAc and washed with sat. NaHCO3. The two phases were partitioned. The organic layer was dried over MgSO4, filtered and the solution was concentrated to dryness. The crude material was purified by silica gel column chromatography eluting with heptane and a gradient of heptane/EtOAc from [100:0] to [1:1] to afford the desired product (3.19 g, 46%).<br>1H NMR (300 MHz, CDCl3, d in ppm): 1.27 (t, 3H, J = 6.0 Hz), 1.67 (s, 6H), 3.62 (s, 2H), 3.72 (s, 3H), 4.26 (q, 2H, J = 6.0 Hz), 6.94-7.00 (m, 2H), 7.74 (d, 1H, J = 6.0 Hz). |
| Ex. 15b | methyl 2-(2,2-dimethyl-3-oxo-3,4-dihydro-2H-1,4-benzoxazin-7-yl)acetate<br>Step 2: ethyl 2-[5-(2-methoxy-2-oxoethyl)-2-nitrophenoxy]-2-methylpropanoate Ex. 15a (3.20 g, 9.83 mmol) was dissolved in glacial acetic acid (30 mL). Iron powder (1.65 g, 29.49 mmol) was added and the mixture was heated at 80° C. for 2 h. The mixture was concentrated to approx. half its volume. Water was added and the aqueous solution was extracted with EtOAc. The organic layer was dried over MgSO4, filtered and the solution was concentrated to dryness. The crude material was purified by silica gel column chromatography eluting with heptane and a gradient of heptane/EtOAc from [100:0] to [1:1] yielding methyl 2-(2,2-dimethyl-3-oxo-3,4-dihydro-2H-1,4-benzoxazin-7-yl)acetate (1.60 g, 65%). |
| Ex. 15 | 2-(2,2-dimethyl-3-oxo-3,4-dihydro-2H-1,4-benzoxazin-7-yl)acetic acid<br>Step 3: methyl 2-(2,2-dimethyl-3-oxo-3,4-dihydro-2H-1,4-benzoxazin-7-yl)acetate Ex. 15b (1.60 g, 6.42 mmol) was dissolved in THF (20 mL). Water (10 mL) was added followed by lithium hydroxide monohydrate (540 mg, 12.84 mmol) and the resulting mixture was stirred at rt for 16 h. The solution was concentrated and the residues were acidified to pH = 2-3 by adding dropwise 2M HCl. The solid formed was collected by filtration, washed with water and dried under vacuum at 60° C. to constant weight to afford 2-(2,2-dimethyl-3-oxo-3,4-dihydro-2H-1,4-benzoxazin-7-yl)acetic acid (1.37 g, 90%) as white solid. 1H NMR (300 MHz, DMSO-d6, d in ppm): 1.38 (s, 9H), 3.47 (s, 2H), 6.81 (s, 3H), 10.57 (s, 1H), 12.31 (br(s), 1H). |

Intermediate Ex.17: 2-(2,2-dioxo-1,3-dihydro-2,1-benzothiazol-5-yl)acetic acid hydrochloride (FIG. 1AG)

TABLE 1.7

| Cpd. | Starting compounds, Reaction conditions and purification, Yield, appearance, $^1$H NMR (solvent) data |
|---|---|
| Ex. 17a | tert-butyl 2-(bromozincio)acetate<br>Step 1: to a solution of zinc dust (3.0 g, 30.26 mmol) in dry THF (30 mL) was added at rt 1,2-dibromoethane (434 µL, 5.04 mmol) under nitrogen atmosphere. The reaction mixture was stirred at 70° C. for 1 min and cooled down to rt. This procedure was repeated 5 times. Me3SiCl (256 µL, 2.02 mmol) was added and the resulting suspension was stirred at rt for 15 min. It was then heated to 65° C. and a few drops of tert-butyl 2-bromoacetate were added. Then a solution of tert-butyl 2-bromoacetate (4.92 g, 25.22 mmol) in dry THF (5 mL) was added at such a rate that reflux was maintained. Upon completion of addition, the reaction mixture was refluxed for an additional 20 min and allowed to cool down to rt. The zinc was allowed to settle and the supernatant was used further without any analysis. Complete conversion was assumed. |
| Ex. 17b | 1-benzyl-5-bromo-1,3-dihydro-2,1-benzothiazole-2,2-dione<br>Step 2: K2CO3 (111 mg, 0.80 mmol) was added to the mixture of 5-bromo-1,3-dihydro-2,1-benzothiazole-2,2-dione (100 mg, 0.40 mmol) in DMF (10 mL) at 0° C. Then, benzyl bromide (50 µL, 0.42 mmol) was added to the reaction mixture. The suspension was stirred at rt for 16 h. The reaction mixture was diluted with EtOAc and water. After phase separation, the organic layer was washed with brine, dried over MgSO4, filtered and the solution was concentrated to dryness. The crude material was purified by flash column chromatography on silica gel eluting with heptane and a gradient of heptane/EtOAc from [100:0] to [50:50]. The desired fractions were combined and concentrated to obtain 1-benzyl-5-bromo-1,3-dihydro-2,1-benzothiazole-2,2-dione (170 mg, quantitative) as white solid. |
| Ex. 17c | tert-butyl 2-(1-benzyl-2,2-dioxo-1,3-dihydro-2,1-benzothiazol-5-yl)acetate<br>Step 3: 1-benzyl-5-bromo-1,3-dihydro-2,1-benzothiazole-2,2-dione Ex. 17b (980 mg, 2.90 mmol), tert-butyl 2-(bromozincio)acetate Ex. 17a (10 mL, 8.70 mmol) and dry THF (9 mL) were charged to a flask and the mixture was degassed by bubbling nitrogen through it for 5 min. Then Pd2(dba)3 (266 mg, 0.29 mmol) and XPhos (277 mg, 0.58 mmol) were added and the solution was stirred at 75° C. for 16 h. The reaction mixture was concentrated to dryness and the residue was diluted with EtOAC and water. After phase separation, the combined organic layer was washed with brine, dried over MgSO4, filtered and the solution was concentrated under reduced pressure. The crude material was purified by flash column chromatography on silica gel eluting with heptane and a gradient of heptane/EtOAc from [100:0] to [50:50]. The desired fractions were combined and concentrated to obtain tert-butyl 2-(1-benzyl-2,2-dioxo-1,3-dihydro-2,1-benzothiazol-5-yl)acetate (1.00 g, 92%) as pale yellow oil. |
| Ex. 17d | tert-butyl 2-(2,2-dioxo-1,3-dihydro-2,1-benzothiazol-5-yl)acetate<br>Step 4: tert-butyl 2-(1-benzyl-2,2-dioxo-1,3-dihydro-2,1-benzothiazol-5-yl)acetate Ex. 17c (1.00 g, 2.68 mmol) was dissolved in EtOH (10 mL). Pd/C 10% (268 mg) was added and the mixture was purged with hydrogen. The reaction mixture was stirred under hydrogen atmosphere at 45° C. for 36 h. Further Pd/C (100 mg) was added to the reaction mixture and the solution was stirred at 45° C. for additional 20 h. The suspension was filtered through a pad of Celite and the solution was concentrated to dryness. The crude material was purified by flash column chromatography on silica gel eluting with heptane and a gradient of heptane/EtOAc from [100:0] to [50:50]. The desired fractions were combined and concentrated to afford tert-butyl 2-(2,2-dioxo-1,3-dihydro-2,1-benzothiazol-5-yl)acetate (623 mg, 47%) as white solid. |
| Ex. 17 | 2-(2,2-dioxo-1,3-dihydro-2,1-benzothiazol-5-yl)acetic acid hydrochloride<br>Step 5: 4N HCl in dioxane (1.10 mL, 4.40 mmol) was added to tert-butyl 2-(2,2-dioxo-1,3-dihydro-2,1-benzothiazol-5-yl)acetate Ex. 17d (623 mg, 2.20 mmol) dissolved in CH2Cl2 (2 mL). The reaction mixture was stirred at rt for 16 h. The precipitate was collected by filtration, washed with Et2O and dried under vacuum until constant weight to afford 2-(2,2-dioxo-1,3-dihydro-2,1-benzothiazol-5-yl)acetic acid hydrochloride (415 mg, 83%).<br>1H NMR (300 MHz, DMSO-d6, d in ppm): 2.47 (s, 2H), 3.44 (s, 2H), 4.44 (s, 2H) 6.70 (d, 1H), 7.06 (d, 1H), 7.10 (s, 1H), 10.33 (s, 1H). |

Intermediate Ex.23:
2-(2-oxo-1,2,3,4-tetrahydroquinolin-6-yl)acetic acid
(FIG. 1AH)

TABLE 1.8

| Cpd. | Starting compounds, Reaction conditions and purification, Yield, appearance, $^1$H NMR (solvent) data |
|---|---|
| Ex. 23a | tert-butyl 6-bromo-3,4-dihydro-2-oxoquinoline-1(2H)-carboxylate<br>Step 1: 6-bromo-1,2,3,4-tetra-hydro-2-quinolinone (5.0 g, 22.12 mmol) was dissolved in CH2Cl2 (100 mL) and triethylamine (3.39 mL, 24.33 mmol) was added followed by 4-(dimethylamino)-pyridine (260 mg, 2.21 mmol) and the portionwise addition of di-tert-butyl dicarbonate(5.07 g, 23.23 mmol), upon which gas evolution was observed. The mixture was stirred at rt for 16 h. The reaction was quenched with water and the two phases were separated. The organic layer was dried over MgSO4, filtered and the solution was concentrated to dryness. The crude material was purified by silica gel column chromatography eluting with heptane and a gradient of heptane/EtOAc from [100:0] to [85:15]. The product fractions were combined and concentrated to dryness to afford tert-butyl 6-bromo-3,4-dihydro-2-oxoquinoline-1(2H)-carboxylate (6.00 g, 83%) as off-white solid.<br>1H NMR (300 MHz, CDCl3, d in ppm): 1.53 (s, 9H), 2.56-2.61 (m, 2H), 2.84-2.89 (m, 2H), 6.79 (d, 1H, J = 9.0 Hz), 7.25-7.27 (m, 2H). |
| Ex. 23b | tert-butyl 2-oxo-6-(tetramethyl-1,3,2-dioxaborolan-2-yl)-1,2,3,4-tetrahydroquinoline-1-carboxylate<br>Step 2: tert-butyl 6-bromo-3,4-dihydro-2-oxoquinoline-1(2H)-carboxylate Ex. 23a (6.00 g, 18.40 mmol) was dissolved in DMF (60 mL). Bis(pinacolato)diboron (5.60 g, 22.10 mmol) and potassium acetate (5.05 g, 51.50 mmol) were added and the resulting suspension was purged with N2. PdCl2(dppf)2 (450 mg, 0.55 mmol) was added and the mixture was heated at 90° C. for 16 h. After cooling to rt, the reaction was quenched with water. The aqueous layer was extracted with EtOAc. The organic layer was washed with brine, dried over MgSO4, filtered and the solution was concentrated to dryness. The crude material was purified by flash column chromatography on silica gel eluting with heptane and a gradient of heptane/EtOAc from [100:0] to [80:20]. The product fractions were combined and concentrated to dryness to afford tert-butyl 2-oxo-6-(tetramethyl-1,3,2-dioxaborolan-2-yl)-1,2,3,4-tetrahydroquinoline-1-carboxylate (4.61 g, 67%) as pale green oil, which solidified upon standing at rt.<br>1H NMR (300 MHz, CDCl3, d in ppm): 1.27 (s, 12H), 1.53 (s, 9H), 2.56-2.61 (m, 2H), 2.87-2.91 (m, 2H), 6.85 (d, 1H, J = 9.0 Hz), 7.56-7.60 (m, 2H). |
| Ex. 23c | tert-butyl 2-(2-oxo-1,2,3,4-tetrahydroquinolin-6-yl)acetate<br>Step 3: tert-butyl 2-oxo-6-(tetramethyl-1,3,2-dioxaborolan-2-yl)-1,2,3,4-tetrahydroquinoline-1-carboxylate Ex. 23b (3.60 g, 9.64 mmol) was dissolved in DMF (30 mL), water (8 mL) was added followed by sodium carbonate (2.04 g, 19.28 mmol) and tert-butylbromo-acetate (5.62 g, 28.90 mmol). The mixture was purged with nitrogen. PdCl2(dppf)2 (400 mg, 0.47 mmol) was added and the resulting suspension was heated under nitrogen atmosphere at 85° C. for 24 h. After cooling to rt, water and EtOAc were added to quench the reaction. The two phases were separated. The organic layer was washed with brine, dried over MgSO4, filtered and the solution was concentrated to dryness. The crude material was purified by silica gel column chromatography eluting with heptane and a gradient of heptane/EtOAc from [100:0] to [50:50]. The product fractions were combined and concentrated to dryness to afford an orange solid. The solid was triturated with Et2O, filtered and dried under vacuum to constant weight. The product was isolated as a white solid (324 mg, 13%). The BOC-protective group was lost during the reaction.<br>1H NMR (300 MHz, CDCl3, d in ppm): 1.40 (s, 9H), 2.40-2.45 (m, 2H), 2.82-2.87 (m, 2H), 3.44 (s, 2H), 8.79 (d, 1H, J = 8.0 Hz), 6.99-7.03 (m, 2H), 10.03 (s, 1H). |
| Ex. 23 | 2-(2-oxo-1,2,3,4-tetrahydroquinolin-6-yl)acetic acid<br>Step 4: the previously synthesized tert-butyl 2-(2-oxo-1,2,3,4-tetrahydroquinolin-6-yl)acetate Ex. 23c (320 mg, 1.24 mmol) was taken up in 4M HCl in dioxane (5 mL), some gas evolution was observed and the mixture was stirred at rt for 60 h. The mixture was concentrated to afford an off-white solid, Et2O was added and the solid was triturated to afford 2-(2-oxo-1,2,3,4-tetrahydroquinolin-6-yl)acetic acid (229 mg, 90%) as white solid.<br>1H NMR (300 MHz, DMSO-d6, d in ppm): 2.40-2.45 (m, 2H), 2.82-2.87 (m, 2H), 3.46 (s, 2H), 6.78 (d, 1H, J = 6.0 Hz), 7.01 (d, 1H, J = 6.0 Hz), 7.05 (s, 1H), 10.03 (s, 1H), 12.25 (br(s), 1H). |

Intermediate Ex.24: 2-(1-methyl-2-oxo-2,3-dihydro-1H-indol-5-yl)acetic acid (FIG. 1AI)

TABLE 1.9

| Cpd. | Starting compounds, Reaction conditions and purification, Yield, appearance, ¹H NMR (solvent) data |
|---|---|
| Ex. 24a<br>Ex. 24b<br>Ex. 24c | methyl 2-(1-methyl-2-oxo-2,3-dihydro-1H-indol-5-yl)acetate<br>and<br>methyl 2-(1,3-dimethyl-2-oxo-2,3-dihydro-1H-indol-5-yl)acetate<br>and<br>methyl 2-(1,3,3-trimethyl-2-oxo-2,3-dihydro-1H-indol-5-yl)acetate<br>Step 1: to a solution of 2-(2-oxo-2,3-dihydro-1H-indol-5-yl)acetic acid Ex. 14 (1 g, 5.23 mmol) in acetonitrile (40 mL) and DMF (10 mL) was added K2CO3 (2.89 g, 20.92 mmol) followed by iodomethane (1.30 mL, 20.92 mmol). The reaction mixture was heated at 70° C. for 3 h. Additional K2CO3 (2 equiv) and iodomethane (1 equiv) were added and the solution was stirred for additional 1 h 30 at 70° C. Water was added to quench the reaction. The aqueous layer was extracted with EtOAc. The combined organic layers were dried over MgSO4, filtered and the solution was concentrated under reduced pressure. The crude material was diluted in acetonitrile (12 mL) in microwave srew cap vial and K2CO3 (3 equiv) followed by iodomethane (3 equiv) were added. The reaction was heated under microwave irradiation at 100° C. for 30 min. The suspension was filtered through pad of Celite, the filtrate was concentrated to dryness. The residue was purified by silica gel column chromatography eluting with cyclohexane/EtOAc (7:3) affording:<br>Ex. 24a: methyl 2-(1-methyl-2-oxo-2,3-dihydro-1H-indol-5-yl)acetate (360 mg, 31%), 1H NMR (300 MHz, CDCl3, d in ppm): 3.21 (s, 3H), 3.53 (s, 2H), 3.61 (s, 2H), 3.71 (s, 3H), 6.78 (d, 1H, J = 8.4 Hz), 7.17-7.21 (m, 2H);<br>Ex. 24b: methyl 2-(1,3-dimethyl-2-oxo-2,3-dihydro-1H-indol-5-yl)acetate (52 mg, 4%), 1H NMR (300 MHz, CDCl3, d in ppm): 1.48 (d, 3H, J = 7.7 Hz), 3.20 (s, 3H), 3.45 (q, 1H, J = 7.6 Hz), 3.62 (s, 2H), 3.71 (s, 3H), 6.78 (d, 1H, J = 8.2 Hz), 7.17-7.21 (m, 2H);<br>Ex. 24c: methyl 2-(1,3,3-trimethyl-2-oxo-2,3-dihydro-1H-indol-5-yl)acetate (80 mg, 6%), 1H NMR (300 MHz, CDCl3, d in ppm): 1.38 (s, 6H), 3.21 (s, 3H), 3.62 (s, 2H), 3.71 (s, 3H), 6.81 (d, 1H, J = 8.0 Hz), 7.13 (d, 1H, J = 1.7 Hz), 7.20 (dd, 1H, J = 7.9 Hz, J = 1.8 Hz). |
| Ex. 24 | 2-(1-methyl-2-oxo-2,3-dihydro-1H-indol-5-yl)acetic acid<br>Step 2: methyl 2-(1-methyl-2-oxo-2,3-dihydro-1H-indol-5-yl)acetate Ex. 24a (75 mg, 0.34 mmol) was dissolved in MeOH/THF (2 mL, 1:1) and NaOH 2N (257 μL, 0.51 mmol) was added. The reaction mixture was heated at 50° C. for 1 h. The solvents were removed under reduced pressure. Water was added followed by 1N citric acid until pH = 5 was reached. The aqueous solution was extracted with EtOAc. The organic layer was dried over MgSO4, filtered and the solution was concentrated under reduced pressure to afford 2-(1-methyl-2-oxo-2,3-dihydro-1H-indol-5-yl)acetic acid (60 mg, 86%) as white solid.<br>1H NMR (300 MHz, DMSO-d6, d in ppm): 3.09 (s, 3H), 3.51 (s, 2H), 3.52 (s, 2H), 6.89 (d, 1H, J = 8.5 Hz), 7.13-7.15 (m, 2H), 12.24 (br(s), 1H). |

Intermediate Ex.25: 2-(3-hydroxy-1,3-dimethyl-2-oxo-2,3-dihydro-1H-indol-5-yl)acetic acid (FIG. 1AI)

TABLE 1.10

| Cpd. | Starting compounds, Reaction conditions and purification, Yield, appearance, ¹H NMR (solvent) data |
|---|---|
| Ex. 25 | 2-(3-hydroxy-1,3-dimethyl-2-oxo-2,3-dihydro-1H-indol-5-yl)acetic acid<br>The previously synthesized methyl 2-(1,3-dimethyl-2-oxo-2,3-dihydro-1H-indol-5-yl)acetate Ex. 24b (50 mg, 0.21 mmol) was dissolved in MeOH (2 mL) and NaOH 2N (161 μL, 0.32 mmol) was added. The reaction mixture was heated at 50° C. for 1 h. The solvents were removed under reduced pressure. Water was added followed by 1N citric acid until pH = 5 was reached. The aqueous solution was extracted with EtOAc. The organic layer was dried over MgSO4, filtered and the solution was concentrated under reduced pressure to afford 2-(3-hydroxy-1,3-dimethyl-2-oxo-2,3-dihydro-1H-indol-5-yl)acetic acid (50 mg, 99%) as white solid.<br>1H NMR (300 MHz, DMSO-d6, d in ppm): 1.36 (s, 3H), 3.07 (s, 3H), 3.53 (s, 2H), 5.91 (s, 1H), 6.91 (d, 1H, J = 7.9 Hz), 7.17 (dd, 1H, J = 8.0Hz, J = 1.7 Hz), 7.23 (d, 1H, J = 1.5 Hz), 12.18 (br(s), 1H). |

Intermediate Ex.26: 2-(1,3,3-trimethyl-2-oxo-2,3-dihydro-1H-indol-5-yl)acetic acid (FIG. 1AI)

TABLE 1.11

| Cpd. | Starting compounds, Reaction conditions and purification, Yield, appearance, $^1$H NMR (solvent) data |
|---|---|
| Ex. 26 | 2-(1,3,3-trimethyl-2-oxo-2,3-dihydro-1H-indol-5-yl)acetic acid<br>The previously synthesized methyl 2-(1,3,3-trimethyl-2-oxo-2,3-dihydro-1H-indol-5-yl)acetate Ex. 24c (75 mg, 0.30 mmol) was dissolved in MeOH/THF (2 mL, 1:1) and NaOH 2N (227 µL, 0.46 mmol) was added. The reaction mixture was heated at 50° C. for 1 h. The solvents were removed under reduced pressure. Water was added followed by 1N citric acid until pH = 5 was reached. The aqueous solution was extracted with EtOAc. The organic layer was dried over MgSO4, filtered and the solution was concentrated under reduced pressure to afford 2-(1,3,3-trimethyl-2-oxo-2,3-dihydro-1H-indol-5-yl)acetic acid (60 mg, 85%) as pale yellow oil.<br>1H NMR (300 MHz, DMSO-d6, d in ppm): 1.24 (s, 6H), 3.11 (s, 3H), 3.50 (s, 3H), 6.93 (d, 1H, J = 7.9 Hz), 7.14 (dd, 1H, J = 7.9 Hz, J = 1.7 Hz), 7.21 (d, 1H, J = 1.4 Hz). |

Intermediate Ex.27: 2-(2-methanesulfonyl-2,3-dihydro-1H-isoindol-5-yl)acetic acid (FIG. 1AJ)

TABLE 1.12

| Cpd. | Starting compounds, Reaction conditions and purification, Yield, appearance, $^1$H NMR (solvent) data |
|---|---|
| Ex. 27a | 5-bromo-2-methanesulfonyl-2,3-dihydro-1H-isoindole<br>Step 1: Et3N (4.22 mL, 30.30 mmol) was added to the mixture of 5-bromoisoindoline hydrochloride (2 g, 10.10 mmol) in CH2Cl2 (35 mL) at 0° C. Then, methanesulfonyl chloride (860 µL, 11.11 mmol) was added to the reaction mixture. The mixture reaction was stirred at rt for 16 h. The solution was diluted with EtOAc and water. After phase separation, the combined organic layers were washed with brine, dried over MgSO4, filtered and the solution was concentrated to dryness. The solid was triturated with diethyl ether and filtered-off to afford the desired product as pale brown solid (2.10 g, 75%). |
| Ex. 27b | methyl 2-(2-methanesulfonyl-2,3-dihydro-1H-isoindol-5-yl)acetate<br>Step 2: 5-bromo-2-methanesulfonyl-2,3-dihydro-1H-isoindole Ex. 27a (1.95 g, 7.06 mmol), methyl acetoacetate (2.28 mL, 21.18 mmol) and potassium phosphate (6.00 g, 28.24 mmol) were charged to a screw cap tube, toluene (30 mL) was added and the mixture was purged with nitrogen for 5 min. Then Pd(OAc)2 (79 mg, 0.35 mmol) followed by di-tert-butyl X-Phos (302 mg, 0.71 mmol) were added and the tube was closed under nitrogen atmosphere. The reaction mixture was stirred at 80° C. for 3 h, then at 120° C. for 16 h. The residue was diluted with EtOAc and water. After phase separation, the combined organic layers were washed with brine, dried over MgSO4, filtered and the solution was concentrated to dryness. The crude material was purified by flash chromatography on silica gel eluting with heptane and a gradient of heptane/EtOAc from [100:0] to [50:50]. The desired fractions were combined and concentrated to obtain methyl 2-(2-methanesulfonyl-2,3-dihydro-1H-isoindol-5-yl)acetate (1.6 g, 84%) as yellow solid. |
| Ex. 27 | 2-(2-methanesulfonyl-2,3-dihydro-1H-isoindol-5-yl)acetic acid<br>Step 3: lithium hydroxide monohydrate (250 mg, 5.94 mmol) was added to the mixture of methyl 2-(2-methanesulfonyl-2,3-dihydro-1H-isoindol-5-yl)acetate Ex. 27b (1.6 g, 5.94 mmol) in THF (18 mL) and water (9 mL) at 0° C. Then, the reaction mixture was stirred at rt for 18 h. EtOAc and water were added to quench the reaction. The two phases were partitioned. 1M HCl was added to the aqueous layer under vigorous stirring until pH = 4 was reached. The aqueous layer was extracted with EtOAc. The combined organic layers were dried over MgSO4 and the solution was concentrated to dryness. The crude material was purified by silica gel column chromatography eluting with heptane and a gradient of heptane/EtOAc from [100:0] to [0:100]. The product fractions were combined and concentrated to dryness. The solid was triturated with diethyl ether and filtered-off. Final drying to constant weight was carried out under vacuum at 65° C. to give 2-(2-methanesulfonyl-2,3-dihydro-1H-isoindol-5-yl)acetic acid (455 mg, 30%).<br>1H NMR (300 MHz, DMSO-d6, d in ppm): 2.97 (s, 3H), 3.58 (s, 2H), 4.61 (s, 4H), 7.18-7.28 (m, 3H), 12.4 (br(s), 1H). |

Intermediate Ex.28: 2-(2-methanesulfonyl-2,3-di-
hydro-1H-isoindol-4-yl)acetic acid (FIG. 1AK)

TABLE 1.13

| Cpd. | Starting compounds, Reaction conditions and purification, Yield, appearance, $^1$H NMR (solvent) data |
| --- | --- |
| Ex. 28a | 4-bromo-2-methanesulfonyl-2,3-dihydro-1H-isoindole<br>Step 1: Et3N (2.51 mL, 18.00 mmol) was added to a solution of 4-bromo-isoindoline hydrochloride (1.41 g, 6.00 mmol) in CH2Cl2 (30 mL) at 0° C. Then, methanesulfonyl chloride (510 µL, 6.60 mmol) was added to the reaction mixture. The solution was stirred at rt for 16 h. The solvent was removed under reduced pressure. The solid was dissolved with EtOAc and water. After phase separation, the combined organic layers were washed with brine, dried over MgSO4, filtered and the solution was concentrated to dryness. The solid was purified by silica gel column chromatography eluting with a gradient of heptane/EtOAc from [100:0] to [50:50]. The product fractions were combined and concentrated to dryness to afford the desired product (918 mg, 55%). |
| Ex. 28b | tert-butyl 2-(2-methanesulfonyl-2,3-dihydro-1H-isoindol-4-yl)acetate<br>Step 2: 4-bromo-2-methanesulfonyl-2,3-dihydro-1H-isoindole Ex. 28a (550 mg, 1.99 mmol), the previously synthesized tert-butyl 2-(bromozincio)acetate (7 mL, 5.98 mmol) and dry THF (5 mL) were placed in flask, the mixture was degassed by nitrogen bubbling for 5 min. Then Pd2(dba)3 (182 mg, 0.20 mmol) and XPhos (190 mg, 0.40 mmol) were incorporated and the reaction mixture was stirred at 75° C. for 16 h. The reaction mixture was concentrated to dryness. The residue was diluted with EtOAc and water. The two phases were separated. The organic layer was dried over MgSO4, filtered and the solution was concentrated under reduced pressure. The crude material was purified twice by flash chromatography on silica gel eluting with heptane and a gradient of heptane/EtOAc from [100:0] to [70:30]. The desired fractions were combined and concentrated to obtain tert-butyl 2-(2-methanesulfonyl-2,3-dihydro-1H-isoindol-4-yl)acetate (560 mg, 90%) as yellow solid. |
| Ex. 28 | 2-(2-methanesulfonyl-2,3-dihydro-1H-isoindol-4-yl)acetic acid<br>Step 3: tert-butyl 2-(2-methanesulfonyl-2,3-dihydro-1H-isoindol-4-yl)acetate Ex. 28b (560 mg, 1.80 mmol) was dissolved in CH2Cl2 (5 mL) and then was added 4M HCl in dioxane (1.8 mL, 7.20 mmol). The reaction mixture was stirring for 20 h at rt. The solid formed was collected by filtration, washed with diethyl ether and dried under vacuum until constant weight to afford 2-(2-methanesulfonyl-2,3-dihydro-1H-isoindol-4-yl)acetic acid (312 mg, 60%) as off-white solid.<br>1H NMR (300 MHz, DMSO-d6, d in ppm): 2.96 (s, 3H), 3.60 (s, 2H), 4.62 (m, 2H), 4.66 (m, 2H), 7.16-7.31 (m, 3H), 12.47 (br(s), 1H). |

Intermediate Ex.29: 2-(1-oxo-2,3-dihydro-1H-inden-
5-yl)acetic acid (FIG. 1AL)

TABLE 1.14

| Cpd. | Starting compounds, Reaction conditions and purification, Yield, appearance, $^1$H NMR (solvent) data |
| --- | --- |
| Ex. 29a | methyl 2-(1-oxo-2,3-dihydro-1H-inden-5-yl)acetate<br>Step 1: 5-bromo-2,3-dihydro-1H-inden-1-one (500 mg, 2.37 mmol), methyl 3-oxobutanoate (767 µL, 7.11 mmol) and potassium phosphate (2.01 g, 9.48 mmol) were diluted with toluene (15 mL). The solution was degassed with N2 for 15 min. Pd(OAc)2 (27 mg, 0.12 mmol) followed by di-tert-butyl X-Phos (101 mg, 0.24 mmol). The reaction mixture was heated at 120° C. for 18 h. The suspension was filtered through a pad of Celite and washed with EtOAc. The filtrate was concentrated to dryness and purified by silica gel column chromatography using cyclohexane/EtOAc (1:1) as eluent. The desired fractions were combined and concentrated under reduced pressure to obtain methyl 2-(1-oxo-2,3-dihydro-1H-inden-5-yl)acetate (361 mg, 75%) as colourless oil.<br>1H NMR (300 MHz, DMSO-d6, d in ppm): 2.60-2.64 (m, 2H), 3.05-3.10 (m, 2H), 3.62 (s, 3H), 3.81 (s, 2H), 7.29-7.36 (m, 1H), 7.45-7.47 (m, 1H), 7.58 (d, 1H, J = 8.1 Hz). |
| Ex. 29 | 2-(1-oxo-2,3-dihydro-1H-inden-5-yl)acetic acid<br>Step 2: methyl 2-(1-oxo-2,3-dihydro-1H-inden-5-yl)acetate Ex. 29a (360 mg, 1.76 mmol) was dissolved in MeOH (10 mL) and 2N NaOH (1.06 mL, 2.12 mmol) was added to the solution. The reaction mixture was stirred at rt for 1 h. The solvents were removed under reduced pressure. Et2O and water were added to the residue. The two phases were partitionated. The aqueous layer was acidified with 1N citric acid until pH = 5 was reached and then extracted with EtOAc. The combined organic layers were dried over MgSO4, filtered and the solution was concentrated to dryness to give 2-(1-oxo-2,3-dihydro-1H-inden-5-yl)acetic acid (290 mg, 87%) as white solid.<br>1H NMR (300 MHz, DMSO-d6, d in ppm): 2.60 (t, 2H, J = 5.8 Hz), 3.07 (t, 2H, |

TABLE 1.14-continued

| Cpd. | Starting compounds, Reaction conditions and purification, Yield, appearance, $^1$H NMR (solvent) data |
|---|---|
| | J = 6.0 Hz), 3.70 (s, 2H), 7.30 (d, 1H, J = 7.9 Hz), 7.45 (s, 1H), 7.57 (d, 1H, J = 7.8 Hz), 12.42 (br(s), 1H). |

Intermediate Ex.30: 2-(7-methyl-2-oxo-2,3-dihydro-1H-indol-5-yl)acetic acid (FIG. 1AM)

TABLE 1.15

| Cpd. | Starting compounds, Reaction conditions and purification, Yield, appearance, $^1$H NMR (solvent) data |
|---|---|
| Ex. 30a | 2-{4-[2-(N-hydroxyimino)acetamido]-3-methylphenyl}acetic acid<br>Step 1: sodium sulfate (992 mg, 6.99 mmol) was added to 2,2,2-trichloroacetaldehyde (755 mg, 5.12 mmol) dissolved in water (5 mL). IThe reaction mixture was stirred at rt for 15 min. Ethyl 2-(4-amino-3-methylphenyl)acetate (900 mg, 4.66 mmol) dissolved in 1N HCl (5 mL) was added dropwise followed by hydroxylamine hydrochloride (809 mg, 11.64 mmol) dissolved in water (5 mL). The resulting solution was heated at 80° C. for 2 h. After cooling to rt, water was added to quench the reaction and the aqueous layer was extracted with EtOAc. The combined organic layer was dried over MgSO4, filtered and the solution was concentrated under reduced pressure. The compound was used as such in the next step. |
| Ex. 30b | 2-(7-methyl-2,3-dioxo-2,3-dihydro-1H-indol-5-yl)acetic acid<br>Step 2: 2-{4-[2-(N-hydroxyimino)acetamido]-3-methylphenyl}acetic acid Ex. 30a was dissolved in conc. H2SO4 (3 mL) and the solution was heated at 50° C. for 2 h. The reaction mixture was poured onto ice. Brine was added and the aqueous solution was extracted with EtOAc. The combined organic layers were dried over MgSO4, filtered and the solution was concentrated under reduced pressure to afford 2-(7-methyl-2,3-dioxo-2,3-dihydro-1H-indol-5-yl)acetic acid (505 mg, 50% over two steps) as orange solid. The compound was used in the next step without further purification.<br>1H NMR (300 MHz, DMSO-d6, d in ppm): 2.17 (s, 3H), 3.52 (s, 2H), 7.23 (s, 1H), 7.30 (s, 1H), 11.05 (s, 1H). |
| Ex. 30 | 2-(7-methyl-2-oxo-2,3-dihydro-1H-indol-5-yl)acetic acid<br>Step 3: to a solution of 2-(7-methyl-2,3-dioxo-2,3-dihydro-1H-indol-5-yl)acetic acid Ex. 30b (505 mg, 2.30 mmol) in MeOH was added hydrazine 50% in water (162 mg, 2.53 mmol). The reaction mixture was heated at 80° C. overnight. After cooling to rt, Et3N (1.921 mL, 13.82 mmol) was added. The solution was heated under microwave irradiation at 140° C. for 1 h 30. Solvent was removed under reduced pressure. The residue was triturated in 1N citric acid. The solid formed was filtered, washed with water and dried under vacuum until constant weight to afford 2-(7-methyl-2-oxo-2,3-dihydro-1H-indol-5-yl)acetic acid (305 mg, 65% over two steps) as pale brown solid.<br>1H NMR (300 MHz, DMSO-d6, d in ppm): 2.16 (s, 3H), 3.43 (s, 2H), 3.44 (s, 2H), 6.85 (s, 1H), 6.90 (s, 1H), 10.36 (s, 1H), 12.12 (br(s), 1H). |

Intermediate Ex.31: 2-[2-oxo-3-(propan-2-ylidene)-2,3-dihydro-1H-indol-5-yl]acetic acid (FIG. 1AN)

TABLE 1.16

| Cpd. | Starting compounds, Reaction conditions and purification, Yield, appearance, $^1$H NMR (solvent) data |
|---|---|
| Ex. 31a | tert-butyl 2-{5-[2-(tert-butoxy)-2-oxoethyl]-2-nitrophenyl}acetate<br>Step 1: 2,4-dibromo-1-nitrobenzene (3.0 g, 10.68 mmol), the previously synthesized tert-butyl 2-(bromozincio)acetate (65 mL, 53.39 mmol) and dry THF (10 mL) were placed in flask, the mixture was degassed by nitrogen bubbling for 5 min. Then XPhos (1.01 g, 2.14 mmol) and Pd2(dba)3 (978 mg, 1.07 mmol) were incorporated and the reaction mixture was stirred at 75° C. for 16 h. The solution was concentrated and the residue was diluted with EtOAc/H2O and the phases were separated. The organic layer was dried over MgSO4, filtered and the solution was concentrated to dryness. The crude material was purified by flash chromatography on silica gel eluting with heptane and a gradient of heptane/EtAc from [100:0] to [50:50]. The desired fractions were combined and concentrated to obtain tert-butyl 2-{5-[2-(tert-butoxy)-2-oxoethyl]-2-nitrophenyl}acetate (2.16 g, 58%) as yellow oil. |
| Ex. 31b | tert-butyl 2-{2-amino-5-[2-(tert-butoxy)-2-oxoethyl]phenyl}acetate<br>Step 2: tert-butyl 2-{5-[2-(tert-butoxy)-2-oxoethyl]-2-nitrophenyl}acetate Ex. 31a (2.16 g, 6.15 mmol) was dissolved in MeOH (120 mL). Then Pd/C 10% (720 mg) |

TABLE 1.16-continued

| Cpd. | Starting compounds, Reaction conditions and purification, Yield, appearance, $^1$H NMR (solvent) data |
|---|---|
| | was added and the reaction mixture was stirrred at rt for 20 h under hydrogen. The solution was filtered over a pad of Celite, washed with EtOAc and concentrated to afford tert-butyl 2-{2-amino-5-[2-(tert-butoxy)-2-oxoethyl]phenyl}acetate (1.90 g, 96%) as orange solid. |
| Ex. 31c | tert-butyl 2-(2-oxo-2,3-dihydro-1H-indol-5-yl)acetate<br>Step 3: tert-butyl 2-{2-amino-5-[2-(tert-butoxy)-2-oxoethyl]phenyl}acetate Ex. 31b (1.90 g, 5.97 mmol) was dissolved in 2-propanol (15 mL). Then glacial acetic acid (3.42 mL, 59.70 mmol) was added, the reaction mixture was heated in a sealed tube at 95° C. for 16 h. Excess of acetic acid was neutralized with NaHCO3 and the solution was concentrated under reduced pressure. The residue was dissolved in EtOAc and washed with sat. NaHCO3. The organic layer was dried over MgSO4, filtered and the solution was concentrated to dryness. The crude material was purified by flash column chromatography on silica gel eluting with heptane/EtOAc [40:60]. Column fractions were combined and concentrated to afford tert-butyl 2-(2-oxo-2,3-dihydro-1H-indol-5-yl)acetate (1.40 g, 95%) as red solid. |
| Ex. 31d | tert-butyl 2-[2-oxo-3-(propan-2-ylidene)-2,3-dihydro-1H-indol-5-yl]acetate<br>Step 4: tert-butyl 2-(2-oxo-2,3-dihydro-1H-indol-5-yl)acetate Ex. 31c (250 mg, 1.01 mmol) was dissolved in acetone (2.5 mL) and absolute EtOH (2.5 mL). Then, piperidine (400 µL, 4.04 mmol) was added, the reaction mixture was stirred at rt for 5 h. The solvents were removed under reduced pressure. EtOAc and water was added to the residue. The organic layer was separated, dried over MgSO4, filtered and the solution was concentrated to dryness. The crude material was purified by silica gel column chromatography eluting with heptane/EtOAc using a gradient from [100:0] to [50:50]. The product fractions were concentrated to dryness to afford tert-butyl 2-[2-oxo-3-(propan-2-ylidene)-2,3-dihydro-1H-indol-5-yl]acetate (223 mg, 77%) as brown oil. |
| Ex. 31 | 2-[2-oxo-3-(propan-2-ylidene)-2,3-dihydro-1H-indol-5-yl]acetic acid<br>Step 5: tert-butyl 2-[2-oxo-3-(propan-2-ylidene)-2,3-dihydro-1H-indol-5-yl]acetate Ex. 31d (270 mg, 1.01 mmol) was dissolved in CH2Cl2 (4 mL). Then, 4M HCl in dioxane (1.5 mL, 6 mmol) was added dropwise. The mixture of reaction was stirred at rt overnight. Solvent was removed under reduced pressure. The solid was triturated in diethyl ether and filtered to give 2-[2-oxo-3-(propan-2-ylidene)-2,3-dihydro-1H-indol-5-yl]acetic acid (126 mg, 50%) as yellow solid.<br>1H NMR (300 MHz, DMSO-d6, d in ppm): 2.32 (s, 3H), 3.54 (s, 2H), 6.75 (d, 1H), 7.05 (d, 1H), 7.44 (s, 1H), 10.38 (s, 1H), 12.24 (s, 1H). |

Intermediate Ex.33: 1-(2-methanesulfonyl-2,3-dihydro-1H-isoindol-5-yl)cyclopropane-1-carboxylic acid (FIG. 1AO)

TABLE 1.17

| Cpd. | Starting compounds, Reaction conditions and purification, Yield, appearance, $^1$H NMR (solvent) data |
|---|---|
| Ex. 33a | bromo[1-(methoxycarbonyl)cyclopropyl]zinc<br>Step 1: to a solution of zinc dust (2.0 g, 30.26 mmol) in dry THF (25 mL) at rt was added 1,2-dibromoethane (434 µL, 5.04 mmol) under N2 atmosphere. The reaction mixture was stirred at 70° C. for 1 min and cooled down to rt. This procedure was repeated 5 times. Chlorotrimethylsilane (256 µL, 2.02 mmol) was added and the resulting suspension was stirred at rt for 15 min. It was the heated to 65° C. and a few drops of methyl 1-bromocyclopropane-1-carboxylate were added. Methyl 1-bromocyclopropane-1-carboxylate (2.61 mL, 25.22 mmol) dissolved in dry THF (5 mL) was added at such a rate that reflux was maintained. Upon completion of addition, the reaction mixture was refluxed for an additional 20 min and allowed to cool down to rt. The zinc was allowed to settle and the supernatant was used further. Complete conversion was assumed. |
| Ex. 33b | 5-bromo-2-methanesulfonyl-2,3-dihydro-1H-isoindole<br>Step 2: to a solution of 5-bromo-isoindoline hydrochloride (450 mg, 1.92 mmol) in CH2Cl2 (8 mL) was added Et3N (801 µL, 5.76 mmol). The reaction mixture was stirred until all material was totally dissolved and then cooled down to 0° C. Methanesulfonyl chloride (161 µL, 2.11 mmol) was added dropwise to the solution and the reaction mixture was stirred at rt for 16 h. The solvent was removed under reduced pressure. The residue was re-dissolved in EtOAc and washed with H2O. The organic layer was dried over MgSO4, filtered and the solution was concentrated to dryness. The crude material was purified by flash silica gel column chromatography eluting with a gradient of CH2Cl2/MeOH from [100:0] to [90:10] to afford 5-bromo-2-methanesulfonyl-2,3-dihydro-1H-isoindole (480 mg, 91%) as white solid. |
| Ex. 33c | methyl 1-(2-methanesulfonyl-2,3-dihydro-1H-isoindol-5-yl)cyclopropane-1-carboxylate |

TABLE 1.17-continued

| Cpd. | Starting compounds, Reaction conditions and purification, Yield, appearance, $^1$H NMR (solvent) data |
|---|---|
| | Step 3: 5-bromo-2-methanesulfonyl-2,3-dihydro-1H-isoindole Ex. 33b (480 mg, 1.74 mmol) and bromo[1-(methoxycarbonyl)cyclopropyl]zinc Ex. 33a (6.5 mL, 5.21 mmol) were dissolved in dry THF (5 mL) and the solution was degassed by nitrogen bubbling for 5 min. Then, XPhos (166 mg, 0.35 mmol) and Pd2(dba)3 (159 mg, 0.17 mmol) were incorporated and the reaction mixture was stirred at 75° C. for 16 h. The reaction mixture was concentrated to dryness and the residue was diluted with EtOAc/H2O. The two layers were partitionated and the organic layer was dried over MgSO4, filtered and the solution was concentrated under reduced pressure. The crude material was purified by flash silica gel column chromatography eluting with a gradient of heptane/EtOAc from [100:0] to [50:50]. The desired fractions were combined and concentrate to obtain methyl 1-(2-methanesulfonyl-2,3-dihydro-1H-isoindol-5-yl)cyclopropane-1-carboxylate (285 mg, 56%) as white solid. |
| Ex. 33 | 1-(2-methanesulfonyl-2,3-dihydro-1H-isoindol-5-yl)cyclopropane-1-carboxylic acid<br>Step 4: methyl 1-(2-methanesulfonyl-2,3-dihydro-1H-isoindol-5-yl)cyclopropane-1-carboxylate Ex. 33c (285 mg, 0.96 mmol) was dissolved in THF/H2O (20 mL/5 mL). Lithium hydroxide monohydrate (81 mg, 1.93 mmol) was added to the solution and the reaction mixture was stirred overnigth at rt. The solvent was removed under reduced pressure. Water was added and pH was adjusted to pH 4 with conc. HCl. The aqueous solution was extracted with EtOAc. The combined organic layers were dried over MgSO4, filtered and the solution was concentrated to dryness. The residue was triturated with tert-butyl methyl ester and then filtered-off to give 1-(2-methanesulfonyl-2,3-dihydro-1H-isoindol-5-yl)cyclopropane-1-carboxylic acid (217 mg, 80%) as white solid.<br>1H NMR (300 MHz, DMSO-d6, d in ppm): 1.12 (d, 2H, J = 2.4 Hz), 1.45 (d, 2H, J = 2.4 Hz), 2.97 (s, 3H), 4.60 (s, 4H), 7.27 (m, 3H). |

Intermediate Ex.34: 2-[3-(2-hydroxyethyl)-1H-indol-5-yl]acetic acid (FIG. 1AP)

TABLE 1.18

| Cpd. | Starting compounds, Reaction conditions and purification, Yield, appearance, $^1$H NMR (solvent) data |
|---|---|
| Ex. 34a | 5-bromo-3-{2-[(tert-butyldimethylsilyl)oxy]ethyl}-1H-indole<br>Step 1: t-butyldimethylsilyl chloride (3.01 g, 20 mmol) was added to a solution of 5-bromotryptophol (4.00 g, 16.65 mmol) and triethylamine (3.23 mL, 23.31 mmol) in CH2Cl2 (45 mL) at 0° C. under N2 atmosphere. The mixture was allowed to reach rt and stirred for 15 h. The reaction was quenched by addition of sat. NH4Cl and the product was extracted with EtOAc. The organic layer was washed with water and brine, dried over MgSO4, filtered and the solution was concentrated to dryness. The residue was purified by flash silica gel column chromatography eluting with heptane and EtOAc. The desired fractions were combined and concentrated to obtain 5-bromo-3-{2-[(tert-butyldimethylsilyl)oxy]ethyl}-1H-indole (5.29 g, 89%). |
| Ex. 34b | 5-bromo-3-{2-[(tert-butyldimethylsilyl)oxy]ethyl}-1-(4-methylbenzenesulfonyl)-1H-indole<br>Step 2: 5-bromo-3-{2-[(tert-butyldimethylsilyl)oxy]ethyl}-1H-indole Ex. 34a (5.29 g, 14.92 mmol) was dissolved in DMF (45 mL). The mixture was cooled to 0° C. and p-toluenesulfonyl chloride (3.41 g, 17.90 mmol) was added. The mixture was stirred at 0° C. for 20 min, then sodium hydride (60% in mineral oil), (660 mg, 16.41 mmol) was added in one portion and the mixture was allowed to warm up to rt and stirred for 2 h. The reaction was quenched by addition of water and the crude was diluted with EtOAc. The organic layer was washed with water and brine, dried over MgSO4, filtered and the solution was concentrated to dryness. The residue was purified by flash silica gel column chromatography with heptane and EtOAc. The desired fractions were combined and concentrated to obtain 5-bromo-3-{2-[(tert-butyldimethylsilyl)oxy]ethyl}-1-(4-methylbenzenesulfonyl)-1H-indole (4.81 g, 63%). |
| Ex. 34c | methyl 2-(3-{2-[(tert-butyldimethylsilyl)oxy]ethyl}-1-(4-methylbenzenesulfonyl)-1H-indol-5-yl)acetate<br>Step 3: 5-bromo-3-{2-[(tert-butyldimethylsilyl)oxy]ethyl}-1-(4-methylbenzenesulfonyl)-1H-indole Ex. 34b (4.81 g, 9.45 mmol), methyl acetoacetate (3.1 mL, 28.35 mmol) and potassium phosphate (8.10 g, 37.80 mmol) were charged to a screw cap tube, toluene (100 mL) was added and the mixture was purged with nitrogen for 5 min. Then, Pd(OAc)2 (110 mg, 0.47 mmol) and di-tert-butyl X-Phos (400 mg, 0.94 mmol) were added and the tube was closed under N2 atmosphere. The reaction mixture was stirred at 120° C. for 15 h. After cooling EtOAc and water were added to the reaction mixture. The two phases were separated, washed with brine, dried over MgSO4, filtered and the solution was concentrated to dryness. The resulting oil was purified by flash |

TABLE 1.18-continued

| Cpd. | Starting compounds, Reaction conditions and purification, Yield, appearance, $^1$H NMR (solvent) data |
|---|---|
| | silica gel column chromatography eluting with heptane and EtOAc. The desired fractions were combined and concentrated to obtain methyl 2-(3-{2-[(tert-butyldimethylsilyl)oxy]ethyl}-1-(4-methylbenzenesulfonyl)-1H-indol-5-yl)acetate (2.02 g, 42%). |
| Ex. 34d | methyl 2-[3-(2-hydroxyethyl)-1-(4-methylbenzenesulfonyl)-1H-indol-5-yl]acetate<br>Step 4: tetrabutylammonium fluoride (1M in THF), (6.03 mL, 6.03 mmol) was added to a solution of methyl 2-(3-{2-[(tert-butyldimethylsilyl)oxy]ethyl}-1-(4-methylbenzenesulfonyl)-1H-indol-5-yl)acetate Ex. 34c (2.02 g, 4.02 mmol) dissolved in THF (12 mL). The mixture was stirred at rt for 3 h. The reaction was diluted with EtOAc and washed with water and then brine. The organic layer was dried over MgSO4, filtered and the solution was concentrated to dryness. The residue was purified by flash silica gel column chromatography eluting with heptane and EtOAc. The desired fractions were combined and concentrated to obtain methyl 2-[3-(2-hydroxyethyl)-1-(4-methylbenzenesulfonyl)-1H-indol-5-yl]acetate (1.18 g, 75%). |
| Ex. 34e | methyl 2-[3-(2-hydroxyethyl)-1H-indol-5-yl]acetate<br>Step 5: methyl 2-[3-(2-hydroxyethyl)-1-(4-methylbenzenesulfonyl)-1H-indol-5-yl]acetate Ex. 34d (1.18 g, 3.05 mmol) was added to a solution of magnesium (370 mg, 15.20 mmol) in dry MeOH (20 mL). The suspension was stirred at rt overnight. The reaction was diluted with CH2Cl2 and washed with 0.5N HCl, sat. NaHCO3 and brine. The organic layer was dried over MgSO4, filtered and the solution was concentrated under reduced pressure. The residue was purified by flash silica gel column chromatography eluting with heptane and EtOAc. The concentration of the appropriate fractions afforded pure methyl 2-[3-(2-hydroxyethyl)-1H-indol-5-yl]acetate (570 mg, 80%). |
| Ex. 34 | 2-[3-(2-hydroxyethyl)-1H-indol-5-yl]acetic acid<br>Step 6: methyl 2-[3-(2-hydroxyethyl)-1H-indol-5-yl]acetate Ex. 34e (570 mg, 2.44 mmol) was dissolved in THF/H2O (8 mL/2 mL) and lithium hydroxide monohydrate (310 mg, 7.32 mmol) was added at 0° C. Then, the reaction mixture was allowed to warm up and stirred at rt for 3 h. The reaction was acidified by addition of 1N HCl and the product was extracted with CH2Cl2. The organic layer was dried over MgSO4, filtered and the solution was concentrated to dryness. The residue was purified by flash silica gel column chromatography eluting with CH2Cl2 and MeOH. After evaporation of the appropriate fractions, the resulting solid was triturated in CH2Cl2 and then filtered to afford 2-[3-(2-hydroxyethyl)-1H-indol-5-yl]acetic acid as a white solid (320 g, 60%).<br>1H NMR (300 MHz, DMSO-d6, d in ppm): 2.81 (t, 2H), 3.57 (s, 2H), 3.63 (t, 2H), 4.61 (br(s), 1H), 6.95 (d, 1H), 7.11 (s, 1H), 7.25 (d, 1H), 7.37 (s, 1H), 10.73 (s, 1H), 12.12 (br(s), 1H). |

Intermediate Ex.35: 1-(3-oxo-3,4-dihydro-2H-1,4-benzoxazin-7-yl)cyclopropane-1-carboxylic acid
(FIG. 1AQ)

TABLE 1.19

| Cpd. | Starting compounds, Reaction conditions and purification, Yield, appearance, $^1$H NMR (solvent) data |
|---|---|
| Ex. 35a | ethyl 2-(5-bromo-2-nitrophenoxy)acetate<br>Step 1: 5-bromo-2-nitrophenol (1.0 g, 4.59 mmol) was dissolved in DMF (10 mL). Potassium carbonate (697 mg, 5.05 mmol) was added followed by ethyl 2-bromoacetate (560 μL, 5.05 mL). The resulting suspension was heated at 50° C. for 2 h. The mixture was cooled to rt and was diluted with EtOAc. Water was added and the phases were separated. The aqueous layer was washed with EtOAc. The combined organic layers were dried over MgSO4, filtered and the solution was concentrated to dryness. The crude material was purified by column chromatography on silica gel eluting with a gradient of Cyclohexane/EtOAc from [100:0] to [85:15]. The product fractions were combined and concentrated to dryness to afford ethyl 2-(5-bromo-2-nitrophenoxy)acetate Ex. 35a (1.24 g, 89%) as pale yellow solid. 1H NMR (300 MHz, DMSO-d6, d in ppm): 1.20 (m, 3H, J = 7.2 Hz), 4.16 (q, 2H, J = 7.2 Hz), 5.08 (s, 2H), 7.37 (dd, 1H, J = 8.7 Hz, J = 1.8 Hz), 7.62 (d, 1H, J = 1.8 Hz), 7.86 (d, 1H, J = 8.7 Hz). |
| Ex. 35b | methyl 1-(3-((ethoxycarbonyl)methoxy)-4-nitrophenyl)cyclopropanecarboxylate<br>Step 2: ethyl 2-(5-bromo-2-nitrophenoxy)acetate Ex. 35a (1.23 g, 4.04 mmol) was dissolved in dry THF (10 mL). The solution was purged with nitrogen and Pd2(dba)3 (278 mg, 0.30 mmol) and XPhos (289 mg, 0.61 mmol) were added to afford a deep red suspension. The freshly prepared bromo[1-(methoxycarbonyl)cyclopropyl]zinc (10.11 mL, 8.09 mmol) was added to the solution. The resulting deep red mixture was heated at 70° C. for 1 h. The reaction |

TABLE 1.19-continued

| Cpd. | Starting compounds, Reaction conditions and purification, Yield, appearance, $^1$H NMR (solvent) data |
|---|---|
|  | mixture was cooled to rt and quenched with water and extracted with EtOAc. The combined organic layers were dried over MgSO4, filtered and the solution was concentrated to dryness. The crude material was adsorbed onto silica gel and purified by column chromatography eluting with a gradient of Cyclohexane/EtOAc from [100:0] to [85:15]. The product fractions were combined and concentrated to dryness to afford methyl 1-(3-((ethoxycarbonyl)methoxy)-4-nitrophenyl)cyclopropanecarboxylate Ex. 35b (1.00 g, 77%) as yellow viscous oil. 1H NMR (300 MHz, DMSO-d6, d in ppm): 1.18 (t, 3H, J = 7.1 Hz), 1.25-1.29 (m, 2H), 1.49-1.53 (m, 2H), 3.56 (s, 3H), 4.15 (q, 2H, J = 4.2 Hz), 5.03 (s, 2H), 7.12 (dd, 1H, J = 8.4 Hz, J = 1.8 Hz), 7.26 (d, 1H, J = 1.5 Hz), 7.81 (d, 1H, J = 8.1 Hz). |
| Ex. 35c | methyl 1-(3,4-dihydro-3-oxo-2H-benzo[b][1,4]oxazin-7-yl)cyclopropanecarboxylate<br>Step 3: methyl 1-(3-((ethoxycarbonyl)methoxy)-4-nitrophenyl)cyclopropanecarboxylate Ex. 35b (1.00 g, 3.09 mmol) was dissolved in glacial acetic acid (10 mL) at rt. Iron powder (1.73 g, 3.09 mmol) was added and the resulting brown suspension was heated at 60° C. for 3 h. Water was added followed by 10% aq. potassium carbonate solution until pH = 6-7 was reached. The aqueous layer was extracted with EtOAc. The organic layer was dried over MgSO4, filtered and the solution was concentrated under vacuum. The crude material was purified by silica gel column chromatography eluting with a gradient of cyclohexane/EtOAc from [100:0] to [1:1]. The product fractions were combined and concentrated to dryness to afford methyl 1-(3,4-dihydro-3-oxo-2H-benzo[b][1,4]oxazin-7-yl)cyclopropanecarboxylate Ex. 35c (631 mg, 83%) as white solid. 1H NMR (300 MHz, DMSO-d6, d in ppm): 1.12-1.15 (m, 2H), 1.40-1.44 (m, 2H), 3.53 (s, 3H), 4.55 (s, 2H), 6.78-6.81 (m, 1H), 6.89-6.91 (m, 2H), 10.68 (br(s), 1H). |
| Ex. 35 | 1-(3-oxo-3,4-dihydro-2H-1,4-benzoxazin-7-yl)cyclopropane-1-carboxylic acid<br>Step 4: methyl 1-(3,4-dihydro-3-oxo-2H-benzo[b][1,4]oxazin-7-yl)cyclopropanecarboxylate Ex. 35c (630 mg, 2.55 mmol) was dissolved in THF/H2O [4:1] (15 mL). Lithium hydroxide monohydrate (321 mg, 7.64 mmol) was added and the mixture was stirred overnight at rt. The organic solvent was removed under reduced pressure and the remaining aqueous layer was acidifed to pH = 3-4 by addition of 3M HCl. The solid formed was collected by filtration, washed with water and dried under vacuum at 40° C. to constant weight to afford 1-(3-oxo-3,4-dihydro-2H-1,4-benzoxazin-7-yl)cyclopropane-1-carboxylic acid Ex. 35 (601 mg, quantitative) as white solid. 1H NMR (300 MHz, DMSO-d6, d in ppm): 1.06-1.09 (m, 2H), 1.37-1.40 (m, 2H), 4.54 (s, 2H), 6.77 (d, 1H, J = 7.5 Hz), 6.87-6.90 (m, 2H), 10.66 (s, 1H), 12.26 (s, 1H). |

Intermediate Ex.36: 1-[3-(2-hydroxyethyl)-1H-indol-5-yl]cyclopropane-1-carboxylic acid (FIG. 1AR)

TABLE 1.20

| Cpd. | Starting compounds, Reaction conditions and purification, Yield, appearance, $^1$H NMR (solvent) data |
|---|---|
| Ex. 36a | 5-bromo-3-{2-[(tert-butyldimethylsilyl)oxy]ethyl}-1H-indole<br>Step 1: imidazole (311 mg, 4.57 mmol) was added to a solution of 2-(5-bromo-1H-dindol-3-yl) ethanol dissolved in DMF (5 mL). The mixture was cooled at 0° C. then tert-butyl dimethyl silyl chloride (485 mg, 3.12 mmol) was added portionwise. The mixture was stirred at rt for 20 h. EtOAc/H2O were added to quench the reaction. After phases separation, the organic layer was dried over MgSO4, filtered and the solution was concentrated under reduced pressure. The crude material was purified by flash column chromatography on silica gel eluting with Heptane/EtOAc [20:80]. Column fractions were combined and concentrated to afford 5-bromo-3-{2-[(tert-butyldimethylsilyl)oxy]ethyl}-1H-indole Ex. 36a (664 mg, 90%) as orange oil. |
| Ex. 36b | methyl 1-(3-{2-[(tert-butyldimethylsilyl)oxy]ethyl}-1H-indol-5-yl)cyclopropane-1-carboxylate<br>Step 2: 5-bromo-3-{2-[(tert-butyldimethylsilyl)oxy]ethyl}-1H-indole Ex. 36a (660 mg, 1.86 mmol) and freshly prepared bromo[1-(methoxycarbonyl)cyclopropyl]zinc (6.5 mL, 5.59 mmol) were dissolved in dry THF (5 mL) and the solution was degassed by nitrogen bubbling for 5 min. Then, XPhos (177 mg, 0.37 mmol) and Pd2(dba)3 (170 mg, 0.19 mmol) were incorporated and the reaction mixture was stirred at 75° C. for 16 h. The reaction mixture was concentrated to dryness and the residue was diluted with EtOAc/H2O. The two layers were partitionated and the organic layer was dried over MgSO4, filtered and the solution was concentrated under reduced pressure. The crude material was purified by flash column chromatography on silica gel eluting with a gradient of Heptane/EtOAc from [100:0] to [50:50]. The |

TABLE 1.20-continued

| Cpd. | Starting compounds, Reaction conditions and purification, Yield, appearance, $^1$H NMR (solvent) data |
|---|---|
| | desired fractions were combined and concentrated to obtain methyl 1-(3-{2-[(tert-butyldimethylsilyl)oxy]ethyl}-1H-indol-5-yl)cyclopropane-1-carboxylate Ex. 36b (660 mg, crude). The desired compound could not be isolated appropriately and it was used as such for the next synthetic step. |
| Ex. 36c | methyl 1-[3-(2-hydroxyethyl)-1H-indol-5-yl]cyclopropane-1-carboxylate Step 3: tetrabutylammonium fluoride solution 1M in THF (3.53 mL, 3.53 mmol) was slowly added to a solution of methyl 1-(3-{2-[(tert-butyldimethylsilyl)oxy]ethyl}-1H-indol-5-yl)cyclopropane-1-carboxylate Ex. 36b (660 mg, 1.76 mmol) diluted in THF (5 mL). The reaction mixture was stirred at rt for 72 h. EtOAc and water were added to quench the reaction. The organic layer was washed with water several times and the aqueous layer was washed with EtOAc. The organic layers were combined, dried over MgSO4, filtered and the solution was concentrated to dryness. The crude material was purified by flash column chromatography on silica gel eluting with a gradient of Heptane/EtOAc [100:0] to [50:50]. Column fractions were combined to afford methyl 1-[3-(2-hydroxyethyl)-1H-indol-5-yl]cyclopropane-1-carboxylate Ex. 36c (268 mg, 59%) as orange solid. |
| Ex. 36 | 1-[3-(2-hydroxyethyl)-1H-indol-5-yl]cyclopropane-1-carboxylic acid Step 4: methyl 1-[3-(2-hydroxyethyl)-1H-indol-5-yl]cyclopropane-1-carboxylate Ex. 36c (268 mg, 1.03 mmol) was dissolved in THF/H2O (8 mL/2 mL). Lithium hydroxide monohydrate (42 mg, 1.03 mmol) was added to the solution and the reaction mixture was stirred overnigth at rt. Additional lithium hydroxide monohydrate (84 mg, 2.06 mmol) was added and the reaction mixture was heated at 50° C. overnight. The solvent was removed under reduced pressure. Water was added and pH was adjusted to pH 4 with conc. HCl. The aqueous solution was extracted with EtOAc. The combined organic layers were dried over MgSO4, filtered and the solution was concentrated to dryness. The residue was purified by flash column chromatography on silica gel eluting with a long gradient of CH2Cl2/MeOH to afford 1-[3-(2-hydroxyethyl)-1H-indol-5-yl]cyclopropane-1-carboxylic acid Ex. 36 (111 mg, 44%) as white solid. 1H NMR (300 MHz, DMSO-d6, d in ppm): 1.18 (s, 2H), 1.48 (s, 2H), 2.86 (t, 2H, J = 7.3 Hz), 3.63-3.70 (m, 2H), 4.64 (t, 1H, J = 5.3 Hz), 7.06 (d, 1H, J = 8.4 Hz), 7.14 (s, 1H), 7.26 (d, 1H, J = 8.3 Hz), 7.44 (s, 1H), 10.75 (s, 1H), 12.10 (br(s), 1H). |

Intermediate Ex.37: 1-(2-oxo-2,3-dihydro-1H-indol-5-yl)cyclopropane-1-carboxylic acid (FIG. 1AS)

TABLE 1.21

| Cpd. | Starting compounds, Reaction conditions and purification, Yield, appearance, $^1$H NMR (solvent) data |
|---|---|
| Ex. 37a | methyl 1-(2-oxoindolin-5-yl)cyclopropanecarboxylate Step 1: 5-bromoindolin-2-one (250 mg, 1.18 mmol) and freshly prepared bromo[1-(methoxycarbonyl)cyclopropyl]zinc (4.42 mL, 3.54 mmol) were dissolved in dry THF (5 mL) and the solution was degassed by nitrogen bubbling for 5 min. Then, XPhos (112 mg, 0.24 mmol) and Pd2(dba)3 (108 mg, 0.12 mmol) were incorporated and the reaction mixture was stirred at 85° C. for 1 h. The reaction mixture was concentrated to dryness. The crude material was purified by column chromatography on silica gel eluting with Cyclohexane/EtOAc (60:40). The desired fractions were combined and concentrated to obtain methyl 1-(2-oxoindolin-5-yl)cyclopropanecarboxylate Ex. 37a (110 mg, 40%) as pale yellow solid. 1H NMR (300 MHz, DMSO-d6, d in ppm): 1.09-1.15 (m, 2H), 1.41-1.47 (m, 2H), 3.43 (s, 2H), 3.52 (s, 3H), 6.72 (d, 1H, J = 7.9 Hz), 7.10 (dd, 1H, J = 8.0 Hz, J = 1.9 Hz), 7.14-7.17 (m, 1H), 10.33 (s, 1H). |
| Ex. 37 | 1-(2-oxo-2,3-dihydro-1H-indol-5-yl)cyclopropane-1-carboxylic acid Step 2: methyl 1-(2-oxoindolin-5-yl)cyclopropanecarboxylate Ex. 37a (60 mg, 0.26 mmol) was dissolved in THF/MeOH (2 mL/3 mL). 5M NaOH (259 μL, 1.30 mmol) was added to the solution and the reaction mixture was stirred at rt for 5 h. The solvent was removed under reduced pressure. Water and EtOAc were added to the solution and the two phases were separated. The pH of the aqueous layer was adjusted to pH = 3-4 with 1M citric acid. The aqueous layer was extracted twice with EtOAc. The combined organic layers were dried over MgSO4, filtered and the solution was concentrated under reduced pressure to afford 1-(2-oxo-2,3-dihydro-1H-indol-5-yl)cyclopropane-1-carboxylic acid Ex. 37 (56 mg, 99%) as off-white solid. 1H NMR (300 MHz, DMSO-d6, d in ppm): 1.12 (q, 2H, J = 3.1 Hz), 1.35-1.45 (m, 2H), 3.43 (s, 2H), 6.71 (d, 1H, J = 7.9 Hz), 7.10 (dd, 1H, J = 8.0 Hz, J = 1.8 Hz), 7.16 (s, 1H), 10.31 (s, 1H), 12.22 (br(s), 1H). |

Intermediate Ex.38: 1-(2,2-dioxo-1,3-dihydro-2,1-benzothiazol-5-yl)cyclopropane-1-carboxylic acid (FIG. 1AT)

TABLE 1.22

| Cpd. | Starting compounds, Reaction conditions and purification, Yield, appearance, $^1$H NMR (solvent) data |
|---|---|
| Ex. 38a | methyl 1-(2,2-dioxo-1,3-dihydro-2,1-benzothiazol-5-yl)cyclopropane-1-carboxylate<br>Step 1: 5-bromo-1,3-dihydro-2,1-benzothiazole-2,2-dione (500 mg, 2.01 mmol) and freshly prepared bromo[1-(methoxycarbonyl)cyclopropyl]zinc (7 mL, 6.05 mmol) were dissolved in dry THF (5 mL) and the solution was degassed by nitrogen bubbling for 5 min. Then, XPhos (191 mg, 0.40 mmol) and Pd2(dba)3 (184 mg, 0.20 mmol) were incorporated and the reaction mixture was stirred at 75° C. for 16 h. The reaction mixture was concentrated to dryness and the residue was diluted with EtOAc/H2O. The two layers were partitionated and the organic layer was dried over MgSO4, filtered and the solution was concentrated under reduced pressure. The crude material was purified by flash column chromatography on silica gel eluting with a gradient of Heptane/EtOAc from [100:0] to [50:50]. The desired fractions were combined and concentrated to obtain methyl 1-(2,2-dioxo-1,3-dihydro-2,1-benzothiazol-5-yl)cyclopropane-1-carboxylate Ex. 38a (198 mg, 37%) as yellow solid. |
| Ex. 38 | 1-(2,2-dioxo-1,3-dihydro-2,1-benzothiazol-5-yl)cyclopropane-1-carboxylic acid<br>Step 2: methyl 1-(2,2-dioxo-1,3-dihydro-2,1-benzothiazol-5-yl)cyclopropane-1-carboxylate Ex. 38a (198 mg, 0.74 mmol) was dissolved in THF/H2O (8 mL/3 mL). Lithium hydroxide monohydrate (62 mg, 1.48 mmol) was added to the solution and the reaction mixture was stirred overnigth at rt. Further lithium hydroxide monohydrate (31 mg, 0.74 mmol) was added and the reaction mixture was heated at 50° C. for 8 h. The solvent was removed under reduced pressure. Water was added and pH was adjusted to pH 4 with 1M HCl. The solid was collected by filtration, triturated in Et2O, filtered-off and dried until constant weight to afford 1-(2,2-dioxo-1,3-dihydro-2,1-benzothiazol-5-yl)cyclopropane-1-carboxylic acid Ex. 38 (157 mg, 84%) as yellow solid. 1H NMR (300 MHz, DMSO-d6, d in ppm): 1.08 (br(s), 2H), 1.41 (br(s), 2H), 4.48 (s, 2H), 6.73 (d, 1H, J = 8.1 Hz), 7.18 (d, 1H), 7.23 (s, 1H). Acidic and sulfonamide protons exchanged with the deuterated solvent. |

Intermediate Ex.39:
2-(3-methyl-1H-indol-5-yl)acetic acid (FIG. 1AU)

TABLE 1.23

| Cpd. | Starting compounds, Reaction conditions and purification, Yield, appearance, $^1$H NMR (solvent) data |
|---|---|
| Ex. 39a | 5-bromo-3-methyl-1-tosyl-1H-indole<br>Step 1: 5-bromo-3-methyl-1H-indole (3.50 g, 16.66 mmol) was dissolved in dimethylacetamide (50 mL). The mixture was purged with N2 and cooled to 0-5° C. Sodium hydride (60% in mineral oil) (800 mg, 19.99 mmol) was added portionwise over 30 min under a flow of N2. Gas evolution was observed upon addition. When the addition was completed the mixture was stirred for 30 min at 0-5° C. p-Toluenesulfonyl chloride (3.80 g, 19.99 mmol) was added in one portion and the mixture was allowed to warm up to rt and stirred overnight. The reaction was quenched with water to form a suspension. EtOAc was added and the phases were separated. The combined organic layers were washed with brine, dried over MgSO4, filtered and the solution was concentrated to dryness. The crude material was purified by column chromatography on silica gel eluting with a gradient of Heptane/EtOAc from [100:0] to [70:30]. The product fractions were combined and concentrated to dryness to afford a pale yellow oil, which solidified upon standing at rt affording 5-bromo-3-methyl-1-tosyl-1H-indole (5.32 g, 88%) as pale yellow solid. |
| Ex. 39b | methyl 2-(3-methyl-1-tosyl-1H-indol-5-yl)acetate<br>Step 2: 5-bromo-3-methyl-1-tosyl-1H-indole Ex. 39a (2.78 g, 8.24 mmol), methyl acetoacetate (2.66 mL, 24.72 mmol) and K3PO4 (7.00 g, 32.96 mmol) were charged to a round bottom flask and suspended in dry toluene (100 mL). The mixture was purged with N2 and tBuXPhos (348 mg, 0.82 mmol) was added followed by Pd(OAc)2 (92 mg, 0.41 mmol). The obtained suspension was heated to 120° C. for 16 h. The mixture was cooled to rt, filtered through a pad of Celite, poured into water and the aqueous layer was extracted with EtOAc. The combined organic layers were dried over MgSO4, filtered and the solution was concentrated to dryness. The crude material was purified by column |

TABLE 1.23-continued

| Cpd. | Starting compounds, Reaction conditions and purification, Yield, appearance, ¹H NMR (solvent) data |
|---|---|
| | chromatography on silica gel eluting with a gradient of Heptane/EtOAc from [100:0] to [70:30]. The product fractions were combined and concentrated to dryness to afford methyl 2-(3-methyl-1-tosyl-1H-indol-5-ypacetate Ex. 39b (2.16 g, 73%) as pale yellow oil. |
| Ex. 39c | methyl 2-(3-methyl-1H-indol-5-yl)acetate<br>Step 3: methyl 2-(3-methyl-1-tosyl-1H-indol-5-yl)acetate Ex. 39b (1.90 g, 5.32 mmol) was dissolved in dry MeOH (95 mL). Magnesium (700 mg, 26.60 mmol) was added and the mixture was stirred overnight at rt. The reaction mixture was concentrated in vacuo. The residues were suspended in EtOAc and a 10% aq. solution of EDTA (disodium salt) was added. The phases were mixed vigorously and the organic layer was separated. The aqueous phase was washed with further EtOAc. The combined organic layers were dried over MgSO4, filtered and the solution was concentrated to dryness. The crude material was purified by column chromatography on silica gel eluting with a gradient of Heptane/EtOAc form [100:0] to [75:25]. The product fractions were combined and concentrated to dryness to afford methyl 2-(3-methyl-1H-indol-5-yl)acetate Ex. 39c (618 mg, 57%) as pale yellow oil. |
| Ex. 39 | 2-(3-methyl-1H-indol-5-yl)acetic acid<br>Step 4: lithium hydroxide monohydrate (150 mg, 3.68 mmol) was added to the mixture of methyl 2-(3-methyl-1H-indol-5-yl)acetate Ex. 39c (618 mg, 3.04 mmol) diluted in THF/H2O (10 mL/5 mL) at 0° C. Then, the reaction mixture was stirred at rt for 16 h. The mixture was diluted with EtOAc and 1M HCl was added under vigorous stirring until pH = 4 was reached. The organic layer was separated, dried over MgSO4, filtered and the solution was concentrated to dryness. The crude material was purified by column chromatography on silica gel eluting with a gradient of CH2Cl2/MeOH from [100:0] to [9:1]. The product fractions were combined and concentrated to dryness. The residue was triturated with diethyl ether and the solid was collected by filtration to give 2-(3-methyl-1H-indol-5-yl)acetic acid Ex. 39 (121 mg, 20%) as white solid. 1H NMR (300 MHz, DMSO-d6, d in ppm): 2.23 (s, 3H), 3.58 (s, 2H), 6.96 (m, 1H), 7.08 (s, 1H), 7.25 (m, 1H), 7.33 (s, 1H), 10.66 (s, 1H), 12.13 (br(s), 1H). |

Intermediate Ex.40: 1-(1-methyl-2,2-dioxo-1,3-di-hydro-2,1-benzothiazol-5-yl)cyclopropane-1-carboxylic acid (FIG. 1AV)

TABLE 1.24

| Cpd. | Starting compounds, Reaction conditions and purification, Yield, appearance, ¹H NMR (solvent) data |
|---|---|
| Ex. 40a | methyl 1-(1-methyl-2,2-dioxo-1,3-dihydro-2,1-benzothiazol-5-yl)cyclopropane-1-carboxylate<br>Step 1: to a solution of previously synthesized methyl 1-(2,2-dioxo-1,3-dihydro-2,1-benzothiazol-5-yl)cyclopropane-1-carboxylate (100 mg, 0.37 mmol) dissolved in dry DMF (2 mL) was added K2CO3 (155 mg, 1.12 mmol) followed by iodomethane (35 µL, 0.56 mmol). The reaction mixture was stirred at rt for 1 h. The reaction mixture was poured onto brine. The aqueous layer was extracted with EtOAc. The combined organic layers were dried over MgSO4, filtered and the solution was concentrated under reduced pressure. The residue was triturated in small amount of cold MeOH and the precipitate was filtered-off to afford methyl 1-(1-methyl-2,2-dioxo-1,3-dihydro-2,1-benzothiazol-5-yl)cyclopropane-1-carboxylate Ex. 40a (56 mg, 53%) as white solid. 1H NMR (300 MHz, DMSO-d6, d in ppm): 1.15 (q, 2H, J = 4.2 Hz), 1.47 (q, 2H, J = 3.7 Hz), 3.02 (s, 3H), 3.53 (s, 3H), 4.61 (s, 2H), 6.87 (d, 1H, J = 8.8 Hz), 7.25-7.35 (m, 2H). |
| Ex. 40 | 1-(1-methyl-2,2-dioxo-1,3-dihydro-2,1-benzothiazol-5-yl)cyclopropane-1-carboxylic acid<br>Step 2: methyl 1-(1-methyl-2,2-dioxo-1,3-dihydro-2,1-benzothiazol-5-yl)cyclopropane-1-carboxylate Ex. 40a (56 mg, 0.20 mmol) was dissolved in THF/MeOH (1 mL/0.5 mL). 5M NaOH (408 µL, 2.04 mmol) was added and the mixture was stirred overnight at rt. The reaction mixture was diluted with sat. NH4Cl and EtOAc. The two phases were separated. The aqueous layer was acidified to pH = 3-4 by addition of 10% citric acid. The aqueous layer was extracted with EtOAc. The combined organic layers were dried over MgSO4, filtered and the solution was concentrated under reduced pressure to afford 1-(1-methyl-2,2-dioxo-1,3-dihydro-2,1-benzothiazol-5-yl)cyclopropane-1-carboxylic acid Ex. 40 (30 mg, 56%) as white solid. 1H NMR (300 MHz, DMSO-d6, d in ppm): 1.10 (q, 2H, J = 4.1 Hz), 1.47 (q, 2H, J = 3.6 Hz), 3.01 (s, 3H), 4.61 (s, 2H), 6.85 (d, 1H, J = 8.7 Hz), 7.25-7.35 (m, 2H), 12.28 (s, 1H). |

Intermediate Ex.41: 1-{1-[2-(benzyloxy)ethyl]-2,3-dihydro-1H-indol-5-yl}cyclopropane-1-carboxylic acid (FIG. 1AW)

TABLE 1.25

| Cpd. | Starting compounds, Reaction conditions and purification, Yield, appearance, $^1$H NMR (solvent) data |
|---|---|
| Ex. 41a | 1-[2-(benzyloxy)ethyl]-5-bromo-2,3-dihydro-1H-indole<br>Step 1: 5-bromo-2,3-dihydro-1H-indole (700 mg, 3.53 mmol) was dissolved in dry acetonitrile (10 mL). K2CO3 (1.47 g, 10.60 mmol) was added to the solution followed by [(2-bromoethoxy)methyl]benzene (616 µL, 3.89 mmol). The microwave vial was sealed and the reaction was heated at 100° C. for 15 min under microwave irradiation. After TLC, no conversion was observed. The reaction was heated for additional 1 h at 120° C. under microwave irradiation. The TLC showed only starting material. Dry DMF (1 mL) was added and the reaction was heated at 120° C. for 1 h under microwave irradiation. After TLC, small conversion was observed. A catalytic amount of tetrabutylammonium bromide was added and the reaction was heated at 120° C. for 1 h under microwave irradiation. The TLC showed complete conversion. The solution was decomposed into water. The aqueous layer was extracted with EtOAc. The combined organic layers were dried over MgSO4, filtered and the solution was concentrated under reduced pressure. The crude material was purified by silica gel column chromatography eluting with cyclohexane/EtOAc (90:10). The desired fractions were combined and concentrated to dryness to afford 1-[2-(benzyloxy)ethyl]-5-bromo-2,3-dihydro-1H-indole Ex. 41a (620 mg, 53%) as colourless oil. 1H NMR (300 MHz, DMSO-d6, d in ppm): 2.85 (t, 2H, J = 8.5 Hz), 3.25 (t, 2H, J = 5.6 Hz), 3.41 (t, 2H, J = 8.5 Hz), 3.62 (t, 2H, J = 5.6 Hz), 4.50 (s, 2H), 6.43 (d, 1H, J = 8.3 Hz), 7.07 (dd, 1H, J = 8.3 Hz, J = 2.1 Hz), 7.13 (m, 1H), 7.22-7.35 (m, 5H). |
| Ex. 41b | methyl 1-{1-[2-(benzyloxy)ethyl]-2,3-dihydro-1H-indol-5-yl}cyclopropane-1-carboxylate<br>Step 2: 1-[2-(benzyloxy)ethyl]-5-bromo-2,3-dihydro-1H-indole Ex. 41a (620 mg, 1.87 mmol) was dissolved in dry THF (5 mL). The solution was purged with nitrogen and Pd2(dba)3 (43 mg, 0.05 mmol) and XPhos (44 mg, 0.09 mmol) were added to the solution. The freshly prepared bromo[1-(methoxycarbonyl)cyclopropyl]zinc (7 mL, 5.60 mmol) was added to the solution. The resulting deep red mixture was heated at 75° C. for 2 h. The reaction mixture was cooled to rt and quenched with water and extracted with EtOAc. The combined organic layers were dried over MgSO4, filtered and the solution was concentrated to dryness. The crude material was purified by column chromatography eluting with Cyclohexane/EtOAc (90:10). The product fractions were combined and concentrated to dryness to afford methyl 1-{1-[2-(benzyloxy)ethyl]-2,3-dihydro-1H-indol-5-yl}cyclopropane-1-carboxylate Ex. 41b (590 mg, 90%) as colourless oil. 1H NMR (300 MHz, DMSO-d6, d in ppm): 1.06 (q, 2H, J = 4.1 Hz), 1.39 (q, 2H, J = 3.5 Hz), 2.84 (t, 2H, J = 8.5 Hz), 3.24 (t, 2H, J = 5.8 Hz), 3.37 (t, 2H, J = 8.3 Hz), 3.51 (s, 3H), 3.63 (t, 2H, J = 5.6 Hz), 4.51 (s, 2H), 6.40 (d, 1H, J = 8.1 Hz), 6.91 (dd, 1H, J = 8.0 Hz, J = 1.9 Hz), 6.95 (d, 1H, J = 1.4 Hz), 7.20-7.40 (m, 5H). |
| Ex. 41 | 1-{1-[2-(benzyloxy)ethyl]-2,3-dihydro-1H-indol-5-yl}cyclopropane-1-carboxylic acid<br>Step 3: methyl 1-{1-[2-(benzyloxy)ethyl]-2,3-dihydro-1H-indol-5-yl}cyclopropane-1-carboxylate Ex. 41b (590 mg, 1.68 mmol) was dissolved in THF/MeOH (2 mL/3 mL). 5M NaOH (1.68 mL, 8.39 mmol) was added and the mixture was stirred at rt for 5 h. The reaction mixture was diluted with brine and EtOAc. The two phases were separated. The aqueous layer was acidified to pH = 5-6 by addition of 10% citric acid. The solid formed was collected by filtration and dried at 40° C. under vacuo until constant weight to afford 1-{1-[2-(benzyloxy)ethyl]-2,3-dihydro-1H-indol-5-yl}cyclopropane-1-carboxylic acid Ex. 41 (425 mg, 75%) as white solid. 1H NMR (300 MHz, DMSO-d6, d in ppm): 1.00 (q, 2H, J = 3.9 Hz), 1.35 (q, 2H, J = 3.4 Hz), 2.84 (t, 2H, J = 8.3 Hz), 3.22 (t, 2H, J = 2.8 Hz), 3.36 (t, 2H, J = 8.2 Hz), 3.63 (t, 2H, J = 5.6 Hz), 4.51 (s, 2H), 6.39 (d, 1H, J = 8.1 Hz), 6.88 (dd, 1H, J = 8.1 Hz, J = 1.9 Hz), 6.95 (d, 1H, J = 1.4 Hz), 7.20-7.40 (m, 5H), 12.02 (br(s), 1H). |

Intermediate Ex.43: 1-(2,2-dioxo-1,3-dihydro-2-benzothiophen-5-yl)cyclopropane-1-carboxylic acid (FIG. 1AY)

TABLE 1.26

| Cpd. | Starting compounds, Reaction conditions and purification, Yield, appearance, $^1$H NMR (solvent) data |
|---|---|
| Ex. 43a | methyl 1-(2,2-dioxo-1,3-dihydro-2-benzothiophen-5-yl)cyclopropane-1-carboxylate |

TABLE 1.26-continued

| Cpd. | Starting compounds, Reaction conditions and purification, Yield, appearance, $^1$H NMR (solvent) data |
|---|---|
| | Step 1: 5-bromo-1,3-dihydro-2-benzothiophene-2,2-dione (475 mg, 1.92 mmol) and freshly prepared bromo[1-(methoxycarbonyl)cyclopropyl]zinc (4.81 mL, 3.84 mmol) were dissolved in dry THF (5 mL) and the solution was degassed by nitrogen bubbling for 5 min. Then, XPhos (183 mg, 0.38 mmol) and Pd2(dba)3 (176 mg, 0.19 mmol) were incorporated and the reaction mixture was stirred at 75° C. for 1 h. The mixture was cooled to rt and quenched with water and extracted with EtOAc. The combined organic layers were dried over MgSO4, filtered and the solution was concentrated to dryness. The crude was adsorbed onto silica gel and purified by column chromatography eluting with a gradient of Cyclohexane/EtOAc from [90:10] to [60:40]. The product fractions were combined and concentrated to dryness to afford a white solid. The solid was triturated with cyclochexane and dried under vacuum at 40° C. to constant weight to afford methyl 1-(2,2-dioxo-1,3-dihydro-2-benzothiophen-5-yl)cyclopropane-1-carboxylate Ex. 43a (254 mg, 50%) as white solid. 1H NMR (300 MHz, DMSO-d6, d in ppm): 1.18-1.22 (m, 2H), 1.47-1.51 (m, 2H), 3.54 (s, 3H), 4.46 (s, 4H), 7.29-7.35 (m, 3H). |
| Ex. 43 | 1-(2,2-dioxo-1,3-dihydro-2-benzothiophen-5-yl)cyclopropane-1-carboxylic acid<br>Step 2: methyl 1-(2,2-dioxo-1,3-dihydro-2-benzothiophen-5-yl)cyclopropane-1-carboxylate Ex. 43a (350 mg, 1.31 mmol) was dissolved in THF/H2O (4 mL/1 mL). Lithium hydroxide monohydrate (260 mg, 3.94 mmol) was added to the solution and the reaction mixture was stirred overnigth at rt. The solvent was removed under reduced pressure. Water was added and pH was adjusted to pH = 3-4 with 3M HCl. The solid was collected by filtration, washed with water and dried until constant weight to afford 1-(2,2-dioxo-1,3-dihydro-2-benzothiophen-5-yl)cyclopropane-1-carboxylic acid Ex. 43 (319 mg, 96%) as white solid. 1H NMR (300 MHz, DMSO-d6, d in ppm): 1.12-1.15 (m, 2H), 1.44-1.47 (m, 2H), 4.45 (s, 4H), 7.30-7.33 (m, 3H). |

Intermediate Ex.46: 2-(2,2-dioxo-1,3-dihydro-2-benzothiophen-5-yl)acetic acid (FIG. 1 BB)

TABLE 1.27

| Cpd. | Starting compounds, Reaction conditions and purification, Yield, appearance, $^1$H NMR (solvent) data |
|---|---|
| Ex. 46a | tert-butyl 2-(2,2-dioxo-1,3-dihydro-2-benzothiophen-5-yl)acetate<br>Step 1: 5-Bromo-1,3-dihydro-benzo(c)thiophene 2,2-dioxide (500 mg, 2.02 mmol), the previously synthesized tert-butyl 2-(bromozincio)acetate (7.60 mL, 6.07 mmol) and dry THF (5 mL) were placed in flask, the mixture was degassed by nitrogen bubbling for 5 min. Then Pd2(dba)3 (185 mg, 0.20 mmol) and XPhos (193 mg, 0.41 mmol) were incorporated and the reaction mixture was stirred at 75° C. for 1 h. The mixture was cooled to rt, EtOAc and water was added and the two-phase mixture was filtered through a pad of Celite. The phases were separated, the organic layer was dried over MgSO4, filtered and the solution was concentrated to dryness. The crude material was purified by column chromatography eluting with a gradient of Cyclohexane/EtOAc from [100:0] to [70:30]. The product fractions were combined and concentrated to dryness. The residue was triturated with Cyclohexane/Et2O [1:1], filtered and dried under vacuum at 40° C. The product tert-butyl 2-(2,2-dioxo-1,3-dihydro-2-benzothiophen-5-yl)acetate Ex. 46a (421 mg, 74%) was isolated as a white fluffy solid. 1H NMR (300 MHz, DMSO-d6, d in ppm): 1.39 (s, 9H), 3.58 (s, 2H), 4.46 (s, 2H), 4.48 (s, 2H), 7.22-7.25 (m, 2H), 7.32 (d, 1H, J = 7.5 Hz). |
| Ex. 46 | 2-(2,2-dioxo-1,3-dihydro-2-benzothiophen-5-yl)acetic acid<br>Step 2: tert-butyl 2-(2,2-dioxo-1,3-dihydro-2-benzothiophen-5-yl)acetate Ex. 46a (200 mg, 0.71 mmol) was dissolved in CH2Cl2 (2 mL) and then was added 4M HCl in dioxane (2 mL, 8 mmol). The reaction mixture was stirring for 6 h at rt. Slow conversion was observed. The reaction mixture was heated at 40° C. for 18 h. The solution was concentrated to dryness to afford a colourless oil. A mixture of Et2O/Cyclohexane was added to the residue and a white precipitate formed. The solid was collected by filtration and dried under vacuum at 40° C. until constant weight to afford 2-(2,2-dioxo-1,3-dihydro-2-benzothiophen-5-yl)acetic acid Ex. 46 (109 mg, 68%) as white solid. 1H NMR (300 MHz, DMSO-d6, d in ppm): 3.59 (s, 2H), 4.45 (s, 2H), 4.47 (s, 2H), 7.26-7.33 (m, 3H), 12.38 (s, 1H). |

Figure 1B:
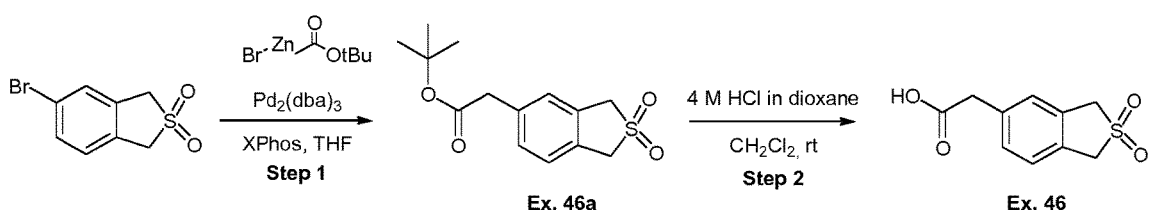
Figure 1B:
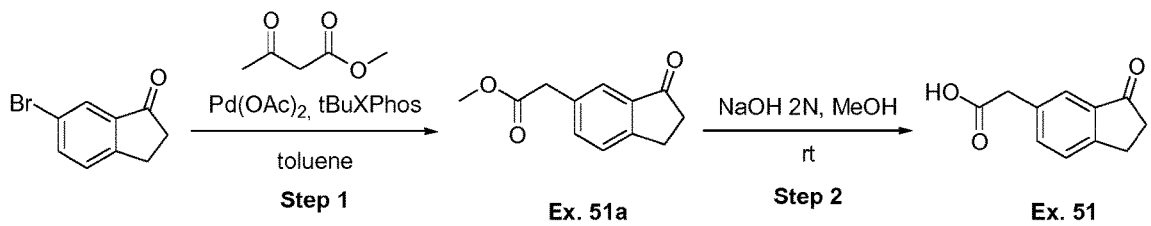
Figure 1B:
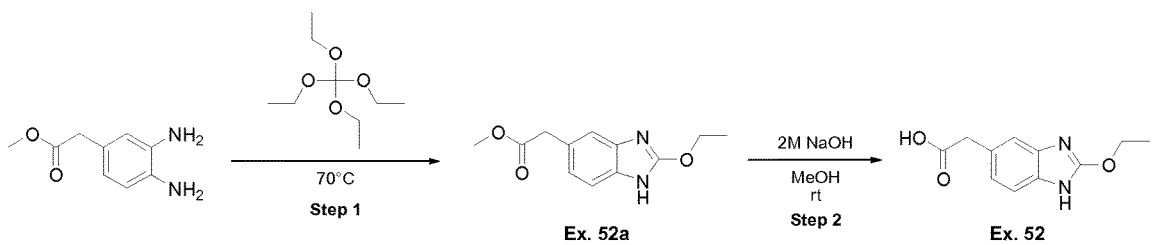
Figure 1B:
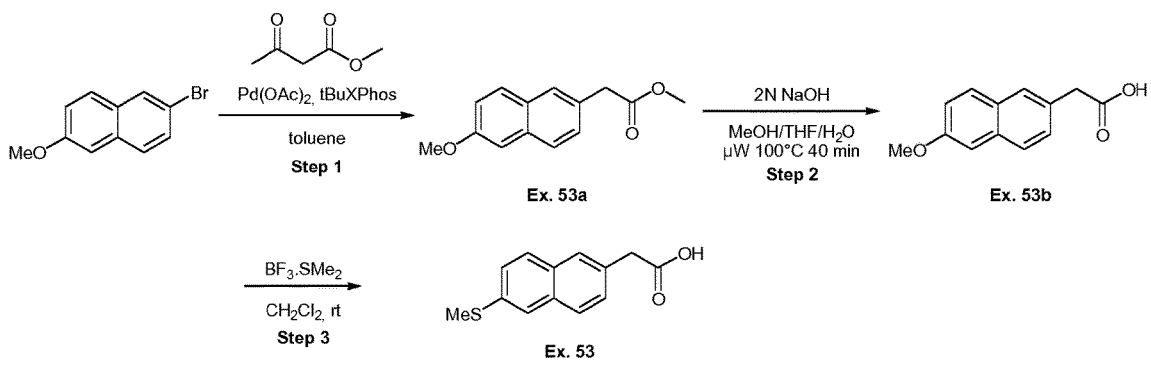
Figure 1B:
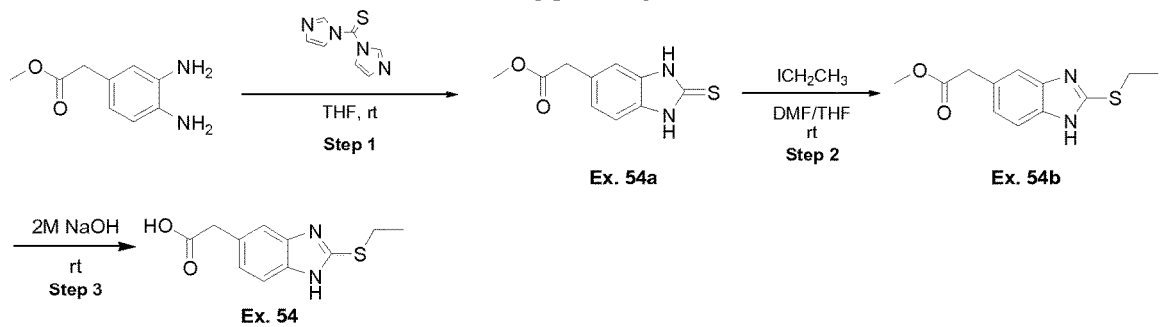
Figure 1B:
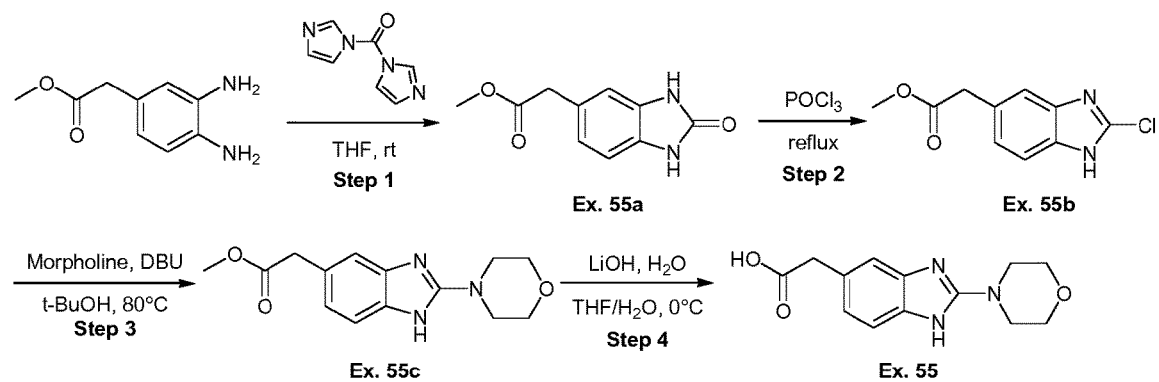
Figure 1B:
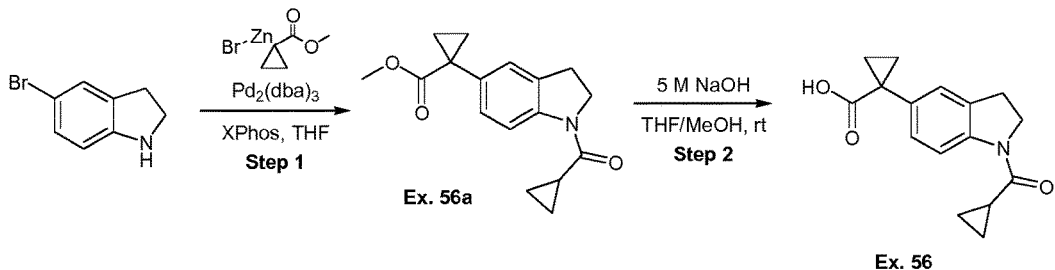
Figure 1B:
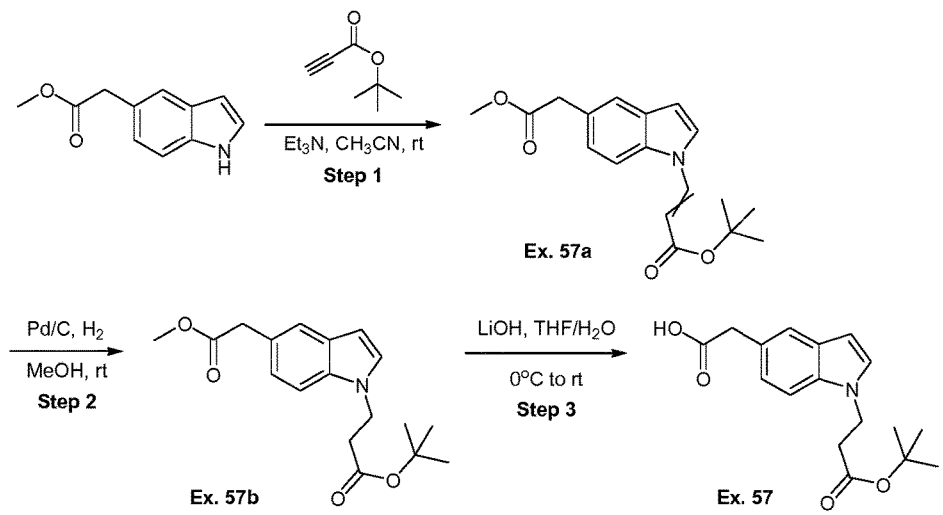
Figure 1B:
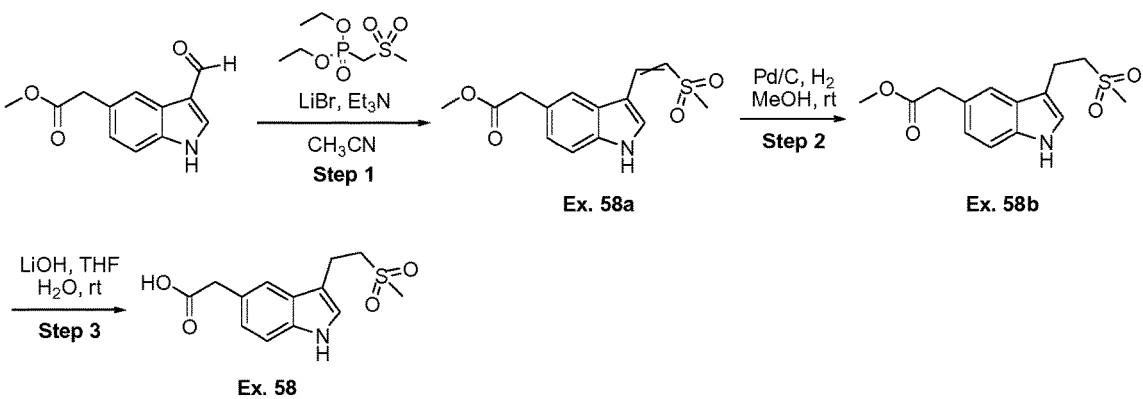
Figure 1B:
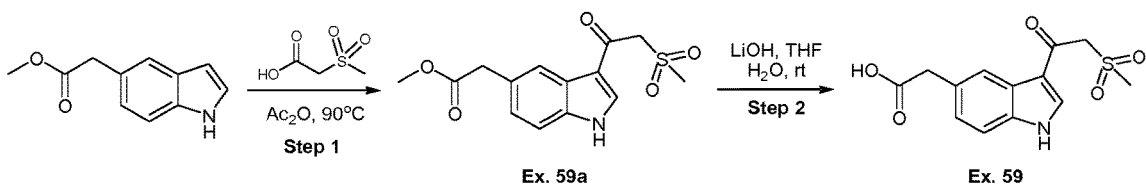

Intermediate Ex.51: 2-(3-oxo-2,3-dihydro-1H-inden-5-yl)acetic acid (FIG. 1BG)

TABLE 1.28

| Cpd. | Starting compounds, Reaction conditions and purification, Yield, appearance, $^1$H NMR (solvent) data |
| --- | --- |
| Ex. 51a | methyl 2-(1-oxo-2,3-dihydro-1H-inden-6-yl)acetate<br>Step 1: 6-bromo-2,3-dihydroinden-1-one (500 mg, 2.37 mmol), methyl acetoacetate (767 µL, 7.11 mmol) and potassium phosphate (2.01 g, 9.48 mmol) were diluted with toluene (15 mL). The solution was degassed with N2 for 15 min. Pd(OAc)2 (27 mg, 0.12 mmol) followed by di-tert-butyl XPhos (101 mg, 0.24 mmol). The reaction mixture was heated overnight at 120° C. The suspension was filtered through a pad of Celite and washed with EtOAc. The filtrate was concentrated to dryness and purified by silica gel column chromatography using Cyclohexane/EtOAc (70:30) as eluent. The desired fractions were combined and concentrated under reduced pressure to obtain methyl 2-(1-oxo-2,3-dihydro-1H-inden-6-yl)acetate Ex. 51a (361 mg, 75%) as pale brown solid. 1H NMR (300 MHz, DMSO-d6, d in ppm): 2.62 (t, 2H, J = 5.8 Hz), 3.07 (t, 2H, J = 6.2 Hz), 3.61 (s, 3H), 3.79 (s, 2H), 7.54-7.55 (m, 2H), 7.59 (s, 1H). |
| Ex. 51 | 2-(3-oxo-2,3-dihydro-1H-inden-5-yl)acetic acid<br>Step 2: methyl 2-(1-oxo-2,3-dihydro-1H-inden-6-yl)acetate Ex. 51a (310 mg, 1.52 mmol) was dissolved in MeOH (10 mL) and 2N NaOH (911 µL, 1.82 mmol) was added to the solution. The reaction mixture was stirred at rt for 2 h. The solvents were removed under reduced pressure. Et2O and water was added to the residue. The two phases were partitionated. The aqueous layer was acidified with 1N citric acid until pH = 5 was reached and then extracted with EtOAc. The combined organic layers were dried over MgSO4, filtered and the solution was concentrated to dryness to give 2-(1-oxo-2,3-dihydro-1H-inden-6-yl)acetic acid Ex. 51 (230 mg, 80%) as pale brown solid. 1H NMR (300 MHz, DMSO-d6, d in ppm): 2.62 (t, 2H, J = 5.7 Hz), 3.07 (t, 2H, J = 6.0 Hz), 3.67 (s, 2H), 7.50-7.57 (m, 3H), 12.39 (s, 1H). |

Intermediate Ex.52: 2-(2-ethoxy-1H-1,3-benzodiazol-5-yl)acetic acid (FIG. 1BH)

TABLE 1.29

| Cpd. | Starting compounds, Reaction conditions and purification, Yield, appearance, $^1$H NMR (solvent) data |
| --- | --- |
| Ex. 52a | Step 1: a solution of methyl 2-(3,4-diaminophenyl)acetate (synthesized following the procedure described in WO2013019682A1) (330 mg, 1.83 mmol) and tetraethyl orthocarbonate (536 µL, 2.56 mmol) was heated overnight at 70° C. After cooling to rt, the crude material was purified by silica gel column chromatography using CH2Cl2/MeOH (90:10) as eluent affording methyl 2-(2-ethoxy-1H-1,3-benzodiazol-5-yl)acetate Ex. 52a (300 mg, 70%) as pale brown solid. 1H NMR (300 MHz, DMSO-d6, d in ppm): 1.37 (t, 3H, J = 7.1 Hz), 3.60 (s, 3H), 3.68 (s, 2H), 4.45 (q, 2H, J = 7.1 Hz), 6.92 (dd, 1H, J = 8.2 Hz, J = 1.6 Hz), 7.10-7.30 (m, 2H), 11.80 (s, 1H). |
| Ex. 52 | 2-(2-ethoxy-1H-1,3-benzodiazol-5-yl)acetic acid<br>Step 2: methyl 2-(2-ethoxy-1H-1,3-benzodiazol-5-yl)acetate Ex. 52a (300 mg, 1.28 mmol) was dissolved in MeOH (3 mL). 2M NaOH (1.28 mL, 2.56 mmol) was added to the solution. The reaction mixture was stirred at rt for 5 h. The solvent was removed under reduced pressure. 1M citric acid was added up pH = 6 was reached. The solid formed was collected by filtration to give 2-(2-ethoxy-1H-1,3-benzodiazol-5-yl)acetic acid Ex. 52 (230 mg, 82%) as off-white solid. 1H NMR (300 MHz, DMSO-d6, d in ppm): 1.37 (t, 3H, J = 8.7 Hz), 3.56 (s, 2H), 4.46 (q, 2H, J = 7.0 Hz), 6.92 (dd, 1H, J = 8.2 Hz, J = 1.6 Hz), 7.17-7.22 (m, 2H), 11.76 (s, 1H). |

Intermediate Ex.53: 2-[6-(methylsulfanyl)naphthalen-2-yl]acetic acid (FIG. 1BI)

TABLE 1.30

| Cpd. | Starting compounds, Reaction conditions and purification, Yield, appearance, $^1$H NMR (solvent) data |
| --- | --- |
| Ex. 53a | methyl 2-(2-methoxynaphthalen-6-yl)acetate<br>Step 1: 2-bromo-6-methoxynaphthalene (500 mg, 2.11 mmol) was weighted into |

TABLE 1.30-continued

| Cpd. | Starting compounds, Reaction conditions and purification, Yield, appearance, $^1$H NMR (solvent) data |
|---|---|
| | a reaction vial. Potassium phosphate (1.79 g, 8.44 mmol) and toluene (15 mL) were added followed by di-tert-butyl Xphos (90 mg, 0.21 mmol) and methyl acetoacetate (807 µL, 6.33 mmol). The mixture was purged with N2 an Pd(OAc)2 (24 mg, 0.11 mmol) was added. The reaction vial was sealed under N2 atmosphere and heated under vigorous stirring at 100° C. for 16 h. Water was added to quench the reaction. The solution was diluted with EtOAc and filtered through a plug of Celite. The phases were separated. The organic layer was dried over MgSO4, filtered and the solution was concentrated to dryness. The crude material was purified by silica gel column chromatography eluting with Cyclohexane/EtOAc (90:10) to afford methyl 2-(2-methoxynaphthalen-6-yl)acetate Ex. 53a (332 mg, 68%) as white solid. |
| Ex. 53b | 2-(2-methoxynaphthalen-6-yl)acetic acid<br>Step 2: methyl 2-(2-methoxynaphthalen-6-yl)acetate Ex. 53a (330 mg, 1.43 mmol) was dissolved in a mixture of MeOH (2 mL), THF (2 mL) and water (2 mL) and introduced in a sealed tube. 5N NaOH (2.90 mL, 14.33 mmol) was added to the solution and the reaction mixture was heated at 100° C. for 40 min under microwave irradiation. The solvent was evaporated under reduced pressure and the residue was washed with water. The solution was acidified with 1N HCl until pH = 1 was reached. The solid was collected by filtration and dried until constant weight to give 2-(2-methoxynaphthalen-6-yl)acetic acid Ex. 53b (270 mg, 87%) as white solid. 1H NMR (300 MHz, DMSO-d6, d in ppm): 3.62 (s, 2H), 3.86 (s, 3H), 7.12 (dd, 1H, J = 2.6 Hz, J = 8.9 Hz), 7.27 (d, 1H, J = 2.6 Hz), 7.35 (dd, 1H, J = 1.8 Hz, J = 8.4 Hz), 7.65 (s, 1H), 7.73 (d, 1H, J = 8.4 Hz), 7.74 (d, 1H, J = 8.9 Hz). |
| Ex. 53 | 2-[6-(methylsulfanyl)naphthalen-2-yl]acetic acid<br>Step 3: to a solution of 2-(2-methoxynaphthalen-6-yl)acetic acid Ex. 53b (270 g, 1.25 mmol) dissolved in CH2Cl2 (3 mL) was added boron trifluoride methyl sulfide complex (1.31 mL, 12.45 mmol). The reaction was stirred at rt over the weekend. The solvent was removed under reduced pressure and the residue was diluted with EtOAc. The combined organic layers were washed with brine and water. The organic layer was dried over MgSO4, filtered and the solution was concentrated under reduced pressure. The crude material was purified by silica gel column chromatography eluting with CH2Cl2/MeOH (95:5) to afford 2-[6-(methylsulfanyl)naphthalen-2-yl]acetic acid Ex. 53 (140 g, 47%) as pale green solid. 1H NMR (300 MHz, DMSO-d6, d in ppm): 2.56 (s, 3H), 3.70 (s, 2H), 7.34-7.43 (m, 2H), 7.65-7.73 (m, 2H), 7.73-7.82 (m, 2H), 12.35 (br(s), 1H). |

Intermediate Ex.54: 2-[2-(ethylsulfanyl)-1H-1,3-benzodiazol-5-yl]acetic acid (FIG. 1BJ)

TABLE 1.31

| Cpd. | Starting compounds, Reaction conditions and purification, Yield, appearance, $^1$H NMR (solvent) data |
|---|---|
| Ex. 54a | methyl 2-(2-sulfanylidene-2,3-dihydro-1H-1,3-benzodiazol-5-yl)acetate<br>Step 1: methyl 2-(3,4-diaminophenyl)acetate (synthesized following the procedure described in WO2013019682A1) (300 mg, 1.66 mmol) was dissolved in dry THF (5 mL) and 1,1'-thiocarbonyldiimidazole (356 mg, 2.00 mmol) was added to the solution. The reaction mixture was stirred at rt for 2 h. The solvent was removed under reduced pressure. The crude material was purified by silica gel column chromatography using CH2Cl2/MeOH (96:4) as eluent affording methyl 2-(2-sulfanylidene-2,3-dihydro-1H-1,3-benzodiazol-5-yl)acetate Ex. 54a (280 mg, 76%) as pale brown solid. 1H NMR (300 MHz, DMSO-d6, d in ppm): 3.62 (s, 3H), 3.72 (s, 2H), 7.01 (dd, 1H, J = 8.0 Hz, J = 1.6 Hz), 7.06 (d, 1H, J = 8.0 Hz), 7.09 (d, 1H, J = 1.6 Hz), 12.51 (s, 2H). |
| Ex. 54b | methyl 2-[2-(ethylsulfanyl)-1H-1,3-benzodiazol-5-yl]acetate<br>Step 2: methyl 2-(2-sulfanylidene-2,3-dihydro-1H-1,3-benzodiazol-5-yl)acetate Ex. 54a (181 mg, 0.81 mmol) was dissolved in a mixture of DMF/THF (2 mL/2 mL) and K2CO3 (340 mg, 2.44 mmol) was added followed by iodoethane (66 µL, 0.82 mmol). The reaction mixture was stirred at rt for 1 h. Water was added to quench the reaction. The aqueous layer was extracted with EtOAc. The combined organic layers were dried over MgSO4, filtered and the solution was concentrated to dryness yielding methyl 2-[2-(ethylsulfanyl)-1H-1,3-benzodiazol-5-yl]acetate Ex. 54b (204 mg, quantitative). The title compound was used at the next step without further purification. 1H NMR (300 MHz, DMSO-d6, d in ppm): 1.36 (t, 3H, J = 7.3 Hz), 3.26 (q, 2H, J = 7.3 Hz), 3.61 (s, 3H); 3.73 (s, 2H), 6.98-7.03 (m, 1H), 7.26-7.30 (m, 1H), 7.40-7.45 (m, 1H), 12.46 (s, 1H). |
| Ex. 54 | 2-[2-(ethylsulfanyl)-1H-1,3-benzodiazol-5-yl]acetic acid<br>Step 3: methyl 2-[2-(ethylsulfanyl)-1H-1,3-benzodiazol-5-yl]acetate Ex. 54b (202 mg, 0.81 mmol) was dissolved in MeOH (4 mL). 2M NaOH (807 µL, 1.61 mmol) was added to the solution. The reaction mixture was stirred at rt for 1 h. The solvent was removed under reduced pressure. 1M citric acid was added up pH = |

TABLE 1.31-continued

| Cpd. | Starting compounds, Reaction conditions and purification, Yield, appearance, $^1$H NMR (solvent) data |
|---|---|
| | 4-5 was reached. The solid formed was collected by filtration to give 2-[2-(ethylsulfanyl)-1H-1,3-benzodiazol-5-yl]acetic acid Ex. 54 (180 mg, 94%) as off-white solid. 1H NMR (300 MHz, DMSO-d6, d in ppm): 1.36 (t, 3H, J = 7.3 Hz), 3.25 (q, 2H, J = 7.4 Hz), 3.59 (s, 2H), 7.00 (dd, 1H, J = 8.2 Hz, J = 1.2 Hz), 7.31 (d, 1H, J = 1.2 Hz), 7.65 (d, 1H, J = 8.2 Hz). The acidic proton exchanged with the deuterated solvent. |

Intermediate Ex.55: 2-[2-(morpholin-4-yl)-1H-1,3-benzodiazol-5-yl]acetic acid (FIG. 1BK)

TABLE 1.32

| Cpd. | Starting compounds, Reaction conditions and purification, Yield, appearance, $^1$H NMR (solvent) data |
|---|---|
| Ex. 55a | methyl 2-(2,3-dihydro-2-oxo-1H-benzo[d]imidazol-5-yl)acetate<br>Step 1: to a solution of methyl 2-(3,4-diaminophenyl)acetate (synthesized following the procedure described in WO2013019682A1) (2.00 g, 11.10 mmol) in THF (30 mL) was added dropwise a solution of 1,1'-carbonyldiimidazole (2.16 g, 13.32 mmol) dissolved in CH2Cl2 (30 mL). The reaction was stirred at rt for 16 h. Tert-butylmethylether (30 mL) wad added to the reaction mixture. The resulting precipitate was collected by filtration and washed with tert-butylmethylether and dried under vacuum to afford methyl 2-(2,3-dihydro-2-oxo-1H-benzo[d]imidazol-5-yl)acetate Ex. 55a (1.42 g, 62%) as pale brown solid. |
| Ex. 55b | methyl 2-(2-chloro-1H-benzo[d]imidazol-5-yl)acetate<br>Step 2: phosphorus oxychloride (1 mL) was added to methyl 2-(2,3-dihydro-2-oxo-1H-benzo[d]imidazol-5-yl)acetate Ex. 55a (100 mg, 0.49 mmol). The reaction mixture was stirred at 90° C. for 4 h. The reaction was quenched by dropwise addition of sat. NaHCO3 solution. CH2Cl2 was added and the phases were separated. The organic layer was dried over MgSO4, filtered and the solution was concentrated under reduced pressure. The crude material was purified by column chromatography eluting with a gradient of Heptane/EtOAc from [100:0] to [50:50]. The product fractions were combined and concentrated to dryness to afford methyl 2-(2-chloro-1H-benzo[d]imidazol-5-yl)acetate Ex. 55b (40 mg, 37%) as white solid. |
| Ex. 55c | methyl 2-(2-morpholino-1H-benzo[d]imidazol-5-yl)acetate<br>Step 3: methyl 2-(2-chloro-1H-benzo[d]imidazol-5-yl)acetate Ex. 55b (380 mg, 1.69 mmol) was dissolved in tert-butanol (12 mL) and then morpholine (580 µL, 6.77 mmol) was added. The reaction mixture was stirred at rt for 72 h. LC-MS did not show conversion. Additional morpholine (290 µL, 3.39 mmol) was added and reaction was stirred at 50° C. for 1 week. LC-MS still did not show conversion. Then 1,8-diazabicyclo[5.4.0]undec-7-ene (250 µL, 1.69 mmol) was added in addition of additional morpholine (290 µL, 3.39 mmol), the mixture reaction was stirred at rt for 72 h. LCMS showed a peak with [M + H]+ = 276.1 (10% of conversion). Morpholine (290 µL, 3.39 mmol) and 1,8-diazabicyclo[5.4.0]undec-7-ene (250 µL, 1.69 mmol) were added and reaction was stirred at rt for 2 weeks. LCMS showed 30% of conversion. The reaction mixture was diluted with EtOAc and water. The organic layer was dried over MgSO4, filtered and the solution was concentrated to dryness. The crude material was purified by column chromatography eluting with a gradient of Heptane/EtOAc from [100:0] to [0:100]. The product fractions were combined and concentrated to afford methyl 2-(2-morpholino-1H-benzo[d]imidazol-5-yl)acetate Ex. 55c (78 mg, 17%) as light yellow oil. |
| Ex. 55 | 2-[2-(morpholin-4-yl)-1H-1,3-benzodiazol-5-yl]acetic acid<br>Step 4: methyl 2-(2-morpholino-1H-benzo[d]imidazol-5-yl)acetate Ex. 55c (78 mg, 0.28 mmol) was dissolved in THF (8 mL). Water (2 mL) was added followed by lithium hydroxide monohydrate (24 mg, 0.57 mmol) and the reaction mixture was stirred overnight at rt. The solvent was removed under reduced pressure. Water was added to the residue and the pH was adjusted to pH = 4 with 1N HCl. The aqueous layer was evaporated to dryness. The crude of the reaction was absorbed onto silica gel and purified by column chromatography eluting a gradient of CH2Cl2/MeOH from [100:0] to [75:25]. The product fractions were combined and concentrated to dryness to afford 2-[2-(morpholin-4-yl)-1H-1,3-benzodiazol-5-yl]acetic acid Ex. 55 (36 mg, 48%) as yellow oil. 1H NMR (300 MHz, DMSO-d6, d in ppm): 3.16 (s, 2H), 3.38-3.45 (m, 4H), 3.69-3.72 (m, 4H), 6.82 (d, 1H), 7.08-7.11 (m, 2H), 8.45 (s, 1H). |

Intermediate Ex.56: 1-(1-cyclopropanecarbonyl-2,3-dihydro-1H-indol-5-yl)cyclopropane-1-carboxylic acid (FIG. 1BL)

TABLE 1.33

| Cpd. | Starting compounds, Reaction conditions and purification, Yield, appearance, ¹H NMR (solvent) data |
|---|---|
| Ex. 56a | methyl 1-(1-cyclopropanecarbonyl-2,3-dihydro-1H-indol-5-yl)cyclopropane-1-carboxylate<br>Step 1: 5-bromoindoline (500 mg, 2.52 mmol) and freshly prepared bromo[1-(methoxycarbonyl)cyclopropyl]zinc (12.62 mL, 10.10 mmol) were dissolved in dry THF (5 mL) and the solution was degassed by nitrogen bubbling for 5 min. Then, XPhos (60 mg, 0.13 mmol) and Pd2(dba)3 (58 mg, 0.06 mmol) were incorporated and the reaction mixture was stirred at 75° C. for 2 h. The reaction mixture was cooled to rt. Water and ice was added to the residue and the aqueous layer was extracted with EtOAc. The combined organic layers were dried over MgSO4, filtered and the solution was concentrated to reduced pressure. The crude material was triturated with a mixture of Et2O/petroleum ether and the solid was collected by filtration. The filtrate was concentrated to dryness to afford methyl 1-(1-cyclopropanecarbonyl-2,3-dihydro-1H-indol-5-yl)cyclopropane-1-carboxylate Ex. 56a (540 mg, 75%). 1H NMR (300 MHz, DMSO-d6, d in ppm): 0.80-0.90 (m, 4H), 1.13 (q, 2H, J = 3.0 Hz), 1.44 (q, 2H, J = 4.1 Hz), 1.85-2.00 (m, 1H), 3.14 (t, 2H, J = 8.1 Hz), 3.52 (s, 3H), 4.27 (t, 2H, J = 7.4 Hz), 7.07 (dd, 1H, J = 8.2 Hz), 7.18 (s, 1H), 7.91 (d, 1H, J = 7.0 Hz). |
| Ex. 56 | 1-(1-cyclopropanecarbonyl-2,3-dihydro-1H-indol-5-yl)cyclopropane-1-carboxylic acid<br>Step 2: methyl 1-(1-cyclopropanecarbonyl-2,3-dihydro-1H-indol-5-yl)cyclopropane-1-carboxylate Ex. 56a (500 mg, 1.75 mmol) was dissolved in MeOH (3 mL) and THF (2 mL). 5M NaOH (1.75 mL, 8.76 mmol) was added and the solution was stirred at rt for 5 h. The reaction was quenched with brine and was extracted with EtOAc. The aqueous layer was acidified with 1M citric acid up pH = 3-4 and the precipitate formed was collected by filtration and washed with water to afford 1-(1-cyclopropanecarbonyl-2,3-dihydro-1H-indol-5-yl)cyclopropane-1-carboxylic acid Ex. 56 (405 mg, 85%) as pale pink solid. 1H NMR (300 MHz, DMSO-d6, d in ppm): 0.80-0.90 (m, 4H), 1.07 (q, 2H, J = 4.0 Hz), 1.40 (q, 2H, J = 3.5 Hz), 1.85-2.00 (m, 1H), 3.14 (t, 2H, J = 8.0 Hz), 4.27 (m, 2H), 7.06 (d, 1H, J = 7.9 Hz), 7.17 (s, 1H), 7.89 (d, 1H, J = 8.4 Hz), 12.20 (br(s), 1H). |

Intermediate Ex.57: 2-{1-[3-(tert-butoxy)-3-oxopropyl]-1H-indol-5-yl}acetic acid (FIG. 1BM)

TABLE 1.34

| Cpd. | Starting compounds, Reaction conditions and purification, Yield, appearance, ¹H NMR (solvent) data |
|---|---|
| Ex. 57a | tert-butyl 3-[5-(2-methoxy-2-oxoethyl)-1H-indol-1-yl]prop-2-enoate<br>Step 1: methyl 2-(1H-indol-5-yl)acetate (5.60 g, 29.60 mmol) was dissolved in acetonitrile (30 mL) and triethylamine (4.54 mL, 32.55 mmol) was added to the solution followed by tert-butyl propiolate (4.46 mL, 32.55 mmol). The solution was stirred at rt for 90 min. The mixture was concentrated to dryness. The residue was dissolved in EtOAc/H2O and, after phases separation, the combined organic layer were washed with brine, dried over MgSO4, filtered and the solution was concentrated under reduced pressure. The crude material was purified by column chromatography on silica gel eluting with a gradient of Heptane/EtOAc from [100:0] to [65:35]. The fractions of the main product were concentrated to dryness to afford a pale yellow solid. This solid was triturated with heptane to obtain tert-butyl 3-[5-(2-methoxy-2-oxoethyl)-1H-indol-1-yl]prop-2-enoate Ex. 57a (6.40 g, 69%) as white solid. |
| Ex. 57b | tert-butyl 3-[5-(2-methoxy-2-oxoethyl)-1H-indol-1-yl]propanoate<br>Step 2: tert-butyl 3-[5-(2-methoxy-2-oxoethyl)-1H-indol-1-yl]prop-2-enoate Ex. 57a (1.15 g, 3.65 mmol) was dissolved in dry MeOH (10 mL) and dry THF (3 mL) and the mixture was purged with N2. Pd/C 5% (58 mg) was added and the N2 atmosphere was replaced by hydrogen and the mixture was stirred at 40° C. for 5 h. TLC showed starting material. The reaction mixture was stirred at rt for additional 72 h. TLC showed still starting material. Additional Pd/C 5% (58 mg) was added and the reaction mixture was stirred at rt for 18 h. LCMS showed total consumption of starting material but 50% of product, [M + H]+ = 318, and 50% of reduced indol ring (indoline), [M + H]+ = 320. The reaction mixture was filtered through a pad of Celite and washed with EtOAc. The filtrate was concentrated to dryness and EtOAc/H2O were added. After phases separation, the product was extracted with EtOAc and the combined organic layer were washed with brine, dried over MgSO4, filtered and the solution was concentrated under reduced pressure. The residue was purified by flash column chromatography on silica gel eluting with heptane and a gradient of CH2Cl2 and CH2Cl2/EtOAc from [100:0] |

TABLE 1.34-continued

| Cpd. | Starting compounds, Reaction conditions and purification, Yield, appearance, $^1$H NMR (solvent) data |
|---|---|
| | to [80:20]. The product fractions were combined and concentrated to dryness to afford tert-butyl 3-[5-(2-methoxy-2-oxoethyl)-1H-indol-1-yl]propanoate Ex. 57b (346 mg, 30%) as yellow oil. During the purification process also 180 mg of indoline derivative was isolated as a yellow oil. |
| Ex. 57 | 2-{1-[3-(tert-butoxy)-3-oxopropyl]-1H-indol-5-yl}acetic acid<br>Step 3: tert-butyl 3-[5-(2-methoxy-2-oxoethyl)-1H-indol-1-yl]propanoate Ex. 57b (346 mg, 1.09 mmol) was dissolved in THF:H2O (9 mL/3 mL) and lithium hydroxide monohydrate (55 mg, 1.31 mmol) was added at 0° C. Then, the reaction mixture was allowed to warm up to rt and stirred at this temperature for 18 h. The reaction mixture was concentrated to dryness and 2M HCl was added at 0° C. until pH = 4 was reached. EtOAc/H2O were added and, after phases separation, the combined organic layer were washed with brine, dried over MgSO4, filtered and the solution was concentrated under reduced pressure. The crude material was purified by flash column chromatography on silica gel eluting with a gradient of CH2Cl2/MeOH from [100:0] to [60:40]. The product fractions were combined and concentrated to dryness affording 2-{1-[3-(tert-butoxy)-3-oxopropyl]-1H-indol-5-yl}acetic acid Ex. 57 (144 mg, 44%) as white solid. 1H NMR (300 MHz, DMSO-d6, d in ppm): 1.36 (s, 9H), 2.73-2.77 (m, 2H), 3.62 (s, 2H), 4.38-4.42 (m, 2H), 6.40 (d, 1H, J = 1.9 Hz), 7.06 (d, 1H, J = 8.3 Hz), 7.34 (d, 1H, J = 2.0 Hz), 7.44 (m, 2H), 12.24 (s, 1H). |

Intermediate Ex.58: 2-[3-(2-methanesulfonylethyl)-1H-indol-5-yl]acetic acid (FIG. 1BN)

TABLE 1.35

| Cpd. | Starting compounds, Reaction conditions and purification, Yield, appearance, $^1$H NMR (solvent) data |
|---|---|
| Ex. 58a | methyl 2-(3-(2-(methylsulfonyl)vinyl)-1H-indol-5-yl)acetate<br>Step 1: methyl 2-(3-formyl-1H-indol-5-yl)acetate (synthesized following the procedure described in WO2016102633) (708 mg, 3.26 mmol) and diethyl(methylsulfonylmethyl) phosphonate (900 mg, 3.91 mmol) were dissolved in acetonitrile (6 mL) and Et3N (6 mL). Lithium bromide (340 mg, 3.91 mmol) was added and the reaction mixture was stirred at rt for 16 h. The reaction mixture was concentrated to dryness and the residue was partitioned between EtOAc and water. After phase separation, the organic layer was washed with brine, dried over MgSO4, filtered and the solution was concentrated under reduced pressure. The crude material was purified by flash column chromatography on silica gel eluting with a gradient of Heptane/EtOAc from [100:0] to [80:20]. The product fractions were combined and concentrated to dryness to afford methyl 2-(3-(2-(methylsulfonyl)vinyl)-1H-indol-5-yl)acetate Ex. 58a (800 mg, 84%) as white solid. |
| Ex. 58b | methyl 2-(3-(2-(methylsulfonyl)ethyl)-1H-indol-5-yl)acetate<br>Step 2: methyl 2-(3-(2-(methylsulfonyl)vinyl)-1H-indol-5-yl)acetate Ex. 58a (800 mg, 2.73 mmol) was dissolved in MeOH (30 mL) and the mixture was purged with N2. Then, Pd/C 10% (80 mg) was added and the N2 atmosphere was replaced by hydrogen and the mixture was stirred at rt for 1 h. The reaction mixture was filtered through a pad of Celite and washed with EtOAc. The solution was concentrated to dryness and the residue was purified by flash column chromatography on silica gel eluting with a gradient of Heptane/EtOAc from [100:0] to [30:70]. The product fractions were combined and concentrated under reduced pressure to afford methyl 2-(3-(2-(methylsulfonyl)ethyl)-1H-indol-5-yl)acetate Ex. 58b (713 mg, 89%) as pale brown oil. |
| Ex. 58 | 2-[3-(2-methanesulfonylethyl)-1H-indol-5-yl]acetic acid<br>Step 3: lithium hydroxide monohydrate (122 mg, 2.90 mmol) was added to the mixture of methyl 2-(3-(2-(methylsulfonyl)ethyl)-1H-indol-5-yl)acetate Ex. 58b (713 mg, 2.41 mmol) diluted in THF/H2O (19 mL/6 mL) at 0° C. Then, the reaction mixture was stirred overnight at rt. The reaction mixture was concentrated to dryness and 2M HCl was added at 0° C. and under vigorous stirring until pH = 4 was reached. The solid formed was collected by filtration and wash with water to afford 2-[3-(2-methanesulfonylethyl)-1H-indol-5-yl]acetic acid Ex. 58 (393 mg, 58%) as pink solid. 1H NMR (300 MHz, DMSO-d6, d in ppm): 3.05 (s, 3H), 3.11-3.17 (m, 2H), 3.45-3.50 (m, 2H), 3.64 (s, 2H), 7.03 (d, 1H, J = 8.3 Hz), 7.27 (s, 1H), 7.32 (d, 1H, J = 8.3 Hz), 7.46 (s, 1H), 10.90 (s, 1H), 12.19 (s, 1H). |

Intermediate Ex.59: 2-[3-(2-methanesulfonylacetyl)-
1H-indol-5-yl]acetic acid (FIG. 1BO)

TABLE 1.36

| Cpd. | Starting compounds, Reaction conditions and purification, Yield, appearance, $^1$H NMR (solvent) data |
|---|---|
| Ex. 59a | methyl 2-(3-(2-(methylsulfonyl)acetyl)-1H-indol-5-yl)acetate<br>Step 1: methyl 2-(1H-indol-5-yl)acetate (500 mg, 2.64 mmol) was added to a solution of methylsulfonylacetic acid (272 µL, 2.91 mmol) diluted in acetic anhydride (4 mL) heated at 85° C. The solution was heated to 90° C. for 18 h. The reaction mixture was filtered and the solid was washed with MeOH yielding methyl 2-(3-(2-(methylsulfonyl)acetyl)-1H-indol-5-yl)acetate Ex. 59a (564 mg, 69%) as a white solid. 1H NMR (300 MHz, DMSO-d6, d in ppm): 3.17 (s, 3H), 3.61 (s, 3H), 3.77 (s, 2H), 4.82 (s, 2H), 7.16 (d, 1H, J = 8.3 Hz), 7.45 (d, 1H, J = 8.3 Hz), 8.09 (s, 1H); 8.56 (s, 1H), 12.22 (s, 1H). |
| Ex. 59 | 2-[3-(2-methanesulfonylacetyl)-1H-indol-5-yl]acetic acid<br>Step 2: lithium hydroxide monohydrate (134 mg, 3.19 mmol) was added to the mixture of methyl 2-(3-(2-(methylsulfonyl)acetyl)-1H-indol-5-yl)acetate Ex. 59a (494 mg, 1.60 mmol) diluted in THF/H2O (9 mL/3 mL) at 0° C. Then, the reaction mixture was stirred overnight at rt. The reaction mixture was concentrated to dryness and 1M HCl was added under vigorous stirring until pH = 4 was reached. The solid formed was collected by filtration and wash with water to afford 2-[3-(2-methanesulfonylacetyl)-1H-indol-5-yl]acetic acid Ex. 59 (468 mg, 99%) as pink solid. 1H NMR (300 MHz, DMSO-d6, d in ppm): 3.20 (s, 3H), 3.68 (s, 2H), 4.85 (s, 2H), 7.19 (d, 1H, J = 8.3 Hz), 7.47 (d, 1H, J = 8.3 Hz), 8.12 (s, 1H), 8.58 (s, 1H), 12.27 (s, 1H). |

Intermediate Ex.61:
1-(1H-indol-5-yl)cyclopropane-1-carboxylic acid
(FIG. 1BQ)

TABLE 1.37

| Cpd. | Starting compounds, Reaction conditions and purification, Yield, appearance, $^1$H NMR (solvent) data |
|---|---|
| Ex. 61a | methyl 1-phenylcyclopropanecarboxylate<br>Step 1: 1-phenylcyclopropanecarboxylic acid (10.00 g, 61.66 mmol) was dissolved in MeOH (150 mL). HCl 4M in dioxane (10 mL) was added and the mixture was heated at 50° C. for 16 h. The solvent was removed under reduced pressure. The residue was partitioned between EtOAc and sat. NaHCO3 solution. The organic layer was dried over MgSO4, filtered and the solution was concentrated to dryness to afford methyl 1-phenylcyclopropanecarboxylate Ex. 61a (10.40 g, 96%) as colorless oil. 1H NMR (300 MHz, CDCl3, d in ppm): 1.22-1.24 (m, 2H), 1.61-1.64 (m, 2H), 3.65 (s, 3H), 7.28-7.39 (m, 5H). |
| Ex. 61b | methyl 1-(4-nitrophenyl)cyclopropanecarboxylate<br>Step 2: methyl 1-phenylcyclopropanecarboxylate Ex. 61a (9.50 g, 53.90 mmol) was dissolved in a mixture of concentrated H2SO4 (25 mL) and CH2Cl2 (25 mL) and cooled at 0° C. Sodium nitrate (4.58 g, 53.90 mmol) was added in portionwise and the mixture was stirred at 0° C. for 2 h and then allowed to warm up to rt. After 36 h, the reaction mixture was quenched with EtOAc and water. The phases were separated, the organic layer was washed with sat. NaHCO3 solution, dried over MgSO4, filtered and the solution was concentrated to dryness. The crude material was purified by column chromatography on silica gel eluting with a gradient of Heptane/EtOAc from [100:0] to [30:70]. The product fractions were combined and concentrated to dryness to afford a colourless oil, which solidified upon standing at rt to give methyl 1-(4-nitrophenyl)cyclopropanecarboxylate Ex. 61b (5.20 g, 44% (uncorrected for impurities)). The product was considered to be suitable for the next synthetic step. 1H NMR (300 MHz, CDCl3, d in ppm): 1.15-1.18 (m, 2H), 1.62-1.66 (m, 2H), 3.57 (s, 3H), 7.44 (d, 2H, J = 8.8 Hz), 8.11 (d, 2H, J = 8.8 Hz). |
| Ex. 61c | methyl 1-(4-aminophenyl)cyclopropanecarboxylate<br>Step 3: methyl 1-(4-nitrophenyl)cyclopropanecarboxylate Ex. 61b (5.20 g, 23.5 mmol) was dissolved in MeOH (100 mL). The solution was purged with N2 and Pd/C 10% (520 mg) was added under N2 atmosphere. The N2 atmosphere was replaced by hydrogen (balloon) and the mixture was stirred at rt for 16 h. The catalyst was removed by filtration through a pad of Celite, the filtrate was concentrated to dryness and purified by column chromatography on silica gel eluting with a gradient of Heptane/EtOAc from [100:0] to [50:50]. The product fractions were combined and concentrated to dryness to afford methyl 1-(4-aminophenyl)cyclopropanecarboxylate Ex. 61c (3.59 g, 80%) as an off-white solid. 1H NMR (300 MHz, CDCl3, d in ppm): 1.03-1.07 (m, 2H), 1.45-1.49 (m, 2H), 3.54-3.55 (m, 5H), 6.56 (d, 2H, J = 8.4 Hz), 7.05 (d, 2H, J = 8.4 Hz). |
| Ex. 61d | methyl 1-(4-amino-3-bromophenyl)cyclopropanecarboxylate<br>Step 4: methyl 1-(4-aminophenyl)cyclopropanecarboxylate Ex. 61c (3.59 g, |

TABLE 1.37-continued

| Cpd. | Starting compounds, Reaction conditions and purification, Yield, appearance, $^1$H NMR (solvent) data |
|---|---|
| | 18.77 mmol) was dissolved in acetonitrile (100 mL). N-bromosuccinimide (3.34 g, 18.77 mmol) was added and the mixture was stirred at rt for 16 h. The mixture was concentrated to dryness. The residue was partitioned between water and EtOAc. The organic layer was separated, dried over MgSO4, filtered and the solution was concentrated to dryness. The residue was purified by column chromatography on silica gel eluting with a gradient of Heptane/EtOAc from [100:0] to [70:30]. The product fractions were combined and concentrated to dryness to afford a pale brown sticky oil which solidified upon standing at rt to give methyl 1-(4-amino-3-bromophenyl)cyclopropanecarboxylate Ex. 61d (4.17 g, 82%) as pale brown solid. 1H NMR (300 MHz, CDCl3, d in ppm): 1.03-1.07 (m, 2H), 1.46-1.49 (m, 2H), 3.55 (s, 3H), 3.99 (br(s), 2H), 6.62 (d, 1H, J = 8.2 Hz), 7.01 (dd, 1H, J = 8.2 Hz, J = 1.8 Hz), 7.31 (d, 1H, J = 1.8 Hz). |
| Ex. 61e | methyl 1-(4-amino-3-(2-(trimethylsilyl)ethynyl)phenyl)cyclopropanecarboxylate<br>Step 5: methyl 1-(4-amino-3-bromophenyl)cyclopropanecarboxylate Ex. 61d (3.90 g, 13.57 mmol) was dissolved in Et3N (50 mL). Ethynyltrimethylsilane (19.18 mL, 135.7 mmol) was added followed by DMAP (33 mg, 0.27 mmol). The mixture was purged with N2 and PdCl2(PPh3)2 (190 mg, 0.27 mmol) was added to the solution. The mixture was heated at 90° C. for 16 h. The reaction was cooled to rt, the solids were removed by filtration through a pad of Celite and washed with EtOAc. The filtrate was concentrated to dryness. The crude material was purified by column chromatography on silica gel eluting with a gradient of Heptane/EtOAc from [100:0] to [75:25]. The product fractions were combined and concentrated to dryness to afford a dark yellow sticky oil, which solidified upon standing at rt to give methyl 1-(4-amino-3-(2-(trimethylsilyl)ethynyl)phenyl)cyclopropanecarboxylate Ex. 61e (1.38 g, 35%) as yellow solid. 1H NMR (300 MHz, CDCl3, d in ppm): 0.27 (s, 9H), 1.11-1.14 (m, 2H), 1.53-1.55 (m, 2H), 3.62 (s, 3H), 4.23 (s, 2H), 6.65 (d, 1H, J = 8.3 Hz), 7.11 (dd, 1H, J = 8.3 Hz, J = 1.9 Hz), 7.28 (s, 1H). |
| Ex. 61f | methyl 1-(1H-indol-5-yl)cyclopropanecarboxylate<br>Step 6: methyl 1-(4-amino-3-(2-(trimethylsilyl)ethynyl)phenyl)cyclopropanecarboxylate Ex. 61e (470 mg, 1.64 mmol) was dissolved in a pressure tube in dry DMF (10 mL). The solution was purged with N2 and CuI (155 mg, 0.82 mmol) was added. The tube was sealed under N2 and heated at 80° C. for 36 h. The mixture was cooled to rt, water and EtOAc were added. The phases were separated and the aqueous layer was washed with EtOAc. The combined organic phases were dried over MgSO4, filtered and the solution was concentrated to dryness. The crude oil was purified by column chromatography on silica gel eluting with a gradient of Heptane/EtOAc from [100:0] to [75:25]. The product fractions were combined and concentrated to dryness to afford methyl 1-(1H-indol-5-yl)cyclopropanecarboxylate Ex. 61f (235 mg, 67%) as yellow oil. 1H NMR (300 MHz, CDCl3, d in ppm): 1.17-1.20 (m, 2H), 1.54-1.57 (m, 2H), 3.54 (s, 3H), 6.45 (s, 1H), 7.12-7.15 (m, 2H), 7.27 (d, 1H, J = 8.4 Hz), 7.53 (s, 1H), 8.08 (br(s), 1H). |
| Ex. 61 | 1-(1H-indol-5-yl)cyclopropane-1-carboxylic acid<br>Step 7: methyl 1-(1H-indol-5-yl)cyclopropanecarboxylate Ex. 61f (355 mg, 1.65 mmol) was dissolved in THF (10 mL). Lithium hydroxide monohydrate (138 mg, 3.30 mmol) dissolved in water (2 mL) was added and the reaction mixture was stirred at rt for 16 h. Further lithium hydroxide monohydrate (2.0 equiv) was added and the reaction mixture was stirred at rt for 60 h. The reaction was quenched with EtOAc. 1M HCl was added until pH = 3-4 was reached. The phases were separated and the organic layer was dried over MgSO4, filtered and the solution was concentrated under reduced pressure. The crude material was purified by column chromatography on silica gel eluting with a gradient of CH2Cl2/MeOH from [100:0] to [95:5]. The product fractions were combined and concentrated to dryness to afford a yellow solid. The solid was triturated with CH2Cl2/MeOH [95:5], filtered and dried under vacuum at 50° C. until constant weight. The product 1-(1H-indol-5-yl)cyclopropane-1-carboxylic acid Ex. 61 (110 mg, 33%) was isolated as a yellow solid. 1H NMR (300 MHz, DMSO-d6, d in ppm): 1.13-1.14 (m, 2H), 1.44-1.45 (m, 2H), 6.36 (s, 1H), 7.06 (dd, 1H, J = 1.3 Hz, J = 8.4 Hz), 7.28-7.32 (m, 2H), 7.45 (s, 1H), 11.00 (s, 1H), 12.07 (br(s), 1H). |

55

Intermediate Ex.64: 2-[3-(methylsulfamoyl)-1H-indol-5-yl]acetic acid (FIG. 1BT)

TABLE 1.38

| Cpd. | Starting compounds, Reaction conditions and purification, Yield, appearance, $^1$H NMR (solvent) data |
|---|---|
| Ex. 64a | 5-((methoxycarbonyl)methyl)-1H-indol-3-sulfonic acid<br>Step 1: methyl 2-(1H-indol-5-yl)acetate (550 mg, 2.91 mmol) was dissolved in pyridine (8 mL). Sulfur trioxide pyridine complex (460 mg, 2.91 mmol) was |

TABLE 1.38-continued

| Cpd. | Starting compounds, Reaction conditions and purification, Yield, appearance, $^1$H NMR (solvent) data |
|---|---|
| | added and the mixture was heated at 120° C. for 2 h. Water and EtOAc were added to quench the reaction. The aqueous layer was separated and concentrated under reduced pressure. The crude was dried under vacuum to afford 5-((methoxycarbonyl)methyl)-1H-indole-3-sulfonic acid Ex. 64a (crude) as an oil. No purification was carried out and the crude was used in the next synthetic step. |
| Ex. 64b | methyl 2-[3-(chlorosulfonyl)-1H-indol-5-yl]acetate<br>Step 2: 5-((methoxycarbonyl)methyl)-1H-indole-3-sulfonic acid Ex. 64a (crude, 2.91 mmol, complete conversion estimated) was dissolved in a mixture of sulfolane/acetonitrile (6 mL/6 mL). The mixture was cooled to 0° C. and phosphorus oxychloride (972 µL, 3.78 mmol) was added dropwise under stirring. Then the mixture was heated at 80° C. for 1 h. The mixture was concentrated to dryness to afford methyl 2-[3-(chlorosulfonyl)-1H-indol-5-yl]acetate Ex. 64b (crude) as an oil. The crude was used in the next synthetic step without any purification. |
| Ex. 64c | methyl 2-[3-(methylsulfamoyl)-1H-indol-5-yl]acetate<br>Step 3: methyl 2-[3-(chlorosulfonyl)-1H-indol-5-yl]acetate Ex. 64b (crude, 2.91 mmol, complete conversion estimated) was dissolved in dry THF (18 mL). The mixture was cooled to 0° C. and pyridine (285 µL, 3.49 mmol) was added. Then, methylamine (2M in THF) (4.36 mL, 8.73 mmol) was added dropwise under stirring. The reaction mixture was stirred overnight at rt. Further methylamine (2M in THF) (4.36 mL, 8.73 mmol) was added to the reaction mixture at 0° C. and the solution was stirred overnight at rt. Water and EtOAc were added to quench the reaction. The organic layer was separated, dried over MgSO4, filtered and the solution was concentrated to dryness. The crude material was purified by column chromatography on silica gel eluting with a gradient of Heptane/EtOAc from [100:0] to [90:10]. The product fractions were combined and concentrated to dryness to afford methyl 2-[3-(methylsulfamoyl)-1H-indol-5-yl]acetate Ex. 64c (crude) as an oil. Residual sulfolane could not be removed at this point and the mixture was used as such in the next synthetic step. |
| Ex. 64 | 2-[3-(methylsulfamoyl)-1H-indol-5-yl]acetic acid<br>Step 4: lithium hydroxide monohydrate (160 mg, 3.90 mmol) was added to a mixture of methyl 2-[3-(methylsulfamoyl)-1H-indol-5-yl]acetate Ex. 64c (1.10 g) diluted in THF/H2O (8 mL/4 mL) at 0° C. The reaction mixture was stirred at rt over the weekend. Water and EtOAc were added to the reaction mixture and the organic layer was separated. 1M HCl was added under vigorous stirring to the aqueous layer until pH = 4 was reached. The aqueous layer was extracted with EtOAc. The organic layer was separated, dried over MgSO4, filtered and the solution was concentrated to dryness. The crude material was purified by column chromatography on silica gel eluting with a gradient of CH2Cl2/MeOH from [100:0] to [90:10]. The product fractions were combined and concentrated to dryness to afford 2-[3-(methylsulfamoyl)-1H-indol-5-yl]acetic acid Ex. 64 (95 mg, 13% over 4 steps) as white solid. 1H NMR (300 MHz, DMSO-d6, d in ppm): 2.32 (d, 3H, J = 5.0 Hz), 3.56 (s, 2H), 7.03 (d, 1H, J = 5.1 Hz), 7.08 (d, 1H, J = 8.5 Hz), 7.37 (d, 1H, J = 8.4 Hz), 7.63 (s, 1H), 7.79 (d, 1H), 11.84 (s, 1H), 12.19 (br(s), 1H). |

Intermediate Ex.65: 2-[3-(morpholine-4-carbonyl)-1H-indol-5-yl]acetic acid (FIG. 1BU)

TABLE 1.39

| Cpd. | Starting compounds, Reaction conditions and purification, Yield, appearance, $^1$H NMR (solvent) data |
|---|---|
| Ex. 65a | 5-bromo-1-tosyl-1H-indole-3-carboxylic acid<br>Step 1: 5-bromo-1H-indole-3-carboxylic acid (3.26 g, 13.6 mmol) was dissolved in dioxane (30 mL). The mixture was purged with nitrogen and cooled to 0-5° C. Sodium Hydride (60% in mineral oil) (1.63 g, 40.8 mmol) was added portionwise over approx. 30 min under a flow of N2. Gas evolution was observed upon addition. When the addition was completed the mixture was stirred for 30 min at 0-5° C. p-Toluenesulfonyl chloride (5.17 g, 27.1 mmol) was dissolved in dioxane (10 mL) and added dropwise over 1 h to the suspension. The reaction mixture was allowed to warm up to rt and stirred at temperature overnight. A white insoluble solid was formed. 1M HCl was added up to pH = 6. The reaction mixture was filtered and washed with CH2Cl2. The combined organic layer were washed with brine, dried over MgSO4, filtered and the solution was concentrated under reduced pressure. The crude material was purified by flash column chromatography on silica gel with a gradient of CH2Cl2/CH2Cl2:MeOH (9:1) from [100:0] to [0:100]. The column fractions were concentrated to dryness to afford 5-bromo-1-tosyl-1H-indole-3-carboxylic acid Ex. 65a (1.47 g, 27%) as pale orange solid. |

TABLE 1.39-continued

| Cpd. | Starting compounds, Reaction conditions and purification, Yield, appearance, $^1$H NMR (solvent) data |
|---|---|
| Ex. 65b | (5-bromo-1-tosyl-1H-indol-3-yl)(morpholino)methanone<br>Step 2: 5-bromo-1-tosyl-1H-indole-3-carboxylic acid Ex. 65a (1.47 g, 3.73 mmol) was dissolved in DMF (30 mL) and (1-cyano-2-ethoxy-2-oxoethylidenaminooxy)dimethylamino-morpholino-carbenium hexafluorophosphate (1.91 g, 4.48 mmol) was added followed by Et3N (1.26 mL, 4.48 mmol) and morpholine (376 μL, 4.48 mmol). The reaction mixture was stirred at 50° C. for 20 h. The reaction mixture was concentrated to dryness. The crude material was purified by flash column chromatography on silica gel using a gradient of Heptane/EtOAc from [100:0] to [20:80]. The desired fractions were concentrated to dryness to afford (5-bromo-1-tosyl-1H-indol-3-yl)(morpholino)methanone Ex. 65b (1.45 g, 84%) as yellow oil. |
| Ex 65c | methyl 2-[1-(4-methylbenzenesulfonyl)-3-(morpholine-4-carbonyl)-1H-indol-5-yl]acetate<br>Step 3: (5-bromo-1-tosyl-1H-indol-3-yl)(morpholino)methanone Ex. 65b (1.45 g, 3.13 mmol), methyl acetoacetate (1 mL, 9.39 mmol) and potassium phosphate (2.65 g, 12.52 mmol) were placed in a screw cap tube, toluene (15 mL) was added and the mixture was degassed by N2 bubbling for 5 min. Then, Pd(OAc)2 (26 mg, 0.16 mmol) and di-tert-butyl XPhos (131 mg, 0.31 mmol) were incorporated and the tube was closed under N2 atmosphere. The reaction mixture was stirred overnight at 120° C. After cooling to rt, the mixture was diluted with water. The aqueous layer was extracted with EtOAc, dried over MgSO4, filtered and the solution was concentrated to dryness. The crude material methyl 2-[1-(4-methylbenzenesulfonyl)-3-(morpholine-4-carbonyl)-1H-indol-5-yl]acetate Ex. 65c (1.54 g, crude) was used as such in the next synthetic step. |
| Ex. 65d | methyl 2-[3-(morpholine-4-carbonyl)-1H-indol-5-yl]acetate<br>Step 4: magnesium (409 mg, 16.80 mmol) was added portionwise to a solution of methyl 2-[1-(4-methylbenzenesulfonyl)-3-(morpholine-4-carbonyl)-1H-indol-5-yl]acetate Ex. 65c (1.54 g, crude) in dry methanol (25 mL). The suspension was stirred at rt for 20 h. Gas formation was observed. The reaction mixture was concentrated and EtOAc/H2O were added. The residu was filtered through a pad of Celite. The two phases were separated. The organic layer was dried over MgSO4, filtered and the solution was concentrated to dryness. The crude material was purified by flash column chromatography on silica gel using a gradient of Heptane/EtOAc from [100:0] to [0:100]. The desired fractions were combined and concentrated to dryness to afford methyl 2-[3-(morpholine-4-carbonyl)-1H-indol-5-yl]acetate Ex. 65d (568 mg, 56%) as white solid. |
| Ex. 65 | 2-[3-(morpholine-4-carbonyl)-1H-indol-5-yl]acetic acid<br>Step 5: methyl 2-[3-(morpholine-4-carbonyl)-1H-indol-5-yl]acetate Ex. 65d (568 mg, 1.88 mmol) was dissolved in THF (5 mL). Water (1.5 mL) was added followed by lithium hydroxide monohydrate (158 mg, 3.76 mmol). The reaction mixture was stirred at rt for 16 h. The solvent was removed under reduced pressure. EtOAc and water were added followed by 1M HCl under vigorous stirring until pH = 4 was reached. The phases were separated. The organic layer was dried over MgSO4, filtered and the solution was concentrated to dryness. The crude material was purified by flash column chromatography on silica gel using a gradient of CH2Cl2/CH2Cl2:MeOH (9:1) from [100:0] to [0:100]. The desired fractions were combined and concentrated to afford 2-[3-(morpholine-4-carbonyl)-1H-indol-5-yl]acetic acid Ex. 65 (112 mg, 21%) as white solid. 1H NMR (300 MHz, DMSO-d6, d in ppm): 3.63 (s, 10H), 7.07-7.10 (d, 1H), 7.38-7.41 (d, 1H), 7.61 (s, 1H), 7.71 (s, 1H), 11.59 (s, 1H), 12.20 (br(s), 1H). |

Intermediate Ex.67: 1-[2-(2-methoxyacetyl)-2,3-dihydro-1H-isoindol-5-yl]cyclopropane-1-carboxylic acid (FIG. 1BW)

TABLE 1.40

| Cpd. | Starting compounds, Reaction conditions and purification, Yield, appearance, $^1$H NMR (solvent) data |
|---|---|
| Ex. 67a | 1-(5-bromoisoindolin-2-yl)-2-methoxyethanone<br>Step 1: to a solution of 5-bromoisoindoline (300 mg, 1.51 mmol) and Et3N (633 μL, 4.54 mmol) in CH2Cl2 (2 mL) was added dropwise 2-methoxyacetyl chloride (208 μL, 2.27 mmol). The reaction mixture was stirred at rt for 1 h. The solution was poured onto a mixture of cold water and CH2Cl2. The phases were separated and the aqueous layer was extracted twice with CH2Cl2. The combined organic layers were dried over MgSO4, filtered and the solution was concentrated to dryness. The residue was triturated in Et2O and filtered-off. The filtrate was concentrated under reduced pressure and triturated with a mixture of Et2O (3 mL) and petroleum ether (3 mL). The solid formed was collected by filtration to afford 1-(5-bromoisoindolin-2-yl)-2-methoxyethanone Ex. 67a (205 mg, 50%) as pale brown solid. 1H NMR (300 MHz, DMSO-d6, d in ppm): |

TABLE 1.40-continued

| Cpd. | Starting compounds, Reaction conditions and purification, Yield, appearance, ¹H NMR (solvent) data |
|---|---|
| | 3.33 (s, 3H), 4.12 (s, 2H), 4.63 (d, 2H, J = 13.4 Hz), 4.75 (d, 2H, J = 12.8 Hz), 7.32 (t, 1H, J = 8.1 Hz), 7.48 (dd, 1H, J = 8.1 Hz, J = 1.9 Hz), 7.58 (d, 1H, J = 8.3 Hz). |
| Ex. 67b | methyl 1-(2-(2-methoxyacetyl)isoindolin-5-yl)cyclopropanecarboxylate<br>Step 2: 1-(5-bromoisoindolin-2-yl)-2-methoxyethanone Ex. 67a (205 mg, 0.76 mmol) and freshly prepared bromo[1-(methoxycarbonyl)cyclopropyl]zinc (1.89 mL, 1.52 mmol) were dissolved in dry THF (2 mL) and the solution was degassed by nitrogen bubbling for 5 min. Then, XPhos (36 mg, 0.08 mmol) and Pd2(dba)3 (35 mg, 0.04 mmol) were incorporated and the reaction mixture was stirred at 75° C. for 16 h. The mixture was cooled to rt and quenched with water and extracted with EtOAc. The combined organic layers were dried over MgSO4, filtered and the solution was concentrated to dryness. The crude was adsorbed onto silica gel and purified by column chromatography eluting with a gradient of Cyclohexane/EtOAc from [20:80] to [0:100]. The product fractions were combined and concentrated to dryness to afford methyl 1-(2-(2-methoxyacetyl)isoindolin-5-yl)cyclopropanecarboxylate Ex. 67b (120 mg, 55%) as white solid. 1H NMR (300 MHz, DMSO-d6, d in ppm): 1.15-1.20 (m, 2H), 1.45-1.50 (m, 2H), 3.33 (s, 3H), 3.53 (s, 3H), 4.12 (s, 2H), 4.63 (s, 2H), 4.74 (s, 2H), 7.20-7.35 (m, 3H). |
| Ex. 67 | 1-[2-(2-methoxyacetyl)-2,3-dihydro-1H-isoindol-5-yl]cyclopropane-1-carboxylic acid<br>Step 3: methyl 1-(2-(2-methoxyacetyl)isoindolin-5-yl)cyclopropanecarboxylate Ex. 67b (120 mg, 0.42 mmol) was dissolved in THF/MeOH (1 mL/1 mL). 5M NaOH (415 µL, 2.07 mmol) was added and the reaction mixture was heated at 100° C. for 5 min under microwave irradiation. Brine was added to quench the reaction. The aqueous layer was acidified with 1M citric acid up pH = 3-4 and was extracted twice with EtOAc. The combined organic layers were dried over MgSO4, filtered and the solution was concentrated under reduced pressure. The residue was triturated with Et2O, filtered, washed with Et2O and dried until constant weight to afford 1-[2-(2-methoxyacetyl)-2,3-dihydro-1H-isoindol-5-yl]cyclopropane-1-carboxylic acid Ex. 67 (40 mg, 35%) as white solid. 1H NMR (300 MHz, DMSO-d6, d in ppm): 1.05-1.15 (m, 2H), 1.40-1.60 (m, 2H), 3.38 (s, 3H), 4.12 (s, 3H), 4.62 (s, 2H), 4.74 (s, 2H), 7.20-7.35 (m, 2H), 12.26 (br(s), 1H). |

Intermediate Ex.68: 2-(1-cyclopropanecarbonyl-2,3-dihydro-1H-indol-5-yl)acetic acid (FIG. 1BX)

TABLE 1.41

| Cpd. | Starting compounds, Reaction conditions and purification, Yield, appearance, ¹H NMR (solvent) data |
|---|---|
| Ex. 68a | (5-bromoindolin-1-yl)(cyclopropyl)methanone<br>Step 1: cyclopropanecarboxylic acid (452 µL, 5.68 mmol) and 5-bromoindoline (750 mg, 3.79 mmol) were dissolved in DMF (7 mL). DMAP (555 mg, 4.54 mmol) and EDCl•HCl (1.60 g, 8.33 mmol) were added to the solution and the reaction mixture was stirred at rt for 12 h. Water was added to quench the reaction. The aqueous layer was extracted with EtOAc. The combined organic layers were washed with 0.25M HCl, water, 5% NaHCO3 and water, dried over MgSO4, filtered and the solution was concentrated to reduced pressure to afford (5-bromoindolin-1-yl)(cyclopropyl)methanone Ex. 68a (998 mg, 99%) as white solid. 1H NMR (300 MHz, DMSO-d6, d in ppm): 0.80-0.90 (m, 4H), 1.94 (m, 1H), 3.18 (t, 2H, J = 8.4 Hz), 4.29 (t, 2H, J = 8.6 Hz), 7.25-7.30 (m, 1H), 7.42 (m, 1H), 7.93 (d, 1H, J = 8.0 Hz). |
| Ex. 68b | tert-butyl 2-(1-cyclopropanecarbonyl-2,3-dihydro-1H-indol-5-yl)acetate<br>Step 2: (5-bromoindolin-1-yl)(cyclopropyl)methanone Ex. 68a (820 mg, 3.08 mmol), the previously synthesized tert-butyl 2-(bromozincio)acetate (5.60 mL, 6.16 mmol) and dry THF (4 mL) were placed in flask, the mixture was degassed by nitrogen bubbling for 5 min. Then Pd2(dba)3 (28 mg, 0.03 mmol) and XPhos (29 mg, 0.06 mmol) were incorporated and the reaction mixture was refluxed for 3 h. The mixture was cooled to rt, EtOAc and water was added and the two-phase mixture was filtered through a pad of Celite. The phases were separated, the organic layer was dried over MgSO4, filtered and the solution was concentrated to dryness. The crude material was purified by column chromatography eluting with Cyclohexane/EtOAc (90:10). The product fractions were combined and concentrated to dryness to give tert-butyl 2-(1-cyclopropanecarbonyl-2,3-dihydro-1H-indol-5-yl)acetate Ex. 68b (900 mg, 97%) as white solid. 1H NMR (300 MHz, DMSO-d6, d in ppm): 0.8-0.9 (m, 4H), 1.38 (s, 9H), 1.85-2.00 (m, 1H), 3.15 (t, 2H, J = 8.0 Hz), 3.46 (s, 2H), 4.27 (t, 2H, J = 7.4 Hz), 6.98 (d, 1H, J = 8.1 Hz), 7.09 (s, 1H), 7.92 (d, 1H, J = 7.3 Hz). |
| Ex. 68 | 2-(1-cyclopropanecarbonyl-2,3-dihydro-1H-indol-5-yl)acetic acid<br>Step 3: tert-butyl 2-(1-cyclopropanecarbonyl-2,3-dihydro-1H-indol-5-yl)acetate Ex. 68b (900 mg, 2.99 mmol) was dissolved in dry CH2Cl2 (5 mL) and 4M HCl in dioxane (3.73 mL, 14.93 mmol) was added to the solution. The reaction |

TABLE 1.41-continued

| Cpd. | Starting compounds, Reaction conditions and purification, Yield, appearance, $^1$H NMR (solvent) data |
|---|---|
| | mixture was stirred overnight at rt. Et2O was added and the precipitate formed was collected by filtration and dried at 40° C. under vacuum until constant weight to give 2-(1-cyclopropanecarbonyl-2,3-dihydro-1H-indol-5-yl)acetic acid Ex. 68 (470 mg, 64%) as pale pink solid. 1H NMR (300 MHz, DMSO-d6, d in ppm): 0.75-0.90 (m, 4H), 1.85-2.00 (m, 1H), 3.15 (t, 2H, J = 8.6 Hz), 3.48 (s, 2H), 4.27 (t, 2H, J = 7.8 Hz), 6.98 (d, 1H, J = 8.5 Hz), 7.11 (s, 1H), 7.92 (d, 1H, J = 7.1 Hz), 12.22 (br(s), 1H). |

Intermediate Ex.69: 1-(2,2-dioxo-1,3-dihydro-4,2,1-benzoxathiazin-6-yl)cyclopropane-1-carboxylic acid (FIG. 1BY)

TABLE 1.42

| Cpd. | Starting compounds, Reaction conditions and purification, Yield, appearance, $^1$H NMR (solvent) data |
|---|---|
| Ex. 69a | 1-chloro-N-(2-methoxyphenyl)methanesulfonamide<br>Step 1: 2-methoxyaniline(6.5 g, 52.78 mmol) was dissolved in CH2Cl2 (150 mL) and Et3N (11.00 mL, 79.17 mmol) was added. The solution was cooled to 0° C. and chloromethanesulfonyl chloride (9.61 g, 58.10 mmol) was added dropwise. The reaction was then warmed to rt and stirred at this temperature overnight. Water was added to quench the reaction. The phases were separated. The aqueous layer was extracted twice with CH2Cl2. The combined organic layers were dried over MgSO4, filtered and the solution was concentrated under reduced pressure. The crude material was purified by silica gel column chromatography eluting with Cyclohexane/EtOAc (80:20). The desired fractions were concentrated to dryness to afford 1-chloro-N-(2-methoxyphenyl)methanesulfonamide Ex. 69a (10.25 g, 72%) as pale brown solid. 1H NMR (300 MHz, DMSO-d6, d in ppm): 3.82 (s, 3H), 4.88 (s, 2H), 6.88-6.95 (m, 1H), 7.03-7.10 (m, 1H), 7.20-7.27 (m, 2H), 9.50 (br(s), 1H). |
| Ex. 69b | 1-chloro-N-(2-hydroxyphenyl)methanesulfonamide<br>Step 2: 1-chloro-N-(2-methoxyphenyl)methanesulfonamide Ex. 69a (10.25 g, 37.84 mmol) was dissolved in CH2Cl2 (200 mL, stabilized with amylene) and the solution was cooled to 0° C. 1M tribromoborane (113.5 mL, 113.5 mmol) was added dropwise over approx. 50 min.<br>The stirring was kept at 0° C. for 1 h 30 and then poured into ice under good stirring. The two phases were separated. The aqueous phase was extracted twice with CH2Cl2. The combined organic layers were washed three times with water, dried over MgSO4, filtered and the solution was concentrated to dryness. The crude material was purified by silica gel column chromatography eluting with Cyclohexane/EtOAc (80:20). The desired fractions were concentrated to dryness to afford 1-chloro-N-(2-hydroxyphenyl)methanesulfonamide Ex. 69b (4.10 g, 49%) as pale brown solid. 1H NMR (300 MHz, DMSO-d6, d in ppm): 4.90 (s, 2H), 6.72-6.80 (m, 1H), 6.87 (dd, 1H, J = 8.1 Hz, J = 1.4 Hz), 7.03-7.10 (m, 1H), 7.16 (dd, 1H, J = 7.8 Hz, J = 1.6 Hz), 9.33 (s, 1H), 9.91 (br(s), 1H). |
| Ex. 69c | 1,3-dihydro-4,2,1-benzoxathiazine-2,2-dione<br>Step 3: 1-chloro-N-(2-hydroxyphenyl)methanesulfonamide Ex. 69b (3.50 g, 14.35 mmol) was dissolved in MeOH (52.5 mL) and K2CO3 (5.95 g, 43.05 mmol) wa added. The solution was distributed in 4 microwave vials. Each vial was heated at 100° C. for 15 min under microwave irradiation. The combined reaction mixture were concentrated under reduced pressure. Water and EtOAc were added to the residue and pH was adjusted with 1N citric acid. After phases separation, the aqueous layer was extracted twice with EtOAc. The combined organic layers were dried over MgSO4, filtered and the solution was concentrated under reduced pressure. The crude material was purified by silica gel column chromatography eluting with Cyclohexane/EtOAc (80:20). The desired fractions were concentrated to dryness to afford 1,3-dihydro-4,2,1-benzoxathiazine-2,2-dione Ex. 69c (1.38 g, 52%) as pale brown solid. 1H NMR (300 MHz, DMSO-d6, d in ppm): 5.19 (s, 2H), 6.80-6.86 (m, 1H), 6.96-7.09 (m, 3H), 10.56 (br(s), 1H). |
| Ex. 69d | 6-bromo-1,3-dihydro-4,2,1-benzoxathiazine-2,2-dione<br>Step 4: 1,3-dihydro-4,2,1-benzoxathiazine-2,2-dione Ex. 69c (1.66 g, 8.94 mmol) was dissolved in CH2Cl2 (30 mL) and the solution was cooled to 0° C. Bromine (503 µL, 9.83 mmol) was added dropwise and the solution was slowly warmed to rt and stirred at this temperature overnight. The precipitate formed was collected by filtration, washed with CH2Cl2 and dried under vacuum to afford a first batch (1.34 g). The filtrate was concentrated under reduced pressure and the precipitate formed was collected by filtration to give a second batch of the |

TABLE 1.42-continued

| Cpd. | Starting compounds, Reaction conditions and purification, Yield, appearance, $^1$H NMR (solvent) data |
|---|---|
| | title compound (630 mg). This two batches were joined to afford 6-bromo-1,3-dihydro-4,2,1-benzoxathiazine-2,2-dione Ex. 69d (1.97 g, 83%) as pale orange solid. 1H NMR (300 MHz, DMSO-d6, d in ppm): 5.24 (s, 2H), 6.78 (d, 1H, J = 8.6 Hz), 7.22 (dd, 1H, J = 8.6 Hz, J = 2.2 Hz), 7.32 (d, 1H, J = 2.2 Hz), 10.77 (s, 1H). |
| Ex. 69e | methyl 1-(2,2-dioxo-1,3-dihydro-4,2,1-benzoxathiazin-6-yl)cyclopropane-1-carboxylate<br>Step 5: 6-bromo-1,3-dihydro-4,2,1-benzoxathiazine-2,2-dione Ex. 69d (1.97 g, 6.44 mmol) was dissolved in dry THF (10 mL). The solution was purged with N2 and Pd2(dba)3 (589 mg, 0.64 mmol) and XPhos (614 mg, 1.29 mmol) were added . The freshly prepared bromo[1-(methoxycarbonyl)cyclopropyl]zinc (24.14 mL, 19.31 mmol) was added to the solution. The reaction mixture was heated overnight at 85° C. The solution was cooled to rt and quenched with water and extracted with EtOAc. The combined organic layers were dried over MgSO4, filtered and the solution was concentrated to dryness. The crude material was adsorbed onto silica gel and purified by column chromatography eluting with Cyclohexane/EtOAc (70:30). The product fractions were combined and concentrated to dryness to afford methyl 1-(2,2-dioxo-1,3-dihydro-4,2,1-benzoxathiazin-6-yl)cyclopropane-1-carboxylate Ex. 69e (1.17 g, 64%) as pale yellow solid. 1H NMR (300 MHz, DMSO-d6, d in ppm): 1.11-1.20 (m, 2H), 1.39-1.49 (m, 2H), 3.54 (s, 3H), 5.18 (s, 2H), 6.75 (d, 1H, J = 8.8 Hz), 6.97-7.04 (m, 2H), 10.54 (br(s), 1H). |
| Ex. 69 | 1-(2,2-dioxo-1,3-dihydro-4,2,1-benzoxathiazin-6-yl)cyclopropane-1-carboxylic acid<br>Step 6: methyl 1-(2,2-dioxo-1,3-dihydro-4,2,1-benzoxathiazin-6-yl)cyclopropane-1-carboxylate Ex. 69e (1.17 g, 4.13 mmol) was dissolved in a mixture of THF/MeOH (10 mL/ 10 mL). 5M NaOH (4.13 mL, 8.26 mmol) was added and the solution was stirred overnight at rt. The solvents were removed under reduced pressure. Water was added to the residue and the solution was extracted with Et2O. The resulting aqueous layer was acidified with 1N citric acid to pH = 3-4 and then extracted with EtOAc. The combined organic layers were dried over MgSO4, filtered and the solution was concentrated under reduced pressure to afford 1-(2,2-dioxo-1,3-dihydro-4,2,1-benzoxathiazin-6-yl)cyclopropane-1-carboxylic acid Ex. 69 (1.10 g, 99%) as white solide. 1H NMR (300 MHz, DMSO-d6, d in ppm): 1.06-1.13 (m, 2H), 1.36-1.44 (m, 2H), 5.15 (s, 2H), 6.73 (d, 1H, J = 8.7 Hz), 6.93-7.03 (m, 2H), 10.51 (br(s), 1H), 12.25 (br(s), 1H). |

Intermediate Ex.70: 1-(2,3-dioxo-2,3-dihydro-1H-indol-5-yl)cyclopropane-1-carboxylic acid (FIG. 1BZ)

TABLE 1.43

| Cpd. | Starting compounds, Reaction conditions and purification, Yield, appearance, $^1$H NMR (solvent) data |
|---|---|
| Ex. 70a | 5'-bromo-1',2'-dihydrospiro[1,3-dioxolane-2,3'-indole]-2'-one<br>Step 1: 5-bromo-2,3-dihydro-1H-indole-2,3-dione (5.00 g, 22.10 mmol) was suspended in toluene (150 mL). Ethane-1,2-diol (12.34 mL, 221 mmol) was added followed by p-toluenesulfonic acid monohydrate (210 mg, 1.11 mmol). The mixture was heated to reflux in a Dean-Stark apparatus for 24 h. The reaction mixture was cooled to rt and concentrated to dryness. The oil was taken up in EtOAc and washed with water. The organic layer was dried over MgSO4, filtered and the solution was concentrated until precipitation started. Diethyl ether was added to the slurry, the mixture was stirred at rt for 1 h and the solid was collected by filtration and washed with a small amount of diethyl ether. The solid was dried under vacuum at 40° C. until constant weight to afford 5'-bromo-1',2'-dihydrospiro[1,3-dioxolane-2,3'-indole]-2'-one Ex. 70a (3.88 g, 65%) as pale yellow solid. 1H NMR (300 MHz, DMSO-d6, d in ppm): 4.23-4.34 (m, 4H), 6.80 (dd, 1H, J = 7.8 Hz, J = 1.2 Hz), 7.49-7.53 (m, 2H), 10.59 (s, 1H). |
| Ex. 70b | methyl 1-{2'-oxo-1',2'-dihydrospiro[1,3-dioxolane-2,3'-indole]-5'-yl}cyclopropane-1-carboxylate<br>Step 2: 5'-bromo-1',2'-dihydrospiro[1,3-dioxolane-2,3'-indole]-2'-one Ex. 70a (500 mg, 1.85 mmol) was dissolved in dry THF (5 mL). The solution was purged with N2 and Pd2(dba)3 (127 mg, 0.14 mmol) and XPhos (132 mg, 0..28 mmol) were added. The freshly prepared bromo[1-(methoxycarbonyl)cyclopropyl]zinc (6.94 mL, 5.55 mmol) was added slowly as a solution in THF (approx. 0.8M, 1.85 mL, 3 eq.). The resulting deep red mixture was heated at 70° C. for 1 h 30. TLC (cyclohexane ethyl acetate [8:2]) showed partial conversion. Heating was continued for 16 h, no change in profile was observed by TLC (still residual starting material present). The mixture was cooled to rt and was quenched with water and EtOAc. The mixture was filtered through a pad of Celite. The aqueous |

TABLE 1.43-continued

| Cpd. | Starting compounds, Reaction conditions and purification, Yield, appearance, $^1$H NMR (solvent) data |
|---|---|
| | phase was separated from the filtrate. The remaining organic layer was dried over MgSO4, filtered and the solution was concentrated to dryness. The crude material was adsorbed onto silica gel and purified by column chromatography eluting with a gradient of Cyclohexane/EtOAc from [100:0] to [85:15]. The product fractions were combined and concentrated to dryness to afford methyl 1-{2'-oxo-1',2'-dihydrospiro[1,3-dioxolane-2,3'-indole]-5'-yl}cyclopropane-1-carboxylate Ex. 70b (190 mg, 36%) as white solid. 1H NMR (300 MHz, DMSO-d6, d in ppm): 1.13-1.17 (m, 2H), 1.44-1.47 (m, 2H), 3.53 (s, 3H), 4.22-4.35 (m, 4H), 6.77 (dd, 1H, J = 7.8 Hz, J = 0.3 Hz), 7.26-7.30 (m, 2H), 10.43 (s, 1H). |
| Ex. 70c | methyl 1-(2,3-dioxo-2,3-dihydro-1H-indol-5-yl)cyclopropane-1-carboxylate<br>Step 3: methyl 1-{2'-oxo-1,2'-dihydrospiro[1,3-dioxolane-2,3'-indole]-5'-yl}cyclopropane-1-carboxylate Ex. 70b (500 mg, 1.73 mmol) was dissolved in methanol (10 mL). 1M HCl (2.0 mL) was added and the reaction mixture was heated at 70° C. for 16 h. LCMS showed complete conversion. The mixture was cooled to rt and water was added to quench the reaction. The solid formed was collected by filtration, washed with water and dried under vacuum at 40° C. until constant weight to give methyl 1-(2,3-dioxo-2,3-dihydro-1H-indol-5-yl)cyclopropane-1-carboxylate Ex. 70c (345 mg, 81%) as orange solid. 1H NMR (300 MHz, DMSO-d6, d in ppm): 1.16-1.20 (m, 2H), 1.45-1.49 (m, 2H), 3.54 (s, 3H), 6.85 (dd, 1H, J = 8.1 Hz, J = 0.3 Hz), 7.44 (d, 1H, J = 2.1 Hz), 7.56 (dd, 1H, J = 8.1 Hz, J = 2.1 Hz), 11.03 (s, 1H). |
| Ex. 70 | 1-(2,3-dioxo-2,3-dihydro-1H-indol-5-yl)cyclopropane-1-carboxylic acid<br>Step 4: methyl 1-(2,3-dioxo-2,3-dihydro-1H-indol-5-yl)cyclopropane-1-carboxylate Ex. 70c (340 mg, 1.39 mmol) was suspended in THF/H2O [4:1] (10 mL). Lithiumhydroxide monohydrate (175 mg, 4.16 mmol) was added and the reaction mixture was stirred at rt for 24 h. LCMS showed complete consumption of the starting material. The organic solvent was removed under reduced pressure and the remaining aqueous solution was acidified to pH = 2-3 by addition of 1M HCl. The mixture was stirred overnight at rt. The solid formed was collected by filtration, washed with water and dried under vacuum at 40° C. until constant weight to afford 1-(2,3-dioxo-2,3-dihydro-1H-indol-5-yl)cyclopropane-1-carboxylic acid (278 mg, 87%) as orange solid. 1H NMR (300 MHz, DMSO-d6, d in ppm): 1.10-1.14 (m, 2H), 1.42-1.45 (m, 2H), 6.84 (d, 1H, J = 8.1 Hz), 7.41 (d, 1H, J = 1.8 Hz), 7.54 (dd, 1H, J = 8.1 Hz, J = 1.8 Hz), 11.01 (s, 1H), 12.38 (br(s), 1H). |

Intermediate Ex.71: 1-(1-acetylindolin-5-yl)cyclopropanecarboxylic acid=1-(1-acetyl-2,3-dihydro-1H-indol-5-yl)cyclopropane-1-carboxylic acid (FIG. 1CA, 1CB)

TABLE 1.44

| Cpd. | Starting compounds, Reaction conditions and purification, Yield, appearance, $^1$H NMR (solvent) data |
|---|---|
| Ex. 71a | 1-(5-bromoindolin-1-yl)ethanone<br>Step 1: to a solution of 5-bromoindoline (600 mg, 3.03 mmol) dissolved in dry CH2Cl2 (2 mL) was added sodium hydrogencarbonate (1.27 g, 15.15 mmol). After few min of stirring, acetyl chloride (248 µL, 3.64 mmol) was slowly added at rt to the solution. The reaction mixture was stirred at rt for 1 h. The solution was poured onto brine. The aqueous layer was extracted with EtOAc. The combined organic layers were dried over MgSO4, filtered and the solution was dried under reduced pressure to afford 1-(5-bromoindolin-1-yl)ethanone Ex. 71a (551 mg, 76%) as white solid. The product was pure enough and used as such in the next synthetic step. 1H NMR (300 MHz, DMSO-d6, d in ppm): 2.13 (s, 3H), 3.13 (t, 2H, J = 8.5 Hz), 4.09 (t, 2H, J = 8.8 Hz), 7.30 (dd, 1H, J = 8.6 Hz, J = 2.1 Hz), 7.40 (d, 1H, J = 0.8 Hz), 7.95 (d, 1H, J = 8.6 Hz). |
| Ex. 71b | methyl 1-(1-acetylindolin-5-yl)cyclopropanecarboxylate<br>Step 2: 1-(5-bromoindolin-1-yl)ethanone Ex. 71a (550 mg, 2.29 mmol) was dissolved in dry THF (4 mL). The solution was purged with N2 and Pd2(dba)3 (21 mg, 0.02 mmol) and XPhos (22 mg, 0.04 mmol) were added to the solution. The freshly prepared bromo[1-(methoxycarbonyl)cyclopropyl]zinc (4.17 mL, 4.58 mmol) was added to the solution. The resulting mixture was heated at reflux for 5 h. The reaction mixture was cooled to rt and quenched with sat. NH4Cl and extracted with EtOAc. The combined organic layers were dried over MgSO4, filtered and the solution was concentrated to dryness. The crude material was purified by silica gel column chromatography eluting with Cyclohexane/EtOAc from [90:10]. The product fractions were combined and concentrated to dryness and the residue was triturated in Et2O. The solid was collected by filtration to afford methyl 1-(1-acetylindolin-5-yl)cyclopropanecarboxylate Ex. 71b (524 mg, 88%) as pale brown solid. 1H NMR (300 MHz, DMSO-d6, d in ppm): 1.13 (q, 2H, J = 4.2 Hz), 1.44 (q, 2H, J = 3.0 Hz), 2.13 (s, 3H), 3.10 (t, 2H, J = 8.4 Hz), 3.52 (s, |

TABLE 1.44-continued

| Cpd. | Starting compounds, Reaction conditions and purification, Yield, appearance, $^1$H NMR (solvent) data |
|---|---|
| | 3H), 4.07 (t, 2H, J = 8.7 Hz), 7.08 (d, 1H, J = 8.3 Hz), 7.16 (s, 1H), 7.92 (d, 1H, J = 8.3 Hz). |
| Ex. 71 | 1-(1-acetylindolin-5-yl)cyclopropanecarboxylic acid = 1-(1-acetyl-2,3-dihydro-1H-indol-5-yl)cyclopropane-1-carboxylic acid<br>Step 3: to a solution of methyl 1-(1-acetylindolin-5-yl)cyclopropanecarboxylate (475 mg, 1.83 mmol) dissolved in MeOH/THF (3 mL/2 mL) was added 5M NaOH (1.83 mL, 9.16 mmol). The solution was stirred at rt for 8 h. The solution was poured onto brine and the aqueous solution was extracted with Et2O twice. The pH of the aqueous layer was then adjusted to pH = 2-3 with 1M citric acid. The solid formed was collected by filtration and dried until constant weight to afford 1-(1-acetylindolin-5-yl)cyclopropanecarboxylic acid Ex. 71 (308 mg, 69%) as pale pink solid. 1H NMR (300 MHz, DMSO-d6, d in ppm): 1.07 (q, 2H, J = 4.8 Hz), 1.40 (q, 2H, J = 3.8 Hz), 2.13 (s, 3H), 3.10 (t, 2H, J = 9.4 Hz), 4.06 (t, 2H, J = 8.8 Hz), 7.06 (d, 1H, J = 7.6 Hz), 7.15 (s, 1H), 7.91 (d, 1H, J = 8.4 Hz), 12.20 (br(s), 1H). |

Intermediate Ex.72: 1-(2-acetylisoindolin-5-yl)cyclopropanecarboxylic acid=1-(2-acetyl-2,3-dihydro-1H-isoindol-5-yl)cyclopropane-1-carboxylic acid (FIG. 1CA, 1CB)

TABLE 1.45

| Cpd. | Starting compounds, Reaction conditions and purification, Yield, appearance, $^1$H NMR (solvent) data |
|---|---|
| Ex. 72a | 1-(6-bromoindolin-1-yl)ethanone<br>Step 1: to a solution of 6-bromoindoline (600 mg, 3.03 mmol) dissolved in dry CH2Cl2 (2 mL) was added sodium hydrogencarbonate (1.27 g, 15.15 mmol). After few min of stirring, acetyl chloride (248 µL, 3.64 mmol) was slowly added at rt to the solution. The reaction mixture was stirred at rt for 1 h. The solution was poured onto brine. The aqueous layer was extracted with EtOAc. The combined organic layers were dried over MgSO4, filtered and the solution was dried under reduced pressure to afford 1-(6-bromoindolin-1-yl)ethanone Ex. 72a (400 mg, 55%) as white solid. The product was pure enough and used as such in the next synthetic step. 1H NMR (300 MHz, DMSO-d6, d in ppm): 2.03 (s, 3H), 4.57 (d, 2H, J = 13.6 Hz), 4.80 (d, 2H, J = 11.9 Hz), 7.25-7.35 (m, 1H), 7.47 (dd, 1H, J = 8.0 Hz, J = 1.9 Hz), 7.57 (d, 1H, J = 7.7 Hz). |
| Ex. 72b | methyl 1-(1-acetylindolin-6-yl)cyclopropanecarboxylate<br>Step 2: 1-(6-bromoindolin-1-yl)ethanone Ex. 72a (400 mg, 1.67 mmol) was dissolved in dry THF (4 mL). The solution was purged with N2 and Pd2(dba)3 (15 mg, 0.02 mmol) and XPhos (16 mg, 0.03 mmol) were added to the solution. The freshly prepared bromo[1-(methoxycarbonyl)cyclopropyl]zinc (3.03 mL, 3.33 mmol) was added to the solution. The resulting mixture was heated at reflux for 5 h. The reaction mixture was cooled to rt and quenched with sat. NH4Cl and extracted with EtOAc. The combined organic layers were dried over MgSO4, filtered and the solution was concentrated to dryness. The crude material was purified by silica gel column chromatography eluting with Cyclohexane/EtOAc from [70:30]. The product fractions were combined and concentrated to dryness to afford methyl 1-(1-acetylindolin-6-yl)cyclopropanecarboxylate Ex. 72b (150 mg, 35%) as white solid. 1H NMR (300 MHz, DMSO-d6, d in ppm): 1.15-1.20 (m, 2H), 1.45-1.50 (m, 2H), 2.04 (s, 3H), 3.53 (s, 3H), 4.57 (s, 2H), 4.79 (s, 2H), 7.25-7.27 (m, 2H), 7.30 (d, 1H, J = 6.4 Hz). |
| Ex. 72 | 1-(2-acetylisoindolin-5-yl)cyclopropanecarboxylic acid = 1-(2-acetyl-2,3-dihydro-1H-isoindol-5-yl)cyclopropane-1-carboxylic acid<br>Step 3: to a solution of methyl 1-(1-acetylindolin-6-yl)cyclopropanecarboxylate Ex. 72b (150 mg, 0.58 mmol) dissolved in MeOH/THF (1.5 mL/ 0.5 mL) was added 5M NaOH (578 µL, 2.89 mmol). The solution was stirred at rt for 8 h. The solution was poured onto brine and the aqueous solution was extracted with Et2O twice. The pH of the aqueous layer was then adjusted to pH = 3-4 with 1M citric acid and extracted with EtOAc. The combined organic layers were dried over MgSO4, filtered and the solution was concentrated under reduced pressure to afford 1-(1-acetylindolin-6-yl)cyclopropanecarboxylic acid Ex. 72 (138 mg, 97%) as yellow oil. 1H NMR (300 MHz, DMSO-d6, d in ppm): 1.11 (q, 2H, J = 4.2 Hz), 1.40 (m, 2H), 2.04 (s, 3H), 4.57 (s, 2H), 4.78 (s, 2H), 7.23-7.25 (m, 2H), 7.28 (d, 1H, J = 6.8 Hz), 12.25 (br(s), 1H). |

Intermediate Ex.75: 1-(1-methyl-2-oxo-2,3-dihydro-1H-indol-5-yl)cyclopropane-1-carboxylic acid (FIG. 1CE)

TABLE 1.46

| Cpd. | Starting compounds, Reaction conditions and purification, Yield, appearance, $^1$H NMR (solvent) data |
|---|---|
| Ex. 75a | methyl 1-(1-methyl-2-oxo-2,3-dihydro-1H-indol-5-yl)cyclopropane-1-carboxylate<br>Step 1: 5-bromo-1-methylindolin-2-one (500 mg, 2.21 mmol) was dissolved in dry THF (5 mL). The solution was purged with N2 and Pd2(dba)3 (127 mg, 0.14 mmol) and XPhos (132 mg, 0.28 mmol) were added to the solution. The freshly prepared bromo[1-(methoxycarbonyl)cyclopropyl]zinc (6.94 mL, 5.55 mmol) was added slowly as a solution in THF (approx. 0.8M). The resulting mixture was heated at 70° C. for 1 h 30. Partial conversion was obersved by LCMS. The mixture was heated at 70° C. overnight, no change in profile. Further Pd2(dba)3 (127 mg, 0.14 mmol) and XPhos (132 mg, 0.28 mmol) were added followed by bromo[1-(methoxycarbonyl)cyclopropyl]zinc (6.94 mL, 5.55 mmol). Heating to 70° C. was continued until almost complete conversion was observed (1 h30). The mixture was cooled to rt and was quenched with water and EtOAc. The mixture was filtered through a pad of Celite. After phases separation, the remaining organic layer was dried over MgSO4, filtered and the solution was concentrated to dryness. The crude material was purified by column chromatography eluting with a gradient of Cyclohexane/EtOAc from [100:0] to [65:35]. The product fractions were combined and concentrated to dryness to afford methyl 1-(1-methyl-2-oxo-2,3-dihydro-1H-indol-5-yl)cyclopropane-1-carboxylate Ex. 75a (99 mg, 18%) as pale orange solid. 1H NMR (300 MHz, DMSO-d6, d in ppm): 1.12-1.16 (m, 2H), 1.44-1.48 (m, 2H), 3.09 (s, 3H), 3.51 (s, 2H), 3.52 (s, 3H), 6.88 (d, 1H, J = 8.7 Hz), 7.21 (d, 1H, J = 1.8 Hz), 7.23 (d, 1H, J = 1.8 Hz). |
| Ex. 75 | 1-(1-methyl-2-oxo-2,3-dihydro-1H-indol-5-yl)cyclopropane-1-carboxylic acid<br>Step 2: methyl 1-(1-methyl-2-oxo-2,3-dihydro-1H-indol-5-yl)cyclopropane-1-carboxylate Ex. 75a (40 mg, 0.16 mmol) was taken up in concentrated H2SO4 (1 mL) and the mixture was stirred overnight at 50° C. The solution was cooled to rt and poured onto ice and water. The pH was adjusted up to pH = 4-5 with 5M NaOH solution. The aqueous layer was extracted with EtOAc. The combined organic layers were dried over MgSO4, filtered and the solution was concentrated under reduced pressure to afford 1-(1-methyl-2-oxo-2,3-dihydro-1H-indol-5-yl)cyclopropane-1-carboxylic acid Ex. 75 (35 mg, 93%) as pale brown solid. 1H NMR (300 MHz, DMSO-d6, d in ppm): 1.05-1.12 (m, 2H), 1.39-1.46 (m, 2H), 3.09 (s, 3H), 3.51 (s, 2H), 6.86 (d, 1H, J = 8.5 Hz), 7.15-7.26 (m, 2H), 12.27 (br(s), 1H). |

Intermediate Ex.76: 1-(1-ethyl-2,2-dioxo-1,3-dihydro-2,1-benzothiazol-5-yl)cyclopropane-1-carboxylic acid (FIG. 1CF)

TABLE 1.47

| Cpd. | Starting compounds, Reaction conditions and purification, Yield, appearance, $^1$H NMR (solvent) data |
|---|---|
| Ex. 76a | methyl 1-(1-ethyl-2,2-dioxo-1,3-dihydro-2,1-benzothiazol-5-yl)cyclopropane-1-carboxylate<br>Step 1: to a previously synthesized methyl 1-(2,2-dioxo-1,3-dihydro-2,1-benzothiazol-5-yl)cyclopropane-1-carboxylate (120 mg, 0.45 mmol) dissolved in dry DMF (10 mL) were added K2CO3 (186 mg, 1.35 mmol) followed by iodoethane (54 μL, 0.67 mmol). After 1 h at rt, TLC showed not total consumption of the starting material. Additional iodoethane (54 μL, 0.67 mmol) and K2CO3 (186 mg, 1.35 mmol) were added to the reaction mixture and the solution was stirred for 5 h. The reaction mixture was quenched with brine. The aqueous solution was extracted with EtOAc, dried over MgSO4, filtered and the solution was concentrated under reduced pressure to afford methyl 1-(1-ethyl-2,2-dioxo-1,3-dihydro-2,1-benzothiazol-5-yl)cyclopropane-1-carboxylate Ex. 76 (70 mg, 53%). 1H NMR (300 MHz, DMSO-d6, d in ppm): 1.15 (q, 2H, J = 4.2 Hz), 1.25 (t, 3H, J = 7.1 Hz), 1.47 (q, 2H, J = 3.7 Hz), 3.53 (s, 3H), 3.61 (q, 2H, J = 7.1 Hz), 4.59 (s, 2H), 6.90 (d, 1H, J = 8.8 Hz), 7.25-7.35 (m, 2H). |
| Ex. 76 | 1-(1-ethyl-2,2-dioxo-1,3-dihydro-2,1-benzothiazol-5-yl)cyclopropane-1-carboxylic acid<br>Step 2: to a solution of methyl 1-(1-ethyl-2,2-dioxo-1,3-dihydro-2,1-benzothiazol-5-yl)cyclopropane-1-carboxylate Ex. 76a (70 mg, 0.24 mmol) dissolved in MeOH/THF (800 μL/200 μL) was added 5M NaOH (237 μL, 1.19 mmol). The solution was stirred overnight at rt. The solution was poured onto sat. NH4Cl and the aqueous solution was extracted with EtOAc twice. The pH of the aqueous layer was then adjusted to pH = 3-4 with 1M citric acid and extracted with EtOAc. The combined organic layers were dried over MgSO4, filtered and |

TABLE 1.47-continued

| Cpd. | Starting compounds, Reaction conditions and purification, Yield, appearance, $^1$H NMR (solvent) data |
|---|---|
| | the solution was concentrated under reduced pressure to afford 1-(1-ethyl-2,2-dioxo-1,3-dihydro-2,1-benzothiazol-5-yl)cyclopropane-1-carboxylic acid Ex. 76 (54 mg, 81%) as pale brown solid. 1H NMR (300 MHz, DMSO-d6, d in ppm): 1.10 (q, 2H, J = 3.0 Hz), 1.25 (t, 3H, J = 7.1 Hz), 1.43 (q, 2H, J = 3.6 Hz), 3.60 (q, 2H, J = 7.1 Hz), 4.58 (s, 2H), 6.87 (d, 1H, J = 5.9 Hz), 7.25-7.35 (m, 2H), 12.22 (s, 1H). |

Intermediate Ex.82: 1-(1-oxo-2,3-dihydro-1H-inden-5-yl)cyclopropane-1-carboxylic acid (FIG. 1CL)

TABLE 1.48

| Cad. | Starting compounds, Reaction conditions and purification, Yield, appearance, $^1$H NMR (solvent) data |
|---|---|
| Ex. 82a | methyl 1-(1-oxo-2,3-dihydro-1H-inden-5-yl)cyclopropane-1-carboxylate<br>Step 1: 5-bromo-1-indanone (200 mg, 9.48 mmol) was dissolved in dry THF (5 mL). The solution was purged with N2 and Pd2(dba)3 (87 mg, 0.09 mmol) and XPhos (90 mg, 0.19 mmol) were added to the solution. The freshly prepared bromo[1-(methoxycarbonyl)cyclopropyl]zinc (3.55 mL, 2.84 mmol) was added slowly as a solution in THF (approx. 0.8M). The resulting mixture was heated at 70° C. for 1 h 30. TLC showed complete conversion. After cooling to rt, the reaction mixture was quenched with water and EtOAc and filtered through a pad of Celite. After phases separation, the remaining organic layer was dried over MgSO4, filtered and the solution was concentrated to dryness. The crude material was adsorbed onto silica gel and purified by column chromatography eluting with a gradient of Cyclohexane/EtOAc from [100:0] to [75:25]. The product fractions were combined and concentrated to dryness. The solid was triturated with a small amount of Et2O, filtered and dried until constant weight to afford methyl 1-(1-oxo-2,3-dihydro-1H-inden-5-yl)cyclopropane-1-carboxylate Ex. 82a (129 mg, 59%) as pale yellow solid. 1H NMR (300 MHz, DMSO-d6, d in ppm): 1.24-1.28 (m, 2H), 1.51-1.55 (m, 2H), 2.60-2.64 (m, 2H), 3.05-3.09 (m, 2H), 3.55 (s, 3H), 7.37-7.40 (m, 1H), 7.53-7.58 (m, 2H). |
| Ex. 82 | 1-(1-oxo-2,3-dihydro-1H-inden-5-yl)cyclopropane-1-carboxylic acid<br>Step 2: methyl 1-(1-oxo-2,3-dihydro-1H-inden-5-yl)cyclopropane-1-carboxylate Ex. 82a (100 mg, 0.43 mmol) was taken up in a mixture of THF and water [4:1] (5 mL). Lithium hydroxide monohydrate (36 mg, 0.87 mmol) was added and the mixture was stirred at rt for 2 h. LCMS showed complete conversion. The organic solvent was removed in vacuo and the remaining aqueous mixture was acidified to pH = 2-3 by addition of 3M HCl. The solid formed was collected by filtration and washed with water. The product contained some impurities and was adsorbed onto silica gel and purified by column chromatography eluting with a gradient of CH2Cl2/MeOH from [100:0] to [95:5]. The product fractions were combined and concentrated to dryness to afford 1-(1-oxo-2,3-dihydro-1H-inden-5-yl)cyclopropane-1-carboxylic acid Ex. 82 (68 mg, 72%) as an off-white solid. 1H NMR (300 MHz, DMSO-d6, d in ppm): 1.18-1.22 (m, 2H), 1.48-1.51 (m, 2H), 2.59-2.63 (m, 2H), 3.05-3.09 (m, 2H), 7.37 (dd, 1H, J = 1.5 Hz, J = 7.8 Hz), 7.51-7.56 (m, 2H), 12.45 (s, 1H) |

Intermediate Ex.84: 1-{2-oxo-1H2H,3H-pyrido[2,3-b][1,4]oxazin-6-yl}cyclopropane-1-carboxylic acid (FIG. 1CN)

TABLE 1.49

| Cpd. | Starting compounds, Reaction conditions and purification, Yield, appearance, $^1$H NMR (solvent) data |
|---|---|
| Ex. 84a | methyl 1-{2-oxo-1H,2H,3H-pyrido[2,3-b][1,4]oxazin-6-yl}cyclopropane-1-carboxylate<br>Step 1: 6-bromo-1h-pyrido[2,3-b][1,4]oxazin-2(3h)-one (970 mg, 4.24 mmol) was dissolved in dry THF (12 mL). The solution was purged with N2 and Pd2(dba)3 (388 mg, 0.42 mmol) and XPhos (404 mg, 0.85 mmol) were added to the solution. The freshly prepared bromo[1-(methoxycarbonyl)cyclopropyl]zinc (3.11 g, 12.71 mmol) was added slowly as a solution in THF (approx. 0.8M). The resulting mixture was heated at 75° C. for 16 h. TLC showed complete conversion. After cooling to rt, the reaction mixture was quenched with water and EtOAc and filtered through a pad of Celite. After phases separation, the remaining organic layer was dried over MgSO4, filtered and the solution was concentrated to dryness. The crude material was adsorbed onto silica gel and |

TABLE 1.49-continued

| Cpd. | Starting compounds, Reaction conditions and purification, Yield, appearance, $^1$H NMR (solvent) data |
|---|---|
| | purified by column chromatography eluting with a gradient of Hexanes/EtOAc from [50:50] to [30:70]. The product fractions were combined and concentrated to dryness. The solid was triturated with a small amount of Et2O, filtered and dried until constant weight to afford methyl 1-{2-oxo-1H,2H,3H-pyrido[2,3-b][1,4]oxazin-6-yl}cyclopropane-1-carboxylate Ex. 84a (500 mg, 34%) as yellowish solid. 1H NMR (400 MHz, DMSO-d6, d in ppm): 1.28 (q, 2H, J = 4.0 Hz), 1.44 (q, 2H, J = 3.9 Hz), 3.58 (s, 3H), 4.75 (s, 2H), 7.10-7.19 (m, 2H), 10.81 (s, 1H). |
| Ex. 84 | 1-{2-oxo-1H,2H,3H-pyrido[2,3-b][1,4]oxazin-6-yl}cyclopropane-1-carboxylic acid<br>Step 2: methyl 1-{2-oxo-1H,2H,3H-pyrido[2,3-b][1,4]oxazin-6-yl}cyclopropane-1-carboxylate Ex. 84a (500 mg, 2.01 mmol) was taken up in a mixture of THF/H2O (15 mL/7.5 mL). Lithium hydroxide monohydrate (254 mg, 6.04 mmol) was added and the mixture was stirred at rt for 7 days. Water and EtOAc were added to quench the reaction. The mixture was acidified to pH = 2-3 by addition of 3M HCl. After phases separation, the organic layer was dried over MgSO4, filtered and the solution was concentrated under reduced pressure. The crude product was purified by flash column chromatography on silica gel eluting with a gradient of CH2Cl2/MeOH. The product fractions were combined and concentrated to dryness to afford 1-{2-oxo-1H,2H,3H-pyrido[2,3-b][1,4]oxazin-6-yl}cyclopropane-1-carboxylic acid Ex. 84 (132 mg, 28%) as pale brown solid. 1H NMR (400 MHz, DMSO-d6, d in ppm): 1.24 (q, 2H, J = 3.7 Hz), 1.41 (q, 2H, J = 3.8 Hz), 4.74 (s, 2H), 7.16 (d, 2H, J = 1.7 Hz), 10.79 (s, 1H), 12.42 (s, 1H). |

Intermediate Ex.85: 1-(3,3-dimethyl-2-oxo-2,3-di-hydro-1H-indol-5-yl)cyclopropane-1-carboxylic acid
(FIG. 1CO)

TABLE 1.50

| Cpd. | Starting compounds, Reaction conditions and purification, Yield, appearance, $^1$H NMR (solvent) data |
|---|---|
| Ex. 85a | 5-bromo-3,3-dimethyl-2,3-dihydro-1H-indol-2-one<br>Step 1: 3,3-dimethyl-2,3-dihydro-1H-indol-2-one (500 mg, 3.10 mmol) was dissolved in dry CH2Cl2 (25 mL). Tetrabutylammonium tribromide (3.74 g, 7.75 mmol) was added portion wise to the solution. The reaction mixture was stirred at rt overnight. Water was added to quench the reaction. After phases separation, the organic layer was dried over MgSO4, filtered and the solution was concentrated under reduced pressure. The crude material was purified by silica gel column chromatography eluting with Cyclohexane/EtOAc (70:30). Product fractions were collected and evaporated to dryness to afford 5-bromo-3,3-dimethyl-2,3-dihydro-1H-indol-2-one Ex. 85a (730 mg, 3.04 mmol) as yellow solid. 1H NMR (300 MHz, DMSO-d6, d in ppm): 1.24 (s, 6H), 6.79 (d, 1H, J = 8.2 Hz), 7.32 (dd, 1H, J = 8.0 Hz = 2.1Hz), 7.52 (d, 1H, J = 2.1 Hz), 10.44 (s, 1H). |
| Ex. 85b | methyl 1-(3,3-dimethyl-2-oxo-2,3-dihydro-1H-indol-5-yl)cyclopropane-1-carboxylate<br>Step 2: 5-bromo-3,3-dimethyl-2,3-dihydro-1H-indol-2-one Ex. 85a (300 mg, 1.25 mmol) was dissolved in dry THF (5 mL). The solution was purged with N2 and Pd2(dba)3 (114 mg, 0.13 mmol) and XPhos (119 mg, 0.25 mmol) were added to the solution. The freshly prepared bromo[1-(methoxycarbonyl)cyclopropyl]zinc (4.69 mL, 3.75 mmol) was added slowly as a solution in THF (approx. 0.8M). The resulting mixture was heated at 85° C. for 1 h. TLC showed not complete conversion. Additional Pd2(dba)3 (228 mg, 0.26 mmol) and XPhos (238 mg, 0.50 mmol) were added to the solution followed by bromo[1-(methoxycarbonyl)cyclopropyl]zinc (9.37 mL, 7.50 mmol). The reaction mixture was stirred at 80° C. for 18 h. After cooling to rt, the reaction was quenched with water and EtOAc and filtered through a pad of Celite. After phases separation, the remaining organic layer was dried over MgSO4, filtered and the solution was concentrated to dryness. The crude material was adsorbed onto silica gel and purified by column chromatography eluting with Cyclohexane/EtOAc (70:30). The product fractions were combined and concentrated to dryness. The solid was triturated with Et2O, filtered and dried until constant weight to afford methyl 1-(3,3-dimethyl-2-oxo-2,3-dihydro-1H-indol-5-yl)cyclopropane-1-carboxylate Ex. 85b (178 mg, 52%) as pale brown solid. 1H NMR (300 MHz, DMSO-d6, d in ppm): 1.11-1.18 (m, 2H), 1.22 (s, 6H), 1.42-1.48 (m, 2H), 3.53 (s, 3H), 6.75 (d, 1H, J = 7.9 Hz), 7.10 (dd, 1H, J = 8.0 Hz, J = 1.8 Hz), 7.23 (d, 1H, J = 1.8 Hz), 10.29 (br(s), 1H). |
| Ex. 85 | 1-(3,3-dimethyl-2-oxo-2,3-dihydro-1H-indol-5-yl)cyclopropane-1-carboxylic acid<br>Step 3: methyl 1-(3,3-dimethyl-2-oxo-2,3-dihydro-1H-indol-5-yl)cyclopropane-1-carboxylate Ex. 85b (170 mg, 0.66 mmol) was taken up in a mixture of THF and |

TABLE 1.50-continued

| Cpd. | Starting compounds, Reaction conditions and purification, Yield, appearance, $^1$H NMR (solvent) data |
|---|---|
| | water [4:1] (5 mL). Lithium hydroxide monohydrate (55 mg, 1.31 mmol) was added and the mixture was stirred at rt overnight. TLC showed not total consumption of the starting material. Additional lithium hydroxide monohydrate (55 mg, 1.31 mmol) was added and the solution was heated at 45° C. for 2 h. The organic solvent was removed in vacuo. Water was added to the residue and the aqueous layer was extracted with Et2O. After phases separation, the remaining aqueous mixture was acidified to pH = 2-3 by addition of 1M citric acid and extracted with EtOAc. The combined organic layers were dried over MgSO4, filtered and the solution was concentrated under reduced pressure to afford 1-(3,3-dimethyl-2-oxo-2,3-dihydro-1H-indol-5-yl)cyclopropane-1-carboxylic acid Ex. 85 (147 mg, 91%) as white solid. 1H NMR (300 MHz, DMSO-d6, d in ppm): 1.05-1.12 (m, 2H), 1.22 (m, 6H), 1.37-1.45 (m, 2H), 6.74 (d, 1H, J = 8.0 Hz), 7.09 (dd, 1H, J = 8.0 Hz, J = 1.8 Hz), 7.22 (d, 1H, J = 1.7 Hz), 10.26 (s, 1H), 12.18 (br(s), 1H). |

Intermediate Ex.86: 2-(2,2-dioxo-1,3-dihydro-4,2,1-benzoxathiazin-6-yl)acetic acid (FIG. 1CP)

TABLE 1.51

| Cpd. | Starting compounds, Reaction conditions and purification, Yield, appearance, $^1$H NMR (solvent) data |
|---|---|
| Ex. 86a | tert-butyl 2-(2,2-dioxo-1,3-dihydro-4,2,1-benzoxathiazin-6-yl)acetate<br>Step 1: the previously synthesized 6-bromo-1,3-dihydro-4,2,1-benzoxathiazine-2,2-dione (300 mg, 1.14 mmol) and tert-butyl 2-(bromozincio)acetate (3.10 mL, 3.41 mmol) were dissolved in dry THF (7 mL) and placed in flask, the mixture was degassed by N2 bubbling for 5 min. Then Pd2(dba)3 (104 mg, 0.11 mmol) and XPhos (108 mg, 0.23 mmol) were incorporated and the reaction mixture was stirred at 85° C. for 2 h. The mixture was cooled to rt and solvent was removed under reduced pressure. The crude material was purified by column chromatography eluting with Cyclohexane/EtOAc (60:40). The product fractions were combined and concentrated to dryness to afford tert-butyl 2-(2,2-dioxo-1,3-dihydro-4,2,1-benzoxathiazin-6-yl)acetate Ex. 86a (251 mg, 74%) as pale brown solid. 1H NMR (300 MHz, DMSO-d6, d in ppm): 1.39 (s, 9H), 3.49 (s, 2H), 5.18 (s, 2H), 6.77 (d, 1H, J = 8.1 Hz), 6.92 (dd, 1H, J = 8.2 Hz, J = 1.9 Hz), 6.95 (d, 1H, J = 1.6 Hz), 10.49 (s, 1H). |
| Ex. 86 | 2-(2,2-dioxo-1,3-dihydro-4,2,1-benzoxathiazin-6-yl)acetic acid<br>Step 2: tert-butyl 2-(2,2-dioxo-1,3-dihydro-4,2,1-benzoxathiazin-6-yl)acetate Ex. 86a (250 mg, 0.84 mmol) was dissolved in MeOH (5 mL). 5M NaOH (835 μL, 4.18 mmol) was added and the reaction mixture was heated at 110° C. for 30 min under microwave irradiation. The solvent was removed under reduced pressure. Water was added to the residue and the aqueous layer was extracted with Et2O. After phases separation, the remaining aqueous layer was acidified up to pH = 2-3 with 1M citric acid and extracted with EtOAc. The combined organic layers were dried over MgSO4, filtered and the solution was concentrated to dryness. The crude material was triturated with Et2O. The solid formed was collected by filtration and dried under vacuum to afford 2-(2,2-dioxo-1,3-dihydro-4,2,1-benzoxathiazin-6-yl)acetic acid Ex. 86 (120 mg, 59%) as pale brown solid. 1H NMR (300 MHz, DMSO-d6, d in ppm): 3.50 (s, 2H), 5.17 (s, 2H), 6.76 (d, 1H, J = 8.1 Hz), 6.92 (dd, 1H, J = 8.1 Hz, J = 1.9 Hz), 6.96 (d, 1H, J = 1.7 Hz), 10.48 (br(s), 1H), 12.29 (br(s), 1H). |

Intermediate Ex.88: 1-(2H-1,3-benzodioxol-5-yl)cyclopropane-1-carboxylic acid (FIG. 1CR)

TABLE 1.52

| Cpd. | Starting compounds, Reaction conditions and purification, Yield, appearance, $^1$H NMR (solvent) data |
|---|---|
| Ex. 88a | methyl 1-(2H-1,3-benzodioxol-5-yl)cyclopropane-1-carboxylate<br>Step 1: 5-bromo-2H-1,3-benzodioxole (1.00 g, 4.97 mmol) was dissolved in dry THF (30 mL). The solution was purged with N2 and Pd2(dba)3 (456 mg, 0.50 mmol) and XPhos (474 mg, 1.00 mmol) were added to the solution. The freshly prepared bromo[1-(methoxycarbonyl)cyclopropyl]zinc (18.66 mL, 14.92 mmol) was added slowly as a solution in THF (approx. 0.8M). The resulting mixture was heated at 75° C. overnight. After cooling to rt, the reaction was quenched with water and EtOAc and filtered through a pad of Celite. After phases separation, the remaining organic layer was dried over MgSO4, filtered and the |

TABLE 1.52-continued

| Cpd. | Starting compounds, Reaction conditions and purification, Yield, appearance, $^1$H NMR (solvent) data |
|---|---|
| | solution was concentrated to dryness. The crude material was purified by column chromatography on silica gel eluting with Cyclohexane/EtOAc (80:20). The product fractions were combined and concentrated to dryness to afford methyl 1-(2H-1,3-benzodioxol-5-yl)cyclopropane-1-carboxylate Ex. 88a (1.00 g, 91%) as orange oil. 1H NMR (300 MHz, DMSO-d6, d in ppm): 1.14 (q, 2H, J = 3.0 Hz), 1.42 (q, 2H, J = 3.1 Hz), 3.53 (s, 3H), 5.99 (s, 2H), 6.75-6.84 (m, 2H), 6.89 (dd, 1H, J = 1.6 Hz, J = 0.5 Hz). |
| Ex. 88 | 1-(2H-1,3-benzodioxol-5-yl)cyclopropane-1-carboxylic acid Step 2: methyl 1-(2H-1,3-benzodioxol-5-yl)cyclopropane-1-carboxylate Ex. 88a (1.00 g, 4.54 mmol) was dissolved in MeOH (40 mL). 5M NaOH (11.35 mL, 22.70 mmol) was added and the resulting solution was distributed in microwave sealed tubes. The reaction mixture was heated at 100° C. for 15 min under microwave irradiation. The solvent was removed under reduced pressure. Water was added to the residue followed by 1M citric acid up to pH = 4-5 was reached. The solid formed was collected by filtration, washed with water and dried under vacuum until constant weight to afford 1-(2H-1,3-benzodioxol-5-yl)cyclopropane-1-carboxylic acid Ex. 88 (630 mg, 67%) as white solid. 1H NMR (300 MHz, DMSO-d6, din ppm): 1.07 (q, 2H, J = 3.0 Hz), 1.38 (q, 2H, J = 3.0 Hz), 5.97 (s, 2H), 6.72-6.83 (m, 2H), 6.86 (d, 1H, J = 1.1 Hz), 12.21 (br(s), 1H). |

Intermediate Ex.91: 1-[1-(oxan-4-ylmethyl)-2,2-dioxo-1,3-dihydro-2,1-benzothiazol-5-yl]cyclopropane-1-carboxylic acid (FIG. 1CU)

TABLE 1.53

| Cpd. | Starting compounds, Reaction conditions and purification, Yield, appearance, $^1$H NMR (solvent) data |
|---|---|
| Ex. 91a | 1-[1-(oxan-4-ylmethyl)-2,2-dioxo-1,3-dihydro-2,1-benzothiazol-5-yl]cyclopropane-1-carboxylate Step 1: to a previously synthesized methyl 1-(2,2-dioxo-1,3-dihydro-2,1-benzothiazol-5-yl)cyclopropane-1-carboxylate (100 mg, 0.37 mmol) dissolved in dry DMF (2 mL) were added K2CO3 (155 mg, 1.12 mmol) followed by 4-bromomethyltetrahydropyran (63 μL, 0.49 mmol). After 4 h at rt, TLC showed not total consumption of the starting material. The reaction was heated at 60° C. for 5 min under microwave irradiation. TLC showed almost total consumption of the starting material. The reaction was heated for additional 5 min at 100° C. under microwave irradiation. TLC showed complete reaction. The mixture was diluted with water. The aqueous solution was extracted with EtOAc, dried over MgSO4, filtered and the solution was concentrated under reduced pressure. The crude material was purified by silica gel column chromatography eluting with Cyclohexane/EtOAc (70:30). The desired fractions were collected and evaporated to dryness to afford methyl 1-[1-(oxan-4-ylmethyl)-2,2-dioxo-1,3-dihydro-2,1-benzothiazol-5-yl]cyclopropane-1-carboxylate Ex. 91a (80 mg, 59%) as colorless oil. 1H NMR (300 MHz, DMSO-d6, d in ppm): 1.15 (q, 2H, J = 4.1 Hz), 1.20-1.35 (m, 2H), 1.47 (q, 2H, J = 3.0 Hz), 1.67 (d, 2H, J = 10.6 Hz), 1.90-2.00 (m, 1H), 3.20-3.25 (m, 2H), 3.35-3.45 (m, 2H), 3.53 (s, 3H), 3.84 (dd, 2H, J = 11.7 Hz, J = 2.9 Hz), 4.62 (s, 2H), 6.91 (d, 1H, J = 8.8 Hz), 7.25-7.35 (m, 2H). |
| Ex. 91 | 1-[1-(oxan-4-ylmethyl)-2,2-dioxo-1,3-dihydro-2,1-benzothiazol-5-yl]cyclopropane-1-carboxylic acid Step 2: to a solution of methyl 1-[1-(oxan-4-ylmethyl)-2,2-dioxo-1,3-dihydro-2,1-benzothiazol-5-yl]cyclopropane-1-carboxylate Ex. 91a (78 mg, 0.21 mmol) dissolved in MeOH/THF (800 μL/200 μL) was added 5M NaOH (213 μL, 1.07 mmol). The solution was stirred overnight at rt. The solution was poured onto sat. NH4Cl and the aqueous solution was extracted with EtOAc twice. The pH of the aqueous layer was then adjusted to pH = 3-4 with 1M citric acid and extracted with EtOAc. The combined organic layers were dried over MgSO4, filtered and the solution was concentrated under reduced pressure to afford 1-[1-(oxan-4-ylmethyl)-2,2-dioxo-1,3-dihydro-2,1-benzothiazol-5-yl]cyclopropane-1-carboxylic acid Ex. 91 (65 mg, 87%) as yellow oil. 1H NMR (300 MHz, DMSO-d6, d in ppm): 1.09 (q, 2H, J = 3.0 Hz), 1.20-1.35 (m, 2H), 1.42 (q, 2H, J = 2.9 Hz), 1.67 (d, 2H, J = 10.9 Hz), 1.85-1.95 (m, 1H), 3.20-3.25 (m, 2H), 3.35-3.45 (m, 2H), 3.84 (dd, 2H, J = 11.1 Hz, J = 2.6 Hz), 4.61 (s, 2H), 6.91 (d, 1H, J = 8.9 Hz), 7.25-7.30 (m, 2H), 12.29 (br(s), 1H). |

Intermediate Ex.92: 1-(7-fluoro-2-oxo-2,3-dihydro-1H-indol-5-yl)cyclopropane-1-carboxylic acid (FIG. 1CV)

TABLE 1.54

| Cpd. | Starting compounds, Reaction conditions and purification, Yield, appearance, ¹H NMR (solvent) data |
| --- | --- |
| Ex. 92a | methyl 1-(7-fluoro-2-oxo-2,3-dihydro-1H-indol-5-yl)cyclopropane-1-carboxylate<br>Step 1: 5-bromo-7-fluorooxindole (250 mg, 1.09 mmol) was dissolved in dry THF (10 mL). The solution was purged with N2 and Pd2(dba)3 (100 mg, 0.11 mmol) and XPhos (104 mg, 0.22 mmol) were added to the solution. The freshly prepared bromo[1-(methoxycarbonyl)cyclopropyl]zinc (4.08 mL, 3.26 mmol) was added slowly as a solution in THF (approx. 0.8M). The resulting mixture was heated at 85° C. for 1 h. After cooling to rt, the solvent was removed under reduced pressure. The crude material was purified by column chromatography on silica gel eluting with Cyclohexane/EtOAc (60:40). The product fractions were combined and concentrated to dryness to afford methyl 1-(7-fluoro-2-oxo-2,3-dihydro-1H-indol-5-yl)cyclopropane-1-carboxylate Ex. 92a (112 mg, 41%) as pale yellow solid. 1H NMR (300 MHz, DMSO-d6, d in ppm): 1.14-1.20 (m, 2H), 1.40-1.48 (m, 2H), 3.48-3.58 (m, 5H), 7.10-7.11 (m, 2H), 10.81 (br(s), 1H). |
| Ex. 92 | 1-(7-fluoro-2-oxo-2,3-dihydro-1H-indol-5-yl)cyclopropane-1-carboxylic acid<br>Step 2: methyl 1-(7-fluoro-2-oxo-2,3-dihydro-1H-indol-5-yl)cyclopropane-1-carboxylate Ex. 92a (100 mg, 0.40 mmol) was dissolced in concentrated sulfuric acid (1.5 mL). The solution was heated at 80° C. for 15 min under microwave irradiations. After cooling to rt, the solution was poured onto a mixture of ice and water. The aqueous layer was extracted with EtOAc. The combined organic layers were washed several times with water, dried over MgSO4, filtered and the solution was concentrated under reduced pressure to afford 1-(7-fluoro-2-oxo-2,3-dihydro-1H-indol-5-yl)cyclopropane-1-carboxylic acid Ex. 92 (75 mg, 79%) as pale brown solid. 1H NMR (300 MHz, DMSO-d6, d in ppm): 1.06-1.14 (m, 2H), 1.37-1.44 (m, 2H), 3.53 (s, 2H), 6.98-7.07 (m, 2H), 10.79 (s, 1H), 12.25 (br(s), 1H). |

Intermediate Ex.93: 1-(3,3-difluoro-2-oxo-2,3-dihydro-1H-indol-5-yl)cyclopropane-1-carboxylic acid (FIG. 1CW)

TABLE 1.55

| Cpd. | Starting compounds, Reaction conditions and purification, Yield, appearance, ¹H NMR (solvent) data |
| --- | --- |
| Ex. 93a | 5-bromo-3,3-difluoro-2,3-dihydro-1H-indol-2-one<br>Step 1: 5-bromoisatin (500 mg, 2.21 mmol) was dissolved in CH2Cl2 (15 mL). (Diethylamino)sulfur trifluoride (731 µL, 5.53 mL) was added and the reaction mixture was stirred at rt for 16 h. The solution was cooled to 0° C. and MeOH was added to quench the reaction. The stirring was kept at 0° C. for 30 min. The solvent was removed under reduced. The residue was purified by silica gel column chromatography eluting with Cyclohexane/EtOAc (70:30). The desired fractions were combined and concentrated to dryness to afford 5-bromo-3,3-difluoro-2,3-dihydro-1H-indol-2-one Ex. 93a (385 mg, 70%) as yellow solid. 1H NMR (300 MHz, DMSO-d6, d in ppm): 6.91-7.00 (m, 1H), 7.66-7.76 (m, 1H), 7.91-7.97 (m, 1H), 11.29 (br(s), 1H). |
| Ex. 93b | methyl 1-(3,3-difluoro-2-oxo-2,3-dihydro-1H-indol-5-yl)cyclopropane-1-carboxylate<br>Step 2: 5-bromo-3,3-difluoro-2,3-dihydro-1H-indol-2-one Ex. 93a (375 mg, 1.51 mmol) was dissolved in dry THF (10 mL). The solution was purged with N2 and Pd2(dba)3 (138 mg, 0.15 mmol) and XPhos (144 mg, 0.30 mmol) were added to the solution. The freshly prepared bromo[1-(methoxycarbonyl)cyclopropyl]zinc (5.67 mL, 4.54 mmol) was added slowly as a solution in THF (approx. 0.8M). The resulting mixture was heated overnight at 85° C. After cooling to rt, the solvent was removed under reduced pressure. The crude material was purified by column chromatography on silica gel eluting with Cyclohexane/EtOAc (70:30). The product fractions were combined and concentrated to dryness to afford methyl 1-(3,3-difluoro-2-oxo-2,3-dihydro-1H-indol-5-yl)cyclopropane-1-carboxylate Ex. 93b (454 mg, 99%) as pale brown oil. 1H NMR (300 MHz, DMSO-d6, d in ppm): 1.19-1.24 (m, 2H), 1.48-1.52 (m, 2H), 3.54 (s, 3H), 6.90-6.96 (m, 1H), 7.44-7.52 (m, 1H), 7.58-7.64 (m, 1H), 11.18 (s, 1H). |
| Ex. 93 | 1-(3,3-difluoro-2-oxo-2,3-dihydro-1H-indol-5-yl)cyclopropane-1-carboxylic acid<br>Step 3: methyl 1-(3,3-difluoro-2-oxo-2,3-dihydro-1H-indol-5-yl)cyclopropane-1-carboxylate Ex. 93b (400 mg, 1.50 mmol) was dissolced in concentrated sulfuric acid (4 mL). The solution was heated at 80° C. for 15 min under microwave irradiations. After cooling to rt, the solution was poured onto a mixture of ice and |

TABLE 1.55-continued

| Cpd. | Starting compounds, Reaction conditions and purification, Yield, appearance, $^1$H NMR (solvent) data |
|---|---|
| | water. The aqueous layer was extracted with EtOAc. The combined organic layers were washed several times with water, dried over MgSO4, filtered and the solution was concentrated under reduced pressure. The crude material was purified by column chromatography on silica gel eluting with CH2Cl2/MeOH (95:5). The product fractions were combined and concentrated to dryness to afford 1-(3,3-difluoro-2-oxo-2,3-dihydro-1H-indol-5-yl)cyclopropane-1-carboxylic acid Ex. 93 (70 mg, 17%) as orange solid. 1H NMR (300 MHz, DMSO-d6, d in ppm): 1.11-1.18 (m, 2H), 1.40-1.48 (m, 2H), 6.91 (d, 1H, J = 8.1 Hz), 7.46 (dd, 1H, J = 8.2 Hz, J = 1.8 Hz), 7.58 (d, 1H, J = 1.7 Hz), 11.16 (s, 1H), 12.36 (br(s), 1H). |

Intermediate Ex.94: 1-[1-(hydroxyimino)-2,3-dihydro-1H-inden-5-yl]cyclopropane-1-carboxylic acid (FIG. 1CX)

TABLE 1.56

| Cpd. | Starting compounds, Reaction conditions and purification, Yield, appearance, $^1$H NMR (solvent) data |
|---|---|
| Ex. 94a | methyl 1-[1-(hydroxyimino)-2,3-dihydro-1H-inden-5-yl]cyclopropane-1-carboxylate<br>Step 1: methyl 1-(1-oxo-2,3-dihydro-1H-inden-5-yl)cyclopropane-1-carboxylate (mixed fractions, 1.7 g containing an estimated 1.0 g, 4.34 mmol of starting material) was dissolved in MeOH (35 mL). Hydroxylamine hydrochloride (604 mg, 8.68 mmol) and potassium acetate (891 mg, 10.9 mmol) were added to the solution. The reaction mixture was heated at 60° C. for 1 h. The solution was cooled to rt and was concentrated to dryness. The residue was partitioned between water and EtOAc. The organic layer was dried over MgSO4, filtered and concentrated under reduced pressure. The crude oil was purified by column chromatography on silica gel eluting with a gradient of Cyclohexane/EtOAc from [100:0] to [60:40]. The product fractions were combined and concentrated to dryness to afford methyl 1-[1-(hydroxyimino)-2,3-dihydro-1H-inden-5-yl]cyclopropane-1-carboxylate Ex. 94a (769 mg, 72%) as yellow foam. The product was found to be stable under chromatographic conditions on silica gel. The product contained some unknown impurity ([M + H]+ = 462) but was considered to be suitable for the next synthetic step. |
| Ex. 94 | 1-[1-(hydroxyimino)-2,3-dihydro-1H-inden-5-yl]cyclopropane-1-carboxylic acid<br>Step 2: methyl 1-[1-(hydroxyimino)-2,3-dihydro-1H-inden-5-yl]cyclopropane-1-carboxylate Ex. 94a (150 mg, 0.62 mmol) was dissolved in dry THF (10 mL). Potassium trimethylsilanolate (157 mg, 1.22 mmol) was added and the mixture was heated at 65° C. for 1 h. Upon heating a pale brown solid precipitated from the reaction mixture. The reaction was monitored by TLC. Full consumption of the starting material was observed after 1 h. The mixture was acidified to pH = 2-3 by addition of 1M HCl. The mixture was concentrated to dryness, adsorbed onto silica gel and purified by column chromatography eluting with a gradient of CH2Cl2/MeOH from [100:0] to [95:5]. The product fractions were combined and concentrated to dryness to afford 1-[1-(hydroxyimino)-2,3-dihydro-1H-inden-5-yl]cyclopropane-1-carboxylic acid Ex. 94 (67 mg, 47%) as pale yellow solid. 1H NMR (300 MHz, DMSO-d6, d in ppm): 1.19-1.22 (m, 2H), 1.57-1.61 (m, 2H), 2.89-2.94 (m, 2H), 3.01-3.06 (m, 2H), 7.25 (dd, 1H, J = 0.9 Hz, J = 8.1 Hz), 7.34 (d, 1H, J = 0.9 Hz), 7.57 (d, 1H, J = 8.1 Hz). The two polar protons exchanged with the deuterated solvent. |

Intermediate Ex.95: 2-[1-(oxan-4-ylmethyl)-2,2-dioxo-1,3-dihydro-2,1-benzothiazol-5-yl]acetic acid (FIG. 1CY)

TABLE 1.57

| Cpd. | Starting compounds, Reaction conditions and purification, Yield, appearance, $^1$H NMR (solvent) data |
|---|---|
| Ex. 95a | 5-bromo-1-(oxan-4-ylmethyl)-1,3-dihydro-2,1-benzothiazole-2,2-dione<br>Step 1: to a solution of 5-bromo-1,3-dihydro-2,1-benzothiazole-2,2-dione (200 mg, 0.81 mmol) dissolved in dry DMF (2 mL) were added potassium carbonate (334 mg, 2.42 mmol) and 4-bromomethyltetrahydropyran (135 µL, 1.05 mmol). The reaction mixture was heated at 60° C. overnight. After cooling to rt, the solution was poured onto water and EtOAc. After phases separation, the |

TABLE 1.57-continued

| Cpd. | Starting compounds, Reaction conditions and purification, Yield, appearance, $^1$H NMR (solvent) data |
|---|---|
| | aqueous layer was extracted with EtOAc. The combined organic layers were dried over MgSO4, filtered and the solution was concentrated under reduced pressure. The crude material was purified by column chromatography on silica gel eluting with Cyclohexane/EtOAc (70:30). The desired fractions were collected and concentrated to dryness to afford 5-bromo-1-(oxan-4-ylmethyl)-1,3-dihydro-2,1-benzothiazole-2,2-dione Ex. 95a (157 mg, 56%) as colourless oil, which solidified to a white solid upon standing at rt. 1H NMR (300 MHz, DMSO-d6, d in ppm): 1.25-1.45 (m, 2H), 1.64 (d, 2H, J = 11.1 Hz), 1.85-2.00 (m, 1H), 3.15-3.30 (m, 2H), 3.40 (d, 2H, J = 7.3 Hz), 3.84 (dd, 2H, J = 11.3 Hz, J = 2.7 Hz), 4.68 (s, 2H), 6.98 (d, 1H, J = 9.2 Hz), 7.45-7.55 (m, 2H). |
| Ex. 95b | tert-butyl 2-[1-(oxan-4-ylmethyl)-2,2-dioxo-1,3-dihydro-2,1-benzothiazol-5-yl]acetate<br>Step 2: 5-bromo-1-(oxan-4-ylmethyl)-1,3-dihydro-2,1-benzothiazole-2,2-dione Ex. 95a (300 mg, 0.87 mmol), the previously synthesized tert-butyl 2-(bromozincio)acetate (2.36 mL, 2.60 mmol) and dry THF (4 mL) were placed in flask, the mixture was degassed by nitrogen bubbling for 5 min. Then Pd2(dba)3 (8 mg, 0.01 mmol) and XPhos (8 mg, 0.02 mmol) were incorporated and the reaction mixture was heated at 80° C. for 5 h. The mixture was cooled to rt, EtOAc and water was added and the two-phase mixture was filtered through a pad of Celite. The phases were separated, the organic layer was dried over MgSO4, filtered and the solution was concentrated to dryness. The crude material was purified by column chromatography eluting with Cyclohexane/EtOAc (80:20). The product fractions were combined and concentrated to dryness to give tert-butyl 2-[1-(oxan-4-ylmethyl)-2,2-dioxo-1,3-dihydro-2,1-benzothiazol-5-yl]acetate Ex. 95b (316 mg, 96%) as yellow solid. 1H NMR (300 MHz, DMSO-d6, d in ppm): 1.20-1.35 (m, 2H), 1.37 (s, 9H), 1.66 (d, 2H, J = 11.1 Hz), 1.85-2.00 (m, 1H), 3.20-3.30 (m, 2H), 3.37 (d, 2H, J = 7.2 Hz), 3.51 (s, 2H), 3.85 (dd, 2H, J = 11.1 Hz, J = 2.7 Hz), 4.64 (s, 2H), 6.94 (d, 1H, J = 8.7 Hz), 7.15-7.25 (m, 2H). |
| Ex. 95 | 2-[1-(oxan-4-ylmethyl)-2,2-dioxo-1,3-dihydro-2,1-benzothiazol-5-yl]acetic acid<br>Step 3: to a solution of tert-butyl 2-[1-(oxan-4-ylmethyl)-2,2-dioxo-1,3-dihydro-2,1-benzothiazol-5-yl]acetate Ex. 95b (316 mg, 0.83 mmol) dissolved in MeOH/THF (2 mL/3 mL) was added 5M NaOH (1.65 mL, 8.28 mmol). The reaction mixture was heated at 100° C. for 10 min under microwave irradiations. After cooling to rt, the solution was poured onto water. The pH was then adjusted to pH = 3-4 with 1M citric acid and the solution was extracted with EtOAc. The combined organic layers were dried over MgSO4, filtered and the solution was concentrated under reduced pressure to afford 2-[1-(oxan-4-ylmethyl)-2,2-dioxo-1,3-dihydro-2,1-benzothiazol-5-yl]acetic acid Ex. 95 (200 mg, 74%) as yellow foam. 1H NMR (300 MHz, DMSO-d6, d in ppm): 1.15-1.35 (m, 2H), 1.66 (d, 2H, J = 12.6 Hz), 1.85-2.00 (m, 1H), 3.15-3.30 (m, 2H), 3.37 (d, 2H, J = 7.1 Hz), 3.52 (s, 2H), 3.85 (dd, 2H, J = 11.9 Hz, J = 2.8 Hz), 4.63 (s, 2H), 6.93 (d, 1H, J = 8.8 Hz), 7.15-7.25 (m, 2H), 12.28 (br(s), 1H). |

Intermediate Ex.96: 1-(2,2-dimethyl-2,4-dihydro-1,3-benzodioxin-7-yl)cyclopropane-1-carboxylic acid
(FIG. 1CZ, 1DA)

TABLE 1.58

| Cpd. | Starting compounds, Reaction conditions and purification, Yield, appearance, $^1$H NMR (solvent) data |
|---|---|
| Ex. 96a | 7-bromo-2,2-dimethyl-2,4-dihydro-1,3-benzodioxine<br>Step 1: 5-bromo-2-(hydroxymethyl)phenol (500 mg, 2.46 mmol) was dissolved in acetone (10 mL). p-Toluenesulfonic acid (42 mg, 0.25 mmol) was added followed by 2,2-dimethoxypropane (1.51 mL, 1.23 mmol) and sodium sulfate (944 mg, 6.65 mmol). The resulting mixture was heated under vigorous stirring at 50° C. for 1 h. After cooling to rt, the mixture was concentrated under reduced pressure and the residue was partitioned between water and EtOAc. The organic layer was dried over MgSO4, filtered and the solution was concentrated to dryness. The crude material was purified by column chromatography on silica gel eluting with a gradient of Cyclohexane/EtOAc from [100:0] to [90:10]. The product fractions were combined and concentrated to dryness to afford 7-bromo-2,2-dimethyl-2,4-dihydro-1,3-benzodioxine Ex. 96a (456 mg, 76%) as colourless oil, which solidified to a white solid upon standing at rt. 1H NMR (300 MHz, DMSO-d6, d in ppm): 1.46 (s, 6H), 4.78 (s, 2H), 7.00 (d, 1H, J = 1.8 Hz), 7.05 (d, 1H, J = 8.1 Hz), 7.08 (dd, 1H, J = 8.1 Hz, J = 1.8 Hz). |
| Ex. 96b | methyl 1-(2,2-dimethyl-2,4-dihydro-1,3-benzodioxin-7-yl)cyclopropane-1-carboxylate<br>Step 2: 7-bromo-2,2-dimethyl-2,4-dihydro-1,3-benzodioxine Ex. 96a (450 mg, 1.85 mmol) was dissolved in dry THF (5 mL). The solution was purged with N2 and Pd2(dba)3 (127 mg, 0.14 mmol) and XPhos (132 mg, 0.28 mmol) were |

TABLE 1.58-continued

| Cpd. | Starting compounds, Reaction conditions and purification, Yield, appearance, ¹H NMR (solvent) data |
|---|---|
| | added. The freshly prepared bromo[1-(methoxycarbonyl)cyclopropyl]zinc (4.63 mL, 3.70 mmol) was added slowly as a solution in THF (approx. 0.8M). The resulting mixture was heated at 70° C. for 2 h. TLC (visualisation with molybdate stain) showed complete conversion. The reaction was then quenched with water and EtOAc and filtered through a pad of Celite. After phases separation, the remaining organic layer was dried over MgSO4, filtered and the solution was concentrated to dryness. The crude material was adsorbed onto silica gel and purified by column chromatography eluting with a gradient of Cyclohexane/EtOAc from [100:0] to [80:20]. The product fractions were combined and concentrated to dryness to afford methyl 1-(2,2-dimethyl-2,4-dihydro-1,3-benzodioxin-7-yl)cyclopropane-1-carboxylate Ex. 96b (293 mg, 60%) as yellow oil. 1H NMR (300 MHz, CDCl3, d in ppm): 1.14-1.17 (m, 2H), 1.41-1.45 (m, 8H), 3.53 (s, 3H), 4.78 (s, 2H), 6.72 (d, 1H, J = 1.5 Hz), 6.84 (dd, 1H, J = 7.8 Hz, J = 1.5 Hz), 6.98 (d, 1H, J = 7.8 Hz). |
| Ex. 96 | 1-(2,2-dimethyl-2,4-dihydro-1,3-benzodioxin-7-yl)cyclopropane-1-carboxylic acid<br>Step 3: methyl 1-(2,2-dimethyl-2,4-dihydro-1,3-benzodioxin-7-yl)cyclopropane-1-carboxylate Ex. 96b (375 mg, 1.43 mmol) was taken up in a mixture of THF and water [4:1] (15 mL). Lithium hydroxide monohydrate (150 mg, 3.57 mmol) was added and the mixture was stirred at rt for 16 h. The organic solvent was removed in vacuo and the residual aqueous layer was acidified to pH = 3-4 by dropwise addition of 3M HCl. The solid formed was collected by filtration, washed with water and dried under vacuum at 40° C. to constant weight to afford 1-(2,2-dimethyl-2,4-dihydro-1,3-benzodioxin-7-yl)cyclopropane-1-carboxylic acid Ex. 96 (230 mg, 84%) as an off-white solid. 1H NMR (300 MHz, DMSO-d6, d in ppm): 1.07-1.11 (m, 2H), 1.37-1.41 (m, 2H), 1.45 (s, 6H), 4.78 (s, 2H), 6.70 (d, 1H, J = 1.5 Hz), 6.84 (dd, 1H, J = 7.8 Hz, J = 1.5 Hz), 6.96 (d, 1H, J = 7.8 Hz), 12.25 (s, 1H). |

Intermediate Ex.97: 1-(2,2-dimethyl-2,4-dihydro-1,3-benzodioxin-6-yl)cyclopropane-1-carboxylic acid
(FIG. 1CZ, 1DA)

TABLE 1.59

| Cpd. | Starting compounds, Reaction conditions and purification, Yield, appearance, ¹H NMR (solvent) data |
|---|---|
| Ex. 97a | 6-bromo-2,2-dimethyl-2,4-dihydro-1,3-benzodioxine<br>Step 1: 4-bromo-2-(hydroxymethyl)phenol (500 mg, 2.46 mmol) was dissolved in acetone (10 mL). p-Toluenesulfonic acid (42 mg, 0.25 mmol) was added followed by 2,2-dimethoxypropane (1.51 mL, 1.23 mmol) and sodium sulfate (944 mg, 6.65 mmol). The resulting mixture was heated under vigorous stirring overnight at 50° C. After cooling to rt, the mixture was concentrated under reduced pressure and the residue was partitioned between water and EtOAc. The organic layer was dried over MgSO4, filtered and the solution was concentrated to dryness. The crude material was purified by column chromatography on silica gel eluting with a gradient of Cyclohexane/EtOAc from [100:0] to [90:10]. The product fractions were combined and concentrated to dryness to afford 6-bromo-2,2-dimethyl-2,4-dihydro-1,3-benzodioxine Ex. 97a (529 mg, 88%) as colourless oil. 1H NMR (300 MHz, DMSO-d6, d in ppm): 1.45 (s, 6H), 4.80 (s, 2H), 6.74-6.77 (m, 1H), 7.29-7.32 (m, 2H). |
| Ex. 97b | methyl 1-(2,2-dimethyl-2,4-dihydro-1,3-benzodioxin-6-yl)cyclopropane-1-carboxylate<br>Step 2: 6-bromo-2,2-dimethyl-2,4-dihydro-1,3-benzodioxine Ex. 97a (500 mg, 2.06 mmol) was dissolved in dry THF (5 mL). The solution was purged with N2 and Pd2(dba)3 (141 mg, 0.15 mmol) and XPhos (147 mg, 0.31 mmol) were added. The freshly prepared bromo[1-(methoxycarbonyl)cyclopropyl]zinc (5.14 mL, 4.11 mmol) was added slowly as a solution in THF (approx. 0.8M). The resulting mixture was heated at 70° C. for 2 h. TLC (visualisation with molybdate stain) showed complete conversion. The reaction was then quenched with water and EtOAc and filtered through a pad of Celite. After phases separation, the remaining organic layer was dried over MgSO4, filtered and the solution was concentrated to dryness. The crude material was adsorbed onto silica gel and purified by column chromatography eluting with a gradient of Cyclohexane/EtOAc from [100:0] to [80:20]. The product fractions were combined and concentrated to dryness to afford methyl 1-(2,2-dimethyl-2,4-dihydro-1,3-benzodioxin-6-yl)cyclopropane-1-carboxylate Ex. 97b (381 mg, 71%) as yellow oil, which solidified upon standing at rt. 1H NMR (300 MHz, CDCl3, d in ppm): 1.11-1.15 (m, 2H), 1.41-1.45 (m, 8H), 3.53 (s, 3H), 4.77 (s, 2H), 6.70 (d, 1H, J = 8.4 Hz), 7.01 (d, 1H, J = 2.1 Hz), 7.10 (dd, 1H, J = 8.4 Hz, J = 2.1 Hz). |
| Ex. 97 | 1-(2,2-dimethyl-2,4-dihydro-1,3-benzodioxin-6-yl)cyclopropane-1-carboxylic acid |

TABLE 1.59-continued

| Cpd. | Starting compounds, Reaction conditions and purification, Yield, appearance, ¹H NMR (solvent) data |
|---|---|
| | Step 3: methyl 1-(2,2-dimethyl-2,4-dihydro-1,3-benzodioxin-6-yl)cyclopropane-1-carboxylate Ex. 97b (375 mg, 1.43 mmol) was taken up in a mixture of THF and water [4:1] (15 mL). Lithium hydroxide monohydrate (150 mg, 3.57 mmol) was added and the mixture was stirred at rt for 16 h. LCMS showed approx 50% conversion. Further lithium hydroxide monohydrate (150 mg, 3.57 mmol) was added and the solution was stirred overnight at rt. The organic solvent was removed in vacuo and the residual aqueous layer was acidified to pH = 3-4 by dropwise addition of 3M HCl. The solid formed was collected by filtration, washed with water and dried under vacuum at 40° C. to constant weight to afford 1-(2,2-dimethyl-2,4-dihydro-1,3-benzodioxin-6-yl)cyclopropane-1-carboxylic acid Ex. 97 (276 mg, 78%) as an off-white solid. 1H NMR (300 MHz, DMSO-d6, d in ppm): 1.04-1.07 (m, 2H), 1.37-1.40 (m, 2H), 1.44 (s, 6H), 4.77 (s, 2H), 6.68 (d, 1H, J = 8.4 Hz), 7.00 (d, 1H, J = 2.1 Hz), 7.09 (dd, 1H, J = 8.4 Hz, J = 2.1 Hz), 12.23 (br(s), 1H). |

Intermediate Ex.98: 1-[3-(1-hydroxy-2-methylpropan-2-yl)-1H-indol-5-yl]cyclopropane-1-carboxylic acid (FIG. 1DB)

TABLE 1.60

| Cpd. | Starting compounds, Reaction conditions and purification, Yield, appearance, ¹H NMR (solvent) data |
|---|---|
| Ex. 98a | ethyl 2-(5-bromo-1H-indol-3-yl)-2-methylpropanoate<br>Step 1 (following the protocol described by Leitch Jamie A. et al. in ACS Catalysis, 2017, 7, 2616-2623): in a microwave vial were introduced 5-bromo-1H-indole (500 mg, 2.55 mmol) and dry dioxane (8 mL). The solution was purged with N2. Potassium acetate (500 mg, 5.10 mmol), dichloro(p-cymene)ruthenium(ii) dimer (78 mg, 0.13 mmol) and ethyl 2-bromo-2-methylpropanoate (1.11 mL, 7.65 mmol) were added to the solution under N2. The vial was sealed and heated at 120° C. for 18 h. The reaction was quenched with sat. NH4Cl and the remaining mixture was extracted with EtOAc. The combined organic layers were washed with sat. NH4Cl. After phases separation, the organic layer was dried over MgSO4, filtered and the solution was concentrated under reduced pressure. The crude material was purified by silica gel column chromatography eluting with Cyclohexane/EtOAc (70:30). The desired fractions were combined and evaporated to dryness to afford ethyl 2-(5-bromo-1H-indol-3-yl)-2-methylpropanoate Ex. 98a (650 mg, 82%) as colourless oil, which solidified to a white solid upon standing at rt. 1H NMR (300 MHz, DMSO-d6, d in ppm): 1.08 (t, 3H, J = 7.1 Hz), 1.56 (s, 6H), 4.02 (q, 2H, J = 7.1 Hz), 7.16 (dd, 1H, J = 8.6 Hz, J = 1.9 Hz), 7.29 (d, 1H, J = 2.6 Hz), 7.32 (dd, 1H, J = 8.6 Hz, J = 0.5 Hz), 7.61 (d, 1H, J = 2.0 Hz), 11.18 (s, 1H). |
| Ex. 98b | 2-(5-bromo-1H-indol-3-yl)-2-methylpropan-1-ol<br>Step 2: ethyl 2-(5-bromo-1H-indol-3-yl)-2-methylpropanoate Ex. 98a (650 mg, 2.10 mmol) was dissolved in dry THF (10 mL). Lithium aluminum hydride (119 mg, 3.14 mmol) was added and the reaction mixture was stirred at rt for 1 h. TLC showed no conversion. The solution was heated at 80° C. overnight. TLC showed still starting material. The solution was cooled to rt and additional lithium aluminum hydride (119 mg, 3.14 mmol) was added. After 2 h of stirring at rt, the mixture was quenched with 220 µL of water followed by 15% NaOH (220 µL) and 660 µL of water under vigorous stirring. The white precipitate was filtered-off. The remaining solution was extracted with EtOAc. The combined organic layers were washed with sat. NH4Cl and then partitionated. The organic layer was dried over MgSO4, filtered and the solution was concentrated under reduced pressure. The crude material was purified by silica gel column chromatography eluting with Cyclohexane/EtOAc (70:30). The product fractions were combined and concentrated to dryness to give 2-(5-bromo-1H-indol-3-yl)-2-methylpropan-1-ol Ex. 98b (425 mg, 76%) as colourless oil, which solidified to a white solid upon standing at rt. 1H NMR (300 MHz, DMSO-d6, d in ppm): 1.30 (s, 6H), 3.51 (d, 2H, J = 5.6 Hz), 4.60 (t, 1H, J = 5.6 Hz), 7.06-7.18 (m, 2H), 7.30 (d, 1H, J = 8.6 Hz), 7.80 (d, 1H, J = 1.8 Hz), 11.01 (s, 1H). |
| Ex. 98c | 5-bromo-3-{1-[(tert-butyldimethylsilyl)oxy]-2-methylpropan-2-yl}-1H-indole<br>Step 3: 2-(5-bromo-1H-indol-3-yl)-2-methylpropan-1-ol Ex. 98b (420 mg, 1.57 mmol) was dissolved in dry DMF (10 mL). Imidazole (0.235 g, 3.446 mmol) was added and the solution was cooled to 0° C. tert-Butyldimethylsilyl chloride (307 mg, 2.04 mmol) was added portion wise and the reaction mixture was warmed up to rt. After 3 h, the reaction was quenched by addition of sat. NH4Cl. The solution was extracted with EtOAc. The combined organic layers were dried over MgSO4, filtered and the solution was concentrated under reduced pressure. The crude material was purified by silica gel column chromatography eluting with Cyclohexane/EtOAc (90:10). The product fractions were combined and concentrated to dryness to give 5-bromo-3-{1-[(tert-butyldimethylsilyl)oxy]-2- |

TABLE 1.60-continued

| Cpd. | Starting compounds, Reaction conditions and purification, Yield, appearance, $^1$H NMR (solvent) data |
|---|---|
| | methylpropan-2-yl}-1H-indole Ex. 98c (590 mg, 98%) as yellow oil. 1H NMR (300 MHz, DMSO-d6, d in ppm): −0.07 (s, 6H), 0.81 (s, 9H), 1.32 (s, 6H), 3.64 (s, 2H), 7.10-7.17 (m, 2H), 7.29 (dd, 1H, J = 8.6 Hz, J = 0.4 Hz), 7.80 (d, 1H, J = 1.9 Hz), 11.03 (s, 1H). |
| Ex. 98d | methyl 1-(3-{1-[(tert-butyldimethylsilyl)oxy]-2-methylpropan-2-yl}-1H-indol-5-yl)cyclopropane-1-carboxylate<br>Step 4: 5-bromo-3-{1-[(tert-butyldimethylsilyl)oxy]-2-methylpropan-2-yl}-1H-indole Ex. 98c (295 mg, 0.77 mmol) was dissolved in dry THF (8 mL). The solution was purged with N2 and Pd2(dba)3 (71 mg, 0.08 mmol) and XPhos (74 mg, 0.15 mmol) were added to the solution. The freshly prepared bromo[1-(methoxycarbonyl)cyclopropyl]zinc (2.89 mL, 2.31 mmol) was added slowly as a solution in THF (approx. 0.8M). The resulting mixture was heated at 80° C. for 1 h. After cooling to rt, the solvent was removed under reduced pressure. The crude material was purified by column chromatography on silica gel eluting with Cyclohexane/EtOAc (90:10). The product fractions were combined and concentrated to dryness to afford methyl 1-(3-{1-[(tert-butyldimethylsilyl)oxy]-2-methylpropan-2-yl}-1H-indol-5-yl)cyclopropane-1-carboxylate Ex. 98d (252 mg, 81%) as yellow oil, which solidified to a yellow solid upon standing at rt. 1H NMR (300 MHz, DMSO-d6, d in ppm): −0.06 (s, 6H), 0.82 (s, 9H), 1.14-1.20 (m, 2H), 1.33 (s, 6H), 1.45-1.51 (m, 2H), 3.50 (s, 3H), 3.67 (s, 2H), 7.00 (dd, 1H, J = 8.4 Hz, J = 1.6 Hz), 7.04 (d, 1H, J = 2.5 Hz), 7.24 (d, 1H, J = 8.3 Hz), 7.55 (s, 1H), 10.78 (s, 1H). |
| Ex. 98 | 1-[3-(1-hydroxy-2-methylpropan-2-yl)-1H-indol-5-yl]cyclopropane-1-carboxylic acid<br>Step 5: to a solution of methyl 1-(3-{1-[(tert-butyldimethylsilyl)oxy]-2-methylpropan-2-yl}-1H-indol-5-yl)cyclopropane-1-carboxylate Ex. 98d (250 mg, 0.62 mmol) dissolved in MeOH/THF (2 mL/2 mL) was added 5M NaOH (1.25 mL, 6.23 mmol). The reaction mixture was heated at 110° C. for 1 h under microwave irradiations. TLC showed still starting material. The reaction mixture was heated by classical heating at 110° C. for 16 h. The solvent was removed under reduced pressure. Water was added and the solution was extracted twice with EtOAc. The pH of the remaining aqueous phase was then adjusted to pH = 3-4 with 1M citric acid and the solution was extracted with EtOAc. The combined organic layers were washed with water. After phases separation, the organic layer was dried over MgSO4, filtered and the solution was concentrated under reduced pressure to afford 1-[3-(1-hydroxy-2-methylpropan-2-yl)-1H-indol-5-yl]cyclopropane-1-carboxylic acid Ex. 98 (155 mg, 84%) as white solid. 1H NMR (300 MHz, DMSO-d6, d in ppm): 1.09-1.16 (m, 2H), 1.31 (s, 6H), 1.42-1.47 (m, 2H), 3.53 (d, 2H, J = 5.6 Hz), 4.55 (t, 1H, J = 5.6 Hz), 6.97-7.04 (m, 2H), 7.22 (d, 1H, J = 8.3 Hz), 7.55 (s, 1H), 10.71 (s, 1H), 12.04 (br(s), 1H). |

Intermediate Ex.100: 1-(1-methyl-2,2-dioxo-1,3-dihydro-4,2,1-benzoxathiazin-6-yl)cyclopropane-1-carboxylic acid (FIG. 1DD)

TABLE 1.61

| Cpd. | Starting compounds, Reaction conditions and purification, Yield, appearance, $^1$H NMR (solvent) data |
|---|---|
| Ex. 100a | Step 1: the previously synthesized 1-(2,2-dioxo-1,3-dihydro-4,2,1-benzoxathiazin-6-yl)cyclopropane-1-carboxylic acid (150 mg, 0.56 mmol) was dissolved in dry DMF (3 mL) and potassium carbonate (231 mg, 1.67 mmol) followed by iodomethane (104 μL, 1.67 mmol) were added to the solution. The reaction mixture was heated at 50° C. for 1 h. The reaction was quenched by the addition of sat. NH4Cl. The resulting mixture was extracted with EtOAc. The combined organic layers were dried over MgSO4, filtered and the solution was concentrated under reduced pressure to afford methyl 1-(1-methyl-2,2-dioxo-1,3-dihydro-4,2,1-benzoxathiazin-6-yl)cyclopropane-1-carboxylate Ex. 100a (160 mg, 96%) as white solid. The compound was pure enough and used for the next step without further purification. 1H NMR (300 MHz, DMSO-d6, d in ppm): 1.15-1.22 (m, 2H), 1.42-1.49 (m, 2H), 3.21 (s, 3H), 3.55 (s, 3H), 5.38 (s, 2H), 7.02 (d, 1H, J = 1.6 Hz), 7.08 (dd, 1H, J = 8.4 Hz, J = 1.8 Hz), 7.13 (d, 1H, J = 8.4 Hz). |
| Ex. 100 | 1-(1-methyl-2,2-dioxo-1,3-dihydro-4,2,1-benzoxathiazin-6-yl)cyclopropane-1-carboxylic acid<br>Step 2: o a solution of methyl 1-(1-methyl-2,2-dioxo-1,3-dihydro-4,2,1-benzoxathiazin-6-yl)cyclopropane-1-carboxylate Ex. 100a (160 mg, 0.54 mmol) dissolved in MeOH/THF (1.5 mL/1.5 mL) was added 2M NaOH (538 μL, 1.08 mmol). The reaction mixture was heated at 110° C. for 20 min under microwave irradiations. After cooling to rt, the solution was concentrated under reduced pressure. Water was added and the solution was extracted twice with Et2O. The pH of the aqueous layer was then adjusted to pH = 3-4 with 1M citric acid |

TABLE 1.61-continued

| Cpd. | Starting compounds, Reaction conditions and purification, Yield, appearance, $^1$H NMR (solvent) data |
|---|---|
| | and the solution was extracted with EtOAc. The combined organic layers were dried over MgSO4, filtered and the solution was concentrated under reduced pressure to afford 1-(1-methyl-2,2-dioxo-1,3-dihydro-4,2,1-benzoxathiazin-6-yl)cyclopropane-1-carboxylic acid Ex. 100 (140 mg, 92%) as white solid. 1H NMR (300 MHz, DMSO-d6, d in ppm): 1.07-1.14 (m, 2H), 1.38-1.46 (m, 2H), 3.20 (s, 3H), 5.36 (s, 2H), 6.99 (d, 1H, J = 1.7 Hz), 7.06 (dd, 1H, J = 8.4 Hz, J = 1.9 Hz), 7.11 (d, 1H, J = 8.4 Hz), 12.35 (br(s), 1H). |

Intermediate Ex.102: 1-(2,2-dimethyl-2H-1,3-benzodioxol-5-yl)cyclopropane-1-carboxylic acid (FIG. 1DF)

TABLE 1.62

| Cpd. | Starting compounds, Reaction conditions and purification, Yield, appearance, $^1$H NMR (solvent) data |
|---|---|
| Ex. 102a | 2,2-dimethyl-2H-1,3-benzodioxole<br>Step 1: benzene-1,2-diol (5.00 g, 45.40 mmol) was dissolved in a mixture of toluene (10 mL) and acetone (4.20 mL, 56.80 mmol). Phosphorus trichloride (1.58 mL, 18.20 mmol) was added dropwise over approx. 10 min (gas evolution was observed). After addition, the stirring was continued for 15 min to afford a two phase mixture. Et3N (7 mL) was added slowly followed by water and EtOAc. The two phases were separated, the organic layer was washed with 10% K2CO3 solution and brine. The organic layer was then dried over MgSO4, filtered and the solution was carefully concentrated under reduced pressure (caution the product has a bp of 50-51° C. at 2-3 mbar). The crude material was purified by silica gel column chromatography eluting with Petroleum ether/EtOAc [90:10]. The product fractions were combined and conentrated to dryness to afford 2,2-dimethyl-2H-1,3-benzodioxole Ex. 102a (3.47 g, 51%) as colourless oil. 1H NMR (300 MHz, DMSO-d6, d in ppm): 1.62 (s, 6H), 6.75-6.83 (m, 4H). |
| Ex. 102b | 5-bromo-2,2-dimethyl-2H-1,3-benzodioxole<br>Step 2: 2,2-dimethyl-2H-1,3-benzodioxole Ex. 102a (1.00 g, 6.66 mmol) was dissolved in dry DMF (20 mL). N-bromosuccinimide (1.19 g, 6.66 mmol) was added portionwise at rt. The mixture was then stirred overnight at this temperature. LCMS showed almost complete consumption of the starting material. The reaction was found to be difficult to monitor by TLC as starting material and product showed the same Rf. The mixture was diluted with water, some brine was added followed by EtOAc. The two phases were separated, the organic layer was dried over MgSO4, filtered and the solution was conentrated to dryness. The crude oil was purified by silica gel column chromatography eluting with Cyclohexane/EtOAc [95:5]. The product fractions were combined and concentrated to dryness to afford 5-bromo-2,2-dimethyl-2H-1,3-benzodioxole Ex. 102b (1.32 g, 86%) as colourless oil. 1H NMR (300 MHz, DMSO-d6, d in ppm): 1.63 (s, 6H), 6.79 (d, 1H, J = 8.1 Hz), 6.95 (dd, 1H, J = 8.1 Hz, J = 2.1 Hz), 7.06 (d, 1H, J = 2.1 Hz) |
| Ex. 102c | methyl 1-(2,2-dimethyl-2H-1,3-benzodioxol-5-yl)cyclopropane-1-carboxylate<br>Step 3: 5-bromo-2,2-dimethyl-2H-1,3-benzodioxole Ex. 102b (600 mg, 2.62 mmol) was dissolved in dry THF (5 mL). The solution was purged with N2 and Pd2(dba)3 (180 mg, 0.20 mmol) and XPhos (187 mg, 0.39 mmol) were added. The freshly prepared bromo[1-(methoxycarbonyl)cyclopropyl]zinc (6.55 mL, 5.24 mmol) was added slowly as a solution in THF (approx. 0.8M). The resulting mixture was heated at 70° C. for 1 h. The solvent was removed under reduced pressure. Water and EtOAc were added to the residue and the resulting mixture was filtered through a pad of Celite. After phases separation, the organic layer was dried over MgSO4, filtered and the solution was concentrated to dryness. The crude material was purified by silica gel column chromatography eluting with a gradient of Cyclohexane/EtOAc from [100:0] to [90:10]. The product fractions were combined and concentrated to dryness to afford methyl 1-(2,2-dimethyl-2H-1,3-benzodioxol-5-yl)cyclopropane-1-carboxylate Ex. 102c (303 mg, 47%) as orange viscous oil. 1H NMR (300 MHz, DMSO-d6, d in ppm): 1.11-1.15 (m, 2H), 1.39-1.43 (m, 2H), 1.62 (s, 6H), 3.53 (s, 3H), 6.71-6.72 (m, 2H), 6.79 (dd, 1H, J = 2.1 Hz, J = 0.6 Hz). |
| Ex. 102 | 1-(2,2-dimethyl-2H-1,3-benzodioxol-5-yl)cyclopropane-1-carboxylic acid<br>Step 4: methyl 1-(2,2-dimethyl-2H-1,3-benzodioxol-5-yl)cyclopropane-1-carboxylate Ex. 102c (300 mg, 1.21 mmol) was taken up in a mixture of THF and water [4:1] (10 mL). Lithium hydroxide monohydrate (152 mg, 3.63 mmol) was added and the mixture was stirred at rt over the weekend. LCMS showed full conversion. The organic solvent was removed in vacuo and the residual aqueous layer was acidified to pH = 3-4 by dropwise addition of 3M HCl. A cloudy solution was formed and the aqueous phase was extracted with EtOAc. The combined organic layers were dried over MgSO4, filtered and the solution |

TABLE 1.62-continued

| Cpd. | Starting compounds, Reaction conditions and purification, Yield, appearance, ¹H NMR (solvent) data |
|---|---|
| | was concentrated to dryness. The crude product was purified by silica gel column chromatography eluting with a gradient of Cyclohexane/EtOAc from [100:0] to [70:30]. The product fractions were combined and concentrated to dryness to afford 1-(2,2-dimethyl-2H-1,3-benzodioxol-5-yl)cyclopropane-1-carboxylic acid Ex. 102 (242 mg, 86%) as pale yellow solid. 1H NMR (300 MHz, DMSO-d6, d in ppm): 1.05-1.09 (m, 2H), 1.36-1.39 (m, 2H), 1.61 (s, 6H), 6.69-6.70 (m, 2H), 6.76-6.77 (m, 1H), 12.20 (s, 1H). |

The following acids are commercially available

TABLE 1.63

| Ex. 9 | 2-(4-methyl-2-oxo-1,2-dihydroquinolin-6-yl)acetic acid (supplier Fluorochem) |
| Ex. 45 | 2-(2-methyl-1H-1,3-benzodiazol-5-yl)acetic acid |
| Ex. 89 | 2-(1H-indol-6-yl)acetic acid |
| Ex. 90 | 2-(1H-indol-5-yl)acetic acid |

Example 1b: Synthesis of Amine Intermediates for the Synthesis of Compounds According to the Invention The following amines were obtained following the procedure described in WO2006035157

TABLE 1.64

| Ex. 7 | 3-methyl-1-[2-(piperidin-1-yl)phenyl]butan-1-amine |

The following amines were obtained following the procedure described in WO2016102633

TABLE 1.65

| Ex. 1 | [4-methyl-2-(piperidin-1-yl)phenyl](phenyl)methanamine |
| Ex. 3 | [4-methyl-2-(morpholin-4-yl)phenyl](phenyl)methanamine hydrochloride |
| Ex. 4 | phenyl[2-(piperidin-1-yl)phenyl]methanamine hydrochloride |
| Ex. 5 | [4-methoxy-2-(piperidin-1-yl)phenyl](phenyl)methanamine |
| Ex. 6 | phenyl[2-(pyrrolidin-1-yl)phenyl]methanamine hydrochloride |
| Ex. 8 | [2-(morpholin-4-yl)phenyl](phenyl)methanamine hydrochloride |
| Ex. 10 | (2,4-dimethylphenyl)(phenyl)methanamine hydrochloride |
| Ex. 16 | [4-methyl-2-(piperidin-1-yl)phenyl](5-methylfuran-2-yl)methanamine |
| Ex. 49 | (2-bromo-4-methylphenyl)(phenyl)methanamine |
| Ex. 50 | [4-methyl-2-(pyrrolidin-1-yl)phenyl](phenyl)methanamine |

The following amines were obtained following the procedure described in WO2013019635

TABLE 1.66

| Ex. 81 | (4-chlorophenyl)(2,4-dimethylphenyl)methanamine hydrochloride |

Intermediate Ex.18: (2-bromo-4-methylphenyl)(5-methylfuran-2-yl)methanamine hydrochloride (FIG. 2A)

TABLE 1.67

| Cpd. | Starting compounds, Reaction conditions and purification, Yield, Appearance, ¹H NMR (solvent) data |
|---|---|
| Ex. 18a | 2-methyl-N-[(5-methylfuran-2-yl)methylidene]propane-2-sulfinamide<br>Step 1: 5-methylfuran-2-carbaldehyde (1.0 g, 9.08 mmol) was dissolved in dry THF (5 mL). Titanium ethoxide (7.62 mL, 36.3 mmol) and 2-methyl-2-propane-sulfinamide (1.76 g, 14.5 mmol) were added to the reaction mixture. The solution was stirred at rt until completion of the reaction. Brine was added to quench the reaction and the solution was stirred vigorously. EtOAc was added and the resulting mixture was filtered on Celite. The two layers were partitionated. The organic layer was dried over MgSO4, filtered and the solution was concentrated under reduced pressure to afford 2-methyl-N-[(5-methylfuran-2-yl)methylidene]propane-2-sulfinamide (1.70 g, 88%) as orange oil. The compound was used as such for the next step. |
| Ex. 18b | N-[(2-bromo-4-methylphenyl)(5-methylfuran-2-yl)methyl]-2-methylpropane-2-sulfinamide<br>Step 2: to a solution of 2-bromo-1-iodo-4-methylbenzene (1.74 g, 5.86 mmol) in dry THF (20 mL) was added a solution of isopropylmagnesium chloride 2M in THF (2.93 mL, 5.86 mmol) at −40° C. Then, 2-methyl-N-[(5-methylfuran-2-yl)methylidene]propane-2-sulfinamide Ex. 18a (1.00 g, 4.69 mmol) diluted in dry THF (5 mL) was added dropwise at −40° C. The reaction was warmed to rt and stirred at that temperature for 3 days. Water was added to quench the reaction. The two layers were partitionated and the organic layer was dried over MgSO4, filtered and the solution was concentrated under reduced pressure. The crude material was purified by silica gel column chromatography using a gradient of hexanes/EtOAc ([8:2] to [6:4]) to afford N-[(2-bromo-4-methylphenyl)(5-methylfuran-2-yl)methyl]-2-methylpropane-2-sulfinamide (541 mg, 30%). |
| Ex. 18 | (2-bromo-4-methylphenyl)(5-methylfuran-2-yl)methanamine hydrochloride<br>Step 3: to a solution of N-[(2-bromo-4-methylphenyl)(5-methylfuran-2-yl)methyl]-2-methylpropane-2-sulfinamide Ex. 18b (540 mg, 1.41 mmol) dissolved in MeOH (5 mL) was added conc. HCl (2.7 mL) at 0° C. The reaction mixture was stirred at this temperature for 1 h. The solvent was removed and then the solid was collected by filtration. The solid was triturated with Et2O and dried until constant |

TABLE 1.67-continued

| Cpd. | Starting compounds, Reaction conditions and purification, Yield, Appearance, $^1$H NMR (solvent) data |
|---|---|
| | weight to afford (2-bromo-4-methylphenyl)(5-methylfuran-2-yl)methanamine hydrochloride (209 mg, 47%) as white solid. 1H NMR (400 MHz, DMSO-d6, d in ppm): 2.25 (d, 3H, J = 1.0 Hz), 2.33 (s, 3H), 5.72 (s, 1H), 6.10 (dd, 1H, J = 3.2 Hz, J = 1.1 Hz), 6.26 (d, 1H, J = 3.2 Hz), 7.35 (dd, 1H, J = 8.2 Hz, J = 1.7 Hz), 7.53-7.59 (m, 1H), 7.68 (d, 1H, J = 8.0 Hz), 9.20 (s, 3H). |

Intermediate Ex.19: (2,4-dimethylphenyl)(5-methyl-furan-2-yl)methanamine (FIG. 2B)

TABLE 1.68

| Cpd. | Starting compounds, Reaction conditions and purification, Yield, Appearance, $^1$H NMR (solvent) data |
|---|---|
| Ex. 19a | 2-methyl-N-[(5-methylfuran-2-yl)methylidene]propane-2-sulfinamide Step 1: 5-methylfuran-2-carbaldehyde (1.0 g, 9.08 mmol) was dissolved in dry THF (5 mL). Titanium ethoxide (7.62 mL, 36.3 mmol) and 2-methyl-2-propane-sulfinamide (1.76 g, 14.5 mmol) were added to the reaction mixture. The solution was stirred at rt until completion of the reaction. Brine was added to quench the reaction and the solution was stirred vigorously. EtOAc was added and the resulting mixture was filtered on Celite. The two layers were partitionated. The organic layer was dried over MgSO4, filtered and the solution was concentrated under reduced pressure to afford 2-methyl-N-[(5-methylfuran-2-yl)methylidene]propane-2-sulfinamide (1.70 g, 88%) as orange oil. The compound was used as such for the next step. |
| Ex. 19b | N-[(2,4-dimethylphenyl)(5-methylfuran-2-yl)methyl]-2-methylpropane-2-sulfinamide Step 2: to a suspension of magnesium powder (239 mg, 9.79 mmol) in dry THF (small amount) was added dropwise 1-bromo-2,4-dimethylbenzene (1.64 g, 8.86 mmol) diluted in dry THF (20 mL) and the reaction was heated at 40° C. After completion of Grignard reagent, 2-methyl-N-[(5-methylfuran-2-yl)methylidene]propane-2-sulfinamide Ex. 19a (995 mg, 4.66 mmol) diluted in THF (10 mL) was added to the solution. The reaction mixture was stirred at rt overnight. Water was added to quench the reaction. The two layers were partitionated and the organic layer was dried over MgSO4, filtered and the solution was concentrated under reduced pressure. The crude material was purified by silica gel column chromatography using a gradient of hexanes/EtOAc ([5:1] to [4:1]) to afford N-[(2,4-dimethylphenyl)(5-methylfuran-2-yl)methyl]-2-methylpropane-2-sulfinamide (1.27 g, 85%) as yellowish oil. |
| Ex. 19 | (2,4-dimethylphenyl)(5-methylfuran-2-yl)methanamine Step 3: to a solution of N-[(2,4-dimethylphenyl)(5-methylfuran-2-yl)methyl]-2-methylpropane-2-sulfinamide Ex. 19b (683 mg, 2.14 mmol) dissolved in dry dioxane (5 mL) was added 4N HCl in dioxane (2.4 mL) at 0° C. The reaction mixture was stirred at this temperature for 2 h and then the solid was collected by filtration. The solid was triturated with Et2O and dried until constant weight to afford (2,4-dimethylphenyl)(5-methylfuran-2-yl)methanamine (194 mg, 36%) as white solid. 1H NMR (400 MHz, DMSO-d6, d in ppm): 2.24 (s, 3H); 2.29 (d, J = 4.7 Hz, 6H), 5.64 (s, 1H), 6.02-6.19 (m, 1H), 6.25 (d, 1H, J = 3.2 Hz), 7.09-7.16 (m, 1H), 7.44 (d, 1H, J = 8.0 Hz), 8.96 (s, 3H). |

Intermediate Ex.20: [4-methoxy-2-(morpholin-4-yl)phenyl](5-methylfuran-2-yl)methanamine hydrochloride (FIG. 2C)

TABLE 1.69

| Cpd. | Starting compounds, Reaction conditions and purification, Yield, Appearance, $^1$H NMR (solvent) data |
|---|---|
| Ex. 20a | 4-methoxy-2-(morpholin-4-yl)benzaldehyde Step 1: a solution of 2-bromo-4-methoxybenzaldehyde (2.0 g, 9.30 mmol), morpholine (1.21 mL, 13.95 mmol), BINAP (232 mg, 0.37 mmol), Pd2(dba)3 (170 mg, 0.19 mmol) and Cs2CO3 (7.56 g, 23.25 mmol) in dry toluene (50 mL) was heated at 110° C. for 3 days. The solution was filtered on Celite and the filtrate was concentrated to dryness. The crude material was purified by silica gel column chromatography using hexanes/EtOAc (4:1) as eluent to afford 4-methoxy-2-(morpholin-4-yl)benzaldehyde (1.29 g, 63%) as yellowish oil. |

TABLE 1.69-continued

| Cpd. | Starting compounds, Reaction conditions and purification, Yield, Appearance, $^1$H NMR (solvent) data |
|---|---|
| Ex. 20b | N-{[4-methoxy-2-(morpholin-4-yl)phenyl]methylidene}-2-methylpropane-2-sulfinamide<br>Step 2: 4-methoxy-2-(morpholin-4-yl)benzaldehyde Ex. 20a (1.29 g, 5.83 mmol) was dissolved in dry THF (25 mL). Titanium ethoxide (2.44 mL, 11.66 mmol) and 2-methyl-2-propane-sulfinamide (707 mg, 5.83 mmol) were added to the reaction mixture. The solution was stirred at rt until completion of the reaction. Brine was added to quench the reaction and the solution was stirred vigorously. EtOAc was added and the resulting mixture was filtered on Celite. The two layers were partitionated. The organic layer was dried over MgSO4, filtered and the solution was concentrated under reduced pressure to afford N-{[4-methoxy-2-(morpholin-4-yl)phenyl]methylidene}-2-methylpropane-2-sulfinamide (1.96 g, quantitative) as yellowish oil. The compound was used as such for the next step. |
| Ex. 20c | N-{[4-methoxy-2-(morpholin-4-yl)phenyl](5-methylfuran-2-yl)methyl}-2-methylpropane-2-sulfinamide<br>Step 3: to a suspension of magnesium powder (323 mg, 13.29 mmol) in dry THF (small amount) was added cat. iodine followed by a dropwise addition of 2-bromo-5-methylfuran (2.04 g, 12.67 mmol) diluted in dry THF (20 mL). The reaction was heated at 40° C. After completion of Grignard reagent, N-{[4-methoxy-2-(morpholin-4-yl)phenyl]methylidene}-2-methylpropane-2-sulfinamide Ex. 20b (1.96 g, 5.83 mmol) diluted in THF (10 mL) was added to the solution. The reaction mixture was stirred at rt overnight. Water was added to quench the reaction. The two layers were partitionated and the organic layer was dried over MgSO4, filtered and the solution was concentrated under reduced pressure. The crude material was purified by silica gel column chromatography using hexanes/EtOAc (1:1) to afford N-{[4-methoxy-2-(morpholin-4-yl)phenyl](5-methylfuran-2-yl)methyl}-2-methylpropane-2-sulfinamide (1.08 g, 44%) as yellowish oil. |
| Ex. 20 | [4-methoxy-2-(morpholin-4-yl)phenyl](5-methylfuran-2-yl)methanamine hydrochloride<br>Step 4: to a solution of N-{[4-methoxy-2-(morpholin-4-yl)phenyl](5-methylfuran-2-yl)methyl}-2-methylpropane-2-sulfinamide Ex. 20c (1.08 g, 2.66 mmol) dissolved in dry dioxane (15 mL) was added 4N HCl in dioxane (1.66 mL) at 0° C. The reaction mixture was stirred at this temperature for 2 h and then the solid was collected by filtration. The solid was washed with Et2O and dried until constant weight to afford [4-methoxy-2-(morpholin-4-yl)phenyl](5-methylfuran-2-yl)methanamine hydrochloride (904 mg, 92%) as white solid.<br>1H NMR (400 MHz, DMSO-d6, d in ppm): 2.24 (d, 3H, J = 1.1 Hz), 2.66-2.83 (m, 4H), 3.67-3.77 (m, 4H), 3.79 (s, 3H), 5.90 (d, 1H, J = 5.7 Hz), 6.05-6.11 (m, 1H), 6.28 (d, 1H, J = 3.2 Hz), 6.86-6.90 (m, 2H), 7.62 (d, 1H, J = 9.4 Hz), 8.95 (s, 3H). |

Intermediate Ex.21:
(2,4-dimethylphenyl)(5-ethylfuran-2-yl)methanamine hydrochloride (FIG. 2D)

TABLE 1.70

| Cpd. | Starting compounds, Reaction conditions and purification, | Yield, Appearance, $^1$H NMR (solvent) data |
|---|---|---|
| Ex. 21a | N-[(5-ethylfuran-2-yl)methylidene]-2-methylpropane-2-sulfinamide<br>Step 1: 5-ethylfuran-2-carbaldehyde (762 µL, 6.48 mmol) was diluted in dry THF (10 mL). Titanium ethoxide (4.07 mL, 19.43 mmol) and 2-methyl-2-propane-sulfinamide (1.04 g, 8.58 mmol) were added to the reaction mixture. The solution was stirred at rt until completion of the reaction. Brine was added to quench the reaction and the solution was stirred vigorously. EtOAc was added and the resulting mixture was filtered on Celite. The two layers were partitionated. The organic layer was dried over MgSO4, filtered and the solution was concentrated under reduced pressure to afford N-[(5-ethylfuran-2-yl)methylidene]-2-methylpropane-2-sulfinamide (1.46 g, quantitative) as colourless oil. The compound was used as such for the next step. | |
| Ex. 21b | N-[(2,4-dimethylphenyl)(5-ethylfuran-2-yl)methyl]-2-methylpropane-2-sulfinamide<br>Step 2: to a suspension of magnesium powder (328 mg, 13.49 mmol) in dry THF (small amount) was added dropwise 2,4-dimethylbromobenzene (2.33 g, 12.59 mmol) dissolved in dry THF (20 mL). The reaction was heated at 40° C. After completion of Grignard reagent, N-[(5-ethylfuran-2-yl)methylidene]-2-methylpropane-2-sulfinamide Ex. 21a (1.46 g, 6.42 mmol) diluted in THF (10 mL) was added to the solution. The reaction mixture was stirred at rt overnight. Water was added to quench the reaction. The two layers were partitionated and the organic layer was dried over MgSO4, filtered and the solution was concentrated under reduced pressure. The crude material was purified by silica | |

TABLE 1.70-continued

| Cpd. | Starting compounds, Reaction conditions and purification, | Yield, Appearance, $^1$H NMR (solvent) data |
|---|---|---|
| | gel column chromatography using hexanes/EtOAc (5:1) to afford N-[(2,4-dimethylphenyl)(5-ethylfuran-2-yl)methyl]-2-methylpropane-2-sulfinamide (1.63 g, 76%) as yellowish oil. | |
| Ex. 21 | (2,4-dimethylphenyl)(5-ethylfuran-2-yl)methanamine hydrochloride Step 3: to a solution of N-[(2,4-dimethylphenyl)(5-ethylfuran-2-yl)methyl]-2-methylpropane-2-sulfinamide Ex. 21b (1.63 g, 4.89 mmol) dissolved in dry dioxane (10 mL) was added 4N HCl in dioxane (4.9 mL) at 0° C. The reaction mixture was stirred at this temperature for 2 h and then the solid was collected by filtration. The solid was washed with Et2O and dried until constant weight to afford (2,4-dimethylphenyl)(5-ethylfuran-2-yl)methanamine hydrochloride (872 mg, 68%) as white solid. 1H NMR (400 MHz, DMSO-d6, d in ppm): 1.15 (t, 3H, J = 7.5 Hz), 2.28 (s, 3H), 2.30 (s, 3H), 2.58 (q, 2H, J = 7.5 Hz), 5.64 (s, 1H), 6.09 (d, 1H, J = 3.2 Hz), 6.27 (d, 1H, J = 3.2 Hz), 7.07 (s, 1H), 7.12 (d, 1H, J = 8.0 Hz), 7.46 (d, 1H, J = 7.9 Hz), 9.01 (s, 3H). | |

Intermediate Ex.22: (2-bromo-4-methoxyphenyl)(5-methylfuran-2-yl)methanamine (FIG. 2E)

TABLE 1.71

| Cpd. | Starting compounds, Reaction conditions and purification, | Yield, Appearance, $^1$H NMR (solvent) data |
|---|---|---|
| Ex. 22a | N-[(2-bromo-4-methoxyphenyl)methylidene]-2-methylpropane-2-sulfinamide Step 1: 2-bromo-4-methoxybenzaldehyde (1 g, 4.65 mmol) was diluted in dry THF (20 mL). Titanium ethoxide (2.92 mL, 13.95 mmol) and 2-methyl-2-propane-sulfinamide (750 mg, 6.19 mmol) were added to the reaction mixture. The solution was stirred at rt until completion of the reaction. Brine was added to quench the reaction and the solution was stirred vigorously. EtOAc was added and the resulting mixture was filtered on Celite. The two layers were partitionated. The organic layer was dried over MgSO4, filtered and the solution was concentrated under reduced pressure to afford N-[(2-bromo-4-methoxyphenyl)methylidene]-2-methylpropane-2-sulfinamide (1.48 g, quantitative) as colourless oil. The compound was used as such for the next step. | |
| Ex. 22b | N-[(2-bromo-4-methoxyphenyl)(5-methylfuran-2-yl)methyl]-2-methylpropane-2-sulfinamide Step 2: to a suspension of magnesium powder (73 mg, 3.00 mmol) in dry THF (small amount) was added dropwise 2-bromo-5-methylfuran (430 mg, 2.67 mmol) dissolved in dry THF (5 mL). The reaction was heated at 40° C. After completion of Grignard reagent, N-[(2-bromo-4-methoxyphenyl)methylidene]-2-methylpropane-2-sulfinamide (500 mg, 1.57 mmol) diluted in THF (5 mL) was added to the solution. The reaction mixture was stirred at rt overnight. Water was added to quench the reaction. The two layers were partitionated and the organic layer was dried over MgSO4, filtered and the solution was concentrated under reduced pressure. The crude material was purified by silica gel column chromatography using hexanes/EtOAc (5:1) to afford N-[(2-bromo-4-methoxyphenyl)(5-methylfuran-2-yl)methyl]-2-methylpropane-2-sulfinamide (440 mg, 70%) as yellowish oil. | |
| Ex. 22 | (2,4-dimethylphenyl)(5-ethylfuran-2-yl)methanamine hydrochloride Step 3: to a solution of N-[(2-bromo-4-methoxyphenyl)(5-methylfuran-2-yl)methyl]-2-methylpropane-2-sulfinamide (880 mg, 2.21 mmol) dissolved in dry dioxane (10 mL) was added 4N HCl in dioxane (2.2 mL) at 0° C. The reaction mixture was stirred at this temperature for 2 h and then the solid was collected by filtration. The solid was washed with Et2O and dried until constant weight to afford (2,4-dimethylphenyl)(5-ethylfuran-2-yl)methanamine hydrochloride (632 mg, 89%) as white solid. 1H NMR (400 MHz, DMSO-d6, d in ppm): 2.25 (s, 3H), 3.81 (s, 3H), 5.71 (s, 1H), 6.10 (d, 1H, J = 2.8 Hz), 6.25 (d, 1H, J = 3.2 Hz), 7.14 (dd, 1H, J = 8.8 Hz, J = 2.6 Hz), 7.29 (d, 1H, J = 2.6 Hz), 7.70 (d, 1H, J = 8.8 Hz), 9.13 (s, 3H). | |

Intermediate Ex.32: (5-chlorofuran-2-yl)(2,4-dimethylphenyl)methanamine (FIG. 2F)

TABLE 1.72

| Cpd. | Starting compounds, Reaction conditions and purification, | Yield, Appearance, $^1$H NMR (solvent) data |
|---|---|---|
| Ex. 32a | 2-methyl-N-[(5-chlorofuran-2-yl)methylidene]propane-2-sulfinamide Step 1: 5-chlorofuran-2-carbaldehyde (1.0 g, 7.66 mmol) was dissolved in dry THF (10 mL). Titanium ethoxide (3.21 mL, 15.3 mmol) and 2-methyl-2-propane-sulfinamide (975 mg, 8.04 mmol) were added to the reaction mixture. The solution was stirred at rt until completion of the reaction. Brine was added to quench the reaction and the solution was stirred vigorously. EtOAc was added and the resulting mixture was filtered on Celite. The two layers were partitioned. The organic layer was dried over MgSO4, filtered and the solution was concentrated under reduced pressure. The crude material was purified by silica gel column chromatography using Cyclohexane/EtOAc [9:1] as eluent to afford 2-methyl-N-[(5-chlorofuran-2-yl)methylidene]propane-2-sulfinamide (1.51 g, 84%) as white solid. | |
| Ex. 32b | N-[(5-chlorofuran-2-yl)(2,4-dimethylphenyl)methyl]-2-methylpropane-2-sulfinamide Step 2: to a solution of 1-bromo-2,4-dimethylbenzene(653 mg, 3.53 mmol) in dry THF (5 mL) was added dropwise n-butyllithium 1.6M (2.21 mL, 3.53 mmol) at −78° C. under N2 atmosphere. The reaction mixture was stirred at −78° C. for 20 minutes. Then, 2-methyl-N-[(5-chlorofuran-2-yl)methylidene]propane-2-sulfinamide Ex. 32a (750 mg, 3.21 mmol) dissolved in dry THF (5 mL) was added dropwise to the solution. The reaction mixture was slowly warmed to rt and kept at this temperature for 2 h under stirring. Sat. NH4Cl was added to quench the reaction. The two layers were partitioned and the organic layer was dried over MgSO4, filtered and the solution was concentrated under reduced pressure. The crude material was purified by silica gel column chromatography using Cyclohexane/EtOAc [8:2] as eluent to afford N-[(5-chlorofuran-2-yl)(2,4-dimethylphenyl)methyl]-2-methylpropane-2-sulfinamide (235 mg, 22%) as yellowish oil. | |
| Ex. 32 | (5-chlorofuran-2-yl)(2,4-dimethylphenyl)methanamine Step 3: to a solution of N-[(5-chlorofuran-2-yl)(2,4-dimethylphenyl)methyl]-2-methylpropane-2-sulfinamide Ex. 32b (230 mg, 0.67 mmol) dissolved in MeOH (2.5 mL) was added 6N HCl (545 µL) at rt. The reaction mixture was stirred overnight at rt. Water was added to quench the reaction. The aqueous layer was washed with Et2O and then basified with NaOH 5N until pH 9-10. The resulting basic aqueous phase was extracted with EtOAc. The combined organic layers were dried over MgSO4, filtered and the solution was concentrated under reduced pressure to afford (5-chlorofuran-2-yl)(2,4-dimethylphenyl)methanamine (130 mg, 82%) as yellow solid. 1H NMR (400 MHz, DMSO-d6, d in ppm): 2.23 (s, 3H), 2.25 (s, 3H), 2.30 (br(s), 2H), 5.11 (s, 1H), 6.21 (dd, 1H, J = 3.3 Hz, J = 0.9 Hz), 6.33 (d, 1H, J = 3.3 Hz), 6.95-6.98 (m, 2H), 7.19 (d, 1H, J = 7.7 Hz). | |

Intermediate Ex.42. 2-[amino(5-methylfuran-2-yl)methyl]-N,N,5-trimethylaniline hydrochloride (FIG. 2G)

TABLE 1.73

| Cpd. | Starting compounds, Reaction conditions and purification, | Yield, Appearance, $^1$H NMR (solvent) data |
|---|---|---|
| Ex. 42a | 2-bromo-N,N,5-trimethylbenzenamine Step 1: a solution of 2-bromo-5-methylaniline (2.00 g, 10.75 mmol), K2CO3 (3.71 g, 2.69 mmol) and iodomethane (3.35 mL, 53.75 mmol) in acetonitrile (60 mL) wa heated at 110° C. for 18 h. After cooling to rt, the inorganic salt was removed through a pad of Celite. The solution was concentrated to dryness. The crude material was purified by silica gel column chromatography eluting with Hexanes/EtOAc (90:10) to afford 2-bromo-N,N,5-trimethylbenzenamine Ex. 42a (2.09 g, 91%). | |
| Ex. 42b | N-{[2-(dimethylamino)-4-methylphenyl](5-methylfuran-2-yl)methyl}-2-methylpropane-2-sulfinamide Step 2: to a suspension of magnesium powder (237 mg, 9.75 mmol) in dry THF (small amount) was added dropwise 2-bromo-N,N,5-trimethylbenzenamine Ex. 42a (2.00 g, 9.38 mmol) diluted in dry THF (4 mL) and the reaction was heated at 40° C. After completion of Grignard reagent, the previously prepared 2-methyl-N-[(5-methylfuran-2-yl)methylidene]propane-2-sulfinamide (800 mg, 3.75 mmol) diluted in THF (4 mL) was added to the solution. The reaction mixture was stirred at rt overnight. Water was added to quench the reaction. The | |

TABLE 1.73-continued

| Cpd. | Starting compounds, Reaction conditions and purification, | Yield, Appearance, ¹H NMR (solvent) data |
|---|---|---|
| | two layers were partitionated and the organic layer was dried over MgSO4, filtered and the solution was concentrated under reduced pressure. The crude material was purified by silica gel column chromatography using a gradient of Hexanes/EtOAc (from [80:20] to [70:30]) to afford N-{[2-(dimethylamino)-4-methylphenyl](5-methylfuran-2-yl)methyl}-2-methylpropane-2-sulfinamide Ex. 42b (980 mg, 75%). | |
| Ex. 42 | 2-[amino(5-methylfuran-2-yl)methyl]-N,N,5-trimethylaniline hydrochloride Step 3: to a solution of N-{[2-(dimethylamino)-4-methylphenyl](5-methylfuran-2-yl)methyl}-2-methylpropane-2-sulfinamide Ex. 42b (980 mg, 2.81 mmol) in dry dioxane (29 mL) was added HCl 4M in dioxane (2.45 mL, 9.80 mmol) at 0° C. The reaction mixture was stirred at this temperature for 2 h. The solid formed was collected by filtration. The residue was triturated with diethyl ether and a mixture of Et2O/EtOAc (9:1) and filtered-off to afford 2-[amino(5-methylfuran-2-yl)methyl]-N,N,5-trimethylaniline hydrochloride Ex. 42 (542 mg, 79%) as off-white solid. 1H NMR (400 MHz, DMSO-d6, d in ppm): 2.25 (d, 3H, J = 1.0 Hz), 2.35 (s, 3H), 2.77 (s, 6H), 6.10 (dd, 2H, J = 3.2 Hz, J = 1.2 Hz), 6.32 (d, 1H, J = 3.2 Hz), 7.18 (s, 1H), 7.38 (s, 1H), 7.59 (d, 1H, J = 8.0 Hz), 9.05 (s, 3H). | |

Intermediate Ex.44: [4-methyl-2-(pyrrolidin-1-yl)phenyl](5-methylfuran-2-yl)methanamine hydrochloride (FIG. 2H)

TABLE 1.74

| Cpd. | Starting compounds, Reaction conditions and purification, | Yield, Appearance, ¹H NMR (solvent) data |
|---|---|---|
| Ex. 44a | 4-methyl-2-(pyrrolidin-1-yl)benzaldehyde Step 1: a solution of 2-bromo-4-methylbenzaldehyde (3.00 g, 15.07 mmol), pyrrolidine (1.87 mL, 22.61 mmol), BINAP (436 mg, 0.75 mmol), Pd2(dba)3 (276 mg, 0.30 mmol) and Cs2CO3 (6.88 g, 21.10 mmol) in dry toluene (60 mL) was heated at 90° C. for two days. Water was added to quench the reaction. The two layers were partitionated and the organic layer was dried over MgSO4, filtered and the solution was concentrated under reduced pressure. The crude material was purified by silica gel column chromatography using Hexanes/EtOAc as eluent (15:1) to afford 4-methyl-2-(pyrrolidin-1-yl)benzaldehyde Ex. 44a (2.08 g, 73%). | |
| Ex. 44b | 2-methyl-N-{[4-methyl-2-(pyrrolidin-1-yl)phenyl]methylidene}propane-2-sulfinamide Step 2: a solution of 4-methyl-2-(pyrrolidin-1-yl)benzaldehyde Ex. 44a (1.00 g, 5.28 mmol), titanium ethoxide (4.32 mL, 20.61 mmol), 2-methyl-propane-sulfinamide (1.23 g, 10.14 mmol) dry THF (30 mL) overnight at rt. Water was added to quench the reaction. The two layers were partitionated and the organic layer was dried over MgSO4, filtered and the solution was concentrated under reduced pressure. The crude material was purified by silica gel column chromatography eluting with a gradient of Hexanes/EtOAc (from [90:10] to [80:20] to [70:30]) to afford 2-methyl-N-{[4-methyl-2-(pyrrolidin-1-yl)phenyl]methylidene}propane-2-sulfinamide Ex. 44b (1.16 g, 75%). | |
| Ex. 44c | 2-methyl-N-{[4-methyl-2-(pyrrolidin-1-yl)phenyl](5-methylfuran-2-yl)methyl}propane-2-sulfinamide Step 3: to a suspension of magnesium powder (96 mg, 3.97 mmol) in dry THF (small amount) was added dropwise 2-bromo-5-methylfurane (614 mg, 3.81 mmol) diluted in dry THF (5 mL) and the reaction was heated at 40° C. After completion of Grignard reagent, the previously prepared 2-methyl-N-{[4-methyl-2-(pyrrolidin-1-yl)phenyl]methylidene}propane-2-sulfinamide Ex. 44b (446 mg, 1.53 mmol) diluted in THF (5 mL) was added to the solution. The reaction mixture was stirred at rt overnight. Water was added to quench the reaction. The two layers were partitionated and the organic layer was dried over MgSO4, filtered and the solution was concentrated under reduced pressure. The crude material was purified by silica gel column chromatography using a gradient of Hexanes/EtOAc (from [80:20] to [70:30]) to afford 2-methyl-N-{[4-methyl-2-(pyrrolidin-1-yl)phenyl](5-methylfuran-2-yl)methyl}propane-2-sulfinamide Ex. 44c (436 mg, 76%). | |
| Ex. 44 | [4-methyl-2-(pyrrolidin-1-yl)phenyl](5-methylfuran-2-yl)methanamine hydrochloride Step 4: to a solution of 2-methyl-N-{[4-methyl-2-(pyrrolidin-1-yl)phenyl](5-methylfuran-2-yl)methyl}propane-2-sulfinamide Ex. 44c (430 mg, 1.15 mmol) in dry dioxane (17 mL) was added HCl 4M in dioxane (1.06 mL, 4.24 mmol) at 0° C. The reaction mixture was stirred at this temperature for 2 h. The solid formed was collected by filtration and washed with diethyl ether to afford [4- | |

TABLE 1.74-continued

| Cpd. | Starting compounds, Reaction conditions and purification, | Yield, Appearance, $^1$H NMR (solvent) data |
|---|---|---|
| | methyl-2-(pyrrolidin-1-yl)phenyl](5-methylfuran-2-yl)methanamine hydrochloride Ex. 44 (244 mg, 91%) as pale orange solid. 1H NMR (400 MHz, DMSO-d6, d in ppm): 2.00 (s, 4H), 2.25 (d, 3H, J = 1.0 Hz), 2.34 (s, 3H), 2.93-3.48 (m, 4H), 5.77 (s, 1H), 6.10 (dd, 1H, J = 1.2 Hz, J = 3.3 Hz), 6.31 (s, 1H), 7.13 (s, 1H), 7.27 (s, 1H), 7.57 (d, 1H, J = 7.9 Hz), 9.00 (s, 3H). One proton hidden by the water peak. | |

Intermediate Ex.47: (5-chlorofuran-2-yl)[4-methyl-2-(piperidin-1-yl)phenyl]methanamine (FIG. 2I)

TABLE 1.75

| Cpd. | Starting compounds, Reaction conditions and purification, | Yield, Appearance, $^1$H NMR (solvent) data |
|---|---|---|
| Ex. 47a | 2-methyl-N-[(5-chlorofuran-2-yl)methylidene]propane-2-sulfinamide Step 1: 5-chlorofuran-2-carbaldehyde (1.0 g, 7.66 mmol) was dissolved in dry THF (10 mL). Titanium ethoxide (3.21 mL, 15.3 mmol) and 2-methyl-2-propane-sulfinamide (975 mg, 8.04 mmol) were added to the reaction mixture. The solution was stirred at rt until completion of the reaction. Brine was added to quench the reaction and the solution was stirred vigorously. EtOAc was added and the resulting mixture was filtered on Celite. The two layers were partitionated. The organic layer was dried over MgSO4, filtered and the solution was concentrated under reduced pressure. The crude material was purified by silica gel column chromatography using Cyclohexane/EtOAc [9:1] as eluent to afford 2-methyl-N-[(5-chlorofuran-2-yl)methylidene]propane-2-sulfinamide Ex. 47a (1.51 g, 84%) as white solid. | |
| Ex. 47b | N-[(5-chlorofuran-2-yl)[4-methyl-2-(piperidin-1-yl)phenyl]methyl]-2-methylpropane-2-sulfinamide Step 2: to a solution of 1-(2-bromo-5-methylphenyl)piperidine (synthesized following the procedure described in PCT Int. Appl. (2016), WO 2016102633) (897 mg, 3.53 mmol) diluted in dry THF (5 mL) was added dropwise nBuLi 1.6M in THF (2.21 mL, 3.53 mmol) at −78° C. and under N2 atmosphere. The stirring was kept at −78° C. for 20 min. 2-Methyl-N-[(5-chlorofuran-2-yl)methylidene]propane-2-sulfinamide Ex. 47a (750 mg, 3.21 mmol) dissolved in dry THF (5 mL) was added dropwise to the solution. The reaction mixture is gently warmed to 0° C. (takes approx. 2 h). Sat. NH4Cl was added to quench the reaction. After few min of stirring, the resulting mixture was extracted with EtOAc. The combined organic layers were dried over MgSO4, filtered and the solution was concentrated under reduced pressure. The crude material was purified by silica gel column chromatography eluting with Cyclohexane/EtOAc (80:20) to afford N-[(5-chlorofuran-2-yl)[4-methyl-2-(piperidin-1-yl)phenyl]methyl]-2-methylpropane-2-sulfinamide Ex. 47b (717 mg, 55%) as white solid. | |
| Ex. 47 | (5-chlorofuran-2-yl)[4-methyl-2-(piperidin-1-yl)phenyl]methanamine Step 3: N-[(5-chlorofuran-2-yl)[4-methyl-2-(piperidin-1-yl)phenyl]methyl]-2-methylpropane-2-sulfinamide Ex. 47b (600 mg, 1.47 mmol) was dissolved in MeOH (6 mL). 6N HCl (1.22 mL, 7.34 mmol) was added to the solution. The reaction mixture was stirred overnight at rt. Water was added to quench the reaction and the aqueous layer was extracted with diethyl ether. After phases separation, the aqueous layer was basified with 5N NaOH up pH = 9-10 and extracted with EtOAc. The combined organic layers were dried over MgSO4, filtered and the solution was concentrated to dryness to afford (5-chlorofuran-2-yl)[4-methyl-2-(piperidin-1-yl)phenyl]methanamine Ex. 47 (360 mg, 81%) as yellowish oil. | |

Intermediate Ex.48: (5-chlorofuran-2-yl)[4-methyl-2-(pyrrolidin-1-yl)phenyl]methanamine hydrochloride (FIG. 2J)

TABLE 1.76

| Cpd. | Starting compounds, Reaction conditions and purification, | Yield, Appearance, $^1$H NMR (solvent) data |
|---|---|---|
| Ex. 48a | 2-methyl-N-[(5-chlorofuran-2-yl)methylidene]propane-2-sulfinamide Step 1: 5-chlorofuran-2-carbaldehyde (1.0 g, 7.66 mmol) was dissolved in dry | |

TABLE 1.76-continued

| Cpd. | Starting compounds, Reaction conditions and purification, | Yield, Appearance, ¹H NMR (solvent) data |
|---|---|---|
| | THF (10 mL). Titanium ethoxide (3.21 mL, 15.3 mmol) and 2-methyl-2-propane-sulfinamide (975 mg, 8.04 mmol) were added to the reaction mixture. The solution was stirred at rt until completion of the reaction. Brine was added to quench the reaction and the solution was stirred vigorously. EtOAc was added and the resulting mixture was filtered on Celite. The two layers were partitionated. The organic layer was dried over MgSO4, filtered and the solution was concentrated under reduced pressure. The crude material was purified by silica gel column chromatography using Cyclohexane/EtOAc [9:1] as eluent to afford 2-methyl-N-[(5-chlorofuran-2-yl)methylidene]propane-2-sulfinamide Ex. 48a (1.51 g, 84%) as white solid. | |
| Ex. 48b | 1-(2-bromo-5-methylphenyl)pyrrolidine Step 2: a solution of 2-bromo-5-methylaniline (1.20 g, 6.45 mmol), 1,4-dibromobutane (1.54 mL, 12.90 mmol) and K2CO3 (2.22 g, 16.12 mmol) dissolved in acetonitrile (50 mL) was refluxed for two days. The solvent was removed under reduced pressure. Water was added to dissolve the inorganic salt. The aqueous layer was extracted with EtOAc. The combined organic layer was dried over MgSO4, filtered and the solution was concentrated to dryness. The residue was purified by silica gel column chromatography using Hexanes (100%) as eluent affording 1-(2-bromo-5-methylphenyl)pyrrolidine Ex. 48b (1.29 g, 83%). | |
| Ex. 48c | 2-methyl-N-{[4-methyl-2-(pyrrolidin-1-yl)phenyl](5-methylfuran-2-yl)methyl}propane-2-sulfinamide Step 3: to a suspension of magnesium powder (151 mg, 6.21 mmol) in dry THF (small amount) was added dropwise 1-(2-bromo-5-methylphenyl)pyrrolidine Ex. 48b (1.29 g, 5.37 mmol) dissolved in dry THF. The reaction was heated at 40° C. After completion of Grignard reagent, 2-methyl-N-[(5-chlorofuran-2-yl)methylidene]propane-2-sulfinamide Ex. 48a (766 mg, 3.28 mmol) diluted in THF (5 mL) was added to the solution. The reaction mixture was stirred at 45° C. overnight. Water was added to quench the reaction. The two layers were partitionated and the organic layer was dried over MgSO4, filtered and the solution was concentrated under reduced pressure. The crude material was purified by silica gel column chromatography using Hexanes/EtOAc (80:20) to afford 2-methyl-N-{[4-methyl-2-(pyrrolidin-1-yl)phenyl](5-methylfuran-2-yl)methyl}propane-2-sulfinamide Ex. 48c (972 mg, 75%) as yellowish oil. | |
| Ex. 48 | (5-chlorofuran-2-yl)[4-methyl-2-(pyrrolidin-1-yl)phenyl]methanamine hydrochloride Step 4: to a solution of 2-methyl-N-{[4-methyl-2-(pyrrolidin-1-yl)phenyl](5-methylfuran-2-yl)methyl}propane-2-sulfinamide Ex. 48c (972 mg, 2.46 mmol) dissolved in dry dioxane (5 mL) was added 4N HCl in dioxane (600 µL) at 0° C. The reaction mixture was stirred at this temperature for 2 h and then the solid was collected by filtration. The solid was washed with Et2O and dried until constant weight to afford (5-chlorofuran-2-yl)[4-methyl-2-(pyrrolidin-1-yl)phenyl]methanamine hydrochloride Ex. 48 (667 mg, 83%) as pale pink solid. 1H NMR (400 MHz, DMSO-d6, d in ppm): 1.99 (s, 4H), 2.34 (s, 3H), 2.88-3.36 (m, 4H), 6.17 (s, 1H), 6.52 (d, 1H, J = 3.4 Hz), 6.55 (d, 1H, J = 3.6 Hz), 7.13 (s, 1H), 7.26 (s, 1H), 7.58 (d, 1H, J = 7.9 Hz), 9.14 (s, 3H). | |

Intermediate Ex.63: [2-(azepan-1-yl)-4-methoxy-phenyl](5-methylfuran-2-yl)methanamine (FIG. 2K)

TABLE 1.77

| Cpd. | Starting compounds, Reaction conditions and purification, | Yield, Appearance, ¹H NMR (solvent) data |
|---|---|---|
| Ex. 63a | 2-(azepan-1-yl)-4-methoxybenzaldehyde Step 1: a solution of 2-bromo-4-methoxybenzaldehyde (0.5 g, 2.33 mmol), hexamethyleneimine (262 µL, 2.33 mmol), BINAP (58 mg, 0.10 mmol), Pd2(dba)3 (43 mg, 0.05 mmol) and Cs2CO3 (1.134 g, 3.48 mmol) in dry toluene (15 mL) was heated at 95° C. for 17 h. Water was added to quench the reaction. The two layers were partitionated and the organic layer was dried over MgSO4, filtered and the solution was concentrated under reduced pressure. The crude material was purified by silica gel column chromatography using Hexanes/EtOAc as eluent ([100:1] to [20:1]) to afford 2-(azepan-1-yl)-4-methoxybenzaldehyde Ex. 63a (526 mg, 96%). | |
| Ex. 63b | N-{[2-(azepan-1-yl)-4-methoxyphenyl]methylidene}-2-methylpropane-2-sulfinamide Step 2: a solution of 2-(azepan-1-yl)-4-methoxybenzaldehyde Ex. 63a (526 mg, 2.25 mmol), titanium ethoxide (1.9 mL, 9.02 mmol), 2-methyl-propane-sulfinamide (276 mg, 2.48 mmol) dry THF at rt. Water was added to quench the reaction. The two layers were partitionated and the organic layer was dried over | |

TABLE 1.77-continued

| Cpd. | Starting compounds, Reaction conditions and purification, | Yield, Appearance, ¹H NMR (solvent) data |
|---|---|---|
| | MgSO4, filtered and the solution was concentrated under reduced pressure. The crude material was pure enough and used in the next step without further purification. | |
| Ex. 63c | N-{[2-(azepan-1-yl)-4-methoxyphenyl](5-methylfuran-2-yl)methyl}-2-methylpropane-2-sulfinamide | |
| | Step 3: to a suspension of magnesium powder (60 mg, 2.46 mmol) in dry THF (small amount) was added dropwise 2-bromo-5-methylfurane (377 mg, 2.34 mmol) diluted in dry THF (5 mL) and the reaction was heated at 40° C. After completion of Grignard reagent, the previously prepared N-{[2-(azepan-1-yl)-4-methoxyphenyl]methylidene}-2-methylpropane-2-sulfinamide Ex. 63b (394 mg, 1.17 mmol) diluted in THF (5 mL) was added to the solution. The reaction mixture was stirred at rt overnight. Water was added to quench the reaction. The two layers were partitionated and the organic layer was dried over MgSO4, filtered and the solution was concentrated under reduced pressure. The crude material was purified by silica gel column chromatography using a gradient of Hexanes/EtOAc to afford N-{[2-(azepan-1-yl)-4-methoxyphenyl](5-methylfuran-2-yl)methyl}-2-methylpropane-2-sulfinamide Ex. 63c (283 mg, 60%) as yellowish oil. | |
| Ex. 63 | [2-(azepan-1-yl)-4-methoxyphenyl](5-methylfuran-2-yl)methanamine | |
| | Step 4: to a solution of N-{[2-(azepan-1-yl)-4-methoxyphenyl](5-methylfuran-2-yl)methyl}-2-methylpropane-2-sulfinamide Ex. 63c (283 mg, 0.70 mmol) in MeOH (5 mL) was added conc. HCl (3.1 mL) at 0° C. The reaction mixture was stirred at this temperature for 2 h and then quench with sat. NaHCO3 to reach ph 7-8. The aqueous layer was extracted with EtOAc. The combined organic layers were dried over MgSO4, filtered and the solution was concentrated under reduced pressure. The residue was purified by silica gel column chromatography using CH2Cl2/EtOAc as eluent ([10:0] to [8:2]) followed by flash silica gel column chromatography using hexanes/EtOAc as eluent to afford [2-(azepan-1-yl)-4-methoxyphenyl](5-methylfuran-2-yl)methanamine Ex. 63 (62 mg, 28%) as yellowish oil. 1H NMR (400 MHz, DMSO-d6, d in ppm): 1.66 (s, 8H), 2.17 (s, 3H), 2.91-3.06 (m, 4H), 3.71 (s, 3H), 5.41 (s, 1H), 5.92 (s, 2H), 6.62 (dd, 1H, J = 8.5 Hz, J = 2.6 Hz), 6.66 (d, 1H, J = 2.6 Hz), 7.23 (d, 1H, J = 8.5 Hz) (NH2 exchange with deuterated solvent). | |

Intermediate Ex.77: (2,4-dimethylphenyl)(6-methylpyridin-2-yl)methanamine dihydrochloride (FIG. 2L)

TABLE 1.78

| Cpd. | Starting compounds, Reaction conditions and purification, | Yield, Appearance, ¹H NMR (solvent) data |
|---|---|---|
| Ex. 77a | (2,4-dimethylphenyl)(6-methylpyridin-2-yl)methanol | |
| | Step 1: in a three-neck round-bottom flask were placed 2-bromo-6-methylpyridine (2.82 g, 16.40 mmol) and dry THF (5.00 mL) under argon atmosphere. The solution was cooled down at −78° C. nBuLi 2.5M in hexanes (6.56 mL, 16.40 mmol) was added dropwise to the solution. The reaction mixture was stirred at −78° C. for 20 min and a solution of 2,4-dimethylbenzaldehyde (2.00 g, 14.91 mmol) dissolved in dry THF (0.5 mL) was added dropwise over 15 min. The reaction mixture was slowly warmed to rt over 2 h. TLC showed full conversion of starting material, and the reaction mixture was poured onto cold brine solution, EtOAc was added and the two phases wereseparated. The organic layer was dried over MgSO4, filtered and the solution was concentrated to dryness. The residue was triturated with a mixture of EtOAc/Hexanes to give (2,4-dimethylphenyl)(6-methylpyridin-2-yl)methanol Ex. 77a (1.65 g, 40%) as light orange solid. 1H NMR (300 MHz, CDCl3, d in ppm): 2.30 (s, 3H), 2.31 (s, 3H), 2.60 (s, 3H), 5.47 (d, 1H, J = 3.3 Hz), 5.87 (d, 1H, J = 3.0 Hz), 6.77 (d, 1H, J = 7.8 Hz), 6.93-7.02 (m, 2H), 7.04 (d, 1H, J = 7.6 Hz), 7.10 (d, 1H, J = 7.7 Hz), 7.47 (t, 1H, J = 7.7 Hz). | |
| Ex. 77b | 2-(2,4-dimethylbenzoyl)-6-methylpyridine | |
| | Step 2: (2,4-dimethylphenyl)(6-methylpyridin-2-yl)methanol Ex. 77a (1.65 g, 7.26 mmol) was dissolved in CH2Cl2 (17 mL), and manganese (IV) oxide (3.79 g, 43.55 mmol) was added. The solution was stirred at rt for 6 h. The reaction mixture was filltered through a pad of celite, and the filtrate was evaporated to dryness to afford 2-(2,4-dimethylbenzoyl)-6-methylpyridine Ex. 77b (1.58 g, 97%) as yellow oil. 1H NMR (300 MHz, CDCl3, d in ppm): 2.38 (s, 3H), 2.41 (s, 3H), 2.59 (s, 3H), 7.04 (d, 1H, J = 8.3 Hz), 7.10 (s, 1H), 7.30 (d, 1H, J = 4.0 Hz), 7.40 (d, 1H, J = 7.8 Hz), 7.69-7.77 (m, 2H). | |
| Ex. 77c | N-[(2,4-dimethylphenyl)(6-methylpyridin-2-yl)methylidene]-2-methylpropane-2-sulfinamide | |

TABLE 1.78-continued

| Cpd. | Starting compounds, Reaction conditions and purification, | Yield, Appearance, ¹H NMR (solvent) data |
|---|---|---|
| | Step 3: 2-(2,4-dimethylbenzoyl)-6-methylpyridine Ex. 77b (1.58 g, 7.01 mmol) was dissolved in THF (16 mL). 2-methylpropane-2-sulfinamide (0.89 g, 7.36 mmol) was added to the solution followed by Ti(OEt)4 (2.94 mL, 14.03 mmol). The reaction mixture was stirred overnight at 60° C. TLC showed not total consumption of the starting material. Additional Ti(OEt)4 (1.47 mL, 7.01 mmol) was added and the stirring was kept at 60° C. over the weekend. The reaction mixture was poured onto a mixture of EtOAc and sat. NH4Cl under vigorous stirring. The inorganic salt was removed by filtration on Celite. The two layers were partitioned and the aqueous layer was washed with sat. NH4Cl. The combined organic layers were dried over MgSO4, filtered and the solution was concentrated under reduced pressure. The crude material was purified by silica gel column chromatography eluting with Hexanes/EtOAc (75:25). Pure fractions were combined and evaporated under reduced pressure. During the evaproration additional products were observed on TLC probably due to decomposition. The resulting oil was conserved at 4° C. The solid was triturated in pentane and filtered off to give N-[(2,4-dimethylphenyl)(6-methylpyridin-2-yl)methylidene]-2-methylpropane-2-sulfinamide Ex. 77c (830 mg, 36%) as yellow solid. 1H NMR (300 MHz, DMSO-d6, d in ppm): 1.19 (s, 9H), 2.00 (s, 3H), 2.33 (s, 3H), 2.37 (s, 3H), 6.92-7.15 (m, 3H), 7.40 (d, 1H, J = 7.6 Hz), 7.86 (t, 1H, J = 7.6 Hz), 7.95 (s, 1H). | |
| Ex. 77d | N-[(2,4-dimethylphenyl)(6-methylpyridin-2-yl)methyl]-2-methylpropane-2-sulfinamide Step 4: N-[(2,4-dimethylphenyl)(6-methylpyridin-2-yl)methylidene]-2-methylpropane-2-sulfinamide Ex. 77c (830 mg, 2.53 mmol) was solubilized in MeOH (8 mL) and NaBH4 (190 mg, 5.05 mmol) was added portion wise at 0° C. The reaction mixture was stirred at this temperature and monitored by TLC. The solution was poured onto cold brine and CH2Cl2 was added. After phases separation, the organic layer was dried over MgSO4, filtered and the solution was concentrated to dryness. The crude material was purified by silica gel column chromatography eluting with CH2Cl2/EtOAc (80:20) containing 1% of MeOH. Pure fractions were combined and evaporated to dryness to give N-[(2,4-dimethylphenyl)(6-methylpyridin-2-yl)methyl]-2-methylpropane-2-sulfinamide Ex. 77d (610 mg, 73%) as a pale yellow oil. 1H NMR (300 MHz, DMSO-d6, d in ppm): 1.12 (s, 9H), 1.14 (s, 8H), 2.22 (s, 3H), 2.23 (s, 3H), 2.28 (s, 3H), 2.36 (s, 3H), 2.41 (s, 3H), 2.46 (s, 3H), 5.63 (d, 1H, J = 4.3 Hz), 5.67 (d, 1H, J = 5.2 Hz), 5.82 (d, 1H, J = 5.3 Hz), 6.02 (d, 1H, J = 4.4 Hz), 6.91-7.01 (m, 4H), 7.04 (d, 1H, J = 7.8 Hz), 7.07-7.13 (m, 2H), 7.15 (d, 1H, J = 3.3 Hz), 7.19 (d, 1H, J = 8.5 Hz), 7.30 (d, 1H, J = 7.8 Hz), 7.65 (td, 2H, J = 7.7 Hz, J = 4.2 Hz). | |
| Ex. 77 | (2,4-dimethylphenyl)(6-methylpyridin-2-yl)methanamine dihydrochloride Step 5: to a solution of N-[(2,4-dimethylphenyl)(6-methylpyridin-2-yl)methyl]-2-methylpropane-2-sulfinamide Ex. 77d (610 mg, 1.85 mmol) dissolved in i-PrOH (6 mL) was added 6N HCl in i-PrOH (1.08 mL, 6.46 mmol). The reaction mixture was stirred at rt for 2 h. White precipitate was observed. Et2O was added to the suspension. The solid was collected by filtration, washed with Et2O and dried until constant weight to afford (2,4-dimethylphenyl)(6-methylpyridin-2-yl)methanamine 2×HCl salt Ex. 77 (450 mg, 23%) as a white solid. 1H NMR (300 MHz, DMSO-d6, d in ppm): 2.25 (s, 3H), 2.44 (s, 3H), 2.57 (s, 3H), 5.72 (q, 1H, J = 5.8 Hz), 6.57 (s, 3H), 7.04 (dd, 1H, J = 7.9 Hz, J = 1.9 Hz), 7.08 (s, 1H), 7.16 (d, 1H, J = 7.8 Hz), 7.27 (dd, 2H, J = 12.3 Hz, J = 7.8 Hz), 7.75 (t, 1H, J = 7.7 Hz), 8.89 (s, 3H). | |

Intermediate Ex.80:
(2,4-dimethylphenyl)(furan-2-yl)methanamine (FIG. 2N)

TABLE 1.79

| Cpd. | Starting compounds, Reaction conditions and purification, | Yield, Appearance, ¹H NMR (solvent) data |
|---|---|---|
| Ex. 80a | N-[furan-2-ylmethylidene]-2-methylpropane-2-sulfinamide Step 1: 2-furaldehyde (930 mg, 9.68 mmol) was dissolved in dry THF (9 mL). 2-methylpropane-2-sulfinamide(1.23 g, 10.16 mmol) was added to the solution followed by Ti(OEt)4 (4.06 mL, 19.36 mmol). The reaction mixture was stirred at rt for 2 days (over the weekend). The solution was poured onto a mixture of EtOAc and sat. NH4Cl under vigorous stirring. The inorganic salt was removed by filtration on Celite. The two layers were partitioned and the organic layer was washed with sat. NH4Cl. The combined organic layers were dried over MgSO4, filtered and the solution was concentrated under reduced pressure. The crude product was purified by silica gel column chromatography using Hexanes/EtOAc (50:50) as eluent to afford the N-[furan-2-ylmethylidene]-2-methylpropane-2-sulfinamide Ex. 80a (1.8 g, 87%) as yellowish solid. 1H NMR (400 MHz, DMSO- | |

TABLE 1.79-continued

| Cpd. | Starting compounds, Reaction conditions and purification, | Yield, Appearance, $^1$H NMR (solvent) data |
|---|---|---|
| | | d6, d in ppm): 1.16 (s, 9H), 6.66-6.85 (m, 1H), 7.31-7.42 (m, 1H), 7.95-8.13 (m, 1H), 8.33 (d, 1H, J = 0.7 Hz). |
| Ex. 80b | N-[(2,4-dimethylphenyl)(furan-2-yl)methyl]-2-methylpropane-2-sulfinamide Step 2: in a three-neck round-bottom flask were placed 1-bromo-2,4-dimethylbenzene (818 mg, 4.42 mmol) and dry THF (8 mL) under argon atmosphere. The solution was cooled down at −78° C. nBuLi 2.5M in hexanes (1.77 mL, 4.42 mmol) was added dropwise to the solution. The reaction mixture was stirred at −78° C. for 20 min and a solution of N-[furan-2-ylmethylidene]-2-methylpropane-2-sulfinamide Ex. 80a (849 mg, 3.98 mmol) dissolved in dry THF (8 mL) was added dropwise. The reaction mixture was slowly warmed to rt. After 18 h, the reaction was finished. Sat. NH4Cl was added to quench the reaction. The aqueous layer was extracted with EtOAc. The combined organic layers were dried over MgSO4, filtered and the solution was concentrated to dryness. The crude material was purified by silica gel flash column chromatography using a gradient of Hexanes/EtOAc to give N-[(2,4-dimethylphenyl)(furan-2-yl)methyl]-2-methylpropane-2-sulfinamide Ex. 80b (800 mg, 65%) as colorless oil. 1H NMR (400 MHz, DMSO-d6, d in ppm): 1.11 (s, 9H), 2.25 (s, 6H), 5.57-5.66 (m, 1H), 5.87-5.96 (m, 1H), 6.19-6.27 (m, 1H), 6.35-6.42 (m, 1H), 6.95-7.03 (m, 2H), 7.24-7.32 (m, 1H), 7.50-7.61 (m, 1H). | |
| Ex. 80 | (2,4-dimethylphenyl)(furan-2-yl)methanamine Step 3: to a solution of N-[(2,4-dimethylphenyl)(furan-2-yl)methyl]-2-methylpropane-2-sulfinamide Ex. 80b (750 g, 2.46 mmol) dissolved in i-PrOH (7.5 mL) was added 6M HCl in i-PrOH (1.02 mL, 6.14 mmol) at 0° C. The reaction mixture was warmed and stirred overnight at rt. The solvent was removed under reduced pressure. The residue was triturated with Et2O, filtered, washed with Et2O and dried under vacuo. The solid was dissolved in water, K2CO3 was added up to pH = 8-9, the emulsion was extracted with EtOAc, all organic layers were combined, dried over MgSO4, filtered and the solution was concentrated under reduced pressure. The crude material was purified using by silica gel flash chromatography eluting with a gradient of Hexanes/EtOAc to give (2,4-dimethylphenyl)(furan-2-yl)methanamine Ex. 80 (360 mg, 72%) as a yellowish oil. 1H NMR (400 MHz, DMSO-d6, d in ppm): 2.15 (s, 2H), 2.23 (s, 3H), 2.26 (s, 3H), 5.16 (s, 1H), 6.10-6.15 (m, 1H), 6.31-6.38 (m, 1H), 6.95 (d, 2H, J = 9.0 Hz), 7.20 (d, 1H, J = 7.7 Hz), 7.45-7.54 (m, 1H). | |

Intermediate Ex.83:
(3-chlorophenyl)(2,4-dimethylphenyl)methanamine hydrochloride (FIG. 2O)

TABLE 1.80

| Cpd. | Starting compounds, Reaction conditions and purification, | Yield, Appearance, $^1$H NMR (solvent) data |
|---|---|---|
| Ex. 83a | N-[(3-chlorophenyl)methylidene]-2-methylpropane-2-sulfinamide Step 1: 3-chlorobenzaldehyde (2.00 g, 14.23 mmol) was dissolved in dry THF (25 mL). 2-methylpropane-2-sulfinamide (1.81 g, 14.94 mmol) was added to the solution followed by Ti(OEt)4 (6.49 g, 28.46 mmol). The reaction mixture was stirred at rt overnight. The reaction mixture was poured onto a mixture of EtOAc and sat. NH4Cl under vigorous stirring. The inorganic salt was removed by filtration on Celite. The two layers were partitionated and the aqueous layer was washed with sat. NH4Cl. The corganic layer was dried over MgSO4, filtered and the solution was concentrated under reduced pressure to afford N-[(3-chlorophenyl)methylidene]-2-methylpropane-2-sulfinamide Ex. 83a (3.36 g, 97%). The crude material was used without further purification for the next step. 1H NMR (400 MHz, DMSO-d6, d in ppm): 1.20 (s, 9H), 7.58 (t, 1H, J = 7.8 Hz), 7.67 (ddd, 1H, J = 8.1 Hz, J = 2.2 Hz, J = 1.2 Hz), 7.93 (dt, 1H, J = 7.7 Hz, J = 1.3 Hz), 8.00 (t, 1H, J = 1.8 Hz), 8.58 (s, 1H). | |
| Ex. 83b | N-[(3-chlorophenyl)(2,4-dimethylphenyl)methyl]-2-methylpropane-2-sulfinamide Step 2: a dried round-bottom flask containing stir bar was charged with magnesium (530 mg, 21.70 mmol), small piece of iodine and dry THF (73 mL) was added under argon. Solution of 1-bromo-2,4-dimethylbenzene (3.65 g, 19.72 mmol) diluted in dry THF (3 mL) was added dropwise to the suspension and the solution was stirred at 50° C. for 60 min. After the formation of Grignard reagent, the reaction mixture was cooled to 0° C., and then N-[(3-chlorophenyl)methylidene]-2-methylpropane-2-sulfinamide Ex. 83a (3.37 g, 13.81 mmol) in dry THF (3 mL) was added dropwise. The resulting mixture was stirred at rt. After the completion of the reaction, the reaction mixture was quenched with sat. NH4Cl and the solution was extracted with EtOAc. The combined organic layers were washed with brine. After phases separation, the | |

TABLE 1.80-continued

| Cpd. | Starting compounds, Reaction conditions and purification, | Yield, Appearance, $^1$H NMR (solvent) data |
|---|---|---|
| | organic layer was dried over MgSO4, filtered and the solution was concentrated under reduced pressure. The crude material was purified by column chromatography on silica gel eluting with a gradient of Hexanes/EtOAc from [90:10] to [60:40] to afford N-[(3-chlorophenyl)(2,4-dimethylphenyl)methyl]-2-methylpropane-2-sulfinamide Ex. 83b (2.30 g, 48%) as yellow oil. 1H NMR (400 MHz, DMSO-d6, din ppm): 1.11 (s, 9H), 2.22 (s, 3H), 2.26 (s, 3H), 5.67 (d, 1H, J = 6.3 Hz), 6.03 (d, 1H, J = 6.3 Hz), 6.98 (s, 1H), 7.04 (d, 1H, J = 8.0 Hz), 7.19-7.27 (m, 1H), 7.26-7.40 (m, 4H). | |
| Ex. 83 | (3-chlorophenyl)(2,4-dimethylphenyl)methanamine hydrochloride Step 3: to a solution of N-[(3-chlorophenyl)(2,4-dimethylphenyl)methyl]-2-methylpropane-2-sulfinamide Ex. 83b (2.30 g, 6.57 mmol) dissolved in iPrOH (23 mL) was added 6N HCl in iPrOH (3.29 mL, 19.72 mmol). The reaction mixture was stirred at rt overnight. Solvent was removed under reduced pressure, small amount of i-PrOH was left and Et2O was added. The solid formed was collected by filtration to give(3-chlorophenyl)(2,4-dimethylphenyl)methanamine hydrochloride Ex. 83 (1.39 g, 75%) as white powder. 1H NMR (400 MHz, DMSO-d6, d in ppm): 2.22 (s, 3H), 2.27 (s, 3H), 5.70 (s, 1H), 6.96-7.23 (m, 2H), 7.29-7.63 (m, 5H), 9.14 (s, 3H). | |

Intermediate Ex.87: (3,5-dimethylpyridin-2-yl)(5-methylfuran-2-yl)methanamine dihydrochloride
(FIG. 2P)

TABLE 1.81

| Cpd. | Starting compounds, Reaction conditions and purification, | Yield, Appearance, $^1$H NMR (solvent) data |
|---|---|---|
| Ex. 87a | (3,5-dimethylpyridin-2-yl)(5-methylfuran-2-yl)methanol Step 1: in a three-neck round-bottom flask were placed 2-bromo-3,5-dimethylpyridine (5.00 g, 26.87 mmol) and dry THF (40 mL) under N2 atmosphere. The solution was cooled down at −78° C. nBuLi 2.5M in hexanes (12.89 mL, 32.25 mmol) was added dropwise to the solution. The reaction mixture was stirred at −78° C. for 20 min and 5-methylfuran-2-carbaldehyde (2.94 mL, 29.56 mmol) dissolved in dry THF (10 mL) was added dropwise to the solution. The reaction mixture was stirred at −78° C. for 30 min and then was slowly warmed to rt and the stirring was kept at this temperature overnight. The reaction was quenched with sat. NH4Cl. The aqueous layer was extracted with EtOAc. The combined organic layers were dried over MgSO4, filtered and the solution was concentrated to dryness. The crude material was purified by silica gel column chromatography eluting with a gradient of Hexanes/EtOAc from [96:4] to [90:10]. The product fractions were collected and evaporated under redcued pressure to afford (3,5-dimethylpyridin-2-yl)(5-methylfuran-2-yl)methanol Ex. 87a (3.29 g, 56%) as orange oil. 1H NMR (400 MHz, CDCl3, d in ppm): 2.13 (s, 3H), 2.24 (d, 3H, J = 0.8 Hz), 2.33 (s, 3H), 5.71 (s, 1H), 5.83-5.86 (m, 2H), 7.28-7.30 (m, 1H), 8.26-8.28 (m, 1H). | |
| Ex. 87b | 3,5-dimethyl-2-(5-methylfuran-2-carbonyl)pyridine Step 2: manganese (IV) oxide (15.80 g, 181.71 mmol) was added to a solution of (3,5-dimethylpyridin-2-yl)(5-methylfuran-2-yl)methanol Ex. 87a (3.29 g, 15.14 mmol) dissolved in CH2Cl2 (40 mL). The resulting mixture was stirred at rt for 16 h. The solution was diluted by CH2Cl2 and filtered through a pad of Celite. The filtrate was concentrated to dryness to afford 3,5-dimethyl-2-(5-methylfuran-2-carbonyl)pyridine Ex. 87b (3.09 g, 95%). The product was pure enough and used at the next synthetic step without further purification. 1H NMR (400 MHz, DMSO-d6, d in ppm): 2.33 (s, 3H), 2.34 (s, 3H), 2.40 (s, 3H), 6.38 (dd, 1H, J = 3.4 Hz, J = 1.0 Hz), 7.19 (dd, 1H, J = 3.5 Hz, J = 0.7 Hz), 7.58-7.64 (m, 1H), 8.33 (dd, 1H, J = 1.4 Hz, J = 0.7 Hz). | |
| Ex. 87c | N-[(3,5-dimethylpyridin-2-yl)(5-methylfuran-2-yl)methylidene]-2-methylpropane-2-sulfinamide Step 3: 3,5-dimethyl-2-(5-methylfuran-2-carbonyl)pyridine Ex. 87b (3.09 g, 14.36 mmol) was dissolved in dry THF (30 mL). 2-methylpropane-2-sulfinamide (1.83 g, 15.07 mmol) was added to the solution followed by Ti(OEt)4 (6.55 g, 28.71 mmol). The reaction mixture was heated at 60° C. for 48 h. The reaction mixture was poured onto a mixture of EtOAc and sat. NH4Cl under vigorous stirring. The inorganic salt was removed by filtration on Celite. After phases separation, the organic layer was washed with sat. NH4Cl. The organic layers was dried over MgSO4, filtered and the solution was concentrated under reduced pressure to afford N-[(3,5-dimethylpyridin-2-yl)(5-methylfuran-2-yl)methylidene]-2-methylpropane-2-sulfinamide Ex. 87c (4.5 g, 98%) as brown oil. The product was pure enough and used at the next synthetic step without further purification. 1H NMR (400 MHz, DMSO-d6, d in ppm): 1.14 (s, 9H), 2.32 (s, 3H), 2.37 (s, | |

TABLE 1.81-continued

| Cpd. | Starting compounds, Reaction conditions and purification, | Yield, Appearance, $^1$H NMR (solvent) data |
|---|---|---|
| Ex. 87d | | 3H), 6.30-6.35 (m, 1H), 6.52 (s, 1H), 7.53 (s, 1H), 8.27 (s, 1H). N-[(3,5-dimethylpyridin-2-yl)(5-methylfuran-2-yl)methyl]-2-methylpropane-2-sulfinamide Step 4: sodium borohydride (4.50 g, 14.13 mmol) was added portion wise to a cooled (0° C.) solution of the N-[(3,5-dimethylpyridin-2-yl)(5-methylfuran-2-yl)methylidene]-2-methylpropane-2-sulfinamide Ex. 87c (5.35 g, 141.31 mmol) in MeOH (45 mL). After addition, the reaction was warmed to rt and stirred overnight at this temperature. The reaction was quenched with sat. NH4Cl. The solution was extracted with EtOAc. After phases separation, the organic layer was dried over MgSO4, filtered and the solution was concentrated under reduced pressure. The crude material was purified by silica gel column chromatography eluting with Hexanes/EtOAc (50:50). The desired fractions were collected and concentrated to dryness to afford N-[(3,5-dimethylpyridin-2-yl)(5-methylfuran-2-yl)methyl]-2-methylpropane-2-sulfinamide Ex. 87d (3.80 g, 84%) as yellowish oil. |
| Ex. 87 | | (3,5-dimethylpyridin-2-yl)(5-methylfuran-2-yl)methanamine dihydrochloride Step 5: to a solution of N-[(3,5-dimethylpyridin-2-yl)(5-methylfuran-2-yl)methyl]-2-methylpropane-2-sulfinamide Ex. 87d (3.80 g, 11.86 mmol) dissolved in iPrOH (15 mL) was added 6N HCl in iPrOH (5.93 mL, 35.57 mmol). The reaction mixture was stirred at rt overnight. Solvent was removed under reduced pressure, small amount of iPrOH was left and Et2O was added. The solid formed was collected by filtration to give (3,5-dimethylpyridin-2-yl)(5-methylfuran-2-yl)methanamine dihydrochloride Ex. 87 (3.19 g, 93%) as yellowish solid. 1H NMR (400 MHz, DMSO-d6, d in ppm): 2.19 (d, 6H, J = 8.6 Hz), 2.30 (s, 3H), 5.79 (d, 1H, J = 5.4 Hz), 6.08 (d, 1H, J = 3.0 Hz), 6.25 (d, 1H, J = 3.0 Hz), 7.52 (s, 1H), 8.35 (s, 1H), 8.86 (s, 1H). |

Intermediate Ex.99: [4-methyl-2-(trifluoromethyl)phenyl](5-methylfuran-2-yl)methanamine hydrochloride (FIG. 2Q)

TABLE 1.82

| Cpd. | Starting compounds, Reaction conditions and purification, | Yield, Appearance, $^1$H NMR (solvent) data |
|---|---|---|
| Ex. 99a | | 2-methyl-N-{[4-methyl-2-(trifluoromethyl)phenyl](5-methylfuran-2-yl)methyl}propane-2-sulfinamide Step 1:: to a suspension of magnesium powder (120 mg, 4.94 mmol) in dry THF (small amount) was added dropwise 1-bromo-4-methyl-2-(trifluoromethyl)benzene (1.12 g, 4.69 mmol) diluted in dry THF (4 mL) and the reaction was heated at 40° C. After completion of Grignard reagent, the previously prepared 2-methyl-N-[(5-methylfuran-2-yl)methylidene]propane-2-sulfinamide (500 mg, 2.34 mmol) diluted in THF (4 mL) was added to the solution. The reaction mixture was stirred at rt overnight. Water was added to quench the reaction. The two layers were partitionated and the organic layer was dried over MgSO4, filtered and the solution was concentrated under reduced pressure. The crude material was purified by silica gel column chromatography using a gradient of Hexanes/EtOAc from [5:1] to [4:1]. The desired fractions were combined and concentrated to dryness to afford 2-methyl-N-{[4-methyl-2-(trifluoromethyl)phenyl](5-methylfuran-2-yl)methyl}propane-2-sulfinamide Ex. 99a (534 mg, 61%) as yellow oil. |
| Ex. 99 | | [4-methyl-2-(trifluoromethyl)phenyl](5-methylfuran-2-yl)methanamine hydrochloride Step 2: to a solution of 2-methyl-N-{[4-methyl-2-(trifluoromethyl)phenyl](5-methylfuran-2-yl)methyl}propane-2-sulfinamide Ex. 99a (534 mg, 1.43 mmol) dissolved in dry dioxane (10 mL) was added HCl 4M in dioxane (900 µL, 6.43 mmol) at 0° C. The reaction mixture was warmed to rt and stirred at rt for 4 h. Et2O was added to the reaction mixture. The solid formed was collected by filtration and washed with Et2O to afford [4-methyl-2-(trifluoromethyl)phenyl](5-methylfuran-2-yl)methanamine hydrochloride Ex. 99 (232 mg, 55%) as yellowish solid. 1H NMR (400 MHz, DMSO-d6, d in ppm): 2.24 (d, 3H, J = 1.0 Hz), 2.43 (s, 3H), 5.59 (s, 1H), 6.10 (dd, 1H, J = 3.2 Hz, 1.2 Hz), 6.26 (d, 1H, J = 3.2 Hz), 7.67 (d, 2H, J = 6.9 Hz), 7.90 (d, 1H, J = 8.5 Hz), 9.25 (s, 3H). |

Intermediate Ex.101: (2-methoxy-4-methylphenyl)(5-methylfuran-2-yl)methanamine (FIG. 2R)

TABLE 1.83

| Cpd. | Starting compounds, Reaction conditions and purification, | Yield, Appearance, $^1$H NMR (solvent) data |
|---|---|---|
| Ex. 101a | | N-[(2-methoxy-4-methylphenyl)(5-methylfuran-2-yl)methyl]-2-methylpropane-2-sulfinamide Step 1:: to a solution of 1-bromo-2-methoxy-4-methylbenzene (1.80 g, 8.95 mmol) dissolved in dry THF (12 mL) was added dropwise isopropylmagnesium chloride solution 2M in THF (5.60 mL, 11.19 mmol). The mixture was then heated at 70° C. for 3 h. After completion of Grignard reagent, the previously prepared 2-methyl-N-[(5-methylfuran-2-yl)methylidene]propane-2-sulfinamide (1.91 g, 8.95 mmol) dissolved in dry THF. The mixture was then heated overnight at 70° C. After cooling to rt, sat. NH4Cl was added followed by EtOAc. The two phases were separated, the resulting organic layer was washed with brine and water. The combined organic layers were dried over MgSO4, filtered and the solution was concentrated under reduced pressure. The crude material was purified by silica gel column chromatography using a gradient of Cyclohexane/EtOAc from [90:10] to [60:40]. The product fractions were combined and concentrated to dryness to afford N-[(2-methoxy-4-methylphenyl)(5-methylfuran-2-yl)methyl]-2-methylpropane-2-sulfinamide Ex. 101a (380 mg, 13%) as brownish oil. |
| Ex. 101 | | (2-methoxy-4-methylphenyl)(5-methylfuran-2-yl)methanamine Step 2: to a solution of N-[(2-methoxy-4-methylphenyl)(5-methylfuran-2-yl)methyl]-2-methylpropane-2-sulfinamide Ex. 101a (375 mg, 1.12 mmol) dissolved in dry dioxane (4 mL) was added HCl 4M in dioxane (1.26 mL, 5.03 mmol) at rt. The reaction mixture was stirred overnight at rt. The solvent was removed under reduced pressure. The residue was diluted with water, pH was adjusted to pH = 8-9 with 1N NaOH and the aqueous solution was extracted twice with EtOAc. The combined organic layers were dried over MgSO4, filtered and the solution was concentrated under reduced pressure. The crude material was purified by silica gel column chromatography eluting with CH2Cl2/MeOH (95:5) to provide (2-methoxy-4-methylphenyl)(5-methylfuran-2-yl)methanamine Ex. 101 (100 mg, 39%) as pale brown oil. 1H NMR (300 MHz, DMSO-d6, d in ppm): 2.16 (s, 3H), 2.27 (s, 3H), 3.74 (s, 3H), 5.20 (s, 1H), 5.87-5.90 (m, 2H), 6.71 (d, 1H, J = 7.8 Hz), 6.78 (s, 1H), 7.13 (d, 1H, J = 7.8 Hz). |

Example 2: Synthesis of the Compounds According to the Invention

Protocol A: to a solution of the substituted acid in DMF (0.25 mmol/mL) were added DMAP (2 to 4 equiv), EDCl.HCl (1 to 1.5 equiv) and the substituted amine (1 equiv). The reaction mixture was stirred at rt. After completion of the reaction (monitored by TLC), sat. NH4Cl or HCl 0.5N was added and the solution was extracted with EtOAc. The organic layer was washed with sat. NH4Cl, dried over MgSO4, filtered and evaporated to dryness under reduced pressure (FIG. 3AA).

Protocol B: to a solution of the substituted amine (1 equiv) and substituted acid (1 equiv) in DMF (0.30 mmol/mL) were added triethylamine (3 equiv) and PyBOP (1 equiv). The reaction mixture was heated at 100° C. for 20 min under microwave irradiation. After cooling to rt, the reaction mixture was quenched with sat. NH4Cl. The solution was extracted with EtOAc. The combined organic layers were washed with sat. NH4Cl, dried over MgSO4, filtered and the solution was concentrated under reduced pressure (FIG. 3AB).

TABLE 2

All the NMR were performed in DMSO-d6

| | Cpd. | Starting compounds, Reaction conditions and purification Yield, MP, Appearance, $^1$H NMR (solvent) data, Mass (ES+ or ES−) data |
|---|---|---|
| 1 | N-{[4-methyl-2-(piperidin-1-yl)phenyl](phenyl)methyl}-2-(3-oxo-3,4-dihydro-2H-1,4-benzoxazin-7-yl)acetamide | From [4-methyl-2-(piperidin-1-yl)phenyl](phenyl)methanamine Ex. 1 and 2-(3-oxo-3,4-dihydro-2H-1,4-benzoxazin-7-yl)acetic acid Ex. 2 following protocol A, DMAP (2.2 equiv), EDCl•HCl (1.1 equiv), 18 h at rt, purification by silica gel column chromatography (Cyclohexane/EtOAc, 6:4), yield 86%, mp: 130° C., appearance: white solid 1H NMR (300 MHz, d in ppm): 1.43-1.60 (m, 6H), 2.23 (s, 3H), 2.48-2.52 (m, 2H), 2.82-287 (m, 2H), 3.42 (s, 2H), 4.52 (s, 2H), 6.54 (d, 1H, J = 8.5 Hz), 6.76-6.88 (m, 4H), 6.94 (s, 1H), 7.10-7.18 (m, 4H), 7.23-7.28 (m, 2H), 8.69 (d, 1H, J = 8.5 Hz), 10.63 (s, 1H); m/z: 470 [M + H]+ (calc. mass: 469). |

TABLE 2-continued

All the NMR were performed in DMSO-d6

| Cpd. | Starting compounds, Reaction conditions and purification Yield, MP, Appearance, $^1$H NMR (solvent) data, Mass (ES+ or ES−) data |
|---|---|
| 2 N-{[4-methyl-2-(morpholin-4-yl)phenyl](phenyl)methyl}-2-(3-oxo-3,4-dihydro-2H-1,4-benzoxazin-7-yl)acetamide | From [4-methyl-2-(morpholin-4-yl)phenyl](phenyl)methanamine hydrochloride Ex. 3 and 2-(3-oxo-3,4-dihydro-2H-1,4-benzoxazin-7-yl)acetic acid Ex. 2 following protocol A, DMAP (2.2 equiv), EDCl•HCl (1.1 equiv), 18 h at rt, purification by silica gel column chromatography (Cyclohexane/EtOAc, 3:7), yield 62%, mp: 235° C., appearance: white solid<br>1H NMR (300 MHz, d in ppm): 2.25 (s, 3H), 2.48-2.54 (m, 2H), 2.86-2.91 (m, 2H), 3.41 (s, 2H), 3.52-3.57 (m, 2H), 3.62-3.67 (m, 2H), 4.52 (s, 2H), 6.58 (d, 1H, J = 8.6 Hz), 6.76-6.84 (m, 3H), 6.91 (d, 1H, J = 7.8 Hz), 6.99 (s, 1H), 7.09 (d, 1H, J = 7.8 Hz), 7.15-7.19 (m, 3H), 7.24-7.30 (m, 2H), 8.74 (d, 1H, J = 8.6 Hz), 10.63 (s, 1H); m/z: 472 [M + H]+ (calc. mass: 471). |
| 3 2-(3-oxo-3,4-dihydro-2H-1,4-benzoxazin-7-yl)-N-{phenyl[2-(piperidin-1-yl)phenyl]methyl}acetamide | From phenyl[2-(piperidin-1-yl)phenyl]methanamine hydrochloride Ex. 4 and 2-(3-oxo-3,4-dihydro-2H-1,4-benzoxazin-7-yl)acetic acid Ex. 2 following protocol A, DMAP (2.2 equiv), EDCl•HCl (1.1 equiv), 18 h at rt, purification by silica gel column chromatography (Cyclohexane/EtOAc, 6:4), yield 83%, mp: 222° C., appearance: white solid<br>1H NMR (300 MHz, d in ppm): 1.46-1.58 (m, 6H), 2.48-2.53 (m, 2H), 2.82-2.88 (m, 2H), 3.43 (s, 2H), 4.51 (s, 2H), 6.59 (d, 1H, J = 8.5 Hz), 6.76-6.84 (m, 3H), 8.81 (dt, 1H, J = 7.8 Hz, J = 1.6 Hz), 7.04-7.18 (m, 5H), 7.19-7.29 (m, 3H), 8.75 (d, 1H, J = 8.6 Hz), 10.63 (s, 1H); m/z: 456 [M + H]+ (calc. mass: 455). |
| 4 N-{[4-methoxy-2-(piperidin-1-yl)phenyl](phenyl)methyl}-2-(3-oxo-3,4-dihydro-2H-1,4-benzoxazin-7-yl)acetamide | From [4-methoxy-2-(piperidin-1-yl)phenyl](phenyl)methanamine Ex. 5 and 2-(3-oxo-3,4-dihydro-2H-1,4-benzoxazin-7-yl)acetic acid Ex. 2 following protocol A, DMAP (2.2 equiv), EDCl•HCl (1.1 equiv), 18 h at rt, purification by silica gel column chromatography (Cyclohexane/EtOAc, 3:7), yield 61%, mp: 162° C., appearance: white solid<br>1H NMR (300 MHz, d in ppm): 1.44-1.58 (m, 6H), 2.48-2.52 (m, 2H), 2.83-2.88 (m, 2H), 3.42 (s, 2H), 3.70 (s, 3H), 4.51 (s, 2H), 6.48 (d, 1H, J = 8.5 Hz), 6.61-6.65 (m, 2H), 6.76-6.84 (m, 3H), 7.08-7.18 (m, 4H), 7.23-7.28 (m, 2H), 8.67 (d, 1H, J = 8.6 Hz), 10.62 (s, 1H); m/z: 486 [M + H]+ (calc. mass: 485). |
| 5 2-(3-oxo-3,4-dihydro-2H-1,4-benzoxazin-7-yl)-N-{phenyl[2-(pyrrolidin-1-yl)phenyl]methyl}acetamide | From phenyl[2-(pyrrolidin-1-yl)phenyl]methanamine hydrochloride Ex. 6 and 2-(3-oxo-3,4-dihydro-2H-1,4-benzoxazin-7-yl)acetic acid Ex. 2 following protocol A, DMAP (2.2 equiv), EDCl•HCl (1.1 equiv), 18 h at rt, purification by silica gel column chromatography (Cyclohexane/EtOAc, 1:1), yield 83%, mp: 207° C., appearance: white solid<br>1H NMR (300 MHz, d in ppm): 1.76-1.78 (m, 4H), 2.80-2.84 (m, 2H), 3.04-3.09 (m, 2H), 3.43 (s, 2H), 4.53 (s, 2H), 6.49 (d, 1H, J = 8.3 Hz), 6.76-6.85 (m, 3H), 6.94 (dt, 1H, J = 7.8 Hz, J = 1.3 Hz), 7.06-7.19 (m, 6H), 7.23-7.28 (m, 2H), 8.78 (d, 1H, J = 8.5 Hz), 10.63 (s, 1H); m/z: 442 [M + H]+ (calc. mass: 441). |
| 6 N-{3-methyl-1-[2-(piperidin-1-yl)phenyl]butyl}-2-(3-oxo-3,4-dihydro-2H-1,4-benzoxazin-7-yl)acetamide | From 3-methyl-1-[2-(piperidin-1-yl)phenyl]butan-1-amine Ex. 7 and 2-(3-oxo-3,4-dihydro-2H-1,4-benzoxazin-7-yl)acetic acid Ex. 2 following protocol A, DMAP (2.2 equiv), EDCl•HCl (1.1 equiv), 18 h at rt, purification by silica gel column chromatography (Cyclohexane/EtOAc, 1:1), yield 48%, mp: 236° C., appearance: white solid<br>1H NMR (300 MHz, d in ppm): 0.84-0.89 (m, 6H), 1.22-1.65 (m, 12H), 2.50-2.6 (m, 2H), 3.00-3.12 (m, 2H), 4.51 (s, 2H), 6.75-6.81 (m, 3H), 7.00-7.17 (m, 3H), 7.26 (dd, 1H, J = 7.5 Hz, J = 1.5 Hz), 8.33 (d, 1H, J = 8.4 Hz), 10.61 (br(s), 1H); m/z: 436 [M + H]+ (calc. mass: 435). |
| 7 N-{[2-(morpholin-4-yl)phenyl](phenyl)methyl}-2-(3-oxo-3,4-dihydro-2H-1,4-benzoxazin-7-yl)acetamide | From [2-(morpholin-4-yl)phenyl](phenyl)methanamine hydrochloride and 2-(3-oxo-3,4-dihydro-2H-1,4-benzoxazin-7-yl)acetic acid Ex. 2 following protocol A, DMAP (2.2 equiv), EDCl•HCl (1.1 equiv), 18 h at rt, purification by silica gel column chromatography (Cyclohexane/EtOAc, 4:6), yield 43%, mp: 216° C., appearance: white solid<br>1H NMR (300 MHz, d in ppm): 2.50-2.54 (m, 2H), 2.88-2.93 (m, 2H), 3.42 (s, 2H), 3.53-3.62 (m, 4H), 4.51 (s, 2H), 6.63 (d, 1H, J = 8.6 Hz), 6.58-6.83 (m, 3H), 7.08-7.13 (m, 1H), |

TABLE 2-continued

All the NMR were performed in DMSO-d6

| Cpd. | | Starting compounds, Reaction conditions and purification Yield, MP, Appearance, $^1$H NMR (solvent) data, Mass (ES+ or ES−) data |
|---|---|---|
| | | 7.16-7.30 (m, 8H), 8.79 (d, 1H, J = 8.6 Hz), 10.62 (s, 1H); m/z: 458 [M + H]+ (calc. mass: 457). |
| 8 | N-{[4-methyl-2-(morpholin-4-yl)phenyl](phenyl)methyl}-2-(4-methyl-2-oxo-1,2-dihydroquinolin-6-yl)acetamide | From [4-methyl-2-(morpholin-4-yl)phenyl](phenyl)methanamine hydrochloride Ex. 3 and 2-(4-methyl-2-oxo-1,2-dihydroquinolin-6-yl)acetic acid Ex. 9 following protocol A, DMAP (2.2 equiv), EDCl•HCl (1.1 equiv), 18 h at rt. After water addition, the precipitate was collected by filtration. The solid was dissolved in CH2Cl2 and the organic layer was washed with citric acid 1M followed by water. The organic layer was dried over MgSO4, filtered and the solution was concentrated under reduced pressure, yield 61%, mp: 158° C., appearance: white solid 1H NMR (300 MHz, d in ppm): 2.24 (s, 3H), 2.34 (d, 3H, J = 0.9 Hz), 2.45-2.55 (m, 2H), 2.84-2.89 (m, 2H), 3.48-3.64 (m, 6H), 6.37 (d, 1H, J = 1.0 Hz), 6.60 (d, 1H, J = 8.6 Hz), 6.90 (d, 1H, J = 8.0 Hz), 6.99 (s, 1H), 7.12-7.28 (m, 7H), 7.37 (dd, 1H, J = 8.4 Hz, J = 1.8 Hz), 7.57 (d, 1H, J = 1.6 Hz), 8.83 (d, 1H, J = 8.7 Hz), 11.53 (br(s), 1H); m/z: 482 [M + H]+ (calc. mass: 481). |
| 9 | N-[(2,4-dimethylphenyl)(phenyl)methyl]-2-(4-methyl-2-oxo-1,2-dihydroquinolin-6-yl)acetamide | From (2,4-dimethylphenyl)(phenyl)methanamine hydrochloride Ex. 10 and 2-(4-methyl-2-oxo-1,2-dihydroquinolin-6-yl)acetic acid Ex. 9 following protocol A, DMAP (2.2 equiv), EDCl•HCl (1.1 equiv), 18 h at rt. After water addition, the precipitate was collected by filtration, triturated with cold MeOH and washed with Et2O, yield 70%, mp: 259° C., appearance: white solid 1H NMR (300 MHz, d in ppm): 2.14 (s, 3H), 2.22 (s, 3H), 2.36 (s, 3H), 3.57 (s, 2H), 6.18 (d, 1H, J = 8.4 Hz), 6.37 (s, 1H), 6.93-7.01 (m, 3H), 7.15-7.25 (m, 4H), 7.27-7.32 (m, 2H), 7.37 (dd, 1H, J = 8.4 Hz, J = 1.8 Hz), 7.57 (m, 1H), 8.91 (d, 1H, J = 8.4 Hz), 11.53 (s, 1H); m/z: 411 [M + H]+ (calc. mass: 410). |
| 10 | N-{[4-methoxy-2-(piperidin-1-yl)phenyl](phenyl)methyl}-2-(4-methyl-2-oxo-1,2-dihydroquinolin-6-yl)acetamide | From [4-methoxy-2-(piperidin-1-yl)phenyl](phenyl)methanamine Ex. 5 and 2-(4-methyl-2-oxo-1,2-dihydroquinolin-6-yl)acetic acid Ex. 9 following protocol A, DMAP (2.2 equiv), EDCl•HCl (1.1 equiv), 18 h at rt. After water addition, the precipitate was collected by filtration. The solid was dissolved in CH2Cl2 and the organic layer was washed with citric acid 1M followed by water. The organic layer was dried over MgSO4, filtered and the solution was concentrated under reduced pressure, yield 65%, mp: 158° C., appearance: white solid 1H NMR (300 MHz, d in ppm): 1.43-1.56 (m, 6H), 2.35 (d, 3H, J = 1.0 Hz), 2.48-2.53 (m, 2H), 2.8-2.9 (m, 2H), 3.58 (s, 2H), 8.77 (s, 3H), 6.37 (d, 1H, J = 0.8 Hz), 6.51 (d, 1H, J = 8.6 Hz), 6.62-6.65 (m, 2H), 7.13-7.22 (m, 4H), 7.24-7.27 (m, 3H), 7.38 (dd, 1H, J = 8.4 Hz, J = 1.8 Hz), 7.57 (d, 1H, J = 1.6 Hz), 8.75 (d, 1H, J = 8.5 Hz), 11.52 (br(s), 1H); m/z: 496 [M + H]+ (calc. mass: 495). |
| 11 | N-{[4-methyl-2-(piperidin-1-yl)phenyl](phenyl)methyl}-2-(4-methyl-2-oxo-1,2-dihydroquinolin-6-yl)acetamide | From [4-methyl-2-(piperidin-1-yl)phenyl](phenyl)methanamine Ex. 1 and 2-(4-methyl-2-oxo-1,2-dihydroquinolin-6-yl)acetic acid Ex. 9 following protocol A, DMAP (2.2 equiv), EDCl•HCl (1.1 equiv), 18 h at rt. After water addition, the precipitate was collected by filtration and washed with Et2O. The solid was dissolved in CH2Cl2 and the organic layer was washed with citric acid 1M followed by water. The organic layer was dried over MgSO4, filtered and the solution was concentrated under reduced pressure, yield 30%, mp: 173° C., appearance: white solid 1H NMR (300 MHz, d in ppm): 1.40-1.56 (m, 6H), 2.22 (s, 3H), 2.35 (s, 3H), 2.48-2.52 (m, 2H), 2.81-2.84 (m, 2H), 3.58 (s, 2H), 6.37 (s, 1H), 6.55 (d, 1H, J = 8.6 Hz), 6.86 (d, 1H, J = 8.0 Hz), 6.93 (s, 1H), 7.13-7.40 (m, 7H), 7.37 (dd, 1H, J = 8.4 Hz, J = 1.8 Hz), 7.57 (d, 1H, J = 1.5 Hz), 8.77 (d, 1H, J = 8.6 Hz), 11.53 (s, 1H); m/z: 480 [M + H]+ (calc. mass: 479). |
| 12 | 2-(2,3-dioxo-1,2,3,4-tetrahydroquinoxalin-6-yl)-N-{phenyl[2- | From phenyl[2-(piperidin-1-yl)phenyl]methanamine hydrochloride Ex. 4 and 2-(2,3-dioxo-1,2,3,4-tetrahydroquinoxalin-6-yl)acetic acid Ex. 11 following protocol A, DMAP (2.2 equiv), EDCl•HCl (1.1 equiv), 2 h at rt, purification by silica gel column chromatography |

TABLE 2-continued

All the NMR were performed in DMSO-d6

| Cpd. | Starting compounds, Reaction conditions and purification Yield, MP, Appearance, ¹H NMR (solvent) data, Mass (ES+ or ES−) data |
|---|---|
| (piperidin-1-yl)phenyl]methyl}acetamide | (CH2Cl2/MeOH, 94:6), yield 37%, mp: 265° C., appearance: white solid<br>1H NMR (300 MHz, d in ppm): 1.45-1,57 (m, 6H), 2.47-2.52 (m, 2H), 2.84-2.89 (m, 2H), 3.49 (s, 2H), 6.58 (d, 1H, J = 8.6 Hz), 6.96-7.03 (m, 2H), 7.04-7.06 (m, 2H), 7.10 (dd, 1H, J = 9.6 Hz, J = 1.4 Hz), 7.14-7.28 (m, 7H), 8.79 (d, 1H, J = 8.5 Hz), 11.88 (br(s), 2H); m/z: 469 [M + H]+ (calc. mass: 468). |
| 13   2-(3-oxo-3,4-dihydro-2H-1,4-benzoxazin-6-yl)-N-{phenyl[2-(piperidin-1-yl)phenyl]methyl}acetamide | From phenyl[2-(piperidin-1-yl)phenyl]methanamine hydrochloride Ex. 4 and 2-(3-oxo-3,4-dihydro-2H-1,4-benzoxazin-6-yl)acetic acid Ex. 12 following protocol A, DMAP (2.2 equiv), EDCl•HCl (1.1 equiv), 2 h at rt. After water addition, the precipitate was collected by filtration and washed with Et2O. The solid was triturated with CH2Cl2 containing small amount of MeOH and filtered-off, yield 38%, mp: 209° C., appearance: white solid<br>1H NMR (300 MHz, d in ppm): 1.46-1.58 (m, 6H), 2.48-2.52 (m, 2H), 2.85-2.89 (m, 2H), 3.42 (s, 2H), 4.50 (s, 2H), 6.58 (d, 1H, J = 8.5 Hz), 6.78-6.85 (m, 3H), 7.06 (m, 1H), 7.12-7.29 (m, 8H), 8.75 (d, 1H, J = 8.5 Hz), 10.69 (br(s), 1H); m/z: 456 [M + H]+ (calc. mass: 455). |
| 14   2-(2,2-difluoro-3-oxo-3,4-dihydro-2H-1,4-benzoxazin-7-yl)-N-{phenyl[2-(piperidin-1-yl)phenyl]methyl}acetamide | From phenyl[2-(piperidin-1-yl)phenyl]methanamine hydrochloride Ex. 4 and 2-(2,2-difluoro-3-oxo-3,4-dihydro-2H-1,4-benzoxazin-7-yl)acetic acid Ex. 13 following protocol A, substituted amine (0.9 equiv), DMAP (2.2 equiv), EDCl•HCl (1.2 equiv), 15 h at rt, purification by silica gel column chromatography (Cyclohexane/EtOAc, 1:1), followed by a second purification by silica gel column chromatography (Cyclohexane/EtOAc, 6:4), yield 2%, mp: 106° C., appearance: white solid<br>1H NMR (300 MHz, d in ppm): 1.40-1.70 (m, 8H), 2.75-2.90 (m, 2H), 3.52 (s, 2H), 6.59 (d, 1H, J = 8.4 Hz), 7.00 (d, 1H, J = 8.1 Hz), 7.01-7.10 (m, 2H), 7.13-7.29 (m, 10H), 8.80 (d, 1H, J = 8.4 Hz); m/z: 492 [M + H]+ (calc. mass: 491). |
| 15   2-(2-oxo-2,3-dihydro-1H-indol-5-yl)-N-{phenyl[2-(piperidin-1-yl)phenyl]methyl}acetamide | From phenyl[2-(piperidin-1-yl)phenyl]methanamine hydrochloride Ex. 4 and 2-(2-oxo-2,3-dihydro-1H-indol-5-yl)acetic acid Ex. 14 following protocol A, DMAP (2.2 equiv), EDCl•HCl (1.1 equiv), 18 h at rt, purification by silica gel column chromatography (Cyclohexane/EtOAc, 3:7), yield 66%, mp: 208° C., appearance: white solid<br>1H NMR (300 MHz, d in ppm): 1.44-1.58 (m, 6H), 2.48-2.52 (m, 2H), 2.85-2.89 (m, 2H), 3.41 (s, 2H), 3.45 (s, 2H), 6.59 (d, 1H, J = 8.5 Hz), 6.70 (d, 1H, J = 7.9 Hz), 7.03-7.09 (m, 3H), 7.12-7.21 (m, 5H), 7.24-7.29 (m, 3H), 8.73 (d, 1H, J = 8.6 Hz), 10.29 (s, 1H); m/z: 440 [M + H]+ (calc. mass: 439). |
| 16   N-{[4-methyl-2-(piperidin-1-yl)phenyl](phenyl)methyl}-2-(2-oxo-2,3-dihydro-1H-indol-5-yl)acetamide | From [4-methyl-2-(piperidin-1-yl)phenyl](phenyl)methanamine hydrochloride Ex. 1 and 2-(2-oxo-2,3-dihydro-1H-indol-5-yl)acetic acid Ex. 14 following protocol A, DMAP (2.2 equiv), EDCl•HCl (1.1 equiv), 18 h at rt, purification by silica gel column chromatography (Cyclohexane/EtOAc, 3:7), yield 67%, mp: 202° C., appearance: white solid<br>1H NMR (300 MHz, d in ppm): 1.39-1.58 (m, 6H), 2.23 (s, 3H), 2.48-2.52 (m, 2H), 2.83-2.86 (m, 2H), 3.41 (s, 2H), 3.44 (s, 2H), 6.53 (d, 1H, J = 8.3 Hz), 6.70 (d, 1H, J = 7.9 Hz), 6.87 (dd, 1H, J = 7.7 Hz, J = 1.1 Hz), 6.94 (d, 1H, J = 1.1 Hz), 7.04 (dd, 1H, J = 8.1 Hz, J = 1.4 Hz), 7.09-7.18 (m, 5H), 7.23-7.28 (m, 2H), 8.67 (d, 1H, J = 8.6 Hz), 10.28 (s, 1H); m/z: 454 [M + H]+ (calc. mass: 453). |
| 17   N-{[2-(morpholin-4-yl)phenyl](phenyl)methyl}-2-(2-oxo-2,3-dihydro-1H-indol-5-yl)acetamide | From [2-(morpholin-4-yl)phenyl](phenyl)methanamine hydrochloride Ex. 8 and 2-(2-oxo-2,3-dihydro-1H-indol-5-yl)acetic acid Ex. 14 following protocol A, DMAP (2.2 equiv), EDCl•HCl (1.1 equiv), 2 h at rt, purification by silica gel column chromatography (CH2Cl2/MeOH, 96:4). The solid was then triturated in Et2O containing small amount of CH2Cl2 and filtered-off, yield 45%, mp: 160° C., appearance: white solid<br>1H NMR (300 MHz, d in ppm): 2.48-2.53 (m, 2H), 2.89-2.94 (m, 2H), 3.41 (s, 2H), 3.44 (s, 2H), 3.53-3.58 (m, 2H), 3.61-3.65 (m, 2H), 6.63 (d, 1H, J = 8.6 Hz), 6.71 (d, 1H, J = 7.9 Hz), 7.06 (dd, 1H, J = 8.0 Hz, J = 1.5 Hz), 7.09 (d, 1H, J = 1.6 Hz), 7.12 (dd, 1H, J = 7.3 Hz, J = 1.6 Hz), 7.16-7.30 (m, 8H), |

TABLE 2-continued

All the NMR were performed in DMSO-d6

| Cpd. | | Starting compounds,<br>Reaction conditions and purification<br>Yield, MP, Appearance, $^1$H NMR (solvent) data, Mass (ES+ or ES−) data |
|---|---|---|
| | | 8.78 (d, 1H, J = 8.6 Hz), 10.29 (s, 1H); m/z: 442 [M + H]+ (calc. mass: 441). |
| 18 | N-{[4-methyl-2-(morpholin-4-yl)phenyl](phenyl)methyl}-2-(2-oxo-2,3-dihydro-1H-indol-5-yl)acetamide | From [4-methyl-2-(morpholin-4-yl)phenyl](phenyl)methanamine hydrochloride Ex. 3 and 2-(2-oxo-2,3-dihydro-1H-indol-5-yl)acetic acid Ex. 14 following protocol A, DMAP (2.2 equiv), EDCl•HCl (1.1 equiv), 2 h at rt, purification by silica gel column chromatography (CH2Cl2/MeOH, 96:4). The solid was then triturated in Et2O containing small amount of CH2Cl2 and filtered-off, yield 53%, mp: 226° C., appearance: white solid<br>1H NMR (300 MHz, d in ppm): 2.25 (s, 3H), 2.48-2.52 (m, 2H), 2.87-2.92 (m, 2H), 3.41 (s, 2H), 3.43 (s, 2H), 3.50-3.56 (m, 2H), 3.61-3.67 (m, 2H), 6.58 (d, 1H, J = 8.6 Hz), 6.70 (d, 1H, J = 7.9 Hz), 6.91 (dd, 1H, J = 7.9 Hz, J = 1.0 Hz), 6.99 (d, 1H, J = 1.2 Hz), 7.04 (dd, 1H, J = 7.9 Hz, J = 1.7 Hz), 7.08 (s, 1H), 7.12 (d, 1H, J = 7.8 Hz), 7.16-7.19 (m, 3H), 7.24-7.29 (m, 2H), 8.72 (d, 1H, J = 8.6 Hz), 10.29 (s, 1H); m/z: 456 [M + H]+ (calc. mass: 455). |
| 19 | 2-(2,2-dimethyl-3-oxo-3,4-dihydro-2H-1,4-benzoxazin-7-yl)-N-{phenyl[2-(piperidin-1-yl)phenyl]methyl}acetamide | From phenyl[2-(piperidin-1-yl)phenyl]methanamine hydrochloride Ex. 4 and 2-(2,2-dimethyl-3-oxo-3,4-dihydro-2H-1,4-benzoxazin-7-yl)acetic acid Ex. 15 following protocol A, substituted amine (0.9 equiv), DMAP (2.2 equiv), EDCl•HCl (1.2 equiv), 4 h at rt, purification by silica gel column chromatography (CH2Cl2/MeOH, 95:5), yield 71%, mp: 190° C., appearance: white solid<br>1H NMR (300 MHz, d in ppm): 1.36 (s, 6H), 1.40-1.65 (m, 6H), 2.50-2.54 (m, 2H), 2.80-2.91 (m, 2H), 3.43 (s, 2H), 6.59 (d, 1H, J = 8.4 Hz), 6.73-6.87 (m, 3H), 7.01-7.09 (m, 1H), 7.11-7.30 (m, 8H), 8.72 (d, 1H, J = 8.5 Hz), 10.53 (br(s), 1H); m/z: 484 [M + H]+ (calc. mass: 483). |
| 20 | 2-(2,3-dioxo-2,3-dihydro-1H-indol-5-yl)-N-{phenyl[2-(piperidin-1-yl)phenyl]methyl}acetamide | From phenyl[2-(piperidin-1-yl)phenyl]methanamine hydrochloride Ex. 4 and 2-(2,3-dioxo-2,3-dihydro-1H-indol-5-yl)acetic acid Ex. 14b following protocol A, substituted amine (0.9 equiv), DMAP (2.2 equiv), EDCl•HCl (1.2 equiv), 18 h at rt, purification by silica gel column chromatography (Cyclohexane/EtOAc, 4:6). The solid was then triturated in Et2O and filtered-off, yield 6%, mp: 227° C., appearance: red solid<br>1H NMR (300 MHz, d in ppm): 1.36-1.68 (m, 6H), 2.52-2.60 (m, 2H), 2.80-2.94 (m, 2H), 3.51 (s, 2H), 6.60 (d, 1H, J = 8.5 Hz), 6.83 (d, 1H, J = 8.0 Hz), 7.02-7.11 (m, 1H), 7.12-7.30 (m, 8H), 7.39 (d, 1H, J = 1.4 Hz), 7.45 (dd, 1H, J = 8.1 Hz, J = 1.8 Hz), 8.80 (d, 1H, J = 8.6 Hz), 10.97 (br(s), 1H); m/z: 454 [M + H]+ (calc. mass: 453). |
| 21 | 2-(2,2-dimethyl-3-oxo-3,4-dihydro-2H-1,4-benzoxazin-7-yl)-N-{[4-methyl-2-(morpholin-4-yl)phenyl](phenyl)methyl}acetamide | From [4-methyl-2-(morpholin-4-yl)phenyl](phenyl)methanamine hydrochloride Ex. 3 and 2-(2,2-dimethyl-3-oxo-3,4-dihydro-2H-1,4-benzoxazin-7-yl)acetic acid Ex. 15 following protocol A, substituted amine (0.9 equiv), DMAP (2.2 equiv), EDCl•HCl (1.2 equiv), 4 h at rt, purification by silica gel column chromatography (CH2Cl2/MeOH, 95:5), yield 76%, mp: 127° C., appearance: white solid<br>1H NMR (300 MHz, d in ppm): 1.36 (s, 6H), 2.25 (s, 3H), 2.50-2.58 (m, 2H), 2.82-2.92 (m, 2H), 3.38-3.44 (m, 2H), 3.49-3.58 (m, 2H), 3.60-3.68 (m, 2H), 6.58 (d, 1H, J = 8.6 Hz), 6.74-6.85 (m, 3H), 6.87-6.93 (m, 1H), 6.99 (s, 1H), 7.07 (d, 1H, J = 7.8 Hz), 7.12-7.21 (m, 3H), 7.22-7.28 (m, 2H), 8.71 (d, 1H, J = 8.6 Hz), 10.53 (br(s), 1H); m/z: 500 [M + H]+ (calc. mass: 499). |
| 22 | 2-(2,3-dioxo-2,3-dihydro-1H-indol-5-yl)-N-{[4-methoxy-2-(piperidin-1-yl)phenyl](phenyl)methyl}acetamide | From [4-methoxy-2-(piperidin-1-yl)phenyl](phenyl)methanamine Ex. 5 and 2-(2,3-dioxo-2,3-dihydro-1H-indol-5-yl)acetic acid Ex. 14b following protocol A, substituted amine (0.9 equiv), DMAP (2.2 equiv), EDCl•HCl (1.2 equiv), 18 h at rt, purification by silica gel column chromatography (Cyclohexane/EtOAc, 4:6). The solid was then triturated in Et2O and filtered-off, yield 13%, mp: 231° C., appearance: red solid<br>1H NMR (300 MHz, d in ppm): 1.37-1.67 (m, 6H), 2.53-2.60 (m, 2H), 2.77-2.92 (m, 2H), 3.49 (s, 2H), 3.70 (s, 3H), 6.49 (d, 1H, J = 8.5 Hz), 6.60-6.68 (m, 2H), 6.83 (d, 1H, J = 8.0 Hz), 7.05-7.20 (m, 4H), 7.21-7.30 (m, 2H), 7.36-7.41 (m, 1H), 7.45 (dd, 1H, J = 8.0 Hz, J = 1.8 Hz), 8.72 (d, 1H, J = 8.4 Hz), 10.97 (br(s), 1H); m/z: 484 [M + H]+ (calc. mass: 483). |

TABLE 2-continued

All the NMR were performed in DMSO-d6

| Cpd. | Starting compounds, Reaction conditions and purification Yield, MP, Appearance, $^1$H NMR (solvent) data, Mass (ES+ or ES−) data |
|---|---|
| 23 2-(2,3-dioxo-2,3-dihydro-1H-indol-5-yl)-N-{[4-methyl-2-(piperidin-1-yl)phenyl](5-methylfuran-2-yl)methyl}acetamide | From [4-methyl-2-(piperidin-1-yl)phenyl](5-methylfuran-2-yl)methanamine Ex. 16 and 2-(2,3-dioxo-2,3-dihydro-1H-indol-5-yl)acetic acid Ex. 14b following protocol A, DMAP (2.2 equiv), EDCl•HCl (1.2 equiv), 18 h at rt, purification by silica gel column chromatography (Cyclohexane/EtOAc, 3:7), yield 30%, mp: 215° C., appearance: orange solid 1H NMR (300 MHz, d in ppm): 1.35-1.65 (m, 6H), 2.17 (s, 3H), 2.24 (s, 3H), 2.50-2.60 (m, 2H), 2.70-2.85 (m, 2H), 3.43 (s, 2H), 5.80 (d, 1H, J = 3.0 Hz), 5.90-5.95 (m, 1H), 6.47 (d, 1H, J = 8.4 Hz), 6.82 (d, 1H, J = 8.1 Hz), 6.89 (d, 1H, J = 8.0 Hz), 6.94 (s, 1H), 7.17 (d, 1H, J = 7.8 Hz), 7.37 (d, 1H, J = 1.5 Hz), 7.43 (dd, 1H, J = 8.1 Hz, J = 1.8 Hz), 8.76 (d, 1H, J = 8.4 Hz), 10.96 (br(s), 1H); m/z: 472 [M + H]+ (calc. mass: 471). |
| 24 N-{[4-methyl-2-(piperidin-1-yl)phenyl](5-methylfuran-2-yl)methyl}-2-(2-oxo-2,3-dihydro-1H-indol-5-yl)acetamide | From [4-methyl-2-(piperidin-1-yl)phenyl](5-methylfuran-2-yl)methanamine Ex. 16 and 2-(2-oxo-2,3-dihydro-1H-indol-5-yl)acetic acid Ex. 14 following protocol A, DMAP (2.2 equiv), EDCl•HCl (1.2 equiv), 18 h at rt, purification by silica gel column chromatography (Cyclohexane/EtOAc, 4:6), yield 80%, mp: 95° C., appearance: white solid 1H NMR (300 MHz, d in ppm): 1.40-1.65 (m, 6H), 2.18 (s, 3H), 2.26 (s, 3H), 2.50-2.60 (m, 2H), 2.70-2.85 (m, 2H), 3.39 (s, 2H), 3.42 (s, 2H), 5.80 (d, 1H, J = 3.0 Hz), 5.90-5.95 (m, 1H), 6.48 (d, 1H, J = 8.3 Hz), 6.70 (d, 1H, J = 7.9 Hz), 6.89 (d, 1H, J = 7.7 Hz), 6.94 (s, 1H), 7.03 (d, 1H, J = 7.9 Hz), 7.08 (s, 1H), 7.18 (dd, 1H, J = 7.8 Hz), 8.77 (d, 1H, J = 8.5 Hz), 10.29 (br(s), 1H); m/z: 458 [M + H]+ (calc. mass: 457). |
| 25 2-(2,2-dimethyl-3-oxo-3,4-dihydro-2H-1,4-benzoxazin-7-yl)-N-{[4-methyl-2-(piperidin-1-yl)phenyl](5-methylfuran-2-yl)methyl}acetamide | From [4-methyl-2-(piperidin-1-yl)phenyl](5-methylfuran-2-yl)methanamine Ex. 16 and 2-(2,2-dimethyl-3-oxo-3,4-dihydro-2H-1,4-benzoxazin-7-yl)acetic acid Ex. 15 following protocol A, substituted amine (0.9 equiv), DMAP (3.2 equiv), EDCl•HCl (1.2 equiv), 18 h at rt, purification by silica gel column chromatography (Cyclohexane/EtOAc, 6:4), yield 43%, mp: 101° C., appearance: white solid 1H NMR (300 MHz, d in ppm): 1.37 (s, 6H), 1.42-1.62 (m, 6H), 2.18 (s, 3H), 2.26 (s, 3H), 2.53-2.62 (m, 2H), 2.73-2.82 (m, 2H), 3.37 (s, 2H), 5.80 (d, 1H, J = 2.6 Hz), 5.93 (dd, 1H, J = 3.0 Hz, J = 1.1 Hz), 6.48 (d, 1H, J = 8.4 Hz), 6.73-6.81 (m, 2H), 6.83 (s, 1H), 6.89 (d, 1H, J = 7.9 Hz), 6.95 (s, 1H), 7.16 (d, 1H, J = 7.8 Hz), 8.79 (d, 1H, J = 8.5 Hz), 10.53 (s, 1H); m/z: 502 [M + H]+ (calc. mass: 501). |
| 26 2-(2,2-dioxo-1,3-dihydro-2,1-benzothiazol-5-yl)-N-{phenyl[2-(piperidin-1-yl)phenyl]methyl}acetamide | From phenyl[2-(piperidin-1-yl)phenyl]methanamine Ex. 4 hydrochloride and 2-(2,2-dioxo-1,3-dihydro-2,1-benzothiazol-5-yl)acetic acid Ex. 17 following protocol A, DMAP (2.2 equiv), EDCl•HCl (1.1 equiv), 2 h at rt, purification by silica gel column chromatography (CH2Cl2/meOH, 97:3), yield 56%, mp: 198° C., appearance: white solid 1H NMR (300 MHz, d in ppm): 1.36-1.58 (m, 6H), 2.48-2.5 (m, 2H), 2.84-2.89 (m, 2H), 3.47 (s, 2H), 4.46 (s, 2H), 6.59 (d, 1H, J = 8.4 Hz), 6.73 (d, 1H, J = 8.0 Hz), 7.04-7.10 (m, 1H), 7.13-7.21 (m, 7H), 7.24-7.29 (m, 3H), 8.75 (d, 1H, J = 8.6 Hz), 10.35 (br(s), 1H); m/z: 476 [M + H]+ (calc. mass: 475). |
| 27 2-(2,2-dioxo-1,3-dihydro-2,1-benzothiazol-5-yl)-N-{[4-methyl-2-(piperidin-1-yl)phenyl](5-methylfuran-2-yl)methyl}acetamide | From [4-methyl-2-(piperidin-1-yl)phenyl](5-methylfuran-2-yl)methanamine Ex. 16 and 2-(2,2-dioxo-1,3-dihydro-2,1-benzothiazol-5-yl)acetic acid Ex. 17 following protocol A, DMAP (3.2 equiv), EDCl•HCl (1.1 equiv), 18 h at rt, purification by silica gel column chromatography (CH2Cl2/EtOAc, 9:1), yield 59%, mp: 108° C., appearance: white solid 1H NMR (300 MHz, d in ppm): 1.40-1.60 (m, 6H), 2.17 (s, 3H), 2.25 (s, 3H), 2.52-2.57 (m, 2H), 2.69-2.83 (m, 2H), 3.40 (s, 2H), 4.46 (s, 2H), 5.81 (d, 1H, J = 3.0 Hz), 5.92 (dd, 1H, J = 3.0 Hz, J = 1.0 Hz), 6.47 (d, 1H, J = 8.4 Hz), 6.72 (d, 1H, J = 7.8 Hz), 6.89 (d, 1H, J = 7.6 Hz), 6.94 (s, 1H), 7.10 (d, 1H, J = 8.4 Hz), 7.13 (s, 1H), 7.17 (d, 1H, J = 7.8 Hz), 8.71 (d, 1H, J = 8.5 Hz), 10.34 (br(s), 1H); m/z: 494 [M + H]+ (calc. mass: 493). |
| 28 N-[(2-bromo-4-methylphenyl)(5-methylfuran-2-yl)methyl]-2- | From (2-bromo-4-methylphenyl)(5-methylfuran-2-yl)methanamine hydrochloride Ex. 18 and 2-(2,2-dioxo-1,3-dihydro-2,1-benzothiazol-5-yl)acetic acid Ex. 17 following protocol A, DMAP (3.2 equiv), EDCl•HCl (1.1 equiv), 18 h at |

TABLE 2-continued

All the NMR were performed in DMSO-d6

| Cpd. | Starting compounds, Reaction conditions and purification Yield, MP, Appearance, $^1$H NMR (solvent) data, Mass (ES+ or ES−) data |
|---|---|
| (2,2-dioxo-1,3-dihydro-2,1-benzothiazol-5-yl)acetamide | rt, purification by silica gel column chromatography (CH2Cl2/EtOAc, 6:4), yield 68%, mp: 102° C., appearance: white solid<br>1H NMR (300 MHz, d in ppm): 2.21 (s, 3H), 2.28 (s, 3H), 3.44 (s, 2H), 4.48 (s, 2H), 5.76 (d, 1H, J = 3.0 Hz), 5.96 (dd, 1H, J = 3.0 Hz, J = 1.0 Hz), 6.23 (d, 1H, J = 8.1 Hz), 6.74 (d, 1H, J = 8.0 Hz), 7.12 (dd, 1H, J = 8.1 Hz, J = 1.7 Hz), 7.15 (s, 1H), 7.20 (dd, 1H, J = 8.0 Hz, J = 1.0 Hz), 7.29 (d, 1H, J = 7.9 Hz), 7.42 (d, 1H, J = 0.8 Hz), 9.06 (d, 1H, J = 8.1 Hz), 10.36 (s, 1H); m/z: 511 [M + Na]+, 513 [M + Na]+ (calc. mass: 488). |
| 29 N-[(2,4-dimethyl phenyl)(5-methylfuran-2-yl)methyl]-2-(2-oxo-2,3-dihydro-1H-indol-5-yl)acetamide | From (2,4-dimethylphenyl)(5-methylfuran-2-yl)methanamine Ex. 19 and 2-(2-oxo-2,3-dihydro-1H-indol-5-yl)acetic acid Ex. 14 following protocol A, substituted amine (0.9 equiv), DMAP (3.2 equiv), EDCl•HCl (1.2 equiv), 18 h at rt, purification by preparative HPLC, yield 56%, mp: 176° C., appearance: white solid<br>1H NMR (300 MHz, d in ppm): 2.17 (s, 3H), 2.20 (s, 3H), 2.23 (s, 3H), 3.40 (s, 2H), 3.41 (s, 2H), 5.84 (d, 1H, J = 2.9 Hz), 5.96 (dd, 1H, J = 3.0 Hz, J = 1.0 Hz), 6.09 (d, 1H, J = 8.3 Hz), 6.70 (d, 1H, J = 7.9 Hz), 6.90-7.13 (m, 5H), 8.89 (d, 1H, J = 8.4 Hz), 10.29 (br(s), 1H); m/z: 389 [M + H]+ (calc. mass: 388). |
| 30 2-(2,2-dimethyl-3-oxo-3,4-dihydro-2H-1,4-benzoxazin-7-yl)-N-{[4-methoxy-2-(morpholin-4-yl)phenyl](5-methylfuran-2-yl)methyl}acetamide | From [4-methoxy-2-(morpholin-4-yl)phenyl](5-methylfuran-2-yl)methanamine hydrochloride Ex. 20 and 2-(2,2-dimethyl-3-oxo-3,4-dihydro-2H-1,4-benzoxazin-7-yl)acetic acid Ex. 15 following protocol A, substituted amine (0.9 equiv), DMAP (3.2 equiv), EDCl•HCl (1.2 equiv), 18 h at rt, purification by preparative HPLC, yield 51%, mp: 99° C., appearance: white solid<br>1H NMR (300 MHz, d in ppm): 1.36 (s, 6H), 2.17 (s, 3H), 2.55-2.63 (m, 2H), 2.75-2.89 (m, 2H), 3.35 (s, 2H), 3.49-3.58 (m, 2H), 3.59-3.67 (m, 2H), 3.73 (s, 3H), 5.84 (d, 1H, J = 3.0 Hz), 5.93 (dd, 1H, J = 2.9 Hz, J = 1.0 Hz), 6.45 (d, 1H, J = 8.4 Hz), 6.66-6.84 (m, 5H), 7.18 (d, 1H, J = 9.1 Hz), 8.72 (d, 1H, J = 8.5 Hz), 10.53 (br(s), 1H); m/z: 520 [M + H]+ (calc. mass: 519). |
| 31 N-[(2-bromo-4-methylphenyl)(5-methylfuran-2-yl)methyl]-2-(3-oxo-3,4-dihydro-2H-1,4-benzoxazin-7-yl)acetamide | From (2-bromo-4-methylphenyl)(5-methylfuran-2-yl)methanamine hydrochloride Ex. 18 and 2-(3-oxo-3,4-dihydro-2H-1,4-benzoxazin-7-yl)acetic acid Ex. 2 following protocol A, DMAP (3.2 equiv), EDCl•HCl (1.1 equiv), 2 h at rt. After sat. NH4Cl addition, the precipitate was collected by filtration and washed with Et2O, yield 65%, mp: 250° C., appearance: white solid<br>1H NMR (300 MHz, d in ppm): 2.21 (s, 3H), 2.28 (s, 3H), 3.40 (s, 2H), 4.52 (s, 2H), 5.76 (d, 1H, J = 2.9 Hz), 5.96 (d, 1H, J = 2.2 Hz), 6.24 (d, 1H, J = 7.9 Hz), 6.76-6.84 (m, 3H), 7.20 (d, 1H, J = 7.7 Hz), 7.29 (d, 1H, J = 7.9 Hz), 7.43 (br(s), 1H), 9.05 (d, 1H, J = 8.0 Hz), 10.63 (s, 1H); m/z: 491 [M + Na]+, 493 [M + Na]+ (calc. mass: 468). |
| 32 N-[(2,4-dimethylphenyl)(5-ethylfuran-2-yl)methyl]-2-(3-oxo-3,4-dihydro-2H-1,4-benzoxazin-7-yl)acetamide | From (2,4-dimethylphenyl)(5-ethylfuran-2-yl)methanamine hydrochloride Ex. 21 and 2-(3-oxo-3,4-dihydro-2H-1,4-benzoxazin-7-yl)acetic acid Ex. 2 following protocol A, DMAP (3.2 equiv), EDCl•HCl (1.1 equiv), 2 h at rt. After sat. NH4Cl addition, the precipitate was collected by filtration and washed with Et2O, yield 73%, mp: 248° C., appearance: white solid<br>1H NMR (300 MHz, d in ppm): 1.12 (t, 3H, J = 7.6 Hz), 2.17 (s, 3H), 2.23 (s, 3H), 2.54 (q, 2H, J = 7.5 Hz), 3.38 (s, 2H), 4.52 (s, 2H), 5.84 (d, 1H, J = 2.6 Hz), 5.97 (d, 1H, J = 3.1 Hz), 6.10 (d, 1H, J = 8.2 Hz), 6.75-6.84 (m, 3H), 6.96-6.98 (m, 2H), 7.07 (d, 1H, J = 8.2 Hz), 8.90 (d, 1H, J = 8.4 Hz), 10.62 (s, 1H); m/z: 441 [M + Na]+ (calc. mass: 418). |
| 33 N-[(2,4-dimethylphenyl)(5-methylfuran-2-yl)methyl]-2-(3-oxo-3,4-dihydro-2H-1,4- | From (2,4-dimethylphenyl)(5-methylfuran-2-yl)methanamine Ex. 19 and 2-(3-oxo-3,4-dihydro-2H-1,4-benzoxazin-7-yl)acetic acid Ex. 2 following protocol A, DMAP (3.2 equiv), EDCl•HCl (1.1 equiv), 2 h at rt. After sat. NH4Cl addition, the Precipitate was collected by filtration and washed with Et2O, yield 87%, mp: 250° C., appearance: white solid |

TABLE 2-continued

All the NMR were performed in DMSO-d6

| Cpd. | Starting compounds, Reaction conditions and purification Yield, MP, Appearance, ¹H NMR (solvent) data, Mass (ES+ or ES−) data |
|---|---|
| benzoxazin-7-yl)acetamide | 1H NMR (300 MHz, d in ppm): 2.17 (s, 3H), 2.20 (s, 3H), 2.23 (s, 3H), 3.38 (s, 2H), 4.52 (s, 2H), 5.84 (d, 1H, J = 2.9 Hz), 5.96 (d, 1H, J = 2.1 Hz), 6.09 (d, 1H), 6.75-6.83 (m, 3H), 6.96-6.98 (m, 2H), 7.08 (d, 1H, J = 8.4 Hz), 8.91 (d, 1H, J = 8.4 Hz), 10.63 (s, 1H); m/z: 427 [M + Na]+ (calc. mass: 404). |
| 34 N-[(2-bromo-4-methoxyphenyl)(5-methylfuran-2-yl)methyl]-2-(3-oxo-3,4-dihydro-2H-1,4-benzoxazin-7-yl)acetamide | From (2-bromo-4-methoxyphenyl)(5-methylfuran-2-yl)methanamine hydrochloride Ex. 22 and 2-(3-oxo-3,4-dihydro-2H-1,4-benzoxazin-7-yl)acetic acid Ex. 2 following protocol A, DMAP (3.2 equiv), EDCl•HCl (1.1 equiv), 2 h at rt. After sat. NH4Cl addition, the precipitate was collected by filtration and washed with Et2O, yleld 79%, mp: 235° C., appearance: white solid<br>1H NMR (300 MHz, d in ppm): 2.21 (s, 3H), 3.39 (s, 2H), 3.76 (s, 3H), 4.52 (s, 2H), 5.77 (d, 1H, J = 2.8 Hz), 5.96 (d, 1H, J = 2.1 Hz), 6.22 (d, 1H, J = 8.1 Hz), 6.79-6.84 (m, 3H), 6.98 (dd, 1H, J = 8.6 Hz, J = 2.6 Hz), 7.16 (d, 1H, J = 2.6 Hz), 7.31 (d, 1H, J = 8.6 Hz), 9.02 (d, 1H, J = 7.9 Hz), 10.63 (s, 1H); m/z: 507 [M + Na]+, 509 [M + Na]+ (calc. mass: 484). |
| 35 N-{[4-methyl-2-(piperidin-1-yl)phenyl](5-methylfuran-2-yl)methyl}-2-(3-oxo-3,4-dihydro-2H-1,4-benzoxazin-7-yl)acetamide | From [4-methyl-2-(piperidin-1-yl)phenyl](5-methylfuran-2-yl)methanamine Ex. 16 and 2-(3-oxo-3,4-dihydro-2H-1,4-benzoxazin-7-yl)acetic acid Ex. 2 following protocol A, DMAP (2.2 equiv), EDCl•HCl (1.1 equiv), 2 h at rt. After sat. NH4Cl addition, the precipitate was collected by filtration and washed with Et2O, yleld 37%, mp: 154° C., appearance: white solid<br>1H NMR (300 MHz, d in ppm): 1.44-1.53 (m, 6H), 2.17 (s, 3H), 2.25 (s, 3H), 2.52-2.56 (m, 2H), 2.75-2.79 (m, 2H), 3.36 (s, 2H), 4.51 (s, 2H), 5.80 (d, 1H, J = 3.1 Hz), 5.92 (d, 1H, J = 3.1 Hz), 6.47 (d, 1H, J = 8.2 Hz), 6.75-6.82 (m, 3H), 6.88 (d, 1H, J = 8.2 Hz), 6.94 (br(s), 1H), 7.17 (d, 1H, J = 7.8 Hz), 8.69 (d, 1H, J = 8.0 Hz), 10.61 (s, 1H); m/z: 474 [M + H]+ (calc. mass: 473). |
| 36 N-[(2-bromo-4-methylphenyl)(5-methylfuran-2-yl)methyl]-2-(2-oxo-1,2,3,4-tetrahydroquinolin-6-yl)acetamide | From (2-bromo-4-methylphenyl)(5-methylfuran-2-yl)methanamine hydrochloride Ex. 18 and 2-(2-oxo-1,2,3,4-tetrahydroquinolin-6-yl)acetic acid Ex. 23 following protocol A, DMAP (3.2 equiv), EDCl•HCl (1.1 equiv), 2 h at rt. After sat. NH4Cl addition, the precipitate was collected by filtration and washed with Et2O, yleld 77%, mp: 188° C., appearance: white solid<br>1H NMR (300 MHz, DMSO-d6, d in ppm): 2.21 (s, 3H), 2.28 (s, 3H), 2.40 (t, 2H, J = 8.0 Hz), 2.81 (t, 2H, J = 7.3 Hz), 3.40 (s, 2H), 5.77 (d, 1H, J = 3.0 Hz), 5.96 (d, 1H, J = 2.3 Hz), 6.24 (d, 1H, J = 8.1 Hz), 6.74 (d, 1H, J = 7.9 Hz), 7.00 (dd, 1H, J = 8.1 Hz, J = 1.9 Hz), 7.02 (s, 1H), 7.20 (d, 1H, J = 8.2 Hz), 7.31 (d, 1H, J = 8.0 Hz), 7.42 (d, 1H), 9.04 (d, 1H, J = 8.3 Hz), 9.99 (s, 1H); m/z: 489 [M + Na]+, 491 [M + Na]+ (calc. mass: 466). |
| 37 2-(3-hydrazinylidene-2-oxo-2,3-dihydro-1H-indol-5-yl)-N-{[4-methyl-2-(piperidin-1-yl)phenyl](5-methylfuran-2-yl)methyl}acetamide | See FIG. 3AC<br>To a solution of previously synthesized 2-(2,3-dioxo-2,3-dihydro-1H-indol-5-yl)-N-{[4-methyl-2-(piperidin-1-yl)phenyl](5-methylfuran-2-yl)methyl}acetamide Ex. 23 (30 mg, 0.064 mmol) in MeOH (2 mL) was added hydrazine hydrate 50% (w/w) (4 mg, 0.07 mmol). The reaction was heated at 100° C. overnight. The solvents were removed under reduced pressure. The crude material was purified by silica gel column chromatography using Cyclohexane/EtOAc (1:1) as eluent to afford Cpd. 37 (5 mg, 16%) as white solid<br>1H NMR (300 MHz, d in ppm): 1.47-2.30 (m, 6H), 2.20 (s, 3H), 2.30 (s, 3H), 2.58-2.66 (m, 2H), 2.71-2.82 (m, 2H), 3.53 (s, 0.8H), 3.56 (s, 1.2H), 5.82-5.83 (m, 1H), 5.86-5.88 (m, 1H), 6.60 (s, 0.4H), 6.63 (s, 0.6H), 6.81-6.99 (m, 2H), 7.10 (s, 1H), 7.10-7.21 (m, 2H), 7.41 (d, 0.4H, J = 1.2 Hz), 7.73 (d, 0.6H, J = 1.1 Hz); m/z: 486 [M + H]+ (calc. mass: 485); mp: n.d. |

TABLE 2-continued

All the NMR were performed in DMSO-d6

| Cpd. | | Starting compounds, Reaction conditions and purification Yield, MP, Appearance, ¹H NMR (solvent) data, Mass (ES+ or ES−) data |
|---|---|---|
| 38 | N-{[4-methyl-2-(piperidin-1-yl)phenyl](5-methylfuran-2-yl)methyl}-2-(1-methyl-2-oxo-2,3-dihydro-1H-indol-5-yl)acetamide | From [4-methyl-2-(piperidin-1-yl)phenyl](5-methylfuran-2-yl)methanamine Ex. 16 and 2-(1-methyl-2-oxo-2,3-dihydro-1H-indol-5-yl)acetic acid Ex. 24 following protocol A, DMAP (3.2 equiv), EDCl•HCl (1.1 equiv), 2 h at rt, purification by silica gel column chromatography (Cyclohexane/EtOAc, 6:4), yield 30%, mp: 215° C., appearance: white solid 1H NMR (300 MHz, d in ppm): 1.39-1.55 (m, 6H), 2.17 (s, 3H), 2.25 (s, 3H), 2.52-2.59 (m, 2H), 2.77-2.81 (m, 2H), 3.08 (s, 3H), 3.42 (s, 2H), 3.49 (s, 2H), 5.80 (d, 1H, J = 3.1 Hz), 5.91-5.93 (m, 1H), 6.48 (d, 1H, J = 8.6 Hz), 6.85-6.91 (m, 2H), 6.94 (s, 1H), 7.12-7.13 (m, 2H), 7.19 (d, 1H, J = 7.8 Hz), 8.69 (d, 1H, J = 8.4 Hz); m/z: 472 [M + H]+ (calc. mass: 471). |
| 39 | 2-(3-hydroxy-1,3-dimethyl-2-oxo-2,3-dihydro-1H-indol-5-yl)-N-{[4-methyl-2-(piperidin-1-yl)phenyl](5-methylfuran-2-yl)methyl}acetamide | From [4-methyl-2-(piperidin-1-yl)phenyl](5-methylfuran-2-yl)methanamine Ex. 16 and 2-(3-hydroxy-1,3-dimethyl-2-oxo-2,3-dihydro-1H-indol-5-yl)acetic acid Ex. 25 following protocol A, DMAP (3.2 equiv), EDCl•HCl (1.1 equiv), 2 h at rt, purification by silica gel column chromatography (Cyclohexane/EtOAc, 6:4), yield 36%, mp: 103° C., appearance: white solid 1H NMR (300 MHz, d in ppm): 1.32 (s, 1.5H), 1.34 (s, 1.5H), 1.39-1.53 (m, 6H), 2.17 (s, 1.5H), 2.18 (s, 1.5H), 2.24 (s, 3H), 2.51-2.56 (m, 2H), 2.71-2.79 (m, 2H), 3.06 (d, 3H, J = 0.9 Hz), 3.43 (s, 2H), 5.81 (d, 1H, J = 3.1 Hz), 5.89 (s, 1H), 5.91-5.93 (m, 1H), 6.49 (d, 1H, J = 8.7 Hz), 6.85-6.91 (m, 2H), 6.94 (s, 1H), 7.14-7.17 (m, 1H), 7.19 (d, 1H, J = 7.9 Hz), 7.22-7.24 (m, 1H), 8.71 (d, 0.5H, J = 8.5 Hz), 8.73 (d, 0.5H, J = 8.2 Hz); m/z: 502 [M + H]+ (calc. mass: 501). |
| 40 | N-{[4-methyl-2-(piperidin-1-yl)phenyl](5-methylfuran-2-yl)methyl}-2-(1,3,3-trimethyl-2-oxo-2,3-dihydro-1H-indol-5-yl)acetamide | From [4-methyl-2-(piperidin-1-yl)phenyl](5-methylfuran-2-yl)methanamine Ex. 16 and 2-(1,3,3-trimethyl-2-oxo-2,3-dihydro-1H-indol-5-yl)acetic acid Ex. 26 following protocol A, DMAP (3.2 equiv), EDCl•HCl (1.1 equiv), 2 h at rt, purification by silica gel column chromatography (Cyclohexane/EtOAc, 6:4), yield 28%, mp: 75° C., appearance: white solid 1H NMR (300 MHz, d in ppm): 1.21 (s, 3H), 1.22 (s, 3H), 1.45-1.54 (m, 6H), 2.17 (s, 3H), 2.24 (s, 3H), 2.52-2.58 (m, 2H), 2.73-2.85 (m, 2H), 3.09 (s, 3H), 3.43 (s, 2H), 5.81 (d, 1H, J = 3.0 Hz), 5.92 (dd, 1H, J = 3.0 Hz, J = 1.1 Hz), 6.49 (d, 1H, J = 8.4 Hz), 6.87 (dd, 1H, J = 7.7 Hz, J = 1.3 Hz), 6.90 (d, 1H, J = 7.8 Hz), 6.92 (d, 1H, J = 0.9 Hz), 7.12 (dd, 1H, J = 8.0 Hz, J = 1.6 Hz), 7.18 (d, 1H, J = 2.1 Hz), 7.20 (d, 1H, J = 4.3 Hz), 8.70 (d, 1H, J = 8.6 Hz); m/z: 500 [M + H]+ (calc. mass: 499). |
| 41 | 2-(2-methanesulfonyl-2,3-dihydro-1H-isoindol-5-yl)-N-{[4-methyl-2-(piperidin-1-yl)phenyl](5-methylfuran-2-yl)methyl}acetamide | From [4-methyl-2-(piperidin-1-yl)phenyl](5-methylfuran-2-yl)methanamine Ex. 16 and 2-(2-methanesulfonyl-2,3-dihydro-1H-isoindol-5-yl)acetic acid Ex. 27 following protocol A, DMAP (2.2 equiv), EDCl•HCl (1.2 equiv), 18 h at rt, purification by silica gel column chromatography (Cyclohexane/EtOAc, 1:1), yield 83%, mp: 83° C., appearance: white solid 1H NMR (300 MHz, d in ppm): 1.46-1.55 (m, 6H), 2.17 (s, 3H), 2.25 (s, 3H), 2.53-2.59 (m, 2H), 2.77-2.81 (m, 2H), 2.95 (s, 3H), 3.48 (s, 2H), 4.57 (s, 4H), 5.81 (d, 1H, J = 3.0 Hz), 5.93 (dd, 1H, J = 3.0 Hz, J = 1.1 Hz), 6.48 (d, 1H, J = 8.3 Hz), 6.89 (d, 1H, J = 7.9 Hz), 6.94 (s, 1H), 7.16-7.24 (m, 4H), 8.76 (d, 1H, J = 8.5 Hz); m/z: 522 [M + H]+ (calc. mass: 521). |
| 42 | 2-[3-(hydroxylmino)-2-oxo-2,3-dihydro-1H-indol-5-yl]-N-{[4-methyl-2-(piperidin-1-yl)phenyl](5-methylfuran-2-yl)methyl}acetamide | See FIG. 3AD A solution of previously synthesized 2-(2,3-dioxo-2,3-dihydro-1H-indol-5-yl)-N-{[4-methyl-2-(piperidin-1-yl)phenyl](5-methylfuran-2-yl)methyl}acetamide Cpd. 23 (16 mg, 0.034 mmol) and hydroxylamine hydrochloride (4 mg, 0.051 mmol) in EtOH (1 mL) was heated at 80° C. overnight. The solvents were removed under reduced pressure. The crude material was purified by silica gel column chromatography using CH2Cl2/MeOH (95:5) as eluent to afford N-{[4-methyl-2-(piperidin-1-yl)phenyl](5-methylfuran-2-yl)methyl}-2-(2-oxo-2,3-dihydro-1H-indol-6-yl)acetamide (11 mg, 67%) as pale yellow solid, mp: n.d. 1H NMR (300 MHz, d in ppm): 1.40-1.58 (m, 6H), 2.16 (s, 3H), 2.24 (s, 3H), 2.50-2.58 (m, 2H), 2.72-2.8 (m, 2H), 3.41 (s, 2H), 5.82 (d, 1H, J = 2.9 Hz), 5.92 (d, 1H, J = 2.0 Hz), 6.45 (d, 1H, J = 8.3 Hz), 6.77 (d, 1H, J = 8.0 Hz), 6.88 (d, 1H, |

TABLE 2-continued

All the NMR were performed in DMSO-d6

| Cpd. | Starting compounds,<br>Reaction conditions and purification<br>Yield, MP, Appearance, $^1$H NMR (solvent) data, Mass (ES+ or ES−) data |
|---|---|
| | J = 8.2 Hz), 6.93 (s, 1H), 7.17 (d, 1H, J = 7.8 Hz), 7.21 (dd, 1H, J = 8.0 Hz, J = 1.6 Hz), 7.88 (s, 1H), 8.74 (d, 1H, J = 8.3 Hz), 10.61 (s, 1H), 13.26 (s, 1H); m/z: 487 [M + H]+ (calc. mass: 486). |
| 43  2-{3-[(dimethyl-1,2-oxazol-4-yl)methylidene]-2-oxo-2,3-dihydro-1H-indol-5-yl}-N-{[4-methyl-2-(piperidin-1-yl)phenyl](5-methylfuran-2-yl)methyl}acetamide | See FIG. 3AE<br>To a solution of previously synthesized N-{[4-methyl-2-(piperidin-1-yl)phenyl](5-methylfuran-2-yl)methyl}-2-(2-oxo-2,3-dihydro-1H-indol-5-yl)acetamide Cpd. 24 (75 mg, 0.16 mmol) and 3,5-dimethyl-1,2-oxazole-4-carbaldehyde (25 mg, 0.20 mmol) in EtOH (2 mL) was added few drops of catalytic piperidine. The reaction mixture was heated at 80° C. overnight. The solvents were removed under reduced pressure. The crude material was purified by silica gel column chromatography using CH2Cl2/MeOH (95:5) as eluent to afford 2-{3-[(dimethyl-1,2-oxazol-4-yl)methylidene]-2-oxo-2,3-dihydro-1H-indol-5-yl}-N-{[4-methyl-2-(piperidin-1-yl)phenyl](5-methylfuran-2-yl)methyl}acetamide (80 mg, 86%) as yellow solid, mp: 128° C.<br>1H NMR (300 MHz, d in ppm): 1.40-1.54 (m, 6H), 2.16 (s, 3H), 2.20 (s, 3H), 2.22 (s, 3H), 2.24 (s, 3H), 2.50-2.60 (m, 2H), 2.71-2.81 (m, 2H), 3.34 (s, 1.5H), 3.44 (s, 0.5H), 5.77 (d, 0.75H, J = 3.0 Hz), 5.82 (d, 0.25H, J = 2.9 Hz), 5.90-5.95 (m, 1H), 6.44 (d, 0.75H, J = 8.3 Hz), 6.49 (d, 0.25H, J = 8.1 Hz), 6.74 (d, 0.25H, J = 7.8 Hz), 6.78 (d, 0.75H, J = 8.0 Hz), 6.85-6.93 (m, 2.75H), 7.11-7.13 (m, 1.75H), 7.20 (s, 0.75H), 7.22 (s, 0.25H), 7.41 (s, 0.25H), 7.51 (s, 0.25H), 8.68 (d, 0.75H, J = 8.5 Hz), 8.72 (d, 0.25H, J = 8.0 Hz), 10.47 (s, 0.25H), 10.57 (s, 0.75H); m/z: 565 [M + H]+ (calc. mass: 564). |
| 44  2-{3-[(2-amino-1,3-thiazol-5-yl)methylidene]-2-oxo-2,3-dihydro-1 H-indol-5-yl}-N-{[4-methyl-2-(piperidin-1-yl)phenyl](5-methylfuran-2-yl)methyl}acetamide | See FIG. 3AE<br>To a solution of previously synthesized N-{[4-methyl-2-(piperidin-1-yl)phenyl](5-methylfuran-2-yl)methyl}-2-(2-oxo-2,3-dihydro-1H-indol-5-yl)acetamide Cpd. 24 (75 mg, 0.16 mmol) and 2-amino-1,3-thiazole-5-carbaldehyde (25 mg, 0.20 mmol) in EtOH (2 mL) was added few drops of catalytic piperidine. The reaction mixture was heated at 80° C. overnight. The precipitate formed was collected by filtration, triturated with small amount of EtOH and dried until constant weight to afford 2-{3-[(2-amino-1,3-thiazol-5-yl)methylidene]-2-oxo-2,3-dihydro-1H-indol-5-yl}-N-{[4-methyl-2-(piperidin-1-yl)phenyl](5-methylfuran-2-yl)methyl}acetamide (55 mg, 59%) as yellow solid, mp: 235° C.<br>1H NMR (300 MHz, d in ppm): 1.40-1.55 (m, 6H), 2.16 (s, 3H), 2.24 (s, 3H), 2.50-2.58 (m, 2H), 2.72-2.78 (m, 2H), 3.42 (s, 2H), 5.81 (d, 1H, J = 2.9 Hz), 5.92 (dd, 1H, J = 2.9 Hz, J = 1.0 Hz), 6.49 (d, 1H, J = 8.6 Hz), 6.68 (d, 1H, J = 8.0 Hz), 6.89 (d, 1H, J = 7.7 Hz), 6.93 (s, 1H), 6.97 (dd, 1H, J = 8.1 Hz, J = 1.4 Hz), 7.20 (d, 1H, J = 7.8 Hz), 7.35 (s, 1H), 7.71 (s, 1H), 7.72 (s, 1H), 7.84 (br(s), 2H), 8.68 (d, 1H, J = 8.5 Hz), 10.32 (s, 1H); m/z: 568 [M + H]+ (calc. mass: 567). |
| 45  2-(1-methyl-2,3-dioxo-2,3-dihydro-1H-indol-5-yl)-N-{[4-methyl-2-(piperidin-1-yl)phenyl](5-methylfuran-2-yl)methyl}acetamide | See FIG. 3AF<br>2-(2,3-dioxo-2,3-dihydro-1H-indol-5-yl)-N-{[4-methyl-2-(piperidin-1-yl)phenyl](5-methylfuran-2-yl)methyl}acetamide Cpd. 23 (100 mg, 0.21 mmol) was dissolved in dry THF (5 mL). The solution was cooled to 0° C. and sodium hydride 60% in oil (17 mg, 0.42 mmol) was added followed by iodomethane (15 μL, 0.23 mmol). The ice bath was removed and the mixture was stirred at rt overnight. The reaction was stopped with water. The aqueous layer was extracted with EtOAc. The organic layer was dried over MgSO4, filtered and the solution was concentrated under reduced pressure. The crude material was purified by silica gel column chromatography using Cyclohexane/EtOAc (6:4) as eluent affording 2-(1-methyl-2,3-dioxo-2,3-dihydro-1H-indol-5-yl)-N-{[4-methyl-2-(piperidin-1-yl)phenyl](5-methylfuran-2-yl)methyl}acetamide (50 mg, 49%) as orange solid, mp: 99° C.<br>1H NMR (300 MHz, d in ppm): 1.40-1.60 (m, 6H), 2.17 (s, 3H), 2.25 (s, 3H), 2.50-2.62 (m, 2H), 2.72-2.84 (m, 2H), 3.11 (s, 3H), 3.47 (s, 2H), 5.80 (d, 1H, J = 3.0 Hz), 5.92 (dd, 1H, J = 2.9 Hz, J = 1.0 Hz), 6.49 (d, 1H, J = 8.7 Hz), 6.89 (d, 1H, J = 7.7 Hz), 6.94 (s, 1H), 7.06 (d, 1H, J = 8.0 Hz), 7.18 (d, 1H, |

TABLE 2-continued

All the NMR were performed in DMSO-d6

| Cpd. | Starting compounds,<br>Reaction conditions and purification<br>Yield, MP, Appearance, $^1$H NMR (solvent) data, Mass (ES+ or ES−) data |
|---|---|
| | J = 7.8 Hz), 7.40 (d, 1H, J = 1.5 Hz), 7.51 (dd, 1H, J = 8.1 Hz, J = 1.8 Hz), 8.78 (d, 1H, J = 8.3 Hz); m/z: 486 [M + H]+ (calc. mass: 485). |
| 46  2-(3-hydroxy-2-oxo-2,3-dihydro-1H-indol-5-yl)-N-{[4-methyl-2-(piperidin-1-yl)phenyl](5-methylfuran-2-yl)methyl}acetamide | See FIG. 3AG<br>2-(2,3-dioxo-2,3-dihydro-1H-indol-5-yl)-N-{[4-methyl-2-(piperidin-1-yl)phenyl](5-methylfuran-2-yl)methyl}acetamide Cpd. 23 (100 mg, 0.21 mmol) was dissolved in EtOH (10 mL). The solution was cooled to 0° C. and sodium borohydride (9 mg, 0.23 mmol) was added. After 10 min at 0° C., the reaction was completed. The reaction was quenched with citric acid 1N. The solvent was removed under reduced pressure. EtOAc was added and the solution was washed with water. The organic layer was dried over MgSO4, filtered and the solution was concentrated under reduced pressure to afford 2-(3-hydroxy-2-oxo-2,3-dihydro-1H-indol-5-yl)-N-{[4-methyl-2-(piperidin-1-yl)phenyl](5-methylfuran-2-yl)methyl}acetamide (75 mg, 75%) as pale brown solid, mp: 110° C.<br>1H NMR (300 MHz, d in ppm): 1.40-1.60 (m, 6H), 2.17 (s, 3H), 2.25 (s, 3H), 2.50-2.60 (m, 2H), 2.76-2.82 (m, 2H), 3.39 (s, 2H), 4.75-4.78 (m, 1H), 5.79-5.81 (m, 1H), 5.90-5.92 (m, 1H), 6.14 (d, 1H, J = 7.7 Hz), 6.47 (d, 1H, J = 8.2 Hz), 6.67 (d, 1H, J = 7.9 Hz), 6.89 (d, 1H, J = 7.7 Hz), 6.94 (s, 1H), 7.06 (d, 1H, J = 7.8 Hz), 7.17-7.20 (m, 2H), 8.71 (d, 1H, J = 8.5 Hz), 10.15 (s, 1H); m/z: 474 [M + H]+ (calc. mass: 473). |
| 47  2-(3-hydroxy-3-methyl-2-oxo-2,3-dihydro-1H-indol-5-yl)-N-{[4-methyl-2-(piperidin-1-yl)phenyl](5-methylfuran-2-yl)methyl}acetamide | See FIG. 3AH<br>To a solution of 2-(2,3-dioxo-2,3-dihydro-1H-indol-5-yl)-N-{[4-methyl-2-(piperidin-1-yl)phenyl](5-methylfuran-2-yl)methyl}acetamide Cpd. 23 (150 mg, 0.32 mmol) dissolved in dry THF (10 mL) was added dropwise methylmagnesium bromide (265 μL, 0.80 mmol) at 0° C. The solution was slowly warmed to rt and stirred at this temperature overnight. TLC show still starting material. The solution was cooled to 0° C. and additionnal methylmagnesium bromide (7.5 equiv) was added dropwise to the mixture. After 2 h, the reaction was stopped with water and neutralized with a solution of citric acid 1N. The aqueous layer was extracted with EtOAc. The combined organic layers were dried over MgSO4, filtered and the solution was concentrated under reduced pressure. The crude material was purified by silica gel column chromatography using Cyclohexane/EtOAc (1:1) as eluent yielding 2-(3-hydroxy-3-methyl-2-oxo-2,3-dihydro-1H-indol-5-yl)-N-{[4-methyl-2-(piperidin-1-yl)phenyl](5-methylfuran-2-yl)methyl}acetamide (50 mg, 32%) as white solid, mp: 112° C.<br>1H NMR (300 MHz, d in ppm): 1.33 (s, 1.5H), 1.34 (s, 1.5H), 1.34-1.62 (m, 6H), 2.16 (s, 1.5H), 2.17 (s, 1.5H), 2.24 (s, 3H), 2.50-2.60 (m, 2H), 2.73-2.84 (m, 2H), 3.39 (s, 1H), 3.40 (s, 1H), 5.80-5.81 (m, 1H), 5.82 (s, 1H), 5.91-5.93 (m, 1H), 6.48 (d, 1H, J = 8.5 Hz), 6.69 (d, 1H, J = 7.8 Hz), 6.88 (d, 0.5H, J = 7.9 Hz), 6.89 (d, 0.5H, J = 8.2 Hz), 6.94 (s, 1H), 7.05 (d, 1H, J = 7.8 Hz), 7.18-7.20 (m, 2H), 8.70 (d, 0.5H, J = 8.3 Hz), 8.71 (d, 0.5H, J = 8.5 Hz), 10.13 (s, 1H); m/z: 488 [M + H]+ (calc. mass: 487). |
| 48  N-{[4-methyl-2-(piperidin-1-yl)phenyl](5-methylfuran-2-yl)methyl}-2-[(3E)-3-(2-methylpropylidene)-2-oxo-2,3-dihydro-1H-indol-5-yl]acetamide | See FIG. 3AE<br>To a solution of previously synthesized N-{[4-methyl-2-(piperidin-1-yl)phenyl](5-methylfuran-2-yl)methyl}-2-(2-oxo-2,3-dihydro-1H-indol-5-yl)acetamide Cpd. 24 (50 mg, 0.11 mmol) and isobutyraldehyde (10 μL, 0.11 mmol) in EtOH (1 mL) was added few drops of catalytic piperidine. The reaction mixture was heated at 90° C. overnight. The solvent was removed under reduced pressure and the crude material was purified by preparative HPLC to give N-{[4-methyl-2-(piperidin-1-yl)phenyl](5-methylfuran-2-yl)methyl}-2-[(3E)-3-(2-methylpropylidene)-2-oxo-2,3-dihydro-1H-indol-5-yl]acetamide (10 mg, 17%) as white solid, mp: 91° C.<br>1H NMR (300 MHz, d in ppm): 1.07-1.15 (m, 3H), 1.23 (s, 3H), 1.36-1.63 (m, 6H), 2.16 (s, 3H), 2.24 (s, 3H), 2.55-2.58 (m, 2H), 2.73-2.81 (m, 2H), 3.39-3.44 (m, 2H), 5.81 (d, 1H, J = 3.03 Hz), 5.90-5.95 (m, 1H), 6.47 (d, 1H, J = 8.55 Hz), 6.52 (s, 0.3H), 6.57 (d, 0.7H, J = 10.0 Hz), 6.73 (d, 1H, J = 7.8 Hz), 6.86 (d, 1H, J = 7.6 Hz), 6.93 (s, 1H), 7.07 (d, 1H, J = 9.1 Hz), |

TABLE 2-continued

All the NMR were performed in DMSO-d6

| Cpd. | | Starting compounds,<br>Reaction conditions and purification<br>Yield, MP, Appearance, $^1$H NMR (solvent) data, Mass (ES+ or ES−) data |
|---|---|---|
| | | 7.17 (d, 1H, J = 7.8 Hz), 7.48 (s, 1H), 8.72 (d, 1H, J = 8.3 Hz), 10.37 (br(s), 1H) (proton on central carbon of isopropyl group is under the pic of DMSO-d6); m/z: 512 [M + H]+ (calc. mass: 511). |
| 49 | N-{[4-methyl-2-(piperidin-1-yl)phenyl](5-methylfuran-2-yl)methyl}-2-(3-methyl-2-oxo-2,3-dihydro-1H-indol-5-yl)acetamide | See FIG. 3AI<br>To a solution of previously synthesized N-{[4-methyl-2-(piperidin-1-yl)phenyl](5-methylfuran-2-yl)methyl}-2-(2-oxo-2,3-dihydro-1H-indol-5-yl)acetamide Cpd. 24 (150 mg, 0.33 mmol) in THF (4 mL) was added (dimethoxymethyl)dimethylamine (78 mg, 0.66 mmol). The reaction mixture was stirred at rt for 3 h, then the solvent was removed under reduced pressure. EtOH (5 mL) was added to the crude and the solution was cooled at 0° C. Sodium borohydride (25 mg, 0.66 mmol) was added to the solution. The reaction mixture was stirred at rt overnight. Citric acid 1N was added to quench the reaction and the aqueous layer was extracted with EtOAc. The combined organic layer was dried over MgSO4, filtered and the solution was concentrated under reduced pressure. The crude material was purified by silica gel column chromatography using CH2Cl2/MeOH (97:3) as eluent to afford N-{[4-methyl-2-(piperidin-1-yl)phenyl](5-methylfuran-2-yl)methyl}-2-(3-methyl-2-oxo-2,3-dihydro-1H-indol-5-yl)acetamide (12 mg, 8%) as white solid, mp: 102° C.<br>1H NMR (300 MHz, d in ppm): 1.24 (d, 1.5H, J = 7.7 Hz), 1.28 (d, 1.5H, J = 7.7 Hz), 1.4-1.62 (m, 6H), 2.16 (s, 1.5H), 2.17 (s, 1.5H), 2.24 (s, 3H), 2.50-2.60 (m, 2H), 2.70-2.82 (m, 2H), 3.29-3.36 (m, 1H), 3.39 (s, 2H), 5.81 (d, 1H, J = 3.0 Hz), 5.90-5.95 (m, 1H), 6.47 (d, 1H, J = 8.6 Hz), 6.70 (d, 1H, J = 7.7 Hz), 6.85-6.89 (m, 0.5H), 6.91-6.94 (m, 0.5H), 6.93 (s, 1H), 7.02 (d, 1H, J = 7.9 Hz), 7.11 (s, 1H), 7.18 (d, 1H, J = 7.7 Hz), 8.67 (d, 0.5H, J = 8.5 Hz), 8.69 (d, 0.5H, J = 9.0 Hz), 10.24 (br(s), 1H); m/z: 472 [M + H]+ (calc. mass: 471) |
| 50 | 2-(2-methanesulfonyl-2,3-dihydro-1H-isoindol-4-yl)-N-{[4-methyl-2-(piperidin-1-yl)phenyl](5-methylfuran-2-yl)methyl}acetamide | From [4-methyl-2-(piperidin-1-yl)phenyl](5-methylfuran-2-yl)methanamine Ex. 16 and 2-(2-methanesulfonyl-2,3-dihydro-1H-isoindol-4-yl)acetic acid Ex. 28 following protocol A, DMAP (3.2 equiv), EDCl•HCl (1.2 equiv), 18 h at rt, purification by silica gel column chromatography (Cyclohexane/EtOAc, 6:4). The solid was then triturated in Et2O and filtered-off, yield 64%, mp: 155° C., appearance: white solid<br>1H NMR (300 MHz, d in ppm): 1.45-1.52 (m, 6H), 2.18 (s, 3H), 2.25 (s, 3H), 2.52-2.59 (m, 2H), 2.76-2.80 (m, 2H), 2.89 (s, 3H), 3.48 (s, 2H), 4.62 (s, 4H), 5.82 (d, 1H, J = 3.1 Hz), 5.93 (dd, 1H, J = 3.0 Hz, J = 1.0 Hz), 6.49 (d, 1H, J = 8.3 Hz), 6.90 (d, 1H, J = 7.9 Hz), 6.94 (s, 1H), 7.15-7.26 (m, 4H), 8.81 (d, 1H, J = 8.4 Hz); m/z: 522 [M + H]+ (calc. mass: 521). |
| 51 | N-{[4-methyl-2-(piperidin-1-yl)phenyl](5-methylfuran-2-yl)methyl}-2-(1-oxo-2,3-dihydro-1H-inden-5-yl)acetamide | From [4-methyl-2-(piperidin-1-yl)phenyl](5-methylfuran-2-yl)methanamine Ex. 16 and 2-(1-oxo-2,3-dihydro-1H-inden-5-yl)acetic acid Ex. 29 following protocol A, DMAP (1.0 equiv), EDCl•HCl (1.1 equiv), 18 h at rt, purification by silica gel column chromatography (Cyclohexane/EtOAc, 7:3), yield 50%, mp: 74° C., appearance: white solid<br>1H NMR (300 MHz, d in ppm): 1.40-1.60 (m, 6H), 2.17 (s, 3H), 2.25 (s, 3H), 2.50-2.60 (m, 4H), 2.76-2.81 (m, 2H), 3.02-3.06 (m, 2H), 3.59 (s, 2H), 5.82 (d, 1H, J = 2.9 Hz), 5.93 (dd, 1H, J = 3.0 Hz, J = 1.0 Hz), 6.50 (d, 1H, J = 8.4 Hz), 6.90 (d, 1H, J = 7.9 Hz), 6.94 (s, 1H), 7.19 (d, 1H, J = 7.8 Hz), 7.28 (d, 1H, J = 8.0 Hz), 7.41 (s, 1H), 7.54 (d, 1H, J = 7.9 Hz), 8.84 (d, 1H, J = 8.4 Hz); m/z: 457 [M + H]+ (calc. mass: 456). |
| 52 | 2-(1-hydroxy-2,3-dihydro-1H-inden-5-yl)-N-{[4-methyl-2-(piperidin-1-yl)phenyl](5-methylfuran-2-yl)methyl}acetamide | See FIG. 3AJ<br>The previously synthesized N-{[4-methyl-2-(piperidin-1-yl)phenyl](5-methylfuran-2-yl)methyl}-2-(1-oxo-2,3-dihydro-1H-inden-5-yl)acetamide Cpd. 51 (120 mg, 0.26 mmol) was dissolved in EtOH (10 mL). The solution was cooled to 0° C. and sodium borohydride (15 mg, 0.39 mmol) was added. The ice bath was removed and the solution was stirred at rt for 2 h. The solvent was removed under reduced pressure and citric acid 1N to neutralized the solution. The aqueous layer was extracted with CH2Cl2. The organic layer was dried over MgSO4, filtered and the solution was |

TABLE 2-continued

All the NMR were performed in DMSO-d6

| Cpd. | Starting compounds, Reaction conditions and purification Yield, MP, Appearance, $^1$H NMR (solvent) data, Mass (ES+ or ES−) data |
|---|---|
| | concentrated under reduced pressure to afford 2-(1-hydroxy-2,3-dihydro-1H-inden-5-yl)-N-{[4-methyl-2-(piperidin-1-yl)phenyl](5-methylfuran-2-yl)methyl}acetamide (83 mg, 67%) as white solid, mp: 97° C., 1H NMR (300 MHz, d in ppm): 1.35-1.55 (m, 6H), 1.67-1.82 (m, 1H), 2.17 (s, 3H), 2.25 (s, 3H), 2.27-2.34 (m, 1H), 2.50-2.70 (m, 3H), 2.73-2.91 (m, 3H), 3.43 (s, 2H), 4.97 (q, 1H, J = 6.2 Hz), 5.12 (d, 1H, J = 5.9 Hz), 5.80 (d, 1H, J = 2.9 Hz), 5.92 (dd, 1H, J = 2.9 Hz, J = 1.0 Hz), 6.48 (d, 1H, J = 9.8 Hz), 6.89 (d, 1H, J = 7.9 Hz), 6.93 (s, 1H), 7.02-7.06 (m, 2H), 7.19 (d, 2H, J = 7.8 Hz), 8.71 (d, 1H, J = 8.5 Hz); m/z: 459 [M + H]+ (calc. mass: 458). |
| 53  2-(3-hydroxy-1-methyl-2-oxo-2,3-dihydro-1H-indol-5-yl)-N-{[4-methyl-2-(piperidin-1-yl)phenyl](5-methylfuran-2-yl)methyl}acetamide | See FIG. 3AK 2-(1-methyl-2,3-dioxo-2,3-dihydro-1H-indol-5-yl)-N-{[4-methyl-2-(piperidin-1-yl)phenyl](5-methylfuran-2-yl)methyl}acetamide Cpd. 45 (15 mg, 0.03 mmol) was dissolved in EtOH (500 µL). The solution was cooled to 0° C. and sodium borohydride (1 mg, 0.04 mmol) was added. After 5 min at 0° C., the reaction was completed. The reaction was quenched with citric acid 1N. The solvent was removed under reduced pressure. EtOAc was added and the solution was washed with water. The organic layer was dried over MgSO4, filtered and the solution was concentrated under reduced pressure to afford 2-(3-hydroxy-1-methyl-2-oxo-2,3-dihydro-1H-indol-5-yl)-N-{[4-methyl-2-(piperidin-1-yl)phenyl](5-methylfuran-2-yl)methyl}acetamide (12 mg, 74%) as white solid, mp: 155° C., 1H NMR (300 MHz, d in ppm): 1.40-1.6 (m, 6H), 2.17 (s, 3H), 2.25 (s, 3H), 2.50-2.62 (m, 2H), 2.72-2.80 (m, 2H), 3.05 (s, 3H), 3.43 (s, 2H), 4.82-4.88 (m, 1H), 5.79-5.82 (m, 1H), 5.90-5.93 (m, 1H), 6.21 (dd, 1H, J = 7.6 Hz, J = 0.5 Hz), 6.48 (d, 1H, J = 8.7 Hz), 6.86 (d, 1H, J = 8.1 Hz), 6.87-6.92 (m, 1H), 6.94 (s, 1H), 7.14-7.21 (m, 2H), 7.23 (s, 1H), 8.72 (d, 1H, J = 8.5 Hz); m/z: 488 [M + H]+ (calc. mass: 487). |
| 54  N-{[4-methyl-2-(piperidin-1-yl)phenyl](5-methylfuran-2-yl)methyl}-2-(7-methyl-2-oxo-2,3-dihydro-1H-indol-5-yl)acetamide | From [4-methyl-2-(piperidin-1-yl)phenyl](5-methylfuran-2-yl)methanamine Ex. 16 and 2-(7-methyl-2-oxo-2,3-dihydro-1H-indol-5-yl)acetic acid Ex. 30 following protocol A, DMAP (1.0 equiv), EDCl•HCl (1.1 equiv), 2 h at rt, purification by silica gel column chromatography (Cyclohexane/EtOAc, 3:7), yield 30%, mp: 237° C., appearance: white solid 1H NMR (300 MHz, d in ppm): 1.40-1.60 (m, 6H), 2.13 (s, 3H), 2.17 (s, 3H), 2.25 (s, 3H), 2.50-2.60 (m, 2H), 2.72-2.82 (m, 2H), 3.34 (s, 2H), 3.41 (s, 2H), 5.80 (d, 1H, J = 2.8 Hz), 5.92 (dd, 1H, J = 3.0 Hz, J = 1.0 Hz), 6.47 (d, 1H, J = 8.4 Hz), 6.83 (s, 1H), 6.85-6.92 (m, 2H), 6.93 (s, 1H), 7.19 (d, 1H, J = 7.8 Hz), 8.66 (d, 1H, J = 8.5 Hz), 10.33 (s, 1H); m/z: 472 [M + H]+ (calc. mass: 471). |
| 55  N-{[4-methyl-2-(piperidin-1-yl)phenyl](5-methylfuran-2-yl)methyl}-2-[2-oxo-3-(propan-2-ylidene)-2,3-dihydro-1H-indol-5-yl]acetamide | From [4-methyl-2-(piperidin-1-yl)phenyl](5-methylfuran-2-yl)methanamine Ex. 16 and 2-[2-oxo-3-(propan-2-ylidene)-2,3-dihydro-1H-indol-5-yl]acetic acid Ex. 31 following protocol A, DMAP (2.2 equiv), EDCl•HCl (1.2 equiv), 18 h at rt, purification by silica gel column chromatography (CH2Cl2/MeOH, 98:2). The solid was triturated in EtOAc and filtered-off, yield 45%, mp: 172° C., appearance: white solid 1H NMR (300 MHz, d in ppm): 1.44-1.53 (m, 6H), 2.16 (s, 3H), 2.24 (s, 3H), 2.25 (s, 3H), 2.55-2.57 (m, 2H), 2.76-2.79 (m, 2H), 3.42 (s, 2H), 5.79 (d, 1H, J = 2.9 Hz), 5.92 (dd, 1H, J = 2.9 Hz, J = 1.0 Hz), 6.47 (d, 1H, J = 8.4 Hz), 6.70 (d, 1H, J = 7.9 Hz), 6.87 (d, 1H, J = 7.9 Hz), 6.93 (s, 1H), 7.03 (dd, 1H, J = 7.9 Hz, J = 1.2 Hz), 7.19 (d, 1H, J = 7.8 Hz), 7.44 (s, 1H), 8.71 (d, 1H, J = 8.5 Hz), 10.33 (s, 1H) (one CH3 group under the pic of DMSO-d6); m/z: 498 [M + H]+ (calc. mass: 497). |
| 56  N-[(5-chlorofuran-2-yl)(2,4-dimethylphenyl)methyl]-1-(2-methanesulfonyl-2,3-dihydro- | From (5-chlorofuran-2-yl)(2,4-dimethylphenyl)methanamine Ex. 23 and 1-(2-methanesulfonyl-2,3-dihydro-1H-isoindol-5-yl)cyclopropane-1-carboxylic acid Ex. 33 following protocol A, DMAP (1.0 equiv), EDCl•HCl (1.1 equiv), 18 h at rt, purification by silica gel column chromatography (Cyclohexane/EtOAc, 1:1), yield 52%, mp: 68° C., appearance: white solid |

TABLE 2-continued

All the NMR were performed in DMSO-d6

| Cpd. | Starting compounds, Reaction conditions and purification Yield, MP, Appearance, $^1$H NMR (solvent) data, Mass (ES+ or ES−) data |
|---|---|
| 1H-isoindol-5-yl)cyclopropane-1-carboxamide | 1H NMR (300 MHz, d in ppm): 0.98-1.02 (m, 2H), 1.31-1.35 (m, 2H), 2.17 (s, 3H), 2.23 (s, 3H), 2.95 (s, 3H), 4.86 (s, 4H), 5.99 (dd, 1H, J = 3.3 Hz, J = 1.1 Hz), 6.18 (d, 1H, J = 8.2 Hz), 6.36 (d, 1H, J = 3.3 Hz), 6.97 (m, 3H), 7.27 (m, 3H), 7.86 (d, 1H); m/z: 499 [M + H]+ (calc. mass: 498)." |
| 57 2-[3-(2-hydroxyethyl)-1H-indol-5-yl]-N-{[4-methyl-2-(piperidin-1-yl)phenyl](5-methylfuran-2-yl)methyl}acetamide | From [4-methyl-2-(piperidin-1-yl)phenyl](5-methylfuran-2-yl)methanamine Ex. 16 and 2-[3-(2-hydroxyethyl)-1H-indol-5-yl]acetic acid Ex. 34 following protocol A, DMAP (1.0 equiv), EDCl•HCl (1.1 equiv), 18 h at rt, purification by silica gel column chromatography (CH2Cl2/MeOH, 98:2), yield 79%, mp: 80° C., appearance: white solid 1H NMR (300 MHz, d in ppm): 1.34-1.64 (m, 6H), 2.16 (s, 3H), 2.24 (s, 3H), 2.50-2.60 (m, 2H), 2.72-2.85 (m, 4H), 3.49 (s, 2H), 3.58-3.66 (m, 2H), 4.60 (t, 1H, J = 5.3 Hz), 5.81 (dd, 1H, J = 3.0 Hz), 5.91 (d, 1H, J = 3.0 Hz, J = 1.0 Hz), 6.48 (d, 1H, J = 8.6 Hz), 6.88 (d, 1H, J = 7.9 Hz), 6.92 (s, 1H), 6.95 (dd, 1H, J = 8.4 Hz, J = 1.5 Hz), 7.08 (d, 1H, J = 2.2 Hz), 7.20 (d, 1H, J = 8.2 Hz), 7.21 (d, 1H, J = 7.8 Hz), 7.36 (s, 1H), 8.65 (d, 1H, J = 8.4 Hz), 10.66 (s, 1H); m/z: 486 [M + H]+ (calc. mass: 485). |
| 58 2-[3-(hydroxymethyl)-1H-indol-5-yl]-N-{[4-methyl-2-(piperidin-1-yl)phenyl](5-methylfuran-2-yl)methyl}acetamide | See FIG. 3AL Step 1: to a solution of 2-(3-formyl-1H-indol-5-yl)acetic acid (200 mg, 0.98 mmol) in DMF (3 mL) were added DMAP (265 mg, 2.17 mmol), EDCl•HCl (208 mg, 1.08 mmol) and the [4-methyl-2-(piperidin-1-yl)phenyl](5-methylfuran-2-yl)methanamine Ex. 16 (280 mg, 0.98 mmol). The reaction mixture was stirred at rt. After completion of the reaction (monitored by TLC), sat. NH4Cl was added and the solution was extracted with EtOAc. The combined organic layer were washed with sat. NH4Cl, dried over MgSO4, filtered and the solution was concentrated under reduced pressure. The crude material was purified by silica gel column chromatography eluting with CH2Cl2/MeOH (98:2) to give 2-(3-formyl-1H-indol-5-yl)-N-((4-methyl-2-(piperidin-1-yl)phenyl)(5-methylfuran-2-yl)methyl)acetamide (377 mg, 82%) as pale yellow solid. 1H NMR (300 MHz, DMSO-d6, d in ppm): 1.42-1.53 (m, 6H), 2.15 (s, 3H), 2.24 (s, 3H), 2.49-2.52 (m, 2H), 2.72-2.79 (m, 2H), 3.54 (s, 2H), 5.82 (d, 1H, J = 2.5 Hz), 5.91 (dd, 1H, J = 2.9 Hz, J = 1.0 Hz), 6.46 (d, 1H, J = 8.4 Hz), 6.88 (d, 1H, J = 7.9 Hz), 6.92 (s, 1H), 7.16 (dd, 1H, J = 8.3 Hz, J = 1.7 Hz), 7.20 (d, 1H, J = 7.8 Hz), 7.38 (d, 1H, J = 8.3 Hz), 8.00 (d, 1H, J = 1.0 Hz), 8.23 (s, 1H), 8.75 (d, 1H, J = 8.5 Hz), 9.89 (s, 1H), 12.05 (br(s), 1H). Step 2: to a previously synthesized 2-(3-formyl-1H-indol-5-yl)-N-((4-methyl-2-(piperidin-1-yl)phenyl)(5-methylfuran-2-yl)methyl)acetamide (100 mg, 0.21 mmol) in anhydrous MeOH (2 mL) was added sodium borohydride (24 mg, 0.64 mmol). The reaction mixture was stirred at rt for 4 h. The reaction was partitioned between water and EtOAc. The pH of the aqueous layer was ajusted to pH = 7-8 with a solution of 10% citric acid. The aqueous phase was extracted with EtOAc. The organic layer was dried over MgSO4, filtered and the solution was concentrated to dryness. The crude material was purified by silica gel column chromatography eluting with CH2Cl2/EtOAc (50:50), yield 50%, mp: 99° C., appearance: white solid 1H NMR (300 MHz, DMSO-d6 in ppm): 1.40-1.65 (m, 6H), 2.16 (s, 3H), 2.24 (s, 3H), 2.5-2.6 (m, 2H), 2.75-2.85 (m, 2H), 3.50 (s, 2H), 4.58 (d, 2H, J = 5.2 Hz), 4.66 (t, 1H, J = 1.2 Hz), 5.81 (d, 1H, J = 2.7 Hz), 5.90-5.95 (m, 1H), 6.47 (d, 1H, J = 8.4 Hz), 6.88 (d, 1H, J = 7.9 Hz), 6.92 (s, 1H), 6.98 (dd, 1H, J = 8.3 Hz, J = 1.6 Hz), 7.10-7.30 (m, 3H), 7.44 (s, 1H), 8.65 (d, 1H, J = 8.5 Hz), 10.74 (s, 1H); m/z: 472 [M + H]+ (calc. mass: 471). |
| 59 N-[(2,4-dimethylphenyl)(5-methylfuran-2-yl)methyl]-1-(3-oxo-3,4-dihydro-2H-1,4-benzoxazin-7-yl)cyclopropane-1-carboxamide | From (2,4-dimethylphenyl)(5-methylfuran-2-yl)methanamine Ex. 19 and 1-(3-oxo-3,4-dihydro-2H-1,4-benzoxazin-7-yl)cyclopropane-1-carboxylic acid Ex. 35 following protocol A, DMAP (1 equiv), EDCl•HCl (1.1 equiv), 2 h at rt. Sat. NH4Cl was added to quench the reaction. The solid formed was collected by filtration and dried until constant weight, yield 73%, mp: 89° C., appearance: white solid 1H NMR (300 MHz, DMSO-d6 in ppm): 0.92-0.99 (m, 2H), 1.21-1.33 (m, 2H), 2.16 (s, 3H), 2.17 (s, 3H), 2.22 (s, |

TABLE 2-continued

All the NMR were performed in DMSO-d6

| Cpd. | Starting compounds, Reaction conditions and purification Yield, MP, Appearance, $^1$H NMR (solvent) data, Mass (ES+ or ES−) data |
|---|---|
| | 3H), 4.55 (s, 2H), 5.76 (d, 1H, J = 3.1 Hz), 5.94 (dd, 1H, J = 3.0 Hz, J = 1.1 Hz), 6.12 (d, 1H, J = 8.2 Hz), 6.83 (d, 1H, J = 8.6 Hz), 6.90-6.96 (m, 5H), 7.45 (d, 1H, J = 8.2 Hz), 10.71 (s, 1H); m/z: 453 [M + Na]+ (calc. mass: 430). |
| 60 N-[(2,4-dimethylphenyl)(5-methylfuran-2-yl)methyl]-1-[3-(2-hydroxyethyl)-1H-indol-5-yl]cyclopropane-1-carboxamide | From (2,4-dimethylphenyl)(5-methylfuran-2-yl)methanamine Ex. 19 and 1-[3-(2-hydroxyethyl)-1H-indol-5-yl]cyclopropane-1-carboxylic acid Ex. 36 following protocol A, DMAP (1 equiv), EDCl•HCl (1.1 equiv), 2 h at rt, purification by silica gel column chromatography (CH2Cl2/EtOAc, 80:20), yield 53%, mp: 77° C., appearance: white solid 1H NMR (300 MHz, DMSO-d6, d in ppm): 0.99-1.10 (m, 2H), 1.29-1.42 (m, 2H), 2.12 (s, 3H), 2.14 (s, 3H), 2.20 (s, 3H), 2.82 (t, 2H, J = 7.3 Hz), 3.57-3.66 (m, 2H), 4.60 (t, 1H, J = 5.4 Hz), 5.74 (d, 1H, J = 3.4 Hz), 5.89 (dd, 1H, J = 3.0 Hz, J = 1.1 Hz), 6.08 (d, 1H, J = 8.3 Hz), 6.65 (d, 1H, J = 8.5 Hz), 6.77 (d, 1H, J = 7.8 Hz), 6.90 (d, 1H, J = 8.0 Hz), 6.94 (s, 1H), 7.07 (dd, 1H, J = 8.3 Hz, J = 1.7 Hz), 7.15 (d, 1H, J = 2.2 Hz), 7.32 (d, 1H, J = 8.3 Hz), 7.53 (d, 1H, J = 1.4 Hz), 10.84 (d, 1H, J = 1.5 Hz); -m/z: 465 [M + Na]+ (calc. mass: 442). |
| 61 N-[(2,4-dimethylphenyl)(5-methylfuran-2-yl)methyl]-1-(2-oxo-2,3-dihydro-1H-indol-5-yl)cyclopropane-1-carboxamide | From (2,4-dimethylphenyl)(5-methylfuran-2-yl)methanamine Ex. 19 and 1-(2-oxo-2,3-dihydro-1H-indol-5-yl)cyclopropane-1-carboxylic acid Ex. 37 following protocol A, DMAP (1.1 equiv), EDCl•HCl (1.1 equiv), over the weekend at rt, purification by silica gel column chromatography (CH2Cl2/EtOAc, 70:30), yield 67%, mp: 85° C., appearance: pale brown solid 1H NMR (300 MHz, DMSO-d6, d in ppm): 0.88-1.01 (m, 2H), 1.21-1.36 (m, 2H), 2.15 (s, 3H), 2.16 (s, 3H), 2.22 (s, 3H), 3.44 (s, 2H), 5.76 (d, 1H, J = 2.9 Hz), 5.93 (dd, 1H, J = 3.0 Hz, J = 1.1 Hz), 6.11 (d, 1H, J = 8.4 Hz), 6.77 (d, 1H, J = 7.9 Hz), 6.88-7.00 (m, 3H), 7.12-7.23 (m, 3H), 10.39 (br(s), 1H); -m/z: 437 [M + Na]+ (calc. mass: 414). |
| 62 N-[(5-chlorofuran-2-yl)(2,4-dimethylphenyl)methyl]-1-[3-(2-hydroxyethyl)-1H-indol-5-yl]cyclopropane-1-carboxamide | From (5-chlorofuran-2-yl)(2,4-dimethylphenyl)methanamine Ex. 32 and 1-[3-(2-hydroxyethyl)-1H-indol-5-yl]cyclopropane-1-carboxylic acid Ex. 36 following protocol A, DMAP (1.1 equiv), EDCl•HCl (1.1 equiv), 2 h at rt, purification by silica gel column chromatography (CH2Cl2/EtOAc, 80:20), yield 63%, mp: 70° C., appearance: white solid 1H NMR (300 MHz, DMSO-d6, d in ppm): 0.97-1.11 (m, 2H), 1.28-1.42 (m, 2H), 2.15 (s, 3H), 2.21 (s, 3H), 2.82 (t, 2H, J = 7.3 Hz), 3.58-3.65 (m, 2H), 4.59 (t, 1H, J = 5.4 Hz), 6.00 (dd, 1H, J = 3.3 Hz, J = 1.1 Hz), 6.14 (d, 1H, J = 8.4 Hz), 6.33 (d, 1H, J = 3.3 Hz), 6.81 (d, 1H, J = 7.8 Hz), 6.92 (d, 1H, J = 7.9 Hz), 6.96 (s, 1H), 7.00 (d, 1H, J = 8.3 Hz), 7.06 (dd, 1H, J = 8.3 Hz, J = 1.7 Hz), 7.14 (d, 1H, J = 2.3 Hz), 7.30 (d, 1H, J = 8.3 Hz), 7.52 (s, 1H), 10.82 (s, 1H); m/z: 485 [M + Na]+, 487 [M + Na]+ (calc. mass: 462). |
| 63 N-[(2,4-dimethylphenyl)(5-methylfuran-2-yl)methyl]-1-(2,2-dioxo-1,3-dihydro-2,1-benzothiazol-5-yl)cyclopropane-1-carboxamide | From (2,4-dimethylphenyl)(5-methylfuran-2-yl)methanamine Ex. 19 and 1-(2,2-dioxo-1,3-dihydro-2,1-benzothiazol-5-yl)cyclopropane-1-carboxylic acid Ex. 38 following protocol A, DMAP (1 equiv), EDCl•HCl (1.1 equiv), 2 h at rt, purification by silica gel column chromatography (Cyclohexane/EtOAc, 70:30), yield 19%, mp: 97° C., appearance: white solid 1H NMR (300 MHz, DMSO-d6, d in ppm): 0.92-1.02 (m, 2H), 1.26-1.36 (m, 2H), 2.15 (s, 3H), 2.17 (s, 3H), 2.22 (s, 3H), 4.47 (s, 2H), 5.75 (d, 1H, J = 3.0 Hz), 5.93 (dd, 1H, J = 3.0 Hz, J = 1.0 Hz), 6.11 (d, 1H, J = 8.2 Hz), 6.77 (d, 1H, J = 8.0 Hz), 6.91-6.98 (m, 3H), 7.22 (dd, 1H, J = 8.2 Hz, J = 1.9 Hz), 7.25 (s, 1H), 7.43 (d, 1H, J = 8.6 Hz), 10.28 (br(s), 1H); m/z: 473 [M + Na]+ (calc. mass: 450). |
| 64 2-(3-methyl-1H-indol-5-yl)-N-{[4-methyl-2-(piperidin-1-yl)phenyl](5-methylfuran-2-yl)methyl}acetamide | From [4-methyl-2-(piperidin-1-yl)phenyl](5-methylfuran-2-yl)methanamine Ex. 16 and 2-(3-methyl-1H-indol-5-y)acetic acid Ex. 39 following protocol A, DMAP (2.2 equiv), EDCl•HCl (1.2 equiv), overnight at rt, purification by silica gel column chromatography (Cyclohexane/EtOAc, 70:30), yield 53%, mp: 68° C., appearance: white solid 1H NMR (300 MHz, DMSO-d6, d in ppm): 1.39-1.55 (m, 6H), 2.16 (s, 3H), 2.20 (d, 3H, J = 1.0 Hz), 2.24 (s, 3H), 2.54-2.57 (m, 2H), 2.77-2.80 (m, 2H), 3.50 (s, 2H), 5.81 (d, 1H, J = 2.7 Hz), 5.91 (dd, 1H, J = 3.0 Hz, J = 1.0 Hz), 6.49 (d, 1H, |

TABLE 2-continued

All the NMR were performed in DMSO-d6

| Cpd. | Starting compounds,<br>Reaction conditions and purification<br>Yield, MP, Appearance, $^1$H NMR (solvent) data, Mass (ES+ or ES−) data |
|---|---|
| | J = 8.5 Hz), 6.88 (d, 1H, J = 7.8 Hz), 6.93 (s, 1H), 6.96 (dd, 1H, J = 8.3 Hz, J = 1.6 Hz), 7.03-7.04 (m, 1H), 7.19 (dd, 1H, J = 8.3 Hz, J = 0.5 Hz), 7.21 (d, 1H, J = 7.8 Hz), 7.31 (s, 1H), 8.66 (d, 1H, J = 8.6 Hz), 10.59 (br(s), 1H); m/z: 456 [M + H]+ (calc. mass: 455). |
| 65 N-[(2,4-dimethylphenyl)(5-methylfuran-2-yl)methyl]-1-(2-methanesulfonyl-2,3-dihydro-1H-isoindol-5-yl)cyclopropane-1-carboxamide | From (2,4-dimethylphenyl)(5-methylfuran-2-yl)methanamine Ex. 19 and 1-(2-methanesulfonyl-2,3-dihydro-1H-isoindol-5-yl)cyclopropane-1-carboxylic acid Ex. 33 following protocol A, DMAP (1 equiv), EDCl•HCl (1.1 equiv), 2 h at rt, no purification was needed, yield 66%, mp: 67° C., appearance: off-white solid<br>1H NMR (300 MHz, DMSO-d6, d in ppm): 0.95-1.05 (m, 2H), 1.28-1.39 (m, 2H), 2.16 (s, 3H), 2.17 (s, 3H), 2.22 (s, 3H), 2.95 (s, 3H), 4.59 (s, 4H), 5.76 (d, 1H, J = 2.8 Hz), 5.94 (dd, 1H, J = 3.0 Hz, J = 1.0 Hz), 6.14 (d, 1H, J = 8.2 Hz), 6.90-6.99 (m, 3H), 7.25-7.33 (m, 3H), 7.53 (d, 1H, J = 8.3 Hz); m/z: 501 [M + Na]+ (calc. mass: 478). |
| 66 1-[3-(2-hydroxyethyl)-1H-indol-5-yl]-N-{[4-methyl-2-(piperidin-1-yl)phenyl](5-methylfuran-2-yl)methyl}cyclopropane-1-carboxamide | From [4-methyl-2-(piperidin-1-yl)phenyl](5-methylfuran-2-yl)methanamine Ex. 16 and 1-[3-(2-hydroxyethyl)-1H-indol-5-yl]cyclopropane-1-carboxylic acid Ex. 36 following protocol A, DMAP (2.2 equiv), EDCl•HCl (1.2 equiv), overnight at rt, purification by silica gel column chromatography (CH2Cl2/MeOH from [97:3] to [95:5]), yield 39%, mp: 95° C., appearance: white solid<br>1H NMR (300 MHz, DMSO-d6, d in ppm): 0.95-1.05 (m, 2H), 1.05-1.64 (m, 6H), 1.29-1.35 (m, 1H), 1.35-1.45 (m, 1H), 2.08 (s, 3H), 2.21 (s, 3H), 2.25-2.35 (m, 2H), 2.5-2.55 (m, 2H), 2.81 (t, 2H, J = 7.5 Hz), 3.59 (q, 2H, J = 5.3 Hz), 4.60 (t, 1H, J = 5.2 Hz), 5.81 (dd, 1H, J = 2.9 Hz), 5.91 (d, 1H, J = 3.1 Hz, J = 1.1 Hz), 6.30 (d, 1H, J = 8.9 Hz), 6.77 (d, 1H, J = 8.5 Hz), 6.83 (d, 1H, J = 8.0 Hz), 6.90 (d, 1H, J = 7.7 Hz), 6.94 (s, 1H), 7.09 (dd, 1H, J = 9.9 Hz, J = 1.5 Hz), 7.15 (d, 1H, J = 2.3 Hz), 7.31 (d, 1H, J = 8.3 Hz), 7.51 (s, 1H), 10.83 (br(s), 1H); m/z: 512 [M + H]+ (calc. mass: 511). |
| 67 N-{[4-methyl-2-(piperidin-1-yl)phenyl](5-methylfuran-2-yl)methyl}-2-(3-oxo-2,3-dihydro-1H-inden-5-yl)acetamide | From [4-methyl-2-(piperidin-1-yl)phenyl](5-methylfuran-2-yl)methanamine Ex. 16 and 2-(3-oxo-2,3-dihydro-1H-inden-5-yl)acetic acid Ex. 51 following protocol A, DMAP (1 equiv), EDCl•HCl (1.1 equiv), overnight at rt, purification by silica gel column chromatography (Cyclohexane/EtOAc, 70:30), yield 49%, mp: 71° C., appearance: white solid<br>1H NMR (300 MHz, DMSO-d6, d in ppm): 1.40-1.63 (m, 6H), 2.17 (s, 3H), 2.25 (s, 3H), 2.53-2.65 (m, 4H), 2.70-2.84 (m, 2H), 3.05 (t, 2H, J = 5.7 Hz), 3.55 (s, 2H), 5.81 (d, 1H, J = 3.4 Hz), 5.92 (dd, 1H, J = 3.0 Hz, J = 1.0 Hz), 6.48 (d, 1H, J = 8.3 Hz), 6.88 (d, 1H, J = 8.0 Hz), 6.93 (s, 1H), 7.17 (d, 1H, J = 7.8 Hz), 7.46-7.56 (m, 3H), 8.79 (d, 1H, J = 8.3 Hz); m/z: 457 [M + H]+ (calc. mass: 456). |
| 68 N-[(2-bromo-4-methylphenyl)(5-methylfuran-2-yl)methyl]-2-[1-(oxan-4-ylmethyl)-2,2-dioxo-1,3-dihydro-2,1-benzothiazol-5-yl]acetamide | From (2-bromo-4-methylphenyl)(5-methylfuran-2-yl)methanamine Ex. 18 and 2-[1-(oxan-4-ylmethyl)-2,2-dioxo-1,3-dihydro-2,1-benzothiazol-5-yl]acetic acid Ex. 95 following protocol A, substituted amine (0.9 equiv), DMAP (1.1 equiv), EDCl•HCl (2.2 equiv), 8 h at rt, purification by silica gel column chromatography (Cyclohexane/EtOAc, 50:50), yield 69%, mp: 92° C., appearance: yellowish solid<br>1H NMR (300 MHz, DMSO-d6, d in ppm): 2.15 (s, 3H), 2.18 (s, 3H), 2.22 (s, 3H), 3.41 (s, 2H), 3.63 (s, 2H), 4.85 (s, 2H), 5.81 (d, 1H, J = 2.9 Hz), 5.95 (q, 1H, J = 3.0 Hz, J = 1.1 Hz), 6.08 (d, 1H, J = 8.6 Hz), 6.75 (d, 1H, J = 8.1 Hz), 6.85-6.95 (m, 2H), 7.15-7.25 (m, 2H), 8.93 (d, 1H, J = 8.3 Hz); m/z: 609 [M + Na]+, 611 [M + Na]+ (calc. mass: 586). |
| 69 N-[(2,4-dimethylphenyl)(5-methylfuran-2-yl)methyl]-1-[1-(2-hydroxyethyl)-1H-indol-5-yl]cyclopropane-1-carboxamide | See FIG. 3AM<br>Step 1: To a solution of 1-{1-[2-(benzyloxy)ethyl]-2,3-dihydro-1H-indol-5-yl}cyclopropane-1-carboxylic acid Ex. 41 (150 mg, 0.45 mmol) in DMF (2 mL) were added DMAP (65 mg, 0.53 mmol), EDCl•HCl (102 mg, 0.53 mmol) and (2,4-dimethylphenyl)(5-methylfuran-2-yl)methanamine Ex. 19 (112 mg, 0.45 mmol). The reaction mixture was stirred at rt for 4 h. Brine was added and the solution was extracted with EtOAc. The organic layer was dried over MgSO4, filtered and the solution was evaporated to dryness. The crude material was purified by silica gel column chromatography eluting with a gradient of cyclohexane/EtOAc from [90:10] to [85:15]. The product fractions were collected and |

TABLE 2-continued

All the NMR were performed in DMSO-d6

| Cpd. | Starting compounds,<br>Reaction conditions and purification<br>Yield, MP, Appearance, $^1$H NMR (solvent) data, Mass (ES+ or ES−) data |
|---|---|
| | evaporated under reduced pressure affording 1-{1-[2-(benzyloxy)ethyl]-2,3-dihydro-1H-indol-5-yl}-N-[(2,4-dimethylphenyl)(5-methylfuran-2-yl)methyl]cyclopropane-1-carboxamide (180 mg, 76%) as white solid. 1H NMR (300 MHz, DMSO-d6, d in ppm): 0.85-0.95 (m, 2H), 1.15-1.35 (m, 2H), 2.14 (s, 6H), 2.21 (s, 3H), 2.86 (t, 2H, J = 7.8 Hz), 3.24 (t, 2H, J = 5.8 Hz), 3.38 (t, 2H, J = 9.2 Hz), 3.62 (t, 2H, J = 5.6 Hz), 4.49 (s, 2H), 5.78 (d, 1H, J = 3.2 Hz), 5.92 (dd, 1H, J = 3.1 Hz, J = 1.1 Hz), 6.05 (d, 1H, J = 8.4 Hz), 6.45 (d, 1H, J = 8.1 Hz), 6.75-6.80 (m, 2H), 6.80-7.05 (m, 4H), 7.20-7.40 (m, 5H).<br>Step 2: 1-{1-[2-(benzyloxy)ethyl]-2,3-dihydro-1H-indol-5-yl}-N-[(2,4-dimethylphenyl)(5-methylfuran-2-yl)methyl]cyclopropane-1-carboxamide (180 mg, 0.34 mmol) was dissolved in MeOH (10 mL). A few amount of 5% Pd/C was added to the solution and the reaction was stirred under H2 atmosphere at rt for 4 h. TLC showed small evolution of the reaction. The reaction mixture was heated at 50° C. After 1 h, LCMS showed two products (starting material and the expected molecule). The heating was kept overnight. LCMS showed no change. The catalyst was removed by filtration. The solvent was evaporated to dryness. The residue was diluted with THF (10 mL) and few amount of 5% Pd/C was added to the solution. The reaction mixture was stirred at rt over the weekend. LCMS showed formation of by-products and the expected molecule. The catalyst was removed by filtration and the solvent was concentrated under reduced pressure. After analysis by LCMS, the expected molecule was found in few amount (444 [M + H]+) and a new compound appeared with a mass of 465 [M + Na]+ which correspond to the oxidation of the indoline moiety to the corresponding indole. This compound was isolated by preparative HPLC and characterized by NMR to afford N-[(2,4-dimethylphenyl)(5-methylfuran-2-yl)methyl]-1-[1-(2-hydroxyethyl)-1H-indol-5-yl]cyclopropane-1-carboxamide (4 mg, 3%) as white solid., yield 0, %, mp: 74° C., appearance: white solid<br>1H NMR (300 MHz, DMSO-d6, d in ppm): 1.02 (d, 2H, J = 3.2 Hz), 1.23 (m, 2H), 2.12 (s, 3H), 2.20 (s, 3H), 3.68 (q, 2H, J = 5.6 Hz), 4.19 (t, 2H, J = 5.7 Hz), 4.85 (t, 1H, J = 5.3 Hz), 5.76 (d, 1H, J = 2.8 Hz), 5.90 (q, 1H, J = 3.1 Hz, J = 1.1 Hz), 6.09 (d, 1H, J = 8.4 Hz), 6.39 (d, 1H, J = 3.1 Hz), 6.74 (d, 1H, J = 8.6 Hz), 6.79 (d, 1H, J = 7.7 Hz), 6.85-6.95 (m, 2H), 7.14 (dd, 1H, J = 8.5 Hz, J = 1.7 Hz), 7.36 (d, 1H, J = 3.1 Hz), 7.47 (d, 1H, J = 8.6 Hz), 7.55 (d, 1H, J = 1.3 Hz); m/z: (calc. mass: 442). |
| 70 N-[(2,4-dimethylphenyl)(5-methylfuran-2-yl)methyl]-1-(1-methyl-2,2-dioxo-1,3-dihydro-2,1-benzothiazol-5-yl)cyclopropane-1-carboxamide | From (2,4-dimethylphenyl)(5-methylfuran-2-yl)methanamine Ex. 19 and 1-(1-methyl-2,2-dioxo-1,3-dihydro-2,1-benzothiazol-5-yl)cyclopropane-1-carboxylic acid Ex. 40 following protocol A, DMAP (1.2 equiv), EDCl•HCl (2.2 equiv), 8 h at rt, purification by silica gel column chromatography (Cyclohexane/EtOAc, 80:20) followed by a second purification by silica gel column chromatography (CH2Cl2/MeOH, 98:2), yield 58%, mp: 70° C., appearance: white solid<br>1H NMR (300 MHz, DMSO-d6, d in ppm): 0.98 (d, 2H, J = 2.8 Hz), 1.25-1.35 (m, 2H), 2.16 (s, 3H), 2.17 (s, 3H), 2.22 (s, 3H), 3.02 (s, 3H), 4.60 (s, 2H), 5.76 (d, 1H, J = 3.2 Hz), 5.93 (q, 1H, J = 3.3 Hz, J = 1.3 Hz), 6.12 (d, 1H, J = 8.3 Hz), 6.91 (d, 1H, J = 8.3 Hz), 6.95 (s, 3H), 7.25-7.35 (m, 2H), 7.51 (d, 1H, J = 8.4 Hz); m/z: 465 [M + H]+ (calc. mass: 464). |
| 71 N-{[2-(dimethylamino)-4-methylphenyl](5-methylfuran-2-yl)methyl}-1-(2,2-dioxo-1,3-dihydro-2,1-benzothiazol-5-yl)cyclopropane-1-carboxamide | From 2-[amino(5-methylfuran-2-yl)methyl]-N,N,5-trimethylaniline Ex. 42 and 1-(2,2-dioxo-1,3-dihydro-2,1-benzothiazol-5-yl)cyclopropane-1-carboxylic acid Ex. 38 following protocol A, DMAP (1 equiv), EDCl•HCl (1.1 equiv), 2 h at rt, purification by silica gel column chromatography (Cyclohexane/EtOAc, 70:30), yield 31%, mp: 107° C., appearance: white solid<br>1H NMR (300 MHz, DMSO-d6, d in ppm): 0.88-1.04 (m, 2H), 1.27-1.39 (m, 2H), 2.13 (s, 3H), 2.18 (s, 6H), 2.23 (s, 3H), 4.49 (s, 2H), 5.79 (dd, 1H, J = 2.9 Hz, J = 0.8 Hz), 5.92 (dd, 1H, J = 3.0 Hz, J = 1.0 Hz), 6.19 (d, 1H, J = 8.5 Hz), 6.82 (d, 1H, J = 8.3 Hz), 6.88 (dd, 1H, J = 7.7 Hz, J = 1.0 Hz), 7.00 (d, 1H, |

TABLE 2-continued

All the NMR were performed in DMSO-d6

| Cpd. | Starting compounds,<br>Reaction conditions and purification<br>Yield, MP, Appearance, $^1$H NMR (solvent) data, Mass (ES+ or ES−) data |
|---|---|
| | J = 0.6 Hz), 7.12 (d, 1H, J = 7.8 Hz), 7.27-7.34 (m, 2H), 7.97 (d, 1H, J = 8.7 Hz), 10.55 (br(s), 1H); m/z: 480 [M + H]+ (calc. mass: 479). |
| 72 N-[(5-chlorofuran-2-yl)(2,4-dimethylphenyl)methyl]-1-(2,2-dioxo-1,3-dihydro-2-benzothiophen-5-yl)cyclopropane-1-carboxamide | From (5-chlorofuran-2-yl)(2,4-dimethylphenyl)methanamine Ex. 32 and 1-(2,2-dioxo-1,3-dihydro-2-benzothiophen-5-yl)cyclopropane-1-carboxylic acid Ex. 43 following protocol A, DMAP (1 equiv), EDCl•HCl (1.1 equiv), overnight at rt, purification by silica gel column chromatography (Cyclohexane/EtOAc, 70:30), yield 57%, mp: 80° C., appearance: white solid<br>1H NMR (300 MHz, DMSO-d6, d in ppm): 0.97-1.11 (m, 2H), 1.30-1.38 (m, 2H), 2.17 (s, 3H), 2.23 (s, 3H), 4.44 (s, 2H), 4.46 (s, 2H), 6.00 (dd, 1H, J = 3.3 Hz, J = 0.9 Hz), 6.18 (d, 1H, J = 8.3 Hz), 6.35 (d, 1H, J = 3.3 Hz), 6.93-7.02 (m, 3H), 7.26-7.36 (m, 3H), 8.06 (d, 1H, J = 8.3 Hz); m/z: 492 [M + Na]+, 494 [M + Na]+ (calc. mass: 469). |
| 73 1-(2-methanesulfonyl-2,3-dihydro-1H-isoindol-5-yl)-N-{[4-methyl-2-(pyrrolidin-1-yl)phenyl](5-methylfuran-2-yl)methyl}cyclopropane-1-carboxamide | From [4-methyl-2-(pyrrolidin-1-yl)phenyl](5-methylfuran-2-yl)methanamine Ex. 44 and 1-(2-methanesulfonyl-2,3-dihydro-1H-isoindol-5-yl)cyclopropane-1-carboxylic acid Ex. 33 following protocol A, DMAP (1 equiv), EDCl•HCl (1.1 equiv), 2 h at rt, purification by silica gel column chromatography (Cyclohexane/EtOAc, 70:30), yield 43%, mp: 84° C., appearance: pale brown solid<br>1H NMR (300 MHz, DMSO-d6, d in ppm): 0.94-1.04 (m, 2H), 1.27-1.38 (m, 2H), 1.54-1.72 (m, 4H), 2.14 (s, 3H), 2.22 (s, 3H), 2.54-2.64 (m, 2H), 2.70-2.84 (m, 2H), 2.96 (s, 3H), 4.46-4.71 (m, 4H), 5.78 (dd, 1H, J = 3.0 Hz, J = 0.8 Hz), 5.93 (dd, 1H, J = 3.0 Hz, J = 1.0 Hz), 6.23 (d, 1H, J = 8.3 Hz), 6.78 (d, 1H, J = 7.9 Hz), 6.91 (s, 1H), 7.04 (d, 1H, J = 7.8 Hz), 7.30-7.35 (m, 3H), 7.47 (d, 1H, J = 8.6 Hz); m/z: 534 [M + H]+ (calc. mass: 533). |
| 74 N-[(2,4-dimethylphenyl)(5-methylfuran-2-yl)methyl]-1-(2,2-dioxo-1,3-dihydro-2-benzothiophen-5-yl)cyclopropane-1-carboxamide | From (2,4-dimethylphenyl)(5-methylfuran-2-yl)methanamine Ex. 19 and 1-(2,2-dioxo-1,3-dihydro-2-benzothiophen-5-yl)cyclopropane-1-carboxylic acid Ex. 43 following protocol A, DMAP (1 equiv), EDCl•HCl (1.1 equiv), 2 h at rt. Sat. NH4Cl was added to quench the reaction. The solid formed was collected by filtration and dried until constant weight, yield 60%, mp: 74° C., appearance: white solid<br>1H NMR (300 MHz, DMSO-d6, d in ppm): 0.97-1.07 (m, 2H), 1.29-1.39 (m, 2H), 2.16 (s, 3H), 2.18 (s, 3H), 2.22 (s, 3H), 4.44 (s, 2H), 4.46 (s, 2H), 5.76 (d, 1H, J = 3.1 Hz), 5.94 (dd, 1H, J = 3.1 Hz, J = 1.0 Hz), 6.13 (d, 1H, J = 8.3 Hz), 6.91-7.00 (m, 3H), 7.30-7.36 (m, 3H), 7.74 (d, 1H, J = 8.3 Hz); m/z: 472 [M + Na]+ (calc. mass: 449). |
| 75 2-(2-methyl-1H-1,3-benzodiazol-5-yl)-N-{[4-methyl-2-(piperidin-1-yl)phenyl](phenyl)methyl}acetamide | From [4-methyl-2-(piperidin-1-yl)phenyl](phenyl)methanamine Ex. 1 and 2-(2-methyl-1H-1,3-benzodiazol-5-yl)acetic acid Ex. 45 following protocol B, substituted amine (1 equiv), substituted acid (1 equiv), PyBOP (1 equiv) and triethylamine (3 equiv), 100° C. for 20 min under microwave irradiation, purification by silica gel column chromatography (CH2Cl2/MeOH, 97:3). The residue was triturated in diethyl ether and filtered-off, yield 7%, mp: 137° C., appearance: white solid<br>1H NMR (300 MHz, DMSO-d6, d in ppm): 1.44-1.74 (m, 6H), 2.24 (s, 3H), 2.46-2.50 (m, 5H), 2.78-2.88 (m, 2H), 3.59 (s, 2H), 6.56 (d, 1H, J = 8.4 Hz), 6.87 (d, 1H, J = 7.1 Hz), 6.94 (s, 1H), 7.03 (d, 1H, J = 8.4 Hz), 7.12-7.35 (m, 8H), 8.70 (d, 1H, J = 8.7 Hz), 12.20 (br(s), 1H); m/z: 453 [M + H]+ (calc. mass: 452). |
| 76 N-{[2-(dimethylamino)-4-methylphenyl](5-methylfuran-2-yl)methyl}-1-(2-methanesulfonyl-2,3-dihydro-1H-isoindol-5-yl)cyclopropane-1-carboxamide | From 2-[amino(5-methylfuran-2-yl)methyl]-N,N,5-trimethylaniline Ex. 42 and 1-(2-methanesulfonyl-2,3-dihydro-1H-isoindol-5-yl)cyclopropane-1-carboxylic acid Ex. 33 following protocol A, DMAP (1 equiv), EDCl•HCl (1.1 equiv), 2 h at rt, purification by silica gel column chromatography (Cyclohexane/EtOAc, 70:30), yield 33%, mp: 70° C., appearance: white solid<br>1H NMR (300 MHz, DMSO-d6, d in ppm): 0.91-1.06 (m, 2H), 1.27-1.37 (m, 2H), 2.14 (s, 3H), 2.21 (s, 6H), 2.23 (s, 3H), 2.96 (s, 3H), 4.60 (s, 2H), 4.61 (s, 2H), 5.77 (dd, 1H, J = 3.0 Hz, J = 0.8 Hz), 5.92 (dd, 1H, J = 3.0 Hz, J = 1.0 Hz), 6.25 (d, 1H, J = 8.5 Hz), 6.87 (dd, 1H, J = 7.8 Hz, J = 0.7 Hz), 6.99 (d, 1H, J = 0.7 Hz), 7.12 (d, 1H, J = 7.8 Hz), 7.30-7.41 (m, 3H), 7.91 (d, 1H, J = 8.6 Hz); m/z: 508 [M + H]+ (calc. mass: 507). |

TABLE 2-continued

All the NMR were performed in DMSO-d6

| Cpd. | Starting compounds, Reaction conditions and purification Yield, MP, Appearance, $^1$H NMR (solvent) data, Mass (ES+ or ES−) data |
|---|---|
| 77 N-[(2-bromo-4-methylphenyl)(5-methylfuran-2-yl)methyl]-2-(2-methyl-1H-1,3-benzodiazol-5-yl)acetamide | From (2-bromo-4-methylphenyl)(5-methylfuran-2-yl)methanamine Ex. 18 and 2-(2-methyl-1H-1,3-benzodiazol-5-yl)acetic acid Ex. 45 following protocol A, DMAP (3.2 equiv), EDCl•HCl (1.2 equiv), overnight at rt, purification by silica gel column chromatography (CH2Cl2/MeOH, 96:4), yield 55%, mp: 209° C., appearance: white solid<br>1H NMR (300 MHz, DMSO-d6, d in ppm): 2.21 (s, 3H), 2.27 (s, 3H), 2.44 (s, 3H), 3.54 (m, 2H), 5.76 (d, 1H, J = 3.0 Hz), 5.95 (dd, 1H, J = 3.0 Hz, J = 1.0 Hz), 6.25 (d, 1H, J = 7.8 Hz), 6.98-7.02 (m, 1H), 7.18 (d, 1H, J = 8.3 Hz), 7.26-7.33 (m, 2H), 7.35-7.38 (m, 1H), 7.41 (m, 1H), 9.05 (d, 1H, J = 8.1 Hz), 12.05 (br(s), 1H); m/z: 452 [M + H]+, 454 [M + H]+ (calc. mass: 451). |
| 78 2-(2,2-dioxo-1,3-dihydro-2-benzothiophen-5-yl)-N-{[4-methyl-2-(piperidin-1-yl)phenyl](5-methylfuran-2-yl)methyl}acetamide | From [4-methyl-2-(piperidin-1-yl)phenyl](5-methylfuran-2-yl)methanamine Ex. 16 and 2-(2,2-dioxo-1,3-dihydro-2-benzothiophen-5-yl)acetic acid Ex. 46 following protocol A, DMAP (1.1 equiv), EDCl•HCl (1.1 equiv), 2 h at rt, purification by silica gel column chromatography (CH2Cl2/EtOAc, 50:50), yield 69%, mp: 87° C., appearance: white solid<br>1H NMR (300 MHz, DMSO-d6, d in ppm): 1.38-1.63 (m, 6H), 2.17 (s, 3H), 2.24 (s, 3H), 2.54-2.63 (m, 2H), 2.74-2.83 (m, 2H), 3.49 (s, 2H), 4.43 (s, 2H), 4.44 (s, 2H), 5.81 (d, 1H, J = 3.0 Hz), 5.92 (dd, 1H, J = 2.9 Hz, J = 1.0 Hz), 6.48 (d, 1H, J = 8.2 Hz), 6.90 (d, 1H, J = 6.0 Hz), 6.94 (s, 1H), 7.18 (d, 1H, J = 7.7 Hz), 7.20-7.29 (m, 3H), 8.78 (d, 1H, J = 8.7 Hz); m/z: 493 [M + H]+ (calc. mass: 492). |
| 79 N-[(5-chlorofuran-2-yl)[4-methyl-2-(piperidin-1-yl)phenyl]methyl]-2-(2-methanesulfonyl-2,3-dihydro-1H-isoindol-5-yl)acetamide | From (5-chlorofuran-2-yl)[4-methyl-2-(piperidin-1-yl)phenyl]methanamine Ex. 47 and 2-(2-methanesulfonyl-2,3-dihydro-1H-isoindol-5-yl)acetic acid Ex. 27 following protocol A, DMAP (1 equiv), EDCl•HCl (1.1 equiv), overnight at rt, purification by silica gel column chromatography (Cyclohexane/EtOAc, 50:50), yield 69%, mp: 143° C., appearance: white solid<br>1H NMR (300 MHz, DMSO-d6, d in ppm): 1.40-1.60 (m, 6H), 2.26 (s, 3H), 2.50-2.58 (m, 2H), 2.75-2.83 (m, 2H), 2.95 (s, 3H), 3.50 (s, 2H), 4.57 (s, 4H), 6.05 (dd, 1H, J = 3.3 Hz, J = 0.9 Hz), 6.35 (d, 1H, J = 3.3 Hz), 6.51 (d, 1H, J = 8.2 Hz), 6.92 (d, 1H, J = 8.0 Hz), 6.97 (s, 1H), 7.16-7.24 (m, 4H), 8.86 (d, 1H, J = 8.3 Hz); m/z: 542 [M + H]+, 544 [M + H]+ (calc. mass: 541). |
| 80 N-[(5-chlorofuran-2-yl)[4-methyl-2-(pyrrolidin-1-yl)phenyl]methyl]-1-(2-methanesulfonyl-2,3-dihydro-1H-isoindol-5-yl)cyclopropane-1-carboxamide | From (5-chlorofuran-2-yl)[4-methyl-2-(pyrrolidin-1-yl)phenyl]methanamine Ex. 48 and 1-(2-methanesulfonyl-2,3-dihydro-1H-isoindol-5-yl)cyclopropane-1-carboxylic acid Ex. 33 following protocol A, DMAP (1 equiv), EDCl•HCl (1.1 equiv), 2 h at rt, purification by silica gel column chromatography (Cyclohexane/EtOAc, 70:30), yield 42%, mp: 82° C., appearance: white solid<br>1H NMR (300 MHz, DMSO-d6, d in ppm): 0.95-1.04 (m, 2H), 1.28-1.38 (m, 2H), 1.56-1.73 (m, 4H), 2.23 (s, 3H), 2.57-2.66 (m, 2H), 2.75-2.86 (m, 2H), 2.96 (s, 3H), 4.59 (m, 4H), 6.01 (dd, 1H, J = 3.3 Hz, J = 1.2 Hz), 6.28 (d, 1H, J = 7.8 Hz), 6.35 (d, 1H, J = 3.3 Hz), 6.80 (dd, 1H, J = 7.7 Hz, J = 1.0 Hz), 6.94 (d, 1H, J = 1.2 Hz), 7.09 (d, 1H, J = 7.7 Hz), 7.30-7.35 (m, 3H), 7.67 (d, 1H, J = 8.3 Hz); m/z: 554 [M + H]+, 556 [M + H]+ (calc. mass: 553). |
| 81 N-[(2-bromo-4-methylphenyl)(phenyl)methyl]-2-(2-methyl-1H-1,3-benzodiazol-5-yl)acetamide | From (2-bromo-4-methylphenyl)(phenyl)methanamine Ex. 49 and 2-(2-methyl-1H-1,3-benzodiazol-5-yl)acetic acid Ex. 45 following protocol B, substituted amine (1 equiv), substituted acid (1 equiv), PyBOP (1 equiv) and triethylamine (3 equiv), 100° C. for 20 min under microwave irradiation, purification by silica gel column chromatography (CH2Cl2/MeOH, 95:5), yield 21%, mp: 138° C., appearance: white solid<br>1H NMR (300 MHz, DMSO-d6, d in ppm): 2.28 (s, 3H), 2.46 (s, 3H), 3.58 (s, 2H), 6.33 (d, 1H, J = 8.2 Hz), 7.03 (d, 1H, J = 8.2 Hz), 7.13-7.16 (m, 2H), 7.18-7.35 (m, 7H), 7.44 (s, 1H), 8.98 (d, 1H, J = 8.1 Hz), 12.08 (s, 1H); m/z: 448 [M + H]+, 450 [M + H]+ (calc. mass: 447). |
| 82 2-(2-methyl-1H-1,3-benzodiazol-5-yl)-N-{[4- | From [4-methyl-2-(pyrrolidin-1-yl)phenyl](phenyl)methanamine Ex. 50 and 2-(2-methyl-1H-1,3-benzodiazol-5-yl)acetic acid Ex. 45 following protocol A, |

TABLE 2-continued

All the NMR were performed in DMSO-d6

| Cpd. | Starting compounds, Reaction conditions and purification Yield, MP, Appearance, ¹H NMR (solvent) data, Mass (ES+ or ES−) data |
|---|---|
| methyl-2-(pyrrolidin-1-yl)phenyl](phenyl)methyl}acetamide | DMAP (2.2 equiv), EDCl•HCl (1.1 equiv), 18 h at rt, purification by silica gel column chromatography (CH2Cl2/MeOH, 95:5). The residue was triturated in diethylether and filtered-off, yield 41%, mp: 132° C., appearance: white solid<br>1H NMR (300 MHz, DMSO-d6, d in ppm): 1.67-4.74 (m, 4H), 2.22 (s, 3H), 2.44 (s, 3H), 2.72-2.78 (m, 2H), 3.01-3.08 (m, 2H), 3.57 (s, 2H), 6.43 (d, 1H, J = 8.1 Hz), 6.74 (d, 1H, J = 7.8 Hz), 6.87 (s, 1H), 6.99-7.38 (m, 9H), 8.70 (d, 1H, J = 8.2 Hz), 12.05 (s, 1H); m/z: 439 [M + H]+ (calc. mass: 438). |
| 83 N-[(5-chlorofuran-2-yl)[4-methyl-2-(piperidin-1-yl)phenyl]methyl]-2-(2-oxo-2,3-dihydro-1H-indol-5-yl)acetamide | From (5-chlorofuran-2-yl)[4-methyl-2-(piperidin-1-yl)phenyl]methanamine Ex. 47 and 2-(2-oxo-2,3-dihydro-1H-indol-5-yl)acetic acid Ex. 14 following protocol A, DMAP (1 equiv), EDCl•HCl (1.1 equiv), overnight at rt, purification by silica gel column chromatography (Cyclohexane/EtOAc, 50:50), yield 64%, mp: 105° C., appearance: white solid<br>1H NMR (300 MHz, DMSO-d6, d in ppm): 1.40-1.60 (m, 6H), 2.25 (s, 3H), 2.50-2.59 (m, 2H), 2.75-2.84 (m, 2H), 3.40 (s, 2H), 3.41 (s, 2H), 6.04 (dd, 1H, J = 3.3 Hz, J = 0.9 Hz), 6.34 (d, 1H, J = 3.3 Hz), 6.49 (d, 1H, J = 8.1 Hz), 6.70 (d, 1H, J = 7.8 Hz), 6.92 (d, 1H, J = 7.9 Hz), 6.97 (s, 1H), 7.02 (d, 1H, J = 8.0 Hz), 7.07 (s, 1H), 7.17 (d, 1H, J = 7.8 Hz), 8.79 (d, 1H, J = 8.4 Hz), 10.29 (s, 1H); m/z: 478 [M + H]+, 480 [M + H]+ (calc. mass: 477). |
| 84 2-[(3Z)-3-hydrazinylidene-2-oxo-2,3-dihydro-1H-indol-5-yl]-N-{[4-methyl-2-(piperidin-1-yl)phenyl](5-methylfuran-2-yl)methyl}acetamide | See FIG. 3AN<br>To a solution of previously synthesized 2-(2,3-dioxo-2,3-dihydro-1H-indol-5-yl)-N-{[4-methyl-2-(piperidin-1-yl)phenyl](5-methylfuran-2-yl)methyl}acetamide Cpd. 23 (100 mg, 0.21 mmol) in MeOH (2 mL) was added hydrazine hydrate 50% (w/w) (15 mg, 0.23 mmol). The reaction was heated at 100° c. overnight. The solvents were removed under reduced pressure. The crude material was purified by silica gel column chromatography using Cyclohexane/EtOAc (6:4) as eluent to afford 2-(3-hydrazinylidene-2-oxo-2,3-dihydro-1H-indol-5-yl)-N-{[4-methyl-2-(piperidin-1-yl)phenyl](5-methylfuran-2-yl)methyl}acetamide Cpd. 84 (35 mg, 34%) as yellow solid, mp: 130° C.<br>1H NMR (300 MHz, DMSO-d6, d in ppm): 1.46-1.60 (m, 6H), 2.20 (s, 3H), 2.30 (s, 3H), 2.59-2.65 (m, 2H), 2.75-2.80 (m, 2H), 3.53 (s, 1.6H), 3.54 (s, 0.4H), 5.83 (d, 1H, J = 3.0 Hz), 5.87 (dd, 1H, J = 3.1 Hz, J = 1.0 Hz), 6.60 (s, 0.8H), 6.61 (s, 0.2H), 6.82 (d, 0.8H, J = 8.0 Hz), 6.85 (d, 0.2H, J = 7.6 Hz), 6.87 (dd, 1H, J = 7.0 Hz, J = 1.9 Hz), 6.99 (d, 1H, J = 1.0 Hz), 7.11 (dd, 0.8H, J = 8.0 Hz, J = 1.7 Hz), 7.16 (d, 1H, J = 7.9 Hz), 7.20 (d, 0.2H, J = 1.8 Hz), 7.41 (d, 0.8H, J = 1.3 Hz), 7.73 (d, 0.2H, J = 1.2 Hz); m/z: 486 [M + H]+ (calc. mass: 485). |
| 85 2-(3-hydroxy-2,3-dihydro-1H-inden-5-yl)-N-{[4-methyl-2-(piperidin-1-yl)phenyl](5-methylfuran-2-yl)methyl}acetamide | See FIG. 3AO<br>The previously synthesized N-{[4-methyl-2-(piperidin-1-yl)phenyl](5-methylfuran-2-yl)methyl}-2-(3-oxo-2,3-dihydro-1H-inden-5-yl)acetamide Cpd. 67 (50 mg, 0.11 mmol) was dissolved in EtOH (5 mL). The solution was cooled to 0° C. and sodium borohydride (6 mg, 0.16 mmol) was added. The ice bath was removed and the solution was stirred at rt for 2 h. The solvent was removed under reduced pressure and 1N citric acid was added to neutralized the solution. The aqueous layer was extracted with CH2Cl2. The organic layer was dried over MgSO4, filtered and the solution was concentrated under reduced pressure. The crude material was purified by silica gel column chromatography eluting with Cyclohexane/EtOAc (70:30), yield 77%, mp: 60° C., appearance: white solid<br>1H NMR (300 MHz, DMSO-d6, d in ppm): 1.46-1.60 (m, 6H), 1.68-1.78 (m, 1H), 2.17 (s, 3H), 2.25 (s, 3H), 2.25-2.35 (m, 1H), 2.55-2.70 (m, 3H), 2.74-2.90 (m, 3H), 3.44 (s, 2H), 4.96-5.00 (m, 1H), 5.16 (d, 1H, J = 6.2 Hz), 5.79-5.81 (m, 1H), 5.90-5.92 (m, 1H), 6.48 (d, 1H, J = 8.3 Hz), 6.89 (d, 1H, J = 8.0 Hz), 6.93 (s, 1H), 7.04-7.10 (m, 2H), 7.19 (dd, 1H, J = 5.8 Hz, J = 1.1 Hz), 7.21 (d, 1H, J = 1.2 Hz), 8.71 (dd, 1H, J = 8.7 Hz, J = 2.4 Hz); m/z: 459 [M + H]+ (calc. mass: 458). |

TABLE 2-continued

All the NMR were performed in DMSO-d6

| Cpd. | Starting compounds, Reaction conditions and purification Yield, MP, Appearance, ¹H NMR (solvent) data, Mass (ES+ or ES−) data |
|---|---|
| 86 N-[(5-chlorofuran-2-yl)(2,4-dimethylphenyl)methyl]-1-(2-oxo-2,3-dihydro-1H-indol-5-yl)cyclopropane-1-carboxamide | From (5-chlorofuran-2-yl)(2,4-dimethylphenyl)methanamine Ex. 32 and 1-(2-oxo-2,3-dihydro-1H-indol-5-yl)cyclopropane-1-carboxylic acid Ex. 37 following protocol A, DMAP (1 equiv), EDCl•HCl (1.1 equiv), overnight at rt, purification by silica gel column chromatography (Cyclohexane/EtOAc, 50:50), yield 26%, mp: 78° C., appearance: white solid 1H NMR (300 MHz, DMSO-d6, d in ppm): 0.91-1.00 (m, 2H), 1.26-1.33 (m, 2H), 2.16 (s, 3H), 2.23 (s, 3H), 3.43 (s, 2H), 5.99 (dd, 1H, J = 3.3 Hz, J = 1.1 Hz), 6.16 (d, 1H, J = 8.5 Hz), 6.35 (d, 1H, J = 3.3 Hz), 6.75 (d, 1H, J = 7.9 Hz), 6.95 (s, 1H), 6.95-7.01 (m, 2H), 7.15 (dd, 1H, J = 7.9 Hz), 7.17 (s, 1H), 7.56 (d, 1H, J = 8.3 Hz), 10.37 (br(s), 1H); m/z: 457 [M + Na]+, 459 [M + Na]+ (calc. mass: 434). |
| 87 N-[(5-chlorofuran-2-yl)(2,4-dimethylphenyl)methyl]-1-(2,2-dioxo-1,3-dihydro-2,1-benzothiazol-5-yl)cyclopropane-1-Carboxamide | From (5-chlorofuran-2-yl)(2,4-dimethylphenyl)methanamine Ex. 32 and 1-(2,2-dioxo-1,3-dihydro-2,1-benzothiazol-5-yl)cyclopropane-1-carboxylic acid Ex. 38 following protocol A, DMAP (1 equiv), EDCl•HCl (1.1 equiv), overnight at rt, purification by silica gel column chromatography (gradient of Cyclohexane/EtOAc, from [80:20] to [70:30]), yield 28%, mp: 86° C., appearance: white solid 1H NMR (300 MHz, DMSO-d6, d in ppm): 0.92-1.17 (m, 2H), 1.26-1.36 (m, 2H), 2.16 (s, 3H), 2.23 (s, 3H), 4.47 (s, 2H), 5.99 (dd, 1H, J = 3.3 Hz, J = 1.1 Hz), 6.16 (d, 1H, J = 7.9 Hz), 6.35 (d, 1H, J = 3.3 Hz), 6.75 (d, 1H, J = 8.0 Hz), 6.94-7.00 (m, 3H), 7.22 (dd, 1H, J = 8.1 Hz, J = 1.9 Hz), 7.24 (s, 1H), 7.79 (d, 1H, J = 8.3 Hz), 10.48 (br(s), 1H); m/z: 493 [M + Na]+, 495 [M + Na]+ (calc. mass: 470). |
| 88a 2-(1H-indol-6-yl)-N-((4-methyl-2-(piperidin-1-yl)phenyl)(5-methylfuran-2-yl)methyl)acetamide | From [4-methyl-2-(piperidin-1-yl)phenyl](5-methylfuran-2-yl)methanamine Ex. 16 and 2-(1H-indol-6-yl)acetic acid Ex. 89 following protocol A, DMAP (1 equiv), EDCl•HCl (1.1 equiv), overnight at rt, purification by silica gel column chromatography (Cyclohexane/EtOAc, 70:30), yield 78%, mp: ND, appearance: white solid 1H NMR (300 MHz, DMSO-d6, d in ppm): 1.45-1.65 (m, 6H), 2.16 (s, 3H), 2.24 (s, 3H), 2.55-2.6 (m, 2H), 2.70-2.85 (m, 2H), 3.51 (s, 2H), 5.80 (d, 1H, J = 2.8 Hz), 5.90-5.95 (m, 1H), 6.34 (t, 1H, J = 2.1 Hz), 6.48 (d, 1H, J = 8.0 Hz), 6.88 (d, 2H, J = 8.1 Hz), 6.92 (s, 1H), 7.18 (d, 1H, J = 7.8 Hz), 7.23-7.30 (m, 2H), 7.40 (d, 1H, J = 8.1 Hz), 8.67 (d, 1H, J = 8.6 Hz), 10.96 (s, 1H). |
| 88 2-[3-(hydroxymethyl)-1H-indol-6-yl]-N-{[4-methyl-2-(piperidin-1-yl)phenyl](5-methylfuran-2-yl)methyl}acetamide | See FIG. 3AP Step 1: to a solution of anhydrous DMF (1 mL) was added phosphorus oxychloride (32 μL, 0.34 mmol) at −10° C. After 30 min, the previously synthesized 2-(1H-indol-6-yl)-N-((4-methyl-2-(piperidin-1-yl)phenyl)(5-methylfuran-2-yl)methyl)acetamide Cpd. 88a (75 mg, 0.17 mmol) dissolved in dry DMF (1 mL) was added dropwise. The reaction mixture was warmed to rt and stirred at this temperature for 5 h. Ice was added to quench the reaction. The pH of the solution was adjusted with Na2CO3 powder to pH = 5-6. The resulting mixture was extracted with EtOAc. The combined organic layers were dried over MgSO4, filtered and the solution was concentrated under reduced pressure. The crude material was purified by silica gel column chromatography eluting with CH2Cl2/MeOH (97:3) to give 2-(3-formyl-1H-indol-6-yl)-N-((4-methyl-2-(piperidin-1-yl)phenyl)(5-methylfuran-2-yl)methyl)acetamide (75 mg, 94%) as white solid. 1H NMR (300 MHz, DMSO-d6, d in ppm): 1.40-1.65 (m, 6H), 2.16 (s, 3H), 2.24 (s, 3H), 2.50-2.60 (m, 2H), 2.70-2.85 (m, 2H), 3.56 (s, 2H), 5.81 (d, 1H, J = 2.9 Hz), 5.90-5.95 (m, 1H), 6.48 (d, 1H, J = 8.2 Hz), 6.88 (d, 1H, J = 7.7 Hz), 6.93 (s, 1H), 7.10 (dd, 1H, J = 8.2 Hz, J = 1.4 Hz), 7.18 (d, 1H, J = 7.8 Hz), 7.39 (s, 1H), 7.94 (d, 1H, J = 7.7 Hz), 8.23 (d, 1H, J = 3.1 Hz), 8.74 (d, 1H, J = 8.2 Hz), 9.88 (s, 1H), 12.06 (br(s), 1H). Step 2: 2-(3-formyl-1H-indol-6-yl)-N-((4-methyl-2-(piperidin-1-yl)phenyl)(5-methylfuran-2-yl)methyl)acetamide (80 mg, 0.17 mmol) in anhydrous MeOH (2 mL) was added sodium borohydride (19 mg, 0.51 mmol). The reaction mixture was stirred at rt for 4 h. Water and ice were added and the precipitate formed was collected by filtration and washed with water, yield 62%, mp: 92° C., appearance: white solid 1H NMR (300 MHz, DMSO-d6, d in ppm): 1.35-1.65 (m, |

TABLE 2-continued

All the NMR were performed in DMSO-d6

| Cpd. | Starting compounds, Reaction conditions and purification Yield, MP, Appearance, $^1$H NMR (solvent) data, Mass (ES+ or ES−) data |
|---|---|
| | 6H), 2.16 (s, 3H), 2.24 (s, 3H), 2.50-2.60 (m, 2H), 2.75-2.85 (m, 2H), 3.51 (s, 2H), 4.58 (d, 2H, J = 5.3 Hz), 4.67 (t, 1H, J = 4.7 Hz), 5.80 (d, 1H, J = 3.0 Hz), 5.90-5.95 (m, 1H), 6.48 (d, 1H, J = 8.2 Hz), 6.85-6.95 (m, 3H), 7.15 (d, 1H, J = 2.3 Hz), 7.18 (d, 1H, J = 7.8 Hz), 7.23 (s, 1H), 7.45 (d, 1H, J = 8.1 Hz), 8.65 (d, 1H, J = 8.4 Hz), 10.75 (s, 1H); m/z: 472 [M + H]+ (calc. mass: 471). |
| 89a 1-(1H-indol-5-yl)-N-((4-methyl-2-(piperidin-1-yl)phenyl)(5-methylfuran-2-yl)methyl)cyclopropanecarboxamide | From [4-methyl-2-(piperidin-1-yl)phenyl](5-methylfuran-2-yl)methanamine Ex. 16 and 1-(1H-indol-5-yl)cyclopropane-1-carboxylic acid Ex. 61 following protocol A, DMAP (1 equiv), EDCl•HCl (1.1 equiv), 5 h at rt, purification by silica gel column chromatography (Cyclohexane/EtOAc, 70:30) followed by a second purification by column chromatography on silica gel eluting with Cyclohexane/EtOAc (80:20), yield 89%, mp: ND, appearance: white solid<br>1H NMR (300 MHz, DMSO-d6, d in ppm): 1.01 (m, 2H), 1.05-1.35 (m, 8H), 2.08 (s, 3H), 2.21 (s, 3H), 2.25-2.35 (m, 2H), 2.50-2.60 (m, 2H), 5.80-5.81 (dd, 1H, J = 3.0 Hz, J = 0.9 Hz), 5.90-5.95 (dd, 1H, J = 3.0 Hz, J = 1.1 Hz), 6.30 (m, 1H, J = 8.6 Hz), 6.39 (m, 1H), 6.76 (d, 1H, J = 8.6 Hz), 6.83 (dd, 1H, J = 6.8 Hz, J = 1.0 Hz), 6.90 (d, 1H, J = 7.8 Hz), 6.94 (s, 1H), 7.10 (dd, 1H, J = 8.4 Hz, J = 1.7 Hz), 7.34 (t, 1H, J = 2.6 Hz), 7.38 (d, 1H, J = 8.4 Hz), 7.55 (d, 1H, J = 1.7 Hz), 11.11 (br(s), 1H). |
| 89 1-[3-(hydroxymethyl)-1H-indol-5-yl]-N-{[4-methyl-2-(piperidin-1-yl)phenyl](5-methylfuran-2-yl)methyl}cyclopropane-1-carboxamide | See FIG. 3AQ<br>Step 1: to a solution of anhydrous DMF (1 mL) was added phosphorus oxychloride (80 µL, 0.86 mmol) at −10° C. After 30 min, the previously synthesized 1-(1H-indol-5-yl)-N-((4-methyl-2-(piperidin-1-yl)phenyl)(5-methylfuran-2-yl)methyl)cyclopropanecarboxamide Cpd. 89a (200 mg, 0.43 mmol) dissolved in dry DMF (1 mL) was added dropwise. The reaction mixture was warmed to rt and stirred at this temperature for 5 h. Ice was added to quench the reaction. The pH of the solution was adjusted with Na2CO3 powder to pH = 5-6. The resulting mixture was extracted with EtOAc. The combined organic layers were dried over MgSO4, filtered and the solution was concentrated under reduced pressure. The crude material was purified by silica gel column chromatography eluting with CH2Cl2/MeOH (97:3) to give 1-(3-formyl-1H-indol-5-yl)-N-((4-methyl-2-(piperidin-1-yl)phenyl)(5-methylfuran-2-yl)methyl)cyclopropanecarboxamide (210 mg, 99%). 1H NMR (300 MHz, DMSO-d6, d in ppm): 1.00-1.30 (m, 8H), 1.30-1.40 (m, 1H), 1.40-1.50 (m, 1H), 2.08 (s, 3H), 2.21 (s, 3H), 2.25-2.35 (m, 2H), 2.45-2.50 (m, 2H), 5.81 (d, 1H, J = 3.1 Hz), 5.90-5.95 (m, 1H), 6.32 (d, 1H, J = 8.4 Hz), 6.83 (d, 1H, J = 6.1 Hz), 6.94 (s, 1H), 6.97 (d, 1H, J = 7.9 Hz), 7.01 (d, 1H, J = 8.6 Hz), 7.30 (dd, 1H, J = 8.3 Hz, J = 1.8 Hz), 7.49 (d, 1H, J = 8.6 Hz), 8.11 (s, 1H), 8.30 (d, 1H, J = 3.1 Hz), 9.92 (s, 1H), 12.15 (br(s), 1H).<br>Step 2: 1-(3-formyl-1H-indol-5-yl)-N-((4-methyl-2-(piperidin-1-yl)phenyl)(5-methylfuran-2-yl)methyl)cyclopropanecarboxamide (80 mg, 0.16 mmol) in anhydrous MeOH (2 mL) was added sodium borohydride (18 mg, 0.48 mmol). The reaction mixture was stirred at rt for 4 h. Water and ice were added and the precipitate formed was collected by filtration and washed with water, yield 62%, mp: 112° C., appearance: white solid1H NMR (300 MHz, DMSO-d6, d in ppm): 0.95-1.05 (m, 2H), 1.10-1.30 (m, 6H), 1.30-1.35 (m, 1H), 1.53-1.45 (m, 3H), 2.21 (s, 3H), 2.25-2.40 (m, 2H), 2.50-2.55 (m, 2H), 4.60 (d, 2H, J = 5.5 Hz), 4.74 (t, 1H, J = 5.0 Hz), 5.81 (d, 1H, J = 2.8 Hz), 5.90-5.95 (m, 1H), 6.32 (d, 1H, J = 9.1 Hz), 6.75 (d, 1H, J = 8.8 Hz), 6.82 (d, 1H, J = 7.1 Hz), 6.90 (d, 1H, J = 7.7 Hz), 6.94 (s, 1H), 7.11 (dd, 1H, J = 8.5 Hz, J = 1.8 Hz), 7.24 (d, 1H, J = 2.3 Hz), 7.34 (d, 1H, J = 8.6 Hz), 7.62 (d, 1H, J = 1.5 Hz), 10.90 (s, 1H); m/z: 498 [M + H]+ (calc. mass: 497). |

TABLE 2-continued

All the NMR were performed in DMSO-d6

| Cpd. | Starting compounds, Reaction conditions and purification Yield, MP, Appearance, ¹H NMR (solvent) data, Mass (ES+ or ES−) data |
|---|---|
| 90 N-[(2-bromo-4-methylphenyl)(phenyl)methyl]-2-(2-ethoxy-1H-1,3-benzodiazol-5-yl)acetamide | From (2-bromo-4-methylphenyl)(phenyl)methanamine Ex. 49 and 2-(2-ethoxy-1H-1,3-benzodiazol-5-yl)acetic acid Ex. 52 following protocol A, substituted amine (0.9 equiv), DMAP (3.2 equiv), EDCL•HCl (1.1 equiv), 1 h30 at rt. Sat. NH4Cl was added to quench the reaction. The brown solid formed was collected by filtration and dried until constant weight. Purification by silica gel column chromatography (CH2Cl2/EtOAC, 80:20), yield 37%, mp: 189° C., appearance: pale brown solid 1H NMR (300 MHz, DMSO-d6, d in ppm): 1.37 (t, 3H, J = 7.0 Hz), 2.28 (s, 3H), 3.54 (s, 2H), 4.45 (q, 2H, J = 7.1 Hz), 6.32 (d, 1H, J = 8.2 Hz), 6.94 (dd, 1H, J = 8.2 Hz, J = 1.6 Hz), 7.12-7.34 (m, 9H), 7.43 (d, 1H, J = 1.6 Hz), 8.95 (d, 1H, J = 8.3 Hz), 11.70 (s, 1H); m/z: 478 [M + H]+, 480 [M + H]+ (calc. mass: 477). |
| 91 N-{[4-methyl-2-(piperidin-1-yl)phenyl](5-methylfuran-2-yl)methyl}-2-[6-(methylsulfanyl)naphthalen-2-yl]acetamide | From [4-methyl-2-(piperidin-1-yl)phenyl](5-methylfuran-2-yl)methanamine Ex. 16 and 2-[6-(methylsulfanyl)naphthalen-2-yl]acetic acid Ex. 53 following protocol A, DMAP (2.2 equiv), EDCl•HCl (2.2 equiv), overnight at rt, purification by silica gel column chromatography (Cyclohexane/EtOAc, 80:20), yield 47%, mp: 134° C., appearance: white solid 1H NMR (300 MHz, DMSO-d6, d in ppm): 1.38-1.59 (m, 6H), 2.17 (s, 3H), 2.24 (s, 3H), 2.53-2.60 (m, 2H), 2.56 (s, 3H), 2.73-2.82 (m, 2H), 3.61 (s, 2H), 5.82 (d, 1H, J = 3.1 Hz), 5.92 (dd, 1H, J = 3.0 Hz, J = 1.1 Hz), 6.51 (d, 1H, J = 8.3 Hz), 6.89 (d, 1H, J = 8.5 Hz), 6.93 (s, 1H), 7.20 (d, 1H, J = 7.8 Hz), 7.33-7.42 (m, 2H), 7.66 (s, 2H), 7.71-7.76 (m, 2H), 8.81 (d, 1H, J = 8.4 Hz); m/z: 499 [M + H]+ (calc. mass: 498). |
| 92 N-[(2-bromo-4-methylphenyl)(phenyl)methyl]-2-[2-(ethylsulfanyl)-1H-1,3-benzodiazol-5-yl]acetamide | From (2-bromo-4-methylphenyl)(phenyl)methanamine Ex. 49 hydrochloride and 2-[2-(ethylsulfanyl)-1H-1,3-benzodiazol-5-yl]acetic acid Ex. 54 following protocol A, substituted amine (0.9 equiv), DMAP (3.2 equiv), EDCl•HCl (1.1 equiv), 1 h30 at rt. Sat. NH4Cl was added to quench the reaction. The brown solid formed was collected by filtration and dried until constant weight. Purification by silica gel column chromatography (CH2Cl2/EtOAC, 80:20), yield 47%, mp: 103° C., appearance: pale brown solid 1H NMR (300 MHz, DMSO-d6, d in ppm): 1.35 (t, 3H, J = 7.1 Hz), 2.28 (s, 3H), 3.25 (q, 2H, J = 7.3 Hz), 3.58 (s, 2H), 6.33 (d, 1H, J = 8.2 Hz), 7.04 (d, 1H, J = 8.1 Hz), 7.13-7.43 (m, 10H), 8.98 (d, 1H, J = 8.2 Hz), 12.41 (s, 1H); m/z: 494 [M + H]+, 496 [M + H]+ (calc. mass: 493). |
| 93 N-{[4-methyl-2-(piperidin-1-yl)phenyl](5-methylfuran-2-yl)methyl}-2-[2-(morpholin-4-yl)-1H-1,3-benzodiazol-5-yl]acetamide | From [4-methyl-2-(piperidin-1-yl)phenyl](5-methylfuran-2-yl)methanamine Ex. 16 and 2-[2-(morpholin-4-yl)-1H-1,3-benzodiazol-5-yl]acetic acid Ex. 55 following protocol A, DMAP (2.2 equiv), EDCl•HCl (1.2 equiv), overnight at rt, purification by silica gel column chromatography eluting with (Cyclohexan/EtOAc, 60:40) and then with CH2Cl2/MeOH (90:10) containing 10% of NH4OH, yield 14%, mp: 125° C., appearance: yellow solid 1H NMR (300 MHz, DMSO-d6, d in ppm): 1.39-1.55 (m, 6H), 2.16 (s, 3H), 2.24 (s, 3H), 2.51-2.57 (m, 2H), 2.76-2.80 (m, 2H), 3.47-3.49 (m, 6H), 3.73 (t, 4H, J = 5.1 Hz), 5.80 (d, 1H, J = 2.9 Hz), 5.91 (dd, 1H, J = 3.0 Hz, J = 1.0 Hz), 6.47 (d, 1H, J = 8.5 Hz), 6.88 (d, 1H, J = 7.9 Hz), 6.93-6.94 (m, 2H), 7.14-7.19 (m, 3H), 8.68 (d, 1H, J = 8.5 Hz), 12.19 (br(s), 1H); m/z: 528 [M + H]+ (calc. mass: 527). |
| 94 N-{[4-methyl-2-(piperidin-1-yl)phenyl](5-methylfuran-2-yl)methyl}-2-[3-(morpholin-4-ylmethyl)-1H-indol-5-yl]acetamide | See FIG. 3AR Step 1: see step 1 of synthesis of Cpd. 58 Step 2: 2-(3-formyl-1H-indol-5-yl)-N-((4-methyl-2-(piperidin-1-yl)phenyl)(5-methylfuran-2-yl)methyl)acetamide (100 mg, 0.21 mmol) was dissolved in CH2Cl2 (1 mL). Molecular sieves 4A were added. Morpholine (20 μL, 0.23 mmol) was added to the suspension. The reaction mixture was stirred at rt for 18 h. TLC showed starting material. Additional morpholine (2 equiv) were added followed by two drops of acetic acid. The reaction mixture was heated at 40° C. for 2 h. After cooling to rt, sodium triacetoxyborohydride (68 mg, 0.32 mmol) was added portionwise to the reaction mixture and the stirring was kept for 1 h. Water was added to quench the reaction. After phases separation, the aqueous layer was extracted twice with CH2Cl2. The combined |

TABLE 2-continued

All the NMR were performed in DMSO-d6

| Cpd. | | Starting compounds, Reaction conditions and purification Yield, MP, Appearance, $^1$H NMR (solvent) data, Mass (ES+ or ES−) data |
|---|---|---|
| | | organic layers were dried over MgSO4, filtered and the solution was concentrated under reduced pressure. The crude material was purified by silica gel column chromatography eluting with CH2Cl2/MeOH (95:5), yield 39%, mp: 100° C., appearance: white solid 1H NMR (300 MHz, DMSO-d6, d in ppm): 1.42-1.54 (m, 6H), 2.16 (s, 3H), 2.24 (s, 3H), 2.30-2.38 (m, 4H), 2.50-2.26 (m, 2H), 2.75-2.81 (m, 2H), 3.50 (s, 2H), 3.50-3.53 (m, 4H), 3.54 (s, 2H), 5.82 (d, 1H, J = 2.6 Hz), 5.91 (dd, 1H, J = 3 Hz, J = 1.1 Hz), 6.48 (d, 1H, J = 8.4 Hz), 6.88 (d, 1H, J = 7.9 Hz), 6.93 (s, 1H), 6.97 (dd, 1H, J = 8.3 Hz, J = 1.6 Hz), 7.17 (d, 1H, J = 2.3 Hz), 7.19 (d, 1H, J = 5.1 Hz), 7.22 (d, 1H, J = 5.5 Hz), 7.46 (s, 1H), 8.65 (d, 1H, J = 8.4 Hz), 10.82 (s, 1H); -m/z: 541 [M + H]+ (calc. mass: 540). |
| 95 | 1-(1-cyclopropanecarbonyl-2,3-dihydro-1H-indol-5-yl)-N-[(2,4-dimethylphenyl)(5-methylfuran-2-yl)methyl]cyclopropane-1-carboxamide | From (2,4-dimethylphenyl)(5-methylfuran-2-yl)methanamine Ex. 19 and 1-(1-cyclopropanecarbonyl-2,3-dihydro-1H-indol-5-yl)cyclopropane-1-carboxylic acid Ex. 56 following protocol A, DMAP (1.2 equiv), EDCl•HCl (1.2 equiv), 4 h at rt, purification by silica gel column chromatography (Cyclohexane/EtOAc, 70:30), yield 53%, mp: 70° C., appearance: white solid 1H NMR (300 MHz, DMSO-d6, d in ppm): 0.85-0.95 (m, 4H), 0.95-1.00 (m, 2H), 1.20-1.35 (m, 2H), 1.90-1.95 (m, 1H), 2.16 (s, 3H), 2.17 (s, 3H), 2.22 (s, 3H), 3.15 (t, 2H, J = 8.4 Hz), 4.28 (m, 2H), 5.76 (d, 1H, J = 3.1 Hz), 5.92 (dd, 1H, J = 3.0 Hz, J = 1.1 Hz), 6.11 (d, 1H, J = 8.3 Hz), 6.85-6.95 (m, 3H), 7.11 (dd, 1H, J = 8.1 Hz, J = 1.9 Hz), 7.20-7.25 (m, 2H), 7.95 (d, 1H, J = 5.5 Hz); m/z: 491 [M + Na]+ (calc. mass: 468). |
| 96 | tert-butyl 3-{5-[({[4-methyl-2-(piperidin-1-yl)phenyl](5-methylfuran-2-yl)methyl}carbamoyl)methyl]-1H-indol-1-yl}propanoate | From [4-methyl-2-(piperidin-1-yl)phenyl](5-methylfuran-2-yl)methanamine Ex. 16 and 2-{1-[3-(tert-butoxy)-3-oxopropyl]-1H-indol-5-yl}acetic acid Ex. 57 following protocol A, DMAP (2.2 equiv), EDCl•HCl (1.2 equiv), overnight at rt, purification by silica gel column chromatography (Cyclohexane/EtOAc, 70:30), yield 89%, mp: 50° C., appearance: white solid 1H NMR (300 MHz, DMSO-d6, d in ppm): 1.31 (s, 9H), 1.45-1.65 (m, 6H), 2.16 (s, 3H), 2.24 (s, 3H), 2.50-2.60 (m, 2H), 2.68 (t, 2H, J = 6.6 Hz), 2.70-2.85 (m, 2H), 3.50 (s, 2H), 4.34 (t, 2H, J = 6.6 Hz), 5.80 (d, 1H, J = 3.1 Hz), 5.90-5.95 (m, 1H), 6.31 (d, 1H, J = 0.6 Hz), 6.48 (d, 1H, J = 8.5 Hz), 6.88 (d, 1H, J = 7.8 Hz), 6.92 (s, 1H), 7.02 (dd, 1H, J = 8.4 Hz, J = 1.7 Hz), 7.19 (d, 1H, J = 7.7 Hz), 7.27 (d, 1H, J = 3.1 Hz), 7.30-7.40 (m, 2H), 8.64 (d, 1H, J = 8.6 Hz); m/z: 569 [M + H]+ (calc. mass: 569). |
| 97 | 3-{5-[({[4-methyl-2-(piperidin-1-yl)phenyl](5-methylfuran-2-yl)methyl}carbamoyl)methyl]-1H-indol-1-yl}propanoic acid | See FIG. 3AS The previously synthesized tert-butyl 3-{5-[({[4-methyl-2-(piperidin-1-yl)phenyl](5-methylfuran-2-yl)methyl}carbamoyl)methyl]-1H-indol-1-yl}propanoate Cpd. 96 (2.20 g, 3.86 mmol) was dissolved in MeOH (16 mL). 5M NaOH (3.86 mL, 19.31 mmol) was added to the solution. The reaction mixture was heated at 100° C. for 45 min under mricrowave irradiation. The solvent was removed under reduced pressure and 1N citric acid was added to the residue up pH = 5 was reached. The solid formed was collected by filtration, washed with water and dried until constant weight, yield 83%, mp: 95° C., appearance: white solid 1H NMR (300 MHz, DMSO-d6, d in ppm): 1.43-1.52 (m, 6H), 2.16 (s, 3H), 2.24 (s, 3H), 2.50-2.57 (m, 2H), 2.68 (t, 2H, J = 6.8 Hz), 2.74-2.76 (m, 2H), 3.50 (s, 2H), 4.34 (t, 2H, J = 6.9 Hz), 5.80 (d, 1H, J = 2.9 Hz), 5.91 (dd, 1H, J = 2.9 Hz, J = 1.0 Hz), 6.31 (d, 1H, J = 2.9 Hz), 6.48 (d, 1H, J = 8.5 Hz), 6.88 (d, 1H, J = 7.9 Hz), 6.93 (s, 1H), 7.02 (dd, 1H, J = 8.5 Hz, J = 1.4 Hz), 7.20 (d, 1H, J = 7.8 Hz), 7.29 (d, 1H, J = 3.1 Hz), 7.34-7.37 (m, 2H), 8.66 (d, 1H, J = 8.5 Hz), 12.35 (br(s), 1H); m/z: 514 [M + H]+ (calc. mass: 513). |
| 98 | 2-[3-(2-methanesulfonylethyl)-1H-indol-5-yl]-N-{[4-methyl-2-(piperidin-1-yl)phenyl](5- | From [4-methyl-2-(piperidin-1-yl)phenyl](5-methylfuran-2-yl)methanamine Ex. 16 and 2-[3-(2-methanesulfonylethyl)-1H-indol-5-yl]acetic acid Ex. 58 following protocol A, substituted amine (0.9 equiv), DMAP (2.2 equiv), EDCl•HCl (1.2 equiv), overnight at rt, purification by preparative HPLC, yield 46%, mp: 107° C., appearance: white solid 1H NMR (300 MHz, DMSO-d6, d in ppm): 1.35-1.63 (m, |

TABLE 2-continued

All the NMR were performed in DMSO-d6

| Cpd. | Starting compounds,<br>Reaction conditions and purification<br>Yield, MP, Appearance, $^1$H NMR (solvent) data, Mass (ES+ or ES−) data |
|---|---|
| methylfuran-2-yl)methyl}acetamide | 6H), 2.16 (s, 3H), 2.24 (s, 3H), 2.52-2.60 (m, 2H), 2.72-2.82 (m, 2H), 2.99 (s, 3H), 3.04-3.13 (m, 2H), 3.37-3.46 (m, 2H), 3.51 (s, 2H), 5.81 (d, 1H, J = 3.0 Hz), 5.90 (dd, 1H, J = 2.9 Hz, J = 0.9 Hz), 6.48 (d, 1H, J = 8.4 Hz), 6.84-6.95 (m, 2H), 7.00 (dd, 1H, J = 8.3 Hz, J = 1.4 Hz), 7.17-7.26 (m, 3H), 7.41 (s, 1H), 8.67 (d, 1H, J = 8.5 Hz), 10.81 (s, 1H); m/z: 548 [M + H]+ (calc. mass: 547). |
| 99 tert-butyl 3-[5-({[(2,4-dimethylphenyl)(5-methylfuran-2-yl)methyl]carbamoyl}methyl)-1H-indol-1-yl]propanoate | From (2,4-dimethylphenyl)(5-methylfuran-2-yl)methanamine Ex. 19 and 2-{1-[3-(tert-butoxy)-3-oxopropyl]-1H-indol-5-yl}acetic acid Ex. 57 following protocol A, substituted amine (0.9 equiv), DMAP (2.2 equiv), EDCl•HCl (1.2 equiv), overnight at rt, purification by preparative HPLC, yield 50%, mp: 39° C., appearance: white solid<br>1H NMR (300 MHz, DMSO-d6, d in ppm): 1.31 (s, 9H), 2.16 (s, 3H), 2.19 (s, 3H), 2.22 (s, 3H), 2.69 (t, 2H, J = 6.6 Hz), 3.52 (s, 2H), 4.34 (t, 2H, J = 6.5 Hz), 5.84 (d, 1H, J = 3.2 Hz), 5.95 (dd, 1H, J = 3.0 Hz, J = 1.0 Hz), 6.11 (d, 1H, J = 8.3 Hz), 6.32 (d, 1H, J = 3.0 Hz, J = 0.5 Hz), 6.92-6.99 (m, 2H), 7.04 (dd, 1H, J = 8.4 Hz, J = 1.6 Hz), 7.10 (d, 1H, J = 8.4 Hz), 7.28 (d, 1H, J = 3.1 Hz), 7.33-7.40 (m, 2H), 8.87 (d, 1H, J = 8.3 Hz); m/z: 501 [M + H]+ (calc. mass: 500). |
| 100 tert-butyl 3-[5-({[(2-bromo-4-methylphenyl)(5-methylfuran-2-yl)methyl]carbamoyl}methyl)-1H-indol-1-yl]propanoate | From (2-bromo-4-methylphenyl)(5-methylfuran-2-yl)methanamine Ex. 18 and 2-{1-[3-(tert-butoxy)-3-oxopropyl-1H-indol-5-yl}acetic acid Ex. 57 following protocol A, substituted amine (0.9 equiv), DMAP (2.2 equiv), EDCl•HCl (1.2 equiv), overnight at rt, purification by silica gel column chromatography (CH2Cl2/EtOAc, 95:5), yield 58%, mp: 149° C., appearance: white solid<br>1H NMR (300 MHz, DMSO-d6, d in ppm): 1.31 (s, 9H), 2.21 (s, 3H), 2.27 (s, 3H), 2.69 (t, 2H, J = 6.6 Hz), 3.53 (s, 2H), 4.34 (t, 2H, J = 6.6 Hz), 5.75 (d, 1H, J = 3.0 Hz), 5.95 (dd, 1H, J = 3.0 Hz, J = 1.0 Hz), 6.26 (d, 1H, J = 8.1 Hz), 6.33 (d, 1H, J = 3.2 Hz), 7.04 (dd, 1H, J = 8.5 Hz, J = 1.5 Hz), 7.17 (d, 1H, J = 7.0 Hz), 7.28 (d, 1H, J = 3.1 Hz), 7.31 (d, 1H, J = 7.9 Hz), 7.34-7.43 (m, 3H), 9.01 (d, 1H, J = 8.2 Hz); m/z: 565 [M + H]+, 567 [M + H]+ (calc. mass: 564). |
| 101 3-[5-({[(2,4-dimethylphenyl)(5-methylfuran-2-yl)methyl]carbamoyl}methyl)-1H-indol-1-yl]propanoic acid | See FIG. 3AS<br>The previously synthesized tert-butyl 3-[5-({[(2,4-dimethylphenyl)(5-methylfuran-2-yl)methyl]carbamoyl}methyl)-1H-indol-1-yl]propanoate Cpd. 99 (45 mg, 0.09 mmol) was dissolved in MeOH (1.5 mL). 5M NaOH (90 µL, 0.45 mmol) was added to the solution. The reaction mixture was heated at 100° C. for 30 min under mricrowave irradiation. The solvent was removed under reduced pressure and 1N citric acid was added to the residue up pH = 4 was reached. The solid formed was collected by filtration, washed with water and dried until constant weight, yield 98%, mp: 65° C., appearance: white solid<br>1H NMR (300 MHz, DMSO-d6, d in ppm): 2.17 (s, 3H), 2.20 (s, 3H), 2.23 (s, 3H), 2.71 (t, 2H, J = 6.8 Hz), 3.52 (s, 2H), 4.35 (t, 2H, J = 6.8 Hz), 5.84 (d, 1H, J = 3.1 Hz), 5.95 (dd, 1H, J = 3.0 Hz, J = 1.0 Hz), 6.11 (d, 1H, J = 8.3 Hz), 6.33 (d, 1H, J = 2.9 Hz), 6.92-7.00 (m, 2H), 7.03 (dd, 1H, J = 8.6 Hz, J = 1.3 Hz), 7.11 (d, 1H, J = 8.4 Hz), 7.29 (d, 1H, J = 3.1 Hz), 7.34-7.42 (m, 2H), 8.88 (d, 1H, J = 8.4 Hz), 12.32 (br(s), 1H); m/z: 445 [M + H]+ (calc. mass: 444). |
| 102 3-[5-({[(2-bromo-4-methylphenyl)(5-methylfuran-2-yl)methyl]carbamoyl}methyl)-1H-indol-1-yl]propanoic acid | See FIG. 3AS<br>The previously synthesized tert-butyl 3-[5-({[(2-bromo-4-methylphenyl)(5-methylfuran-2-yl)methyl]carbamoyl}methyl)-1H-indol-1-yl]propanoate Cpd. 100 (45 mg, 0.09 mmol) was dissolved in MeOH (1.5 mL). 5M NaOH (00 µL, 0.40 mmol) was added to the solution. The reaction mixture was heated at 100° C. for 30 min under mricrowave irradiation. The solvent was removed under reduced pressure and 1N citric acid was added to the residue up pH = 4 was reached. The solid formed was collected by filtration, washed with water and dried until constant weight, yield 99%, mp: 70° C., appearance: white solid<br>1H NMR (300 MHz, DMSO-d6, d in ppm): 2.21 (s, 3H), 2.27 (s, 3H), 2.71 (t, 2H, J = 6.8 Hz), 3.53 (s, 2H), 4.35 (t, 2H, J = 6.7 Hz), 5.76 (d, 1H, J = 3.0 Hz), 5.95 (dd, 1H, J = 3.0 Hz, |

TABLE 2-continued

All the NMR were performed in DMSO-d6

| Cpd. | | Starting compounds,<br>Reaction conditions and purification<br>Yield, MP, Appearance, ¹H NMR (solvent) data, Mass (ES+ or ES−) data |
|---|---|---|
| 103 | 2-[3-(2-methanesulfonylacetyl)-1H-indol-5-yl]-N-{[4-methyl-2-(piperidin-1-yl)phenyl](5-methylfuran-2-yl)methyl}acetamide | J = 0.9 Hz), 6.26 (d, 1H, J = 8.2 Hz), 6.33 (d, 1H, J = 3.1 Hz), 7.04 (dd, 1H, J = 8.6 Hz, J = 1.3 Hz), 7.18 (d, 1H, J = 8.2 Hz), 7.28-7.43 (m, 5H), 9.03 (d, 1H, J = 8.2 Hz), 12.28 (br(s), 1H); m/z: 509 [M + H]+, 511 [M + H]+ (calc. mass: 508).<br>From [4-methyl-2-(piperidin-1-yl)phenyl](5-methylfuran-2-yl)methanamine Ex. 16 and 2-[3-(2-methanesulfonylacetyl)-1H-indol-5-yl]acetic acid Ex. 59 following protocol A, DMAP (2.2 equiv), EDCl•HCl (1.1 equiv), overnight at rt, purification by silica gel column chromatography (CH2Cl2/EtOAc, 60:40), yield 76%, mp: 139° C., appearance: white solid<br>1H NMR (300 MHz, DMSO-d6, d in ppm): 1.42-1.53 (m, 6H), 2.16 (s, 3H), 2.24 (s, 3H), 2.50-2.56 (m, 2H), 2.72-2.77 (m, 2H), 3.15 (s, 3H), 3.55 (s, 2H), 4.79 (s, 2H), 5.83 (d, 1H, J = 3.0 Hz), 5.91 (dd, 1H, J = 2.9 Hz, J = 1.0 Hz), 6.47 (d, 1H, J = 8.4 Hz), 6.88 (d, 1H, J = 7.9 Hz), 6.92 (s, 1H), 7.16 (dd, 1H, J = 8.4 Hz, J = 1.6 Hz), 7.20 (d, 1H, J = 7.8 Hz), 7.38 (d, 1H, J = 8.2 Hz), 8.11 (s, 1H), 8.51 (s, 1H), 8.75 (d, 1H, J = 8.4 Hz), 12.14 (br(s), 1H); m/z: 562 [M + H]+ (calc. mass: 561). |
| 104 | N-[(2-bromo-4-methylphenyl)(5-methylfuran-2-yl)methyl]-2-[3-(2-methanesulfonylacetyl)-1H-indol-5-yl]acetamide | From (2-bromo-4-methylphenyl)(5-methylfuran-2-yl)methanamine Ex. 18 and 2-[3-(2-methanesulfonylacetyl)-1H-indol-5-yl]acetic acid Ex. 59 following protocol A, DMAP (3.2 equiv), EDCl•HCl (1.1 equiv), overnight at rt, purification by silica gel column chromatography (CH2Cl2/EtOAc, 60:40), yield 70%, mp: 206° C., appearance: white solid<br>1H NMR (300 MHz, DMSO-d6, d in ppm): 2.20 (s, 3H), 2.26 (s, 3H), 3.16 (s, 3H), 3.53-3.63 (m, 2H), 4.80 (s, 2H), 5.78 (d, 1H, J = 2.7 Hz), 5.96 (dd, 1H, J = 3.1 Hz, J = 1.1 Hz), 6.23 (d, 1H, J = 8.3 Hz), 7.15-7.20 (m, 2H), 7.35-7.40 (m, 3H), 8.15 (d, 1H, J = 1.0 Hz), 8.51 (s, 1H), 9.13 (d, 1H, J = 8.1 Hz), 12.16 (br(s), 1H); m/z: 579 [M + Na]+, 581 [M + Na]+ (calc. mass: 556). |
| 106a | 2-(1H-indol-5-yl)-N-{[4-methyl-2-(piperidin-1-yl)phenyl](5-methylfuran-2-yl)methyl}acetamide | From [4-methyl-2-(piperidin-1-yl)phenyl](5-methylfuran-2-yl)methanamine Ex. 16 and 2-(1H-indol-5-yl)acetic acid Ex. 90 following protocol A, DMAP (2.2 equiv), EDCl•HCl (1.2 equiv), overnight at rt, purification by silica gel column chromatography (Cyclohexane/EtOAc, 60:40), yield 79%, mp: ND, appearance: white solid<br>1H NMR (300 MHz, DMSO-d6, din ppm): 1.40-1.65 (m, 6H), 2.17 (s, 3H), 2.24 (s, 3H), 2.50-2.60 (m, 2H), 2.70-2.85 (m, 2H), 3.49 (s, 2H), 5.80 (d, 1H, J = 3.1 Hz), 5.90-5.95 (m, 1H), 6.32 (m, 1H), 6.49 (d, 1H, J = 8.5 Hz), 6.87 (d, 1H, J = 8.2 Hz), 6.92 (s, 1H), 6.97 (dd, 1H, J = 8.3 Hz, J = 1.7 Hz), 7.19 (d, 1H, J = 7.8 Hz), 7.23-7.30 (m, 2H), 7.38 (s, 1H), 8.63 (d, 1H, J = 8.3 Hz), 10.70 (br(s), 1H). |
| 106 | 2-(1-methanesulfonyl-1H-indol-5-yl)-N-{[4-methyl-2-(piperidin-1-yl)phenyl](5-methylfuran-2-yl)methyl}acetamide | See FIG. 3AT<br>2-(1H-indol-5-yl)-N-{[4-methyl-2-(piperidin-1-yl)phenyl](5-methylfuran-2-yl)methyl}acetamide Cpd. 106a (50 mg, 0.11 mmol) was dissolved in dry THF (2 mL).<br>Tetrabutylammonium hydrogen sulfate (4 mg, 0.01 mmol) was added to the solution followed by 12M NaOH (944 µL, 0.11 mmol). After 5 min of stirring, methanesulfonyl chloride (13 µL, 0.17 mmol) was added to the reaction mixture and the solution was stirred at rt for 1 h. The solvent was removed under reduced pressure. Water and EtOAc was added to the residue. After phase separation, the organic layer was dried over MgSO4, filtered and the solution was concentrated to dryness. The crude material was purified by silica gel column chromatography eluting with CH2Cl2/EtOAc (95:5), yield 42%, mp: 83° C., appearance: white solid<br>1H NMR (300 MHz, DMSO-d6, d in ppm): 1.35-1.60 (m, 6H), 2.17 (s, 3H), 2.24 (s, 3H), 2.50-2.60 (m, 2H), 2.65-2.85 (m, 2H), 3.36 (s, 3H), 3.56 (s, 2H), 5.81 (d, 1H, J = 3.0 Hz), 5.90-5.95 (m, 1H), 6.48 (d, 1H, J = 8.2 Hz), 6.78 (dd, 1H, J = 3.7 Hz, J = 0.7 Hz), 6.88 (d, 1H, J = 8.2 Hz), 6.93 (s, 1H), 7.20 (d, 1H, J = 7.8 Hz), 7.25 (dd, 1H, J = 8.6 Hz, J = 1.7 Hz), 7.5-7.55 (m, 2H), 7.72 (d, 1H, J = 8.6 Hz), 8.78 (d, 1H, J = 8.5 Hz); m/z: 520 [M + H]+ (calc. mass: 519). |

TABLE 2-continued

All the NMR were performed in DMSO-d6

| Cpd. | Starting compounds, Reaction conditions and purification Yield, MP, Appearance, $^1$H NMR (solvent) data, Mass (ES+ or ES−) data |
|---|---|
| 107 N-[(2,4-dimethylphenyl)(5-methylfuran-2-yl)methyl]-2-[3-(2-methanesulfonylacetyl)-1H-indol-5-yl]acetamide | From (2,4-dimethylphenyl)(5-methylfuran-2-yl)methanamine Ex. 19 and 2-[3-(2-methanesulfonylacetyl)-1H-indol-5-yl]acetic acid Ex. 59 following protocol A, substituted amine (0.9 equiv), DMAP (3.2 equiv), EDCl•HCl (1.2 equiv), overnight at rt, purification by preparative HPLC, yield 68%, mp: 213° C., appearance: white solid<br>1H NMR (300 MHz, DMSO-d6, d in ppm): 2.16 (s, 3H), 2.19 (s, 3H), 2.21 (s, 3H), 3.16 (s, 3H), 3.57 (s, 2H), 4.80 (s, 2H), 5.86 (d, 1H, J = 2.9 Hz), 5.95 (dd, 1H, J = 3.0 Hz, J = 1.0 Hz), 6.10 (d, 1H, J = 8.4 Hz), 6.92-7.00 (m, 2H), 7.11 (d, 1H, J = 7.6 Hz), 7.17 (dd, 1H, J = 8.4 Hz, J = 1.6 Hz), 7.38 (d, 1H, J = 8.5 Hz), 8.14 (s, 1H), 8.51 (s, 1H), 8.97 (d, 1H, J = 8.3 Hz), 12.15 (br(s), 1H) ; m/z: 515 [M + Na]+ (calc. mass: 492). |
| 108 N-[(2,4-dimethylphenyl)(5-methylfuran-2-yl)methyl]-1-(1H-indol-5-yl)cyclopropane-1-carboxamide | From (2,4-dimethylphenyl)(5-methylfuran-2-yl)methanamine Ex. 19 and 1-(1H-indol-5-yl)cyclopropane-1-carboxylic acid Ex. 61 following protocol A, substituted amine (0.9 equiv), DMAP (3.2 equiv), EDCl•HCl (1.2 equiv), overnight at rt, purification by preparative HPLC, yield 47%, mp: 62° C., appearance: white solid<br>1H NMR (300 MHz, DMSO-d6, d in ppm): 0.96-1.09 (m, 2H), 1.25-1.42 (m, 2H), 2.11 (s, 3H), 2.13 (s, 3H), 2.20 (s, 3H), 5.76 (s, 1H), 5.90 (s, 1H), 6.07 (d, 1H, J = 7.8 Hz), 6.40 (s, 1H), 6.66 (d, 1H, J = 8.0 Hz), 6.77 (d, 1H, J = 7.4 Hz), 6.85-6.98 (m, 2H), 7.10 (d, 1H, J = 8.5 Hz), 7.30-7.45 (m, 2H), 7.56 (s, 1H), 11.12 (br(s), 1H); m/z: 399 [M + H]+ (calc. mass: 398). |
| 110 tert-butyl 3-{5-[({[2-(azepan-1-yl)-4-methoxyphenyl](5-methylfuran-2-yl)methyl}carbamoyl)methyl]-1H-indol-1-yl}propanoate | From [2-(azepan-1-yl)-4-methoxyphenyl](5-methylfuran-2-yl)methanamine Ex. 63 and 2-{1-[3-(tert-butoxy)-3-oxopropyl]-1H-indol-5-yl}acetic acid Ex. 57 following protocol A, substituted amine (0.9 equiv), DMAP (3.2 equiv), EDCl•HCl (1.2 equiv), overnight at rt, purification by preparative HPLC, yield 53%, mp: 57° C., appearance: white solid<br>1H NMR (300 MHz, DMSO-d6, d in ppm): 1.31 (s, 9H), 1.42-1.65 (m, 8H), 2.17 (s, 3H), 2.69 (t, 2H, J = 6.5 Hz), 2.76-2.89 (m, 2H), 2.90-3.02 (m, 2H), 3.49 (s, 2H), 3.70 (s, 3H), 4.34 (t, 2H, J = 6.4 Hz), 5.72 (d, 1H, J = 2.7 Hz), 5.90 (dd, 1H, J = 3.0 Hz, J = 1.0 Hz), 6.32 (d, 1H, J = 2.5 Hz), 6.53 (d, 1H, J = 8.1 Hz), 6.59-6.70 (m, 2H), 7.03 (dd, 1H, J = 8.4 Hz, J = 1.6 Hz), 7.23 (d, 1H, J = 9.3 Hz), 7.27 (d, 1H, J = 3.1 Hz), 7.31-7.41 (m, 2H), 8.65 (d, 1H, J = 8.5 Hz); m/z: 600 [M + H]+ (calc. mass: 599). |
| 111 3-{5-[({[2-(azepan-1-yl)-4-methoxyphenyl](5-methylfuran-2-yl)methyl}carbamoyl)methyl]-1H-indol-1-yl}propanoic acid | FIG. 3AS<br>The previously synthesized tert-butyl 3-{5-[({[2-(azepan-1-yl)-4-methoxyphenyl](5-methylfuran-2-yl)methyl}carbamoyl)methyl]-1H-indol-1-yl}propanoate Cpd. 110 (32 mg, 0.05 mmol) was dissolved in MeOH (1.5 mL). 5M NaOH (53 µL, 0.26 mmol) was added to the solution. The reaction mixture was heated at 100° C. for 30 min under mricrowave irradiation. The solvent was removed under reduced pressure and 1N citric acid was added to the residue up pH = 4 was reached. The solid formed was collected by filtration, washed with water and dried until constant weight, yield 84%, mp: 80° C., appearance: white solid<br>1H NMR (300 MHz, DMSO-d6, din ppm): 1.41-1.69 (m, 8H), 2.18 (s, 3H), 2.70 (t, 2H, J = 6.8 Hz), 2.77-2.89 (m, 2H), 2.89-3.02 (m, 2H), 3.49 (s, 2H), 3.71 (s, 3H), 4.35 (t, 2H, J = 6.9 Hz), 5.72 (d, 1H, J = 3.2 Hz), 5.88-5.94 (m, 1H), 6.32 (d, 1H, J = 3.1 Hz), 6.53 (d, 1H, J = 8.6 Hz), 6.62-6.71 (m, 2H), 7.03 (dd, 1H, J = 8.6 Hz, J = 1.5 Hz), 7.23 (d, 1H, J = 9.3 Hz), 7.29 (d, 1H, J = 3.2 Hz), 7.33-7.41 (m, 2H), 8.67 (d, 1H, J = 8.9 Hz), 12.25 (br(s), 1H); m/z: 544 [M + H]+ (calc. mass: 543). |
| 112 N-[(5-chlorofuran-2-yl)[4-methyl-2-(pyrrolidin-1-yl)phenyl]methyl]-2-[3-(2-methanesulfonylethyl)-1H-indol-5-yl]acetamide | From (5-chlorofuran-2-yl)[4-methyl-2-(pyrrolidin-1-yl)phenyl]methanamine Ex. 48 and 2-[3-(2-methanesulfonylethyl)-1H-indol-5-yl]acetic acid Ex. 58 following protocol A, DMAP (3.2 equiv), EDCl•HCl (1.2 equiv), overnight at rt, purification by silica gel column chromatography (CH2Cl2/MeOH, 98:2), yield 51%, mp: 83° C., appearance: off-white solid<br>1H NMR (300 MHz, DMSO-d6, d in ppm): 1.72-1.76 (m, 4H), 2.23 (s, 3H), 2.84-2.88 (m, 2H), 2.99 (s, 3H), |

TABLE 2-continued

All the NMR were performed in DMSO-d6

| Cpd. | | Starting compounds, Reaction conditions and purification Yield, MP, Appearance, ¹H NMR (solvent) data, Mass (ES+ or ES−) data |
|---|---|---|
| | | 3.00-3.11 (m, 4H), 3.39-3.45 (m, 2H), 3.53 (s, 2H), 6.03 (dd, 1H, J = 3.4 Hz, J = 1.1 Hz), 6.33 (d, 1H, J = 3.3 Hz), 6.36 (d, 1H, J = 8.2 Hz), 6.79 (d, 1H, J = 7.7 Hz), 6.86 (s, 1H), 7.00 (dd, 1H, J = 8.3 Hz, J = 1.4 Hz), 7.15 (d, 1H, J = 7.8 Hz), 7.20 (d, 1H, J = 2.2 Hz), 7.24 (d, 1H, J = 8.4 Hz), 7.42 (s, 1H), 8.81 (d, 1H, J = 8.2 Hz), 10.82 (d, 1H, J = 2.1 Hz); m/z: 554 [M + H]+, 556 [M + H]+ (calc. mass: 553). |
| 113 | N-{[4-methyl-2-(piperidin-1-yl)phenyl](5-methylfuran-2-yl)methyl}-2-[1-(oxan-4-ylmethyl)-1H-indol-5-yl]acetamide | See FIG. 3AT To a solution of 2-(1H-indol-5-yl)-N-{[4-methyl-2-(piperidin-1-yl)phenyl](5-methylfuran-2-yl)methyl}acetamide Cpd. 106a (70 mg, 0.16 mmol) dissolved in dry THF (1 mL) was added sodium hydride (60% in meneral oil) (11 mg, 0.48 mmol). After few min of stirring, 4-(bromomethyl)-tetrahydro-2H-pyran (57 mg, 0.32 mmol) was added and the reaction mixture was stirred at rt for two days. Water was added to the reaction and the aqueous layer was extracted with EtOAc. The organic layer was dried over MgSO4, filtered and the solution was concentrated under reduced pressure. The crude material was purified by preparative HPLC, yield 12%, mp: 67° C., appearance: pale green solid 1H NMR (300 MHz, DMSO-d6, d in ppm): 1.26-1.35 (m, 4H), 1.37-1.58 (m, 6H), 1.94-2.02 (m, 1H), 2.16 (s, 3H), 2.24 (s, 3H), 2.53-2.61 (m, 2H), 2.71-2.80 (m, 2H), 3.12-3.23 (m, 2H), 3.49 (s, 2H), 3.73-3.83 (m, 2H), 4.02 (d, 2H, J = 7.3 Hz), 5.80 (d, 1H, J = 3.2 Hz), 5.89-5.93 (m, 1H), 6.32 (d, 1H, J = 3.3 Hz), 6.46 (d, 1H, J = 7.9 Hz), 6.87 (d, 1H, J = 7.5 Hz), 6.92 (s, 1H), 7.01 (dd, 1H, J = 8.4 Hz, J = 2.0 Hz), 7.18 (d, 1H, J = 7.7 Hz), 7.28 (d, 1H, J = 3.1 Hz), 7.34-7.42 (m, 2H), 8.65 (d, 1H, J = 8.4 Hz); m/z: 540 [M + H]+ (calc. mass: 539). |
| 114 | N-{[4-methyl-2-(piperidin-1-yl)phenyl](5-methylfuran-2-yl)methyl}-2-[1-(morpholine-4-carbonyl)-1H-indol-6-yl]acetamide | See FIG. 3AU Step 1: to a solution of 1,1′-carbonyldiimidazole (3.07 g, 18.93 mmol) in THF (20 mL) was added morpholine (1.57 g, 17.99 mmol) at rt, and then the mixture was refluxed for 12 h. After cooling to rt, the mixture was concentrated under reduced pressure. CH2Cl2 and water were added to quench the reaction. The pH of the solution was ajusted to pH = 8 with 1N HCl. The organic layer was separated, dried over MgSO4, filtered and the solution was concentrated under reduced pressure to afford 4-[(1H-imidazol-1-yl)carbonyl]morpholine (2.75 g, 84%) as white solid. 1H NMR (300 MHz, DMSO-d6, d in ppm): 3.49 (t, 4H, J = 4.5 Hz), 3.65 (t, 4H, J = 3.7 Hz), 7.02 (dd, 1H, J = 1.4 Hz, J = 0.9 Hz), 7.47 (t, 1H, J = 1.4 Hz), 8.03 (t, 1H, J = 1.1 Hz). Step 2: to a solution of 2-(1H-indol-6-yl)-N-((4-methyl-2-(piperidin-1-yl)phenyl)(5-methylfuran-2-yl)methyl)acetamide Cpd. 88a (75 mg, 0.17 mmol) dissolved in dry acetonitrile (2 mL) was added 4-[(1H-imidazol-1-yl)carbonyl]morpholine (46 mg, 0.26 mmol) followed by 1,8-diazabicyclo[5.4.0]undec-7-ene (5 μL, 0.03 mmol). The reaction mixture was stirred overnight at rt. Additional 4-[(1H-imidazol-1-yl)carbonyl]morpholine (46 mg, 0.26 mmol) and 1,8-diazabicyclo[5.4.0]undec-7-ene (5 μL, 0.03 mmol) were added to the reaction mixture and the stirring was kept for 4 h. Water was added to the reaction and the aqueous layer was extracted with EtOAc. The organic layer was dried over MgSO4, filtered and the solution was concentrated under reduced pressure. The crude material was purified by silica gel column chromatography eluting with Cyclohexane/EtOAc (70:30) to give N-{[4-methyl-2-(piperidin-1-yl)phenyl](5-methylfuran-2-yl)methyl}-2-[1-(morpholine-4-carbonyl)-1H-indol-6-yl]acetamide, yield 53%, mp: 85° C., appearance: white solid 1H NMR (300 MHz, DMSO-d6, d in ppm): 1.40-1.60 (m, 6H), 2.16 (s, 3H), 2.24 (s, 3H), 2.5-2.55 (m, 2H), 2.75-2.85 (m, 2H), 3.46 (t, 4H, J = 2.3 Hz), 3.56 (s, 2H), 3.66 (t, 4H, J = 4.8 Hz), 5.82 (d, 1H, J = 2.6 Hz), 5.90-5.95 (m, 1H), 6.47 (m, 1H, J = 8.7 Hz), 6.60 (d, 1H, J = 2.9 Hz), 6.87 (d, 1H, J = 7.3 Hz), 6.92 (s, 1H), 7.07 (dd, 1H, J = 8.1 Hz, J = 1.4 Hz), 7.18 (d, 1H, J = 7.7 Hz), 7.45-7.53 (m, 2H), 7.56 (s, 1H), 8.76 (d, 1H, J = 8.8 Hz); m/z: 555 [M + H]+ (calc. mass: 554). |

TABLE 2-continued

All the NMR were performed in DMSO-d6

| Cpd. | Starting compounds, Reaction conditions and purification Yield, MP, Appearance, $^1$H NMR (solvent) data, Mass (ES+ or ES−) data |
|---|---|
| 115 N-{[4-methyl-2-(piperidin-1-yl)phenyl](5-methylfuran-2-yl)methyl}-2-[3-(methylsulfamoyl)-1H-indol-5-yl]acetamide | From [4-methyl-2-(piperidin-1-yl)phenyl](5-methylfuran-2-yl)methanamine Ex. 16 and 2-[3-(methylsulfamoyl)-1H-indol-5-yl]acetic acid Ex. 64 following protocol A, DMAP (2.2 equiv), EDCl•HCl (1.2 equiv), overnight at rt, purification by silica gel column chromatography (Cyclohexan/EtOAc, 50:50), yield 74%, mp: 119° C., appearance: white solid 1H NMR (300 MHz, DMSO-d6, d in ppm): 1.43-1.53 (m, 6H), 2.16 (s, 3H), 2.24 (s, 3H), 2.36 (d, 3H, J = 5.1 Hz), 2.51-2.57 (m, 2H), 2.76-2.80 (m, 2H), 3.54 (s, 2H), 5.82 (d, 1H, J = 3.0 Hz), 5.91 (dd, 1H, J = 3.0 Hz, J = 1.0 Hz), 6.48 (d, 1H, J = 8.4 Hz), 6.88 (d, 1H, J = 7.8 Hz), 6.93 (s, 1H), 7.02 (q, 1H, J = 5.1 Hz), 7.15 (dd, 1H, J = 8.5 Hz, J = 1.6 Hz), 7.20 (d, 1H, J = 7.8 Hz), 7.38 (d, 1H, J = 8.4 Hz), 7.70 (s, 1H), 7.82 (d, 1H, J = 2.8 Hz), 8.73 (d, 1H, J = 8.5 Hz), 11.84 (br(s), 1H); m/z: 535 [M + H]+ (calc. mass: 534). |
| 116 N-{[4-methyl-2-(piperidin-1-yl)phenyl](5-methylfuran-2-yl)methyl}-2-[1-(morpholine-4-carbonyl)-1H-indol-5-yl]acetamide | See FIG. 3AX To a solution of previously synthesized 2-(1H-indol-5-yl)-N-{[4-methyl-2-(piperidin-1-yl)phenyl](5-methylfuran-2-yl)methyl}acetamide Cpd. 106a (94 mg, 0.21 mmol) dissolved in dry acetonitrile (2 mL) was added the previously synthesized 4-[(1H-imidazol-1-yl)carbonyl]morpholine (58 mg, 0.32 mmol) followed by 1,8-diazabicyclo[5.4.0]undec-7-ene (6 µL, 0.04 mmol). The reaction mixture was stirred overnight at rt. Additional 4-[(1H-imidazol-1-yl)carbonyl]morpholine (58 mg, 0.32 mmol) and 1,8-diazabicyclo[5.4.0]undec-7-ene (6 µL, 0.04 mmol) were added to the reaction mixture and the stirring was kept for 4 h. Water was added to the reaction and the aqueous layer was extracted with EtOAc. The organic layer was dried over MgSO4, filtered and the solution was concentrated under reduced pressure. The crude material was purified by silica gel column chromatography eluting with Cyclohexane/EtOAc (70:30) to give N-{[4-methyl-2-(piperidin-1-yl)phenyl](5-methylfuran-2-yl)methyl}-2-[1-(morpholine-4-carbonyl)-1H-indol-5-yl]acetamide Cpd. 116, yield 64%, mp: 88° C., appearance: pale blue solid 1H NMR (300 MHz, DMSO-d6, d in ppm): 1.40-1.60 (m, 6H), 2.17 (s, 3H), 2.24 (s, 3H), 2.5-2.55 (m, 2H), 2.75-2.85 (m, 2H), 3.48 (t, 4H, J = 4.5 Hz), 3.53 (s, 2H), 3.67 (t, 4H, J = 5.2 Hz), 5.82 (d, 1H, J = 2.9 Hz), 5.90-5.95 (m, 1H), 6.47 (m, 1H, J = 8.6 Hz), 6.60 (dd, 1H, J = 3.5 Hz, J = 0.6 Hz), 6.88 (d, 1H, J = 7.7 Hz), 6.93 (s, 1H), 7.15 (dd, 1H, J = 8.4 Hz, J = 1.6 Hz), 7.20 (d, 1H, J = 7.7 Hz), 7.45 (d, 1H, J = 0.9 Hz), 7.50 (d, 1H, J = 3.5 Hz), 7.54 (d, 1H, J = 8.5 Hz), 8.72 (d, 1H, J = 8.4 Hz); m/z: 555 [M + H]+ (calc. mass: 554). |
| 117 2-[3-(2-methanesulfonylacetyl)-1H-indol-6-yl]-N-{[4-methyl-2-(piperidin-1-yl)phenyl](5-methylfuran-2-yl)methyl}acetamide | See FIG. 3AY To a solution of previously synthesized 2-(1H-indol-6-yl)-N-((4-methyl-2-(piperidin-1-yl)phenyl)(5-methylfuran-2-yl)methyl)acetamide Cpd. 88a (60 mg, 0.14 mmol) dissolved in dry CH2Cl2 (2 mL) was added Et3N (38 µL, 0.27 mmol) followed by 2-methanesulfonylacetyl chloride (53 mg, 0.34 mmol). The reaction mixture was stirred overnight at rt. TLC showed not total consumption of the starting material. Additional 2-methanesulfonylacetyl chloride (53 mg, 0.34 mmol) and Et3N (38 µL, 0.27 mmol) were added to the reaction mixture. After 4 h, water was added to quench the reaction. The mixture was extracted with EtOAc. After phases separation, the organic layer was dried over MgSO4, filtered and the solution was concentrated to dryness. The crude material was purified by silica gel column chromatography eluting with CH2Cl2/MeOH (98:2), yield 33%, mp: 85° C., appearance: white solid 1H NMR (300 MHz, DMSO-d6, d in ppm): 1.40-1.60 (m, 6H), 2.16 (s, 3H), 2.24 (s, 3H), 2.5-2.55 (m, 2H), 2.75-2.85 (m, 2H), 3.15 (s, 3H), 3.56 (s, 2H), 4.79 (s, 2H), 5.82 (d, 1H, J = 3.1 Hz), 5.90-5.95 (m, 1H), 6.48 (m, 1H, J = 8.2 Hz), 6.88 (d, 1H, J = 7.3 Hz), 6.93 (s, 1H), 7.12 (d, 1H, J = 9.5 Hz), 7.18 (d, 1H, J = 7.8 Hz), 7.38 (s, 1H), 8.04 (d, 1H, J = 8.1 Hz), 8.51 (d, 1H, J = 3.2 Hz), 8.73 (d, 1H, J = 8.3 Hz), 12.15 (s, 1H); m/z: 562 [M + H]+ (calc. mass: 561). |

US 11,052,092 B2

TABLE 2-continued

All the NMR were performed in DMSO-d6

| Cpd. | Starting compounds, Reaction conditions and purification Yield, MP, Appearance, $^1$H NMR (solvent) data, Mass (ES+ or ES−) data |
|---|---|
| 118 N-{[4-methyl-2-(piperidin-1-yl)phenyl](5-methylfuran-2-yl)methyl}-2-[1-(oxane-4-carbonyl)-1H-indol-5-yl]acetamide | See FIG. 3AT<br>To a solution of previously synthesized 2-(1H-indol-5-yl)-N-((4-methyl-2-(piperidin-1-yl)phenyl)(5-methylfuran-2-yl)methyl)acetamide Cpd. 106a (80 mg, 0.18 mmol) dissolved in dry CH2Cl2 were added DMAP (44 mg, 0.36 mmol) and tetrahydro-2H-pyran-4-carbonyl chloride (40 mg, 0.27 mmol) at 0° C. and under N2 atmosphere. After few min of stirring, Et3N (76 µL, 0.54 mmol) was added and the reaction mixture was stirred overnight at rt. Water was added to quench the reaction. The aqueous layer was extracted with EtOAc. The combined organic layers were dried over MgSO4, filtered and the solution was concentrated under reduced pressure. The crude material was purified by silica gel column chromatography eluting with Cyclohexane/EtOAc (50:50), yield 65%, mp: 96° C., appearance: white solid<br>1H NMR (300 MHz, DMSO-d6, d in ppm): 1.45-1.60 (m, 6H), 1.65-1.85 (m, 4H), 2.16 (s, 3H), 2.24 (s, 3H), 2.55-2.6 (m, 3H), 2.70-2.80 (m, 2H), 3.45-3.53 (m, 2H), 3.54 (s, 2H), 3.85-3.95 (m, 2H), 5.80 (d, 1H, J = 3.0 Hz), 5.90-5.95 (m, 1H), 6.49 (d, 1H, J = 8.2 Hz), 6.71 (dd, 1H, J = 3.8 Hz, J = 0.6 Hz), 6.88 (dd, 1H, J = 9.5 Hz, J = 1.2 Hz), 6.93 (s, 1H), 7.15-7.25 (m, 2H), 7.46 (d, 1H, J = 1.1 Hz), 8.03 (d, 1H, J = 3.9 Hz), 8.23 (d, 1H, J = 8.5 Hz), 8.74 (d, 1H, J = 8.3 Hz); m/z: 554 [M + H]+ (calc. mass: 553). |
| 119 1-[3-(methanesulfonamidomethyl)-1H-indol-5-yl]-N-{[4-methyl-2-(piperidin-1-yl)phenyl](5-methylfuran-2-yl)methyl}cyclopropane-1-carboxamide | See FIG. 3AZ<br>To a solution of previously synthesized 1-(3-formyl-1H-indol-5-yl)-N-((4-methyl-2-(piperidin-1-yl)phenyl)(5-methylfuran-2-yl)methyl)cyclopropanecarboxamide (see Step 1 of Cpd. 89) (136 mg, 0.27 mmol) dissolved in dry toluene (4 mL) was added methanesulfonamide (39 mg, 0.41 mmol) followed by titanium (IV) ethoxide (115 µL, 0.55 mmol). The reaction mixture was stirred at 110° C. for 3 h. After cooling to rt, the solvent was removed under reduced pressure. Anhydrous MeOH (4 mL) was added and the reaction mixture was cooled to 0° C. Sodium hydride (83 mg, 2.20 mmol) was added portionwise to the solution and the reaction mixture was stirred at rt for 2 h. LCMS showed incomplete conversion of the starting material. Additional sodium borohydride (83 mg, 2.20 mmol) was added and the reaction mixture was stirred overnight at rt. Water and ice were added to quench the reaction. The solid formed was collected by filtration, washed with water and dried under vacuo until constant weight, yield 32%, mp: 109° C., appearance: white solid<br>1H NMR (300 MHz, DMSO-d6, d in ppm): 1.0-1.1 (m, 2H), 1.12-1.35 (m, 7H), 1.35-1.45 (m, 1H), 2.08 (s, 3H), 2.21 (s, 3H), 2.25-2.40 (m, 2H), 2.50-2.55 (m, 2H), 2.71 (s, 3H), 4.26 (d, 2H, J = 6.1 Hz), 5.82 (d, 1H, J = 3.0 Hz), 5.85-5.95 (m, 1H), 6.32 (d, 1H), 6.69 (d, 1H, J = 8.9 Hz), 6.83 (d, 1H, J = 8.7 Hz), 6.90 (d, 1H, J = 7.8 Hz), 6.94 (s, 1H), 7.14 (dd, 1H, J = 8.4 Hz, J = 1.7 Hz), 7.25-7.40 (m, 3H), 7.70 (s, 1H), 11.03 (s, 1H); m/z: 575 [M + H]+ (calc. mass: 574). |
| 120 N-{[4-methyl-2-(piperidin-1-yl)phenyl](5-methylfuran-2-yl)methyl}-2-[3-(morpholine-4-carbonyl)-1H-indol-5-yl]acetamide | From [4-methyl-2-(piperidin-1-yl)phenyl](5-methylfuran-2-yl)methanamine Ex. 16 and 2-[3-(morpholine-4-carbonyl)-1H-indol-5-yl]acetic acid Ex. 65 following protocol A, DMAP (1 equiv), EDCl•HCl (1.1 equiv), 3 h at rt, purification by silica gel column chromatography (CH2Cl2/MeOH, 95:5), yield 53%, mp: 124° C., appearance: white solid<br>1H NMR (300 MHz, DMSO-d6, d in ppm): 1.40-1.60 (m, 6H), 2.16 (s, 3H), 2.24 (s, 3H), 2.50-2.54 (m, 2H), 2.75-2.80 (m, 2H), 3.52 (s, 2H), 3.53-3.60 (m, 8H), 5.81 (d, 1H, J = 2.8 Hz), 5.90 (dd, 1H, J = 3.0 Hz, J = 1.0 Hz), 6.47 (d, 1H, J = 8.4 Hz), 6.87 (d, 1H, J = 7.7 Hz), 6.91 (s, 1H), 7.05 (dd, 1H, J = 8.4 Hz, J = 1.6 Hz), 7.19 (d, 1H, J = 7.8 Hz), 7.32 (d, 1H, J = 8.3 Hz), 7.57 (s, 1H), 7.64 (d, 1H, J = 2.7 Hz), 7.80 (d, 1H, J = 8.5 Hz), 11.49 (s, 1H); m/z: 555 [M + H]+ (calc. mass: 554). |
| 122 N-[(2,4-dimethylphenyl)(5-methylfuran-2-yl)methyl]-1-[2-(2- | From (2,4-dimethylphenyl)(5-methylfuran-2-yl)methanamine Ex. 19 and 1-[2-(2-methoxyacetyl)-2,3-dihydro-1H-isoindol-5-yl]cyclopropane-1-carboxylic acid Ex. 67 following protocol A, DMAP (1 equiv), EDCl•HCl (1.1 equiv), overnight at rt, purification by silica gel column chromatography |

TABLE 2-continued

All the NMR were performed in DMSO-d6

| Cpd. | | Starting compounds, Reaction conditions and purification Yield, MP, Appearance, $^1$H NMR (solvent) data, Mass (ES+ or ES−) data |
|---|---|---|
| | methoxyacetyl)-2,3-dihydro-1H-isoindol-5-yl]cyclopropane-1-carboxamide | (CH2Cl2/MeOH, 97:3) followed by a second purification on silica gel column chromatography (gradient of Cyclohexane/EtOAc, from [30:70] to [20:80]). The residue was then triturated in Et2O and filtered-off. The solvent was concentrated under reduced pressure to afford the title compound, yield 58%, mp: 55° C., appearance: off-white solid<br>1H NMR (300 MHz, DMSO-d6, d in ppm): 0.95-1.05 (m, 2H), 1.25-1.40 (m, 2H), 2.16 (s, 3H), 2.17 (s, 3H), 2.22 (s, 3H), 3.33 (d, 3H, J = 1.2 Hz), 4.12 (d, 2H, J = 2.0 Hz), 4.63 (s, 2H), 4.74 (s, 2H), 5.80 (m, 1H), 5.93 (d, 1H, J = 3.0 Hz), 6.12 (d, 1H, J = 8.4 Hz), 6.90-7.00 (m, 3H), 7.25-7.40 (m, 3H), 7.45 (d, 1H, J = 8.7 Hz); m/z: 495 [M + Na]+ (calc. mass: 472). |
| 123 | 2-(1-cyclopropanecarbonyl-2,3-dihydro-1H-indol-5-yl)-N-{[4-methyl-2-(piperidin-1-yl)phenyl](5-methylfuran-2-yl)methyl}acetamide | From [4-methyl-2-(piperidin-1-yl)phenyl](5-methylfuran-2-yl)methanamine Ex. 16 and 2-(1-cyclopropanecarbonyl-2,3-dihydro-1H-indol-5-yl)acetic acid Ex. 68 following protocol A, DMAP (1.2 equiv), EDCl•HCl (2.2 equiv), 8 h at rt, purification by trituration in MeOH and filtration, yield 74%, mp: 94° C., appearance: white solid<br>1H NMR (300 MHz, DMSO-d6, d in ppm): 0.80-0.90 (m, 4H), 1.40-1.55 (m, 6H), 1.85-1.95 (m, 1H), 2.17 (s, 3H), 2.25 (s, 3H), 2.55-2.60 (m, 2H), 2.75-2.85 (m, 2H), 3.11 (t, 2H, J = 8.5 Hz), 3.39 (s, 2H), 4.25 (t, 2H, J = 7.8 Hz), 5.80 (d, 1H, J = 3.1 Hz), 5.92 (dd, 1H, J = 2.9 Hz, J = 1.0 Hz), 6.48 (d, 1H, J = 8.4 Hz), 6.88 (d, 1H, J = 7.4 Hz), 6.94 (s, 1H), 6.97 (d, 1H, J = 7.1 Hz), 7.09 (s, 1H), 7.17 (d, 1H, J = 7.7 Hz), 7.88 (d, 1H, J = 5.5 Hz), 8.69 (d, 1H, J = 8.5 Hz); m/z: 512 [M + H]+ (calc. mass: 511). |
| 124 | N-[(2,4-dimethylphenyl)(5-methylfuran-2-yl)methyl]-1-(2,2-dioxo-1,3-dihydro-4,2,1-benzoxathiazin-6-yl)cyclopropane-1-carboxamide | From (2,4-dimethylphenyl)(5-methylfuran-2-yl)methanamine Ex. 19 and 1-(2,2-dioxo-1,3-dihydro-4,2,1-benzoxathiazin-6-yl)cyclopropane-1-carboxylic acid Ex. 69 following protocol A, DMAP (1.1 equiv), EDCl•HCl (1.1 equiv), 2 h at rt, purification by silica gel column chromatography (Cyclohexane/EtOAc, 70:30), yield 52%, mp: 96° C., appearance: white solid<br>1H NMR (300 MHz, DMSO-d6, d in ppm): 0.92-1.02 (m, 2H), 1.22-1.34 (m, 2H), 2.16 (s, 3H), 2.18 (s, 3H), 2.22 (s, 3H), 5.17 (s, 2H), 5.76 (d, 1H, J = 3.0 Hz), 5.93 (dd, 1H, J = 3.0 Hz, J = 1.0 Hz), 6.13 (d, 1H, J = 8.5 Hz), 6.75-6.80 (m, 1H), 6.91-7.05 (m, 5H), 7.63 (d, 1H, J = 8.3 Hz), 10.56 (s, 1H); m/z: 489 [M + Na]+ (calc. mass: 466). |
| 125 | N-[(2,4-dimethylphenyl)(5-methylfuran-2-yl)methyl]-1-(2,3-dioxo-2,3-dihydro-1H-indol-5-yl)cyclopropane-1-carboxamide | From (2,4-dimethylphenyl)(5-methylfuran-2-yl)methanamine Ex. 19 and 1-(2,3-dioxo-2,3-dihydro-1H-indol-5-yl)cyclopropane-1-carboxylic acid Ex. 70 following protocol A, DMAP (1.2 equiv), EDCl•HCl (1.2 equiv), 2 h at rt, purification by silica gel column chromatography (CH2Cl2/EtOAc, 95:5), yield 53%, mp: 192° C., appearance: orange solid<br>1H NMR (300 MHz, DMSO-d6, d in ppm): 0.93-1.04 (m, 2H), 1.25-1.37 (m, 2H), 2.16 (s, 3H), 2.18 (s, 3H), 2.22 (s, 3H), 5.72 (dd, 1H, J = 3.0 Hz, J = 0.6 Hz), 5.93 (dd, 1H, J = 3.0 Hz, J = 1.0 Hz), 6.14 (d, 1H, J = 8.3 Hz), 6.87 (d, 1H, J = 7.8 Hz), 6.90-7.01 (m, 3H), 7.44 (d, 1H, J = 1.6 Hz), 7.54 (dd, 1H, J = 8.1 Hz, J = 2.0 Hz), 7.85 (d, 1H, J = 8.4 Hz), 11.05 (s, 1H); m/z: 427 [M − H]− (calc. mass: 428). |
| 126 | 1-(1-acetyl-2,3-dihydro-1H-indol-5-yl)-N-[(2,4-dimethylphenyl)(5-methylfuran-2-yl)methyl]cyclopropane-1-carboxamide | From (2,4-dimethylphenyl)(5-methylfuran-2-yl)methanamine Ex. 19 and 1-(1-acetyl-2,3-dihydro-1H-indol-5-yl)cyclopropane-1-carboxylic acid Ex. 71 following protocol A, DMAP (1.2 equiv), EDCl•HCl (2.2 equiv), 8 h at rt, purification by silica gel column chromatography (Cyclohexane/EtOAc, 50:50), yield 60%, mp: 75° C., appearance: white solid<br>1H NMR (300 MHz, DMSO-d6, d in ppm): 0.96 (d, 2H, J = 2.7 Hz), 1.20-1.35 (m, 2H), 2.13 (s, 3H), 2.16 (s, 3H), 2.17 (s, 3H), 2.22 (s, 3H), 3.10 (t, 2H, J = 8.4 Hz), 4.08 (t, 2H, J = 8.6 Hz), 5.77 (d, 1H, J = 3.0 Hz), 5.93 (dd, 1H, J = 3.0 Hz, J = 1.0 Hz), 6.12 (d, 1H, J = 8.3 Hz), 6.85-7.00 (m, 3H), 7.13 (d, 1H, J = 8.4 Hz), 7.17-7.20 (m, 2H), 7.97 (d, 1H, J = 8.3 Hz); m/z: 465 [M + Na]+ (calc. mass: 442). |
| 127 | 1-(2-acetyl-2,3-dihydro-1H-isoindol-5-yl)-N-[(2,4- | From (2,4-dimethylphenyl)(5-methylfuran-2-yl)methanamine Ex. 19 and 1-(2-acetyl-2,3-dihydro-1H-isoindol-5-yl)cyclopropane-1-carboxylic acid Ex. 72 following protocol A, DMAP (1.2 equiv), EDCl•HCl (2.2 equiv), 8 h at rt, |

TABLE 2-continued

All the NMR were performed in DMSO-d6

| Cpd. | | Starting compounds, Reaction conditions and purification Yield, MP, Appearance, $^1$H NMR (solvent) data, Mass (ES+ or ES−) data |
|---|---|---|
| | dimethylphenyl)(5-methyl-2-yl)methyl]cyclopropane-1-carboxamide | purification by silica gel column chromatography (Cyclohexane/EtOAc, 50:50), yield 14%, mp: 72° C., appearance: white solid 1H NMR (300 MHz, DMSO-d6, d in ppm): 1.00 (s, 2H), 1.20-1.25 (m, 2H), 2.04 (d, 3H, J = 1.7 Hz), 2.16 (s, 3H), 2.17 (s, 3H), 2.22 (s, 3H), 4.57 (s, 2H), 4.79 (t, 2H), 5.76 (m, 1H), 5.93 (m, 1H), 6.13 (d, 1H, J = 8.3 Hz), 6.90-7.00 (m, 3H), 7.20-7.35 (m, 3H), 7.45 (d, 1H, J = 8.3 Hz); m/z: 465 [M + Na]+ (calc. mass: 442). |
| 130 | N-[(2,4-dimethylphenyl)(5-methylfuran-2-yl)methyl]-1-(1-methyl-2-oxo-2,3-dihydro-1H-indol-5-yl)cyclopropane-1-carboxamide | From (2,4-dimethylphenyl)(5-methylfuran-2-yl)methanamine Ex. 19 and 1-(1-methyl-2-oxo-2,3-dihydro-1H-indol-5-yl)cyclopropane-1-carboxylic acid Ex. 75 following protocol A, DMAP (1.2 equiv), EDCl•HCl (1.1 equiv), 8 h at rt, purification by silica gel column chromatography (Cyclohexane/EtOAc, 70:30), yield 31%, mp: 72° C., appearance: white solid 1H NMR (300 MHz, DMSO-d6, d in ppm): 0.91-1.02 (m, 2H), 1.24-1.37 (m, 2H), 2.15 (s, 3H), 2.16 (s, 3H), 2.22 (s, 3H), 3.10 (s, 3H), 3.52 (s, 2H), 5.76 (d, 1H, J = 3.1 Hz), 5.93 (dd, 1H, J = 3.0 Hz, J = 0.9 Hz), 6.12 (d, 1H, J = 8.5 Hz), 6.86-6.99 (m, 4H), 7.20-7.31 (m, 3H); m/z: 451 [M + Na]+ (calc. mass: 428). |
| 131 | N-[(2-bromo-4-methylphenyl)(5-methylfuran-2-yl)methyl]-1-(2,2-dioxo-1,3-dihydro-4,2,1-benzoxathiazin-6-yl)cyclopropane-1-carboxamide | From (2-bromo-4-methylphenyl)(5-methylfuran-2-yl)methanamine Ex. 18 and 1-(2,2-dioxo-1,3-dihydro-4,2,1-benzoxathiazin-6-yl)cyclopropane-1-carboxylic acid Ex. 69 following protocol A, DMAP (1.2 equiv), EDCl•HCl (1.1 equiv), 8 h at rt, purification by silica gel column chromatography (Cyclohexane/EtOAc, 70:30) followed by a second purification on silica gel column chromatography (CH2Cl2/Cyclohexane/EtOAc, 50:30:20), yield 7%, mp: 112° C., appearance: white solid 1H NMR (300 MHz, DMSO-d6, d in ppm): 0.93-1.03 (m, 2H), 1.24-1.35 (m, 2H), 2.18 (s, 3H), 2.27 (s, 3H), 5.15 (s, 2H), 5.68 (d, 1H, J = 3.1 Hz), 5.93 (dd, 1H, J = 3.1 Hz, J = 1.1 Hz), 6.26 (d, 1H, J = 8.0 Hz), 6.76 (d, 1H, J = 8.7 Hz), 6.96-7.04 (m, 2H), 7.14-7.25 (m, 2H), 7.42 (s, 1H), 7.90 (d, 1H, J = 8.2 Hz), 10.56 (br(s), 1H); m/z: 529 [M + H]+, 531 [M + H]+ (calc. mass: 530). |
| 132 | N-[(2,4-dimethylphenyl)(5-methylfuran-2-yl)methyl]-1-(1-ethyl-2,2-dioxo-1,3-dihydro-2,1-benzothiazol-5-yl)cyclopropane-1-carboxamide | From (2,4-dimethylphenyl)(5-methylfuran-2-yl)methanamine Ex. 19 and 1-(1-ethyl-2,2-dioxo-1,3-dihydro-2,1-benzothiazol-5-yl)cyclopropane-1-carboxylic acid Ex. 76 following protocol A, DMAP (1.2 equiv), EDCl•HCl (2.2 equiv), 8 h at rt, purification by silica gel column chromatography (Cyclohexane/EtOAc, 70:30) followed by a second purification on silica gel column chromatography (Cyclohexane/EtOAc, 80:20), yield 27%, mp: 68° C., appearance: white solid 1H NMR (300 MHz, DMSO-d6, d in ppm): 0.98 (d, 2H, J = 2.5 Hz), 1.25 (t, 3H, J = 7.1 Hz), 1.28-1.35 (m, 2H), 2.16 (s, 3H), 2.17 (s, 3H), 2.22 (s, 3H), 3.61 (q, 2H, J = 7.1 Hz), 4.58 (s, 2H), 5.76 (d, 1H, J = 2.6 Hz), 5.93 (q, 1H, J = 3.1 Hz, J = 1.1 Hz), 6.12 (d, 1H, J = 8.3 Hz), 6.90-7.00 (m, 4H), 7.28-7.35 (m, 2H), 7.51 (d, 1H, J = 8.2 Hz); m/z: 501 [M + Na]+ (calc. mass: 478). |
| 133 | N-{[2-(dimethylamino)-4-methylphenyl](5-methylfuran-2-yl)methyl}-1-(1-methyl-2,2-dioxo-1,3-dihydro-2,1-benzothiazol-5-yl)cyclopropane-1-carboxamide | From 2-[amino(5-methylfuran-2-yl)methyl]-N,N,5-trimethylaniline Ex. 42 and 1-(1-methyl-2,2-dioxo-1,3-dihydro-2,1-benzothiazol-5-yl)cyclopropane-1-carboxylic acid Ex. 40 following protocol A, DMAP (1.2 equiv), EDCl•HCl (2.2 equiv), 8 h at rt, purification by silica gel column chromatography (CH2Cl2/MeOH, 98:2) followed by a second purification on silica gel column chromatography (CH2Cl2/EtOAc, 90:10), yield 15%, mp: 73° C., appearance: white solid 1H NMR (300 MHz, DMSO-d6, d in ppm): 0.90-1.00 (m, 2H), 1.25-1.4 (m, 2H), 2.13 (s, 3H), 2.18 (s, 6H), 2.23 (s, 3H), 3.03 (s, 3H), 4.65 (s, 2H), 5.78 (d, 1H, J = 2.1 Hz), 5.92 (q, 1H, J = 3.0 Hz, J = 1.1 Hz), 6.21 (d, 1H, J = 8.3 Hz), 6.88 (d, 1H, J = 8.0 Hz), 6.95 (d, 1H, J = 8.2 Hz), 7.00 (s, 1H), 7.13 (d, 1H, J = 7.8 Hz), 7.37 (s, 1H), 7.40 (d, 1H, J = 8.2 Hz), 7.97 (d, 1H, J = 8.3 Hz); m/z: 494 [M + H]+ (calc. mass: 493). |
| 134 | N-[(5-chlorofuran-2-yl)(2,4- | From (5-chlorofuran-2-yl)(2,4-dimethylphenyl)methanamine Ex. 32 and 1-(3-oxo-3,4-dihydro-2H-1,4-benzoxazin-7-yl)cyclopropane-1-carboxylic acid Ex. 35 following protocol |

| Cpd. | Starting compounds, Reaction conditions and purification Yield, MP, Appearance, $^1$H NMR (solvent) data, Mass (ES+ or ES−) data |
|---|---|
| dimethylphenyl)methyl]-1-(3-oxo-3,4-dihydro-2H-1,4-benzoxazin-7-yl)cyclopropane-1-carboxamide | A, DMAP (1.1 equiv), EDCl•HCl (1.1 equiv), 5 h at rt. After completion of the reaction, the solution was poured into ice and water. The solid formed was collected by filtration and dried under vacuo until constant weight, yield 31%, mp: 94° C., appearance: white solid 1H NMR (300 MHz, DMSO-d6, d in ppm): 0.90-1.02 (m, 2H), 1.23-1.30 (m, 2H), 2.16 (s, 3H), 2.23 (s, 3H), 4.54 (s, 2H), 6.00 (dd, 1H, J = 5.2 Hz, J = 1.1 Hz), 6.16 (d, 1H, J = 8.4 Hz), 6.35 (d, 1H, J = 3.3 Hz), 6.82 (d, 1H, J = 8.3 Hz), 6.87-6.92 (m, 2H), 6.92-7.00 (m, 3H), 7.76 (d, 1H, J = 8.2 Hz), 10.70 (s, 1H); m/z: 473 [M + Na]+, 475 [M + Na]+ (calc. mass: 450). |
| 135 N-[(2-bromo-4-methylphenyl)(5-methylfuran-2-yl)methyl]-1-(3-oxo-3,4-dihydro-2H-1,4-benzoxazin-7-yl)cyclopropane-1-carboxamide | From (2-bromo-4-methylphenyl)(5-methylfuran-2-yl)methanamine Ex. 18 and 1-(3-oxo-3,4-dihydro-2H-1,4-benzoxazin-7-yl)cyclopropane-1-carboxylic acid Ex. 35 following protocol A, DMAP (1.1 equiv), EDCl•HCl (1.1 equiv), 5 h at rt. After completion of the reaction, the solution was poured into ice and water. The solid formed was collected by filtration, washed with Et2O and dried under vacuo until constant weight, yield 5%, mp: 82° C., appearance: white solid 1H NMR (300 MHz, DMSO-d6, d in ppm): 0.94-0.99 (m, 2H), 1.24-1.29 (m, 2H), 2.18 (s, 3H), 2.27 (s, 3H), 4.55 (s, 2H), 5.68 (d, 1H, J = 3.2 Hz), 5.92-5.95 (m, 1H), 6.26 (d, 1H, J = 8.0 Hz), 6.83 (d, 1H, J = 8.5 Hz), 6.90-6.95 (m, 2H), 7.15-7.22 (m, 2H), 7.41 (s, 1H), 7.76 (d, 1H, J = 8.1 Hz), 10.70 (s, 1H); m/z: 517 [M + Na]+, 519 [M + Na]+ (calc. mass: 494). |
| 136 N-[(2,4-dimethylphenyl)(6-methylpyridin-2-yl)methyl]-1-(3-oxo-3,4-dihydro-2H-1,4-benzoxazin-7-yl)cyclopropane-1-carboxamide | From (2,4-dimethylphenyl)(6-methylpyridin-2-yl)methanamine Ex. 77 and 1-(3-oxo-3,4-dihydro-2H-1,4-benzoxazin-7-yl)cyclopropane-1-carboxylic acid Ex. 35 following protocol A, DMAP (1.1 equiv), EDCl•HCl (1.1 equiv), overnight at rt. After completion of the reaction, the solution was poured into ice and water. The solid formed was collected by filtration and dried under vacuo until constant weight, yield 16%, mp: 94° C., appearance: white solid 1H NMR (300 MHz, DMSO-d6, d in ppm): 0.92-0.98 (m, 2H), 1.20-1.25 (m, 2H), 2.17 (s, 3H), 2.30 (s, 3H), 2.32 (s, 3H), 4.59 (d, 2H, J = 1.2 Hz), 5.94 (d, 1H, J = 6.3 Hz), 6.76 (d, 1H, J = 7.8 Hz), 6.83-7.02 (m, 6H), 7.07 (d, 1H, J = 7.8 Hz), 7.54 (t, 1H, J = 7.7 Hz), 7.91 (d, 1H, J = 6.6 Hz), 10.82 (s, 1H); m/z: 442 [M + H]+ (calc. mass: 441). |
| 137 1-(2H-1,3-benzodioxol-5-yl)-N-[(2,4-dimethylphenyl)(5-methylfuran-2-yl)methyl]cyclopropane-1-carboxamide | From (2,4-dimethylphenyl)(5-methylfuran-2-yl)methanamine Ex. 19 and 1-(2H-1,3-benzodioxol-5-yl)cyclopropane-1-carboxylic acid Ex. 88 following protocol A, DMAP (2.2 equiv), EDCl•HCl (2.2 equiv), overnight at rt. After completion of the reaction, the solution was poured into ice and water. The solid formed was collected by filtration and dried under vacuo until constant weight, yield 46%, mp: 52° C., appearance: yellow solid 1H NMR (300 MHz, DMSO-d6, d in ppm): 0.92-1.01 (m, 2H), 1.23-1.31 (m, 2H), 2.15 (s, 3H), 2.17 (s, 3H), 2.22 (s, 3H), 5.77 (d, 1H, J = 3.1 Hz), 5.94 (dd, 1H, J = 3.0 Hz, J = 1.0 Hz), 6.00 (s, 2H), 6.11 (d, 1H, J = 8.4 Hz), 6.81-6.89 (m, 2H), 6.89-6.97 (m, 4H), 7.30 (d, 1H, J = 8.3 Hz); m/z: 426 [M + Na]+ (calc. mass: 403). |
| 139 N-[(2,4-dimethylphenyl)(furan-2-yl)methyl]-1-(3-oxo-3,4-dihydro-2H-1,4-benzoxazin-7-yl)cyclopropane-1-carboxamide | From (2,4-dimethylphenyl)(furan-2-yl)methanamine Ex. 80 and 1-(3-oxo-3,4-dihydro-2H-1,4-benzoxazin-7-yl)cyclopropane-1-carboxylic acid Ex. 35 following protocol A, DMAP (2.1 equiv), EDCl•HCl (2.1 equiv), overnight at rt. After completion of the reaction, the solution was poured into ice and water. The solid formed was collected by filtration and dried under vacuo until constant weight, yield 45%, mp: 180° C., appearance: pale yellow solid 1H NMR (300 MHz, DMSO-d6, d in ppm): 0.92-1.00 (m, 2H), 1.24-1.31 (m, 2H), 2.16 (s, 3H), 2.22 (s, 3H), 4.55 (s, 2H), 5.92-5.96 (m, 1H), 6.18 (d, 1H, J = 8.6 Hz), 6.35 (dd, 1H, J = 3.2 Hz, J = 2.0 Hz), 6.82 (d, 1H, J = 8.4 Hz), 6.87-7.00 (m, 5H), 7.50 (d, 1H, J = 8.4 Hz), 7.53-7.57 (m, 1H), 10.71 (s, 1H); m/z: 417 [M + H]+ (calc. mass: 416). |
| 140 N-[(4-chlorophenyl)(2,4- | From (4-chlorophenyl)(2,4-dimethylphenyl)methanamine Ex. 81 and 1-(3-oxo-3,4-dihydro-2H-1,4-benzoxazin-7-yl)cyclopropane-1-carboxylic acid Ex. 35 following protocol |

TABLE 2-continued

All the NMR were performed in DMSO-d6

| Cpd. | Starting compounds, Reaction conditions and purification Yield, MP, Appearance, $^1$H NMR (solvent) data, Mass (ES+ or ES−) data |
|---|---|
| dimethylphenyl)methyl]-1-(3-oxo-3,4-dihydro-2H-1,4-benzoxazin-7-yl)cyclopropane-1-carboxamide | A, DMAP (2.1 equiv), EDCl•HCl (2.1 equiv), overnight at rt. After completion of the reaction, the solution was poured into ice and water. The solid formed was collected by filtration and dried under vacuo until constant weight, yield 37%, mp: 99° C., appearance: white solid 1H NMR (300 MHz, DMSO-d6, d in ppm): 0.91-0.99 (m, 2H), 1.27 (q, 2H, J = 3.3 Hz), 2.12 (s, 3H), 2.22 (s, 3H), 4.54 (s, 2H), 6.19 (d, 1H, J = 8.5 Hz), 6.81 (dd, 2H, J = 7.9 Hz, J = 1.1 Hz), 6.87-6.95 (m, 3H), 6.97 (s, 1H), 7.09 (d, 2H, J = 8.4 Hz), 7.35 (d, 2H, J = 8.5 Hz), 7.51 (d, 1H, J = 8.5 Hz), 10.69 (s, 1H); m/z: 461 [M + H]+, 463 [M + H]+ (calc. mass: 460). |
| 141 N-[(2,4-dimethylphenyl)(5-methylfuran-2-yl)methyl]-1-(1-oxo-2,3-dihydro-1H-inden-5-yl)cyclopropane-1-carboxamide- | From (2,4-dimethylphenyl)(5-methylfuran-2-yl)methanamine Ex. 19 and 1-(1-oxo-2,3-dihydro-1H-inden-5-yl)cyclopropane-1-carboxylic acid Ex. 82 following protocol A, DMAP (1.1 equiv), EDCl•HCl (1.1 equiv), overnight at rt, purification by silica gel column chromatography (Cyclohexane/EtOAc, 70:30), yield 45%, mp: 56° C., appearance: white solid 1H NMR (300 MHz, DMSO-d6, d in ppm): 1.06-1.17 (m, 2H), 1.35-1.43 (m, 2H), 2.18 (s, 6H), 2.23 (s, 3H), 2.59-2.65 (m, 2H), 3.01-3.10 (m, 2H), 5.74 (d, 1H, J = 3.0 Hz), 5.94 (dd, 1H, J = 3.1 Hz, J = 1.1 Hz), 6.18 (d, 1H, J = 8.3 Hz), 6.89-7.04 (m, 3H), 7.32 (dd, 1H, J = 8.0 Hz, J = 1.5 Hz), 7.47 (d, 1H, J = 0.7 Hz), 7.56 (d, 1H, J = 8.0 Hz), 8.04 (d, 1H, J = 8.3 Hz); m/z: 436 [M + Na]+ (calc. mass: 413). |
| 142 1-(2,3-dihydro-1H-indol-5-yl)-N-[(2,4-dimethylphenyl)(5-methylfuran-2-yl)methyl]cyclopropane-1-carboxamide | See FIG. 3BA The previously synthesized 1-(1-acetyl-2,3-dihydro-1H-indol-5-yl)-N-[(2,4-dimethylphenyl)(5-methylfuran-2-yl)methyl]cyclopropane-1-carboxamide Cpd. 126 (30 mg, 0.07 mmol) was dissolved in MeOH/THF (500 μL/500 μL). 5M NaOH (136 μL, 0.68 mmol) was added and the solution was stirred at rt for 2 days (over the weekend). TLC showed no conversion. The reaction mixture was heated at 120° C. for 1 h under microwave irradiation. After cooling to rt, sat. NH4Cl was added to quench the reaction. The aqueous layer was extracted with EtOAc. The combined organic layers were dried over MgSO4, filtered and the solution was concentrated under reduced pressure. The crude material was purified by column chromatography on silica gel eluting with CH2Cl2/MeOH (98:2). The desired fractions were collected and evaporated under reduced pressure, yield 55%, mp: 57° C., appearance: white solid 1H NMR (300 MHz, DMSO-d6, d in ppm): 0.90 (d, 2H, J = 2.8 Hz), 1.20-1.30 (m, 2H), 2.15 (s, 3H), 2.15 (s, 3H), 2.22 (s, 3H), 2.87 (t, 2H, J = 8.6 Hz), 3.35-3.40 (m, 2H), 5.54 (br(s), 1H), 5.78 (d, 1H, J = 2.6 Hz), 5.94 (dd, 1H, J = 3.0 Hz, J = 1.0 Hz), 6.06 (d, 1H, J = 8.2 Hz), 6.44 (d, 1H, J = 7.9 Hz), 6.72 (d, 1H, J = 8.4 Hz), 6.83 (d, 1H, J = 7.6 Hz), 6.85-7.00 (m, 3H), 7.02 (s, 1H); m/z: 401 [M + H]+ (calc. mass: 400). |
| 143 N-[(3-chlorophenyl)(2,4-dimethylphenyl)methyl]-1-(3-oxo-3,4-dihydro-2H-1,4-benzoxazin-7-yl)cyclopropane-1-carboxamide | From (3-chlorophenyl)(2,4-dimethylphenyl)methanamine Ex. 83 and 1-(3-oxo-3,4-dihydro-2H-1,4-benzoxazin-7-yl)cyclopropane-1-carboxylic acid Ex. 35 following protocol A, DMAP (2.1 equiv), EDCl•HCl (2.1 equiv), overnight at rt. After completion of the reaction, the solution was poured into ice and water. The solid formed was collected by filtration and dried under vacuo until constant weight, yield 56%, mp: 181° C., appearance: white solid 1H NMR (300 MHz, DMSO-d6, d in ppm): 0.91-1.02 (m, 2H), 1.24-1.32 (m, 2H), 2.14 (s, 3H), 2.22 (s, 3H), 4.53 (s, 2H), 6.21 (d, 1H, J = 8.4 Hz), 6.81 (dd, 2H, J = 7.8 Hz, J = 2.3 Hz), 6.87-6.95 (m, 3H), 6.98 (s, 1H), 7.03-7.11 (m, 2H), 7.26-7.35 (m, 2H), 7.63 (d, 1H, J = 8.4 Hz), 10.69 (s, 1H); m/z: 461 [M + H]+, 463 [M + H]+ (calc. mass: 460). |
| 144 N-[(2,4-dimethylphenyl)-(5-methylfuran-2-yl)methyl]-1-{2-oxo-1H,2H,3H-pyrido[2,3-b][1,4]oxazin-6-yl}cyclopropane- | From (2,4-dimethylphenyl)(5-methylfuran-2-yl)methanamine Ex. 19 and 1-{2-oxo-1H,2H,3H-pyrido[2,3-b][1,4]oxazin-6-yl}cyclopropane-1-carboxylic acid Ex. 84 following protocol A, DMAP (2.1 equiv), EDCl•HCl (2.1 equiv), overnight at rt. After completion of the reaction, the solution was poured into ice and water. The solid formed was collected by filtration and dried under vacuo until constant weight, yield 54%, mp: 84° C., appearance: white solid 1H NMR (300 MHz, DMSO-d6, d in ppm): 1.06-1.19 (m, |

TABLE 2-continued

All the NMR were performed in DMSO-d6

| Cpd. | | Starting compounds,<br>Reaction conditions and purification<br>Yield, MP, Appearance, $^1$H NMR (solvent) data, Mass (ES+ or ES−) data |
|---|---|---|
| | 1-carboxamide | 2H), 1.24-1.33 (m, 2H), 2.19 (s, 3H), 2.22 (s, 3H), 2.23 (s, 3H), 4.76 (s, 2H), 5.83 (d, 1H, J = 3.0 Hz), 5.95 (dd, 1H, J = 3.0 Hz, J = 1.0 Hz), 6.21 (d, 1H, J = 8.1 Hz), 6.91 (d, 1H, J = 7.9 Hz), 6.94-7.01 (m, 2H), 7.08 (d, 1H, J = 8.4 Hz), 7.15 (d, 1H, J = 8.0 Hz), 8.76 (d, 1H, J = 8.3 Hz), 10.79 (s, 1H); m/z: 432 [M + H]+ (calc. mass: 431). |
| 145 | N-[(5-chlorofuran-2-yl)[4-methyl-2-(piperidin-1-yl)phenyl]methyl]-1-(3-oxo-3,4-dihydro-2H-1,4-benzoxazin-7-yl)cyclopropane-1-carboxamide | From (5-chlorofuran-2-yl)[4-methyl-2-(piperidin-1-yl)phenyl]methanamine Ex. 47 and 1-(3-oxo-3,4-dihydro-2H-1,4-benzoxazin-7-yl)cyclopropane-1-carboxylic acid Ex. 35 following protocol A, DMAP (2.1 equiv), EDCl•HCl (2.1 equiv), overnight at rt. After completion of the reaction, the solution was poured into ice and water. The solid formed was collected by filtration and dried under vacuo until constant weight, yield 36%, mp: 199° C., appearance: white solid<br>1H NMR (300 MHz, DMSO-d6, d in ppm): 0.92-1.01 (m, 2H), 1.24-1.49 (m, 8H), 2.25 (s, 3H), 2.37-2.46 (m, 2H), 2.55-2.65 (m, 2H), 4.54 (s, 2H), 6.03 (dd, 1H, J = 3.3 Hz, J = 1.2 Hz), 6.34 (d, 1H, J = 3.3 Hz), 6.39 (d, 1H, J = 8.4 Hz), 6.83 (d, 1H, J = 8.0 Hz), 6.89 (d, 1H, J = 7.6 Hz), 6.92-6.98 (m, 2H), 7.01 (s, 1H), 7.09 (d, 1H, J = 7.8 Hz), 7.47 (d, 1H, J = 8.7 Hz), 10.72 (s, 1H); m/z: 520 [M + H]+, 522 [M + H]+ (calc. mass: 519). |
| 146 | 1-(3,3-dimethyl-2-oxo-2,3-dihydro-1H-indol-5-yl)-N-[(2,4-dimethylphenyl)(5-methylfuran-2-yl)methyl]cyclopropane-1-carboxamide | From (2,4-dimethylphenyl)(5-methylfuran-2-yl)methanamine Ex. 19 and 1-(3,3-dimethyl-2-oxo-2,3-dihydro-1H-indol-5-yl)cyclopropane-1-carboxylic acid Ex. 85 following protocol A, DMAP (1.1 equiv), EDCl•HCl (1.1 equiv), 2 h at rt, purification by silica gel column chromatography (Cyclohexane/EtOAc, 70:30), yield 69%, mp: 82° C., appearance: white solid<br>1H NMR (300 MHz, DMSO-d6, d in ppm): 0.92-1.05 (m, 2H), 1.22 (s, 6H), 1.27-1.35 (m, 2H), 2.14 (s, 6H), 2.21 (s, 3H), 5.75 (d, 1H, J = 3.1 Hz), 5.92 (dd, 1H, J = 3.0 Hz, J = 1.0 Hz), 6.09 (d, 1H, J = 8.4 Hz), 6.80 (d, 1H, J = 7.9 Hz), 6.86-6.96 (m, 3H), 7.02 (d, 1H, J = 8.5 Hz), 7.15 (dd, 1H, J = 8.0 Hz, J = 1.8 Hz), 7.30 (d, 1H, J = 1.7 Hz), 10.34 (s, 1H); m/z: 465 [M + Na]+ (calc. mass: 442). |
| 147 | N-[(2-bromo-4-methoxyphenyl)(5-methylfuran-2-yl)methyl]-1-(2,2-dioxo-1,3-dihydro-4,2,1-benzoxathiazin-6-yl)cyclopropane-1-carboxamide | From (2-bromo-4-methoxyphenyl)(5-methylfuran-2-yl)methanamine Ex. 22 and 1-(2,2-dioxo-1,3-dihydro-4,2,1-benzoxathiazin-6-yl)cyclopropane-1-carboxylic acid Ex. 69 following protocol A, DMAP (1.1 equiv), EDCl•HCl (1.1 equiv), 2 h at rt, purification by silica gel column chromatography (Cyclohexane/EtOAc, 70:30), yield 46%, mp: 115° C., appearance: white solid<br>1H NMR (300 MHz, DMSO-d6, d in ppm): 0.90-1.09 (m, 2H), 1.20-1.36 (m, 2H), 2.19 (s, 3H), 3.76 (s, 3H), 5.17 (s, 2H), 5.69 (d, 1H, J = 3.0 Hz), 5.93 (dd, 1H, J = 3.0 Hz, J = 1.1 Hz), 6.25 (d, 1H, J = 8.2 Hz), 6.77 (d, 1H, J = 8.7 Hz), 6.95 (dd, 1H, J = 8.7 Hz, J = 2.6 Hz), 6.98-7.05 (m, 2H), 7.15 (d, 1H, J = 2.6 Hz), 7.23 (d, 1H, J = 8.6 Hz), 7.90 (d, 1H, J = 8.1 Hz), 10.56 (s, 1H); m/z: 545 [M − H]−, 547 [M − H]− (calc. mass: 546). |
| 148 | N-{[2-(dimethylamino)-4-methylphenyl](5-methylfuran-2-yl)methyl}-1-(2,2-dioxo-1,3-dihydro-4,2,1-benzoxathiazin-6-yl)cyclopropane-1-carboxamide | From 2-[amino(5-methylfuran-2-yl)methyl]-N,N,5-trimethylaniline Ex. 42 and 1-(2,2-dioxo-1,3-dihydro-4,2,1-benzoxathiazin-6-yl)cyclopropane-1-carboxylic acid Ex. 69 following protocol A, DMAP (1.1 equiv), EDCl•HCl (1.1 equiv), 2 h at rt, purification by silica gel column chromatography (Cyclohexane/EtOAc, 70:30), yield 35%, mp: 105° C., appearance: white solid<br>1H NMR (300 MHz, DMSO-d6, d in ppm): 0.89-1.08 (m, 2H), 1.21-1.38 (m, 2H), 2.14 (s, 3H), 2.23 (s, 6H), 2.24 (s, 3H), 5.13-5.22 (m, 2H), 5.75-5.78 (m, 1H), 5.90-5.94 (m, 1H), 6.22 (d, 1H, J = 8.7 Hz), 6.82 (d, 1H, J = 8.7 Hz), 6.88 (d, 1H, J = 8.2 Hz), 7.00-7.09 (m, 3H), 7.13 (d, 1H, J = 7.8 Hz), 8.04 (d, 1H, J = 8.6 Hz), 10.62 (s, 1H); m/z: 496 [M + H]+ (calc. mass: 495). |
| 149 | N-[(5-chlorofuran-2-yl)(2,4-dimethylphenyl)methyl]-1-(2,2-dioxo-1,3-dihydro-4,2,1- | From (5-chlorofuran-2-yl)(2,4-dimethylphenyl)methanamine Ex. 32 and 1-(2,2-dioxo-1,3-dihydro-4,2,1-benzoxathiazin-6-yl)cyclopropane-1-carboxylic acid Ex. 69 following protocol A, DMAP (1.1 equiv), EDCl•HCl (1.1 equiv), 2 h at rt, purification by silica gel column chromatography (Cyclohexane/EtOAc, 70:30), yield 47%, mp: 102° C., appearance: white solid |

TABLE 2-continued

All the NMR were performed in DMSO-d6

| Cpd. | Starting compounds, Reaction conditions and purification Yield, MP, Appearance, $^1$H NMR (solvent) data, Mass (ES+ or ES−) data |
|---|---|
| benzoxathiazin-6-yl)cyclopropne-1-carboxamide | 1H NMR (300 MHz, DMSO-d6, d in ppm): 0.91-1.04 (m, 2H), 1.23-1.34 (m, 2H), 2.16 (s, 3H), 2.23 (s, 3H), 5.16 (s, 2H), 6.00 (dd, 1H, J = 3.3 Hz, J = 1.1 Hz), 6.17 (d, 1H, J = 8.4 Hz), 6.35 (d, 1H, J = 3.3 Hz), 6.76 (d, 1H, J = 8.7 Hz), 6.93-7.04 (m, 5H), 7.94 (d, 1H, J = 8.1 Hz), 10.56 (s, 1H); m/z: 485 [M − H]−, 487 [M − H]− (calc. mass: 486). |
| 150 N-[(2-bromo-4-methylphenyl)(5-methylfuran-2-yl)methyl]-2-(2,2-dioxo-1,3-dihydro-4,2,1-benzoxathiazin-6-yl)acetamide | From (2-bromo-4-methylphenyl)(5-methylfuran-2-yl)methanamine Ex. 18 and 2-(2,2-dioxo-1,3-dihydro-4,2,1-benzoxathiazin-6-yl)acetic acid Ex. 86 following protocol A, DMAP (2.1 equiv), EDCl•HCl (2.1 equiv), 2 h at rt. After completion of the reaction, the solution was poured into sat. NH4Cl. The solid formed was collected by filtration and dried under vacuo until constant weight, yield 84%, mp: 116° C., appearance: pale brown solid 1H NMR (300 MHz, DMSO-d6, d in ppm): 2.21 (s, 3H), 2.27 (s, 3H), 3.43 (s, 2H), 5.14 (s, 2H), 5.77 (d, 1H, J = 3.1 Hz), 5.96 (dd, 1H, J = 3.0 Hz, J = 1.1 Hz), 6.23 (d, 1H, J = 8.1 Hz), 6.73 (d, 1H, J = 8.2 Hz), 6.90 (dd, 1H, J = 8.1 Hz, J = 1.9 Hz), 6.94 (d, 1H, J = 1.7 Hz), 7.20 (d, 1H, J = 7.2 Hz), 7.29 (d, 1H, J = 7.9 Hz), 7.40-7.45 (m, 1H), 9.07 (d, 1H, J = 8.1 Hz), 10.40 (br(s), 1H); m/z: 527 [M + Na]+, 529 [M + Na]+ (calc. mass: 504). |
| 152 3-[5-(1-{[(2,4-dimethylphenyl)(5-methylfuran-2-yl)methyl]carbamoyl}cyclopropyl)-1H-indol-1-yl]propanoic acid | See FIG. 3BC Step 1: to a previously synthesized N-[(2,4-dimethylphenyl)(5-methylfuran-2-yl)methyl]-1-(1H-indol-5-yl)cyclopropane-1-carboxamide Cpd. 108 (150 mg, 0.38 mmol) dissolved in dry DMF (1 mL) was added sodium hydride (60% in mineral oil) (45 mg, 1.13 mmol) at rt. After 15 min of stirring, tert-butyl 3-bromopropanoate (188 µL, 1.13 mmol) was added and the reaction mixture was heated at 110° C. for 15 min under microwave irradiation. TLC showed not total consumption of the starting material. Additional sodium hydride (60% in mineral oil) (45 mg, 1.13 mmol) and tert-butyl 3-bromopropanoate (188 µL, 1.13 mmol) were added to the solution and the reaction mixture was heated at 110° C. for 15 min under microwave irradiation. After cooling to rt, water was added to quench the reaction. The pH was adjusted to pH = 4-5 with 1M citric acid. The resulting aqueous solution was extracted with EtOAc. The combined organic layers were dried over MgSO4, filtered and the solution was concentrated under reduced pressure. A mixture of tert-butyl 3-[5-(1-{[(2,4-dimethylphenyl)(5-methylfuran-2-yl)methyl]carbamoyl}cyclopropyl)-1H-indol-1-yl]propanoate and 3-[5-(1-{[(2,4-dimethylphenyl)(5-methylfuran-2-yl)methyl]carbamoyl}cyclopropyl)-1H-indol-1-yl]propanoic acid was observed. The mixture was used as such for the next step. 1H NMR (300 MHz, DMSO-d6, d in ppm): 0.98-1.07 (m, 2H), 1.23 (s, 9H), 1.30-1.36 (m, 2H), 2.12 (s, 3H), 2.14 (s, 3H), 2.20 (s, 3H), 2.68-2.75 (m, 2H), 4.37 (t, 2H, J = 6.4 Hz), 5.75 (d, 1H, J = 2.9 Hz), 5.90 (dd, 1H, J = 3.0 Hz, J = 1.0 Hz), 6.09 (d, 1H, J = 8.3 Hz), 6.35-6.45 (m, 1H), 6.67-6.80 (m, 2H), 6.86-6.90 (m, 2H), 7.16 (dd, 1H, J = 8.3 Hz, J = 1.6 Hz), 7.36 (d, 1H, J = 3.1 Hz), 7.48 (d, 1H, J = 8.2 Hz), 7.55 (d, 1H, J = 1.3 Hz) (ester derivative). Step 2: tert-butyl 3-[5-(1-{[(2,4-dimethylphenyl)(5-methylfuran-2-yl)methyl]carbamoyl}cyclopropyl)-1H-indol-1-yl]propanoate (170 mg, 0.32 mmol) was dissolved in MeOH (2 mL). 5M NaOH (323 µL, 1.61 mmol) was added and the reaction mixture was heated at 110° C. for 30 min under microwave irradiation. The solvent was removed under reduced pressure. Water was added to the residue and the aqueous layer was extracted with Et2O. After phases separation, the remaining aqueous layer was acidified up to pH = 5 with 1M citric acid and extracted with EtOAc. The combined organic layers were dried over MgSO4, filtered and the solution was concentrated to dryness. The crude material was purified by silica gel column chromatography eluting with Cyclohexane/EtOAc (60:40), yield 27%, mp: 78° C., appearance: white solid 1H NMR (300 MHz, DMSO-d6, d in ppm): 0.97-1.08 (m, 2H), 1.27-1.42 (m, 2H), 2.12 (s, 3H), 2.14 (s, 3H), 2.20 (s, 3H), 2.73 (t, 2H, J = 6.8 Hz), 4.38 (t, 2H, J = 6.7 Hz), 5.76 (d, |

TABLE 2-continued

All the NMR were performed in DMSO-d6

Figure 3B:
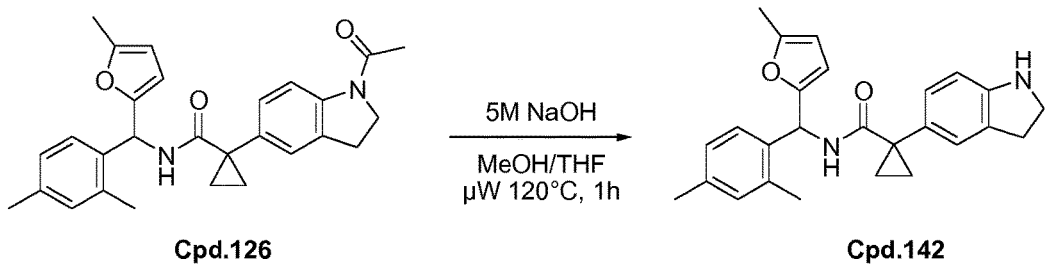
Figure 3B:
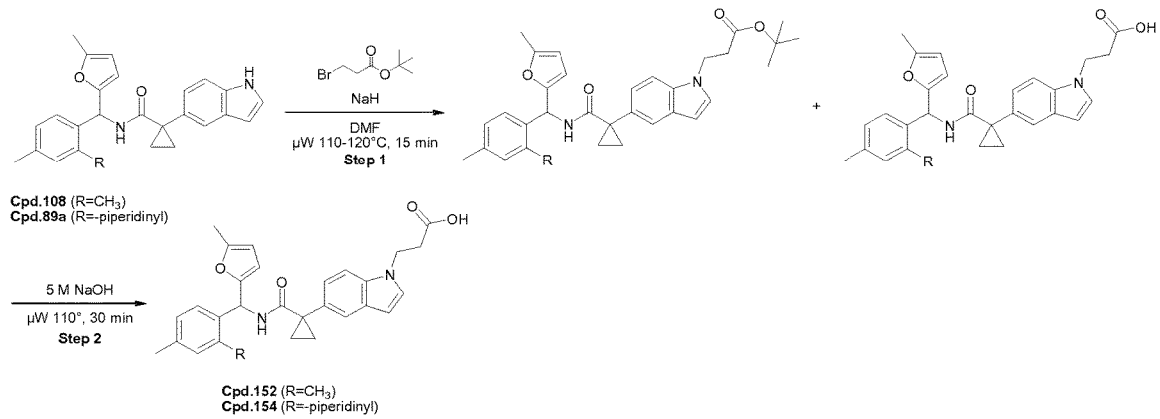

| Cpd. | | Starting compounds, Reaction conditions and purification Yield, MP, Appearance, $^1$H NMR (solvent) data, Mass (ES+ or ES−) data |
|---|---|---|
| | | 1H, J = 3.1 Hz), 5.90 (dd, 1H, J = 3.0 Hz, J = 1.0 Hz), 6.09 (d, 1H, J = 8.4 Hz), 6.39 (d, 1H, J = 2.7 Hz), 6.77-6.86 (m, 2H), 6.90 (d, 1H, J = 8.0 Hz), 6.93 (br(s), 1H), 7.15 (dd, 1H, J = 8.5 Hz, J = 1.6 Hz), 7.36 (d, 1H, J = 3.1 Hz), 7.49 (d, 1H, J = 8.5 Hz), 7.54 (d, 1H, J = 1.3 Hz), 12.34 (br(s), 1H); m/z: 469 [M − H]− (calc. mass: 470). |
| 153 | N-[(3,5-dimethylpyridin-2-yl)(5-methylfuran-2-yl)methyl]-1-(2,2-dioxo-1,3-dihydro-4,2,1-benzoxathiazin-6-yl)cyclopropane-1-carboxamide | From (3,5-dimethylpyridin-2-yl)(5-methylfuran-2-yl)methanamine Ex. 87 and 1-(2,2-dioxo-1,3-dihydro-4,2,1-benzoxathiazin-6-yl)cyclopropane-1-carboxylic acid Ex. 69 following protocol A, DMAP (1.1 equiv), EDCl•HCl (1.1 equiv), 2 h at rt, purification by silica gel column chromatography (Cyclohexane/EtOAc, 60:40), yield 56%, mp: 189° C., appearance: white solid<br>1H NMR (300 MHz, DMSO-d6, d in ppm): 0.88-1.11 (m, 2H), 1.27-1.39 (m, 2H), 2.11 (s, 3H), 2.20 (s, 3H), 2.22 (s, 3H), 5.24 (s, 2H), 5.86-5.92 (m, 2H), 6.08 (d, 1H, J = 7.4 Hz), 6.86 (d, 1H, J = 8.7 Hz), 7.04-7.10 (m, 2H), 7.38-7.42 (m, 1H), 7.55 (d, 1H, J = 7.6 Hz), 8.06 (d, 1H, J = 2.0 Hz), 10.69 (s, 1H); m/z: 468 [M + H]+ (calc. mass: 467). |
| 154 | 3-{5-[1-({[4-methyl-2-(piperidin-1-yl)phenyl](5-methylfuran-2-yl)methyl}carbamoyl)cyclopropyl]-1H-indol-1-yl}propanoic acid | See FIG. 3BC<br>Step 1: to a previously synthesized 1-(1H-indol-5-yl)-N-((4-methyl-2-(piperidin-1-yl)phenyl)(5-methylfuran-2-yl)methyl)cyclopropanecarboxamide Cpd. 89a (100 mg, 0.21 mmol) dissolved in dry DMF (1 mL) was added sodium hydride (60% in mineral oil) (10 mg, 0.26 mmol) at rt. After 15 min of stirring, tert-butyl 3-bromopropanoate (71 μL, 0.43 mmol) was added and the reaction mixture was stirred at rt for 3 h. TLC showed no reaction. Additional sodium hydride (25 mg, 6.43 mmol) and tert-butyl 3-bromopropanoate (107 μL, 6.42 mmol) were added to the solution and the reaction mixture was heated at 120° C. for 15 min under microwave irradiation. After cooling to rt, water was added to quench the reaction. The pH was adjusted to pH = 4-5 with 1M citric acid. The resulting aqueous solution was extracted with EtOAc. The combined organic layers were dried over MgSO4, filtered and the solution was concentrated under reduced pressure. A mixture of tert-butyl 3-{5-[1-({[4-methyl-2-(piperidin-1-yl)phenyl](5-methylfuran-2-yl)methyl}carbamoyl)cyclopropyl]-1H-indol-1-yl}propanoate and 3-{5-[1-({[4-methyl-2-(piperidin-1-yl)phenyl](5-methylfuran-2-yl)methyl}carbamoyl)cyclopropyl]-1H-indol-1-yl}propanoic acid was observed. The mixture was used as such for the next step. 1H NMR (300 MHz, DMSO-d6, d in ppm): 0.94-1.45 (m, 19H), 2.09 (s, 3H), 2.21 (s, 3H), 2.24-2.35 (m, 2H), 2.42-2.48 (m, 2H), 2.69-2.75 (m, 2H), 4.36 (t, 2H, J = 6.5 Hz), 5.79-5.82 (m, 1H), 5.88-5.92 (m, 1H), 6.30 (d, 1H, J = 9.0 Hz), 6.37-6.41 (m, 1H), 6.80-6.97 (m, 4H), 7.16 (dd, 1H, J = 8.4 Hz, J = 1.7 Hz), 7.35 (d, 1H, J = 3.2 Hz), 7.48 (d, 1H, J = 8.6 Hz), 7.55 (d, 1H, J = 1.3 Hz) (ester derivative).<br>Step 2: tert-butyl 3-{5-[1-({[4-methyl-2-(piperidin-1-yl)phenyl](5-methylfuran-2-yl)methyl}carbamoyl)cyclopropyl]-1H-indol-1-yl}propanoate (130 mg, 0.22 mmol) was dissolved in MeOH (2 mL). 5M NaOH (218 μL, 1.09 mmol) was added and the reaction mixture was heated at 110° C. for 30 min under microwave irradiation. The solvent was removed under reduced pressure. Water was added to the residue and the aqueous layer was extracted with Et2O. After phases separation, the remaining aqueous layer was acidified up to pH = 5 with 1M citric acid and extracted with EtOAc. The combined organic layers were dried over MgSO4, filtered and the solution was concentrated to dryness. The crude material was purified by silica gel column chromatography eluting with Cyclohexane/EtOAc (60:40), yield 31%, mp: 90° C., appearance: white solid<br>1H NMR (300 MHz, DMSO-d6, d in ppm): 0.95-1.46 (m, 10H), 2.09 (s, 3H), 2.21 (s, 3H), 2.24-2.35 (m, 2H), 2.40-2.48 (m, 2H), 2.72 (t, 2H, J = 6.8 Hz), 4.37 (t, 2H, J = 6.7 Hz), 5.81 (d, 1H, J = 3.0 Hz), 5.90 (dd, 1H, J = 3.0 Hz, J = 1.0 Hz), 6.30 (d, 1H, J = 8.9 Hz), 6.38 (d, 1H, J = 2.7 Hz), 6.84 (d, 1H, J = 7.5 Hz), 6.91 (d, 1H, J = 8.8 Hz), 6.94-6.98 (m, 2H), 7.17 (dd, 1H, J = 8.4 Hz, J = 1.6 Hz), 7.35 (d, 1H, J = 3.2 Hz), 7.49 (d, |

TABLE 2-continued

All the NMR were performed in DMSO-d6

| Cpd. | Starting compounds,<br>Reaction conditions and purification<br>Yield, MP, Appearance, $^1$H NMR (solvent) data, Mass (ES+ or ES−) data |
|---|---|
| | 1H, J = 8.5 Hz), 7.54 (d, 1H, J = 1.3 Hz), 12.34 (br(s), 1H); m/z: 540 [M + H]+ (calc. mass: 539). |
| 155 N-[(2,4-dimethylphenyl)(5-methylfuran-2-yl)methyl]-1-(1-hydroxy-2,3-dihydro-1H-inden-5-yl)cyclopropane-1-carboxamide | See FIG. 3BD<br>The previously synthesized N-[(2,4-dimethylphenyl)(5-methylfuran-2-yl)methyl]-1-(1-oxo-2,3-dihydro-1H-inden-5-yl)cyclopropane-1-carboxamide Cpd. 141 (115 mg, 0.28 mmol) was dissolved in EtOH (5 mL). The solution was cooled to 0° C. and sodium borohydride (16 mg, 0.42 mmol) was added. The ice bath was removed and the solution was stirred at rt for 2 h. The solvent was removed under reduced pressure. Water and 1N citric acid was added to neutralized the solution. The aqueous layer was extracted with EtOAc. The organic layer was dried over MgSO4, filtered and the solution was concentrated under reduced pressure. The product was pure and no purification was done., yield 85%, mp: 58° C., appearance: white solid<br>1H NMR (300 MHz, DMSO-d6, d in ppm): 0.95-1.02 (m, 2H), 1.25-1.34 (m, 2H), 1.69-1.83 (m, 1H), 2.15 (s, 3H), 2.16 (s, 3H), 2.22 (s, 3H), 2.29-2.38 (m, 1H), 2.61-2.70 (m, 1H), 2.81-2.94 (m, 2H), 4.97-5.05 (m, 1H), 5.20 (dd, 1H, J = 5.9 Hz, J = 0.8 Hz), 5.75-5.79 (m, 1H), 5.91-5.96 (m, 1H), 6.11 (d, 1H, J = 8.2 Hz), 6.90-6.97 (m, 3H), 7.14-7.21 (m, 2H), 7.24-7.31 (m, 2H); m/z: 438 [M + Na]+ (calc. mass: 415). |
| 156 N-{[2-(dimethylamino)-4-methylphenyl](5-methylfuran-2-yl)methyl}-1-(3-oxo-3,4-dihydro-2H-1,4-benzoxazin-7-yl)cyclopropane-1-carboxamide | From 2-[amino(5-methylfuran-2-yl)methyl]-N,N,5-trimethylaniline Ex. 42 and 1-(3-oxo-3,4-dihydro-2H-1,4-benzoxazin-7-yl)cyclopropane-1-carboxylic acid Ex. 35 following protocol A, DMAP (2.2 equiv), EDCI•HCl (2.2 equiv), overnight at rt. After completion of the reaction, the solution was poured into ice and water. The solid formed was collected by filtration and dried under vacuo until constant weight, yield 41%, mp: 99° C., appearance: white solid<br>1H NMR (300 MHz, DMSO-d6, d in ppm): 0.90-1.02 (m, 2H), 1.22-1.35 (m, 2H), 2.13 (s, 3H), 2.24 (s, 3H), 2.25 (s, 6H), 4.55 (s, 2H), 5.76 (dd, 1H, J = 3.2 Hz, J = 1.1 Hz), 5.92 (dd, 1H, J = 2.9 Hz, J = 1.0 Hz), 6.24 (d, 1H, J = 9.3 Hz), 6.84-6.91 (m, 2H), 6.93-7.04 (m, 3H), 7.12 (d, 1H, J = 7.9 Hz), 7.90 (d, 1H, J = 8.9 Hz), 10.74 (s, 1H); m/z: 460 [M + H]+ (calc. mass: 459). |
| 157 N-[(2,4-dimethylphenyl)(5-methylfuran-2-yl)methyl]-1-[1-(oxan-4-ylmethyl)-2,2-dioxo-1,3-dihydro-2,1-benzothiazol-5-yl]cyclopropane-1-carboxamide | From (2,4-dimethylphenyl)(5-methylfuran-2-yl)methanamine Ex. 19 and 1-[1-(oxan-4-ylmethyl)-2,2-dioxo-1,3-dihydro-2,1-benzothiazol-5-yl]cyclopropane-1-carboxylic acid Ex. 91 following protocol A, DMAP (1.1 equiv), EDCI•HCl (2.2 equiv), 2 h at rt, purification by silica gel column chromatography (Cyclohexane/EtOAc, 70:30) followed by a second purification by silica gel column chromatography (CH2Cl2/MeOH, 98:2), yield 59%, mp: 76° C., appearance: white solid<br>1H NMR (300 MHz, DMSO-d6, d in ppm): 0.90-1.10 (m, 2H), 1.15-1.4 (m, 4H), 1.66 (d, 2H, J = 14.4 Hz), 1.85-2.0 (m, 1H), 2.15 (s, 3H), 2.17 (s, 3H), 2.22 (s, 3H), 3.15-3.3 (m, 2H), 3.35-3.45 (m, 2H), 3.85 (dd, 2H, J = 11.3 Hz, J = 2.6 Hz), 4.60 (s, 2H), 5.75 (m, 1H), 5.93 (q, 1H, J = 3.0 Hz, J = 1.0 Hz), 6.12 (d, 1H, J = 8.3 Hz), 6.88-7.0 (m, 4H), 7.25-7.35 (m, 2H), 7.55 (d, 1H, J = 8.1 Hz); m/z: 571 [M + Na]+ (calc. mass: 548). |
| 158 N-[(2,4-dimethylphenyl)(5-methylfuran-2-yl)methyl]-1-(7-fluoro-2-oxo-2,3-dihydro-1H-indol-5-yl)cyclopropane-1-carboxamide | From (2,4-dimethylphenyl)(5-methylfuran-2-yl)methanamine Ex. 19 and 1-(7-fluoro-2-oxo-2,3-dihydro-1H-indol-5-yl)cyclopropane-1-carboxylic acid Ex. 92 following protocol A, DMAP (1.1 equiv), EDCI•HCl (1.1 equiv), overnight at rt, purification by silica gel column chromatography (Cyclohexane/EtOAc, 70:30), yield 31%, mp: 102° C., appearance: white solid<br>1H NMR (300 MHz, DMSO-d6, d in ppm): 0.91-1.06 (m, 2H), 1.21-1.37 (m, 2H), 2.16 (s, 3H), 2.18 (s, 3H), 2.22 (s, 3H), 3.52 (s, 2H), 5.73 (d, 1H, J = 3.4 Hz), 5.93 (dd, 1H, J = 3.0 Hz, J = 1.0 Hz), 6.15 (d, 1H, J = 8.6 Hz), 6.88-7.11 (m, 5H), 7.69 (d, 1H, J = 8.3 Hz), 10.85 (s, 1H); m/z: 455 [M + Na]+ (calc. mass: 432). |
| 159 1-(3,3-difluoro-2-oxo-2,3-dihydro-1H-indol-5-yl)-N- | From (2,4-dimethylphenyl)(5-methylfuran-2-yl)methanamine Ex. 19 and 1-(3,3-difluoro-2-oxo-2,3-dihydro-1H-indol-5-yl)cyclopropane-1-carboxylic acid Ex. 93 following protocol A, DMAP (1.1 equiv), EDCI•HCl (1.1 equiv), overnight at rt, |

TABLE 2-continued

All the NMR were performed in DMSO-d6

| Cpd. | Starting compounds, Reaction conditions and purification Yield, MP, Appearance, $^1$H NMR (solvent) data, Mass (ES+ or ES−) data |
|---|---|
| [(2,4-dimethylphenyl)(5-methylfuran-2-yl)methyl]cyclopropane-1-carboxamide | purification by silica gel column chromatography (Cyclohexane/EtOAc, 80:20), yield 57%, mp: 177° C., appearance: white solid<br>1H NMR (300 MHz, DMSO-d6, d in ppm): 0.95-1.08 (m, 2H), 1.27-1.38 (m, 2H), 2.16 (s, 3H), 2.17 (s, 3H), 2.22 (s, 3H), 5.71 (dd, 1H, J = 3.0 Hz, J = 0.5 Hz), 5.93 (dd, 1H, J = 3.0 Hz, J = 1.0 Hz), 6.15 (d, 1H, J = 8.1 Hz), 6.89-6.98 (m, 3H), 7.00 (d, 1H, J = 7.8 Hz), 7.45 (dd, 1H, J = 8.1 Hz, J = 1.5 Hz), 7.55-7.62 (m, 1H), 7.91 (d, 1H, J = 8.4 Hz), 11.18 (s, 1H); m/z: 449 [M − H]− (calc. mass: 450). |
| 160 N-[(5-chlorofuran-2-yl)(2,4-dimethylphenyl)methyl]-1-(1-methyl-2,2-dioxo-1,3-dihydro-2,1-benzothiazol-5-yl)cyclopropane-1-carboxamide | From (5-chlorofuran-2-yl)(2,4-dimethylphenyl)methanamine Ex. 32 and 1-(1-methyl-2,2-dioxo-1,3-dihydro-2,1-benzothiazol-5-yl)cyclopropane-1-carboxylic acid Ex. 40 following protocol A, DMAP (1.1 equiv), EDCl•HCl (2.2 equiv), 2 h at rt, purification by silica gel column chromatography (Cyclohexane/EtOAc, 70:30), yield 39%, mp: 70° C., appearance: white solid<br>1H NMR (300 MHz, DMSO-d6, d in ppm): 0.90-1.10 (m, 2H), 1.25-1.35 (m, 2H), 2.16 (s, 3H), 2.23 (s, 3H), 3.02 (s, 3H), 4.60 (s, 2H), 5.98 (q, 1H, J = 3.3 Hz, J = 1.1 Hz), 6.16 (d, 1H, J = 7.5 Hz), 6.35 (d, 1H, J = 3.3 Hz), 6.89 (d, 1H, J = 8.2 Hz), 6.97 (s, 3H), 7.25-7.35 (m, 2H), 7.83 (d, 1H, J = 8.2 Hz); m/z: 483 [M − H]−, 485 [M − H]− (calc. mass: 484). |
| 161 1-(2H-1,3-benzodioxol-5-yl)-N-[(2-bromo-4-methylphenyl)(5-methylfuran-2-yl)methyl]cyclopropane-1-carboxamide | From (2-bromo-4-methylphenyl)(5-methylfuran-2-yl)methanamine Ex. 18 and 1-(2H-1,3-benzodioxol-5-yl)cyclopropane-1-carboxylic acid Ex. 88 following protocol A, DMAP (3 equiv), EDCl•HCl (3 equiv), overnight at rt. After completion of the reaction, the solution was poured into ice and water. The solid formed was collected by filtration and dried under vacuo until constant weight, yield 35%, mp: 55° C., appearance: white solid<br>1H NMR (300 MHz, DMSO-d6, d in ppm): 0.90-1.04 (m, 2H), 1.19-1.28 (m, 2H), 2.18 (s, 3H), 2.27 (s, 3H), 5.69 (d, 1H, J = 3.7 Hz), 5.93 (dd, 1H, J = 3.1 Hz, J = 1.0 Hz), 6.00 (s, 2H), 6.25 (d, 1H, J = 7.7 Hz), 6.73-7.00 (m, 3H), 7.12-7.26 (m, 2H), 7.41 (s, 1H), 7.62 (d, 1H, J = 8.2 Hz); m/z: 468 [M + H]+, 470 [M + H]+ (calc. mass: 467). |
| 162 N-{[4-methyl-2-(piperidin-1-yl)phenyl](5-methylfuran-2-yl)methyl}-1-[1-(oxan-4-ylmethyl)-2,2-dioxo-1,3-dihydro-2,1-benzothiazol-5-yl]cyclopropane-1-carboxamide | From [4-methyl-2-(piperidin-1-yl)phenyl](5-methylfuran-2-yl)methanamine Ex. 16 and 1-[1-(oxan-4-ylmethyl)-2,2-dioxo-1,3-dihydro-2,1-benzothiazol-5-yl]cyclopropane-1-carboxylic acid Ex. 91 following protocol A, DMAP (1.1 equiv), EDCl•HCl (2.2 equiv), 2 h at rt, purification by silica gel column chromatography (Cyclohexane/EtOAc, 70:30), yield 61%, mp: 87° C., appearance: white solid<br>1H NMR (300 MHz, DMSO-d6, d in ppm): 0.90-1.00 (m, 2H), 1.10-1.45 (m, 10H), 1.66 (d, 2H, J = 11.2 Hz), 1.85-2.00 (m, 1H), 2.12 (s, 3H), 2.24 (s, 3H), 2.30-2.40 (m, 2H), 2.50-2.60 (m, 2H), 3.15-3.30 (m, 2H), 3.38 (d, 2H, J = 7.3 Hz), 3.85 (dd, 2H, J = 11.2 Hz, J = 2.6 Hz), 4.60 (s, 2H), 5.82 (d, 1H, J = 2.2 Hz), 5.92 (q, 1H, J = 3.0 Hz, J = 1.0 Hz), 6.32 (d, 1H, J = 9.0 Hz), 6.87 (d, 1H, J = 6.8 Hz), 6.95-7.0 (m, 2H), 7.08 (d, 1H, J = 7.7 Hz), 7.30-7.40 (m, 3H); m/z: 618 [M + H]+ (calc. mass: 617). |
| 163 N-[(2-bromo-4-methylphenyl)(5-methylfuran-2-yl)methyl]-1-[1-(oxan-4-ylmethyl)-2,2-dioxo-1,3-dihydro-2,1-benzothiazol-5-yl]cyclopropane-1-carboxamide | From (2-bromo-4-methylphenyl)(5-methylfuran-2-yl)methanamine Ex. 18 and 1-[1-(oxan-4-ylmethyl)-2,2-dioxo-1,3-dihydro-2,1-benzothiazol-5-yl]cyclopropane-1-carboxylic acid Ex. 91 following protocol A, DMAP (1.1 equiv), EDCl•HCl (2.2 equiv), 2 h at rt, purification by silica gel column chromatography (Cyclohexane/EtOAc, 70:30), yield 70%, mp: 85° C., appearance: white solid<br>1H NMR (300 MHz, DMSO-d6, d in ppm): 0.98 (d, 2H, J = 2.7 Hz), 1.20-1.35 (m, 4H), 1.66 (d, 2H, J = 10.9 Hz), 1.85-2.00 (m, 1H), 2.17 (s, 3H), 2.27 (s, 3H), 3.15-3.30 (m, 2H), 3.39 (d, 2H, J = 7.3 Hz), 3.85 (dd, 2H, J = 11.7 Hz, J = 3.2 Hz), 4.61 (s, 2H), 5.68 (d, 1H, J = 2.5 Hz), 5.93 (q, 1H, J = 3.0 Hz, J = 1.1 Hz), 6.25 (d, 1H, J = 8.2 Hz), 6.96 (d, 1H, J = 9.0 Hz), 7.10-7.25 (m, 2H), 7.25-7.35 (m, 2H), 7.41 (s, 1H), 7.83 (d, 1H, J = 8.1 Hz); m/z: 635 [M + H]+, 637 [M + H]+ (calc. mass: 612). |
| 164 1-(2H-1,3-benzodioxol-5-yl)-N-{[4-methyl-2-(piperidin-1- | From [4-methyl-2-(piperidin-1-yl)phenyl](5-methylfuran-2-yl)methanamine Ex. 16 and 1-(2H-1,3-benzodioxol-5-yl)cyclopropane-1-carboxylic acid Ex. 88 following protocol A, DMAP (3 equiv), EDCl•HCl (3 equiv), overnight at rt, |

TABLE 2-continued

All the NMR were performed in DMSO-d6

| Cpd. | Starting compounds, Reaction conditions and purification Yield, MP, Appearance, $^1$H NMR (solvent) data, Mass (ES+ or ES−) data |
|---|---|
| yl)phenyl](5-methylfuran-2-yl)methyl}cyclopropane-1-carboxamide | purification by silica gel column chromatography (Cyclohexane/EtOAc, 80:20), yield 31%, mp: 51° C., appearance: white solid<br>1H NMR (300 MHz, DMSO-d6, d in ppm): 0.90-0.99 (m, 2H), 1.23-1.47 (m, 8H), 2.12 (s, 3H), 2.24 (s, 3H), 2.39-2.46 (m, 2H), 2.55-2.62 (m, 2H), 5.81 (d, 1H, J = 2.3 Hz), 5.92 (dd, 1H, J = 3.0 Hz, J = 1.1 Hz), 5.96-6.03 (m, 2H), 6.34 (d, 1H, J = 8.4 Hz), 6.83-6.91 (m, 3H), 6.92-7.00 (m, 2H), 7.03 (d, 1H, J = 7.8 Hz), 7.17 (d, 1H, J = 8.9 Hz); m/z: 473 [M + H]+ (calc. mass: 472). |
| 165 N-[(2,4-dimethylphenyl)(5-methylfuran-2-yl)methyl]-1-[1-(hydroxyimino)-2,3-dihydro-1H-inden-5-yl]cyclopropane-1-carboxamide | From (2,4-dimethylphenyl)(5-methylfuran-2-yl)methanamine Ex. 19 and 1-[1-(hydroxyimino)-2,3-dihydro-1H-inden-5-yl]cyclopropane-1-carboxylic acid Ex. 94 following protocol A, DMAP (1.1 equiv), EDCl•HCl (1.1 equiv), overnight at rt, purification by silica gel column chromatography (Cyclohexane/EtOAc, 70:30), yield 41%, mp: 68° C., appearance: white solid<br>1H NMR (300 MHz, DMSO-d6, d in ppm): 0.99-1.06 (m, 2H), 1.30-1.33 (m, 2H), 2.16 (s, 3H), 2.16 (s, 3H), 2.22 (s, 3H), 2.74-2.79 (m, 2H), 2.93-2.97 (m, 2H), 5.74-5.75 (m, 1H), 5.92-5.93 (m, 1H), 6.14 (d, 1H, J = 8.1 Hz), 6.94-6.95 (m, 3H), 7.20 (dd, 1H, J = 8.1 Hz, J = 1.5 Hz), 7.29-7.31 (m, 1H), 7.48 (d, 1H, J = 8.1 Hz), 7.62 (d, 1H, J = 8.4 Hz), 10.81 (s, 1H); m/z: 429 [M + H]+ (calc. mass: 428). |
| 166 N-[(2,4-dimethylphenyl)(5-methylfuran-2-yl)methyl]-2-[1-(oxan-4-ylmethyl)-2,2-dioxo-1,3-dihydro-2,1-benzothiazol-5-yl]acetamide | From (2,4-dimethylphenyl)(5-methylfuran-2-yl)methanamine Ex. 19 and 2-[1-(oxan-4-ylmethyl)-2,2-dioxo-1,3-dihydro-2,1-benzothiazol-5-yl]acetic acid Ex. 95 following protocol A, substituted amine (0.9 equiv), DMAP (1.1 equiv), EDCl•HCl (2.2 equiv), 8 h at rt, purification by silica gel column chromatography (Cyclohexane/EtOAc, 50:50), yield 57%, mp: 83° C., appearance: white solid<br>1H NMR (300 MHz, DMSO-d6, d in ppm): 1.20-1.35 (m, 2H), 1.65 (d, 2H, J = 14.9 Hz), 1.80-2.00 (m, 1H), 2.17 (s, 3H), 2.20 (s, 3H), 2.23 (s, 3H), 3.15-3.30 (m, 2H), 3.36 (d, 2H, J = 7.3 Hz), 3.44 (s, 2H), 3.84 (d, 2H, J = 8.0 Hz), 4.61 (s, 2H), 5.85 (d, 1H, J = 3.1 Hz), 5.95 (q, 1H, J = 2.9 Hz, J = 1.0 Hz), 6.10 (d, 1H, J = 8.2 Hz), 6.90-7.00 (m, 3H), 7.09 (d, 1H, J = 8.0 Hz), 7.15-7.25 (m, 2H), 8.93 (d, 1H, J = 8.3 Hz); m/z: 545 [M + Na]+ (calc. mass: 522). |
| 167 N-{[4-methyl-2-(piperidin-1-yl)phenyl](5-methylfuran-2-yl)methyl}-2-[1-(oxan-4-ylmethyl)-2,2-dioxo-1,3-dihydro-2,1-benzothiazol-5-yl]acetamide | From [4-methyl-2-(piperidin-1-yl)phenyl](5-methylfuran-2-yl)methanamine Ex. 16 and 2-[1-(oxan-4-ylmethyl)-2,2-dioxo-1,3-dihydro-2,1-benzothiazol-5-yl]acetic acid Ex. 95 following protocol A, substituted amine (0.9 equiv), DMAP (1.1 equiv), EDCl•HCl (2.2 equiv), 8 h at rt, purification by silica gel column chromatography (Cyclohexane/EtOAc, 50:50), yield 60%, mp: 85° C., appearance: white solid<br>1H NMR (300 MHz, DMSO-d6, d in ppm): 1.20-1.35 (m, 2H), 1.40-1.60 (m, 6H), 1.65 (d, 2H, J = 12.4 Hz), 1.90-2.00 (m, 1H), 2.17 (s, 3H), 2.25 (s, 3H), 2.50-2.60 (m, 2H), 2.70-2.80 (m, 2H), 3.15-3.30 (m, 2H), 3.36 (d, 2H, J = 7.1 Hz), 3.42 (s, 2H), 3.84 (d, 2H, J = 9.0 Hz), 4.60 (s, 2H), 5.81 (d, 1H, J = 2.9 Hz), 5.91 (q, 1H, J = 3.0 Hz, J = 1.0 Hz), 6.46 (d, 1H, J = 8.2 Hz), 6.85-6.95 (m, 3H), 7.15-7.25 (m, 3H), 8.72 (d, 1H, J = 8.3 Hz); m/z: 592 [M + H]+ (calc. mass: 591). |
| 168 1-(2,2-dimethyl-2,4-dihydro-1,3-benzodioxin-7-yl)-N-[(2,4-dimethylphenyl)(5-methylfuran-2-yl)methyl]cyclopropane-1-carboxamide | From (2,4-dimethylphenyl)(5-methylfuran-2-yl)methanamine Ex. 19 and 1-(2,2-dimethyl-2,4-dihydro-1,3-benzodioxin-7-yl)cyclopropane-1-carboxylic acid Ex. 96 following protocol A, DMAP (1.1 equiv), EDCl•HCl (1.1 equiv), 5 h at rt, purification by silica gel column chromatography (Cyclohexane/EtOAc, 80:20), yield 61%, mp: ND, appearance: colourless oil<br>1H NMR (300 MHz, DMSO-d6, d in ppm): 0.98-0.99 (m, 2H), 1.23-1.28 (m, 2H), 1.44 (s, 6H), 2.15 (s, 3H), 2.16 (s, 3H), 2.22 (s, 3H), 4.78 (s, 2H), 5.75-5.76 (m, 1H), 5.92-5.93 (m, 1H), 6.12 (s, 1H, J = 8.1 Hz), 6.74 (d, 1H, J = 1.8 Hz), 6.86 (dd, 1H, J = 7.8 Hz, J = 1.8 Hz), 6.93-6.95 (m, 3H), 7.02 (d, 1H, J = 8.1 Hz), 7.46 (d, 1H, J = 8.4 Hz); m/z: 446 [M + H]+ (calc. mass: 445). |
| 169 1-(2,2-dimethyl-2,4-dihydro-1,3-benzodioxin-6-yl)-N-[(2,4-dimethylphenyl)(5- | From (2,4-dimethylphenyl)(5-methylfuran-2-yl)methanamine Ex. 19 and 1-(2,2-dimethyl-2,4-dihydro-1,3-benzodioxin-6-yl)cyclopropane-1-carboxylic acid Ex. 97 following protocol A, DMAP (1.1 equiv), EDCl•HCl (1.1 equiv), 5 h at rt, purification by silica gel column chromatography |

TABLE 2-continued

All the NMR were performed in DMSO-d6

| Cpd. | Starting compounds, Reaction conditions and purification Yield, MP, Appearance, $^1$H NMR (solvent) data, Mass (ES+ or ES−) data |
|---|---|
| methylfuran-2-yl)methyl]cyclopropane-1-carboxamide | (Cyclohexane/EtOAc, 80:20), yield 63%, mp: ND, appearance: colourless oil<br>1H NMR (300 MHz, DMSO-d6, d in ppm): 0.95-0.96 (m, 2H), 1.25-1.28 (m, 2H), 1.44 (s, 6H), 2.15 (s, 3H), 2.16 (s, 3H), 2.22 (s, 3H), 4.77 (s, 2H), 5.75-5.76 (m, 1H), 5.92-5.93 (m, 1H), 6.10 (d, 1H, J = 7.8 Hz), 6.75 (d, 1H, J = 8.4 Hz), 6.93-6.94 (m, 3H), 7.04 (d, 1H, J = 2.1 Hz), 7.13 (dd, 1H, J = 8.4 Hz, J = 2.1 Hz), 7.26 (d, 1H, J = 8.1 Hz); m/z: 446 [M + H]+ (calc. mass: 445). |
| 170 N-[(2,4-dimethylphenyl)(5-methylfuran-2-yl)methyl]-1-[3-(1-hydroxy-2-methylpropan-2-yl)-1H-indol-5-yl]cyclopropane-1-carboxamide | From (2,4-dimethylphenyl)(5-methylfuran-2-yl)methanamine Ex. 19 and 1-[3-(1-hydroxy-2-methylpropan-2-yl)-1H-indol-5-yl]cyclopropane-1-carboxylic acid Ex. 98 following protocol A, DMAP (1.1 equiv), EDCl•HCl (1.1 equiv), 2 h at rt, purification by silica gel column chromatography (Cyclohexane/EtOAc, 80:20) followed by a second purification by silica gel chromatography (Cyclohexane/CH2Cl2/EtOAc, 50:30:20), yield 49%, mp: 194° C., appearance: white solid<br>1H NMR (300 MHz, DMSO-d6, d in ppm): 0.96-1.11 (m, 2H), 1.31 (s, 6H), 1.33-1.40 (m, 2H), 2.11 (s, 3H), 2.13 (s, 3H), 2.20 (s, 3H), 3.54 (d, 2H, J = 5.5 Hz), 4.58 (t, 1H, J = 5.7 Hz), 5.71 (d, 1H, J = 3.0 Hz), 5.88 (dd, 1H, J = 3.0 Hz, J = 1.0 Hz), 6.07 (d, 1H, J = 8.3 Hz), 6.58 (d, 1H, J = 8.5 Hz), 6.75 (d, 1H, J = 7.8 Hz), 6.88 (d, 1H, J = 7.9 Hz), 6.93 (s, 1H), 7.03-7.10 (m, 2H), 7.32 (d, 1H, J = 8.3 Hz), 7.70 (s, 1H), 10.86 (s, 1H); m/z: 493 [M + Na]+ (calc. mass: 470). |
| 171 1-(2,2-dioxo-1,3-dihydro-4,2,1-benzoxathiazin-6-yl)-N-{[4-methyl-2-(trifluoromethyl)phenyl](5-methylfuran-2-yl)methyl}cyclopropane-1-carboxamide | From [4-methyl-2-(trifluoromethyl)phenyl](5-methylfuran-2-yl)methanamine Ex. 99 and 1-(2,2-dioxo-1,3-dihydro-4,2,1-benzoxathiazin-6-yl)cyclopropane-1-carboxylic acid Ex. 69 following protocol A, DMAP (1.1 equiv), EDCl•HCl (1.1 equiv), 2 h at rt, purification by silica gel column chromatography (CH2Cl2/EtOAc, 90:10), yield 37%, mp: 100° C., appearance: white solid<br>1H NMR (300 MHz, DMSO-d6, d in ppm): 0.93-1.01 (m, 2H), 1.19-1.32 (m, 2H), 2.17 (s, 3H), 2.36 (s, 3H), 5.15 (s, 2H), 5.65 (d, 1H, J = 3.3 Hz), 5.91-5.93 (m, 1H), 6.34 (d, 1H, J = 7.8 Hz), 6.75 (d, 1H, J = 8.4 Hz), 6.95-6.98 (m, 2H), 7.46-7.50 (m, 3H), 7.98 (d, 1H, J = 7.8 Hz), 10.34 (br(s), 1H); m/z: 519 [M − H]− (calc. mass: 520). |
| 172 N-[(2,4-dimethylphenyl)(5-methylfuran-2-yl)methyl]-1-(1-methyl-2,2-dioxo-1,3-dihydro-4,2,1-benzoxathiazin-6-yl)cyclopropane-1-carboxamide | From (2,4-dimethylphenyl)(5-methylfuran-2-yl)methanamine Ex. 19 and 1-(1-methyl-2,2-dioxo-1,3-dihydro-4,2,1-benzoxathiazin-6-yl)cyclopropane-1-carboxylic acid Ex. 100 following protocol A, DMAP (1.1 equiv), EDCl•HCl (1.1 equiv), overnight at rt, purification by silica gel column chromatography (Cyclohexane/EtOAc, 70:30), yield 52%, mp: 65° C., appearance: white solid<br>1H NMR (300 MHz, DMSO-d6, d in ppm): 0.95-1.05 (m, 2H), 1.22-1.36 (m, 2H), 2.17 (s, 3H), 2.18 (s, 3H), 2.23 (s, 3H), 3.20 (s, 3H), 5.37 (s, 2H), 5.76 (d, 1H, J = 3.0 Hz), 5.94 (dd, 1H, J = 3.0 Hz, J = 1.0 Hz), 6.13 (d, 1H, J = 8.3 Hz), 6.91-7.01 (m, 3H), 7.02 (d, 1H, J = 1.9 Hz), 7.06 (dd, 1H, J = 8.4 Hz, J = 2.0 Hz), 7.15 (d, 1H, J = 8.5 Hz), 7.79 (d, 1H, J = 8.2 Hz); m/z: 503 [M + Na]+ (calc. mass: 480). |
| 173 N-[(2-bromo-4-methylphenyl)(5-methylfuran-2-yl)methyl]-1-(1-methyl-2,2-dioxo-1,3-dihydro-4,2,1-benzoxathiazin-6-yl)cyclopropane-1-carboxamide | From (2-bromo-4-methylphenyl)(5-methylfuran-2-yl)methanamine Ex. 18 and 1-(1-methyl-2,2-dioxo-1,3-dihydro-4,2,1-benzoxathiazin-6-yl)cyclopropane-1-carboxylic acid Ex. 100 following protocol A, DMAP (1.1 equiv), EDCl•HCl (1.1 equiv), overnight at rt, purification by silica gel column chromatography (Cyclohexane/EtOAc, 70:30), yield 51%, mp: 71° C., appearance: white solid<br>1H NMR (300 MHz, DMSO-d6, d in ppm): 0.95-1.06 (m, 2H), 1.22-1.36 (m, 2H), 2.19 (s, 3H), 2.28 (s, 3H), 3.20 (s, 3H), 5.37 (s, 2H), 5.68 (dd, 1H, J = 3.1 Hz, J = 0.6 Hz), 5.93 (dd, 1H, J = 3.0 Hz, J = 1.0 Hz), 6.27 (d, 1H, J = 8.1 Hz), 7.02 (d, 1H, J = 1.9 Hz), 7.06 (dd, 1H, J = 8.4 Hz, J = 2.0 Hz), 7.11-7.20 (m, 2H), 7.22 (d, 1H, J = 7.9 Hz), 7.42 (s, 1H), 8.05 (d, 1H, J = 8.1 Hz); m/z: 567 [M + Na]+, 569 [M + Na]+ (calc. mass: 544). |
| 174 1-(2,2-dioxo-1,3-dihydro-4,2,1-benzoxathiazin-6-yl)-N-[(2-methoxy-4- | From (2-methoxy-4-methylphenyl)(5-methylfuran-2-yl)methanamine Ex. 101 and 1-(2,2-dioxo-1,3-dihydro-4,2,1-benzoxathiazin-6-yl)cyclopropane-1-carboxylic acid Ex. 69 following protocol A, DMAP (1.1 equiv), EDCl•HCl (1.1 equiv), overnight at rt, purification by silica gel column |

TABLE 2-continued

All the NMR were performed in DMSO-d6

| Cpd. | Starting compounds, Reaction conditions and purification Yield, MP, Appearance, $^1$H NMR (solvent) data, Mass (ES+ or ES−) data |
|---|---|
| methylphenyl)(5-methylfuran-2-yl)methyl]cyclopropane-1-carboxamide | chromatography (CH2Cl2/EtOAc, 90:10), yield 58%, mp: 107° C., appearance: white solid 1H NMR (300 MHz, DMSO-d6, d in ppm): 0.93-1.01 (m, 2H), 1.25-1.36 (m, 2H), 2.14 (s, 3H), 2.26 (s, 3H), 3.51 (s, 3H), 5.19 (s, 2H), 5.67-5.68 (m, 1H), 5.87-5.89 (m, 1H), 6.05 (d, 1H, J = 9.0 Hz), 6.68-6.71 (m, 1H), 6.76-6.77 (m, 1H), 6.82-6.85 (m, 1H), 7.02-7.09 (m, 3H), 7.30 (d, 1H, J = 9.0 Hz), 10.65 (br(s), 1H); m/z: 505 [M + Na]+ (calc. mass: 482). |
| 175 1-(2,2-dimethyl-2H-1,3-benzodioxol-5-yl)-N-[(2,4-dimethylphenyl)(5-methylfuran-2-yl)methyl]cyclopropane-1-carboxamide | From (2,4-dimethylphenyl)(5-methylfuran-2-yl)methanamine Ex. 19 and 1-(2,2-dimethyl-2H-1,3-benzodioxol-5-yl)cyclopropane-1-carboxylic acid Ex. 102 following protocol A, DMAP (1.1 equiv), EDCl•HCl (1.1 equiv), overnight at rt, purification by silica gel column chromatography (Cyclohexane/EtOAc, 70:30), yield 73%, mp: ND, appearance: viscous colourless oil 1H NMR (300 MHz, DMSO-d6, d in ppm): 0.95-0.97 (m, 2H), 1.19-1.27 (m, 2H), 1.61 (s, 6H), 2.14 (s, 3H), 2.16 (s, 3H), 2.21 (s, 3H), 5.76-5.77 (m, 1H), 5.92-5.94 (m, 1H), 6.08 (d, 1H, J = 8.1 Hz), 6.77-6.78 (m, 2H), 6.81-6.82 (m, 1H), 6.93-6.94 (m, 3H), 7.27 (d, 1H, J = 8.4 Hz); m/z: 432 [M + H]+ (calc. mass: 431). |

Example 3: RORE Luciferase/RORγt Transactivation Assay

It is well known that RORγ binds to a conserved non-coding sequence (CNS) enhancer element in the IL-17 promoter. Accordingly, we have used in this assay a luciferase reporter gene construct that contains the human IL-17 promoter fragment with RORγ-specific CNS enhancer element and a RORγt overexpressing plasmid, to indirectly assess the effect of compounds on RORγ activity. Inhibition of RORγ activity by test compounds will result in a decrease in luciferase activity in COS-7 cells transfected with the reporter construct.

COS-7 Cell Line Culture

Monkey Kidney COS-7 cell line are maintained in a standard culture medium Dulbecco's modified Eagle's minimal (DMEM) medium supplemented with 10% fetal calf serum, 1% sodium pyruvate, 1% essential amino acids and 1% antibiotics at 37° C. in a humidified atmosphere of 5% CO02 and 95% air. Culture medium was changed every 2 days.

Construct Descriptions

The 4.3 Kb human IL-17 promoter containing the RORγ-specific CNS enhancer element was PCR amplified from human genomic DNA and cloned into a pGL3-TKLuc2Cp reporter plasmid. To overexpress RORγt, the full-length cDNA of human RORγt (identical to published sequence NM 001001523) was cloned without any restriction into pcdna3.1DV5-His-topo to generate the RORyt overexpression plasmid "RORyt_FL_h_pcDNA3.1DV5-His-TOPO_1".

COS-7 Cell Transfection

The luciferase reporter plasmid and the RORγt overexpression plasmid were transfected into COS-7 cell line using 4 µLJetPEI™/µg of DNA. Briefly, 150 ng of DNA (ration ½ between RORE-Tk Luc2Cp and cDNA RORγt or the empty vector for the negative control) was served to transfect adherent COS-7 cells in a 225 cm3 culture flask, in complete medium (see cos-7 cell line culture). Cells were incubated for 24 hours in a humidified atmosphere of 5% CO02 and 95% air Cells were then detached (using trypsin) and washed by centrifugation at 300 g for 10 minutes. Cell pellet was resuspended in serum free/phenol red free DMEM and seeded in 384 well plates at a density of 10000 cells/well and then incubated for 4 h at 37° C.

Assay

Compounds were dissolved in 100% DMSO to obtain 10 mM stock solutions. For each compound, test concentrations were diluted in serum free/phenol red free DMEM using the Genesis Freedom 200™ (TECAN) and added to the cells to obtain a 0.3% DMSO final concentration (in a final volume of 40 µL per well). T091317 was used as reference compound. Cells were incubated in presence of compounds for an additional 20 h at 37° C. in a humidified atmosphere of 5% CO02 and 95% air The luciferase activity was then measured with 40 µL/well steady-Glo Luciferase assay system (Promega, Madison, Wis.) and after incubation at room temperature for 30 minutes. The luminescence was estimated using the Ultra384 reader (TECAN). Data were collected and analyzed using GraphPad Prism software (GraphPad Software V5.02, San Diego Calif. USA). IC50 in µM and Emax in % were reported for each compound.

Results:

Effect of reference compound on RORγt activity: in this assay, reference compound T091317 showed on RORγt activity inhibition with $IC_{50}$ of 0.2 µM and an Emax of 83.7% Several compounds belonging to formula (I) or (Ia) inhibit the high transcriptional activity of RORγ at different levels. In particular, Cpd.7 displayed an $IC_{50}$ superior to 10 µM. Some compounds displayed an $IC_{50}$ comprised between 1 and 10 µM in particular Cpds 2-3, 5-6, 9-11, 13, 15, 17-18, 20, 22, 26, 29-30 and 140. Cpds 1, 4, 16, 21, 23, 25, 28, 32-34, 36, 39-40, 42-46, 48, 50-51, 55, 67, 96, 99-102, 104, 107, 110, 141, 148, 150, 153, 159, 161, 164, and 168-169 displayed an $IC_{50}$ comprised between 0.1 and 1 µM.

Cpds 16, 24, 27, 31, 35, 37-38, 41, 47, 49, 52-54, 56-58, 62-66, 69-85, 87-88, 90-95, 97-98, 103, 106, 108, 111-120, 124-127, 130-133, 136-137, 139, 142-147, 149, 152, 155-156, 158, 160, 162-163, 165-167, and 170-171 displayed an $IC_{50}$ comprised between 0.01 and 0.1 µM.

Best compounds (such as Cpds. 59-61, 86, 89, 123, 134-135, 154, and 157) displayed an $IC_{50}$ inferior to 0.01 µM.

Further, the major part of compounds from this chemical series showed no cytotoxic effect at 30 µM as judged from the reporter signal obtained from cells transfected with the empty vector that was used as negative control in this experiment.

Example 4: FRET

General Considerations

Time-resolved FRET (TR-FRET) RORγt coactivator assay was used to identify RORγ modulator compounds with ligand-dependent coactivator displacement. The assay uses a d2-labeled anti-GST antibody, synthetic N-terminally biotinylated peptide which is derived from nuclear receptor coactivator protein RIP140, and a RORγt ligand-binding domain (RORγt-LBD) that is tagged with glutathione-S-transferase (GST). The influence of compounds on the RORγ-peptide interaction relies on the binding dependent energy transfer from a donor to an acceptor fluorophor attached to the binding partner of interest. Because RORγ is constitutively active, streptavidin-terbium conjugate labeled-coactivator peptide is recruited in the absence of ligand and the terbium d2 on the anti-GST antibody is excited at 340 nm, energy is transferred to the terbium label on the coactivator peptide and detected as emission at 665 nm. For reduction of background from compound fluorescence, TR-FRET method makes use of generic fluorophore labels and time resolved detection.

Assay

The assays were done in a final volume of 20 µl in a 384 well plate in a CHAPS buffer (2 mM CHAPS; 1 mM DTT, 2 mM EDTA; 0.1% BSA), containing 20 nM recombinantly expressed RORγ-LBD fused to GST, 30 nM N-terminally biotinylated peptide, 1 nM streptavidin-terbium conjugate and 20 nM d2 labeled-anti-GST. Test compounds were diluted using 10 mM stock solution. The range of the final compound concentrations used in this test was from 0.3 nM to 30 µM (logarithmic scale). DMSO content of the samples was kept at 1%. The assay was equilibrated for 2 hours in the dark at room temperature in 384 well plates (Falcon). The signal was detected by an Ultra384 reader (TECAN). The results were visualized by plotting the ratio between the emitted light at 665 nm and 620 nm. A basal level of RORγ-peptide formation is observed in the absence of added compound. Compounds that promote coactivator displacement induce a concentration-dependent decrease in time-resolved fluorescent signal. Data were collected and analyzed using GraphPad Prism software (GraphPad Software V5.02, San Diego Calif. USA). IC50 in µM and Emax in % were reported for each compound.

Results:

Effect of reference compound on RORγt activity: in this assay, reference compound T091317 showed on RORγt activity inhibition with $IC_{50}$ of 0.097 µM and an Emax of 37%

Several compounds belonging to formula (I) or (Ia) inhibit the ligand-dependent coactivator-RORγt binding.

Cpds 12, 19-20, 32, and 50 displayed an IC50 comprised between 1 µM and 10 µM.

Cpds 1, 3, 7-8, 11, 18, 21-23, 25, 30, 34, 40, 43-45, 48, 64, 91-92, 100, and 118, displayed an IC50 comprised between 0.1 µM and 1 µM.

Cpds.2, 4-5, 9, 15-16, 26, 81-82, 90, 98-99, and 101-102 displayed an $IC_{50}$ between 0.01 µM and 0.1 µM.

Best compounds (such as Cpds.24, 27, 52-53, 59-60, 63, 71, 74, 77, 86-87, 124-125, 127, and 130) displayed an $IC_{50}$ inferior to 0.01 µM.

Example 5: IL-17 Secretion from EL4 Murine Lymphoma

Murine EL-4 lymphoma cell line overexpressing human RORγt was used in this functional assay to assess compound ability to inhibit IL-17 cytokine secretion.

EL-4 Cell Transfection

EL-4 cells are maintained in a standard culture medium RPMI supplemented with 10% fetal calf serum, 1% sodium pyruvate, 1% essential amino acids and 1% antibiotics at 37° C. in a humidified atmosphere of 5% CO02 and 95% air. Culture medium was changed every 2 days. EL4 cells were transfected with a plasmid encoding hRORγt (sequence identical to published sequence NM 001001523). Transfection of EL4 cells was achieved with Amaxa electroporation apparatus (Amaxa Biosystems, Germany), as per the manufacturer's protocols, for the EL4 cells (Amaxa Cell Line Nucleofector Kit L, Amaxa Biosystems). Briefly, 1 µg of DNA/1 million cells was served to transfect EL-4 cells. Cell/DNA suspension was transferred into certified cuvette and the electroporation of RORγt plasmid was carried out using appropriate Nucleofector® program.

IL-17 Secretion Assay

Cells were seeded in 96 well plates at a density of 150000 cells/I well then treated with compounds of this invention at indicated concentrations and incubated for 24 hours at 37° C. in a humidified atmosphere of 5% C02 and 95% air. EL-4 cells were pretreated with test compounds (RORγ modulators) and stimulated with PMA (10 ng/mL) and ionomycin (1 µM final concentration) in the presence of test compound concentrations for additional 24 h at 37° C. in a humidified atmosphere of 5% C02 and 95% air. Subsequently, supernatants were collected (after centrifugation at 300 g for 10 minutes) to determine the concentrations of IL-17 by HTRF (CisBio, France) or ELISA (R&D Systems Europe) according to the manufacturer's protocols.

Results:

Many of the compounds listed above were evaluated for IL-17 secretion inhibition in human RORγt-transfected EL4 Tcells. Data from this assay correlate with the activity observed in RORE Tk luc/RORγt assay.

Cpd. 2 and 5 displayed an IC50 comprised superior to 10 µM.

Cpd. 3, 10-11, 25, 28, 44, 104, and 107 displayed an IC50 comprised between 1 µM and 10 µM.

Cpds. 1, 4, 16, 23, 27, 31, 33, 36-39, 42, 47, 52-53, 71-72, 74-84, 90-92, 97, 106, 111-112, 114-115, 117, 124, and 126 displayed an IC50 comprised between 0.1 µM and 1 µM.

Best compounds (such as Cpds. 24, 35, 41, 54, 57-62, 64, 73, 86-89, 93-94, 98, 103, 108, 116, 118-120, 125, 127 and 130) displayed an IC50 inferior to 0.1 µM.

Example 6: Experimental Autoimmune Encephalomyelitis (EAE) Study 8-10 week old, female C57BL/6 mice were purchased from Janvier Lab (St Berthevin, France) and housed for one week before the start of the studies. EAE was induced by immunization with an emulsion of peptide antigen MOG35-55 (Myelin Oligodendrocyte Glycoprotein) (MMEVGWYRSPFSRVVHLYRNG, SEQ ID NO: 1) in complete Freund's Adjuvant (CFA), followed by administration of Pertussis Toxin (PTX) in PBS on the day of immunization and day 1 post immunization, following manufacturer recommendation (Hooke, Kit MOG35-55/CFA Emulsion PTX). Animals were treated with drug beginning 2 days before peptide injection. Animals were randomized into groups for treatment by weight, so that the average weight of each group was similar. The groups were segregated by cage. Compounds according to the invention were suspended in Labrafil (M1944 CS) by sonication and animals were dosed twice daily by gavage with 5 mL/kg body weight. The daily doses of Cpd.24 were 30 and 60 mg/kg (b.i.d.) by gavage. Clinical assessment of EAE was performed daily according to the following criteria: 0) no disease, 1) limp tail, 2) limp tail and weakness on hind legs 3) limp tail and complete paralysis of hind legs or paralysis of one front one hind leg, 4) limp tail, complete hind leg and partial front leg paralysis and 5) complete paralysis or death.

Data are expressed as (FIG. 4A) mean (+/−SEM) of clinical score for each group per day and (FIG. 4B). Area under curve (AUC) of clinical score for each group through in vivo protocol duration.

Statistical evaluation of differences between the experimental groups was determined by using two-way Anova followed by a Bonferroni post test. **$p<0.005$, Vehicle compared with treatments.

Results

This example shows that Cpd.24 RORγ modulator is able to delay the onset of EAE when the compound was administered p/os at 60 mg/kg (b.i.d.) for 20 days. Clinical disease score improvement was apparent with Cpd.24 by day 15 and maintained through in vivo protocol duration (FIGS. 4A & B).

Example 7: Imiquimod (IMQ) Induced Psoriasis Study 8-10 weeks C57BL/6 female mice received a daily topical dose of 62.5 mg/mouse IMQ cream (Aldara® cream 5%; 3M pharmaceuticals, Sweden) on the shaved back and the right ear for 7 consecutive days. Control mice were treated similarly with a control vehicle cream (Vaseline). Test compound (Cpd 24) was orally administered daily from day 0 to day 7 at 3 mg/mL (30 mg/kg). Test compound was given 8 hours before IMQ application. Mice were killed at day 7, 4 h after the last test compound treatment to analyse skin inflammation parameters.

The severity of inflammation of the back skin was determined using the following criteria. An objective scoring system was developed based on the clinical Psoriasis Area and Severity Index (PASI), except that for the mouse model the affected skin area is not taken into account in the overall score. Erythema, scaling, and thickening were scored independently on a scale from 0 to 4: 0: none; 1: slight; 2: moderate; 3: marked; 4: severe. The cumulative score (erythema plus scaling plus thickening) served as a measure of the severity of inflammation (scale 0-12).

Ear skin tissue were homogenized in PBS containing a protease inhibitor cocktail (P8340, Sigma-Aldrich) by Ultra Turrax, centrifuged and the supernatant was discarded. The pellet was resuspended in 0.5 mL PBS containing 0.5% hexadecyltrimethyl ammonium bromide (HTAB) and 5 mM ethylene-diamine tetra-acetic acid (EDTA). Following centrifugation, 100 μL of supernatants were placed in test tubes with 200 μL PBS-HTAB-EDTA, 1 mL Hanks' balanced salt solution (HBSS), 100 μL of o-dianisidine dihydrochloride (1.25 mg/mL), and 100 μL H2O2 0.05%. After 15 min of incubation at 37° C. in an agitator, the reaction was stopped with 100 μL NaN3 1%. The MPO activity was determined as absorbance at 460 nm in comparison with medium.

Statistical evaluation of differences between the experimental groups was determined by using two-way Anova followed by a Bonferroni post test. *** $p<0.001$, IMQ-Vehicle compared with treatment.

Results

In this experiment, no adverse effect was observed after compound test administration. Orally treatment with 30 mpk Cpd 24 induced a significant decrease of cumulative score at day 5 compared to control treatment (FIG. 5A). The effect of test compound on the extent of inflammation was tested using MPO activity marker. GFE6030 treatment reduced MPO activity in ear homogenates in comparison with IMQ-vehicle group (FIG. 5B).

REFERENCES

Armarego W L F, Chai C L L (2009) *Purification of Laboratory Chemicals (Sixth Edition)*: ELSEVIER.

Bauer M (2004) *Polymorphisme et stabilité*, Paris, FRANCE: Editions de sante.

Crispin J C, Oukka M, Bayliss G, Cohen R A, Van Beek C A, Stillman I E, Kyttaris V C, Juang Y-T, Tsokos G C (2008) Expanded Double Negative T Cells in Patients with Systemic Lupus Erythematosus Produce IL-17 and Infiltrate the Kidneys. *The Journal of Immunology* 181: 8761-8766

Dang Eric V, Barbi J, Yang H-Y, Jinasena D, Yu H, Zheng Y, Bordman Z, Fu J, Kim Y, Yen H-R, Luo W, Zeller K, Shimoda L, Topalian Suzanne L, Semenza Gregg L, Dang Chi V, Pardoll Drew M, Pan F (2011) Control of TH17/Treg Balance by Hypoxia-Inducible Factor 1. *Cell* 146: 772-784

Eberl G, Marmon S, Sunshine M J, Rennert P D, Choi Y, Littman D R (2004) An essential function for the nuclear receptor RORgamma(t) in the generation of fetal lymphoid tissue inducer cells. *Nat Immunol* 5: 64-73

Erdemir D, Lee A Y, Myerson A S (2007) Polymorph selection: the role of nucleation, crystal growth and molecular modeling. *Curr Opin Drug Discov Devel* 10: 746-755

Furuzawa-Carballeda J, Vargas-Rojas M I, Cabral A R (2007) Autoimmune inflammation from the Th17 perspective. *Autoimmunity Reviews* 6: 169-175

Gennaro A (2000) *Remington: The Science and Practice of Pharmacy*—20th edition: Baltimore, Md.; Lippincott Williams & Wilkins.

He Y-W, Deftos M L, Ojala E W, Bevan M J (1998) RORγt, a Novel Isoform of an Orphan Receptor, Negatively Regulates Fas Ligand Expression and IL-2 Production in T Cells. *Immunity* 9: 797-806

Hirose T, Smith R J, Jetten A M (1994) ROR-γ: The Third Member of ROR/RZR Orphan Receptor Subfamily That Is Highly Expressed in Skeletal Muscle. *Biochemical and Biophysical Research Communications* 205: 1976-1983

Korn T, Bettelli E, Oukka M, Kuchroo V K (2009) IL-17 and Th17 Cells. *Annual Review of Immunology* 27: 485-517

Kumar L, Amin A, Bansal A K (2007) An overview of automated systems relevant in pharmaceutical salt screening. *Drug Discov Today* 12: 1046-1053

Lipp M, Muller G (2004) Lymphoid organogenesis: getting the green light from RORgamma(t). *Nat Immunol* 5: 12-14

Liu S-J, Tsai J-P, Shen C-R, Sher Y-P, Hsieh C-L, Yeh Y-C, Chou A-H, Chang S-R, Hsiao K-N, Yu F-W, Chen H-W (2007) Induction of a distinct CD8 Tnc17 subset by transforming growth factor-β and interleukin-6. *Journal of Leukocyte Biology* 82: 354-360

Lubberts E, Koenders M I, Oppers-Walgreen B, van den Bersselaar L, Coenen-de Roo C J J, Joosten L A B, van den Berg W B (2004) Treatment with a neutralizing anti-murine interleukin-17 antibody after the onset of collagen-induced arthritis reduces joint inflammation, cartilage destruction, and bone erosion. *Arthritis & Rheumatism* 50: 650-659

Mahato R, Narang A (2011) *Pharmaceutical Dosage Forms and Drug Delivery, Second Edition*: CRC Press.

Morissette S L, Almarsson O, Peterson M L, Remenar J F, Read M J, Lemmo A V, Ellis S, Cima M J, Gardner C R (2004) High-throughput crystallization: polymorphs, salts, co-crystals and solvates of pharmaceutical solids. *Adv Drug Deliv Rev* 56: 275-300

Murdoch J R, Lloyd C M (2010) Resolution of Allergic Airway Inflammation and Airway Hyperreactivity Is Mediated by IL-17-producing γδT Cells. *American Journal of Respiratory and Critical Care Medicine* 182: 464-476

Mutlib A E (2008) Application of stable isotope-labeled compounds in metabolism and in metabolism-mediated toxicity studies. *Chem Res Toxicol* 21: 1672-1689

Ortiz M A, Piedrafita F J, Pfahl M, Maki R (1995) TOR: a new orphan receptor expressed in the thymus that can modulate retinoid and thyroid hormone signals. *Molecular Endocrinology* 9: 1679-1691

Rachitskaya A V, Hansen A M, Horai R, Li Z, Villasmil R, Luger D, Nussenblatt R B, Caspi R R (2008) Cutting Edge: NKT Cells Constitutively Express IL-23 Receptor and RORγt and Rapidly Produce IL-17 upon Receptor Ligation in an IL-6-Independent Fashion. *Journal of immunology* (Baltimore, Md.: 1950) 180: 5167-5171

Reddy I K, Mehvar R (2004) Chirality in Drug Design and Development: CRC Press.

Rowe R, Sheskey P, Weller P, Rowe R, Sheskey P, Weller P (2003) *Handbook of Pharmaceutical Excipients*, 4th Edition.

Skepner J, Ramesh R, Trocha M, Schmidt D, Baloglu E, Lobera M, Carlson T, Hill J, Orband-Miller L A, Barnes A, Boudjelal M, Sundrud M, Ghosh S, Yang J (2014) Pharmacologic inhibition of RORgammat regulates Th17 signature gene expression and suppresses cutaneous inflammation in vivo. *J Immunol* 192: 2564-2575

Solt L A, Kumar N, Nuhant P, Wang Y, Lauer J L, Liu J, Istrate M A, Kamenecka T M, Roush W R, Vidovic D, Schurer S C, Xu J, Wagoner G, Drew P D, Griffin P R, Burris T P (2011) Suppression of TH17 differentiation and autoimmunity by a synthetic ROR ligand. *Nature* 472: 491-494

Stahl P, Wermuth C (2002) *Handbook of Pharmaceutical Salts: Properties, Selection, and Use*: Verlag Helvetica Chimica Acta, Zürich, Switzerland, and Wiley-VCH, Weinheim, Germany.

Stockinger B, Veldhoen M, Martin B (2007) Th17 T cells: Linking innate and adaptive immunity. *Seminars in Immunology* 19: 353-361

Tuskey A, Behm B W (2014) Profile of ustekinumab and its potential in patients with moderate-to-severe Crohn's disease. *Clinical and Experimental Gastroenterology* 7: 173-179

Wuts P G M, Greene T W (2007) *Greene's Protective Groups in Organic Synthesis, Fourth Edition*: John Wiley & Sons.

Yamashita T, Iwakura T, Matsui K, Kawaguchi H, Obana M, Hayama A, Maeda M, Izumi Y, Komuro I, Ohsugi Y, Fujimoto M, Naka T, Kishimoto T, Nakayama H, Fujio Y (2011) *IL-6-mediated Th17 differentiation through RORγt is essential for the initiation of experimental autoimmune myocarditis*, Vol. 91.

Yang X O, Pappu B, Nurieva R, Akimzhanov A, Kang H S, Chung Y, Ma L, Shah B, Panopoulos A D, Schluns K, Watowich S S, Tian Q, Jetten A M, Dong C (2008) TH17 lineage differentiation is programmed by orphan nuclear receptors RORα and RORγ. *Immunity* 28: 29-39

Yin S X, Grosso J A (2008) Selecting and controlling API crystal form for pharmaceutical development—strategies and processes. *Curr Opin Drug Discov Devel* 11: 771-777

The invention claimed is:

1. A compound of formula (I), or a pharmaceutically acceptable salt thereof:

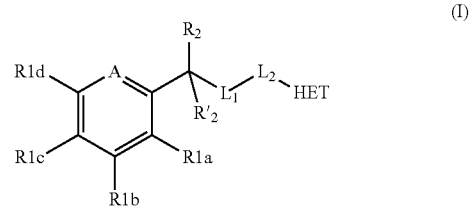

in which,

A is a C-R1e group;

R1a is a halogen atom, a nitrile group, a nitro group (NO2), a (C1-C6) alkyl group, a (C1-C6) alkyloxy group, a (C1-C6) alkylthio group, a —NH2 group, a (C1-C6) alkylamino group, a (C1-C6)dialkylamino group or a heterocyclic group;

R1b is a hydrogen atom, a (C1-C6)alkyloxy group, a (C1-C6)alkyl group or a heterocyclic group;

R1c is a hydrogen atom, a halogen atom, a (C1-C6)alkyl group, a (C1-C6)alkyloxy group, a (C1-C6)alkylthio group, a heterocyclic group, a cyano group, an amido group or a hydroxyl group;

R1d and R1e are, independently, a hydrogen atom, a halogen atom, a (C1-C6)alkyloxy group or an (C1-C6) alkyl group;

R2 is an unsubstituted, branched (C3-C6)alkyl group; an (C2-C6)alkynyl group; a (C3-C14)cycloalkyl group; an (C6-C14)aryl group optionally substituted by a (C1-C6)alkyl group or a halogen; a 5-membered heteroaryl group containing an oxygen or a nitrogen atom optionally substituted by a ($C_1$-$C_6$)alkyl group or a halogen; or a 6-membered heteroaryl group containing at least one nitrogen atom optionally substituted by a ($C_1$-$C_6$) alkyl group or a halogen;

R'2 is a hydrogen atom; an (C1-C6)alkyl group; an (C2-C6)alkynyl group; a (C3-C14)cycloalkyl group; a (C6-C14)aryl group optionally substituted by a ($C_1$-$C_6$) alkyl group or a halogen; or a heterocyclic group optionally substituted by a (C1-C6)alkyl group or a halogen;

or R2 and R2' can form, together with the carbon atom to which they are attached, a cycloalkyl group or a heterocycloalkyl group;

L1 is a —NH—CO— or —CO—NH— group;

L2 represents a CR4R'4 group;

R4 and R'4 are independently, a hydrogen atom or a (C1-C6)alkyl group;

or R4 and R'4 can form, together with the carbon atom to which they are attached, a cycloalkyl group;

HET is one of the following bicyclic groups:

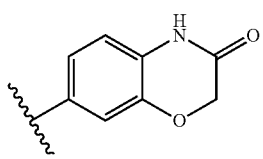
HET1

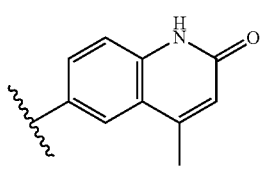
HET2

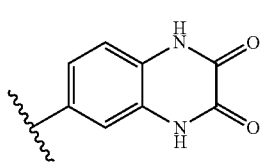
HET3

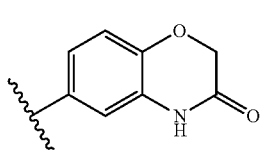
HET4

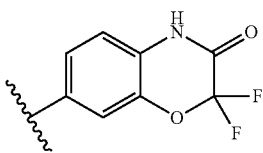
HET5

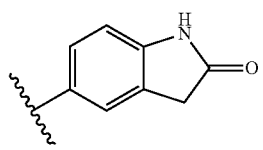
HET6

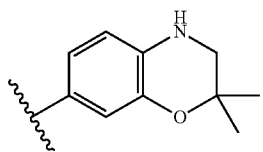
HET7

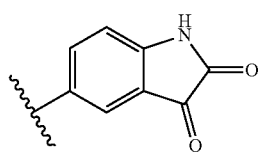
HET8

-continued

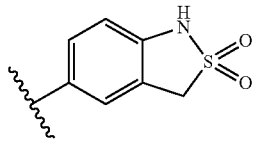
HET9

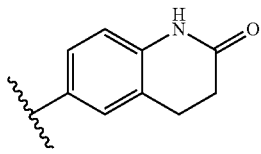
HET10

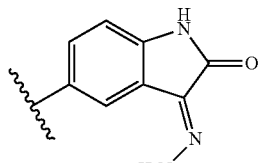
HET11

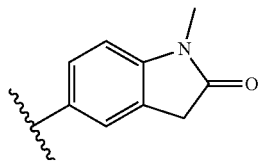
HET12

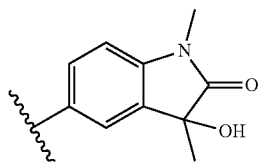
HET13

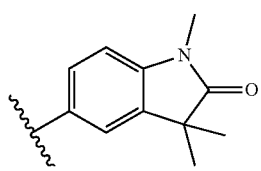
HET14

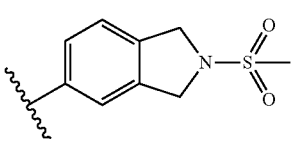
HET15

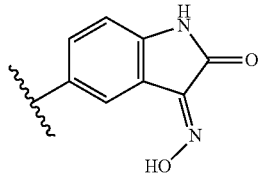
HET16

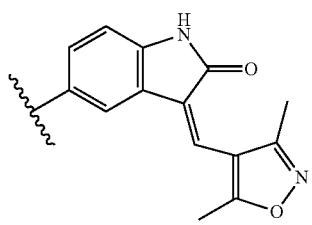
HET17

| | |
|---|---|
| HET18 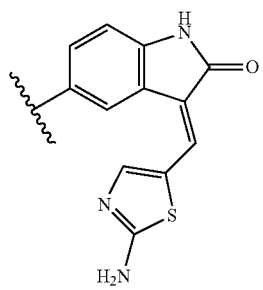 | HET26 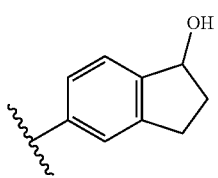 |
| HET19 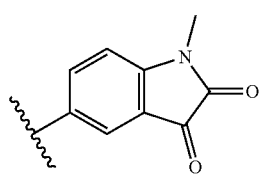 | HET27 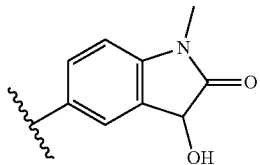 |
| HET20 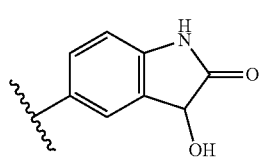 | HET28 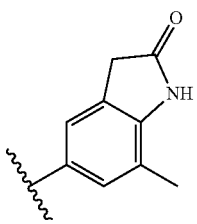 |
| HET21 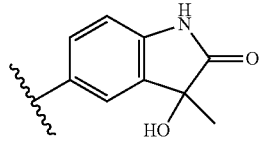 | HET29 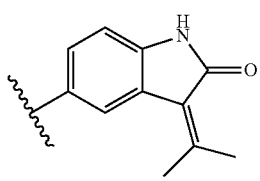 |
| HET22 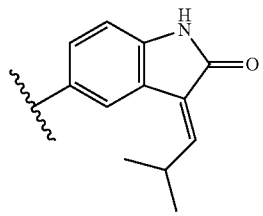 | HET30 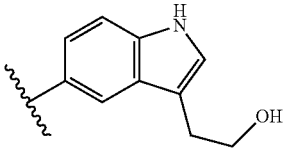 |
| HET23 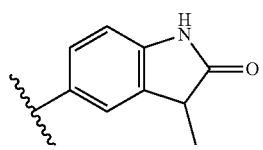 | HET31 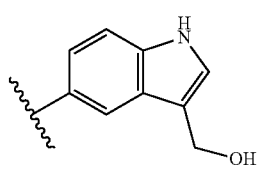 |
| HET24 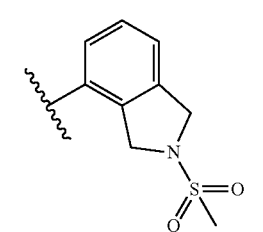 | HET32 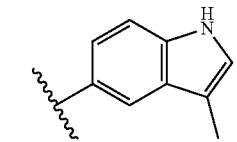 |
| HET25 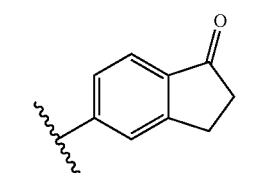 | HET33 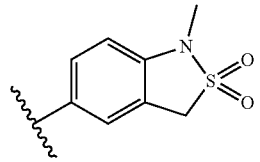 |
| | HET34 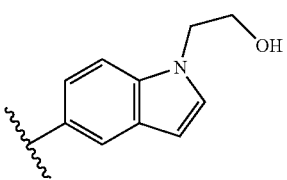 |

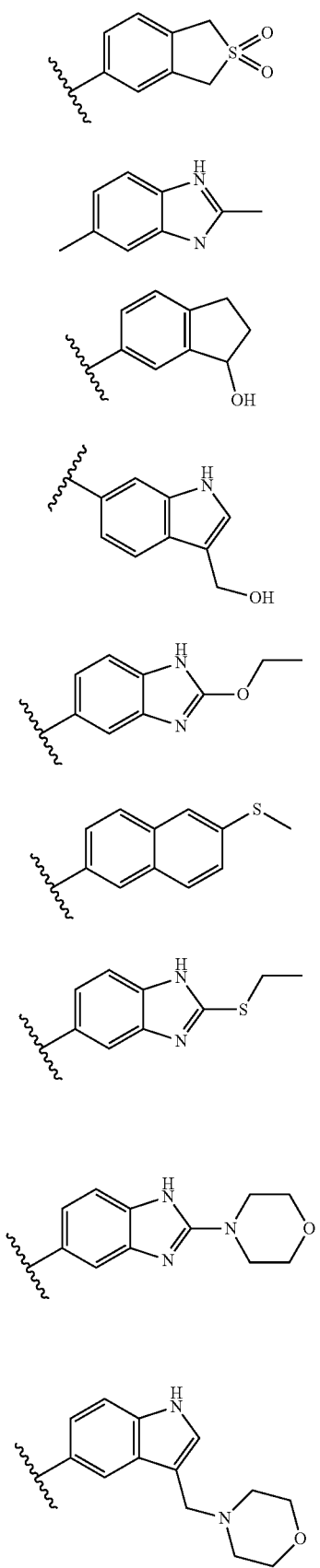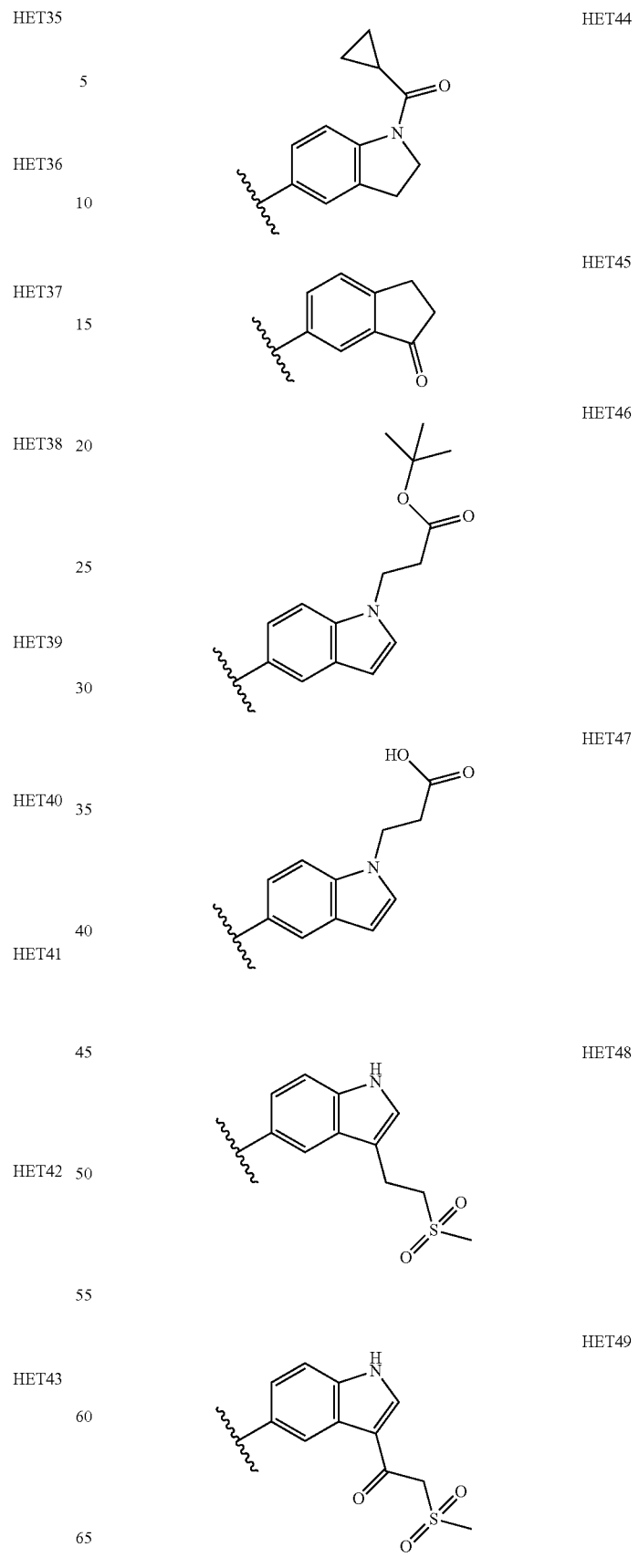

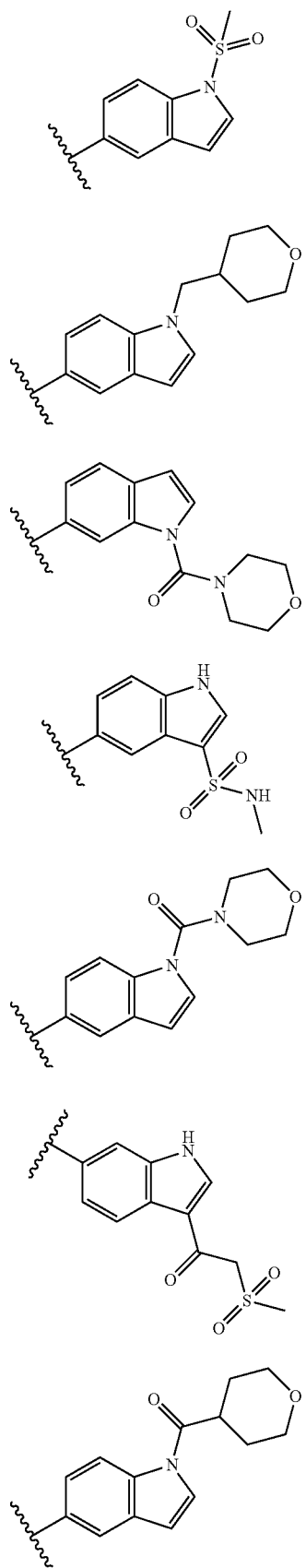
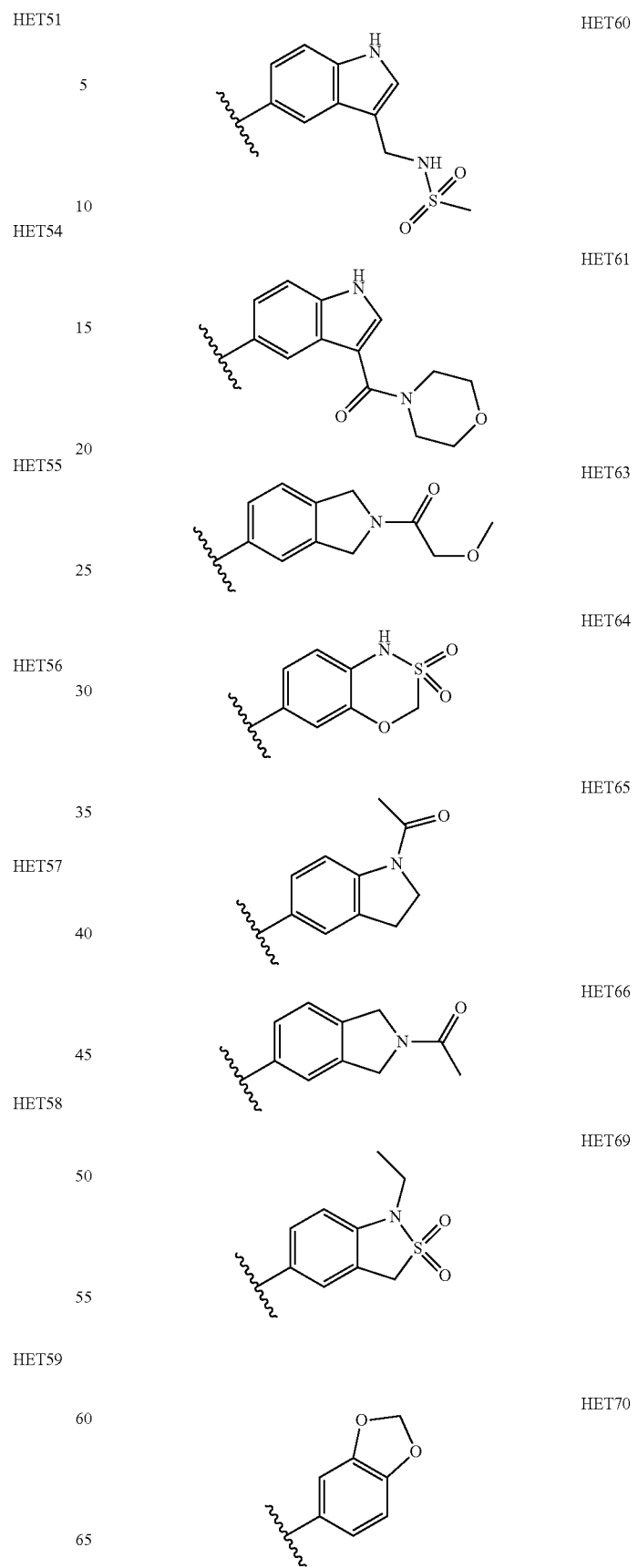

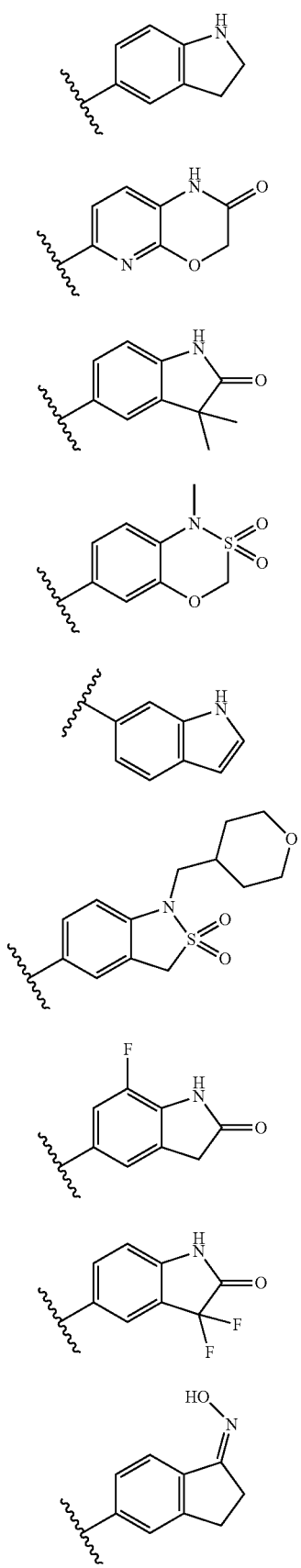

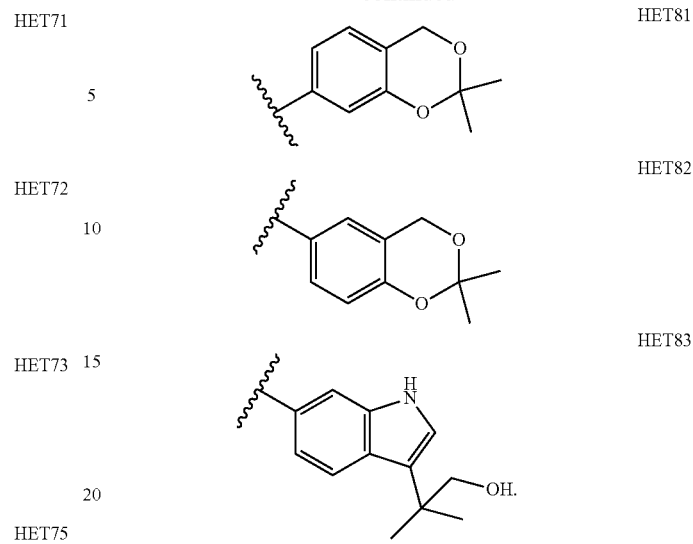

2. The compound according to claim 1, wherein:
R1a is a halogen atom, a nitrile group, a nitro group (NO2), a (C1-C6)alkyl group, a (C1-C6) alkyloxy group, a (C1-C6)alkylthio group, an amino group, a (C1-C6) alkylamino group, a (C1-C6)dialkylamino group, a piperidinyl group, a pyrrolidinyl group, an azepanyl, piperazinyl, or morpholinyl group, wherein said piperidinyl, pyrrolidinyl, azepanyl, piperazinyl, or morpholinyl group can be optionally substituted by at least one (C1-C6)alkyl groups.

3. The compound according to claim 1, wherein:
R1a is a halogen atom, a (C1-C6) alkyl group, a piperidinyl group (such as a piperidin-1-yl group), a morpholinyl group (such as morpholin-4-yl group), a piperazinyl group (such as a piperazin-1-yl), an azepanyl group (such as an azepan-1-yl) or a pyrrolidinyl group (such as a pyrrolidin-1-yl group).

4. The compound according to claim 1, wherein:
R1a is a halogen atom, a nitrile group, a nitro group (NO2), a (C1-C6)alkyl group, a (C1-C6)alkyloxy group, a (C1-C6)alkylthio group, an amino group, a (C1-C6)alkylamino group, a (C1-C6)dialkylamino group, a piperidinyl group, a pyrrolidinyl group, an azepanyl group, wherein said piperidinyl, pyrrolidinyl, azepanyl, piperazinyl, or morpholinyl group can be optionally substituted by at least one (C1-C6)alkyl groups;
R1b is a hydrogen atom;
R1c is a hydrogen atom, a (C1-C6)alkyl group, or a (C1-C6)alkyloxy group;
R1d is a hydrogen atom;
R1e is a hydrogen atom;
R2 is a (C3-C6)alkyl group, an (C6-C14)aryl group, or a heteroaryl group, and R'2 is a hydrogen atom.

5. The compound according to claim 1, wherein:
R1a is a halogen atom (such as bromine), a (C1-C6)alkyl group (such as a methyl or ethyl group, in particular a methyl group), a piperidinyl group, a pyrrolidinyl group, an azepanyl group, wherein said piperidinyl, pyrrolidinyl, azepanyl, piperazinyl, or morpholinyl group can be optionally substituted by at least one (C1-C6)alkyl groups;
R1b is a hydrogen atom;

R1c is a hydrogen, a (C1-C6)alkyl group (such as a methyl or ethyl group, in particular a methyl group), or a (C1-C6)alkoxy group (such as a methoxy or a an ethoxy group, in particular a methoxy group);

R1d and R1e are hydrogen atoms;

R2 is a (C3-C6)alkyl group (such as an isobutyl group), a phenyl group or a heterocyclic group (such as a substituted or unsubstituted furanyl group, in particular a 5-methylfuranyl group or a 5-ethylfuranyl group, more particularly a 5-methylfuran-2-yl group);

L1 represents a NH—CO— group,

L2 is a CH2 group or a cyclopropyl group of formula (III)

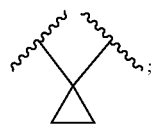

(III)

HET is chosen in the list:

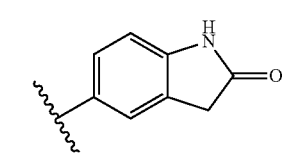

HET1

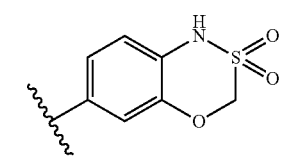

HET6

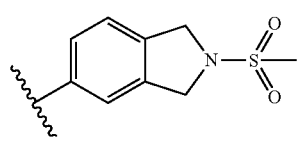

HET64

HET15

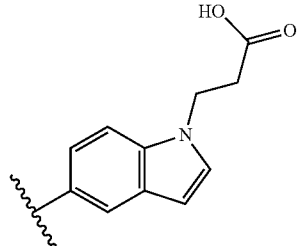

HET9

HET47

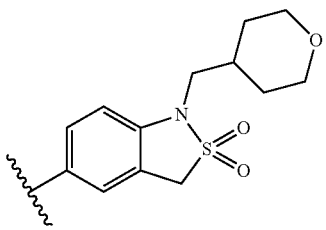

HET77

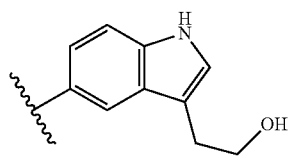

HET30

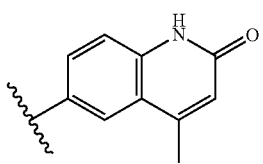

HET2

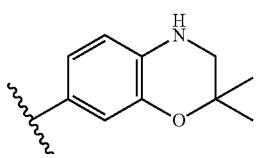

HET7

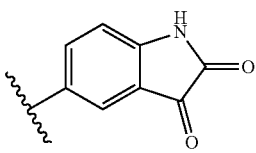

HET8

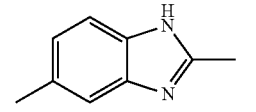

HET36

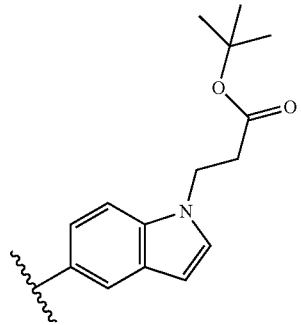

HET46

HET70

6. The compound according to claim 1, wherein:
R1a is a heterocyclic group (in particular a piperidinyl group (such as a piperidin-1-yl group)) or a (C1-C6)

alkyl group (such as a methyl or ethyl group, in particular a methyl group);
R1c is a (C1-C6)alkyl group (such as a methyl or ethyl group, in particular a methyl group);
R2 is a heterocyclic group (such as a substituted or unsubstituted furanyl group, in particular a 5-methylfuranyl group or a 5-ethylfuranyl group or a 5-chlorofuranyl, more particularly a 5-chlorofuran-2-yl group);
L1 represents a NH—CO— group, L2 is a CR4R'4 group (such as a cyclopropyl group of formula (III) or cyclobutyl of formula (IV)

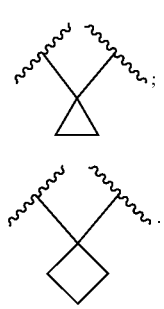

(III)

(IV)

7. The compound according to claim 1, wherein:
R1a represents a halogen, in particular a bromine atom; a (C1-C6)alkyl group, in particular a methyl group; a heterocyclic group, in particular a piperadin-1-yl group, a piperazin-1-yl group, or an azepan-1-yl group; a di(C1-C6)alkylamaino group, in particular a N(CH3)2 group;
R1b, R1d and R1e represent hydrogen atoms;
R1c is a (C1-C6)alkyl group, in particular a methyl group, or a (C1-C6)alkyloxy group, in particular a methoxy group;
R2 represents a 5 membered heteroaryl group containing an oxygen or a nitrogen atom optionally substituted by a $(C_1-C_6)$alkyl group or a halogen, in particular a furan-1-yl group, a 5-methylfuran-2-yl group or a 5-chlorofuran-2-yl group; a (C6-C14)aryl group optionally substituted by a $(C_1-C_6)$alkyl group, in particular a phenyl group optionally substituted by one or more methyl group or by a chlorine atom; or a heterocyclic group optionally substituted by a $(C_1-C_6)$alkyl group, in particular a 6-methylpyridin-2-yl;
R'2 is a hydrogen atom;
L1 represents a NH—CO group; and
L2 represents a (C1-C6)alkyl group, in particular a CH2- group, or a CR4R'4 group, in particular a cyclopropyl group of formula (III)

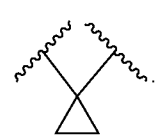

(III)

8. The compound according to claim 1, wherein:
R1a represents a halogen, in particular a bromine atom; a (C1-C6)alkyl group, in particular a methyl group; a heterocyclic group, in particular a piperadin-1-yl group, or a piperazin-1-yl group;
R1b, R1d and R1e represent a hydrogen atom;

R1c is a (C1-C6)alkyl group, in particular a methyl group;
R2 represents a 5 membered heteroaryl group containing an oxygen or a nitrogen atom optionally substituted by a (C1-C6)alkyl group or a halogen, in particular a 5-methylfuran-2-yl group or a 5-chlorofuran-2-yl group;
R'2 is a hydrogen atom;
L1 represents a NH—CO group;
L2 represents a (C1-C6)alkyl group, in particular a CH2- group, or a CR4R'4 group, in particular a cyclopropyl group of formula (III)

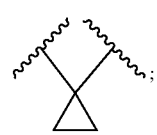

(III)

and
HET is HET1, HET6, HET30, HET38, HET44, HET47, HET67 or HET77.

9. The compound according to claim 1, characterized in that it is selected from:
N-{[4-methyl-2-(piperidin-1-yl)phenyl](phenyl)methyl}-2-(3-oxo-3,4-dihydro-2H-1,4-benzoxazin-7-yl)acetamide;
N-{[4-methyl-2-(morpholin-4-yl)phenyl](phenyl)methyl}-2-(3-oxo-3,4-dihydro-2H-1,4-benzoxazin-7-yl)acetamide;
2-(3-oxo-3,4-dihydro-2H-1,4-benzoxazin-7-yl)-N-{phenyl[2-(piperidin-1-yl)phenyl]methyl}acetamide;
N-{[4-methoxy-2-(piperidin-1-yl)phenyl](phenyl)methyl}-2-(3-oxo-3,4-dihydro-2H-1,4-benzoxazin-7-yl)acetamide;
2-(3-oxo-3,4-dihydro-2H-1,4-benzoxazin-7-yl)-N-{phenyl[2-(pyrrolidin-1-yl)phenyl]methyl}acetamide;
N-{3-methyl-1-[2-(piperidin-1-yl)phenyl]butyl}-2-(3-oxo-3,4-dihydro-2H-1,4-benzoxazin-7-yl)acetamide;
N-{[2-(morpholin-4-yl)phenyl](phenyl)methyl}-2-(3-oxo-3,4-dihydro-2H-1,4-benzoxazin-7-yl)acetamide;
N-{[4-methyl-2-(morpholin-4-yl)phenyl](phenyl)methyl}-2-(4-methyl-2-oxo-1,2-dihydroquinolin-6-yl)acetamide;
N-[(2,4-dimethylphenyl)(phenyl)methyl]-2-(4-methyl-2-oxo-1,2-dihydroquinolin-6-yl)acetamide;
N-{[4-methoxy-2-(piperidin-1-yl)phenyl](phenyl)methyl}-2-(4-methyl-2-oxo-1,2-dihydroquinolin-6-yl)acetamide;
N-{[4-methyl-2-(piperidin-1-yl)phenyl](phenyl)methyl}-2-(4-methyl-2-oxo-1,2-dihydroquinolin-6-yl)acetamide;
2-(2,3-dioxo-1,2,3,4-tetrahydroquinoxalin-6-yl)-N-{phenyl[2-(piperidin-1-yl)phenyl]methyl}acetamide;
2-(3-oxo-3,4-dihydro-2H-1,4-benzoxazin-6-yl)-N-{phenyl[2-(piperidin-1-yl)phenyl]methyl}acetamide;
2-(2,2-difluoro-3-oxo-3,4-dihydro-2H-1,4-benzoxazin-7-yl)-N-{phenyl[2-(piperidin-1-yl)phenyl]methyl}acetamide;
2-(2-oxo-2,3-dihydro-1H-indol-5-yl)-N-{phenyl[2-(piperidin-1-yl)phenyl]methyl}acetamide;
N-{[4-methyl-2-(piperidin-1-yl)phenyl](phenyl)methyl}-2-(2-oxo-2,3-dihydro-1H-indol-5-yl)acetamide;
N-{[2-(morpholin-4-yl)phenyl](phenyl)methyl}-2-(2-oxo-2,3-dihydro-1H-indol-5-yl)acetamide;

N-{[4-methyl-2-(morpholin-4-yl)phenyl](phenyl)
methyl}-2-(2-oxo-2,3-dihydro-1H-indol-5-yl)acet-
amide;
2-(2,2-dimethyl-3-oxo-3,4-dihydro-2H-1,4-benzoxazin-
7-yl)-N-{phenyl[2-(piperidin-1-yl)phenyl]
methyl}acetamide;
2-(2,3-dioxo-2,3-dihydro-1H-indol-5-yl)-N-{phenyl[2-
(piperidin-1-yl)phenyl]methyl}acetamide;
2-(2,2-dimethyl-3-oxo-3,4-dihydro-2H-1,4-benzoxazin-
7-yl)-N-{[4-methyl-2-(morpholin-4-yl)phenyl](phe-
nyl)methyl}acetamide;
2-(2,3-dioxo-2,3-dihydro-1H-indol-5-yl)-N-{[4-
methoxy-2-(piperidin-1-yl)phenyl](phenyl)
methyl}acetamide;
2-(2,3-dioxo-2,3-dihydro-1H-indol-5-yl)-N-{[4-methyl-
2-(piperidin-1-yl)phenyl](5-methylfuran-2-yl)
methyl}acetamide;
N-{[4-methyl-2-(piperidin-1-yl)phenyl](5-methylfuran-
2-yl)methyl}-2-(2-oxo-2,3-dihydro-1H-indol-5-yl)ac-
etamide;
2-(2,2-dimethyl-3-oxo-3,4-dihydro-2H-1,4-benzoxazin-
7-yl)-N-{[4-methyl-2-(piperidin-1-yl)phenyl](5-meth-
ylfuran-2-yl)methyl}acetamide;
2-(2,2-dioxo-1,3-dihydro-2,1-benzothiazol-5-yl)-N-{phe-
nyl[2-(piperidin-1-yl)phenyl]methyl}acetamide;
2-(2,2-dioxo-1,3-dihydro-2,1-benzothiazol-5-yl)-N-{[4-
methyl-2-(piperidin-1-yl)phenyl](5-methylfuran-2-yl)
methyl}acetamide;
N-[(2-bromo-4-methylphenyl)(5-methylfuran-2-yl)
methyl]-2-(2,2-dioxo-1,3-dihydro-2,1-benzothiazol-5-
yl)acetamide;
N-[(2,4-dimethylphenyl)(5-methylfuran-2-yl)methyl]-2-
(2-oxo-2,3-dihydro-1H-indol-5-yl)acetamide;
2-(2,2-dimethyl-3-oxo-3,4-dihydro-2H-1,4-benzoxazin-
7-yl)-N-{[4-methoxy-2-(morpholin-4-yl)phenyl](5-
methylfuran-2-yl)methyl}acetamide;
N-[(2-bromo-4-methylphenyl)(5-methylfuran-2-yl)
methyl]-2-(3-oxo-3,4-dihydro-2H-1,4-benzoxazin-7-
yl)acetamide;
N-[(2,4-dimethylphenyl)(5-ethylfuran-2-yl)methyl]-2-(3-
oxo-3,4-dihydro-2H-1,4-benzoxazin-7-yl)acetamide;
N-[(2,4-dimethylphenyl)(5-methylfuran-2-yl)methyl]-2-
(3-oxo-3,4-dihydro-2H-1,4-benzoxazin-7-yl)acet-
amide;
N-[(2-bromo-4-methoxyphenyl)(5-methylfuran-2-yl)
methyl]-2-(3-oxo-3,4-dihydro-2H-1,4-benzoxazin-7-
yl)acetamide;
N-{[4-methyl-2-(piperidin-1-yl)phenyl](5-methylfuran-
2-yl)methyl}-2-(3-oxo-3,4-dihydro-2H-1,4-benzo-
xazin-7-yl)acetamide;
N-[(2-bromo-4-methylphenyl)(5-methylfuran-2-yl)
methyl]-2-(2-oxo-1,2,3,4-tetrahydroquinolin-6-yl)ac-
etamide;
2-(3-hydrazinylidene-2-oxo-2,3-dihydro-1H-indol-5-yl)-
N-{[4-methyl-2-(piperidin-1-yl)phenyl](5-methyl-
furan-2-yl)methyl}acetamide;
N-{[4-methyl-2-(piperidin-1-yl)phenyl](5-methylfuran-
2-yl)methyl}-2-(1-methyl-2-oxo-2,3-dihydro-1H-in-
dol-5-yl)acetamide;
2-(3-hydroxy-1,3-dimethyl-2-oxo-2,3-dihydro-1H-indol-
5-yl)-N-{[4-methyl-2-(piperidin-1-yl)phenyl](5-meth-
ylfuran-2-yl)methyl}acetamide;
N-{[4-methyl-2-(piperidin-1-yl)phenyl](5-methylfuran-
2-yl)methyl}-2-(1,3,3-trimethyl-2-oxo-2,3-dihydro-
1H-indol-5-yl)acetamide;
2-(2-methanesulfonyl-2,3-dihydro-1H-isoindol-5-yl)-N-{
[4-methyl-2-(piperidin-1-yl)phenyl](5-methylfuran-2-
yl)methyl}acetamide;
2-[3-(hydroxyimino)-2-oxo-2,3-dihydro-1H-indol-5-yl]-
N-{[4-methyl-2-(piperidin-1-yl)phenyl](5-methyl-
furan-2-yl)methyl}acetamide;
2-{3-[(dimethyl-1,2-oxazol-4-yl)methylidene]-2-oxo-2,
3-dihydro-1H-indol-5-yl}-N-{[4-methyl-2-(piperidin-
1-yl)phenyl](5-methylfuran-2-yl)methyl}acetamide;
2-{3-[(2-amino-1,3-thiazol-5-yl)methylidene]-2-oxo-2,3-
dihydro-1H-indol-5-yl}-N-{[4-methyl-2-(piperidin-1-
yl)phenyl](5-methylfuran-2-yl)methyl}acetamide;
2-(1-methyl-2,3-dioxo-2,3-dihydro-1H-indol-5-yl)-N-
{[4-methyl-2-(piperidin-1-yl)phenyl](5-methylfuran-
2-yl)methyl}acetamide;
2-(3-hydroxy-2-oxo-2,3-dihydro-1H-indol-5-yl)-N-{[4-
methyl-2-(piperidin-1-yl)phenyl](5-methylfuran-2-yl)
methyl}acetamide;
2-(3-hydroxy-3-methyl-2-oxo-2,3-dihydro-1H-indol-5-
yl)-N-{[4-methyl-2-(piperidin-1-yl)phenyl](5-methyl-
furan-2-yl)methyl}acetamide;
N-{[4-methyl-2-(piperidin-1-yl)phenyl](5-methylfuran-
2-yl)methyl}-2-[(3E)-3-(2-methylpropylidene)-2-oxo-
2,3-dihydro-1H-indol-5-yl]acetamide;
N-{[4-methyl-2-(piperidin-1-yl)phenyl](5-methylfuran-
2-yl)methyl}-2-(3-methyl-2-oxo-2,3-dihydro-1H-in-
dol-5-yl)acetamide;
2-(2-methanesulfonyl-2,3-dihydro-1H-isoindol-4-yl)-N-
{[4-methyl-2-(piperidin-1-yl)phenyl](5-methylfuran-
2-yl)methyl}acetamide;
N-{[4-methyl-2-(piperidin-1-yl)phenyl](5-methylfuran-
2-yl)methyl}-2-(1-oxo-2,3-dihydro-1H-inden-5-yl)ac-
etamide;
2-(1-hydroxy-2,3-dihydro-1H-inden-5-yl)-N-{[4-methyl-
2-(piperidin-1-yl)phenyl](5-methylfuran-2-yl)
methyl}acetamide;
2-(3-hydroxy-1-methyl-2-oxo-2,3-dihydro-1H-indol-5-
yl)-N-{[4-methyl-2-(piperidin-1-yl)phenyl](5-methyl-
furan-2-yl)methyl}acetamide;
N-{[4-methyl-2-(piperidin-1-yl)phenyl](5-methylfuran-
2-yl)methyl}-2-(7-methyl-2-oxo-2,3-dihydro-1H-in-
dol-5-yl)acetamide;
N-{[4-methyl-2-(piperidin-1-yl)phenyl](5-methylfuran-
2-yl)methyl}-2-[2-oxo-3-(propan-2-ylidene)-2,3-di-
hydro-1H-indol-5-yl]acetamide;
N-[(5-chlorofuran-2-yl)(2,4-dimethylphenyl)methyl]-1-
(2-methanesulfonyl-2,3-dihydro-1H-isoindol-5-yl)cy-
clopropane-1-carboxamide;
2-[3-(2-hydroxyethyl)-1H-indol-5-yl]-N-{[4-methyl-2-
(piperidin-1-yl)phenyl](5-methylfuran-2-yl)
methyl}acetamide;
2-[3-(hydroxymethyl)-1H-indol-5-yl]-N-{[4-methyl-2-
(piperidin-1-yl)phenyl](5-methylfuran-2-yl)
methyl}acetamide;
N-[(2,4-dimethylphenyl)(5-methylfuran-2-yl)methyl]-1-
(3-oxo-3,4-dihydro-2H-1,4-benzoxazin-7-yl)cyclopro-
pane-1-carboxamide;
N-[(2,4-dimethylphenyl)(5-methylfuran-2-yl)methyl]-1-
[3-(2-hydroxyethyl)-1H-indol-5-yl]cyclopropane-1-
carboxamide;
N-[(2,4-dimethylphenyl)(5-methylfuran-2-yl)methyl]-1-
(2-oxo-2,3-dihydro-1H-indol-5-yl)cyclopropane-1-car-
boxamide;
N-[(5-chlorofuran-2-yl)(2,4-dimethylphenyl)methyl]-1-
[3-(2-hydroxyethyl)-1H-indol-5-yl]cyclopropane-1-
carboxamide;

N-[(2,4-dimethylphenyl)(5-methylfuran-2-yl)methyl]-1-(2,2-dioxo-1,3-dihydro-2,1-benzothiazol-5-yl)cyclopropane-1-carboxamide;

2-(3-methyl-1H-indol-5-yl)-N-{[4-methyl-2-(piperidin-1-yl)phenyl](5-methylfuran-2-yl)methyl}acetamide;

N-[(2,4-dimethylphenyl)(5-methylfuran-2-yl)methyl]-1-(2-methanesulfonyl-2,3-dihydro-1H-isoindol-5-yl)cyclopropane-1-carboxamide;

1-[3-(2-hydroxyethyl)-1H-indol-5-yl]-N-{[4-methyl-2-(piperidin-1-yl)phenyl](5-methylfuran-2-yl)methyl}cyclopropane-1-carboxamide;

N-{[4-methyl-2-(piperidin-1-yl)phenyl](5-methylfuran-2-yl)methyl}-2-(3-oxo-2,3-dihydro-1H-inden-5-yl)acetamide;

N-[(2-bromo-4-methylphenyl)(5-methylfuran-2-yl)methyl]-2-[1-(oxan-4-ylmethyl)-2,2-dioxo-1,3-dihydro-2,1-benzothiazol-5-yl]acetamide;

N-[(2,4-dimethylphenyl)(5-methylfuran-2-yl)methyl]-1-[1-(2-hydroxyethyl)-1H-indol-5-yl]cyclopropane-1-carboxamide;

N-[(2,4-dimethylphenyl)(5-methylfuran-2-yl)methyl]-1-(1-methyl-2,2-dioxo-1,3-dihydro-2,1-benzothiazol-5-yl)cyclopropane-1-carboxamide;

N-{[2-(dimethylamino)-4-methylphenyl](5-methylfuran-2-yl)methyl}-1-(2,2-dioxo-1,3-dihydro-2, 1-benzothiazol-5-yl)cyclopropane-1-carboxamide;

N-[(5-chlorofuran-2-yl)(2,4-dimethylphenyl)methyl]-1-(2,2-dioxo-1,3-dihydro-2-benzothiophen-5-yl)cyclopropane-1-carboxamide;

1-(2-methanesulfonyl-2,3-dihydro-1H-isoindol-5-yl)-N-{[4-methyl-2-(pyrrolidin-1-yl)phenyl](5-methylfuran-2-yl)methyl}cyclopropane-1-carboxamide;

N-[(2,4-dimethylphenyl)(5-methylfuran-2-yl)methyl]-1-(2,2-dioxo-1,3-dihydro-2-benzothiophen-5-yl)cyclopropane-1-carboxamide;

2-(2-methyl-1H-1,3-benzodiazol-5-yl)-N-{[4-methyl-2-(piperidin-1-yl)phenyl](phenyl)methyl}acetamide;

N-{[2-(dimethylamino)-4-methylphenyl](5-methylfuran-2-yl)methyl}-1-(2-methanesulfonyl-2,3-dihydro-1H-isoindol-5-yl)cyclopropane-1-carboxamide;

N-[(2-bromo-4-methylphenyl)(5-methylfuran-2-yl)methyl]-2-(2-methyl-1H-1,3-benzodiazol-5-yl)acetamide;

2-(2,2-dioxo-1,3-dihydro-2-benzothiophen-5-yl)-N-{[4-methyl-2-(piperidin-1-yl)phenyl](5-methylfuran-2-yl)methyl}acetamide;

N-[(5-chlorofuran-2-yl)[4-methyl-2-(piperidin-1-yl)phenyl]methyl]-2-(2-methanesulfonyl-2,3-dihydro-1H-isoindol-5-yl)acetamide;

N-[(5-chlorofuran-2-yl)[4-methyl-2-(pyrrolidin-1-yl)phenyl]methyl]-1-(2-methanesulfonyl-2,3-dihydro-1H-isoindol-5-yl)cyclopropane-1-carboxamide;

N-[(2-bromo-4-methylphenyl)(phenyl)methyl]-2-(2-methyl-1H-1,3-benzodiazol-5-yl)acetamide;

2-(2-methyl-1H-1,3-benzodiazol-5-yl)-N-{[4-methyl-2-(pyrrolidin-1-yl)phenyl](phenyl)methyl}acetamide;

N-[(5-chlorofuran-2-yl)[4-methyl-2-(piperidin-1-yl)phenyl]methyl]-2-(2-oxo-2,3-dihydro-1H-indol-5-yl)acetamide;

2-[(3Z)-3-hydrazinylidene-2-oxo-2,3-dihydro-1H-indol-5-yl]-N-{[4-methyl-2-(piperidin-1-yl)phenyl](5-methylfuran-2-yl)methyl}acetamide;

2-(3-hydroxy-2,3-dihydro-1H-inden-5-yl)-N-{[4-methyl-2-(piperidin-1-yl)phenyl](5-methylfuran-2-yl)methyl}acetamide;

N-[(5-chlorofuran-2-yl)(2,4-dimethylphenyl)methyl]-1-(2-oxo-2,3-dihydro-1H-indol-5-yl)cyclopropane-1-carboxamide;

N-[(5-chlorofuran-2-yl)(2,4-dimethylphenyl)methyl]-1-(2,2-dioxo-1,3-dihydro-2,1-benzothiazol-5-yl)cyclopropane-1-carboxamide;

2-(1H-indol-6-yl)-N-((4-methyl-2-(piperidin-1-yl)phenyl)(5-methylfuran-2-yl)methyl)acetamide;

2-[3-(hydroxymethyl)-1H-indol-6-yl]-N-{[4-methyl-2-(piperidin-1-yl)phenyl](5-methylfuran-2-yl)methyl}acetamide;

1-(1H-indol-5-yl)-N-((4-methyl-2-(piperidin-1-yl)phenyl)(5-methylfuran-2-yl)methyl)cyclopropanecarboxamide;

1-[3-(hydroxymethyl)-1H-indol-5-yl]-N-{[4-methyl-2-(piperidin-1-yl)phenyl](5-methylfuran-2-yl)methyl}cyclopropane-1-carboxamide;

N-[(2-bromo-4-methylphenyl)(phenyl)methyl]-2-(2-ethoxy-1H-1,3-benzodiazol-5-yl)acetamide;

N-{[4-methyl-2-(piperidin-1-yl)phenyl](5-methylfuran-2-yl)methyl}-2-[6-(methylsulfanyl)naphthalen-2-yl]acetamide;

N-[(2-bromo-4-methylphenyl)(phenyl)methyl]-2-[2-(ethylsulfanyl)-1H-1,3-benzodiazol-5-yl]acetamide;

N-{[4-methyl-2-(piperidin-1-yl)phenyl](5-methylfuran-2-yl)methyl}-2-[2-(morpholin-4-yl)-1H-1,3-benzodiazol-5-yl]acetamide;

N-{[4-methyl-2-(piperidin-1-yl)phenyl](5-methylfuran-2-yl)methyl}-2-[3-(morpholin-4-ylmethyl)-1H-indol-5-yl]acetamide;

1-(1-cyclopropanecarbonyl-2,3-dihydro-1H-indol-5-yl)-N-[(2,4-dimethylphenyl)(5-methylfuran-2-yl)methyl]cyclopropane-1-carboxamide;

tert-butyl 3-{5-[({[4-methyl-2-(piperidin-1-yl)phenyl](5-methylfuran-2-yl)methyl}carbamoyl)methyl]-1H-indol-1-yl}propanoate;

3-{5-[({[4-methyl-2-(piperidin-1-yl)phenyl](5-methylfuran-2-yl)methyl}carbamoyl)methyl]1H-indol-1-yl}propanoic acid;

2-[3-(2-methanesulfonylethyl)-1H-indol-5-yl]-N-{[4-methyl-2-(piperidin-1-yl)phenyl](5-methylfuran-2-yl)methyl}acetamide;

tert-butyl 3-[5-({[(2,4-dimethylphenyl)(5-methylfuran-2-yl)methyl]carbamoyl}methyl)-1H-indol-1-yl]propanoate;

tert-butyl 3-[5-({[(2-bromo-4-methylphenyl)(5-methylfuran-2-yl)methyl]carbamoyl}methyl)-1H-indol-1-yl]propanoate;

3-[5-({[(2,4-dimethylphenyl)(5-methylfuran-2-yl)methyl]carbamoyl}methyl)-1H-indol-1-yl]propanoic acid;

3-[5-({[(2-bromo-4-methylphenyl)(5-methylfuran-2-yl)methyl]carbamoyl}methyl)-1H-indol-1-yl]propanoic acid;

2-[3-(2-methanesulfonylacetyl)-1H-indol-5-yl]-N-{[4-methyl-2-(piperidin-1-yl)phenyl](5-methylfuran-2-yl)methyl}acetamide;

N-[(2-bromo-4-methylphenyl)(5-methylfuran-2-yl)methyl]-2-[3-(2-methanesulfonylacetyl)-1H-indol-5-yl]acetamide;

2-(1H-indol-5-yl)-N-{[4-methyl-2-(piperidin-1-yl)phenyl](5-methylfuran-2-yl)methyl}acetamide;

2-(1-methanesulfonyl-1H-indol-5-yl)-N-{[4-methyl-2-(piperidin-1-yl)phenyl](5-methylfuran-2-yl)methyl}acetamide;

N-[(2,4-dimethylphenyl)(5-methylfuran-2-yl)methyl]-2-[3-(2-methanesulfonylacetyl)-1H-indol-5-yl]acetamide;

N-[(2,4-dimethylphenyl)(5-methylfuran-2-yl)methyl]-1-(1H-indol-5-yl)cyclopropane-1-carboxamide;

tert-butyl 3-{5-[({[2-(azepan-1-yl)-4-methoxyphenyl](5-methylfuran-2-yl)methyl}carbamoyl)methyl]-1H-indol-1-yl}propanoate;

3-{5-[({[2-(azepan-1-yl)-4-methoxyphenyl](5-methylfuran-2-yl)methyl}carbamoyl)methyl]-1H-indol-1-yl}propanoic acid;

N-[(5-chlorofuran-2-yl)[4-methyl-2-(pyrrolidin-1-yl)phenyl]methyl]-2-[3-(2-methanesulfonylethyl)-1H-indol-5-yl]acetamide;

N-{[4-methyl-2-(piperidin-1-yl)phenyl](5-methylfuran-2-yl)methyl}-2-[1-(oxan-4-ylmethyl)-1H-indol-5-yl]acetamide;

N-{[4-methyl-2-(piperidin-1-yl)phenyl](5-methylfuran-2-yl)methyl}-2-[1-(morpholine-4-carbonyl)-1H-indol-6-yl]acetamide;

N-{[4-methyl-2-(piperidin-1-yl)phenyl](5-methylfuran-2-yl)methyl}-2-[3-(methylsulfamoyl)-1H-indol-5-yl]acetamide;

N-{[4-methyl-2-(piperidin-1-yl)phenyl](5-methylfuran-2-yl)methyl}-2-[1-(morpholine-4-carbonyl)-1H-indol-5-yl]acetamide;

2-[3-(2-methanesulfonylacetyl)-1H-indol-6-yl]-N-{[4-methyl-2-(piperidin-1-yl)phenyl](5-methylfuran-2-yl)methyl}acetamide;

N-{[4-methyl-2-(piperidin-1-yl)phenyl](5-methylfuran-2-yl)methyl}-2-[1-(oxane-4-carbonyl)-1H-indol-5-yl]acetamide;

1-[3-(methanesulfonamidomethyl)-1H-indol-5-yl]-N-{[4-methyl-2-(piperidin-1-yl)phenyl](5-methylfuran-2-yl)methyl}cyclopropane-1-carboxamide;

N-{[4-methyl-2-(piperidin-1-yl)phenyl](5-methylfuran-2-yl)methyl}-2-[3-(morpholine-4-carbonyl)-1H-indol-5-yl]acetamide;

N-[(2,4-dimethylphenyl)(5-methylfuran-2-yl)methyl]-1-[2-(2-methoxyacetyl)-2,3-dihydro-1H-isoindol-5-yl]cyclopropane-1-carboxamide;

2-(1-cyclopropanecarbonyl-2,3-dihydro-1H-indol-5-yl)-N-{[4-methyl-2-(piperidin-1-yl)phenyl](5-methylfuran-2-yl)methyl}acetamide;

N-[(2,4-dimethylphenyl)(5-methylfuran-2-yl)methyl]-1-(2,2-dioxo-1,3-dihydro-4,2,1-benzoxathiazin-6-yl)cyclopropane-1-carboxamide;

N-[(2,4-dimethylphenyl)(5-methylfuran-2-yl)methyl]-1-(2,3-dioxo-2,3-dihydro-1H-indol-5-yl)cyclopropane-1-carboxamide;

1-(1-acetyl-2,3-dihydro-1H-indol-5-yl)-N-[(2,4-dimethylphenyl)(5-methylfuran-2-yl)methyl]cyclopropane-1-carboxamide;

1-(2-acetyl-2,3-dihydro-1H-isoindol-5-yl)-N-[(2,4-dimethylphenyl)(5-methylfuran-2-yl)methyl]cyclopropane-1-carboxamide;

N-[(2,4-dimethylphenyl)(5-methylfuran-2-yl)methyl]-1-(1-methyl-2-oxo-2,3-dihydro-1H-indol-5-yl)cyclopropane-1-carboxamide;

N-[(2-bromo-4-methylphenyl)(5-methylfuran-2-yl)methyl]-1-(2,2-dioxo-1,3-dihydro-4,2,1-benzoxathiazin-6-yl)cyclopropane-1-carboxamide;

N-[(2,4-dimethylphenyl)(5-methylfuran-2-yl)methyl]-1-(1-ethyl-2,2-dioxo-1,3-dihydro-2,1-benzothiazol-5-yl)cyclopropane-1-carboxamide;

N-{[2-(dimethylamino)-4-methylphenyl](5-methylfuran-2-yl)methyl}-1-(1-methyl-2,2-dioxo-1,3-dihydro-2,1-benzothiazol-5-yl)cyclopropane-1-carboxamide;

N-[(5-chlorofuran-2-yl)(2,4-dimethylphenyl)methyl]-1-(3-oxo-3,4-dihydro-2H-1,4-benzoxazin-7-yl)cyclopropane-1-carboxamide;

N-[(2-bromo-4-methylphenyl)(5-methylfuran-2-yl)methyl]-1-(3-oxo-3,4-dihydro-2H-1,4-benzoxazin-7-yl)cyclopropane-1-carboxamide;

N-[(2,4-dimethylphenyl)(6-methylpyridin-2-yl)methyl]-1-(3-oxo-3,4-dihydro-2H-1,4-benzoxazin-7-yl)cyclopropane-1-carboxamide;

1-(2H-1,3-benzodioxol-5-yl)-N-[(2,4-dimethylphenyl)(5-methylfuran-2-yl)methyl]cyclopropane-1-carboxamide;

N-[(2,4-dimethylphenyl)(furan-2-yl)methyl]-1-(3-oxo-3,4-dihydro-2H-1,4-benzoxazin-7-yl)cyclopropane-1-carboxamide;

N-[(4-chlorophenyl)(2,4-dimethylphenyl)methyl]-1-(3-oxo-3,4-dihydro-2H-1,4-benzoxazin-7-yl)cyclopropane-1-carboxamide;

N-[(2,4-dimethylphenyl)(5-methylfuran-2-yl)methyl]-1-(1-oxo-2,3-dihydro-1H-inden-5-yl)cyclopropane-1-carboxamide;

1-(2,3-dihydro-1H-indol-5-yl)-N-[(2,4-dimethylphenyl)(5-methylfuran-2-yl)methyl]cyclopropane-1-carboxamide;

N-[(3-chlorophenyl)(2,4-dimethylphenyl)methyl]-1-(3-oxo-3,4-dihydro-2H-1,4-benzoxazin-7-yl)cyclopropane-1-carboxamide;

N-[(2,4-dimethylphenyl)(5-methylfuran-2-yl)methyl]-1-{2-oxo-1H,2H,3H-pyrido[2,3-b][1,4]oxazin-6-yl}cyclopropane-1-carboxamide;

N-[(5-chlorofuran-2-yl)[4-methyl-2-(piperidin-1-yl)phenyl]methyl]-1-(3-oxo-3,4-dihydro-2H-1,4-benzoxazin-7-yl)cyclopropane-1-carboxamide;

1-(3,3-dimethyl-2-oxo-2,3-dihydro-1H-indol-5-yl)-N-[(2,4-dimethylphenyl)(5-methylfuran-2-yl)methyl]cyclopropane-1-carboxamide;

N-[(2-bromo-4-methoxyphenyl)(5-methylfuran-2-yl)methyl]-1-(2,2-dioxo-1,3-dihydro-4,2,1-benzoxathiazin-6-yl)cyclopropane-1-carboxamide;

N-{[2-(dimethylamino)-4-methylphenyl](5-methylfuran-2-yl)methyl}-1-(2,2-dioxo-1,3-dihydro-4,2,1-benzoxathiazin-6-yl)cyclopropane-1-carboxamide;

N-[(5-chlorofuran-2-yl)(2,4-dimethylphenyl)methyl]-1-(2,2-dioxo-1,3-dihydro-4,2,1-benzoxathiazin-6-yl)cyclopropane-1-carboxamide;

N-[(2-bromo-4-methylphenyl)(5-methylfuran-2-yl)methyl]-2-(2,2-dioxo-1,3-dihydro-4,2,1-benzoxathiazin-6-yl)acetamide;

3-[5-(1{[(2,4-dimethylphenyl)(5-methylfuran-2-yl)methyl]carbamoyl}cyclopropyl)-1H-indol-1-yl]propanoic acid;

3-{5-[1-({[4-methyl-2-(piperidin-1-yl)phenyl](5-methylfuran-2-yl)methyl}carbamoyl)cyclopropyl]-1H-indol-1-yl}propanoic acid;

N-[(2,4-dimethylphenyl)(5-methylfuran-2-yl)methyl]-1-(1-hydroxy-2,3-dihydro-1H-inden-5-yl)cyclopropane-1-carboxamide;

N-{[2-(dimethylamino)-4-methylphenyl](5-methylfuran-2-yl)methyl}-1-(3-oxo-3,4-dihydro-2H-1,4-benzoxazin-7-yl)cyclopropane-1-carboxamide;

N-[(2,4-dimethylphenyl)(5-methylfuran-2-yl)methyl]-1-[1-(oxan-4-ylmethyl)-2,2-dioxo-1,3-dihydro-2,1-benzothiazol-5-yl]cyclopropane-1-carboxamide;

N-[(2,4-dimethylphenyl)(5-methylfuran-2-yl)methyl]-1-(7-fluoro-2-oxo-2,3-dihydro-1H-indol-5-yl)cyclopropane-1-carboxamide;

1-(3,3-difluoro-2-oxo-2,3-dihydro-1H-indol-5-yl)-N-[(2,4-dimethylphenyl)(5-methylfuran-2-yl)methyl]cyclopropane-1-carboxamide;

N-[(5-chlorofuran-2-yl)(2,4-dimethylphenyl)methyl]-1-(1-methyl-2,2-dioxo-1,3-dihydro-2,1-benzothiazol-5-yl)cyclopropane-1-carboxamide;

1-(2H-1,3-benzodioxol-5-yl)-N-[(2-bromo-4-methylphenyl)(5-methylfuran-2-yl)methyl]cyclopropane-1-carboxamide;

N-{[4-methyl-2-(piperidin-1-yl)phenyl](5-methylfuran-2-yl)methyl}-1-[1-(oxan-4-ylmethyl)-2,2-dioxo-1,3-dihydro-2,1-benzothiazol-5-yl]cyclopropane-1-carboxamide;

N-[(2-bromo-4-methylphenyl)(5-methylfuran-2-yl)methyl]-1-[1-(oxan-4-ylmethyl)-2,2-dioxo-1,3-dihydro-2,1-benzothiazol-5-yl]cyclopropane-1-carboxamide;

1-(2H-1,3-benzodioxol-5-yl)-N-{[4-methyl-2-(piperidin-1-yl)phenyl](5-methylfuran-2-yl)methyl}cyclopropane-1-carboxamide;

N-[(2,4-dimethylphenyl)(5-methylfuran-2-yl)methyl]-1-[1-(hydroxyimino)-2,3-dihydro-1H-inden-5-yl]cyclopropane-1-carboxamide;

N-[(2,4-dimethylphenyl)(5-methylfuran-2-yl)methyl]-2-[1-(oxan-4-ylmethyl)-2,2-dioxo-1,3-dihydro-2,1-benzothiazol-5-yl]acetamide;

N-{[4-methyl-2-(piperidin-1-yl)phenyl](5-methylfuran-2-yl)methyl}-2-[1-(oxan-4-ylmethyl)-2,2-dioxo-1,3-dihydro-2,1-benzothiazol-5-yl]acetamide;

1-(2,2-dimethyl-2,4-dihydro-1,3-benzodioxin-7-yl)-N-[(2,4-dimethylphenyl)(5-methylfuran-2-yl)methyl]cyclopropane-1-carboxamide;

1-(2,2-dimethyl-2,4-dihydro-1,3-benzodioxin-6-yl)-N-[(2,4-dimethylphenyl)(5-methylfuran-2-yl)methyl]cyclopropane-1-carboxamide;

N-[(2,4-dimethylphenyl)(5-methylfuran-2-yl)methyl]-1-[3-(1-hydroxy-2-methylpropan-2-yl)-1H-indol-5-yl]cyclopropane-1-carboxamide;

1-(2,2-dioxo-1,3-dihydro-4,2,1-benzoxathiazin-6-yl)-N-{[4-methyl-2-(trifluoromethyl)phenyl](5-methylfuran-2-yl)methyl}cyclopropane-1-carboxamide;

N-[(2,4-dimethylphenyl)(5-methylfuran-2-yl)methyl]-1-(1-methyl-2,2-dioxo-1,3-dihydro-4,2,1-benzoxathiazin-6-yl)cyclopropane-1-carboxamide;

N-[(2-bromo-4-methylphenyl)(5-methylfuran-2-yl)methyl]-1-(1-methyl-2,2-dioxo-1,3-dihydro-4,2,1-benzoxathiazin-6-yl)cyclopropane-1-carboxamide;

1-(2,2-dioxo-1,3-dihydro-4,2,1-benzoxathiazin-6-yl)-N-[(2-methoxy-4-methylphenyl)(5-methylfuran-2-yl)methyl]cyclopropane-1-carboxamide; and 1-(2,2-dimethyl-2H-1,3-benzodioxol-5-yl)-N-[(2,4-dimethylphenyl)(5-methylfuran-2-yl)methyl]cyclopropane-1-carboxamide.

10. A combination product comprising:
i) a compound of formula (I) as defined in claim 1, or a pharmaceutically acceptable salt thereof; and
ii) another therapeutically active agent, such as a PPAR activator.

11. The combination product according to claim 10, component ii) is Elafibranor or seladelpar, saroglitazar, lanifibranor, pioglitazone or a pharmaceutically acceptable salt thereof.

12. The combination product according to claim 10, wherein the combination product is a composition comprising components i) and ii) and a pharmaceutically acceptable carrier.

13. The combination product according to claim 10, wherein the combination product is a kit of parts comprising components i) and ii), for sequential, separate or simultaneous use.

14. The combination product according to claim 10, wherein components i) and ii) are formulated in an injectable suspension, a gel, an oil, a pill, a tablet, a suppository, a powder, a capsule, an aerosol, an ointment, a cream, a patch, or means of galenic forms for a prolonged and/or slow release.

15. A method for the treatment of an autoimmune disease, an autoimmune-related disease, an inflammatory disease, a metabolic disease, a fibrotic disease or a cholestatic disease, wherein said method comprises administering to a subject in need thereof a therapeutically effective amount of a compound according to claim 1.

16. A method for the treatment of an autoimmune disease, an autoimmune-related disease, an inflammatory disease, a metabolic disease, a fibrotic disease or a cholestatic disease, wherein said method comprises administering to a subject in need thereof a therapeutically effective amount of the combination product according to claim 10.

* * * * *